(12) United States Patent
Aertgeerts et al.

(10) Patent No.: US 7,241,604 B1
(45) Date of Patent: Jul. 10, 2007

(54) CRYSTALLIZATION OF 11-BETA-HYDROXYSTEROID DEHYDROGENASE TYPE 1

(75) Inventors: Kathleen Aertgeerts, San Diego, CA (US); Oleg Brodsky, San Diego, CA (US); Ellen Chi, Del Mar, CA (US); Mark T. Hilgers, San Diego, CA (US); David J. Hosfield, San Diego, CA (US); Robert J. Skene, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 586 days.

(21) Appl. No.: 10/800,024

(22) Filed: Mar. 12, 2004

(51) Int. Cl.
*C12N 9/04* (2006.01)
*C12N 9/00* (2006.01)

(52) U.S. Cl. ........................................ 435/190; 435/183

(58) Field of Classification Search ................. 435/190
See application file for complete search history.

(56) References Cited

OTHER PUBLICATIONS

Stulnig et al. 11-Beta-Hydroxysteroid Dehydrogenase Type 1 in obesity and Type 2 Diabetes. Diabetologia. 2004. vol. 47, pp. 1-11.*

* cited by examiner

*Primary Examiner*—David J. Steadman
*Assistant Examiner*—Suzanne M. Noakes
(74) *Attorney, Agent, or Firm*—David J. Weitz

(57) ABSTRACT

Provided are crystals relating to 11-Beta-Hydroxysteroid Dehydrogenase type 1 and its various uses.

9 Claims, 213 Drawing Sheets

FIGURE 1

Amino acid sequence for full-length human wild type HSD11B1 [SEQ. ID No. 1]
(Residues 24-292 are underlined)

```
  1 MAFMKKYLLP ILGLFMAYYY YSANEEFRPE MLQGKKVIVT GASKGIGREM AYHLAKMGAH
 61 VVVTARSKET LQKVVSHCLE LGAASAHYIA GTMEDMTFAE QFVAQAGKLM GGLDMLILNH
121 ITNTSLNLFH DDIHHVRKSM EVNFLSYVVL TVAALPMLKQ SNGSIVVVSS LAGKVAYPMV
181 AAYSASKFAL DGFFSSIRKE YSVSRVNVSI TLCVLGLIDT ETAMKAVSGI VHMQAAPKEE
241 CALEIIKGGA LRQEEVYYDS SLWTTLLIRN PCRKILEFLY STSYNMDRFI NK
```

Human cDNA sequence encoding residues 24-292 of HSD11B1 [SEQ. ID No. 2]

```
  1 AACGAGGAAT TCAGACCAGA GATGCTCCAA GGAAAGAAAG TGATTGTCAC AGGGGCCAGC
 61 AAAGGGATCG GAAGAGAGAT GGCTTATCAT CTGGCGAAGA TGGGAGCCCA TGTGGTGGTG
121 ACAGCGAGGT CAAAAGAAAC TCTACAGAAG GTGGTATCCC ACTGCCTGGA GCTTGGAGCA
181 GCCTCAGCAC ACTACATTGC TGGCACCATG GAAGACATGA CCTTCGCAGA GCAATTTGTT
241 GCCCAAGCAG GAAAGCTCAT GGGAGGACTA GACATGCTCA TTCTCAACCA CATCACCAAC
301 ACTTCTTTGA ATCTTTTTCA TGATGATATT CACCATGTGC GCAAAAGCAT GGAAGTCAAC
361 TTCCTCAGTT ACGTGGTCCT GACTGTAGCT GCCTTGCCCA TGCTGAAGCA GAGCAATGGA
421 AGCATTGTTG TCGTCTCCTC TCTGGCTGGG AAAGTGGCTT ATCCAATGGT TGCTGCCTAT
481 TCTGCAAGCA AGTTTGCTTT GGATGGGTTC TTCTCCTCCA TCAGAAAGGA ATATTCAGTG
541 TCCAGGGTCA ATGTATCAAT CACTCTCTGT GTTCTTGGCC TCATAGACAC AGAAACAGCC
601 ATGAAGGCAG TTTCTGGGAT AGTCCATATG CAAGCAGCTC CAAAGGAGGA ATGTGCCCTG
661 GAGATCATCA AAGGGGAGC TCTGCGCCAA GAAGAAGTGT ATTATGACAG CTCACTCTGG
721 ACCACTCTTC TGATCAGAAA TCCATGCAGG AAGATCCTGG AATTTCTCTA CTCAACGAGC
781 TATAATATGG ACAGATTCAT AAACAAG
```

Human cDNA sequence encoding residues 24-258 of HSD11B1 [SEQ. ID No. 3]

```
  1 AACGAGGAAT TCAGACCAGA GATGCTCCAA GGAAAGAAAG TGATTGTCAC AGGGGCCAGC
 61 AAAGGGATCG GAAGAGAGAT GGCTTATCAT CTGGCGAAGA TGGGAGCCCA TGTGGTGGTG
121 ACAGCGAGGT CAAAAGAAAC TCTACAGAAG GTGGTATCCC ACTGCCTGGA GCTTGGAGCA
181 GCCTCAGCAC ACTACATTGC TGGCACCATG GAAGACATGA CCTTCGCAGA GCAATTTGTT
241 GCCCAAGCAG GAAAGCTCAT GGGAGGACTA GACATGCTCA TTCTCAACCA CATCACCAAC
301 ACTTCTTTGA ATCTTTTTCA TGATGATATT CACCATGTGC GCAAAAGCAT GGAAGTCAAC
361 TTCCTCAGTT ACGTGGTCCT GACTGTAGCT GCCTTGCCCA TGCTGAAGCA GAGCAATGGA
421 AGCATTGTTG TCGTCTCCTC TCTGGCTGGG AAAGTGGCTT ATCCAATGGT TGCTGCCTAT
481 TCTGCAAGCA AGTTTGCTTT GGATGGGTTC TTCTCCTCCA TCAGAAAGGA ATATTCAGTG
541 TCCAGGGTCA ATGTATCAAT CACTCTCTGT GTTCTTGGCC TCATAGACAC AGAAACAGCC
601 ATGAAGGCAG TTTCTGGGAT AGTCCATATG CAAGCAGCTC CAAAGGAGGA ATGTGCCCTG
661 GAGATCATCA AAGGGGAGC TCTGCGCCAA GAAGAAGTGT ATTAT
```

FIGURE 1 (cont.)

Human cDNA sequence encoding residues 24-267 of HSD11B1 [SEQ. ID No. 4]

```
  1 AACGAGGAAT TCAGACCAGA GATGCTCCAA GGAAAGAAAG TGATTGTCAC AGGGGCCAGC
 61 AAAGGGATCG GAAGAGAGAT GGCTTATCAT CTGGCGAAGA TGGGAGCCCA TGTGGTGGTG
121 ACAGCGAGGT CAAAAGAAAC TCTACAGAAG GTGGTATCCC ACTGCCTGGA GCTTGGAGCA
181 GCCTCAGCAC ACTACATTGC TGGCACCATG AAGACATGA CCTTCGCAGA GCAATTTGTT
241 GCCCAAGCAG GAAAGCTCAT GGGAGGACTA GACATGCTCA TTCTCAACCA CATCACCAAC
301 ACTTCTTTGA ATCTTTTTCA TGATGATATT CACCATGTGC GCAAAAGCAT GGAAGTCAAC
361 TTCCTCAGTT ACGTGGTCCT GACTGTAGCT GCCTTGCCCA TGCTGAAGCA GAGCAATGGA
421 AGCATTGTTG TCGTCTCCTC TCTGGCTGGG AAAGTGGCTT ATCCAATGGT TGCTGCCTAT
481 TCTGCAAGCA AGTTTGCTTT GGATGGGTTC TTCTCCTCCA TCAGAAAGGA ATATTCAGTG
541 TCCAGGGTCA ATGTATCAAT CACTCTCTGT GTTCTTGGCC TCATAGACAC AGAAACAGCC
601 ATGAAGGCAG TTTCTGGGAT AGTCCATATG CAAGCAGCTC CAAAGGAGGA ATGTGCCCTG
661 GAGATCATCA AAGGGGAGC TCTGCGCCAA GAAGAAGTGT ATTATGACAG CTCACTCTGG
721 ACCACTCTTC TG
```

**Amino acid sequence for residues 24-292 of HSB11B1 with a
N-terminal MKHQHQHQHQHQHQQPL tag [SEQ. ID No. 5]**
(N-terminal MKHQHQHQHQHQHQQPL tag is underlined)

```
  1 MKHQHQHQHQ HQHQQPLNEE FRPEMLQGKK VIVTGASKGI GREMAYHLAK MGAHVVVTAR
 61 SKETLQKVVS HCLELGAASA HYIAGTMEDM TFAEQFVAQA GKLMGGLDML ILNHITNTSL
121 NLFHDDIHHV RKSMEVNFLS YVVLTVAALP MLKQSNGSIV VVSSLAGKVA YPMVAAYSAS
181 KFALDGFFSS IRKEYSVSRV NVSITLCVLG LIDTETAMKA VSGIVHMQAA PKEECALEII
241 KGGALRQEEV YYDSSLWTTL LIRNPCRKIL EFLYSTSYNM DRFINK
```

**Amino acid sequence for residues 24-258 of HSB11B1 with a
N-terminal MKHQHQHQHQHQHQQPL tag [SEQ. ID No. 6]**
(N-terminal MKHQHQHQHQHQHQQPL tag is underlined)

```
  1 MKHQHQHQHQ HQHQQPLNEE FRPEMLQGKK VIVTGASKGI GREMAYHLAK MGAHVVVTAR
 61 SKETLQKVVS HCLELGAASA HYIAGTMEDM TFAEQFVAQA GKLMGGLDML ILNHITNTSL
121 NLFHDDIHHV RKSMEVNFLS YVVLTVAALP MLKQSNGSIV VVSSLAGKVA YPMVAAYSAS
181 KFALDGFFSS IRKEYSVSRV NVSITLCVLG LIDTETAMKA VSGIVHMQAA PKEECALEII
241 KGGALRQEEV YY
```

FIGURE 1 (cont.)

Amino acid sequence for residues 24-267 of HSB11B1 with a N-terminal MKHQHQHQHQHQHQQPL tag [SEQ. ID No. 7]
(N-terminal MKHQHQHQHQHQHQQPL tag is underlined)

```
  1 MKHQHQHQHQ HQHQQPLNEE FRPEMLQGKK VIVTGASKGI GREMAYHLAK MGAHVVVTAR
 61 SKETLQKVVS HCLELGAASA HYIAGTMEDM TFAEQFVAQA GKLMGGLDML ILNHITNTSL
121 NLFHDDIHHV RKSMEVNFLS YVVLTVAALP MLKQSNGSIV VVSSLAGKVA YPMVAAYSAS
181 KFALDGFFSS IRKEYSVSRV NVSITLCVLG LIDTETAMKA VSGIVHMQAA PKEECALEII
241 KGGALRQEEV YYDSSLWTTL L
```

DNA sequence encoding PCR Primer hsd1_24-f [SEQ. ID No. 8]

5'-AACGAGGAATTCAGACCAGAGATG-3'

DNA sequence encoding PCR Primer hsd1_292-r [SEQ. ID No. 9]

5'-CTTGTTTATGAATCTGTCCATATTATAGC-3'

DNA sequence encoding PCR Primer hsdC272Sqcf [SEQ. ID No. 10]
(Mutation is underlined)

5'-TCAGAAATCCATCCAGGAAGATC-3'

DNA sequence encoding PCR Primer hsdC272Sqcr [SEQ. ID No. 11]
(Mutation is underlined)

5'-GATCTTCCTGGATGGATTTCTGA-3'

DNA sequence encoding PCR Primer hsd1-258-r [SEQ. ID No. 12]

5'-ATAATACACTTCTTCTTGGCGCAGAGC-3'

FIGURE 1 (cont.)

DNA sequence encoding PCR Primer hsd1-267-r [SEQ. ID No. 13]

5'-CAGAAGAGTGGTCCAGAGTGAGCTGTC-3'

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | GLN | A | 21 | -12.232 | 14.783 | 31.949 | 1.00 | 34.55 |
| 3 | CA | GLN | A | 21 | -11.286 | 15.836 | 31.476 | 1.00 | 34.70 |
| 5 | CB | GLN | A | 21 | -11.956 | 17.212 | 31.532 | 1.00 | 35.11 |
| 8 | CG | GLN | A | 21 | -12.533 | 17.649 | 30.189 | 1.00 | 35.61 |
| 11 | CD | GLN | A | 21 | -13.101 | 19.051 | 30.220 | 1.00 | 36.87 |
| 12 | OE1 | GLN | A | 21 | -12.372 | 20.017 | 30.461 | 1.00 | 38.31 |
| 13 | NE2 | GLN | A | 21 | -14.403 | 19.172 | 29.969 | 1.00 | 37.37 |
| 16 | C | GLN | A | 21 | -9.970 | 15.838 | 32.268 | 1.00 | 34.48 |
| 17 | O | GLN | A | 21 | -9.911 | 15.342 | 33.403 | 1.00 | 34.44 |
| 21 | N | PRO | A | 22 | -8.919 | 16.400 | 31.670 | 1.00 | 34.07 |
| 22 | CA | PRO | A | 22 | -7.573 | 16.317 | 32.244 | 1.00 | 33.86 |
| 24 | CB | PRO | A | 22 | -6.670 | 16.646 | 31.052 | 1.00 | 33.90 |
| 27 | CG | PRO | A | 22 | -7.479 | 17.534 | 30.194 | 1.00 | 33.94 |
| 30 | CD | PRO | A | 22 | -8.920 | 17.161 | 30.405 | 1.00 | 34.04 |
| 33 | C | PRO | A | 22 | -7.315 | 17.298 | 33.386 | 1.00 | 33.79 |
| 34 | O | PRO | A | 22 | -7.820 | 18.426 | 33.379 | 1.00 | 33.70 |
| 35 | N | LEU | A | 23 | -6.516 | 16.854 | 34.352 | 1.00 | 33.49 |
| 37 | CA | LEU | A | 23 | -6.107 | 17.679 | 35.484 | 1.00 | 33.36 |
| 39 | CB | LEU | A | 23 | -5.162 | 16.893 | 36.400 | 1.00 | 33.10 |
| 42 | CG | LEU | A | 23 | -5.648 | 15.524 | 36.887 | 1.00 | 31.96 |
| 44 | CD1 | LEU | A | 23 | -4.562 | 14.843 | 37.699 | 1.00 | 31.41 |
| 48 | CD2 | LEU | A | 23 | -6.939 | 15.666 | 37.691 | 1.00 | 31.02 |
| 52 | C | LEU | A | 23 | -5.396 | 18.925 | 34.972 | 1.00 | 33.76 |
| 53 | O | LEU | A | 23 | -4.495 | 18.821 | 34.138 | 1.00 | 34.09 |
| 54 | N | ASN | A | 24 | -5.806 | 20.095 | 35.461 | 1.00 | 34.10 |
| 56 | CA | ASN | A | 24 | -5.178 | 21.358 | 35.071 | 1.00 | 34.24 |
| 58 | CB | ASN | A | 24 | -6.202 | 22.502 | 35.048 | 1.00 | 34.53 |
| 61 | CG | ASN | A | 24 | -7.037 | 22.520 | 33.771 | 1.00 | 35.51 |
| 62 | OD1 | ASN | A | 24 | -6.639 | 21.969 | 32.735 | 1.00 | 37.89 |
| 63 | ND2 | ASN | A | 24 | -8.199 | 23.159 | 33.838 | 1.00 | 36.53 |
| 66 | C | ASN | A | 24 | -4.020 | 21.660 | 36.016 | 1.00 | 34.03 |
| 67 | O | ASN | A | 24 | -4.070 | 22.594 | 36.823 | 1.00 | 34.44 |
| 68 | N | GLU | A | 25 | -2.982 | 20.834 | 35.896 | 1.00 | 33.40 |
| 70 | CA | GLU | A | 25 | -1.819 | 20.849 | 36.775 | 1.00 | 32.65 |
| 72 | CB | GLU | A | 25 | -2.016 | 19.876 | 37.950 | 1.00 | 33.09 |
| 75 | CG | GLU | A | 25 | -3.368 | 19.968 | 38.652 | 1.00 | 34.76 |
| 78 | CD | GLU | A | 25 | -3.357 | 19.372 | 40.053 | 1.00 | 36.52 |
| 79 | OE1 | GLU | A | 25 | -3.945 | 19.991 | 40.971 | 1.00 | 38.22 |
| 80 | OE2 | GLU | A | 25 | -2.768 | 18.283 | 40.238 | 1.00 | 37.54 |

FIGURE 3 (cont.)

| A | B | C | D | E | F | G | H | I | J |
|---|---|---|---|---|---|---|---|---|---|
| 81  | C   | GLU | A | 25 | -0.590 | 20.414 | 35.984 | 1.00 | 31.40 |
| 82  | O   | GLU | A | 25 | -0.700 | 19.640 | 35.033 | 1.00 | 31.29 |
| 83  | N   | GLU | A | 26 |  0.578 | 20.907 | 36.379 | 1.00 | 29.78 |
| 85  | CA  | GLU | A | 26 |  1.840 | 20.407 | 35.838 | 1.00 | 28.67 |
| 87  | CB  | GLU | A | 26 |  3.001 | 21.338 | 36.217 | 1.00 | 29.19 |
| 90  | CG  | GLU | A | 26 |  3.969 | 21.624 | 35.075 | 1.00 | 31.46 |
| 93  | CD  | GLU | A | 26 |  5.341 | 22.076 | 35.559 | 1.00 | 34.18 |
| 94  | OE1 | GLU | A | 26 |  5.408 | 22.956 | 36.447 | 1.00 | 35.78 |
| 95  | OE2 | GLU | A | 26 |  6.358 | 21.552 | 35.049 | 1.00 | 36.07 |
| 96  | C   | GLU | A | 26 |  2.084 | 19.012 | 36.414 | 1.00 | 26.71 |
| 97  | O   | GLU | A | 26 |  1.740 | 18.751 | 37.565 | 1.00 | 26.21 |
| 98  | N   | PHE | A | 27 |  2.673 | 18.115 | 35.626 | 1.00 | 24.64 |
| 100 | CA  | PHE | A | 27 |  3.035 | 16.800 | 36.146 | 1.00 | 23.28 |
| 102 | CB  | PHE | A | 27 |  3.579 | 15.881 | 35.054 | 1.00 | 22.53 |
| 105 | CG  | PHE | A | 27 |  4.011 | 14.541 | 35.573 | 1.00 | 19.85 |
| 106 | CD1 | PHE | A | 27 |  3.069 | 13.558 | 35.848 | 1.00 | 18.53 |
| 108 | CE1 | PHE | A | 27 |  3.459 | 12.318 | 36.343 | 1.00 | 16.99 |
| 110 | CZ  | PHE | A | 27 |  4.798 | 12.053 | 36.578 | 1.00 | 17.51 |
| 112 | CE2 | PHE | A | 27 |  5.751 | 13.028 | 36.312 | 1.00 | 17.43 |
| 114 | CD2 | PHE | A | 27 |  5.355 | 14.268 | 35.817 | 1.00 | 19.22 |
| 116 | C   | PHE | A | 27 |  4.097 | 16.934 | 37.232 | 1.00 | 23.06 |
| 117 | O   | PHE | A | 27 |  5.033 | 17.733 | 37.107 | 1.00 | 22.79 |
| 118 | N   | ARG | A | 28 |  3.936 | 16.145 | 38.291 | 1.00 | 22.98 |
| 120 | CA  | ARG | A | 28 |  4.934 | 15.998 | 39.348 | 1.00 | 23.01 |
| 122 | CB  | ARG | A | 28 |  4.439 | 16.647 | 40.643 | 1.00 | 23.40 |
| 125 | CG  | ARG | A | 28 |  3.938 | 18.086 | 40.518 | 1.00 | 25.90 |
| 128 | CD  | ARG | A | 28 |  3.365 | 18.660 | 41.820 | 1.00 | 28.75 |
| 131 | NE  | ARG | A | 28 |  3.024 | 17.607 | 42.783 | 1.00 | 31.44 |
| 133 | CZ  | ARG | A | 28 |  1.797 | 17.135 | 43.028 | 1.00 | 33.22 |
| 134 | NH1 | ARG | A | 28 |  0.723 | 17.618 | 42.406 | 1.00 | 33.85 |
| 137 | NH2 | ARG | A | 28 |  1.645 | 16.161 | 43.919 | 1.00 | 34.64 |
| 140 | C   | ARG | A | 28 |  5.133 | 14.497 | 39.585 | 1.00 | 22.27 |
| 141 | O   | ARG | A | 28 |  4.146 | 13.764 | 39.645 | 1.00 | 21.88 |
| 142 | N   | PRO | A | 29 |  6.375 | 14.024 | 39.725 | 1.00 | 22.03 |
| 143 | CA  | PRO | A | 29 |  6.615 | 12.592 | 39.984 | 1.00 | 21.92 |
| 145 | CB  | PRO | A | 29 |  8.146 | 12.482 | 40.116 | 1.00 | 22.04 |
| 148 | CG  | PRO | A | 29 |  8.687 | 13.864 | 40.124 | 1.00 | 22.46 |
| 151 | CD  | PRO | A | 29 |  7.629 | 14.791 | 39.629 | 1.00 | 22.27 |
| 154 | C   | PRO | A | 29 |  5.912 | 12.050 | 41.238 | 1.00 | 21.82 |
| 155 | O   | PRO | A | 29 |  5.594 | 10.864 | 41.285 | 1.00 | 21.34 |
| 156 | N   | GLU | A | 30 |  5.639 | 12.918 | 42.210 | 1.00 | 22.04 |
| 158 | CA  | GLU | A | 30 |  4.942 | 12.537 | 43.439 | 1.00 | 21.97 |
| 160 | CB  | GLU | A | 30 |  4.927 | 13.714 | 44.428 | 1.00 | 22.77 |
| 163 | CG  | GLU | A | 30 |  6.284 | 14.045 | 45.032 | 1.00 | 25.13 |
| 166 | CD  | GLU | A | 30 |  7.203 | 14.841 | 44.109 | 1.00 | 28.25 |
| 167 | OE1 | GLU | A | 30 |  6.724 | 15.477 | 43.136 | 1.00 | 27.88 |
| 168 | OE2 | GLU | A | 30 |  8.428 | 14.830 | 44.366 | 1.00 | 31.81 |
| 169 | C   | GLU | A | 30 |  3.506 | 12.060 | 43.185 | 1.00 | 20.96 |
| 170 | O   | GLU | A | 30 |  2.905 | 11.404 | 44.034 | 1.00 | 20.81 |

FIGURE 3 (cont.)

| A | B | C | D | E | F | G | H | I | J |
|---|---|---|---|---|---|---|---|---|---|
| 171 | N | MET | A | 31 | 2.956 | 12.387 | 42.017 | 1.00 | 20.01 |
| 173 | CA | MET | A | 31 | 1.632 | 11.905 | 41.615 | 1.00 | 19.63 |
| 175 | CB | MET | A | 31 | 1.238 | 12.500 | 40.265 | 1.00 | 19.55 |
| 178 | CG | MET | A | 31 | 0.889 | 13.982 | 40.301 | 1.00 | 20.10 |
| 181 | SD | MET | A | 31 | 0.664 | 14.600 | 38.617 | 1.00 | 20.54 |
| 182 | CE | MET | A | 31 | -0.093 | 16.225 | 38.936 | 1.00 | 21.81 |
| 186 | C | MET | A | 31 | 1.541 | 10.378 | 41.515 | 1.00 | 19.10 |
| 187 | O | MET | A | 31 | 0.446 | 9.821 | 41.554 | 1.00 | 19.75 |
| 188 | N | LEU | A | 32 | 2.682 | 9.714 | 41.373 | 1.00 | 18.13 |
| 190 | CA | LEU | A | 32 | 2.725 | 8.252 | 41.285 | 1.00 | 17.38 |
| 192 | CB | LEU | A | 32 | 3.612 | 7.816 | 40.111 | 1.00 | 17.46 |
| 195 | CG | LEU | A | 32 | 2.980 | 7.731 | 38.720 | 1.00 | 17.94 |
| 197 | CD1 | LEU | A | 32 | 2.512 | 9.091 | 38.269 | 1.00 | 18.76 |
| 201 | CD2 | LEU | A | 32 | 1.841 | 6.724 | 38.688 | 1.00 | 18.52 |
| 205 | C | LEU | A | 32 | 3.219 | 7.576 | 42.567 | 1.00 | 16.75 |
| 206 | O | LEU | A | 32 | 3.230 | 6.351 | 42.659 | 1.00 | 15.57 |
| 207 | N | GLN | A | 33 | 3.646 | 8.362 | 43.552 | 1.00 | 16.57 |
| 209 | CA | GLN | A | 33 | 4.127 | 7.807 | 44.814 | 1.00 | 16.81 |
| 211 | CB | GLN | A | 33 | 4.609 | 8.928 | 45.728 | 1.00 | 17.03 |
| 214 | CG | GLN | A | 33 | 5.457 | 8.466 | 46.880 | 1.00 | 19.55 |
| 217 | CD | GLN | A | 33 | 6.117 | 9.637 | 47.587 | 1.00 | 23.05 |
| 218 | OE1 | GLN | A | 33 | 7.250 | 9.530 | 48.046 | 1.00 | 27.78 |
| 219 | NE2 | GLN | A | 33 | 5.408 | 10.754 | 47.669 | 1.00 | 25.68 |
| 222 | C | GLN | A | 33 | 3.028 | 7.014 | 45.513 | 1.00 | 16.02 |
| 223 | O | GLN | A | 33 | 1.937 | 7.522 | 45.745 | 1.00 | 16.34 |
| 224 | N | GLY | A | 34 | 3.311 | 5.752 | 45.806 | 1.00 | 15.47 |
| 226 | CA | GLY | A | 34 | 2.361 | 4.880 | 46.467 | 1.00 | 15.31 |
| 229 | C | GLY | A | 34 | 1.225 | 4.385 | 45.596 | 1.00 | 14.97 |
| 230 | O | GLY | A | 34 | 0.354 | 3.670 | 46.079 | 1.00 | 15.08 |
| 231 | N | LYS | A | 35 | 1.225 | 4.750 | 44.314 | 1.00 | 14.68 |
| 233 | CA | LYS | A | 35 | 0.165 | 4.321 | 43.415 | 1.00 | 14.53 |
| 235 | CB | LYS | A | 35 | 0.068 | 5.226 | 42.183 | 1.00 | 14.81 |
| 238 | CG | LYS | A | 35 | -0.308 | 6.681 | 42.513 | 1.00 | 17.15 |
| 241 | CD | LYS | A | 35 | -1.702 | 6.801 | 43.120 | 1.00 | 19.83 |
| 244 | CE | LYS | A | 35 | -2.113 | 8.262 | 43.286 | 1.00 | 21.68 |
| 247 | NZ | LYS | A | 35 | -3.354 | 8.403 | 44.107 | 1.00 | 23.59 |
| 251 | C | LYS | A | 35 | 0.396 | 2.877 | 43.010 | 1.00 | 13.89 |
| 252 | O | LYS | A | 35 | 1.526 | 2.409 | 42.973 | 1.00 | 14.09 |
| 253 | N | LYS | A | 36 | -0.690 | 2.183 | 42.705 | 1.00 | 12.71 |
| 255 | CA | LYS | A | 36 | -0.654 | 0.758 | 42.404 | 1.00 | 12.37 |
| 257 | CB | LYS | A | 36 | -1.731 | 0.036 | 43.200 | 1.00 | 12.74 |
| 260 | CG | LYS | A | 36 | -1.494 | 0.132 | 44.706 | 1.00 | 13.40 |
| 263 | CD | LYS | A | 36 | -2.719 | -0.178 | 45.534 | 1.00 | 15.94 |
| 266 | CE | LYS | A | 36 | -2.455 | 0.188 | 46.986 | 1.00 | 18.33 |
| 269 | NZ | LYS | A | 36 | -3.393 | -0.468 | 47.929 | 1.00 | 20.06 |
| 273 | C | LYS | A | 36 | -0.875 | 0.605 | 40.907 | 1.00 | 11.85 |
| 274 | O | LYS | A | 36 | -1.941 | 0.931 | 40.390 | 1.00 | 11.45 |
| 275 | N | VAL | A | 37 | 0.143 | 0.112 | 40.215 | 1.00 | 11.52 |
| 277 | CA | VAL | A | 37 | 0.165 | 0.160 | 38.758 | 1.00 | 11.10 |

FIGURE 3 (cont.)

| A | B | C | D | E | F | G | H | I | J |
|---|---|---|---|---|---|---|---|---|---|
| 279 | CB | VAL | A | 37 | 1.191 | 1.208 | 38.268 | 1.00 | 11.41 |
| 281 | CG1 | VAL | A | 37 | 1.122 | 1.363 | 36.747 | 1.00 | 11.58 |
| 285 | CG2 | VAL | A | 37 | 0.980 | 2.540 | 38.981 | 1.00 | 11.66 |
| 289 | C | VAL | A | 37 | 0.544 | -1.178 | 38.165 | 1.00 | 11.35 |
| 290 | O | VAL | A | 37 | 1.497 | -1.799 | 38.614 | 1.00 | 11.33 |
| 291 | N | ILE | A | 38 | -0.229 | -1.613 | 37.168 | 1.00 | 10.79 |
| 293 | CA | ILE | A | 38 | 0.103 | -2.755 | 36.327 | 1.00 | 10.52 |
| 295 | CB | ILE | A | 38 | -1.178 | -3.554 | 36.002 | 1.00 | 10.81 |
| 297 | CG1 | ILE | A | 38 | -1.610 | -4.393 | 37.205 | 1.00 | 10.48 |
| 300 | CD1 | ILE | A | 38 | -2.994 | -4.972 | 37.059 | 1.00 | 10.29 |
| 304 | CG2 | ILE | A | 38 | -0.992 | -4.439 | 34.768 | 1.00 | 11.87 |
| 308 | C | ILE | A | 38 | 0.718 | -2.251 | 35.031 | 1.00 | 10.89 |
| 309 | O | ILE | A | 38 | 0.208 | -1.306 | 34.441 | 1.00 | 10.31 |
| 310 | N | VAL | A | 39 | 1.808 | -2.870 | 34.598 | 1.00 | 10.26 |
| 312 | CA | VAL | A | 39 | 2.365 | -2.610 | 33.270 | 1.00 | 10.58 |
| 314 | CB | VAL | A | 39 | 3.762 | -1.963 | 33.321 | 1.00 | 10.68 |
| 316 | CG1 | VAL | A | 39 | 4.175 | -1.452 | 31.917 | 1.00 | 10.52 |
| 320 | CG2 | VAL | A | 39 | 3.830 | -0.856 | 34.332 | 1.00 | 12.19 |
| 324 | C | VAL | A | 39 | 2.491 | -3.934 | 32.542 | 1.00 | 10.20 |
| 325 | O | VAL | A | 39 | 3.166 | -4.850 | 33.016 | 1.00 | 10.02 |
| 326 | N | THR | A | 40 | 1.848 | -4.042 | 31.387 | 1.00 | 10.58 |
| 328 | CA | THR | A | 40 | 2.006 | -5.228 | 30.546 | 1.00 | 10.42 |
| 330 | CB | THR | A | 40 | 0.681 | -5.670 | 29.887 | 1.00 | 10.70 |
| 332 | OG1 | THR | A | 40 | 0.339 | -4.780 | 28.814 | 1.00 | 11.23 |
| 334 | CG2 | THR | A | 40 | -0.487 | -5.633 | 30.880 | 1.00 | 11.34 |
| 338 | C | THR | A | 40 | 3.080 | -5.018 | 29.491 | 1.00 | 10.31 |
| 339 | O | THR | A | 40 | 3.491 | -3.890 | 29.207 | 1.00 | 10.39 |
| 340 | N | GLY | A | 41 | 3.554 | -6.117 | 28.921 | 1.00 | 10.43 |
| 342 | CA | GLY | A | 41 | 4.661 | -6.046 | 27.984 | 1.00 | 10.23 |
| 345 | C | GLY | A | 41 | 5.852 | -5.312 | 28.571 | 1.00 | 10.53 |
| 346 | O | GLY | A | 41 | 6.459 | -4.466 | 27.921 | 1.00 | 10.66 |
| 347 | N | ALA | A | 42 | 6.204 | -5.665 | 29.804 | 1.00 | 11.06 |
| 349 | CA | ALA | A | 42 | 7.131 | -4.864 | 30.608 | 1.00 | 11.17 |
| 351 | CB | ALA | A | 42 | 6.475 | -4.508 | 31.930 | 1.00 | 11.81 |
| 355 | C | ALA | A | 42 | 8.496 | -5.503 | 30.837 | 1.00 | 11.69 |
| 356 | O | ALA | A | 42 | 9.270 | -5.029 | 31.672 | 1.00 | 11.39 |
| 357 | N | SER | A | 43 | 8.823 | -6.526 | 30.052 | 1.00 | 11.89 |
| 359 | CA | SER | A | 43 | 10.103 | -7.227 | 30.178 | 1.00 | 12.12 |
| 361 | CB | SER | A | 43 | 9.949 | -8.672 | 29.731 | 1.00 | 12.15 |
| 364 | OG | SER | A | 43 | 9.611 | -8.763 | 28.365 | 1.00 | 11.52 |
| 366 | C | SER | A | 43 | 11.220 | -6.549 | 29.384 | 1.00 | 12.17 |
| 367 | O | SER | A | 43 | 12.416 | -6.793 | 29.619 | 1.00 | 12.38 |
| 368 | N | LYS | A | 44 | 10.820 | -5.712 | 28.424 | 1.00 | 12.05 |
| 370 | CA | LYS | A | 44 | 11.759 | -4.964 | 27.601 | 1.00 | 12.04 |
| 372 | CB | LYS | A | 44 | 12.334 | -5.864 | 26.511 | 1.00 | 12.93 |
| 375 | CG | LYS | A | 44 | 11.288 | -6.514 | 25.634 | 1.00 | 14.58 |
| 378 | CD | LYS | A | 44 | 11.886 | -7.587 | 24.753 | 1.00 | 17.65 |
| 381 | CE | LYS | A | 44 | 10.870 | -8.193 | 23.815 | 1.00 | 19.54 |
| 384 | NZ | LYS | A | 44 | 11.571 | -9.041 | 22.777 | 1.00 | 20.14 |

FIGURE 3 (cont.)

| A | B | C | D | E | F | G | H | I | J |
|---|---|---|---|---|---|---|---|---|---|
| 388 | C | LYS | A | 44 | 11.046 | -3.765 | 26.984 | 1.00 | 11.35 |
| 389 | O | LYS | A | 44 | 9.868 | -3.525 | 27.253 | 1.00 | 11.04 |
| 390 | N | GLY | A | 45 | 11.774 | -3.005 | 26.181 | 1.00 | 10.96 |
| 392 | CA | GLY | A | 45 | 11.202 | -1.938 | 25.394 | 1.00 | 10.30 |
| 395 | C | GLY | A | 45 | 10.609 | -0.858 | 26.260 | 1.00 | 9.82 |
| 396 | O | GLY | A | 45 | 11.096 | -0.577 | 27.358 | 1.00 | 10.41 |
| 397 | N | ILE | A | 46 | 9.553 | -0.233 | 25.754 | 1.00 | 10.01 |
| 399 | CA | ILE | A | 46 | 8.899 | 0.868 | 26.445 | 1.00 | 10.09 |
| 401 | CB | ILE | A | 46 | 7.858 | 1.523 | 25.506 | 1.00 | 10.12 |
| 403 | CG1 | ILE | A | 46 | 8.563 | 2.073 | 24.248 | 1.00 | 11.19 |
| 406 | CD1 | ILE | A | 46 | 7.676 | 2.092 | 22.999 | 1.00 | 12.47 |
| 410 | CG2 | ILE | A | 46 | 7.070 | 2.616 | 26.245 | 1.00 | 11.56 |
| 414 | C | ILE | A | 46 | 8.270 | 0.437 | 27.767 | 1.00 | 9.79 |
| 415 | O | ILE | A | 46 | 8.339 | 1.162 | 28.738 | 1.00 | 10.38 |
| 416 | N | GLY | A | 47 | 7.681 | -0.756 | 27.804 | 1.00 | 9.59 |
| 418 | CA | GLY | A | 47 | 7.094 | -1.268 | 29.036 | 1.00 | 9.73 |
| 421 | C | GLY | A | 47 | 8.103 | -1.361 | 30.163 | 1.00 | 10.00 |
| 422 | O | GLY | A | 47 | 7.810 | -0.966 | 31.285 | 1.00 | 10.21 |
| 423 | N | ARG | A | 48 | 9.291 | -1.886 | 29.873 | 1.00 | 10.41 |
| 425 | CA | ARG | A | 48 | 10.353 | -1.953 | 30.876 | 1.00 | 10.68 |
| 427 | CB | ARG | A | 48 | 11.582 | -2.668 | 30.315 | 1.00 | 10.34 |
| 430 | CG | ARG | A | 48 | 12.798 | -2.614 | 31.216 | 1.00 | 11.49 |
| 433 | CD | ARG | A | 48 | 13.926 | -3.512 | 30.774 | 1.00 | 12.74 |
| 436 | NE | ARG | A | 48 | 14.373 | -3.169 | 29.432 | 1.00 | 13.41 |
| 438 | CZ | ARG | A | 48 | 15.214 | -3.903 | 28.720 | 1.00 | 15.06 |
| 439 | NH1 | ARG | A | 48 | 15.757 | -5.002 | 29.235 | 1.00 | 17.63 |
| 442 | NH2 | ARG | A | 48 | 15.550 | -3.519 | 27.501 | 1.00 | 15.73 |
| 445 | C | ARG | A | 48 | 10.715 | -0.557 | 31.368 | 1.00 | 10.85 |
| 446 | O | ARG | A | 48 | 10.857 | -0.338 | 32.567 | 1.00 | 10.29 |
| 447 | N | GLU | A | 49 | 10.861 | 0.390 | 30.445 | 1.00 | 10.84 |
| 449 | CA | GLU | A | 49 | 11.181 | 1.761 | 30.823 | 1.00 | 11.07 |
| 451 | CB | GLU | A | 49 | 11.457 | 2.643 | 29.593 | 1.00 | 11.30 |
| 454 | CG | GLU | A | 49 | 12.669 | 2.235 | 28.757 | 1.00 | 14.01 |
| 457 | CD | GLU | A | 49 | 13.953 | 2.069 | 29.550 | 1.00 | 17.08 |
| 458 | OE1 | GLU | A | 49 | 14.716 | 1.118 | 29.260 | 1.00 | 18.76 |
| 459 | OE2 | GLU | A | 49 | 14.218 | 2.886 | 30.463 | 1.00 | 19.04 |
| 460 | C | GLU | A | 49 | 10.088 | 2.384 | 31.676 | 1.00 | 10.74 |
| 461 | O | GLU | A | 49 | 10.377 | 3.162 | 32.576 | 1.00 | 10.84 |
| 462 | N | MET | A | 50 | 8.828 | 2.047 | 31.405 | 1.00 | 9.94 |
| 464 | CA | MET | A | 50 | 7.736 | 2.562 | 32.214 | 1.00 | 10.51 |
| 466 | CB | MET | A | 50 | 6.377 | 2.235 | 31.580 | 1.00 | 10.23 |
| 469 | CG | MET | A | 50 | 6.094 | 3.123 | 30.376 | 1.00 | 11.02 |
| 472 | SD | MET | A | 50 | 4.428 | 3.013 | 29.708 | 1.00 | 12.32 |
| 473 | CE | MET | A | 50 | 4.435 | 1.396 | 28.956 | 1.00 | 11.67 |
| 477 | C | MET | A | 50 | 7.833 | 2.019 | 33.641 | 1.00 | 10.42 |
| 478 | O | MET | A | 50 | 7.681 | 2.770 | 34.587 | 1.00 | 10.58 |
| 479 | N | ALA | A | 51 | 8.104 | 0.722 | 33.773 | 1.00 | 10.80 |
| 481 | CA | ALA | A | 51 | 8.254 | 0.094 | 35.088 | 1.00 | 10.78 |
| 483 | CB | ALA | A | 51 | 8.515 | -1.410 | 34.950 | 1.00 | 11.65 |

FIGURE 3 (cont.)

| A | B | C | D | E | F | G | H | I | J |
|---|---|---|---|---|---|---|---|---|---|
| 487 | C | ALA | A | 51 | 9.391 | 0.781 | 35.852 | 1.00 | 10.88 |
| 488 | O | ALA | A | 51 | 9.242 | 1.067 | 37.023 | 1.00 | 11.23 |
| 489 | N | TYR | A | 52 | 10.487 | 1.091 | 35.166 | 1.00 | 11.08 |
| 491 | CA | TYR | A | 52 | 11.634 | 1.747 | 35.806 | 1.00 | 11.71 |
| 493 | CB | TYR | A | 52 | 12.854 | 1.742 | 34.881 | 1.00 | 11.74 |
| 496 | CG | TYR | A | 52 | 13.489 | 0.375 | 34.674 | 1.00 | 11.90 |
| 497 | CD1 | TYR | A | 52 | 13.093 | -0.740 | 35.429 | 1.00 | 13.42 |
| 499 | CE1 | TYR | A | 52 | 13.672 | -1.986 | 35.239 | 1.00 | 14.70 |
| 501 | CZ | TYR | A | 52 | 14.650 | -2.135 | 34.300 | 1.00 | 14.86 |
| 502 | OH | TYR | A | 52 | 15.222 | -3.383 | 34.128 | 1.00 | 16.48 |
| 504 | CE2 | TYR | A | 52 | 15.067 | -1.055 | 33.544 | 1.00 | 14.46 |
| 506 | CD2 | TYR | A | 52 | 14.478 | 0.189 | 33.725 | 1.00 | 14.43 |
| 508 | C | TYR | A | 52 | 11.296 | 3.157 | 36.274 | 1.00 | 11.75 |
| 509 | O | TYR | A | 52 | 11.662 | 3.528 | 37.387 | 1.00 | 12.11 |
| 510 | N | HIS | A | 53 | 10.588 | 3.933 | 35.459 | 1.00 | 11.95 |
| 512 | CA | HIS | A | 53 | 10.145 | 5.266 | 35.887 | 1.00 | 11.93 |
| 514 | CB | HIS | A | 53 | 9.420 | 6.005 | 34.771 | 1.00 | 11.83 |
| 517 | CG | HIS | A | 53 | 10.335 | 6.612 | 33.755 | 1.00 | 12.67 |
| 518 | ND1 | HIS | A | 53 | 11.257 | 7.590 | 34.070 | 1.00 | 14.65 |
| 520 | CE1 | HIS | A | 53 | 11.902 | 7.948 | 32.972 | 1.00 | 16.59 |
| 522 | NE2 | HIS | A | 53 | 11.439 | 7.232 | 31.963 | 1.00 | 15.09 |
| 524 | CD2 | HIS | A | 53 | 10.463 | 6.384 | 32.427 | 1.00 | 14.67 |
| 526 | C | HIS | A | 53 | 9.219 | 5.195 | 37.095 | 1.00 | 12.21 |
| 527 | O | HIS | A | 53 | 9.378 | 5.963 | 38.041 | 1.00 | 12.17 |
| 528 | N | LEU | A | 54 | 8.255 | 4.280 | 37.055 | 1.00 | 12.00 |
| 530 | CA | LEU | A | 54 | 7.314 | 4.105 | 38.156 | 1.00 | 12.64 |
| 532 | CB | LEU | A | 54 | 6.258 | 3.051 | 37.797 | 1.00 | 12.10 |
| 535 | CG | LEU | A | 54 | 5.289 | 3.488 | 36.690 | 1.00 | 13.21 |
| 537 | CD1 | LEU | A | 54 | 4.571 | 2.280 | 36.101 | 1.00 | 13.57 |
| 541 | CD2 | LEU | A | 54 | 4.284 | 4.506 | 37.224 | 1.00 | 13.66 |
| 545 | C | LEU | A | 54 | 8.038 | 3.717 | 39.451 | 1.00 | 12.92 |
| 546 | O | LEU | A | 54 | 7.679 | 4.173 | 40.540 | 1.00 | 13.14 |
| 547 | N | ALA | A | 55 | 9.055 | 2.880 | 39.321 | 1.00 | 13.26 |
| 549 | CA | ALA | A | 55 | 9.860 | 2.432 | 40.442 | 1.00 | 14.00 |
| 551 | CB | ALA | A | 55 | 10.822 | 1.351 | 39.998 | 1.00 | 13.49 |
| 555 | C | ALA | A | 55 | 10.616 | 3.616 | 41.041 | 1.00 | 14.38 |
| 556 | O | ALA | A | 55 | 10.606 | 3.809 | 42.245 | 1.00 | 14.77 |
| 557 | N | LYS | A | 56 | 11.230 | 4.430 | 40.196 | 1.00 | 14.87 |
| 559 | CA | LYS | A | 56 | 11.919 | 5.649 | 40.651 | 1.00 | 15.88 |
| 561 | CB | LYS | A | 56 | 12.582 | 6.363 | 39.470 | 1.00 | 16.35 |
| 564 | CG | LYS | A | 56 | 13.856 | 5.709 | 38.953 | 1.00 | 19.70 |
| 567 | CD | LYS | A | 56 | 14.552 | 6.604 | 37.919 | 1.00 | 23.16 |
| 570 | CE | LYS | A | 56 | 15.285 | 5.796 | 36.858 | 1.00 | 25.02 |
| 573 | NZ | LYS | A | 56 | 14.361 | 5.036 | 35.976 | 1.00 | 27.17 |
| 577 | C | LYS | A | 56 | 10.957 | 6.617 | 41.372 | 1.00 | 15.91 |
| 578 | O | LYS | A | 56 | 11.357 | 7.323 | 42.303 | 1.00 | 16.11 |
| 579 | N | MET | A | 57 | 9.689 | 6.626 | 40.965 | 1.00 | 15.83 |
| 581 | CA | MET | A | 57 | 8.668 | 7.483 | 41.584 | 1.00 | 15.88 |
| 583 | CB | MET | A | 57 | 7.552 | 7.789 | 40.578 | 1.00 | 16.41 |

FIGURE 3 (cont.)

| A | B | C | D | E | F | G | H | I | J |
|---|---|---|---|---|---|---|---|---|---|
| 586 | CG | MET | A | 57 | 7.991 | 8.614 | 39.368 | 1.00 | 18.42 |
| 589 | SD | MET | A | 57 | 6.650 | 8.703 | 38.147 | 1.00 | 24.07 |
| 590 | CE | MET | A | 57 | 7.518 | 9.019 | 36.632 | 1.00 | 23.59 |
| 594 | C | MET | A | 57 | 8.066 | 6.885 | 42.859 | 1.00 | 15.40 |
| 595 | O | MET | A | 57 | 7.229 | 7.520 | 43.502 | 1.00 | 15.81 |
| 596 | N | GLY | A | 58 | 8.469 | 5.666 | 43.217 | 1.00 | 14.66 |
| 598 | CA | GLY | A | 58 | 7.997 | 5.016 | 44.430 | 1.00 | 13.88 |
| 601 | C | GLY | A | 58 | 6.607 | 4.408 | 44.332 | 1.00 | 13.58 |
| 602 | O | GLY | A | 58 | 5.887 | 4.296 | 45.326 | 1.00 | 13.18 |
| 603 | N | ALA | A | 59 | 6.219 | 4.008 | 43.126 | 1.00 | 13.47 |
| 605 | CA | ALA | A | 59 | 4.971 | 3.280 | 42.924 | 1.00 | 13.36 |
| 607 | CB | ALA | A | 59 | 4.545 | 3.362 | 41.460 | 1.00 | 13.40 |
| 611 | C | ALA | A | 59 | 5.097 | 1.813 | 43.347 | 1.00 | 13.24 |
| 612 | O | ALA | A | 59 | 6.200 | 1.278 | 43.489 | 1.00 | 12.97 |
| 613 | N | HIS | A | 60 | 3.952 | 1.187 | 43.590 | 1.00 | 13.02 |
| 615 | CA | HIS | A | 60 | 3.832 | -0.268 | 43.609 | 1.00 | 12.98 |
| 617 | CB | HIS | A | 60 | 2.626 | -0.690 | 44.448 | 1.00 | 13.48 |
| 620 | CG | HIS | A | 60 | 2.721 | -0.306 | 45.893 | 1.00 | 14.08 |
| 621 | ND1 | HIS | A | 60 | 3.332 | -1.104 | 46.833 | 1.00 | 16.67 |
| 623 | CE1 | HIS | A | 60 | 3.250 | -0.525 | 48.020 | 1.00 | 16.27 |
| 625 | NE2 | HIS | A | 60 | 2.604 | 0.619 | 47.882 | 1.00 | 16.07 |
| 627 | CD2 | HIS | A | 60 | 2.256 | 0.776 | 46.561 | 1.00 | 16.82 |
| 629 | C | HIS | A | 60 | 3.603 | -0.733 | 42.167 | 1.00 | 12.86 |
| 630 | O | HIS | A | 60 | 2.716 | -0.226 | 41.492 | 1.00 | 12.45 |
| 631 | N | VAL | A | 61 | 4.385 | -1.704 | 41.705 | 1.00 | 12.71 |
| 633 | CA | VAL | A | 61 | 4.287 | -2.179 | 40.321 | 1.00 | 12.60 |
| 635 | CB | BVAL | A | 61 | 5.476 | -1.744 | 39.410 | 0.35 | 12.73 |
| 636 | CB | AVAL | A | 61 | 5.554 | -1.779 | 39.520 | 0.65 | 13.40 |
| 639 | CG1 | BVAL | A | 61 | 5.453 | -0.238 | 39.173 | 0.35 | 12.42 |
| 640 | CG1 | AVAL | A | 61 | 5.313 | -1.870 | 38.038 | 0.65 | 13.96 |
| 647 | CG2 | BVAL | A | 61 | 6.823 | -2.200 | 39.971 | 0.35 | 12.03 |
| 648 | CG2 | AVAL | A | 61 | 6.022 | -0.370 | 39.906 | 0.65 | 13.70 |
| 655 | C | VAL | A | 61 | 4.121 | -3.697 | 40.240 | 1.00 | 12.53 |
| 656 | O | VAL | A | 61 | 4.782 | -4.459 | 40.958 | 1.00 | 12.29 |
| 657 | N | VAL | A | 62 | 3.235 | -4.131 | 39.358 | 1.00 | 11.15 |
| 659 | CA | VAL | A | 62 | 3.206 | -5.520 | 38.934 | 1.00 | 11.52 |
| 661 | CB | VAL | A | 62 | 1.911 | -6.233 | 39.294 | 1.00 | 11.40 |
| 663 | CG1 | VAL | A | 62 | 1.906 | -7.661 | 38.747 | 1.00 | 12.59 |
| 667 | CG2 | VAL | A | 62 | 1.731 | -6.241 | 40.797 | 1.00 | 12.96 |
| 671 | C | VAL | A | 62 | 3.424 | -5.512 | 37.435 | 1.00 | 11.25 |
| 672 | O | VAL | A | 62 | 2.688 | -4.867 | 36.699 | 1.00 | 12.25 |
| 673 | N | VAL | A | 63 | 4.450 | -6.221 | 36.994 | 1.00 | 11.10 |
| 675 | CA | VAL | A | 63 | 4.777 | -6.317 | 35.586 | 1.00 | 10.89 |
| 677 | CB | VAL | A | 63 | 6.276 | -5.979 | 35.315 | 1.00 | 11.00 |
| 679 | CG1 | VAL | A | 63 | 7.221 | -6.835 | 36.140 | 1.00 | 11.07 |
| 683 | CG2 | VAL | A | 63 | 6.522 | -4.511 | 35.596 | 1.00 | 12.45 |
| 687 | C | VAL | A | 63 | 4.447 | -7.701 | 35.041 | 1.00 | 10.25 |
| 688 | O | VAL | A | 63 | 4.464 | -8.705 | 35.769 | 1.00 | 10.68 |
| 689 | N | THR | A | 64 | 4.178 | -7.753 | 33.749 | 1.00 | 10.04 |

FIGURE 3 (cont.)

| A | B | C | D | E | F | G | H | I | J |
|---|---|---|---|---|---|---|---|---|---|
| 691 | CA | THR | A | 64 | 3.937 | -9.010 | 33.080 | 1.00 | 10.00 |
| 693 | CB | THR | A | 64 | 2.437 | -9.391 | 33.174 | 1.00 | 10.15 |
| 695 | OG1 | THR | A | 64 | 2.204 | -10.714 | 32.660 | 1.00 | 11.09 |
| 697 | CG2 | THR | A | 64 | 1.543 | -8.446 | 32.352 | 1.00 | 11.35 |
| 701 | C | THR | A | 64 | 4.470 | -9.026 | 31.638 | 1.00 | 10.09 |
| 702 | O | THR | A | 64 | 4.730 | -7.978 | 31.031 | 1.00 | 10.64 |
| 703 | N | ALA | A | 65 | 4.636 | -10.257 | 31.163 | 1.00 | 10.16 |
| 705 | CA | ALA | A | 65 | 5.165 | -10.672 | 29.862 | 1.00 | 10.42 |
| 707 | CB | ALA | A | 65 | 6.556 | -10.118 | 29.610 | 1.00 | 11.04 |
| 711 | C | ALA | A | 65 | 5.197 | -12.210 | 29.918 | 1.00 | 10.80 |
| 712 | O | ALA | A | 65 | 4.872 | -12.802 | 30.952 | 1.00 | 10.46 |
| 713 | N | ARG | A | 66 | 5.591 | -12.867 | 28.840 | 1.00 | 10.82 |
| 715 | CA | ARG | A | 66 | 5.682 | -14.338 | 28.854 | 1.00 | 11.03 |
| 717 | CB | ARG | A | 66 | 5.707 | -14.890 | 27.430 | 1.00 | 11.05 |
| 720 | CG | ARG | A | 66 | 4.372 | -14.734 | 26.716 | 1.00 | 11.27 |
| 723 | CD | ARG | A | 66 | 4.404 | -15.115 | 25.278 | 1.00 | 12.07 |
| 726 | NE | ARG | A | 66 | 5.361 | -14.290 | 24.571 | 1.00 | 11.37 |
| 728 | CZ | ARG | A | 66 | 5.763 | -14.509 | 23.336 | 1.00 | 12.92 |
| 729 | NH1 | ARG | A | 66 | 6.662 | -13.706 | 22.798 | 1.00 | 12.82 |
| 732 | NH2 | ARG | A | 66 | 5.242 | -15.503 | 22.618 | 1.00 | 14.26 |
| 735 | C | ARG | A | 66 | 6.892 | -14.869 | 29.617 | 1.00 | 11.29 |
| 736 | O | ARG | A | 66 | 6.803 | -15.915 | 30.257 | 1.00 | 12.14 |
| 737 | N | SER | A | 67 | 8.008 | -14.149 | 29.570 | 1.00 | 11.42 |
| 739 | CA | SER | A | 67 | 9.293 | -14.685 | 30.032 | 1.00 | 11.75 |
| 741 | CB | BSER | A | 67 | 10.409 | -14.158 | 29.131 | 0.35 | 11.87 |
| 742 | CB | ASER | A | 67 | 10.453 | -14.176 | 29.168 | 0.65 | 12.08 |
| 747 | OG | BSER | A | 67 | 10.027 | -14.220 | 27.769 | 0.35 | 12.52 |
| 748 | OG | ASER | A | 67 | 11.720 | -14.530 | 29.737 | 0.65 | 12.89 |
| 751 | C | SER | A | 67 | 9.585 | -14.345 | 31.489 | 1.00 | 11.44 |
| 752 | O | SER | A | 67 | 9.877 | -13.190 | 31.808 | 1.00 | 11.69 |
| 753 | N | LYS | A | 68 | 9.583 | -15.356 | 32.360 | 1.00 | 11.26 |
| 755 | CA | LYS | A | 68 | 9.923 | -15.139 | 33.771 | 1.00 | 11.27 |
| 757 | CB | LYS | A | 68 | 9.662 | -16.401 | 34.609 | 1.00 | 11.34 |
| 760 | CG | LYS | A | 68 | 10.568 | -17.594 | 34.335 | 1.00 | 12.53 |
| 763 | CD | LYS | A | 68 | 10.143 | -18.781 | 35.222 | 1.00 | 13.11 |
| 766 | CE | LYS | A | 68 | 11.021 | -20.016 | 35.001 | 1.00 | 16.27 |
| 769 | NZ | LYS | A | 68 | 10.706 | -20.680 | 33.702 | 1.00 | 18.42 |
| 773 | C | LYS | A | 68 | 11.361 | -14.650 | 33.951 | 1.00 | 11.49 |
| 774 | O | LYS | A | 68 | 11.639 | -13.855 | 34.832 | 1.00 | 11.62 |
| 775 | N | GLU | A | 69 | 12.269 | -15.093 | 33.093 | 1.00 | 11.72 |
| 777 | CA | GLU | A | 69 | 13.684 | -14.765 | 33.248 | 1.00 | 12.60 |
| 779 | CB | GLU | A | 69 | 14.536 | -15.604 | 32.293 | 1.00 | 12.93 |
| 782 | CG | GLU | A | 69 | 14.568 | -17.098 | 32.602 | 1.00 | 15.40 |
| 785 | CD | GLU | A | 69 | 13.375 | -17.900 | 32.088 | 1.00 | 17.93 |
| 786 | OE1 | GLU | A | 69 | 13.265 | -19.076 | 32.512 | 1.00 | 20.49 |
| 787 | OE2 | GLU | A | 69 | 12.539 | -17.393 | 31.286 | 1.00 | 19.00 |
| 788 | C | GLU | A | 69 | 13.942 | -13.270 | 33.033 | 1.00 | 12.29 |
| 789 | O | GLU | A | 69 | 14.681 | -12.639 | 33.801 | 1.00 | 12.43 |
| 790 | N | THR | A | 70 | 13.337 | -12.690 | 31.997 | 1.00 | 12.70 |

FIGURE 3 (cont.)

| A | B | C | D | E | F | G | H | I | J |
|---|---|---|---|---|---|---|---|---|---|
| 792 | CA | THR | A | 70 | 13.512 | -11.260 | 31.758 | 1.00 | 12.75 |
| 794 | CB | THR | A | 70 | 13.143 | -10.886 | 30.309 | 1.00 | 12.84 |
| 796 | OG1 | THR | A | 70 | 11.836 | -11.368 | 29.989 | 1.00 | 13.41 |
| 798 | CG2 | THR | A | 70 | 14.038 | -11.607 | 29.347 | 1.00 | 14.60 |
| 802 | C | THR | A | 70 | 12.732 | -10.420 | 32.757 | 1.00 | 12.50 |
| 803 | O | THR | A | 70 | 13.203 | -9.369 | 33.186 | 1.00 | 12.61 |
| 804 | N | LEU | A | 71 | 11.554 | -10.895 | 33.156 | 1.00 | 11.60 |
| 806 | CA | LEU | A | 71 | 10.765 | -10.210 | 34.173 | 1.00 | 11.45 |
| 808 | CB | LEU | A | 71 | 9.402 | -10.878 | 34.346 | 1.00 | 11.15 |
| 811 | CG | LEU | A | 71 | 8.397 | -10.646 | 33.214 | 1.00 | 11.01 |
| 813 | CD1 | LEU | A | 71 | 7.222 | -11.628 | 33.327 | 1.00 | 9.87 |
| 817 | CD2 | LEU | A | 71 | 7.915 | -9.219 | 33.171 | 1.00 | 11.18 |
| 821 | C | LEU | A | 71 | 11.477 | -10.162 | 35.534 | 1.00 | 11.37 |
| 822 | O | LEU | A | 71 | 11.360 | -9.176 | 36.248 | 1.00 | 11.15 |
| 823 | N | GLN | A | 72 | 12.203 | -11.220 | 35.882 | 1.00 | 10.98 |
| 825 | CA | GLN | A | 72 | 12.960 | -11.254 | 37.134 | 1.00 | 10.60 |
| 827 | CB | GLN | A | 72 | 13.709 | -12.589 | 37.294 | 1.00 | 11.07 |
| 830 | CG | GLN | A | 72 | 12.790 | -13.743 | 37.730 | 1.00 | 10.55 |
| 833 | CD | GLN | A | 72 | 13.374 | -15.117 | 37.461 | 1.00 | 11.91 |
| 834 | OE1 | GLN | A | 72 | 14.606 | -15.275 | 37.343 | 1.00 | 13.99 |
| 835 | NE2 | GLN | A | 72 | 12.505 | -16.120 | 37.368 | 1.00 | 11.52 |
| 838 | C | GLN | A | 72 | 13.945 | -10.099 | 37.190 | 1.00 | 10.98 |
| 839 | O | GLN | A | 72 | 14.104 | -9.460 | 38.229 | 1.00 | 11.15 |
| 840 | N | LYS | A | 73 | 14.589 | -9.833 | 36.054 | 1.00 | 11.09 |
| 842 | CA | LYS | A | 73 | 15.587 | -8.770 | 35.977 | 1.00 | 12.13 |
| 844 | CB | LYS | A | 73 | 16.356 | -8.855 | 34.657 | 1.00 | 12.43 |
| 847 | CG | LYS | A | 73 | 17.224 | -10.090 | 34.529 | 1.00 | 16.37 |
| 850 | CD | LYS | A | 73 | 17.931 | -10.129 | 33.181 | 1.00 | 20.53 |
| 853 | CE | LYS | A | 73 | 18.880 | -11.304 | 33.072 | 1.00 | 23.16 |
| 856 | NZ | LYS | A | 73 | 19.965 | -11.013 | 32.093 | 1.00 | 26.57 |
| 860 | C | LYS | A | 73 | 14.947 | -7.393 | 36.128 | 1.00 | 11.61 |
| 861 | O | LYS | A | 73 | 15.511 | -6.498 | 36.773 | 1.00 | 11.60 |
| 862 | N | VAL | A | 74 | 13.763 | -7.222 | 35.547 | 1.00 | 11.01 |
| 864 | CA | VAL | A | 74 | 13.026 | -5.965 | 35.662 | 1.00 | 11.03 |
| 866 | CB | VAL | A | 74 | 11.790 | -5.935 | 34.740 | 1.00 | 10.98 |
| 868 | CG1 | VAL | A | 74 | 10.895 | -4.714 | 35.020 | 1.00 | 11.97 |
| 872 | CG2 | VAL | A | 74 | 12.228 | -5.950 | 33.283 | 1.00 | 11.47 |
| 876 | C | VAL | A | 74 | 12.618 | -5.736 | 37.119 | 1.00 | 11.47 |
| 877 | O | VAL | A | 74 | 12.789 | -4.644 | 37.646 | 1.00 | 11.95 |
| 878 | N | VAL | A | 75 | 12.100 | -6.768 | 37.774 | 1.00 | 11.13 |
| 880 | CA | VAL | A | 75 | 11.670 | -6.618 | 39.167 | 1.00 | 11.29 |
| 882 | CB | VAL | A | 75 | 10.963 | -7.887 | 39.686 | 1.00 | 11.21 |
| 884 | CG1 | VAL | A | 75 | 9.587 | -7.987 | 39.048 | 1.00 | 12.05 |
| 888 | CG2 | VAL | A | 75 | 10.857 | -7.884 | 41.213 | 1.00 | 12.11 |
| 892 | C | VAL | A | 75 | 12.867 | -6.251 | 40.050 | 1.00 | 11.60 |
| 893 | O | VAL | A | 75 | 12.780 | -5.349 | 40.866 | 1.00 | 12.45 |
| 894 | N | SER | A | 76 | 13.984 | -6.941 | 39.879 | 1.00 | 11.86 |
| 896 | CA | SER | A | 76 | 15.142 | -6.672 | 40.732 | 1.00 | 12.00 |
| 898 | CB | BSER | A | 76 | 16.280 | -7.677 | 40.495 | 0.35 | 11.95 |

FIGURE 3 (cont.)

| A | B | C | D | E | F | G | H | I | J |
|---|---|---|---|---|---|---|---|---|---|
| 899 | CB  | ASER | A | 76 | 16.273 | -7.656 | 40.417 | 0.65 | 11.99 |
| 904 | OG  | BSER | A | 76 | 16.798 | -7.610 | 39.181 | 0.35 | 12.85 |
| 905 | OG  | ASER | A | 76 | 17.471 | -7.307 | 41.083 | 0.65 | 13.95 |
| 908 | C   | SER  | A | 76 | 15.611 | -5.227 | 40.555 | 1.00 | 11.96 |
| 909 | O   | SER  | A | 76 | 15.910 | -4.549 | 41.544 | 1.00 | 12.62 |
| 910 | N   | HIS  | A | 77 | 15.658 | -4.741 | 39.315 | 1.00 | 12.03 |
| 912 | CA  | HIS  | A | 77 | 16.065 | -3.356 | 39.071 | 1.00 | 12.50 |
| 914 | CB  | HIS  | A | 77 | 16.358 | -3.081 | 37.592 | 1.00 | 12.58 |
| 917 | CG  | HIS  | A | 77 | 17.169 | -1.840 | 37.378 | 1.00 | 13.91 |
| 918 | ND1 | HIS  | A | 77 | 16.723 | -0.767 | 36.639 | 1.00 | 17.25 |
| 920 | CE1 | HIS  | A | 77 | 17.642 |  0.183 | 36.646 | 1.00 | 15.02 |
| 922 | NE2 | HIS  | A | 77 | 18.662 | -0.230 | 37.370 | 1.00 | 18.45 |
| 924 | CD2 | HIS  | A | 77 | 18.391 | -1.490 | 37.846 | 1.00 | 15.70 |
| 926 | C   | HIS  | A | 77 | 15.030 | -2.362 | 39.603 | 1.00 | 12.87 |
| 927 | O   | HIS  | A | 77 | 15.392 | -1.303 | 40.108 | 1.00 | 12.83 |
| 928 | N   | CYS  | A | 78 | 13.742 | -2.704 | 39.513 | 1.00 | 12.49 |
| 930 | CA  | CYS  | A | 78 | 12.700 | -1.831 | 40.057 | 1.00 | 13.15 |
| 932 | CB  | CYS  | A | 78 | 11.298 | -2.379 | 39.797 | 1.00 | 13.29 |
| 935 | SG  | CYS  | A | 78 | 10.711 | -2.122 | 38.109 | 1.00 | 13.56 |
| 936 | C   | CYS  | A | 78 | 12.897 | -1.623 | 41.553 | 1.00 | 13.28 |
| 937 | O   | CYS  | A | 78 | 12.791 | -0.511 | 42.044 | 1.00 | 14.09 |
| 938 | N   | LEU  | A | 79 | 13.218 | -2.691 | 42.270 | 1.00 | 14.18 |
| 940 | CA  | LEU  | A | 79 | 13.446 | -2.596 | 43.710 | 1.00 | 14.52 |
| 942 | CB  | LEU  | A | 79 | 13.615 | -3.987 | 44.334 | 1.00 | 14.79 |
| 945 | CG  | LEU  | A | 79 | 12.357 | -4.860 | 44.310 | 1.00 | 14.95 |
| 947 | CD1 | LEU  | A | 79 | 11.252 | -4.252 | 45.167 | 1.00 | 15.22 |
| 951 | CD2 | LEU  | A | 79 | 12.641 | -6.279 | 44.769 | 1.00 | 16.43 |
| 955 | C   | LEU  | A | 79 | 14.654 | -1.705 | 44.000 | 1.00 | 15.07 |
| 956 | O   | LEU  | A | 79 | 14.601 | -0.870 | 44.900 | 1.00 | 15.81 |
| 957 | N   | GLU  | A | 80 | 15.723 | -1.866 | 43.221 | 1.00 | 15.55 |
| 959 | CA  | GLU  | A | 80 | 16.935 | -1.047 | 43.386 | 1.00 | 16.56 |
| 961 | CB  | GLU  | A | 80 | 18.011 | -1.450 | 42.380 | 1.00 | 17.26 |
| 964 | CG  | GLU  | A | 80 | 18.625 | -2.810 | 42.629 | 1.00 | 20.78 |
| 967 | CD  | GLU  | A | 80 | 19.649 | -3.182 | 41.576 | 1.00 | 24.94 |
| 968 | OE1 | GLU  | A | 80 | 19.496 | -2.760 | 40.403 | 1.00 | 28.44 |
| 969 | OE2 | GLU  | A | 80 | 20.605 | -3.904 | 41.912 | 1.00 | 28.97 |
| 970 | C   | GLU  | A | 80 | 16.656 |  0.427 | 43.184 | 1.00 | 16.04 |
| 971 | O   | GLU  | A | 80 | 17.267 |  1.271 | 43.833 | 1.00 | 16.11 |
| 972 | N   | LEU  | A | 81 | 15.758 |  0.727 | 42.250 | 1.00 | 15.33 |
| 974 | CA  | LEU  | A | 81 | 15.416 |  2.098 | 41.885 | 1.00 | 15.28 |
| 976 | CB  | LEU  | A | 81 | 14.747 |  2.133 | 40.505 | 1.00 | 15.44 |
| 979 | CG  | LEU  | A | 81 | 15.650 |  1.925 | 39.291 | 1.00 | 15.54 |
| 981 | CD1 | LEU  | A | 81 | 14.792 |  1.810 | 38.042 | 1.00 | 16.22 |
| 985 | CD2 | LEU  | A | 81 | 16.648 |  3.073 | 39.142 | 1.00 | 16.85 |
| 989 | C   | LEU  | A | 81 | 14.503 |  2.776 | 42.902 | 1.00 | 15.16 |
| 990 | O   | LEU  | A | 81 | 14.324 |  3.986 | 42.837 | 1.00 | 16.04 |
| 991 | N   | GLY  | A | 82 | 13.913 |  1.996 | 43.808 | 1.00 | 14.81 |
| 993 | CA  | GLY  | A | 82 | 13.121 |  2.526 | 44.906 | 1.00 | 14.83 |
| 996 | C   | GLY  | A | 82 | 11.621 |  2.302 | 44.839 | 1.00 | 14.21 |

FIGURE 3 (cont.)

| A | B | C | D | E | F | G | H | I | J |
|---|---|---|---|---|---|---|---|---|---|
| 997 | O | GLY | A | 82 | 10.860 | 3.018 | 45.502 | 1.00 | 14.46 |
| 998 | N | ALA | A | 83 | 11.181 | 1.298 | 44.080 | 1.00 | 14.08 |
| 1000 | CA | ALA | A | 83 | 9.769 | 0.937 | 44.043 | 1.00 | 13.64 |
| 1002 | CB | ALA | A | 83 | 9.555 | -0.264 | 43.159 | 1.00 | 13.43 |
| 1006 | C | ALA | A | 83 | 9.281 | 0.622 | 45.447 | 1.00 | 13.43 |
| 1007 | O | ALA | A | 83 | 10.009 | 0.008 | 46.239 | 1.00 | 13.84 |
| 1008 | N | ALA | A | 84 | 8.061 | 1.049 | 45.754 | 1.00 | 13.78 |
| 1010 | CA | ALA | A | 84 | 7.405 | 0.686 | 47.012 | 1.00 | 13.71 |
| 1012 | CB | ALA | A | 84 | 6.060 | 1.361 | 47.116 | 1.00 | 13.87 |
| 1016 | C | ALA | A | 84 | 7.269 | -0.835 | 47.109 | 1.00 | 14.03 |
| 1017 | O | ALA | A | 84 | 7.489 | -1.426 | 48.166 | 1.00 | 14.84 |
| 1018 | N | SER | A | 85 | 6.909 | -1.453 | 45.988 | 1.00 | 13.29 |
| 1020 | CA | SER | A | 85 | 7.021 | -2.893 | 45.800 | 1.00 | 13.20 |
| 1022 | CB | SER | A | 85 | 5.827 | -3.645 | 46.390 | 1.00 | 13.35 |
| 1025 | OG | SER | A | 85 | 4.598 | -3.252 | 45.790 | 1.00 | 14.56 |
| 1027 | C | SER | A | 85 | 7.109 | -3.168 | 44.307 | 1.00 | 12.37 |
| 1028 | O | SER | A | 85 | 6.757 | -2.323 | 43.489 | 1.00 | 12.68 |
| 1029 | N | ALA | A | 86 | 7.600 | -4.352 | 43.969 | 1.00 | 12.05 |
| 1031 | CA | ALA | A | 86 | 7.664 | -4.793 | 42.583 | 1.00 | 12.00 |
| 1033 | CB | ALA | A | 86 | 8.940 | -4.323 | 41.942 | 1.00 | 11.85 |
| 1037 | C | ALA | A | 86 | 7.564 | -6.311 | 42.523 | 1.00 | 11.93 |
| 1038 | O | ALA | A | 86 | 8.251 | -7.028 | 43.259 | 1.00 | 12.29 |
| 1039 | N | HIS | A | 87 | 6.722 | -6.790 | 41.621 | 1.00 | 11.65 |
| 1041 | CA | HIS | A | 87 | 6.483 | -8.207 | 41.437 | 1.00 | 11.60 |
| 1043 | CB | HIS | A | 87 | 5.317 | -8.692 | 42.313 | 1.00 | 12.09 |
| 1046 | CG | HIS | A | 87 | 5.554 | -8.517 | 43.785 | 1.00 | 13.44 |
| 1047 | ND1 | HIS | A | 87 | 6.340 | -9.377 | 44.524 | 1.00 | 17.92 |
| 1049 | CE1 | HIS | A | 87 | 6.388 | -8.957 | 45.776 | 1.00 | 16.57 |
| 1051 | NE2 | HIS | A | 87 | 5.660 | -7.861 | 45.879 | 1.00 | 17.01 |
| 1053 | CD2 | HIS | A | 87 | 5.137 | -7.557 | 44.645 | 1.00 | 14.10 |
| 1055 | C | HIS | A | 87 | 6.164 | -8.471 | 39.977 | 1.00 | 11.09 |
| 1056 | O | HIS | A | 87 | 5.713 | -7.570 | 39.268 | 1.00 | 11.49 |
| 1057 | N | TYR | A | 88 | 6.392 | -9.701 | 39.535 | 1.00 | 10.73 |
| 1059 | CA | TYR | A | 88 | 5.947 | -10.132 | 38.215 | 1.00 | 10.46 |
| 1061 | CB | TYR | A | 88 | 7.133 | -10.492 | 37.306 | 1.00 | 10.59 |
| 1064 | CG | TYR | A | 88 | 7.764 | -11.840 | 37.554 | 1.00 | 9.92 |
| 1065 | CD1 | TYR | A | 88 | 7.255 | -13.001 | 36.974 | 1.00 | 9.00 |
| 1067 | CE1 | TYR | A | 88 | 7.854 | -14.244 | 37.205 | 1.00 | 9.09 |
| 1069 | CZ | TYR | A | 88 | 8.965 | -14.312 | 38.018 | 1.00 | 9.49 |
| 1070 | OH | TYR | A | 88 | 9.579 | -15.516 | 38.278 | 1.00 | 9.96 |
| 1072 | CE2 | TYR | A | 88 | 9.481 | -13.156 | 38.600 | 1.00 | 9.29 |
| 1074 | CD2 | TYR | A | 88 | 8.883 | -11.947 | 38.364 | 1.00 | 9.22 |
| 1076 | C | TYR | A | 88 | 4.990 | -11.304 | 38.303 | 1.00 | 10.75 |
| 1077 | O | TYR | A | 88 | 5.003 | -12.078 | 39.263 | 1.00 | 11.28 |
| 1078 | N | ILE | A | 89 | 4.164 | -11.424 | 37.268 | 1.00 | 10.68 |
| 1080 | CA | ILE | A | 89 | 3.364 | -12.611 | 36.995 | 1.00 | 10.79 |
| 1082 | CB | ILE | A | 89 | 1.885 | -12.382 | 37.341 | 1.00 | 10.72 |
| 1084 | CG1 | ILE | A | 89 | 1.714 | -11.935 | 38.800 | 1.00 | 11.92 |
| 1087 | CD1 | ILE | A | 89 | 0.302 | -11.432 | 39.127 | 1.00 | 13.15 |

FIGURE 3 (cont.)

| A | B | C | D | E | F | G | H | I | J |
|---|---|---|---|---|---|---|---|---|---|
| 1091 | CG2 | ILE | A | 89 | 1.074 | -13.641 | 37.062 | 1.00 | 9.95 |
| 1095 | C | ILE | A | 89 | 3.525 | -12.875 | 35.493 | 1.00 | 10.85 |
| 1096 | O | ILE | A | 89 | 3.233 | -12.000 | 34.673 | 1.00 | 11.61 |
| 1097 | N | ALA | A | 90 | 4.023 | -14.051 | 35.140 | 1.00 | 10.55 |
| 1099 | CA | ALA | A | 90 | 4.302 | -14.397 | 33.742 | 1.00 | 10.70 |
| 1101 | CB | ALA | A | 90 | 5.570 | -15.207 | 33.639 | 1.00 | 10.74 |
| 1105 | C | ALA | A | 90 | 3.147 | -15.176 | 33.120 | 1.00 | 11.23 |
| 1106 | O | ALA | A | 90 | 2.527 | -16.038 | 33.765 | 1.00 | 12.05 |
| 1107 | N | GLY | A | 91 | 2.887 | -14.889 | 31.851 | 1.00 | 10.85 |
| 1109 | CA | GLY | A | 91 | 1.882 | -15.600 | 31.082 | 1.00 | 10.47 |
| 1112 | C | GLY | A | 91 | 1.696 | -14.986 | 29.712 | 1.00 | 10.22 |
| 1113 | O | GLY | A | 91 | 2.231 | -13.917 | 29.428 | 1.00 | 9.99 |
| 1114 | N | THR | A | 92 | 0.936 | -15.669 | 28.866 | 1.00 | 9.93 |
| 1116 | CA | THR | A | 92 | 0.657 | -15.178 | 27.526 | 1.00 | 10.41 |
| 1118 | CB | THR | A | 92 | 0.827 | -16.257 | 26.455 | 1.00 | 10.56 |
| 1120 | OG1 | THR | A | 92 | 0.475 | -15.684 | 25.182 | 1.00 | 11.31 |
| 1122 | CG2 | THR | A | 92 | -0.159 | -17.429 | 26.633 | 1.00 | 10.99 |
| 1126 | C | THR | A | 92 | -0.730 | -14.560 | 27.442 | 1.00 | 10.36 |
| 1127 | O | THR | A | 92 | -1.737 | -15.120 | 27.916 | 1.00 | 10.23 |
| 1128 | N | MET | A | 93 | -0.779 | -13.395 | 26.816 | 1.00 | 10.51 |
| 1130 | CA | MET | A | 93 | -2.038 | -12.683 | 26.609 | 1.00 | 11.22 |
| 1132 | CB | MET | A | 93 | -1.800 | -11.185 | 26.500 | 1.00 | 11.80 |
| 1135 | CG | MET | A | 93 | -1.251 | -10.588 | 27.779 | 1.00 | 11.98 |
| 1138 | SD | MET | A | 93 | -2.484 | -10.548 | 29.090 | 1.00 | 12.19 |
| 1139 | CE | MET | A | 93 | -1.541 | -9.735 | 30.364 | 1.00 | 14.00 |
| 1143 | C | MET | A | 93 | -2.826 | -13.224 | 25.417 | 1.00 | 11.82 |
| 1144 | O | MET | A | 93 | -3.869 | -12.679 | 25.063 | 1.00 | 12.97 |
| 1145 | N | GLU | A | 94 | -2.353 | -14.320 | 24.837 | 1.00 | 11.81 |
| 1147 | CA | GLU | A | 94 | -3.161 | -15.153 | 23.946 | 1.00 | 12.85 |
| 1149 | CB | GLU | A | 94 | -2.281 | -16.196 | 23.228 | 1.00 | 13.18 |
| 1152 | CG | GLU | A | 94 | -1.299 | -15.621 | 22.209 | 1.00 | 16.19 |
| 1155 | CD | GLU | A | 94 | -0.479 | -16.681 | 21.469 | 1.00 | 21.92 |
| 1156 | OE1 | GLU | A | 94 | -0.925 | -17.841 | 21.384 | 1.00 | 24.75 |
| 1157 | OE2 | GLU | A | 94 | 0.625 | -16.358 | 20.958 | 1.00 | 25.43 |
| 1158 | C | GLU | A | 94 | -4.259 | -15.887 | 24.727 | 1.00 | 13.03 |
| 1159 | O | GLU | A | 94 | -5.275 | -16.278 | 24.154 | 1.00 | 14.15 |
| 1160 | N | ASP | A | 95 | -4.031 | -16.074 | 26.029 | 1.00 | 12.98 |
| 1162 | CA | ASP | A | 95 | -4.912 | -16.836 | 26.919 | 1.00 | 13.19 |
| 1164 | CB | ASP | A | 95 | -4.048 | -17.699 | 27.839 | 1.00 | 13.08 |
| 1167 | CG | ASP | A | 95 | -4.842 | -18.496 | 28.843 | 1.00 | 15.34 |
| 1168 | OD1 | ASP | A | 95 | -6.065 | -18.292 | 28.968 | 1.00 | 18.18 |
| 1169 | OD2 | ASP | A | 95 | -4.306 | -19.369 | 29.550 | 1.00 | 17.42 |
| 1170 | C | ASP | A | 95 | -5.754 | -15.842 | 27.710 | 1.00 | 12.94 |
| 1171 | O | ASP | A | 95 | -5.253 | -15.184 | 28.610 | 1.00 | 13.26 |
| 1172 | N | MET | A | 96 | -7.025 | -15.715 | 27.345 | 1.00 | 13.06 |
| 1174 | CA | MET | A | 96 | -7.905 | -14.734 | 27.979 | 1.00 | 13.39 |
| 1176 | CB | MET | A | 96 | -9.220 | -14.608 | 27.206 | 1.00 | 13.93 |
| 1179 | CG | MET | A | 96 | -9.088 | -14.107 | 25.752 | 1.00 | 14.60 |
| 1182 | SD | MET | A | 96 | -8.169 | -12.588 | 25.540 | 1.00 | 17.02 |

FIGURE 3 (cont.)

| A | B | C | D | E | F | G | H | I | J |
|---|---|---|---|---|---|---|---|---|---|
| 1183 | CE | MET | A | 96 | -7.076 | -12.983 | 24.190 | 1.00 | 17.40 |
| 1187 | C | MET | A | 96 | -8.175 | -15.068 | 29.450 | 1.00 | 13.40 |
| 1188 | O | MET | A | 96 | -8.461 | -14.179 | 30.261 | 1.00 | 13.30 |
| 1189 | N | THR | A | 97 | -8.098 | -16.347 | 29.796 | 1.00 | 13.67 |
| 1191 | CA | THR | A | 97 | -8.214 | -16.758 | 31.190 | 1.00 | 13.83 |
| 1193 | CB | THR | A | 97 | -8.342 | -18.289 | 31.281 | 1.00 | 14.66 |
| 1195 | OG1 | THR | A | 97 | -9.548 | -18.697 | 30.624 | 1.00 | 16.10 |
| 1197 | CG2 | THR | A | 97 | -8.507 | -18.739 | 32.722 | 1.00 | 16.08 |
| 1201 | C | THR | A | 97 | -7.034 | -16.256 | 32.008 | 1.00 | 13.48 |
| 1202 | O | THR | A | 97 | -7.203 | -15.772 | 33.126 | 1.00 | 13.67 |
| 1203 | N | PHE | A | 98 | -5.827 | -16.355 | 31.459 | 1.00 | 12.78 |
| 1205 | CA | PHE | A | 98 | -4.686 | -15.751 | 32.114 | 1.00 | 12.66 |
| 1207 | CB | PHE | A | 98 | -3.372 | -16.021 | 31.371 | 1.00 | 12.69 |
| 1210 | CG | PHE | A | 98 | -2.231 | -15.214 | 31.917 | 1.00 | 12.56 |
| 1211 | CD1 | PHE | A | 98 | -1.638 | -15.563 | 33.122 | 1.00 | 12.44 |
| 1213 | CE1 | PHE | A | 98 | -0.633 | -14.794 | 33.661 | 1.00 | 13.10 |
| 1215 | CZ | PHE | A | 98 | -0.203 | -13.655 | 33.005 | 1.00 | 12.78 |
| 1217 | CE2 | PHE | A | 98 | -0.793 | -13.286 | 31.815 | 1.00 | 11.98 |
| 1219 | CD2 | PHE | A | 98 | -1.812 | -14.061 | 31.281 | 1.00 | 12.33 |
| 1221 | C | PHE | A | 98 | -4.877 | -14.243 | 32.300 | 1.00 | 12.89 |
| 1222 | O | PHE | A | 98 | -4.621 | -13.719 | 33.380 | 1.00 | 13.16 |
| 1223 | N | ALA | A | 99 | -5.323 | -13.539 | 31.259 | 1.00 | 12.45 |
| 1225 | CA | ALA | A | 99 | -5.505 | -12.094 | 31.345 | 1.00 | 12.51 |
| 1227 | CB | ALA | A | 99 | -6.081 | -11.565 | 30.050 | 1.00 | 12.81 |
| 1231 | C | ALA | A | 99 | -6.400 | -11.728 | 32.521 | 1.00 | 13.01 |
| 1232 | O | ALA | A | 99 | -6.059 | -10.866 | 33.329 | 1.00 | 12.89 |
| 1233 | N | GLU | A | 100 | -7.536 | -12.405 | 32.614 | 1.00 | 13.24 |
| 1235 | CA | GLU | A | 100 | -8.514 | -12.154 | 33.682 | 1.00 | 14.37 |
| 1237 | CB | GLU | A | 100 | -9.741 | -13.027 | 33.442 | 1.00 | 15.48 |
| 1240 | CG | GLU | A | 100 | -10.888 | -12.773 | 34.399 | 1.00 | 18.83 |
| 1243 | CD | GLU | A | 100 | -12.142 | -13.545 | 34.029 | 1.00 | 23.35 |
| 1244 | OE1 | GLU | A | 100 | -13.227 | -13.169 | 34.534 | 1.00 | 29.89 |
| 1245 | OE2 | GLU | A | 100 | -12.051 | -14.535 | 33.250 | 1.00 | 27.70 |
| 1246 | C | GLU | A | 100 | -7.939 | -12.455 | 35.072 | 1.00 | 14.40 |
| 1247 | O | GLU | A | 100 | -8.068 | -11.653 | 36.012 | 1.00 | 14.51 |
| 1248 | N | GLN | A | 101 | -7.277 | -13.601 | 35.192 | 1.00 | 13.99 |
| 1250 | CA | GLN | A | 101 | -6.755 | -14.052 | 36.482 | 1.00 | 13.85 |
| 1252 | CB | GLN | A | 101 | -6.368 | -15.528 | 36.411 | 1.00 | 14.54 |
| 1255 | CG | GLN | A | 101 | -7.578 | -16.445 | 36.262 | 1.00 | 16.77 |
| 1258 | CD | GLN | A | 101 | -7.210 | -17.912 | 36.220 | 1.00 | 19.86 |
| 1259 | OE1 | GLN | A | 101 | -6.037 | -18.267 | 36.075 | 1.00 | 23.22 |
| 1260 | NE2 | GLN | A | 101 | -8.213 | -18.770 | 36.342 | 1.00 | 22.94 |
| 1263 | C | GLN | A | 101 | -5.571 | -13.202 | 36.921 | 1.00 | 12.95 |
| 1264 | O | GLN | A | 101 | -5.389 | -12.942 | 38.107 | 1.00 | 12.65 |
| 1265 | N | PHE | A | 102 | -4.782 | -12.759 | 35.952 | 1.00 | 11.29 |
| 1267 | CA | PHE | A | 102 | -3.635 | -11.890 | 36.205 | 1.00 | 11.14 |
| 1269 | CB | PHE | A | 102 | -2.900 | -11.561 | 34.893 | 1.00 | 10.88 |
| 1272 | CG | PHE | A | 102 | -1.997 | -10.370 | 34.992 | 1.00 | 11.18 |
| 1273 | CD1 | PHE | A | 102 | -0.815 | -10.444 | 35.699 | 1.00 | 11.95 |

FIGURE 3 (cont.)

| A | B | C | D | E | F | G | H | I | J |
|---|---|---|---|---|---|---|---|---|---|
| 1275 | CE1 | PHE | A | 102 | 0.004 | -9.334 | 35.825 | 1.00 | 12.28 |
| 1277 | CZ | PHE | A | 102 | -0.368 | -8.135 | 35.234 | 1.00 | 12.23 |
| 1279 | CE2 | PHE | A | 102 | -1.540 | -8.057 | 34.527 | 1.00 | 12.61 |
| 1281 | CD2 | PHE | A | 102 | -2.350 | -9.165 | 34.406 | 1.00 | 11.71 |
| 1283 | C | PHE | A | 102 | -4.054 | -10.597 | 36.896 | 1.00 | 11.08 |
| 1284 | O | PHE | A | 102 | -3.465 | -10.201 | 37.883 | 1.00 | 10.92 |
| 1285 | N | VAL | A | 103 | -5.054 | -9.912 | 36.359 | 1.00 | 11.35 |
| 1287 | CA | VAL | A | 103 | -5.486 | -8.654 | 36.972 | 1.00 | 11.51 |
| 1289 | CB | VAL | A | 103 | -6.579 | -7.966 | 36.126 | 1.00 | 12.22 |
| 1291 | CG1 | VAL | A | 103 | -7.225 | -6.809 | 36.874 | 1.00 | 12.63 |
| 1295 | CG2 | VAL | A | 103 | -5.992 | -7.486 | 34.820 | 1.00 | 12.03 |
| 1299 | C | VAL | A | 103 | -5.993 | -8.864 | 38.394 | 1.00 | 11.31 |
| 1300 | O | VAL | A | 103 | -5.670 | -8.087 | 39.280 | 1.00 | 11.15 |
| 1301 | N | ALA | A | 104 | -6.777 | -9.914 | 38.608 | 1.00 | 11.51 |
| 1303 | CA | ALA | A | 104 | -7.302 | -10.215 | 39.939 | 1.00 | 11.36 |
| 1305 | CB | ALA | A | 104 | -8.237 | -11.427 | 39.888 | 1.00 | 11.80 |
| 1309 | C | ALA | A | 104 | -6.155 | -10.454 | 40.918 | 1.00 | 11.39 |
| 1310 | O | ALA | A | 104 | -6.152 | -9.944 | 42.050 | 1.00 | 11.48 |
| 1311 | N | GLN | A | 105 | -5.180 | -11.236 | 40.480 | 1.00 | 11.24 |
| 1313 | CA | GLN | A | 105 | -4.032 | -11.570 | 41.313 | 1.00 | 11.16 |
| 1315 | CB | GLN | A | 105 | -3.162 | -12.626 | 40.607 | 1.00 | 11.09 |
| 1318 | CG | GLN | A | 105 | -2.058 | -13.218 | 41.485 | 1.00 | 11.80 |
| 1321 | CD | GLN | A | 105 | -1.302 | -14.363 | 40.816 | 1.00 | 13.24 |
| 1322 | OE1 | GLN | A | 105 | -0.073 | -14.480 | 40.961 | 1.00 | 15.47 |
| 1323 | NE2 | GLN | A | 105 | -2.023 | -15.214 | 40.112 | 1.00 | 12.86 |
| 1326 | C | GLN | A | 105 | -3.201 | -10.333 | 41.639 | 1.00 | 11.06 |
| 1327 | O | GLN | A | 105 | -2.813 | -10.115 | 42.783 | 1.00 | 11.09 |
| 1328 | N | ALA | A | 106 | -2.896 | -9.535 | 40.614 | 1.00 | 10.33 |
| 1330 | CA | ALA | A | 106 | -2.081 | -8.338 | 40.779 | 1.00 | 10.58 |
| 1332 | CB | ALA | A | 106 | -1.789 | -7.689 | 39.415 | 1.00 | 11.01 |
| 1336 | C | ALA | A | 106 | -2.743 | -7.337 | 41.719 | 1.00 | 10.76 |
| 1337 | O | ALA | A | 106 | -2.093 | -6.760 | 42.591 | 1.00 | 10.67 |
| 1338 | N | GLY | A | 107 | -4.038 | -7.137 | 41.536 | 1.00 | 11.50 |
| 1340 | CA | GLY | A | 107 | -4.789 | -6.222 | 42.368 | 1.00 | 12.10 |
| 1343 | C | GLY | A | 107 | -4.904 | -6.709 | 43.799 | 1.00 | 12.51 |
| 1344 | O | GLY | A | 107 | -4.855 | -5.913 | 44.743 | 1.00 | 12.78 |
| 1345 | N | LYS | A | 108 | -5.083 | -8.007 | 43.991 | 1.00 | 12.80 |
| 1347 | CA | LYS | A | 108 | -5.153 | -8.532 | 45.343 | 1.00 | 13.03 |
| 1349 | CB | LYS | A | 108 | -5.596 | -9.987 | 45.350 | 1.00 | 13.47 |
| 1352 | CG | LYS | A | 108 | -5.960 | -10.484 | 46.728 | 1.00 | 15.78 |
| 1355 | CD | LYS | A | 108 | -6.618 | -11.834 | 46.677 | 1.00 | 19.13 |
| 1358 | CE | LYS | A | 108 | -6.632 | -12.475 | 48.046 | 1.00 | 21.25 |
| 1361 | NZ | LYS | A | 108 | -7.594 | -13.604 | 48.096 | 1.00 | 23.85 |
| 1365 | C | LYS | A | 108 | -3.814 | -8.374 | 46.065 | 1.00 | 12.69 |
| 1366 | O | LYS | A | 108 | -3.776 | -8.068 | 47.262 | 1.00 | 13.21 |
| 1367 | N | LEU | A | 109 | -2.726 | -8.602 | 45.342 | 1.00 | 12.65 |
| 1369 | CA | LEU | A | 109 | -1.393 | -8.472 | 45.909 | 1.00 | 12.45 |
| 1371 | CB | LEU | A | 109 | -0.340 | -8.905 | 44.884 | 1.00 | 12.67 |
| 1374 | CG | LEU | A | 109 | 1.111 | -8.728 | 45.334 | 1.00 | 13.11 |

FIGURE 3 (cont.)

| A | B | C | D | E | F | G | H | I | J |
|---|---|---|---|---|---|---|---|---|---|
| 1376 | CD1 | LEU | A | 109 | 2.042 | -9.118 | 44.188 | 1.00 | 14.19 |
| 1380 | CD2 | LEU | A | 109 | 1.413 | -9.539 | 46.591 | 1.00 | 13.65 |
| 1384 | C | LEU | A | 109 | -1.127 | -7.033 | 46.358 | 1.00 | 12.52 |
| 1385 | O | LEU | A | 109 | -0.657 | -6.800 | 47.471 | 1.00 | 12.92 |
| 1386 | N | MET | A | 110 | -1.460 | -6.065 | 45.500 | 1.00 | 12.89 |
| 1388 | CA | MET | A | 110 | -1.206 | -4.661 | 45.805 | 1.00 | 12.79 |
| 1390 | CB | MET | A | 110 | -1.080 | -3.840 | 44.513 | 1.00 | 12.79 |
| 1393 | CG | MET | A | 110 | 0.142 | -4.178 | 43.690 | 1.00 | 11.94 |
| 1396 | SD | MET | A | 110 | 0.422 | -3.011 | 42.350 | 1.00 | 12.63 |
| 1397 | CE | MET | A | 110 | -0.927 | -3.461 | 41.269 | 1.00 | 13.51 |
| 1401 | C | MET | A | 110 | -2.277 | -4.042 | 46.718 | 1.00 | 13.49 |
| 1402 | O | MET | A | 110 | -2.071 | -2.963 | 47.271 | 1.00 | 14.30 |
| 1403 | N | GLY | A | 111 | -3.409 | -4.720 | 46.881 | 1.00 | 13.28 |
| 1405 | CA | GLY | A | 111 | -4.519 | -4.191 | 47.663 | 1.00 | 13.54 |
| 1408 | C | GLY | A | 111 | -5.317 | -3.114 | 46.948 | 1.00 | 13.50 |
| 1409 | O | GLY | A | 111 | -5.878 | -2.227 | 47.586 | 1.00 | 14.56 |
| 1410 | N | GLY | A | 112 | -5.361 | -3.203 | 45.623 | 1.00 | 13.00 |
| 1412 | CA | GLY | A | 112 | -6.103 | -2.282 | 44.782 | 1.00 | 12.55 |
| 1415 | C | GLY | A | 112 | -5.346 | -2.001 | 43.489 | 1.00 | 12.44 |
| 1416 | O | GLY | A | 112 | -4.335 | -2.641 | 43.189 | 1.00 | 12.46 |
| 1417 | N | LEU | A | 113 | -5.836 | -1.022 | 42.737 | 1.00 | 11.74 |
| 1419 | CA | LEU | A | 113 | -5.280 | -0.680 | 41.429 | 1.00 | 11.64 |
| 1421 | CB | LEU | A | 113 | -5.802 | -1.629 | 40.351 | 1.00 | 11.77 |
| 1424 | CG | LEU | A | 113 | -5.151 | -1.465 | 38.971 | 1.00 | 12.59 |
| 1426 | CD1 | LEU | A | 113 | -3.678 | -1.873 | 38.978 | 1.00 | 13.81 |
| 1430 | CD2 | LEU | A | 113 | -5.919 | -2.252 | 37.916 | 1.00 | 14.21 |
| 1434 | C | LEU | A | 113 | -5.660 | 0.745 | 41.072 | 1.00 | 11.50 |
| 1435 | O | LEU | A | 113 | -6.850 | 1.092 | 41.061 | 1.00 | 11.30 |
| 1436 | N | ASP | A | 114 | -4.644 | 1.554 | 40.778 | 1.00 | 11.48 |
| 1438 | CA | ASP | A | 114 | -4.784 | 2.953 | 40.378 | 1.00 | 11.86 |
| 1440 | CB | ASP | A | 114 | -3.778 | 3.817 | 41.139 | 1.00 | 11.83 |
| 1443 | CG | ASP | A | 114 | -4.011 | 3.807 | 42.635 | 1.00 | 13.40 |
| 1444 | OD1 | ASP | A | 114 | -5.098 | 4.235 | 43.099 | 1.00 | 16.22 |
| 1445 | OD2 | ASP | A | 114 | -3.152 | 3.390 | 43.427 | 1.00 | 14.98 |
| 1446 | C | ASP | A | 114 | -4.579 | 3.186 | 38.890 | 1.00 | 11.53 |
| 1447 | O | ASP | A | 114 | -5.151 | 4.109 | 38.336 | 1.00 | 11.55 |
| 1448 | N | MET | A | 115 | -3.743 | 2.374 | 38.239 | 1.00 | 11.65 |
| 1450 | CA | MET | A | 115 | -3.446 | 2.581 | 36.821 | 1.00 | 12.03 |
| 1452 | CB | MET | A | 115 | -2.270 | 3.550 | 36.646 | 1.00 | 12.51 |
| 1455 | CG | MET | A | 115 | -1.948 | 3.910 | 35.194 | 1.00 | 13.35 |
| 1458 | SD | MET | A | 115 | -0.643 | 5.145 | 35.023 | 1.00 | 17.9 |
| 1459 | CE | MET | A | 115 | -1.525 | 6.634 | 35.502 | 1.00 | 18.97 |
| 1463 | C | MET | A | 115 | -3.151 | 1.254 | 36.134 | 1.00 | 11.70 |
| 1464 | O | MET | A | 115 | -2.366 | 0.441 | 36.633 | 1.00 | 12.00 |
| 1465 | N | LEU | A | 116 | -3.780 | 1.061 | 34.981 | 1.00 | 11.39 |
| 1467 | CA | LEU | A | 116 | -3.604 | -0.119 | 34.157 | 1.00 | 11.20 |
| 1469 | CB | LEU | A | 116 | -4.957 | -0.748 | 33.859 | 1.00 | 11.28 |
| 1472 | CG | LEU | A | 116 | -4.973 | -1.946 | 32.922 | 1.00 | 11.66 |
| 1474 | CD1 | LEU | A | 116 | -4.340 | -3.129 | 33.611 | 1.00 | 13.53 |

FIGURE 3 (cont.)

| A | B | C | D | E | F | G | H | I | J |
|---|---|---|---|---|---|---|---|---|---|
| 1478 | CD2 | LEU | A | 116 | -6.398 | -2.256 | 32.505 | 1.00 | 12.30 |
| 1482 | C | LEU | A | 116 | -2.944 | 0.329 | 32.861 | 1.00 | 11.25 |
| 1483 | O | LEU | A | 116 | -3.557 | 1.040 | 32.070 | 1.00 | 11.10 |
| 1484 | N | ILE | A | 117 | -1.690 | -0.049 | 32.659 | 1.00 | 10.76 |
| 1486 | CA | ILE | A | 117 | -0.968 | 0.336 | 31.445 | 1.00 | 11.16 |
| 1488 | CB | ILE | A | 117 | 0.443 | 0.864 | 31.754 | 1.00 | 11.32 |
| 1490 | CG1 | ILE | A | 117 | 0.365 | 2.048 | 32.718 | 1.00 | 12.14 |
| 1493 | CD1 | ILE | A | 117 | 1.718 | 2.649 | 33.085 | 1.00 | 13.08 |
| 1497 | CG2 | ILE | A | 117 | 1.163 | 1.261 | 30.448 | 1.00 | 10.59 |
| 1501 | C | ILE | A | 117 | -0.907 | -0.879 | 30.539 | 1.00 | 10.80 |
| 1502 | O | ILE | A | 117 | -0.235 | -1.864 | 30.846 | 1.00 | 10.59 |
| 1503 | N | LEU | A | 118 | -1.609 | -0.784 | 29.417 | 1.00 | 10.45 |
| 1505 | CA | LEU | A | 118 | -1.732 | -1.854 | 28.434 | 1.00 | 10.13 |
| 1507 | CB | LEU | A | 118 | -3.190 | -1.930 | 27.966 | 1.00 | 10.43 |
| 1510 | CG | LEU | A | 118 | -4.186 | -2.138 | 29.110 | 1.00 | 10.25 |
| 1512 | CD1 | LEU | A | 118 | -5.625 | -2.049 | 28.624 | 1.00 | 11.52 |
| 1516 | CD2 | LEU | A | 118 | -3.927 | -3.471 | 29.815 | 1.00 | 11.22 |
| 1520 | C | LEU | A | 118 | -0.797 | -1.568 | 27.268 | 1.00 | 10.22 |
| 1521 | O | LEU | A | 118 | -1.015 | -0.627 | 26.509 | 1.00 | 10.36 |
| 1522 | N | ASN | A | 119 | 0.251 | -2.377 | 27.144 | 1.00 | 9.88 |
| 1524 | CA | ASN | A | 119 | 1.373 | -2.063 | 26.285 | 1.00 | 9.94 |
| 1526 | CB | ASN | A | 119 | 2.490 | -1.486 | 27.186 | 1.00 | 9.71 |
| 1529 | CG | ASN | A | 119 | 3.851 | -1.440 | 26.525 | 1.00 | 10.86 |
| 1530 | OD1 | ASN | A | 119 | 4.697 | -2.319 | 26.739 | 1.00 | 13.48 |
| 1531 | ND2 | ASN | A | 119 | 4.082 | -0.410 | 25.750 | 1.00 | 7.73 |
| 1534 | C | ASN | A | 119 | 1.844 | -3.237 | 25.425 | 1.00 | 9.70 |
| 1535 | O | ASN | A | 119 | 2.441 | -3.008 | 24.379 | 1.00 | 9.57 |
| 1536 | N | HIS | A | 120 | 1.582 | -4.477 | 25.836 | 1.00 | 9.31 |
| 1538 | CA | HIS | A | 120 | 2.054 | -5.640 | 25.081 | 1.00 | 9.34 |
| 1540 | CB | HIS | A | 120 | 1.725 | -6.947 | 25.840 | 1.00 | 9.57 |
| 1543 | CG | HIS | A | 120 | 0.262 | -7.147 | 26.072 | 1.00 | 9.97 |
| 1544 | ND1 | HIS | A | 120 | -0.567 | -7.799 | 25.184 | 1.00 | 13.43 |
| 1546 | CE1 | HIS | A | 120 | -1.793 | -7.812 | 25.668 | 1.00 | 8.49 |
| 1548 | NE2 | HIS | A | 120 | -1.797 | -7.183 | 26.823 | 1.00 | 12.74 |
| 1550 | CD2 | HIS | A | 120 | -0.527 | -6.745 | 27.091 | 1.00 | 7.45 |
| 1552 | C | HIS | A | 120 | 1.493 | -5.733 | 23.665 | 1.00 | 8.99 |
| 1553 | O | HIS | A | 120 | 0.395 | -5.263 | 23.376 | 1.00 | 9.09 |
| 1554 | N | ILE | A | 121 | 2.270 | -6.356 | 22.783 | 1.00 | 8.63 |
| 1556 | CA | ILE | A | 121 | 1.820 | -6.755 | 21.457 | 1.00 | 9.34 |
| 1558 | CB | ILE | A | 121 | 2.261 | -5.744 | 20.363 | 1.00 | 9.34 |
| 1560 | CG1 | ILE | A | 121 | 3.767 | -5.475 | 20.427 | 1.00 | 10.84 |
| 1563 | CD1 | ILE | A | 121 | 4.297 | -4.741 | 19.213 | 1.00 | 12.35 |
| 1567 | CG2 | ILE | A | 121 | 1.466 | -4.461 | 20.477 | 1.00 | 9.17 |
| 1571 | C | ILE | A | 121 | 2.398 | -8.118 | 21.134 | 1.00 | 9.37 |
| 1572 | O | ILE | A | 121 | 3.435 | -8.527 | 21.693 | 1.00 | 10.57 |
| 1573 | N | THR | A | 122 | 1.754 | -8.821 | 20.215 | 1.00 | 9.61 |
| 1575 | CA | THR | A | 122 | 2.313 | -10.050 | 19.670 | 1.00 | 10.09 |
| 1577 | CB | THR | A | 122 | 1.200 | -10.854 | 18.965 | 1.00 | 10.32 |
| 1579 | OG1 | THR | A | 122 | 1.633 | -12.200 | 18.744 | 1.00 | 10.54 |

FIGURE 3 (cont.)

| A | B | C | D | E | F | G | H | I | J |
|---|---|---|---|---|---|---|---|---|---|
| 1581 | CG2 | THR | A | 122 | 0.878 | -10.304 | 17.564 | 1.00 | 11.01 |
| 1585 | C | THR | A | 122 | 3.471 | -9.689 | 18.719 | 1.00 | 11.46 |
| 1586 | O | THR | A | 122 | 3.517 | -8.593 | 18.153 | 1.00 | 11.55 |
| 1587 | N | ASN | A | 123 | 4.415 | -10.604 | 18.560 | 1.00 | 12.38 |
| 1589 | CA | ASN | A | 123 | 5.573 | -10.352 | 17.721 | 1.00 | 14.10 |
| 1591 | CB | ASN | A | 123 | 6.510 | -11.580 | 17.710 | 1.00 | 14.39 |
| 1594 | CG | ASN | A | 123 | 7.260 | -11.784 | 19.026 | 1.00 | 16.38 |
| 1595 | OD1 | ASN | A | 123 | 7.229 | -10.951 | 19.942 | 1.00 | 18.79 |
| 1596 | ND2 | ASN | A | 123 | 7.963 | -12.916 | 19.119 | 1.00 | 20.92 |
| 1599 | C | ASN | A | 123 | 5.108 | -10.017 | 16.295 | 1.00 | 15.12 |
| 1600 | O | ASN | A | 123 | 4.309 | -10.743 | 15.696 | 1.00 | 14.58 |
| 1601 | N | THR | A | 124 | 5.568 | -8.874 | 15.791 | 1.00 | 16.97 |
| 1603 | CA | THR | A | 124 | 5.209 | -8.388 | 14.458 | 1.00 | 18.57 |
| 1605 | CB B | THR | A | 124 | 4.234 | -7.233 | 14.498 | 0.35 | 18.86 |
| 1606 | CB A | THR | A | 124 | 4.159 | -7.217 | 14.567 | 0.65 | 19.42 |
| 1609 | OG1B | THR | A | 124 | 4.870 | -6.055 | 15.006 | 0.35 | 18.93 |
| 1610 | OG1A | THR | A | 124 | 4.240 | -6.326 | 13.445 | 0.65 | 19.80 |
| 1613 | CG2B | THR | A | 124 | 3.176 | -7.493 | 15.473 | 0.35 | 17.53 |
| 1614 | CG2A | THR | A | 124 | 4.413 | -6.269 | 15.740 | 0.65 | 18.06 |
| 1621 | C | THR | A | 124 | 6.461 | -7.944 | 13.728 | 1.00 | 20.02 |
| 1622 | O | THR | A | 124 | 7.250 | -7.176 | 14.274 | 1.00 | 21.64 |
| 1623 | N | SER | A | 125 | 6.621 | -8.423 | 12.509 | 1.00 | 20.65 |
| 1625 | CA | SER | A | 125 | 7.668 | -7.921 | 11.617 | 1.00 | 21.51 |
| 1627 | CB | SER | A | 125 | 8.614 | -9.046 | 11.217 | 1.00 | 21.79 |
| 1630 | OG | SER | A | 125 | 7.940 | -10.023 | 10.464 | 1.00 | 25.57 |
| 1632 | C | SER | A | 125 | 7.052 | -7.278 | 10.376 | 1.00 | 20.50 |
| 1633 | O | SER | A | 125 | 5.899 | -7.530 | 10.027 | 1.00 | 20.85 |
| 1634 | N | LEU | A | 126 | 7.836 | -6.435 | 9.716 | 1.00 | 19.49 |
| 1636 | CA | LEU | A | 126 | 7.371 | -5.755 | 8.521 | 1.00 | 18.41 |
| 1638 | CB | LEU | A | 126 | 8.286 | -4.575 | 8.220 | 1.00 | 18.30 |
| 1641 | CG | LEU | A | 126 | 8.235 | -3.516 | 9.306 | 1.00 | 18.14 |
| 1643 | CD1 | LEU | A | 126 | 9.363 | -2.543 | 9.152 | 1.00 | 17.70 |
| 1647 | CD2 | LEU | A | 126 | 6.892 | -2.814 | 9.235 | 1.00 | 17.14 |
| 1651 | C | LEU | A | 126 | 7.367 | -6.693 | 7.322 | 1.00 | 17.29 |
| 1652 | O | LEU | A | 126 | 8.410 | -7.166 | 6.914 | 1.00 | 17.61 |
| 1653 | N | ASN | A | 127 | 6.195 | -6.945 | 6.753 | 1.00 | 16.29 |
| 1655 | CA | ASN | A | 127 | 6.081 | -7.737 | 5.532 | 1.00 | 16.45 |
| 1657 | CB | ASN | A | 127 | 6.286 | -9.230 | 5.831 | 1.00 | 17.25 |
| 1660 | CG | ASN | A | 127 | 7.737 | -9.691 | 5.641 | 1.00 | 20.22 |
| 1661 | OD1 | ASN | A | 127 | 8.280 | -10.409 | 6.483 | 1.00 | 25.21 |
| 1662 | ND2 | ASN | A | 127 | 8.361 | -9.279 | 4.545 | 1.00 | 23.68 |
| 1665 | C | ASN | A | 127 | 4.722 | -7.538 | 4.872 | 1.00 | 15.39 |
| 1666 | O | ASN | A | 127 | 3.754 | -7.186 | 5.547 | 1.00 | 14.23 |
| 1667 | N | LEU | A | 128 | 4.665 | -7.732 | 3.558 | 1.00 | 14.25 |
| 1669 | CA | LEU | A | 128 | 3.399 | -7.753 | 2.833 | 1.00 | 14.12 |
| 1671 | CB | LEU | A | 128 | 3.610 | -8.129 | 1.371 | 1.00 | 14.18 |
| 1674 | CG | LEU | A | 128 | 4.298 | -7.140 | 0.433 | 1.00 | 15.65 |
| 1676 | CD1 | LEU | A | 128 | 4.803 | -7.900 | -0.784 | 1.00 | 17.00 |
| 1680 | CD2 | LEU | A | 128 | 3.373 | -6.025 | 0.013 | 1.00 | 16.03 |

FIGURE 3 (cont.)

| A | B | C | D | E | F | G | H | I | J |
|---|---|---|---|---|---|---|---|---|---|
| 1684 | C | LEU | A | 128 | 2.500 | -8.803 | 3.456 | 1.00 | 14.04 |
| 1685 | O | LEU | A | 128 | 2.964 | -9.867 | 3.849 | 1.00 | 14.34 |
| 1686 | N | PHE | A | 129 | 1.209 | -8.509 | 3.539 | 1.00 | 13.84 |
| 1688 | CA | PHE | A | 129 | 0.243 | -9.529 | 3.904 | 1.00 | 13.46 |
| 1690 | CB | PHE | A | 129 | -1.152 | -8.913 | 3.997 | 1.00 | 12.86 |
| 1693 | CG | PHE | A | 129 | -2.220 | -9.909 | 4.301 | 1.00 | 11.79 |
| 1694 | CD1 | PHE | A | 129 | -2.281 | -10.515 | 5.545 | 1.00 | 12.71 |
| 1696 | CE1 | PHE | A | 129 | -3.258 | -11.469 | 5.818 | 1.00 | 11.64 |
| 1698 | CZ | PHE | A | 129 | -4.177 | -11.791 | 4.857 | 1.00 | 12.44 |
| 1700 | CE2 | PHE | A | 129 | -4.126 | -11.192 | 3.614 | 1.00 | 12.68 |
| 1702 | CD2 | PHE | A | 129 | -3.144 | -10.251 | 3.338 | 1.00 | 12.21 |
| 1704 | C | PHE | A | 129 | 0.308 | -10.645 | 2.857 | 1.00 | 14.16 |
| 1705 | O | PHE | A | 129 | 0.375 | -10.386 | 1.659 | 1.00 | 14.99 |
| 1706 | N | HIS | A | 130 | 0.347 | -11.892 | 3.313 | 1.00 | 14.55 |
| 1708 | CA | HIS | A | 130 | 0.555 | -13.042 | 2.431 | 1.00 | 14.96 |
| 1710 | CB | HIS | A | 130 | 2.043 | -13.456 | 2.416 | 1.00 | 15.55 |
| 1713 | CG | HIS | A | 130 | 2.616 | -13.749 | 3.766 | 1.00 | 17.64 |
| 1714 | ND1 | HIS | A | 130 | 2.910 | -12.765 | 4.686 | 1.00 | 19.86 |
| 1716 | CE1 | HIS | A | 130 | 3.398 | -13.319 | 5.783 | 1.00 | 21.52 |
| 1718 | NE2 | HIS | A | 130 | 3.421 | -14.628 | 5.611 | 1.00 | 21.53 |
| 1720 | CD2 | HIS | A | 130 | 2.945 | -14.923 | 4.356 | 1.00 | 19.41 |
| 1722 | C | HIS | A | 130 | -0.361 | -14.210 | 2.815 | 1.00 | 14.69 |
| 1723 | O | HIS | A | 130 | 0.089 | -15.345 | 2.967 | 1.00 | 15.10 |
| 1724 | N | ASP | A | 131 | -1.656 | -13.904 | 2.950 | 1.00 | 13.78 |
| 1726 | CA | ASP | A | 131 | -2.715 | -14.885 | 3.234 | 1.00 | 13.69 |
| 1728 | CB | ASP | A | 131 | -2.770 | -15.988 | 2.172 | 1.00 | 13.91 |
| 1731 | CG | ASP | A | 131 | -3.050 | -15.457 | 0.777 | 1.00 | 16.42 |
| 1732 | OD1 | ASP | A | 131 | -3.608 | -14.346 | 0.647 | 1.00 | 17.50 |
| 1733 | OD2 | ASP | A | 131 | -2.746 | -16.101 | -0.255 | 1.00 | 20.24 |
| 1734 | C | ASP | A | 131 | -2.598 | -15.501 | 4.621 | 1.00 | 13.16 |
| 1735 | O | ASP | A | 131 | -3.233 | -16.526 | 4.915 | 1.00 | 13.46 |
| 1736 | N | ASP | A | 132 | -1.803 | -14.856 | 5.468 | 1.00 | 12.72 |
| 1738 | CA | ASP | A | 132 | -1.529 | -15.356 | 6.809 | 1.00 | 12.58 |
| 1740 | CB | ASP | A | 132 | -0.125 | -14.955 | 7.315 | 1.00 | 13.30 |
| 1743 | CG | ASP | A | 132 | 0.222 | -13.480 | 7.089 | 1.00 | 14.42 |
| 1744 | OD1 | ASP | A | 132 | -0.096 | -12.916 | 6.015 | 1.00 | 15.68 |
| 1745 | OD2 | ASP | A | 132 | 0.888 | -12.821 | 7.928 | 1.00 | 17.43 |
| 1746 | C | ASP | A | 132 | -2.642 | -14.911 | 7.753 | 1.00 | 12.19 |
| 1747 | O | ASP | A | 132 | -2.423 | -14.097 | 8.643 | 1.00 | 12.09 |
| 1748 | N | ILE | A | 133 | -3.832 | -15.481 | 7.548 | 1.00 | 12.08 |
| 1750 | CA | ILE | A | 133 | -4.990 | -15.203 | 8.392 | 1.00 | 12.44 |
| 1752 | CB | ILE | A | 133 | -6.229 | -16.000 | 7.916 | 1.00 | 12.91 |
| 1754 | CG1 | ILE | A | 133 | -6.642 | -15.566 | 6.508 | 1.00 | 14.29 |
| 1757 | CD1 | ILE | A | 133 | -7.344 | -16.624 | 5.762 | 1.00 | 17.50 |
| 1761 | CG2 | ILE | A | 133 | -7.410 | -15.826 | 8.896 | 1.00 | 13.56 |
| 1765 | C | ILE | A | 133 | -4.678 | -15.507 | 9.850 | 1.00 | 12.67 |
| 1766 | O | ILE | A | 133 | -5.167 | -14.819 | 10.725 | 1.00 | 12.42 |
| 1767 | N | HIS | A | 134 | -3.847 | -16.521 | 10.116 | 1.00 | 12.82 |
| 1769 | CA | HIS | A | 134 | -3.482 | -16.869 | 11.496 | 1.00 | 12.94 |

FIGURE 3 (cont.)

| A | B | C | D | E | F | G | H | I | J |
|---|---|---|---|---|---|---|---|---|---|
| 1771 | CB | HIS | A | 134 | -2.568 | -18.134 | 11.568 | 1.00 | 13.10 |
| 1774 | CG | HIS | A | 134 | -1.196 | -17.966 | 10.970 | 1.00 | 13.12 |
| 1775 | ND1 | HIS | A | 134 | -0.148 | -17.371 | 11.643 | 1.00 | 15.93 |
| 1777 | CE1 | HIS | A | 134 | 0.922 | -17.355 | 10.867 | 1.00 | 16.69 |
| 1779 | NE2 | HIS | A | 134 | 0.617 | -17.945 | 9.724 | 1.00 | 16.50 |
| 1781 | CD2 | HIS | A | 134 | -0.699 | -18.345 | 9.766 | 1.00 | 15.53 |
| 1783 | C | HIS | A | 134 | -2.853 | -15.694 | 12.229 | 1.00 | 12.68 |
| 1784 | O | HIS | A | 134 | -3.078 | -15.492 | 13.420 | 1.00 | 12.80 |
| 1785 | N | HIS | A | 135 | -2.060 | -14.908 | 11.513 | 1.00 | 12.08 |
| 1787 | CA | HIS | A | 135 | -1.415 | -13.753 | 12.103 | 1.00 | 11.63 |
| 1789 | CB | HIS | A | 135 | -0.262 | -13.260 | 11.242 | 1.00 | 11.67 |
| 1792 | CG | HIS | A | 135 | 0.395 | -12.023 | 11.763 | 1.00 | 14.39 |
| 1793 | ND1 | HIS | A | 135 | 1.177 | -12.007 | 12.902 | 1.00 | 16.83 |
| 1795 | CE1 | HIS | A | 135 | 1.639 | -10.784 | 13.091 | 1.00 | 17.41 |
| 1797 | NE2 | HIS | A | 135 | 1.181 | -10.007 | 12.130 | 1.00 | 17.28 |
| 1799 | CD2 | HIS | A | 135 | 0.399 | -10.757 | 11.287 | 1.00 | 16.70 |
| 1801 | C | HIS | A | 135 | -2.389 | -12.613 | 12.327 | 1.00 | 10.53 |
| 1802 | O | HIS | A | 135 | -2.247 | -11.899 | 13.293 | 1.00 | 10.95 |
| 1803 | N | VAL | A | 136 | -3.366 | -12.453 | 11.436 | 1.00 | 9.47 |
| 1805 | CA | VAL | A | 136 | -4.389 | -11.437 | 11.621 | 1.00 | 9.90 |
| 1807 | CB | VAL | A | 136 | -5.338 | -11.354 | 10.435 | 1.00 | 10.24 |
| 1809 | CG1 | VAL | A | 136 | -6.392 | -10.270 | 10.664 | 1.00 | 11.29 |
| 1813 | CG2 | VAL | A | 136 | -4.542 | -11.061 | 9.171 | 1.00 | 10.36 |
| 1817 | C | VAL | A | 136 | -5.179 | -11.764 | 12.876 | 1.00 | 9.81 |
| 1818 | O | VAL | A | 136 | -5.443 | -10.895 | 13.702 | 1.00 | 10.06 |
| 1819 | N | ARG | A | 137 | -5.564 | -13.026 | 13.022 | 1.00 | 10.01 |
| 1821 | CA | ARG | A | 137 | -6.323 | -13.448 | 14.193 | 1.00 | 10.98 |
| 1823 | CB | ARG | A | 137 | -6.807 | -14.889 | 14.047 | 1.00 | 11.57 |
| 1826 | CG | ARG | A | 137 | -7.654 | -15.347 | 15.227 | 1.00 | 15.06 |
| 1829 | CD B | ARG | A | 137 | -8.058 | -16.806 | 15.159 | 0.35 | 16.94 |
| 1830 | CD A | ARG | A | 137 | -8.019 | -16.814 | 15.183 | 0.65 | 19.73 |
| 1835 | NE B | ARG | A | 137 | -8.946 | -17.072 | 14.028 | 0.35 | 18.67 |
| 1836 | NE A | ARG | A | 137 | -9.318 | -17.062 | 14.571 | 0.65 | 24.03 |
| 1839 | CZ B | ARG | A | 137 | -10.264 | -17.288 | 14.107 | 0.35 | 20.30 |
| 1840 | CZ A | ARG | A | 137 | -9.537 | -17.327 | 13.281 | 0.65 | 27.17 |
| 1841 | NH1B | ARG | A | 137 | -10.897 | -17.284 | 15.276 | 0.35 | 20.86 |
| 1842 | NH1A | ARG | A | 137 | -8.550 | -17.355 | 12.386 | 0.65 | 26.90 |
| 1847 | NH2B | ARG | A | 137 | -10.958 | -17.522 | 12.999 | 0.35 | 22.20 |
| 1848 | NH2A | ARG | A | 137 | -10.779 | -17.547 | 12.874 | 0.65 | 29.51 |
| 1853 | C | ARG | A | 137 | -5.513 | -13.292 | 15.473 | 1.00 | 10.70 |
| 1854 | O | ARG | A | 137 | -6.004 | -12.764 | 16.468 | 1.00 | 10.51 |
| 1855 | N | LYS | A | 138 | -4.257 | -13.727 | 15.456 | 1.00 | 11.26 |
| 1857 | CA | LYS | A | 138 | -3.411 | -13.620 | 16.636 | 1.00 | 11.78 |
| 1859 | CB | LYS | A | 138 | -2.072 | -14.322 | 16.430 | 1.00 | 12.91 |
| 1862 | CG | LYS | A | 138 | -1.176 | -14.257 | 17.659 | 1.00 | 14.66 |
| 1865 | CD | LYS | A | 138 | -0.040 | -15.240 | 17.576 | 1.00 | 19.77 |
| 1868 | CE | LYS | A | 138 | -0.517 | -16.649 | 17.846 | 1.00 | 22.64 |
| 1871 | NZ | LYS | A | 138 | 0.610 | -17.541 | 18.166 | 1.00 | 26.76 |
| 1875 | C | LYS | A | 138 | -3.189 | -12.164 | 17.026 | 1.00 | 11.49 |

FIGURE 3 (cont.)

| A | B | C | D | E | F | G | H | I | J |
|---|---|---|---|---|---|---|---|---|---|
| 1876 | O | LYS | A | 138 | -3.230 | -11.818 | 18.207 | 1.00 | 10.94 |
| 1877 | N | SER | A | 139 | -2.997 | -11.298 | 16.037 | 1.00 | 10.79 |
| 1879 | CA | SER | A | 139 | -2.859 | -9.871 | 16.305 | 1.00 | 10.57 |
| 1881 | CB | SER | A | 139 | -2.588 | -9.096 | 15.019 | 1.00 | 10.68 |
| 1884 | OG | SER | A | 139 | -1.315 | -9.439 | 14.525 | 1.00 | 11.59 |
| 1886 | C | SER | A | 139 | -4.106 | -9.314 | 16.979 | 1.00 | 10.43 |
| 1887 | O | SER | A | 139 | -4.027 | -8.544 | 17.940 | 1.00 | 9.90 |
| 1888 | N | MET | A | 140 | -5.261 | -9.708 | 16.467 | 1.00 | 10.90 |
| 1890 | CA | MET | A | 140 | -6.512 | -9.206 | 16.998 | 1.00 | 11.57 |
| 1892 | CB | MET | A | 140 | -7.677 | -9.587 | 16.082 | 1.00 | 12.12 |
| 1895 | CG | MET | A | 140 | -7.762 | -8.817 | 14.763 | 1.00 | 16.15 |
| 1898 | SD | MET | A | 140 | -7.573 | -6.992 | 14.809 | 1.00 | 21.70 |
| 1899 | CE | MET | A | 140 | -8.504 | -6.669 | 16.270 | 1.00 | 15.65 |
| 1903 | C | MET | A | 140 | -6.709 | -9.734 | 18.415 | 1.00 | 11.62 |
| 1904 | O | MET | A | 140 | -7.138 | -9.002 | 19.291 | 1.00 | 11.76 |
| 1905 | N | GLU | A | 141 | -6.332 | -10.978 | 18.679 | 1.00 | 10.59 |
| 1907 | CA | GLU | A | 141 | -6.524 | -11.531 | 20.034 | 1.00 | 11.31 |
| 1909 | CB | GLU | A | 141 | -6.344 | -13.050 | 20.027 | 1.00 | 12.33 |
| 1912 | CG | GLU | A | 141 | -7.429 | -13.796 | 19.269 | 1.00 | 15.26 |
| 1915 | CD | GLU | A | 141 | -8.648 | -14.108 | 20.113 | 1.00 | 20.89 |
| 1916 | OE1 | GLU | A | 141 | -9.742 | -14.249 | 19.529 | 1.00 | 23.63 |
| 1917 | OE2 | GLU | A | 141 | -8.536 | -14.203 | 21.357 | 1.00 | 23.33 |
| 1918 | C | GLU | A | 141 | -5.579 | -10.902 | 21.069 | 1.00 | 11.00 |
| 1919 | O | GLU | A | 141 | -5.991 | -10.503 | 22.154 | 1.00 | 11.40 |
| 1920 | N | VAL | A | 142 | -4.297 | -10.835 | 20.740 | 1.00 | 10.88 |
| 1922 | CA | VAL | A | 142 | -3.290 | -10.372 | 21.678 | 1.00 | 10.28 |
| 1924 | CB | VAL | A | 142 | -1.885 | -10.889 | 21.288 | 1.00 | 10.65 |
| 1926 | CG1 | VAL | A | 142 | -0.793 | -10.288 | 22.187 | 1.00 | 10.71 |
| 1930 | CG2 | VAL | A | 142 | -1.879 | -12.406 | 21.336 | 1.00 | 10.42 |
| 1934 | C | VAL | A | 142 | -3.289 | -8.850 | 21.787 | 1.00 | 10.10 |
| 1935 | O | VAL | A | 142 | -3.265 | -8.298 | 22.885 | 1.00 | 10.60 |
| 1936 | N | ASN | A | 143 | -3.301 | -8.170 | 20.652 | 1.00 | 9.47 |
| 1938 | CA | ASN | A | 143 | -3.140 | -6.725 | 20.660 | 1.00 | 9.48 |
| 1940 | CB | ASN | A | 143 | -2.684 | -6.219 | 19.290 | 1.00 | 9.32 |
| 1943 | CG | ASN | A | 143 | -1.345 | -6.783 | 18.841 | 1.00 | 10.46 |
| 1944 | OD1 | ASN | A | 143 | -0.684 | -7.552 | 19.545 | 1.00 | 9.61 |
| 1945 | ND2 | ASN | A | 143 | -0.938 | -6.389 | 17.633 | 1.00 | 10.58 |
| 1948 | C | ASN | A | 143 | -4.408 | -5.961 | 21.021 | 1.00 | 9.84 |
| 1949 | O | ASN | A | 143 | -4.328 | -4.795 | 21.388 | 1.00 | 10.52 |
| 1950 | N | PHE | A | 144 | -5.567 | -6.588 | 20.829 | 1.00 | 9.68 |
| 1952 | CA | PHE | A | 144 | -6.865 | -5.922 | 20.997 | 1.00 | 9.57 |
| 1954 | CB | PHE | A | 144 | -7.627 | -5.760 | 19.669 | 1.00 | 9.80 |
| 1957 | CG | PHE | A | 144 | -9.049 | -5.350 | 19.870 | 1.00 | 10.47 |
| 1958 | CD1 | PHE | A | 144 | -9.336 | -4.092 | 20.350 | 1.00 | 11.74 |
| 1960 | CE1 | PHE | A | 144 | -10.640 | -3.717 | 20.609 | 1.00 | 11.53 |
| 1962 | CZ | PHE | A | 144 | -11.677 | -4.612 | 20.401 | 1.00 | 10.73 |
| 1964 | CE2 | PHE | A | 144 | -11.409 | -5.864 | 19.930 | 1.00 | 11.08 |
| 1966 | CD2 | PHE | A | 144 | -10.081 | -6.244 | 19.682 | 1.00 | 10.03 |
| 1968 | C | PHE | A | 144 | -7.732 | -6.642 | 22.033 | 1.00 | 9.49 |

FIGURE 3 (cont.)

| A | B | C | D | E | F | G | H | I | J |
|---|---|---|---|---|---|---|---|---|---|
| 1969 | O | PHE | A | 144 | -8.063 | -6.063 | 23.067 | 1.00 | 9.71 |
| 1970 | N | LEU | A | 145 | -8.123 | -7.889 | 21.782 | 1.00 | 9.31 |
| 1972 | CA | LEU | A | 145 | -9.106 | -8.515 | 22.666 | 1.00 | 9.76 |
| 1974 | CB | BLEU | A | 145 | -9.561 | -9.878 | 22.139 | 0.35 | 9.81 |
| 1975 | CB | ALEU | A | 145 | -9.553 | -9.871 | 22.125 | 0.65 | 9.88 |
| 1980 | CG | BLEU | A | 145 | -10.389 | -9.860 | 20.855 | 0.35 | 10.79 |
| 1981 | CG | ALEU | A | 145 | -10.759 | -10.487 | 22.823 | 0.65 | 11.38 |
| 1984 | CD1 | BLEU | A | 145 | -10.573 | -11.282 | 20.349 | 0.35 | 11.81 |
| 1985 | CD1 | ALEU | A | 145 | -11.991 | -9.628 | 22.657 | 0.65 | 12.52 |
| 1992 | CD2 | BLEU | A | 145 | -11.742 | -9.191 | 21.065 | 0.35 | 11.10 |
| 1993 | CD2 | ALEU | A | 145 | -10.987 | -11.869 | 22.264 | 0.65 | 11.08 |
| 2000 | C | LEU | A | 145 | -8.576 | -8.648 | 24.082 | 1.00 | 9.40 |
| 2001 | O | LEU | A | 145 | -9.307 | -8.425 | 25.025 | 1.00 | 9.84 |
| 2002 | N | SER | A | 146 | -7.295 | -8.978 | 24.256 | 1.00 | 9.35 |
| 2004 | CA | SER | A | 146 | -6.752 | -9.101 | 25.604 | 1.00 | 9.51 |
| 2006 | CB | SER | A | 146 | -5.335 | -9.691 | 25.572 | 1.00 | 9.94 |
| 2009 | OG | SER | A | 146 | -4.396 | -8.717 | 25.179 | 1.00 | 10.50 |
| 2011 | C | SER | A | 146 | -6.814 | -7.766 | 26.366 | 1.00 | 9.75 |
| 2012 | O | SER | A | 146 | -6.995 | -7.743 | 27.581 | 1.00 | 9.24 |
| 2013 | N | TYR | A | 147 | -6.692 | -6.651 | 25.652 | 1.00 | 9.39 |
| 2015 | CA | TYR | A | 147 | -6.786 | -5.338 | 26.285 | 1.00 | 9.36 |
| 2017 | CB | TYR | A | 147 | -6.460 | -4.203 | 25.309 | 1.00 | 9.59 |
| 2020 | CG | TYR | A | 147 | -4.993 | -3.950 | 25.019 | 1.00 | 9.05 |
| 2021 | CD1 | TYR | A | 147 | -4.069 | -4.994 | 24.912 | 1.00 | 9.72 |
| 2023 | CE1 | TYR | A | 147 | -2.724 | -4.742 | 24.602 | 1.00 | 9.40 |
| 2025 | CZ | TYR | A | 147 | -2.296 | -3.434 | 24.439 | 1.00 | 9.98 |
| 2026 | OH | TYR | A | 147 | -0.974 | -3.132 | 24.148 | 1.00 | 10.82 |
| 2028 | CE2 | TYR | A | 147 | -3.205 | -2.395 | 24.522 | 1.00 | 9.58 |
| 2030 | CD2 | TYR | A | 147 | -4.535 | -2.654 | 24.820 | 1.00 | 9.53 |
| 2032 | C | TYR | A | 147 | -8.192 | -5.123 | 26.859 | 1.00 | 9.43 |
| 2033 | O | TYR | A | 147 | -8.350 | -4.530 | 27.928 | 1.00 | 10.12 |
| 2034 | N | VAL | A | 148 | -9.202 | -5.595 | 26.138 | 1.00 | 9.73 |
| 2036 | CA | VAL | A | 148 | -10.592 | -5.487 | 26.576 | 1.00 | 9.95 |
| 2038 | CB | VAL | A | 148 | -11.564 | -5.868 | 25.456 | 1.00 | 10.11 |
| 2040 | CG1 | VAL | A | 148 | -11.354 | -4.975 | 24.232 | 1.00 | 10.02 |
| 2044 | CG2 | VAL | A | 148 | -12.994 | -5.761 | 25.933 | 1.00 | 10.49 |
| 2048 | C | VAL | A | 148 | -10.824 | -6.375 | 27.807 | 1.00 | 9.78 |
| 2049 | O | VAL | A | 148 | -11.442 | -5.950 | 28.788 | 1.00 | 9.93 |
| 2050 | N | VAL | A | 149 | -10.312 | -7.601 | 27.768 | 1.00 | 9.80 |
| 2052 | CA | VAL | A | 149 | -10.434 | -8.526 | 28.904 | 1.00 | 10.03 |
| 2054 | CB | VAL | A | 149 | -9.860 | -9.924 | 28.540 | 1.00 | 10.01 |
| 2056 | CG1 | VAL | A | 149 | -9.764 | -10.828 | 29.767 | 1.00 | 9.96 |
| 2060 | CG2 | VAL | A | 149 | -10.705 | -10.562 | 27.460 | 1.00 | 10.49 |
| 2064 | C | VAL | A | 149 | -9.759 | -7.968 | 30.156 | 1.00 | 10.03 |
| 2065 | O | VAL | A | 149 | -10.320 | -7.994 | 31.253 | 1.00 | 10.05 |
| 2066 | N | LEU | A | 150 | -8.562 | -7.425 | 29.984 | 1.00 | 10.31 |
| 2068 | CA | LEU | A | 150 | -7.843 | -6.821 | 31.095 | 1.00 | 10.36 |
| 2070 | CB | LEU | A | 150 | -6.463 | -6.365 | 30.651 | 1.00 | 10.73 |
| 2073 | CG | LEU | A | 150 | -5.505 | -7.498 | 30.293 | 1.00 | 10.27 |

FIGURE 3 (cont.)

| A | B | C | D | E | F | G | H | I | J |
|---|---|---|---|---|---|---|---|---|---|
| 2075 | CD1 | LEU | A | 150 | -4.352 | -6.974 | 29.438 | 1.00 | 9.37 |
| 2079 | CD2 | LEU | A | 150 | -4.964 | -8.221 | 31.529 | 1.00 | 10.66 |
| 2083 | C | LEU | A | 150 | -8.615 | -5.643 | 31.692 | 1.00 | 10.37 |
| 2084 | O | LEU | A | 150 | -8.681 | -5.488 | 32.911 | 1.00 | 10.38 |
| 2085 | N | THR | A | 151 | -9.218 | -4.844 | 30.823 | 1.00 | 10.48 |
| 2087 | CA | THR | A | 151 | -10.010 | -3.698 | 31.241 | 1.00 | 10.79 |
| 2089 | CB | THR | A | 151 | -10.419 | -2.865 | 30.009 | 1.00 | 10.86 |
| 2091 | OG1 | THR | A | 151 | -9.260 | -2.244 | 29.452 | 1.00 | 12.66 |
| 2093 | CG2 | THR | A | 151 | -11.333 | -1.705 | 30.392 | 1.00 | 12.19 |
| 2097 | C | THR | A | 151 | -11.227 | -4.117 | 32.052 | 1.00 | 10.65 |
| 2098 | O | THR | A | 151 | -11.502 | -3.535 | 33.100 | 1.00 | 10.75 |
| 2099 | N | VAL | A | 152 | -11.960 | -5.113 | 31.565 | 1.00 | 10.74 |
| 2101 | CA | VAL | A | 152 | -13.139 | -5.622 | 32.263 | 1.00 | 10.86 |
| 2103 | CB | VAL | A | 152 | -13.815 | -6.755 | 31.450 | 1.00 | 11.39 |
| 2105 | CG1 | VAL | A | 152 | -14.831 | -7.510 | 32.269 | 1.00 | 12.64 |
| 2109 | CG2 | VAL | A | 152 | -14.462 | -6.196 | 30.145 | 1.00 | 11.40 |
| 2113 | C | VAL | A | 152 | -12.725 | -6.121 | 33.645 | 1.00 | 11.38 |
| 2114 | O | VAL | A | 152 | -13.421 | -5.887 | 34.636 | 1.00 | 11.46 |
| 2115 | N | ALA | A | 153 | -11.591 | -6.804 | 33.723 | 1.00 | 10.80 |
| 2117 | CA | ALA | A | 153 | -11.148 | -7.358 | 35.005 | 1.00 | 11.47 |
| 2119 | CB | ALA | A | 153 | -10.009 | -8.341 | 34.794 | 1.00 | 11.43 |
| 2123 | C | ALA | A | 153 | -10.717 | -6.267 | 35.975 | 1.00 | 11.90 |
| 2124 | O | ALA | A | 153 | -10.873 | -6.410 | 37.187 | 1.00 | 12.37 |
| 2125 | N | ALA | A | 154 | -10.178 | -5.174 | 35.441 | 1.00 | 11.38 |
| 2127 | CA | ALA | A | 154 | -9.612 | -4.110 | 36.260 | 1.00 | 11.55 |
| 2129 | CB | ALA | A | 154 | -8.488 | -3.419 | 35.507 | 1.00 | 11.90 |
| 2133 | C | ALA | A | 154 | -10.630 | -3.070 | 36.691 | 1.00 | 11.82 |
| 2134 | O | ALA | A | 154 | -10.391 | -2.341 | 37.648 | 1.00 | 11.16 |
| 2135 | N | LEU | A | 155 | -11.750 | -2.973 | 35.987 | 1.00 | 12.39 |
| 2137 | CA | LEU | A | 155 | -12.607 | -1.791 | 36.134 | 1.00 | 12.82 |
| 2139 | CB | LEU | A | 155 | -13.740 | -1.756 | 35.101 | 1.00 | 12.77 |
| 2142 | CG | LEU | A | 155 | -14.514 | -0.431 | 35.006 | 1.00 | 15.39 |
| 2144 | CD1 | LEU | A | 155 | -15.632 | -0.564 | 33.976 | 1.00 | 17.15 |
| 2148 | CD2 | LEU | A | 155 | -13.602 | 0.739 | 34.655 | 1.00 | 17.18 |
| 2152 | C | LEU | A | 155 | -13.173 | -1.615 | 37.544 | 1.00 | 12.83 |
| 2153 | O | LEU | A | 155 | -13.194 | -0.492 | 38.021 | 1.00 | 12.68 |
| 2154 | N | PRO | A | 156 | -13.640 | -2.675 | 38.211 | 1.00 | 12.68 |
| 2155 | CA | PRO | A | 156 | -14.124 | -2.510 | 39.594 | 1.00 | 12.84 |
| 2157 | CB | PRO | A | 156 | -14.466 | -3.937 | 40.017 | 1.00 | 13.08 |
| 2160 | CG | PRO | A | 156 | -14.799 | -4.628 | 38.743 | 1.00 | 13.53 |
| 2163 | CD | PRO | A | 156 | -13.830 | -4.055 | 37.740 | 1.00 | 12.49 |
| 2166 | C | PRO | A | 156 | -13.091 | -1.843 | 40.525 | 1.00 | 12.92 |
| 2167 | O | PRO | A | 156 | -13.441 | -0.907 | 41.251 | 1.00 | 12.97 |
| 2168 | N | MET | A | 157 | -11.838 | -2.283 | 40.465 | 1.00 | 12.85 |
| 2170 | CA | MET | A | 157 | -10.765 | -1.671 | 41.246 | 1.00 | 12.60 |
| 2172 | CB | MET | A | 157 | -9.483 | -2.510 | 41.171 | 1.00 | 12.58 |
| 2175 | CG | MET | A | 157 | -9.530 | -3.778 | 41.991 | 1.00 | 12.57 |
| 2178 | SD | MET | A | 157 | -7.980 | -4.666 | 41.958 | 1.00 | 14.98 |
| 2179 | CE | MET | A | 157 | -7.953 | -5.260 | 40.271 | 1.00 | 15.15 |

FIGURE 3 (cont.)

| A | B | C | D | E | F | G | H | I | J |
|---|---|---|---|---|---|---|---|---|---|
| 2183 | C | MET | A | 157 | -10.482 | -0.232 | 40.803 | 1.00 | 12.35 |
| 2184 | O | MET | A | 157 | -10.263 | 0.640 | 41.640 | 1.00 | 12.09 |
| 2185 | N | LEU | A | 158 | -10.508 | 0.023 | 39.496 | 1.00 | 12.12 |
| 2187 | CA | LEU | A | 158 | -10.266 | 1.368 | 38.983 | 1.00 | 12.51 |
| 2189 | CB | LEU | A | 158 | -10.066 | 1.346 | 37.469 | 1.00 | 12.39 |
| 2192 | CG | LEU | A | 158 | -8.788 | 0.628 | 37.016 | 1.00 | 12.88 |
| 2194 | CD1 | LEU | A | 158 | -8.797 | 0.481 | 35.503 | 1.00 | 13.53 |
| 2198 | CD2 | LEU | A | 158 | -7.556 | 1.368 | 37.469 | 1.00 | 13.52 |
| 2202 | C | LEU | A | 158 | -11.394 | 2.329 | 39.371 | 1.00 | 12.39 |
| 2203 | O | LEU | A | 158 | -11.148 | 3.499 | 39.609 | 1.00 | 12.45 |
| 2204 | N | LYS | A | 159 | -12.620 | 1.824 | 39.449 | 1.00 | 13.18 |
| 2206 | CA | LYS | A | 159 | -13.756 | 2.635 | 39.889 | 1.00 | 14.15 |
| 2208 | CB | LYS | A | 159 | -15.069 | 1.894 | 39.640 | 1.00 | 14.39 |
| 2211 | CG | LYS | A | 159 | -15.513 | 1.911 | 38.187 | 1.00 | 15.23 |
| 2214 | CD | LYS | A | 159 | -16.683 | 0.953 | 37.933 | 1.00 | 17.07 |
| 2217 | CE | LYS | A | 159 | -17.364 | 1.231 | 36.602 | 1.00 | 19.52 |
| 2220 | NZ | LYS | A | 159 | -18.301 | 0.142 | 36.175 | 1.00 | 20.70 |
| 2224 | C | LYS | A | 159 | -13.605 | 2.998 | 41.369 | 1.00 | 15.38 |
| 2225 | O | LYS | A | 159 | -13.919 | 4.117 | 41.781 | 1.00 | 15.86 |
| 2226 | N | GLN | A | 160 | -13.112 | 2.050 | 42.158 | 1.00 | 15.84 |
| 2228 | CA | GLN | A | 160 | -12.839 | 2.278 | 43.577 | 1.00 | 16.84 |
| 2230 | CB | GLN | A | 160 | -12.348 | 0.982 | 44.224 | 1.00 | 17.43 |
| 2233 | CG | GLN | A | 160 | -12.344 | 0.967 | 45.729 | 1.00 | 21.62 |
| 2236 | CD | GLN | A | 160 | -13.631 | 0.403 | 46.284 | 1.00 | 26.11 |
| 2237 | OE1 | GLN | A | 160 | -14.560 | 1.154 | 46.580 | 1.00 | 29.04 |
| 2238 | NE2 | GLN | A | 160 | -13.701 | -0.928 | 46.402 | 1.00 | 29.33 |
| 2241 | C | GLN | A | 160 | -11.808 | 3.391 | 43.808 | 1.00 | 16.54 |
| 2242 | O | GLN | A | 160 | -11.930 | 4.165 | 44.760 | 1.00 | 17.68 |
| 2243 | N | SER | A | 161 | -10.807 | 3.475 | 42.938 | 1.00 | 15.57 |
| 2245 | CA | SER | A | 161 | -9.701 | 4.422 | 43.081 | 1.00 | 14.86 |
| 2247 | CB | SER | A | 161 | -8.376 | 3.721 | 42.759 | 1.00 | 15.18 |
| 2250 | OG | SER | A | 161 | -8.316 | 3.375 | 41.386 | 1.00 | 14.71 |
| 2252 | C | SER | A | 161 | -9.814 | 5.667 | 42.191 | 1.00 | 14.85 |
| 2253 | O | SER | A | 161 | -8.935 | 6.527 | 42.227 | 1.00 | 14.62 |
| 2254 | N | ASN | A | 162 | -10.884 | 5.772 | 41.411 | 1.00 | 14.79 |
| 2256 | CA | ASN | A | 162 | -10.988 | 6.811 | 40.378 | 1.00 | 15.06 |
| 2258 | CB | ASN | A | 162 | -11.199 | 8.198 | 40.992 | 1.00 | 15.40 |
| 2261 | CG | ASN | A | 162 | -12.416 | 8.254 | 41.888 | 1.00 | 17.57 |
| 2262 | OD1 | ASN | A | 162 | -13.511 | 7.885 | 41.480 | 1.00 | 19.52 |
| 2263 | ND2 | ASN | A | 162 | -12.224 | 8.699 | 43.126 | 1.00 | 21.95 |
| 2266 | C | ASN | A | 162 | -9.734 | 6.811 | 39.516 | 1.00 | 14.16 |
| 2267 | O | ASN | A | 162 | -9.111 | 7.851 | 39.292 | 1.00 | 14.61 |
| 2268 | N | GLY | A | 163 | -9.370 | 5.615 | 39.056 | 1.00 | 13.36 |
| 2270 | CA | GLY | A | 163 | -8.097 | 5.359 | 38.410 | 1.00 | 12.86 |
| 2273 | C | GLY | A | 163 | -8.062 | 5.641 | 36.925 | 1.00 | 12.81 |
| 2274 | O | GLY | A | 163 | -8.877 | 6.377 | 36.398 | 1.00 | 12.37 |
| 2275 | N | SER | A | 164 | -7.097 | 5.028 | 36.247 | 1.00 | 12.80 |
| 2277 | CA | SER | A | 164 | -6.765 | 5.379 | 34.876 | 1.00 | 13.04 |
| 2279 | CB | SER | A | 164 | -5.600 | 6.363 | 34.868 | 1.00 | 13.40 |

FIGURE 3 (cont.)

| A | B | C | D | E | F | G | H | I | J |
|---|---|---|---|---|---|---|---|---|---|
| 2282 | OG | SER | A | 164 | -5.888 | 7.538 | 35.611 | 1.00 | 15.44 |
| 2284 | C | SER | A | 164 | -6.368 | 4.148 | 34.085 | 1.00 | 12.49 |
| 2285 | O | SER | A | 164 | -5.697 | 3.260 | 34.614 | 1.00 | 13.06 |
| 2286 | N | ILE | A | 165 | -6.787 | 4.120 | 32.825 | 1.00 | 12.11 |
| 2288 | CA | ILE | A | 165 | -6.377 | 3.128 | 31.839 | 1.00 | 11.44 |
| 2290 | CB | ILE | A | 165 | -7.613 | 2.488 | 31.157 | 1.00 | 11.74 |
| 2292 | CG1 | ILE | A | 165 | -8.518 | 1.821 | 32.197 | 1.00 | 13.03 |
| 2295 | CD1 | ILE | A | 165 | -9.872 | 1.441 | 31.667 | 1.00 | 13.40 |
| 2299 | CG2 | ILE | A | 165 | -7.182 | 1.502 | 30.075 | 1.00 | 12.06 |
| 2303 | C | ILE | A | 165 | -5.515 | 3.829 | 30.796 | 1.00 | 11.39 |
| 2304 | O | ILE | A | 165 | -5.897 | 4.877 | 30.272 | 1.00 | 11.10 |
| 2305 | N | VAL | A | 166 | -4.347 | 3.264 | 30.514 | 1.00 | 11.09 |
| 2307 | CA | VAL | A | 166 | -3.458 | 3.790 | 29.483 | 1.00 | 11.11 |
| 2309 | CB | VAL | A | 166 | -2.079 | 4.175 | 30.062 | 1.00 | 11.42 |
| 2311 | CG1 | VAL | A | 166 | -1.124 | 4.655 | 28.965 | 1.00 | 12.56 |
| 2315 | CG2 | VAL | A | 166 | -2.246 | 5.226 | 31.161 | 1.00 | 13.43 |
| 2319 | C | VAL | A | 166 | -3.308 | 2.708 | 28.434 | 1.00 | 11.10 |
| 2320 | O | VAL | A | 166 | -2.929 | 1.580 | 28.749 | 1.00 | 11.97 |
| 2321 | N | VAL | A | 167 | -3.628 | 3.060 | 27.195 | 1.00 | 10.73 |
| 2323 | CA | VAL | A | 167 | -3.582 | 2.151 | 26.062 | 1.00 | 10.77 |
| 2325 | CB | VAL | A | 167 | -4.935 | 2.123 | 25.327 | 1.00 | 10.86 |
| 2327 | CG1 | VAL | A | 167 | -4.875 | 1.225 | 24.097 | 1.00 | 11.39 |
| 2331 | CG2 | VAL | A | 167 | -6.045 | 1.673 | 26.282 | 1.00 | 11.58 |
| 2335 | C | VAL | A | 167 | -2.489 | 2.636 | 25.119 | 1.00 | 10.62 |
| 2336 | O | VAL | A | 167 | -2.558 | 3.743 | 24.596 | 1.00 | 10.55 |
| 2337 | N | VAL | A | 168 | -1.475 | 1.810 | 24.900 | 1.00 | 10.22 |
| 2339 | CA | VAL | A | 168 | -0.361 | 2.201 | 24.049 | 1.00 | 10.27 |
| 2341 | CB | VAL | A | 168 | 0.984 | 1.606 | 24.515 | 1.00 | 9.63 |
| 2343 | CG1 | VAL | A | 168 | 2.117 | 2.099 | 23.622 | 1.00 | 10.86 |
| 2347 | CG2 | VAL | A | 168 | 1.252 | 1.988 | 25.943 | 1.00 | 9.25 |
| 2351 | C | VAL | A | 168 | -0.654 | 1.806 | 22.616 | 1.00 | 10.04 |
| 2352 | O | VAL | A | 168 | -0.931 | 0.646 | 22.308 | 1.00 | 10.47 |
| 2353 | N | SER | A | 169 | -0.617 | 2.810 | 21.750 | 1.00 | 10.28 |
| 2355 | CA | SER | A | 169 | -0.841 | 2.641 | 20.318 | 1.00 | 9.68 |
| 2357 | CB | SER | A | 169 | -2.273 | 3.092 | 19.970 | 1.00 | 9.85 |
| 2360 | OG | SER | A | 169 | -2.623 | 2.745 | 18.638 | 1.00 | 10.29 |
| 2362 | C | SER | A | 169 | 0.244 | 3.361 | 19.514 | 1.00 | 10.36 |
| 2363 | O | SER | A | 169 | 1.365 | 3.545 | 20.001 | 1.00 | 11.28 |
| 2364 | N | SER | A | 170 | -0.079 | 3.769 | 18.291 | 1.00 | 9.75 |
| 2366 | CA | SER | A | 170 | 0.897 | 3.796 | 17.215 | 1.00 | 9.23 |
| 2368 | CB | SER | A | 170 | 0.989 | 2.401 | 16.584 | 1.00 | 10.00 |
| 2371 | OG | SER | A | 170 | 1.023 | 1.394 | 17.582 | 1.00 | 11.18 |
| 2373 | C | SER | A | 170 | 0.457 | 4.753 | 16.141 | 1.00 | 9.33 |
| 2374 | O | SER | A | 170 | -0.739 | 4.920 | 15.906 | 1.00 | 9.26 |
| 2375 | N | LEU | A | 171 | 1.415 | 5.317 | 15.415 | 1.00 | 8.94 |
| 2377 | CA | LEU | A | 171 | 1.076 | 6.055 | 14.202 | 1.00 | 9.38 |
| 2379 | CB | LEU | A | 171 | 2.324 | 6.525 | 13.456 | 1.00 | 9.67 |
| 2382 | CG | LEU | A | 171 | 3.122 | 7.641 | 14.131 | 1.00 | 10.64 |
| 2384 | CD1 | LEU | A | 171 | 2.294 | 8.904 | 14.291 | 1.00 | 13.15 |

FIGURE 3 (cont.)

| A | B | C | D | E | F | G | H | I | J |
|---|---|---|---|---|---|---|---|---|---|
| 2388 | CD2 | LEU | A | 171 | 4.354 | 7.912 | 13.294 | 1.00 | 10.42 |
| 2392 | C | LEU | A | 171 | 0.223 | 5.196 | 13.266 | 1.00 | 9.37 |
| 2393 | O | LEU | A | 171 | -0.720 | 5.698 | 12.673 | 1.00 | 8.49 |
| 2394 | N | ALA | A | 172 | 0.531 | 3.898 | 13.180 | 1.00 | 9.28 |
| 2396 | CA | ALA | A | 172 | -0.200 | 2.977 | 12.317 | 1.00 | 9.84 |
| 2398 | CB | ALA | A | 172 | 0.667 | 1.744 | 11.983 | 1.00 | 9.62 |
| 2402 | C | ALA | A | 172 | -1.539 | 2.558 | 12.925 | 1.00 | 9.83 |
| 2403 | O | ALA | A | 172 | -2.225 | 1.690 | 12.384 | 1.00 | 10.17 |
| 2404 | N | GLY | A | 173 | -1.882 | 3.163 | 14.061 | 1.00 | 9.67 |
| 2406 | CA | GLY | A | 173 | -3.196 | 3.089 | 14.665 | 1.00 | 9.91 |
| 2409 | C | GLY | A | 173 | -4.021 | 4.354 | 14.431 | 1.00 | 9.85 |
| 2410 | O | GLY | A | 173 | -5.139 | 4.451 | 14.949 | 1.00 | 10.98 |
| 2411 | N | LYS | A | 174 | -3.481 | 5.306 | 13.658 | 1.00 | 9.32 |
| 2413 | CA | LYS | A | 174 | -4.178 | 6.560 | 13.325 | 1.00 | 9.25 |
| 2415 | CB | LYS | A | 174 | -3.560 | 7.745 | 14.062 | 1.00 | 9.54 |
| 2418 | CG | LYS | A | 174 | -3.833 | 7.755 | 15.551 | 1.00 | 9.69 |
| 2421 | CD | LYS | A | 174 | -5.304 | 8.057 | 15.845 | 1.00 | 10.41 |
| 2424 | CE | LYS | A | 174 | -5.570 | 8.386 | 17.304 | 1.00 | 11.00 |
| 2427 | NZ | LYS | A | 174 | -7.027 | 8.698 | 17.564 | 1.00 | 10.52 |
| 2431 | C | LYS | A | 174 | -4.218 | 6.844 | 11.819 | 1.00 | 9.39 |
| 2432 | O | LYS | A | 174 | -5.151 | 7.486 | 11.328 | 1.00 | 10.14 |
| 2433 | N | VAL | A | 175 | -3.213 | 6.377 | 11.099 | 1.00 | 10.06 |
| 2435 | CA | VAL | A | 175 | -3.185 | 6.449 | 9.651 | 1.00 | 10.50 |
| 2437 | CB | VAL | A | 175 | -2.324 | 7.627 | 9.133 | 1.00 | 10.72 |
| 2439 | CG1 | VAL | A | 175 | -0.872 | 7.431 | 9.479 | 1.00 | 11.95 |
| 2443 | CG2 | VAL | A | 175 | -2.857 | 8.952 | 9.680 | 1.00 | 11.47 |
| 2447 | C | VAL | A | 175 | -2.673 | 5.119 | 9.126 | 1.00 | 10.60 |
| 2448 | O | VAL | A | 175 | -2.152 | 4.296 | 9.886 | 1.00 | 11.55 |
| 2449 | N | ALA | A | 176 | -2.837 | 4.908 | 7.830 | 1.00 | 11.32 |
| 2451 | CA | ALA | A | 176 | -2.532 | 3.628 | 7.218 | 1.00 | 11.97 |
| 2453 | CB | ALA | A | 176 | -3.555 | 3.311 | 6.138 | 1.00 | 12.29 |
| 2457 | C | ALA | A | 176 | -1.119 | 3.584 | 6.631 | 1.00 | 11.96 |
| 2458 | O | ALA | A | 176 | -0.624 | 4.559 | 6.080 | 1.00 | 12.93 |
| 2459 | N | TYR | A | 177 | -0.493 | 2.423 | 6.769 | 1.00 | 11.82 |
| 2461 | CA | TYR | A | 177 | 0.819 | 2.128 | 6.231 | 1.00 | 11.75 |
| 2463 | CB | TYR | A | 177 | 1.833 | 2.043 | 7.372 | 1.00 | 12.18 |
| 2466 | CG | TYR | A | 177 | 2.184 | 3.341 | 8.045 | 1.00 | 10.90 |
| 2467 | CD1 | TYR | A | 177 | 1.415 | 3.836 | 9.081 | 1.00 | 11.58 |
| 2469 | CE1 | TYR | A | 177 | 1.736 | 5.023 | 9.725 | 1.00 | 11.10 |
| 2471 | CZ | TYR | A | 177 | 2.858 | 5.713 | 9.360 | 1.00 | 12.21 |
| 2472 | OH | TYR | A | 177 | 3.150 | 6.879 | 10.028 | 1.00 | 11.86 |
| 2474 | CE2 | TYR | A | 177 | 3.654 | 5.248 | 8.330 | 1.00 | 11.31 |
| 2476 | CD2 | TYR | A | 177 | 3.309 | 4.055 | 7.677 | 1.00 | 11.35 |
| 2478 | C | TYR | A | 177 | 0.799 | 0.752 | 5.585 | 1.00 | 11.78 |
| 2479 | O | TYR | A | 177 | 0.170 | -0.165 | 6.123 | 1.00 | 12.50 |
| 2480 | N | PRO | A | 178 | 1.579 | 0.537 | 4.535 | 1.00 | 11.47 |
| 2481 | CA | PRO | A | 178 | 1.759 | -0.829 | 4.046 | 1.00 | 11.34 |
| 2483 | CB | PRO | A | 178 | 2.470 | -0.625 | 2.721 | 1.00 | 11.47 |
| 2486 | CG | PRO | A | 178 | 3.283 | 0.594 | 2.963 | 1.00 | 11.38 |

FIGURE 3 (cont.)

| A | B | C | D | E | F | G | H | I | J |
|---|---|---|---|---|---|---|---|---|---|
| 2489 | CD | PRO | A | 178 | 2.441 | 1.495 | 3.812 | 1.00 | 11.15 |
| 2492 | C | PRO | A | 178 | 2.640 | -1.592 | 5.027 | 1.00 | 11.07 |
| 2493 | O | PRO | A | 178 | 3.340 | -0.979 | 5.830 | 1.00 | 11.92 |
| 2494 | N | MET | A | 179 | 2.612 | -2.917 | 4.939 | 1.00 | 10.90 |
| 2496 | CA | MET | A | 179 | 3.525 | -3.838 | 5.620 | 1.00 | 10.85 |
| 2498 | CB | MET | A | 179 | 5.002 | -3.405 | 5.504 | 1.00 | 11.24 |
| 2501 | CG | MET | A | 179 | 5.431 | -2.934 | 4.106 | 1.00 | 12.33 |
| 2504 | SD | MET | A | 179 | 4.958 | -4.077 | 2.815 | 1.00 | 16.35 |
| 2505 | CE | MET | A | 179 | 5.406 | -3.132 | 1.336 | 1.00 | 16.92 |
| 2509 | C | MET | A | 179 | 3.194 | -4.123 | 7.082 | 1.00 | 10.20 |
| 2510 | O | MET | A | 179 | 3.893 | -4.908 | 7.735 | 1.00 | 10.26 |
| 2511 | N | VAL | A | 180 | 2.133 | -3.498 | 7.589 | 1.00 | 10.46 |
| 2513 | CA | VAL | A | 180 | 1.686 | -3.690 | 8.958 | 1.00 | 10.18 |
| 2515 | CB | VAL | A | 180 | 2.099 | -2.510 | 9.876 | 1.00 | 10.81 |
| 2517 | CG1 | VAL | A | 180 | 3.601 | -2.493 | 10.074 | 1.00 | 11.63 |
| 2521 | CG2 | VAL | A | 180 | 1.624 | -1.172 | 9.314 | 1.00 | 10.87 |
| 2525 | C | VAL | A | 180 | 0.170 | -3.866 | 9.015 | 1.00 | 10.05 |
| 2526 | O | VAL | A | 180 | -0.467 | -3.440 | 9.976 | 1.00 | 10.08 |
| 2527 | N | ALA | A | 181 | -0.405 | -4.535 | 8.017 | 1.00 | 9.27 |
| 2529 | CA | ALA | A | 181 | -1.882 | -4.636 | 7.917 | 1.00 | 9.51 |
| 2531 | CB | ALA | A | 181 | -2.275 | -5.403 | 6.690 | 1.00 | 9.85 |
| 2535 | C | ALA | A | 181 | -2.556 | -5.226 | 9.160 | 1.00 | 9.14 |
| 2536 | O | ALA | A | 181 | -3.494 | -4.640 | 9.697 | 1.00 | 9.12 |
| 2537 | N | ALA | A | 182 | -2.109 | -6.396 | 9.596 | 1.00 | 9.20 |
| 2539 | CA | ALA | A | 182 | -2.663 | -7.049 | 10.769 | 1.00 | 9.32 |
| 2541 | CB | ALA | A | 182 | -2.004 | -8.400 | 10.945 | 1.00 | 9.17 |
| 2545 | C | ALA | A | 182 | -2.498 | -6.209 | 12.031 | 1.00 | 9.02 |
| 2546 | O | ALA | A | 182 | -3.424 | -6.082 | 12.843 | 1.00 | 9.75 |
| 2547 | N | TYR | A | 183 | -1.315 | -5.630 | 12.214 | 1.00 | 8.82 |
| 2549 | CA | TYR | A | 183 | -1.044 | -4.806 | 13.378 | 1.00 | 8.63 |
| 2551 | CB | TYR | A | 183 | 0.420 | -4.406 | 13.328 | 1.00 | 8.65 |
| 2554 | CG | TYR | A | 183 | 0.886 | -3.376 | 14.321 | 1.00 | 8.36 |
| 2555 | CD1 | TYR | A | 183 | 1.344 | -3.748 | 15.578 | 1.00 | 8.05 |
| 2557 | CE1 | TYR | A | 183 | 1.825 | -2.832 | 16.477 | 1.00 | 8.32 |
| 2559 | CZ | TYR | A | 183 | 1.842 | -1.497 | 16.136 | 1.00 | 7.64 |
| 2560 | OH | TYR | A | 183 | 2.376 | -0.557 | 16.978 | 1.00 | 9.96 |
| 2562 | CE2 | TYR | A | 183 | 1.387 | -1.095 | 14.891 | 1.00 | 8.43 |
| 2564 | CD2 | TYR | A | 183 | 0.911 | -2.026 | 14.000 | 1.00 | 8.34 |
| 2566 | C | TYR | A | 183 | -1.923 | -3.561 | 13.370 | 1.00 | 8.82 |
| 2567 | O | TYR | A | 183 | -2.487 | -3.184 | 14.378 | 1.00 | 9.23 |
| 2568 | N | SER | A | 184 | -2.007 | -2.907 | 12.221 | 1.00 | 9.00 |
| 2570 | CA | SER | A | 184 | -2.782 | -1.672 | 12.094 | 1.00 | 9.32 |
| 2572 | CB | BSER | A | 184 | -2.661 | -1.084 | 10.688 | 0.35 | 9.53 |
| 2573 | CB | ASER | A | 184 | -2.593 | -1.106 | 10.683 | 0.65 | 9.67 |
| 2578 | OG | BSER | A | 184 | -1.412 | -0.455 | 10.514 | 0.35 | 10.17 |
| 2579 | OG | ASER | A | 184 | -3.287 | 0.105 | 10.502 | 0.65 | 10.17 |
| 2582 | C | SER | A | 184 | -4.245 | -1.938 | 12.404 | 1.00 | 9.29 |
| 2583 | O | SER | A | 184 | -4.893 | -1.165 | 13.124 | 1.00 | 9.06 |
| 2584 | N | ALA | A | 185 | -4.761 | -3.056 | 11.910 | 1.00 | 8.76 |

FIGURE 3 (cont.)

| A | B | C | D | E | F | G | H | I | J |
|---|---|---|---|---|---|---|---|---|---|
| 2586 | CA | ALA | A | 185 | -6.148 | -3.426 | 12.198 | 1.00 | 8.85 |
| 2588 | CB | ALA | A | 185 | -6.494 | -4.761 | 11.598 | 1.00 | 8.88 |
| 2592 | C | ALA | A | 185 | -6.354 | -3.454 | 13.707 | 1.00 | 8.75 |
| 2593 | O | ALA | A | 185 | -7.371 | -2.954 | 14.226 | 1.00 | 8.86 |
| 2594 | N | SER | A | 186 | -5.415 | -4.070 | 14.426 | 1.00 | 8.55 |
| 2596 | CA | SER | A | 186 | -5.557 | -4.211 | 15.869 | 1.00 | 8.54 |
| 2598 | CB | SER | A | 186 | -4.570 | -5.252 | 16.424 | 1.00 | 9.15 |
| 2601 | OG | SER | A | 186 | -3.249 | -4.756 | 16.482 | 1.00 | 9.38 |
| 2603 | C | SER | A | 186 | -5.461 | -2.879 | 16.609 | 1.00 | 8.52 |
| 2604 | O | SER | A | 186 | -6.173 | -2.648 | 17.583 | 1.00 | 8.63 |
| 2605 | N | LYS | A | 187 | -4.580 | -1.985 | 16.159 | 1.00 | 8.62 |
| 2607 | CA | LYS | A | 187 | -4.427 | -0.694 | 16.814 | 1.00 | 8.42 |
| 2609 | CB | LYS | A | 187 | -3.070 | -0.062 | 16.490 | 1.00 | 8.79 |
| 2612 | CG | LYS | A | 187 | -1.852 | -0.869 | 16.992 | 1.00 | 9.32 |
| 2615 | CD | LYS | A | 187 | -1.827 | -0.991 | 18.513 | 1.00 | 8.80 |
| 2618 | CE | LYS | A | 187 | -0.421 | -1.296 | 19.029 | 1.00 | 10.25 |
| 2621 | NZ | LYS | A | 187 | -0.381 | -1.481 | 20.519 | 1.00 | 8.76 |
| 2625 | C | LYS | A | 187 | -5.576 | 0.263 | 16.470 | 1.00 | 8.49 |
| 2626 | O | LYS | A | 187 | -6.017 | 1.012 | 17.336 | 1.00 | 8.32 |
| 2627 | N | PHE | A | 188 | -6.056 | 0.246 | 15.230 | 1.00 | 8.45 |
| 2629 | CA | PHE | A | 188 | -7.278 | 0.966 | 14.873 | 1.00 | 8.30 |
| 2631 | CB | PHE | A | 188 | -7.648 | 0.779 | 13.402 | 1.00 | 8.39 |
| 2634 | CG | PHE | A | 188 | -7.051 | 1.812 | 12.463 | 1.00 | 8.04 |
| 2635 | CD1 | PHE | A | 188 | -7.864 | 2.716 | 11.792 | 1.00 | 8.36 |
| 2637 | CE1 | PHE | A | 188 | -7.326 | 3.645 | 10.894 | 1.00 | 9.29 |
| 2639 | CZ | PHE | A | 188 | -5.952 | 3.701 | 10.679 | 1.00 | 8.98 |
| 2641 | CE2 | PHE | A | 188 | -5.128 | 2.801 | 11.327 | 1.00 | 9.29 |
| 2643 | CD2 | PHE | A | 188 | -5.672 | 1.862 | 12.225 | 1.00 | 8.93 |
| 2645 | C | PHE | A | 188 | -8.433 | 0.479 | 15.761 | 1.00 | 8.62 |
| 2646 | O | PHE | A | 188 | -9.204 | 1.290 | 16.261 | 1.00 | 8.60 |
| 2647 | N | ALA | A | 189 | -8.540 | -0.828 | 15.964 | 1.00 | 8.26 |
| 2649 | CA | ALA | A | 189 | -9.620 | -1.377 | 16.807 | 1.00 | 8.33 |
| 2651 | CB | ALA | A | 189 | -9.559 | -2.888 | 16.848 | 1.00 | 8.27 |
| 2655 | C | ALA | A | 189 | -9.547 | -0.826 | 18.221 | 1.00 | 8.44 |
| 2656 | O | ALA | A | 189 | -10.574 | -0.525 | 18.826 | 1.00 | 9.04 |
| 2657 | N | LEU | A | 190 | -8.339 | -0.683 | 18.761 | 1.00 | 8.88 |
| 2659 | CA | LEU | A | 190 | -8.194 | -0.119 | 20.098 | 1.00 | 9.01 |
| 2661 | CB | LEU | A | 190 | -6.741 | -0.085 | 20.544 | 1.00 | 9.20 |
| 2664 | CG | LEU | A | 190 | -6.083 | -1.417 | 20.904 | 1.00 | 9.09 |
| 2666 | CD1 | LEU | A | 190 | -4.596 | -1.193 | 21.064 | 1.00 | 10.39 |
| 2670 | CD2 | LEU | A | 190 | -6.645 | -2.024 | 22.173 | 1.00 | 9.95 |
| 2674 | C | LEU | A | 190 | -8.768 | 1.288 | 20.168 | 1.00 | 8.96 |
| 2675 | O | LEU | A | 190 | -9.393 | 1.646 | 21.144 | 1.00 | 8.84 |
| 2676 | N | ASP | A | 191 | -8.509 | 2.100 | 19.150 | 1.00 | 9.44 |
| 2678 | CA | ASP | A | 191 | -9.001 | 3.469 | 19.116 | 1.00 | 9.93 |
| 2680 | CB | ASP | A | 191 | -8.433 | 4.175 | 17.890 | 1.00 | 9.70 |
| 2683 | CG | ASP | A | 191 | -8.724 | 5.656 | 17.848 | 1.00 | 10.93 |
| 2684 | OD1 | ASP | A | 191 | -9.300 | 6.226 | 18.803 | 1.00 | 10.92 |
| 2685 | OD2 | ASP | A | 191 | -8.353 | 6.323 | 16.869 | 1.00 | 10.94 |

FIGURE 3 (cont.)

| A | B | C | D | E | F | G | H | I | J |
|---|---|---|---|---|---|---|---|---|---|
| 2686 | C | ASP | A | 191 | -10.526 | 3.465 | 19.097 | 1.00 | 9.95 |
| 2687 | O | ASP | A | 191 | -11.170 | 4.129 | 19.909 | 1.00 | 10.49 |
| 2688 | N | GLY | A | 192 | -11.118 | 2.682 | 18.199 | 1.00 | 9.32 |
| 2690 | CA | GLY | A | 192 | -12.564 | 2.629 | 18.110 | 1.00 | 9.37 |
| 2693 | C | GLY | A | 192 | -13.189 | 2.187 | 19.415 | 1.00 | 9.15 |
| 2694 | O | GLY | A | 192 | -14.144 | 2.810 | 19.896 | 1.00 | 10.23 |
| 2695 | N | PHE | A | 193 | -12.658 | 1.107 | 19.995 | 1.00 | 9.24 |
| 2697 | CA | PHE | A | 193 | -13.226 | 0.556 | 21.238 | 1.00 | 9.38 |
| 2699 | CB | PHE | A | 193 | -12.603 | -0.793 | 21.619 | 1.00 | 9.61 |
| 2702 | CG | PHE | A | 193 | -13.322 | -1.467 | 22.751 | 1.00 | 10.09 |
| 2703 | CD1 | PHE | A | 193 | -12.887 | -1.331 | 24.052 | 1.00 | 10.77 |
| 2705 | CE1 | PHE | A | 193 | -13.593 | -1.930 | 25.097 | 1.00 | 12.22 |
| 2707 | CZ | PHE | A | 193 | -14.725 | -2.660 | 24.819 | 1.00 | 11.76 |
| 2709 | CE2 | PHE | A | 193 | -15.161 | -2.807 | 23.536 | 1.00 | 12.81 |
| 2711 | CD2 | PHE | A | 193 | -14.473 | -2.207 | 22.499 | 1.00 | 11.18 |
| 2713 | C | PHE | A | 193 | -13.058 | 1.500 | 22.413 | 1.00 | 9.54 |
| 2714 | O | PHE | A | 193 | -14.029 | 1.860 | 23.072 | 1.00 | 9.87 |
| 2715 | N | PHE | A | 194 | -11.824 | 1.891 | 22.687 | 1.00 | 9.19 |
| 2717 | CA | PHE | A | 194 | -11.552 | 2.684 | 23.880 | 1.00 | 9.61 |
| 2719 | CB | PHE | A | 194 | -10.075 | 2.618 | 24.262 | 1.00 | 9.96 |
| 2722 | CG | PHE | A | 194 | -9.719 | 1.322 | 24.943 | 1.00 | 10.17 |
| 2723 | CD1 | PHE | A | 194 | -9.227 | 0.244 | 24.226 | 1.00 | 10.38 |
| 2725 | CE1 | PHE | A | 194 | -8.938 | -0.964 | 24.861 | 1.00 | 11.43 |
| 2727 | CZ | PHE | A | 194 | -9.148 | -1.106 | 26.225 | 1.00 | 12.52 |
| 2729 | CE2 | PHE | A | 194 | -9.640 | -0.044 | 26.947 | 1.00 | 11.80 |
| 2731 | CD2 | PHE | A | 194 | -9.937 | 1.163 | 26.306 | 1.00 | 10.54 |
| 2733 | C | PHE | A | 194 | -12.099 | 4.093 | 23.806 | 1.00 | 9.59 |
| 2734 | O | PHE | A | 194 | -12.484 | 4.651 | 24.814 | 1.00 | 9.70 |
| 2735 | N | SER | A | 195 | -12.141 | 4.663 | 22.612 | 1.00 | 10.39 |
| 2737 | CA | SER | A | 195 | -12.743 | 5.980 | 22.427 | 1.00 | 10.54 |
| 2739 | CB | SER | A | 195 | -12.388 | 6.553 | 21.058 | 1.00 | 10.93 |
| 2742 | OG | SER | A | 195 | -10.998 | 6.759 | 20.940 | 1.00 | 10.86 |
| 2744 | C | SER | A | 195 | -14.257 | 5.933 | 22.622 | 1.00 | 11.03 |
| 2745 | O | SER | A | 195 | -14.850 | 6.887 | 23.107 | 1.00 | 10.66 |
| 2746 | N | SER | A | 196 | -14.886 | 4.815 | 22.265 | 1.00 | 10.79 |
| 2748 | CA | SER | A | 196 | -16.317 | 4.636 | 22.494 | 1.00 | 11.34 |
| 2750 | CB | BSER | A | 196 | -16.833 | 3.434 | 21.714 | 0.35 | 11.27 |
| 2751 | CB | ASER | A | 196 | -16.844 | 3.395 | 21.764 | 0.65 | 11.24 |
| 2756 | OG | BSER | A | 196 | -16.762 | 3.705 | 20.325 | 0.35 | 11.84 |
| 2757 | OG | ASER | A | 196 | -18.198 | 3.103 | 22.111 | 0.65 | 11.84 |
| 2760 | C | SER | A | 196 | -16.608 | 4.490 | 23.976 | 1.00 | 11.43 |
| 2761 | O | SER | A | 196 | -17.517 | 5.147 | 24.504 | 1.00 | 11.84 |
| 2762 | N | ILE | A | 197 | -15.856 | 3.649 | 24.679 | 1.00 | 11.39 |
| 2764 | CA | ILE | A | 197 | -16.154 | 3.482 | 26.100 | 1.00 | 12.56 |
| 2766 | CB | ILE | A | 197 | -15.563 | 2.192 | 26.723 | 1.00 | 13.89 |
| 2768 | CG1 | ILE | A | 197 | -14.057 | 2.144 | 26.648 | 1.00 | 14.45 |
| 2771 | CD1 | ILE | A | 197 | -13.456 | 1.071 | 27.548 | 1.00 | 16.54 |
| 2775 | CG2 | ILE | A | 197 | -16.198 | 0.933 | 26.111 | 1.00 | 14.40 |
| 2779 | C | ILE | A | 197 | -15.800 | 4.742 | 26.890 | 1.00 | 12.22 |

FIGURE 3 (cont.)

| A | B | C | D | E | F | G | H | I | J |
|---|---|---|---|---|---|---|---|---|---|
| 2780 | O | ILE | A | 197 | -16.446 | 5.036 | 27.887 | 1.00 | 12.16 |
| 2781 | N | ARG | A | 198 | -14.859 | 5.553 | 26.401 | 1.00 | 12.12 |
| 2783 | CA | ARG | A | 198 | -14.606 | 6.844 | 27.039 | 1.00 | 12.80 |
| 2785 | CB | ARG | A | 198 | -13.487 | 7.619 | 26.346 | 1.00 | 13.27 |
| 2788 | CG | ARG | A | 198 | -13.020 | 8.826 | 27.144 | 1.00 | 14.48 |
| 2791 | CD | ARG | A | 198 | -12.051 | 9.729 | 26.426 | 1.00 | 14.81 |
| 2794 | NE | ARG | A | 198 | -10.717 | 9.141 | 26.267 | 1.00 | 13.09 |
| 2796 | CZ | ARG | A | 198 | -10.156 | 8.816 | 25.103 | 1.00 | 13.72 |
| 2797 | NH1 | ARG | A | 198 | -10.827 | 8.929 | 23.964 | 1.00 | 13.58 |
| 2800 | NH2 | ARG | A | 198 | -8.921 | 8.330 | 25.070 | 1.00 | 14.23 |
| 2803 | C | ARG | A | 198 | -15.879 | 7.689 | 27.048 | 1.00 | 12.92 |
| 2804 | O | ARG | A | 198 | -16.217 | 8.286 | 28.066 | 1.00 | 13.72 |
| 2805 | N | LYS | A | 199 | -16.574 | 7.721 | 25.919 | 1.00 | 12.71 |
| 2807 | CA | LYS | A | 199 | -17.831 | 8.469 | 25.815 | 1.00 | 13.22 |
| 2809 | CB | LYS | A | 199 | -18.274 | 8.557 | 24.354 | 1.00 | 13.79 |
| 2812 | CG | LYS | A | 199 | -17.408 | 9.553 | 23.565 | 1.00 | 15.53 |
| 2815 | CD | LYS | A | 199 | -17.547 | 9.396 | 22.078 | 1.00 | 17.33 |
| 2818 | CE | LYS | A | 199 | -16.587 | 10.314 | 21.310 | 1.00 | 16.43 |
| 2821 | NZ | LYS | A | 199 | -16.358 | 11.685 | 21.864 | 1.00 | 15.91 |
| 2825 | C | LYS | A | 199 | -18.912 | 7.872 | 26.719 | 1.00 | 13.58 |
| 2826 | O | LYS | A | 199 | -19.685 | 8.610 | 27.328 | 1.00 | 13.87 |
| 2827 | N | GLU | A | 200 | -18.948 | 6.546 | 26.813 | 1.00 | 12.75 |
| 2829 | CA | GLU | A | 200 | -19.884 | 5.871 | 27.708 | 1.00 | 13.49 |
| 2831 | CB | GLU | A | 200 | -19.849 | 4.360 | 27.500 | 1.00 | 13.22 |
| 2834 | CG | GLU | A | 200 | -20.362 | 3.940 | 26.141 | 1.00 | 14.14 |
| 2837 | CD | GLU | A | 200 | -20.343 | 2.440 | 25.930 | 1.00 | 14.08 |
| 2838 | OE1 | GLU | A | 200 | -20.600 | 2.019 | 24.788 | 1.00 | 15.20 |
| 2839 | OE2 | GLU | A | 200 | -20.087 | 1.691 | 26.890 | 1.00 | 14.89 |
| 2840 | C | GLU | A | 200 | -19.601 | 6.224 | 29.161 | 1.00 | 13.89 |
| 2841 | O | GLU | A | 200 | -20.529 | 6.496 | 29.914 | 1.00 | 13.96 |
| 2842 | N | TYR | A | 201 | -18.329 | 6.278 | 29.547 | 1.00 | 14.36 |
| 2844 | CA | TYR | A | 201 | -17.983 | 6.609 | 30.934 | 1.00 | 15.15 |
| 2846 | CB | TYR | A | 201 | -16.494 | 6.357 | 31.232 | 1.00 | 15.43 |
| 2849 | CG | TYR | A | 201 | -16.083 | 4.893 | 31.212 | 1.00 | 15.96 |
| 2850 | CD1 | TYR | A | 201 | -17.019 | 3.875 | 31.009 | 1.00 | 17.82 |
| 2852 | CE1 | TYR | A | 201 | -16.646 | 2.539 | 30.991 | 1.00 | 19.88 |
| 2854 | CZ | TYR | A | 201 | -15.327 | 2.195 | 31.150 | 1.00 | 20.30 |
| 2855 | OH | TYR | A | 201 | -14.979 | 0.858 | 31.108 | 1.00 | 24.41 |
| 2857 | CE2 | TYR | A | 201 | -14.368 | 3.168 | 31.350 | 1.00 | 19.93 |
| 2859 | CD2 | TYR | A | 201 | -14.750 | 4.524 | 31.381 | 1.00 | 18.36 |
| 2861 | C | TYR | A | 201 | -18.366 | 8.045 | 31.253 | 1.00 | 16.36 |
| 2862 | O | TYR | A | 201 | -18.743 | 8.351 | 32.385 | 1.00 | 16.24 |
| 2863 | N | SER | A | 202 | -18.297 | 8.921 | 30.258 | 1.00 | 17.53 |
| 2865 | CA | SER | A | 202 | -18.686 | 10.314 | 30.468 | 1.00 | 19.44 |
| 2867 | CB | SER | A | 202 | -18.355 | 11.181 | 29.255 | 1.00 | 19.61 |
| 2870 | OG | SER | A | 202 | -18.724 | 12.536 | 29.491 | 1.00 | 22.68 |
| 2872 | C | SER | A | 202 | -20.167 | 10.422 | 30.799 | 1.00 | 20.40 |
| 2873 | O | SER | A | 202 | -20.544 | 11.153 | 31.711 | 1.00 | 21.05 |
| 2874 | N | VAL | A | 203 | -21.007 | 9.695 | 30.070 | 1.00 | 21.19 |

FIGURE 3 (cont.)

| A | B | C | D | E | F | G | H | I | J |
|---|---|---|---|---|---|---|---|---|---|
| 2876 | CA | VAL | A | 203 | -22.453 | 9.794 | 30.294 | 1.00 | 21.92 |
| 2878 | CB | VAL | A | 203 | -23.268 | 9.420 | 29.044 | 1.00 | 22.11 |
| 2880 | CG1 | VAL | A | 203 | -22.967 | 10.392 | 27.923 | 1.00 | 23.12 |
| 2884 | CG2 | VAL | A | 203 | -23.012 | 7.998 | 28.612 | 1.00 | 22.69 |
| 2888 | C | VAL | A | 203 | -22.919 | 8.984 | 31.504 | 1.00 | 22.02 |
| 2889 | O | VAL | A | 203 | -23.911 | 9.344 | 32.143 | 1.00 | 22.21 |
| 2890 | N | SER | A | 204 | -22.189 | 7.921 | 31.841 | 1.00 | 21.78 |
| 2892 | CA | SER | A | 204 | -22.536 | 7.056 | 32.967 | 1.00 | 22.12 |
| 2894 | CB B | SER | A | 204 | -22.225 | 5.588 | 32.650 | 0.35 | 22.13 |
| 2895 | CB A | SER | A | 204 | -22.186 | 5.600 | 32.657 | 0.65 | 22.30 |
| 2900 | OG B | SER | A | 204 | -20.846 | 5.383 | 32.402 | 0.35 | 21.81 |
| 2901 | OG A | SER | A | 204 | -22.758 | 5.185 | 31.430 | 0.65 | 22.86 |
| 2904 | C | SER | A | 204 | -21.825 | 7.499 | 34.246 | 1.00 | 22.25 |
| 2905 | O | SER | A | 204 | -21.966 | 6.860 | 35.283 | 1.00 | 22.52 |
| 2906 | N | ARG | A | 205 | -21.071 | 8.596 | 34.155 | 1.00 | 22.50 |
| 2908 | CA | ARG | A | 205 | -20.340 | 9.175 | 35.284 | 1.00 | 22.65 |
| 2910 | CB | ARG | A | 205 | -21.320 | 9.885 | 36.227 | 1.00 | 23.63 |
| 2913 | CG | ARG | A | 205 | -22.129 | 10.955 | 35.495 | 1.00 | 26.42 |
| 2916 | CD | ARG | A | 205 | -22.691 | 12.073 | 36.368 | 1.00 | 30.05 |
| 2919 | NE | ARG | A | 205 | -23.130 | 13.213 | 35.557 | 1.00 | 33.49 |
| 2921 | CZ | ARG | A | 205 | -23.802 | 14.266 | 36.021 | 1.00 | 36.30 |
| 2922 | NH1 | ARG | A | 205 | -24.128 | 14.354 | 37.308 | 1.00 | 37.68 |
| 2925 | NH2 | ARG | A | 205 | -24.152 | 15.243 | 35.192 | 1.00 | 37.47 |
| 2928 | C | ARG | A | 205 | -19.436 | 8.157 | 35.997 | 1.00 | 21.75 |
| 2929 | O | ARG | A | 205 | -19.429 | 8.043 | 37.225 | 1.00 | 22.16 |
| 2930 | N | VAL | A | 206 | -18.699 | 7.398 | 35.187 | 1.00 | 19.77 |
| 2932 | CA | VAL | A | 206 | -17.629 | 6.521 | 35.636 | 1.00 | 18.53 |
| 2934 | CB | VAL | A | 206 | -17.510 | 5.273 | 34.710 | 1.00 | 18.32 |
| 2936 | CG1 | VAL | A | 206 | -16.294 | 4.434 | 35.069 | 1.00 | 18.31 |
| 2940 | CG2 | VAL | A | 206 | -18.787 | 4.427 | 34.778 | 1.00 | 18.64 |
| 2944 | C | VAL | A | 206 | -16.342 | 7.347 | 35.607 | 1.00 | 17.65 |
| 2945 | O | VAL | A | 206 | -15.908 | 7.799 | 34.536 | 1.00 | 16.81 |
| 2946 | N | ASN | A | 207 | -15.729 | 7.545 | 36.775 | 1.00 | 16.60 |
| 2948 | CA | ASN | A | 207 | -14.577 | 8.449 | 36.912 | 1.00 | 16.29 |
| 2950 | CB B | ASN | A | 207 | -14.622 | 9.176 | 38.266 | 0.35 | 16.45 |
| 2951 | CB A | ASN | A | 207 | -14.604 | 9.166 | 38.264 | 0.65 | 16.92 |
| 2956 | CG B | ASN | A | 207 | -13.582 | 10.292 | 38.384 | 0.35 | 16.63 |
| 2957 | CG A | ASN | A | 207 | -15.857 | 9.996 | 38.459 | 0.65 | 18.02 |
| 2958 | OD1B | ASN | A | 207 | -13.182 | 10.663 | 39.490 | 0.35 | 18.02 |
| 2959 | OD1A | ASN | A | 207 | -16.218 | 10.807 | 37.606 | 0.65 | 20.91 |
| 2960 | ND2B | ASN | A | 207 | -13.150 | 10.834 | 37.253 | 0.35 | 16.67 |
| 2961 | ND2A | ASN | A | 207 | -16.529 | 9.798 | 39.589 | 0.65 | 20.96 |
| 2966 | C | ASN | A | 207 | -13.267 | 7.691 | 36.742 | 1.00 | 15.34 |
| 2967 | O | ASN | A | 207 | -12.395 | 7.690 | 37.617 | 1.00 | 15.45 |
| 2968 | N | VAL | A | 208 | -13.158 | 7.030 | 35.597 | 1.00 | 14.20 |
| 2970 | CA | VAL | A | 208 | -11.942 | 6.343 | 35.195 | 1.00 | 13.45 |
| 2972 | CB | VAL | A | 208 | -12.183 | 4.834 | 35.064 | 1.00 | 13.22 |
| 2974 | CG1 | VAL | A | 208 | -10.943 | 4.118 | 34.514 | 1.00 | 13.60 |
| 2978 | CG2 | VAL | A | 208 | -12.592 | 4.249 | 36.418 | 1.00 | 13.16 |

FIGURE 3 (cont.)

| A | B | C | D | E | F | G | H | I | J |
|---|---|---|---|---|---|---|---|---|---|
| 2982 | C | VAL | A | 208 | -11.505 | 6.942 | 33.871 | 1.00 | 12.86 |
| 2983 | O | VAL | A | 208 | -12.270 | 6.951 | 32.912 | 1.00 | 13.43 |
| 2984 | N | SER | A | 209 | -10.281 | 7.459 | 33.826 | 1.00 | 11.80 |
| 2986 | CA | SER | A | 209 | -9.765 | 8.080 | 32.606 | 1.00 | 12.06 |
| 2988 | CB | SER | A | 209 | -8.677 | 9.108 | 32.923 | 1.00 | 11.61 |
| 2991 | OG | SER | A | 209 | -7.560 | 8.535 | 33.583 | 1.00 | 12.01 |
| 2993 | C | SER | A | 209 | -9.226 | 7.029 | 31.658 | 1.00 | 11.87 |
| 2994 | O | SER | A | 209 | -8.808 | 5.964 | 32.090 | 1.00 | 11.60 |
| 2995 | N | ILE | A | 210 | -9.218 | 7.350 | 30.365 | 1.00 | 11.74 |
| 2997 | CA | ILE | A | 210 | -8.645 | 6.501 | 29.326 | 1.00 | 12.08 |
| 2999 | CB | ILE | A | 210 | -9.750 | 5.893 | 28.448 | 1.00 | 12.81 |
| 3001 | CG1 | ILE | A | 210 | -10.628 | 4.959 | 29.278 | 1.00 | 13.18 |
| 3004 | CD1 | ILE | A | 210 | -11.876 | 4.539 | 28.563 | 1.00 | 13.74 |
| 3008 | CG2 | ILE | A | 210 | -9.173 | 5.164 | 27.241 | 1.00 | 14.13 |
| 3012 | C | ILE | A | 210 | -7.730 | 7.382 | 28.490 | 1.00 | 11.61 |
| 3013 | O | ILE | A | 210 | -8.176 | 8.382 | 27.934 | 1.00 | 11.26 |
| 3014 | N | THR | A | 211 | -6.464 | 6.992 | 28.398 | 1.00 | 11.71 |
| 3016 | CA | THR | A | 211 | -5.444 | 7.714 | 27.653 | 1.00 | 11.63 |
| 3018 | CB | THR | A | 211 | -4.251 | 8.069 | 28.580 | 1.00 | 12.61 |
| 3020 | OG1 | THR | A | 211 | -4.692 | 8.889 | 29.671 | 1.00 | 12.57 |
| 3022 | CG2 | THR | A | 211 | -3.212 | 8.896 | 27.852 | 1.00 | 13.19 |
| 3026 | C | THR | A | 211 | -4.948 | 6.814 | 26.532 | 1.00 | 12.06 |
| 3027 | O | THR | A | 211 | -4.465 | 5.723 | 26.810 | 1.00 | 12.41 |
| 3028 | N | LEU | A | 212 | -5.064 | 7.270 | 25.288 | 1.00 | 11.47 |
| 3030 | CA | LEU | A | 212 | -4.572 | 6.541 | 24.118 | 1.00 | 11.73 |
| 3032 | CB | LEU | A | 212 | -5.599 | 6.573 | 22.985 | 1.00 | 11.89 |
| 3035 | CG | LEU | A | 212 | -5.247 | 5.792 | 21.716 | 1.00 | 13.42 |
| 3037 | CD1 | LEU | A | 212 | -6.179 | 6.146 | 20.556 | 1.00 | 14.83 |
| 3041 | CD2 | LEU | A | 212 | -5.280 | 4.298 | 21.994 | 1.00 | 14.25 |
| 3045 | C | LEU | A | 212 | -3.279 | 7.207 | 23.674 | 1.00 | 11.71 |
| 3046 | O | LEU | A | 212 | -3.255 | 8.403 | 23.412 | 1.00 | 11.69 |
| 3047 | N | CYS | A | 213 | -2.200 | 6.432 | 23.594 | 1.00 | 11.78 |
| 3049 | CA | CYS | A | 213 | -0.899 | 6.986 | 23.257 | 1.00 | 12.57 |
| 3051 | CB | CYS | A | 213 | 0.158 | 6.442 | 24.214 | 1.00 | 12.33 |
| 3054 | SG | CYS | A | 213 | -0.269 | 6.724 | 25.947 | 1.00 | 15.88 |
| 3055 | C | CYS | A | 213 | -0.585 | 6.617 | 21.826 | 1.00 | 11.97 |
| 3056 | O | CYS | A | 213 | -0.706 | 5.458 | 21.451 | 1.00 | 14.09 |
| 3057 | N | VAL | A | 214 | -0.220 | 7.604 | 21.025 | 1.00 | 10.58 |
| 3059 | CA | VAL | A | 214 | 0.099 | 7.413 | 19.617 | 1.00 | 9.96 |
| 3061 | CB | VAL | A | 214 | -0.691 | 8.407 | 18.758 | 1.00 | 9.46 |
| 3063 | CG1 | VAL | A | 214 | -0.307 | 8.283 | 17.279 | 1.00 | 11.00 |
| 3067 | CG2 | VAL | A | 214 | -2.199 | 8.211 | 18.965 | 1.00 | 11.02 |
| 3071 | C | VAL | A | 214 | 1.587 | 7.650 | 19.439 | 1.00 | 10.01 |
| 3072 | O | VAL | A | 214 | 2.042 | 8.791 | 19.547 | 1.00 | 10.72 |
| 3073 | N | LEU | A | 215 | 2.326 | 6.569 | 19.184 | 1.00 | 9.51 |
| 3075 | CA | LEU | A | 215 | 3.784 | 6.592 | 19.172 | 1.00 | 9.51 |
| 3077 | CB | LEU | A | 215 | 4.333 | 5.450 | 20.014 | 1.00 | 9.27 |
| 3080 | CG | LEU | A | 215 | 3.845 | 5.345 | 21.453 | 1.00 | 10.33 |
| 3082 | CD1 | LEU | A | 215 | 4.611 | 4.249 | 22.149 | 1.00 | 10.27 |

FIGURE 3 (cont.)

| A | B | C | D | E | F | G | H | I | J |
|---|---|---|---|---|---|---|---|---|---|
| 3086 | CD2 | LEU | A | 215 | 3.975 | 6.671 | 22.180 | 1.00 | 12.44 |
| 3090 | C | LEU | A | 215 | 4.361 | 6.478 | 17.768 | 1.00 | 9.30 |
| 3091 | O | LEU | A | 215 | 3.993 | 5.607 | 16.989 | 1.00 | 9.46 |
| 3092 | N | GLY | A | 216 | 5.305 | 7.354 | 17.481 | 1.00 | 9.64 |
| 3094 | CA | GLY | A | 216 | 6.161 | 7.204 | 16.325 | 1.00 | 9.54 |
| 3097 | C | GLY | A | 216 | 7.254 | 6.202 | 16.613 | 1.00 | 10.04 |
| 3098 | O | GLY | A | 216 | 7.137 | 5.367 | 17.517 | 1.00 | 9.95 |
| 3099 | N | LEU | A | 217 | 8.331 | 6.296 | 15.846 | 1.00 | 9.88 |
| 3101 | CA | LEU | A | 217 | 9.442 | 5.348 | 15.968 | 1.00 | 9.63 |
| 3103 | CB | LEU | A | 217 | 10.387 | 5.462 | 14.782 | 1.00 | 9.73 |
| 3106 | CG | LEU | A | 217 | 11.633 | 4.582 | 14.836 | 1.00 | 9.78 |
| 3108 | CD1 | LEU | A | 217 | 11.287 | 3.105 | 14.786 | 1.00 | 11.38 |
| 3112 | CD2 | LEU | A | 217 | 12.544 | 4.940 | 13.675 | 1.00 | 10.79 |
| 3116 | C | LEU | A | 217 | 10.209 | 5.573 | 17.254 | 1.00 | 9.53 |
| 3117 | O | LEU | A | 217 | 10.713 | 6.676 | 17.500 | 1.00 | 9.71 |
| 3118 | N | ILE | A | 218 | 10.292 | 4.521 | 18.064 | 1.00 | 9.84 |
| 3120 | CA | ILE | A | 218 | 10.954 | 4.544 | 19.367 | 1.00 | 10.10 |
| 3122 | CB | ILE | A | 218 | 9.973 | 4.157 | 20.509 | 1.00 | 10.68 |
| 3124 | CG1 | ILE | A | 218 | 8.611 | 4.868 | 20.367 | 1.00 | 10.23 |
| 3127 | CD1 | ILE | A | 218 | 8.679 | 6.406 | 20.385 | 1.00 | 10.45 |
| 3131 | CG2 | ILE | A | 218 | 10.593 | 4.418 | 21.872 | 1.00 | 11.90 |
| 3135 | C | ILE | A | 218 | 12.102 | 3.542 | 19.306 | 1.00 | 10.59 |
| 3136 | O | ILE | A | 218 | 11.950 | 2.463 | 18.748 | 1.00 | 11.02 |
| 3137 | N | ASP | A | 219 | 13.239 | 3.882 | 19.904 | 1.00 | 10.63 |
| 3139 | CA | ASP | A | 219 | 14.461 | 3.072 | 19.734 | 1.00 | 10.92 |
| 3141 | CB | ASP | A | 219 | 15.698 | 3.950 | 19.938 | 1.00 | 11.57 |
| 3144 | CG | ASP | A | 219 | 15.847 | 4.431 | 21.346 | 1.00 | 12.72 |
| 3145 | OD1 | ASP | A | 219 | 16.832 | 5.159 | 21.603 | 1.00 | 17.04 |
| 3146 | OD2 | ASP | A | 219 | 15.067 | 4.157 | 22.263 | 1.00 | 13.80 |
| 3147 | C | ASP | A | 219 | 14.551 | 1.799 | 20.599 | 1.00 | 10.52 |
| 3148 | O | ASP | A | 219 | 15.630 | 1.428 | 21.088 | 1.00 | 11.55 |
| 3149 | N | THR | A | 220 | 13.445 | 1.079 | 20.730 | 1.00 | 10.56 |
| 3151 | CA | THR | A | 220 | 13.486 | -0.234 | 21.356 | 1.00 | 10.32 |
| 3153 | CB | THR | A | 220 | 12.060 | -0.775 | 21.601 | 1.00 | 10.52 |
| 3155 | OG1 | THR | A | 220 | 11.409 | -1.005 | 20.341 | 1.00 | 10.00 |
| 3157 | CG2 | THR | A | 220 | 11.193 | 0.247 | 22.334 | 1.00 | 10.69 |
| 3161 | C | THR | A | 220 | 14.239 | -1.232 | 20.480 | 1.00 | 10.14 |
| 3162 | O | THR | A | 220 | 14.325 | -1.076 | 19.267 | 1.00 | 10.03 |
| 3163 | N | GLU | A | 221 | 14.783 | -2.275 | 21.090 | 1.00 | 10.29 |
| 3165 | CA | GLU | A | 221 | 15.470 | -3.321 | 20.324 | 1.00 | 11.82 |
| 3167 | CB | GLU | A | 221 | 15.967 | -4.433 | 21.243 | 1.00 | 12.41 |
| 3170 | CG | GLU | A | 221 | 16.656 | -5.585 | 20.515 | 1.00 | 17.63 |
| 3173 | CD | GLU | A | 221 | 17.681 | -6.346 | 21.348 | 1.00 | 25.15 |
| 3174 | OE1 | GLU | A | 221 | 17.473 | -7.562 | 21.582 | 1.00 | 29.83 |
| 3175 | OE2 | GLU | A | 221 | 18.719 | -5.757 | 21.739 | 1.00 | 30.76 |
| 3176 | C | GLU | A | 221 | 14.581 | -3.891 | 19.223 | 1.00 | 10.51 |
| 3177 | O | GLU | A | 221 | 15.037 | -4.102 | 18.096 | 1.00 | 10.36 |
| 3178 | N | THR | A | 222 | 13.306 | -4.125 | 19.537 | 1.00 | 10.29 |
| 3180 | CA | THR | A | 222 | 12.375 | -4.592 | 18.538 | 1.00 | 10.08 |

FIGURE 3 (cont.)

| A | B | C | D | E | F | G | H | I | J |
|---|---|---|---|---|---|---|---|---|---|
| 3182 | CB | THR | A | 222 | 11.003 | -4.767 | 19.175 | 1.00 | 10.12 |
| 3184 | OG1 | THR | A | 222 | 11.080 | -5.848 | 20.104 | 1.00 | 11.30 |
| 3186 | CG2 | THR | A | 222 | 9.959 | -5.155 | 18.136 | 1.00 | 11.15 |
| 3190 | C | THR | A | 222 | 12.304 | -3.682 | 17.320 | 1.00 | 10.05 |
| 3191 | O | THR | A | 222 | 12.422 | -4.148 | 16.189 | 1.00 | 10.05 |
| 3192 | N | ALA | A | 223 | 12.117 | -2.382 | 17.540 | 1.00 | 10.23 |
| 3194 | CA | ALA | A | 223 | 12.030 | -1.451 | 16.430 | 1.00 | 9.76 |
| 3196 | CB | ALA | A | 223 | 11.614 | -0.088 | 16.901 | 1.00 | 9.78 |
| 3200 | C | ALA | A | 223 | 13.341 | -1.373 | 15.654 | 1.00 | 9.93 |
| 3201 | O | ALA | A | 223 | 13.335 | -1.310 | 14.432 | 1.00 | 10.36 |
| 3202 | N | MET | A | 224 | 14.455 | -1.408 | 16.363 | 1.00 | 10.57 |
| 3204 | CA | MET | A | 224 | 15.745 | -1.230 | 15.695 | 1.00 | 10.91 |
| 3206 | CB | MET | A | 224 | 16.828 | -0.887 | 16.705 | 1.00 | 11.45 |
| 3209 | CG | MET | A | 224 | 16.596 | 0.451 | 17.424 | 1.00 | 11.79 |
| 3212 | SD | MET | A | 224 | 16.480 | 1.911 | 16.350 | 1.00 | 14.5 |
| 3213 | CE | MET | A | 224 | 14.771 | 1.998 | 15.995 | 1.00 | 15.91 |
| 3217 | C | MET | A | 224 | 16.098 | -2.458 | 14.863 | 1.00 | 11.87 |
| 3218 | O | MET | A | 224 | 16.793 | -2.355 | 13.857 | 1.00 | 11.83 |
| 3219 | N | LYS | A | 225 | 15.578 | -3.613 | 15.251 | 1.00 | 12.68 |
| 3221 | CA | LYS | A | 225 | 15.725 | -4.817 | 14.446 | 1.00 | 14.34 |
| 3223 | CB | LYS | A | 225 | 15.419 | -6.052 | 15.302 | 1.00 | 14.91 |
| 3226 | CG | LYS | A | 225 | 16.580 | -6.440 | 16.197 | 1.00 | 19.32 |
| 3229 | CD | LYS | A | 225 | 16.299 | -7.717 | 16.970 | 1.00 | 24.07 |
| 3232 | CE | LYS | A | 225 | 17.430 | -8.057 | 17.917 | 1.00 | 26.90 |
| 3235 | NZ | LYS | A | 225 | 18.628 | -8.593 | 17.203 | 1.00 | 29.50 |
| 3239 | C | LYS | A | 225 | 14.814 | -4.780 | 13.209 | 1.00 | 14.21 |
| 3240 | O | LYS | A | 225 | 15.182 | -5.293 | 12.159 | 1.00 | 15.40 |
| 3241 | N | ALA | A | 226 | 13.642 | -4.156 | 13.330 | 1.00 | 13.78 |
| 3243 | CA | ALA | A | 226 | 12.643 | -4.146 | 12.258 | 1.00 | 13.40 |
| 3245 | CB | ALA | A | 226 | 11.256 | -3.895 | 12.843 | 1.00 | 13.11 |
| 3249 | C | ALA | A | 226 | 12.910 | -3.134 | 11.138 | 1.00 | 13.23 |
| 3250 | O | ALA | A | 226 | 12.699 | -3.436 | 9.969 | 1.00 | 13.27 |
| 3251 | N | VAL | A | 227 | 13.356 | -1.930 | 11.480 | 1.00 | 12.92 |
| 3253 | CA | VAL | A | 227 | 13.503 | -0.868 | 10.476 | 1.00 | 13.22 |
| 3255 | CB | VAL | A | 227 | 13.304 | 0.552 | 11.076 | 1.00 | 13.18 |
| 3257 | CG1 | VAL | A | 227 | 11.923 | 0.675 | 11.717 | 1.00 | 13.18 |
| 3261 | CG2 | VAL | A | 227 | 14.424 | 0.921 | 12.046 | 1.00 | 14.17 |
| 3265 | C | VAL | A | 227 | 14.851 | -0.965 | 9.737 | 1.00 | 13.49 |
| 3266 | O | VAL | A | 227 | 15.706 | -1.784 | 10.090 | 1.00 | 13.51 |
| 3267 | N | SER | A | 228 | 15.012 | -0.132 | 8.711 | 1.00 | 13.96 |
| 3269 | CA | SER | A | 228 | 16.142 | -0.200 | 7.791 | 1.00 | 14.64 |
| 3271 | CB | SER | A | 228 | 15.655 | -0.693 | 6.427 | 1.00 | 15.09 |
| 3274 | OG | SER | A | 228 | 16.690 | -0.626 | 5.454 | 1.00 | 17.17 |
| 3276 | C | SER | A | 228 | 16.872 | 1.133 | 7.626 | 1.00 | 14.31 |
| 3277 | O | SER | A | 228 | 16.260 | 2.198 | 7.534 | 1.00 | 14.90 |
| 3278 | N | GLY | A | 229 | 18.196 | 1.067 | 7.586 | 1.00 | 14.06 |
| 3280 | CA | GLY | A | 229 | 19.010 | 2.186 | 7.148 | 1.00 | 13.99 |
| 3283 | C | GLY | A | 229 | 18.900 | 3.389 | 8.062 | 1.00 | 14.34 |
| 3284 | O | GLY | A | 229 | 18.809 | 3.241 | 9.281 | 1.00 | 13.98 |

FIGURE 3 (cont.)

| A | B | C | D | E | F | G | H | I | J |
|---|---|---|---|---|---|---|---|---|---|
| 3285 | N | ILE | A | 230 | 18.881 | 4.586 | 7.479 | 1.00 | 14.68 |
| 3287 | CA | ILE | A | 230 | 18.909 | 5.810 | 8.272 | 1.00 | 15.19 |
| 3289 | CB | ILE | A | 230 | 19.153 | 7.066 | 7.400 | 1.00 | 15.60 |
| 3291 | CG1 | ILE | A | 230 | 18.015 | 7.295 | 6.402 | 1.00 | 16.97 |
| 3294 | CD1 | ILE | A | 230 | 18.010 | 8.693 | 5.829 | 1.00 | 19.57 |
| 3298 | CG2 | ILE | A | 230 | 20.492 | 6.976 | 6.696 | 1.00 | 16.66 |
| 3302 | C | ILE | A | 230 | 17.655 | 6.019 | 9.108 | 1.00 | 14.94 |
| 3303 | O | ILE | A | 230 | 17.651 | 6.870 | 9.989 | 1.00 | 15.39 |
| 3304 | N | VAL | A | 231 | 16.606 | 5.249 | 8.841 | 1.00 | 15.06 |
| 3306 | CA | VAL | A | 231 | 15.406 | 5.304 | 9.675 | 1.00 | 15.19 |
| 3308 | CB | VAL | A | 231 | 14.317 | 4.319 | 9.170 | 1.00 | 15.25 |
| 3310 | CG1 | VAL | A | 231 | 13.105 | 4.285 | 10.119 | 1.00 | 15.04 |
| 3314 | CG2 | VAL | A | 231 | 13.891 | 4.690 | 7.750 | 1.00 | 15.23 |
| 3318 | C | VAL | A | 231 | 15.768 | 5.040 | 11.137 | 1.00 | 15.39 |
| 3319 | O | VAL | A | 231 | 15.167 | 5.629 | 12.025 | 1.00 | 15.53 |
| 3320 | N | HIS | A | 232 | 16.748 | 4.170 | 11.390 | 1.00 | 15.81 |
| 3322 | CA | HIS | A | 232 | 17.231 | 3.918 | 12.757 | 1.00 | 16.19 |
| 3324 | CB | HIS | A | 232 | 18.475 | 3.018 | 12.782 | 1.00 | 15.89 |
| 3327 | CG | HIS | A | 232 | 18.254 | 1.631 | 12.249 | 1.00 | 14.26 |
| 3328 | ND1 | HIS | A | 232 | 17.805 | 0.589 | 13.030 | 1.00 | 16.24 |
| 3330 | CE1 | HIS | A | 232 | 17.730 | -0.505 | 12.294 | 1.00 | 13.18 |
| 3332 | NE2 | HIS | A | 232 | 18.122 | -0.215 | 11.070 | 1.00 | 13.71 |
| 3334 | CD2 | HIS | A | 232 | 18.458 | 1.112 | 11.018 | 1.00 | 10.97 |
| 3336 | C | HIS | A | 232 | 17.575 | 5.216 | 13.495 | 1.00 | 16.92 |
| 3337 | O | HIS | A | 232 | 17.352 | 5.321 | 14.694 | 1.00 | 18.81 |
| 3338 | N | MET | A | 233 | 18.127 | 6.192 | 12.781 | 1.00 | 17.36 |
| 3340 | CA | MET | A | 233 | 18.622 | 7.421 | 13.410 | 1.00 | 17.67 |
| 3342 | CB | MET | A | 233 | 19.733 | 8.021 | 12.547 | 1.00 | 18.33 |
| 3345 | CG | MET | A | 233 | 20.915 | 7.057 | 12.391 | 1.00 | 20.88 |
| 3348 | SD | MET | A | 233 | 22.408 | 7.841 | 11.894 | 1.00 | 26.90 |
| 3349 | CE | MET | A | 233 | 22.816 | 8.658 | 13.404 | 1.00 | 25.25 |
| 3353 | C | MET | A | 233 | 17.509 | 8.439 | 13.668 | 1.00 | 17.20 |
| 3354 | O | MET | A | 233 | 17.734 | 9.486 | 14.273 | 1.00 | 17.30 |
| 3355 | N | GLN | A | 234 | 16.306 | 8.104 | 13.226 | 1.00 | 16.57 |
| 3357 | CA | GLN | A | 234 | 15.149 | 8.973 | 13.327 | 1.00 | 16.31 |
| 3359 | CB | GLN | A | 234 | 14.430 | 8.974 | 11.973 | 1.00 | 17.11 |
| 3362 | CG | GLN | A | 234 | 15.384 | 9.358 | 10.831 | 1.00 | 17.53 |
| 3365 | CD | GLN | A | 234 | 14.822 | 9.234 | 9.417 | 1.00 | 19.66 |
| 3366 | OE1 | GLN | A | 234 | 15.417 | 9.778 | 8.473 | 1.00 | 23.54 |
| 3367 | NE2 | GLN | A | 234 | 13.717 | 8.538 | 9.254 | 1.00 | 18.05 |
| 3370 | C | GLN | A | 234 | 14.230 | 8.503 | 14.458 | 1.00 | 15.78 |
| 3371 | O | GLN | A | 234 | 13.066 | 8.894 | 14.510 | 1.00 | 16.20 |
| 3372 | N | ALA | A | 235 | 14.763 | 7.674 | 15.357 | 1.00 | 14.80 |
| 3374 | CA | ALA | A | 235 | 14.009 | 7.147 | 16.497 | 1.00 | 14.83 |
| 3376 | CB | ALA | A | 235 | 14.516 | 5.770 | 16.848 | 1.00 | 14.44 |
| 3380 | C | ALA | A | 235 | 14.104 | 8.048 | 17.713 | 1.00 | 14.74 |
| 3381 | O | ALA | A | 235 | 15.145 | 8.677 | 17.962 | 1.00 | 16.24 |
| 3382 | N | ALA | A | 236 | 13.027 | 8.100 | 18.486 | 1.00 | 12.99 |
| 3384 | CA | ALA | A | 236 | 12.997 | 8.819 | 19.751 | 1.00 | 12.70 |

FIGURE 3 (cont.)

| A | B | C | D | E | F | G | H | I | J |
|---|---|---|---|---|---|---|---|---|---|
| 3386 | CB | ALA | A | 236 | 11.606 | 9.349 | 20.015 | 1.00 | 12.97 |
| 3390 | C | ALA | A | 236 | 13.445 | 7.893 | 20.888 | 1.00 | 12.58 |
| 3391 | O | ALA | A | 236 | 13.287 | 6.676 | 20.801 | 1.00 | 12.11 |
| 3392 | N | PRO | A | 237 | 13.985 | 8.449 | 21.965 | 1.00 | 12.73 |
| 3393 | CA | PRO | A | 237 | 14.469 | 7.630 | 23.088 | 1.00 | 12.81 |
| 3395 | CB | PRO | A | 237 | 15.226 | 8.626 | 23.974 | 1.00 | 13.23 |
| 3398 | CG | PRO | A | 237 | 15.042 | 9.967 | 23.379 | 1.00 | 13.72 |
| 3401 | CD | PRO | A | 237 | 14.199 | 9.889 | 22.188 | 1.00 | 13.31 |
| 3404 | C | PRO | A | 237 | 13.360 | 6.949 | 23.884 | 1.00 | 12.51 |
| 3405 | O | PRO | A | 237 | 12.389 | 7.585 | 24.290 | 1.00 | 12.66 |
| 3406 | N | LYS | A | 238 | 13.513 | 5.654 | 24.113 | 1.00 | 11.91 |
| 3408 | CA | LYS | A | 238 | 12.494 | 4.887 | 24.831 | 1.00 | 11.86 |
| 3410 | CB | LYS | A | 238 | 12.829 | 3.389 | 24.808 | 1.00 | 12.07 |
| 3413 | CG | LYS | A | 238 | 14.183 | 3.006 | 25.404 | 1.00 | 12.85 |
| 3416 | CD | LYS | A | 238 | 14.478 | 1.541 | 25.156 | 1.00 | 13.91 |
| 3419 | CE | LYS | A | 238 | 15.728 | 1.099 | 25.895 | 1.00 | 15.43 |
| 3422 | NZ | LYS | A | 238 | 16.074 | -0.331 | 25.644 | 1.00 | 17.83 |
| 3426 | C | LYS | A | 238 | 12.259 | 5.362 | 26.262 | 1.00 | 12.41 |
| 3427 | O | LYS | A | 238 | 11.145 | 5.262 | 26.772 | 1.00 | 12.64 |
| 3428 | N | GLU | A | 239 | 13.301 | 5.875 | 26.919 | 1.00 | 12.99 |
| 3430 | CA | GLU | A | 239 | 13.148 | 6.368 | 28.285 | 1.00 | 14.06 |
| 3432 | CB | GLU | A | 239 | 14.503 | 6.733 | 28.904 | 1.00 | 15.10 |
| 3435 | CG | GLU | A | 239 | 14.388 | 7.171 | 30.358 | 1.00 | 18.88 |
| 3438 | CD | GLU | A | 239 | 15.720 | 7.442 | 31.039 | 1.00 | 23.63 |
| 3439 | OE1 | GLU | A | 239 | 15.780 | 8.402 | 31.834 | 1.00 | 27.51 |
| 3440 | OE2 | GLU | A | 239 | 16.697 | 6.692 | 30.808 | 1.00 | 28.46 |
| 3441 | C | GLU | A | 239 | 12.226 | 7.575 | 28.318 | 1.00 | 13.62 |
| 3442 | O | GLU | A | 239 | 11.351 | 7.657 | 29.178 | 1.00 | 13.63 |
| 3443 | N | GLU | A | 240 | 12.406 | 8.500 | 27.380 | 1.00 | 13.23 |
| 3445 | CA | GLU | A | 240 | 11.571 | 9.704 | 27.321 | 1.00 | 13.79 |
| 3447 | CB | GLU | A | 240 | 12.157 | 10.747 | 26.353 | 1.00 | 14.47 |
| 3450 | CG | GLU | A | 240 | 11.373 | 12.055 | 26.303 | 1.00 | 18.33 |
| 3453 | CD | GLU | A | 240 | 12.038 | 13.136 | 25.454 | 1.00 | 22.78 |
| 3454 | OE1 | GLU | A | 240 | 11.851 | 13.149 | 24.210 | 1.00 | 24.01 |
| 3455 | OE2 | GLU | A | 240 | 12.755 | 13.987 | 26.031 | 1.00 | 26.83 |
| 3456 | C | GLU | A | 240 | 10.134 | 9.349 | 26.929 | 1.00 | 13.09 |
| 3457 | O | GLU | A | 240 | 9.168 | 9.859 | 27.509 | 1.00 | 12.73 |
| 3458 | N | CYS | A | 241 | 10.008 | 8.464 | 25.954 | 1.00 | 12.39 |
| 3460 | CA | CYS | A | 241 | 8.709 | 7.983 | 25.510 | 1.00 | 12.17 |
| 3462 | CB | CYS | A | 241 | 8.893 | 6.903 | 24.454 | 1.00 | 12.41 |
| 3465 | SG | CYS | A | 241 | 7.346 | 6.166 | 23.884 | 1.00 | 13.2 |
| 3466 | C | CYS | A | 241 | 7.901 | 7.441 | 26.677 | 1.00 | 11.60 |
| 3467 | O | CYS | A | 241 | 6.749 | 7.835 | 26.884 | 1.00 | 11.86 |
| 3468 | N | ALA | A | 242 | 8.517 | 6.552 | 27.445 | 1.00 | 11.18 |
| 3470 | CA | ALA | A | 242 | 7.882 | 5.954 | 28.624 | 1.00 | 11.17 |
| 3472 | CB | ALA | A | 242 | 8.838 | 4.954 | 29.306 | 1.00 | 11.30 |
| 3476 | C | ALA | A | 242 | 7.399 | 6.990 | 29.628 | 1.00 | 11.69 |
| 3477 | O | ALA | A | 242 | 6.306 | 6.880 | 30.158 | 1.00 | 12.03 |
| 3478 | N | LEU | A | 243 | 8.218 | 7.998 | 29.897 | 1.00 | 12.30 |

FIGURE 3 (cont.)

| A | B | C | D | E | F | G | H | I | J |
|---|---|---|---|---|---|---|---|---|---|
| 3480 | CA | LEU | A | 243 | 7.835 | 9.038 | 30.842 | 1.00 | 12.71 |
| 3482 | CB | LEU | A | 243 | 9.016 | 9.957 | 31.163 | 1.00 | 13.30 |
| 3485 | CG | LEU | A | 243 | 8.728 | 11.016 | 32.233 | 1.00 | 14.81 |
| 3487 | CD1 | LEU | A | 243 | 8.259 | 10.409 | 33.534 | 1.00 | 17.02 |
| 3491 | CD2 | LEU | A | 243 | 9.956 | 11.876 | 32.464 | 1.00 | 16.27 |
| 3495 | C | LEU | A | 243 | 6.641 | 9.837 | 30.323 | 1.00 | 12.58 |
| 3496 | O | LEU | A | 243 | 5.713 | 10.093 | 31.067 | 1.00 | 13.14 |
| 3497 | N | GLU | A | 244 | 6.634 | 10.181 | 29.041 | 1.00 | 12.66 |
| 3499 | CA | GLU | A | 244 | 5.509 | 10.933 | 28.475 | 1.00 | 13.16 |
| 3501 | CB | GLU | A | 244 | 5.800 | 11.388 | 27.042 | 1.00 | 13.53 |
| 3504 | CG | GLU | A | 244 | 6.884 | 12.456 | 26.905 | 1.00 | 15.47 |
| 3507 | CD | GLU | A | 244 | 6.668 | 13.672 | 27.802 | 1.00 | 18.14 |
| 3508 | OE1 | GLU | A | 244 | 7.661 | 14.149 | 28.385 | 1.00 | 21.51 |
| 3509 | OE2 | GLU | A | 244 | 5.520 | 14.166 | 27.928 | 1.00 | 20.54 |
| 3510 | C | GLU | A | 244 | 4.191 | 10.145 | 28.522 | 1.00 | 12.61 |
| 3511 | O | GLU | A | 244 | 3.115 | 10.729 | 28.712 | 1.00 | 13.71 |
| 3512 | N | ILE | A | 245 | 4.268 | 8.827 | 28.374 | 1.00 | 12.09 |
| 3514 | CA | ILE | A | 245 | 3.086 | 7.972 | 28.501 | 1.00 | 11.82 |
| 3516 | CB | ILE | A | 245 | 3.400 | 6.522 | 28.110 | 1.00 | 11.22 |
| 3518 | CG1 | ILE | A | 245 | 3.666 | 6.437 | 26.607 | 1.00 | 11.30 |
| 3521 | CD1 | ILE | A | 245 | 4.237 | 5.125 | 26.206 | 1.00 | 10.91 |
| 3525 | CG2 | ILE | A | 245 | 2.237 | 5.596 | 28.474 | 1.00 | 11.57 |
| 3529 | C | ILE | A | 245 | 2.562 | 8.033 | 29.936 | 1.00 | 12.26 |
| 3530 | O | ILE | A | 245 | 1.370 | 8.235 | 30.145 | 1.00 | 11.84 |
| 3531 | N | ILE | A | 246 | 3.452 | 7.881 | 30.910 | 1.00 | 12.36 |
| 3533 | CA | ILE | A | 246 | 3.061 | 7.944 | 32.321 | 1.00 | 12.96 |
| 3535 | CB | ILE | A | 246 | 4.256 | 7.606 | 33.245 | 1.00 | 13.20 |
| 3537 | CG1 | ILE | A | 246 | 4.616 | 6.114 | 33.116 | 1.00 | 13.37 |
| 3540 | CD1 | ILE | A | 246 | 6.015 | 5.764 | 33.620 | 1.00 | 13.81 |
| 3544 | CG2 | ILE | A | 246 | 3.939 | 7.962 | 34.694 | 1.00 | 13.32 |
| 3548 | C | ILE | A | 246 | 2.471 | 9.317 | 32.663 | 1.00 | 13.52 |
| 3549 | O | ILE | A | 246 | 1.467 | 9.400 | 33.376 | 1.00 | 14.24 |
| 3550 | N | LYS | A | 247 | 3.094 | 10.383 | 32.164 | 1.00 | 13.79 |
| 3552 | CA | LYS | A | 247 | 2.634 | 11.744 | 32.454 | 1.00 | 14.92 |
| 3554 | CB | LYS | A | 247 | 3.561 | 12.782 | 31.834 | 1.00 | 15.40 |
| 3557 | CG | LYS | A | 247 | 4.929 | 12.946 | 32.496 | 1.00 | 18.06 |
| 3560 | CD | LYS | A | 247 | 5.528 | 14.312 | 32.153 | 1.00 | 22.18 |
| 3563 | CE | LYS | A | 247 | 6.996 | 14.233 | 31.799 | 1.00 | 24.53 |
| 3566 | NZ | LYS | A | 247 | 7.476 | 15.495 | 31.166 | 1.00 | 24.96 |
| 3570 | C | LYS | A | 247 | 1.220 | 11.944 | 31.916 | 1.00 | 14.92 |
| 3571 | O | LYS | A | 247 | 0.358 | 12.487 | 32.609 | 1.00 | 14.25 |
| 3572 | N | GLY | A | 248 | 0.987 | 11.495 | 30.685 | 1.00 | 14.56 |
| 3574 | CA | GLY | A | 248 | -0.323 | 11.566 | 30.064 | 1.00 | 14.78 |
| 3577 | C | GLY | A | 248 | -1.385 | 10.851 | 30.873 | 1.00 | 14.66 |
| 3578 | O | GLY | A | 248 | -2.468 | 11.383 | 31.084 | 1.00 | 15.08 |
| 3579 | N | GLY | A | 249 | -1.078 | 9.641 | 31.326 | 1.00 | 14.70 |
| 3581 | CA | GLY | A | 249 | -1.990 | 8.881 | 32.153 | 1.00 | 14.83 |
| 3584 | C | GLY | A | 249 | -2.277 | 9.551 | 33.486 | 1.00 | 14.79 |
| 3585 | O | GLY | A | 249 | -3.432 | 9.624 | 33.905 | 1.00 | 15.25 |

FIGURE 3 (cont.)

| A | B | C | D | E | F | G | H | I | J |
|---|---|---|---|---|---|---|---|---|---|
| 3586 | N | ALA | A | 250 | -1.233 | 10.037 | 34.150 | 1.00 | 14.46 |
| 3588 | CA | ALA | A | 250 | -1.383 | 10.697 | 35.450 | 1.00 | 14.16 |
| 3590 | CB | ALA | A | 250 | -0.026 | 11.039 | 36.026 | 1.00 | 14.16 |
| 3594 | C | ALA | A | 250 | -2.241 | 11.948 | 35.352 | 1.00 | 14.08 |
| 3595 | O | ALA | A | 250 | -3.025 | 12.241 | 36.265 | 1.00 | 14.84 |
| 3596 | N | LEU | A | 251 | -2.101 | 12.681 | 34.249 | 1.00 | 13.91 |
| 3598 | CA | LEU | A | 251 | -2.840 | 13.928 | 34.031 | 1.00 | 14.09 |
| 3600 | CB | LEU | A | 251 | -2.024 | 14.891 | 33.156 | 1.00 | 14.26 |
| 3603 | CG | LEU | A | 251 | -0.724 | 15.384 | 33.794 | 1.00 | 15.23 |
| 3605 | CD1 | LEU | A | 251 | 0.090 | 16.174 | 32.789 | 1.00 | 16.39 |
| 3609 | CD2 | LEU | A | 251 | -1.010 | 16.207 | 35.036 | 1.00 | 16.11 |
| 3613 | C | LEU | A | 251 | -4.211 | 13.680 | 33.397 | 1.00 | 13.99 |
| 3614 | O | LEU | A | 251 | -4.947 | 14.627 | 33.113 | 1.00 | 14.70 |
| 3615 | N | ARG | A | 252 | -4.546 | 12.413 | 33.161 | 1.00 | 13.35 |
| 3617 | CA | ARG | A | 252 | -5.861 | 12.021 | 32.657 | 1.00 | 13.70 |
| 3619 | CB | ARG | A | 252 | -6.947 | 12.389 | 33.678 | 1.00 | 13.81 |
| 3622 | CG | ARG | A | 252 | -6.669 | 11.842 | 35.062 | 1.00 | 13.84 |
| 3625 | CD | ARG | A | 252 | -7.733 | 12.183 | 36.087 | 1.00 | 13.80 |
| 3628 | NE | ARG | A | 252 | -8.904 | 11.295 | 36.082 | 1.00 | 13.43 |
| 3630 | CZ | ARG | A | 252 | -8.958 | 10.089 | 36.647 | 1.00 | 13.38 |
| 3631 | NH1 | ARG | A | 252 | -7.903 | 9.566 | 37.267 | 1.00 | 13.53 |
| 3634 | NH2 | ARG | A | 252 | -10.092 | 9.397 | 36.601 | 1.00 | 14.15 |
| 3637 | C | ARG | A | 252 | -6.151 | 12.625 | 31.265 | 1.00 | 14.05 |
| 3638 | O | ARG | A | 252 | -7.292 | 12.949 | 30.924 | 1.00 | 13.82 |
| 3639 | N | GLN | A | 253 | -5.096 | 12.772 | 30.463 | 1.00 | 14.24 |
| 3641 | CA | GLN | A | 253 | -5.219 | 13.221 | 29.084 | 1.00 | 14.68 |
| 3643 | CB | GLN | A | 253 | -3.841 | 13.537 | 28.488 | 1.00 | 15.44 |
| 3646 | CG | GLN | A | 253 | -3.119 | 14.683 | 29.126 | 1.00 | 18.33 |
| 3649 | CD | GLN | A | 253 | -1.741 | 14.927 | 28.502 | 1.00 | 18.88 |
| 3650 | OE1 | GLN | A | 253 | -1.439 | 14.439 | 27.399 | 1.00 | 24.01 |
| 3651 | NE2 | GLN | A | 253 | -0.919 | 15.675 | 29.195 | 1.00 | 23.09 |
| 3654 | C | GLN | A | 253 | -5.893 | 12.160 | 28.221 | 1.00 | 14.73 |
| 3655 | O | GLN | A | 253 | -5.687 | 10.960 | 28.419 | 1.00 | 14.76 |
| 3656 | N | GLU | A | 254 | -6.691 | 12.593 | 27.257 | 1.00 | 14.58 |
| 3658 | CA | GLU | A | 254 | -7.359 | 11.641 | 26.376 | 1.00 | 14.78 |
| 3660 | CB | GLU | A | 254 | -8.500 | 12.296 | 25.619 | 1.00 | 15.34 |
| 3663 | CG | GLU | A | 254 | -9.619 | 12.674 | 26.572 | 1.00 | 18.01 |
| 3666 | CD | GLU | A | 254 | -10.911 | 13.085 | 25.905 | 1.00 | 21.86 |
| 3667 | OE1 | GLU | A | 254 | -11.774 | 13.602 | 26.638 | 1.00 | 25.73 |
| 3668 | OE2 | GLU | A | 254 | -11.082 | 12.878 | 24.685 | 1.00 | 23.79 |
| 3669 | C | GLU | A | 254 | -6.350 | 10.996 | 25.434 | 1.00 | 14.10 |
| 3670 | O | GLU | A | 254 | -6.396 | 9.805 | 25.203 | 1.00 | 12.59 |
| 3671 | N | GLU | A | 255 | -5.431 | 11.786 | 24.902 | 1.00 | 14.29 |
| 3673 | CA | GLU | A | 255 | -4.430 | 11.253 | 23.984 | 1.00 | 14.94 |
| 3675 | CB | GLU | A | 255 | -4.854 | 11.456 | 22.514 | 1.00 | 15.32 |
| 3678 | CG | GLU | A | 255 | -6.153 | 10.719 | 22.161 | 1.00 | 17.27 |
| 3681 | CD | GLU | A | 255 | -6.493 | 10.670 | 20.673 | 1.00 | 20.11 |
| 3682 | OE1 | GLU | A | 255 | -7.174 | 9.689 | 20.251 | 1.00 | 22.21 |
| 3683 | OE2 | GLU | A | 255 | -6.133 | 11.613 | 19.931 | 1.00 | 21.72 |

FIGURE 3 (cont.)

| A | B | C | D | E | F | G | H | I | J |
|---|---|---|---|---|---|---|---|---|---|
| 3684 | C | GLU | A | 255 | -3.058 | 11.858 | 24.242 | 1.00 | 15.03 |
| 3685 | O | GLU | A | 255 | -2.938 | 13.016 | 24.660 | 1.00 | 16.89 |
| 3686 | N | VAL | A | 256 | -2.040 | 11.039 | 24.028 | 1.00 | 14.51 |
| 3688 | CA | VAL | A | 256 | -0.643 | 11.451 | 24.046 | 1.00 | 14.15 |
| 3690 | CB | VAL | A | 256 | 0.154 | 10.654 | 25.100 | 1.00 | 13.96 |
| 3692 | CG1 | VAL | A | 256 | 1.649 | 10.938 | 24.997 | 1.00 | 15.69 |
| 3696 | CG2 | VAL | A | 256 | -0.363 | 10.939 | 26.515 | 1.00 | 14.47 |
| 3700 | C | VAL | A | 256 | -0.079 | 11.170 | 22.659 | 1.00 | 13.85 |
| 3701 | O | VAL | A | 256 | -0.284 | 10.094 | 22.106 | 1.00 | 14.72 |
| 3702 | N | TYR | A | 257 | 0.604 | 12.145 | 22.086 | 1.00 | 12.90 |
| 3704 | CA | TYR | A | 257 | 1.284 | 11.965 | 20.819 | 1.00 | 12.32 |
| 3706 | CB | TYR | A | 257 | 0.776 | 12.965 | 19.781 | 1.00 | 12.68 |
| 3709 | CG | TYR | A | 257 | -0.619 | 12.658 | 19.299 | 1.00 | 13.34 |
| 3710 | CD1 | TYR | A | 257 | -1.729 | 13.026 | 20.043 | 1.00 | 17.02 |
| 3712 | CE1 | TYR | A | 257 | -3.020 | 12.734 | 19.601 | 1.00 | 16.67 |
| 3714 | CZ | TYR | A | 257 | -3.186 | 12.041 | 18.417 | 1.00 | 16.83 |
| 3715 | OH | TYR | A | 257 | -4.453 | 11.728 | 17.964 | 1.00 | 18.33 |
| 3717 | CE2 | TYR | A | 257 | -2.096 | 11.652 | 17.672 | 1.00 | 15.55 |
| 3719 | CD2 | TYR | A | 257 | -0.817 | 11.954 | 18.119 | 1.00 | 15.03 |
| 3721 | C | TYR | A | 257 | 2.764 | 12.178 | 21.076 | 1.00 | 12.67 |
| 3722 | O | TYR | A | 257 | 3.159 | 13.207 | 21.635 | 1.00 | 12.40 |
| 3723 | N | TYR | A | 258 | 3.574 | 11.195 | 20.695 | 1.00 | 12.14 |
| 3725 | CA | TYR | A | 258 | 5.012 | 11.228 | 20.957 | 1.00 | 12.17 |
| 3727 | CB | TYR | A | 258 | 5.382 | 10.400 | 22.194 | 1.00 | 12.26 |
| 3730 | CG | TYR | A | 258 | 6.847 | 10.529 | 22.532 | 1.00 | 12.49 |
| 3731 | CD1 | TYR | A | 258 | 7.761 | 9.585 | 22.087 | 1.00 | 13.64 |
| 3733 | CE1 | TYR | A | 258 | 9.085 | 9.706 | 22.351 | 1.00 | 14.93 |
| 3735 | CZ | TYR | A | 258 | 9.552 | 10.781 | 23.061 | 1.00 | 15.74 |
| 3736 | OH | TYR | A | 258 | 10.899 | 10.886 | 23.312 | 1.00 | 18.74 |
| 3738 | CE2 | TYR | A | 258 | 8.678 | 11.756 | 23.507 | 1.00 | 15.65 |
| 3740 | CD2 | TYR | A | 258 | 7.325 | 11.623 | 23.235 | 1.00 | 14.56 |
| 3742 | C | TYR | A | 258 | 5.811 | 10.766 | 19.741 | 1.00 | 12.04 |
| 3743 | O | TYR | A | 258 | 5.584 | 9.686 | 19.190 | 1.00 | 12.46 |
| 3744 | N | ASP | A | 259 | 6.746 | 11.613 | 19.332 | 1.00 | 11.98 |
| 3746 | CA | ASP | A | 259 | 7.596 | 11.362 | 18.189 | 1.00 | 12.06 |
| 3748 | CB | ASP | A | 259 | 6.877 | 11.734 | 16.890 | 1.00 | 12.28 |
| 3751 | CG | ASP | A | 259 | 7.592 | 11.199 | 15.662 | 1.00 | 12.82 |
| 3752 | OD1 | ASP | A | 259 | 8.255 | 11.972 | 14.928 | 1.00 | 13.50 |
| 3753 | OD2 | ASP | A | 259 | 7.567 | 9.997 | 15.367 | 1.00 | 13.61 |
| 3754 | C | ASP | A | 259 | 8.871 | 12.199 | 18.309 | 1.00 | 12.75 |
| 3755 | O | ASP | A | 259 | 8.907 | 13.196 | 19.023 | 1.00 | 14.17 |
| 3756 | N | SER | A | 260 | 9.915 | 11.803 | 17.593 | 1.00 | 12.69 |
| 3758 | CA | SER | A | 260 | 11.133 | 12.606 | 17.553 | 1.00 | 12.78 |
| 3760 | CB | SER | A | 260 | 12.245 | 11.818 | 16.859 | 1.00 | 13.14 |
| 3763 | OG | SER | A | 260 | 11.902 | 11.533 | 15.525 | 1.00 | 14.29 |
| 3765 | C | SER | A | 260 | 10.946 | 13.983 | 16.882 | 1.00 | 12.78 |
| 3766 | O | SER | A | 260 | 11.763 | 14.883 | 17.090 | 1.00 | 13.36 |
| 3767 | N | SER | A | 261 | 9.891 | 14.148 | 16.086 | 1.00 | 12.92 |
| 3769 | CA | SER | A | 261 | 9.662 | 15.385 | 15.342 | 1.00 | 13.13 |

FIGURE 3 (cont.)

| A | B | C | D | E | F | G | H | I | J |
|---|---|---|---|---|---|---|---|---|---|
| 3771 | CB | SER | A | 261 | 9.726 | 15.110 | 13.847 | 1.00 | 13.52 |
| 3774 | OG | SER | A | 261 | 9.558 | 16.314 | 13.106 | 1.00 | 15.49 |
| 3776 | C | SER | A | 261 | 8.316 | 16.047 | 15.645 | 1.00 | 12.86 |
| 3777 | O | SER | A | 261 | 7.282 | 15.391 | 15.669 | 1.00 | 12.36 |
| 3778 | N | LEU | A | 262 | 8.345 | 17.365 | 15.810 | 1.00 | 13.43 |
| 3780 | CA | LEU | A | 262 | 7.111 | 18.146 | 15.922 | 1.00 | 13.79 |
| 3782 | CB | LEU | A | 262 | 7.411 | 19.585 | 16.344 | 1.00 | 14.71 |
| 3785 | CG | LEU | A | 262 | 7.796 | 19.741 | 17.812 | 1.00 | 16.69 |
| 3787 | CD1 | LEU | A | 262 | 8.483 | 21.061 | 18.024 | 1.00 | 18.30 |
| 3791 | CD2 | LEU | A | 262 | 6.575 | 19.622 | 18.706 | 1.00 | 18.44 |
| 3795 | C | LEU | A | 262 | 6.295 | 18.149 | 14.632 | 1.00 | 13.50 |
| 3796 | O | LEU | A | 262 | 5.077 | 18.334 | 14.671 | 1.00 | 13.90 |
| 3797 | N | TRP | A | 263 | 6.940 | 17.954 | 13.485 | 1.00 | 12.96 |
| 3799 | CA | TRP | A | 263 | 6.191 | 17.805 | 12.251 | 1.00 | 12.95 |
| 3801 | CB | TRP | A | 263 | 7.105 | 17.575 | 11.054 | 1.00 | 13.21 |
| 3804 | CG | TRP | A | 263 | 7.833 | 18.797 | 10.591 | 1.00 | 13.06 |
| 3805 | CD1 | TRP | A | 263 | 8.963 | 19.336 | 11.132 | 1.00 | 13.15 |
| 3807 | NE1 | TRP | A | 263 | 9.358 | 20.436 | 10.409 | 1.00 | 13.91 |
| 3809 | CE2 | TRP | A | 263 | 8.471 | 20.632 | 9.382 | 1.00 | 13.01 |
| 3810 | CD2 | TRP | A | 263 | 7.497 | 19.615 | 9.469 | 1.00 | 12.54 |
| 3811 | CE3 | TRP | A | 263 | 6.470 | 19.589 | 8.517 | 1.00 | 13.69 |
| 3813 | CZ3 | TRP | A | 263 | 6.448 | 20.570 | 7.525 | 1.00 | 14.28 |
| 3815 | CH2 | TRP | A | 263 | 7.422 | 21.570 | 7.475 | 1.00 | 14.58 |
| 3817 | CZ2 | TRP | A | 263 | 8.441 | 21.625 | 8.389 | 1.00 | 14.67 |
| 3819 | C | TRP | A | 263 | 5.202 | 16.647 | 12.387 | 1.00 | 12.67 |
| 3820 | O | TRP | A | 263 | 4.068 | 16.737 | 11.925 | 1.00 | 13.16 |
| 3821 | N | THR | A | 264 | 5.631 | 15.575 | 13.048 | 1.00 | 12.43 |
| 3823 | CA | THR | A | 264 | 4.772 | 14.414 | 13.260 | 1.00 | 12.40 |
| 3825 | CB | THR | A | 264 | 5.601 | 13.208 | 13.720 | 1.00 | 12.33 |
| 3827 | OG1 | THR | A | 264 | 6.631 | 12.927 | 12.761 | 1.00 | 13.89 |
| 3829 | CG2 | THR | A | 264 | 4.745 | 11.949 | 13.762 | 1.00 | 13.45 |
| 3833 | C | THR | A | 264 | 3.675 | 14.672 | 14.275 | 1.00 | 12.94 |
| 3834 | O | THR | A | 264 | 2.493 | 14.489 | 13.973 | 1.00 | 13.32 |
| 3835 | N | THR | A | 265 | 4.044 | 15.080 | 15.488 | 1.00 | 12.88 |
| 3837 | CA | THR | A | 265 | 3.043 | 15.176 | 16.542 | 1.00 | 13.43 |
| 3839 | CB | THR | A | 265 | 3.653 | 15.379 | 17.924 | 1.00 | 13.61 |
| 3841 | OG1 | THR | A | 265 | 4.476 | 16.544 | 17.950 | 1.00 | 13.50 |
| 3843 | CG2 | THR | A | 265 | 4.581 | 14.223 | 18.285 | 1.00 | 14.31 |
| 3847 | C | THR | A | 265 | 2.030 | 16.277 | 16.270 | 1.00 | 13.30 |
| 3848 | O | THR | A | 265 | 0.882 | 16.148 | 16.656 | 1.00 | 14.73 |
| 3849 | N | LEU | A | 266 | 2.439 | 17.346 | 15.595 | 1.00 | 13.38 |
| 3851 | CA | LEU | A | 266 | 1.478 | 18.412 | 15.285 | 1.00 | 13.34 |
| 3853 | CB | LEU | A | 266 | 2.175 | 19.760 | 15.049 | 1.00 | 13.45 |
| 3856 | CG | LEU | A | 266 | 2.923 | 20.354 | 16.251 | 1.00 | 14.57 |
| 3858 | CD1 | LEU | A | 266 | 3.639 | 21.633 | 15.849 | 1.00 | 14.76 |
| 3862 | CD2 | LEU | A | 266 | 1.997 | 20.630 | 17.449 | 1.00 | 16.72 |
| 3866 | C | LEU | A | 266 | 0.573 | 18.063 | 14.107 | 1.00 | 13.75 |
| 3867 | O | LEU | A | 266 | -0.626 | 18.331 | 14.158 | 1.00 | 14.43 |
| 3868 | N | LEU | A | 267 | 1.117 | 17.479 | 13.045 | 1.00 | 13.89 |

FIGURE 3 (cont.)

| A | B | C | D | E | F | G | H | I | J |
|---|---|---|---|---|---|---|---|---|---|
| 3870 | CA | LEU | A | 267 | 0.325 | 17.246 | 11.835 | 1.00 | 14.09 |
| 3872 | CB | LEU | A | 267 | 1.210 | 17.160 | 10.583 | 1.00 | 14.83 |
| 3875 | CG | LEU | A | 267 | 1.934 | 18.451 | 10.207 | 1.00 | 15.97 |
| 3877 | CD1 | LEU | A | 267 | 2.932 | 18.187 | 9.095 | 1.00 | 16.94 |
| 3881 | CD2 | LEU | A | 267 | 0.954 | 19.541 | 9.797 | 1.00 | 18.16 |
| 3885 | C | LEU | A | 267 | -0.557 | 16.008 | 11.918 | 1.00 | 14.25 |
| 3886 | O | LEU | A | 267 | -1.567 | 15.928 | 11.219 | 1.00 | 13.84 |
| 3887 | N | ILE | A | 268 | -0.189 | 15.039 | 12.758 | 1.00 | 14.62 |
| 3889 | CA | ILE | A | 268 | -0.932 | 13.783 | 12.823 | 1.00 | 15.29 |
| 3891 | CB | ILE | A | 268 | -0.044 | 12.644 | 13.406 | 1.00 | 15.57 |
| 3893 | CG1 | ILE | A | 268 | -0.572 | 11.270 | 12.972 | 1.00 | 18.61 |
| 3896 | CD1 | ILE | A | 268 | -0.268 | 10.952 | 11.536 | 1.00 | 20.22 |
| 3900 | CG2 | ILE | A | 268 | 0.071 | 12.769 | 14.928 | 1.00 | 16.48 |
| 3904 | C | ILE | A | 268 | -2.228 | 13.949 | 13.625 | 1.00 | 15.51 |
| 3905 | O | ILE | A | 268 | -3.153 | 13.132 | 13.514 | 1.00 | 15.43 |
| 3906 | N | ARG | A | 269 | -2.306 | 14.995 | 14.444 | 1.00 | 15.82 |
| 3908 | CA | ARG | A | 269 | -3.547 | 15.260 | 15.167 | 1.00 | 16.27 |
| 3910 | CB | ARG | A | 269 | -3.358 | 16.396 | 16.173 | 1.00 | 17.51 |
| 3913 | CG | ARG | A | 269 | -2.544 | 15.963 | 17.385 | 1.00 | 21.13 |
| 3916 | CD | ARG | A | 269 | -2.787 | 16.788 | 18.636 | 1.00 | 26.97 |
| 3919 | NE | ARG | A | 269 | -1.784 | 16.495 | 19.660 | 1.00 | 31.40 |
| 3921 | CZ | ARG | A | 269 | -1.731 | 17.060 | 20.860 | 1.00 | 34.49 |
| 3922 | NH1 | ARG | A | 269 | -0.755 | 16.721 | 21.698 | 1.00 | 36.54 |
| 3925 | NH2 | ARG | A | 269 | -2.641 | 17.955 | 21.233 | 1.00 | 36.22 |
| 3928 | C | ARG | A | 269 | -4.703 | 15.553 | 14.207 | 1.00 | 15.45 |
| 3929 | O | ARG | A | 269 | -4.535 | 16.209 | 13.184 | 1.00 | 15.18 |
| 3930 | N | ASN | A | 270 | -5.875 | 15.021 | 14.544 | 1.00 | 14.09 |
| 3932 | CA | ASN | A | 270 | -7.104 | 15.241 | 13.782 | 1.00 | 13.41 |
| 3934 | CB | ASN | A | 270 | -7.590 | 13.872 | 13.270 | 1.00 | 13.09 |
| 3937 | CG | ASN | A | 270 | -8.893 | 13.927 | 12.462 | 1.00 | 13.39 |
| 3938 | OD1 | ASN | A | 270 | -9.536 | 12.880 | 12.232 | 1.00 | 13.86 |
| 3939 | ND2 | ASN | A | 270 | -9.261 | 15.110 | 11.992 | 1.00 | 13.50 |
| 3942 | C | ASN | A | 270 | -8.148 | 15.912 | 14.688 | 1.00 | 13.21 |
| 3943 | O | ASN | A | 270 | -9.079 | 15.250 | 15.128 | 1.00 | 12.55 |
| 3944 | N | PRO | A | 271 | -7.996 | 17.206 | 14.995 | 1.00 | 13.34 |
| 3945 | CA | PRO | A | 271 | -8.950 | 17.903 | 15.877 | 1.00 | 13.52 |
| 3947 | CB | PRO | A | 271 | -8.372 | 19.327 | 15.969 | 1.00 | 13.91 |
| 3950 | CG | PRO | A | 271 | -7.529 | 19.468 | 14.753 | 1.00 | 13.93 |
| 3953 | CD | PRO | A | 271 | -6.916 | 18.111 | 14.553 | 1.00 | 13.66 |
| 3956 | C | PRO | A | 271 | -10.378 | 17.921 | 15.331 | 1.00 | 13.69 |
| 3957 | O | PRO | A | 271 | -11.315 | 17.977 | 16.131 | 1.00 | 13.14 |
| 3958 | N | SER | A | 272 | -10.548 | 17.822 | 14.016 | 1.00 | 13.03 |
| 3960 | CA | SER | A | 272 | -11.885 | 17.781 | 13.433 | 1.00 | 13.46 |
| 3962 | CB | SER | A | 272 | -11.828 | 17.710 | 11.912 | 1.00 | 14.11 |
| 3965 | OG | SER | A | 272 | -11.399 | 18.963 | 11.391 | 1.00 | 17.11 |
| 3967 | C | SER | A | 272 | -12.707 | 16.612 | 13.937 | 1.00 | 13.00 |
| 3968 | O | SER | A | 272 | -13.921 | 16.728 | 14.067 | 1.00 | 13.00 |
| 3969 | N | ARG | A | 273 | -12.068 | 15.474 | 14.176 | 1.00 | 12.78 |
| 3971 | CA | ARG | A | 273 | -12.801 | 14.324 | 14.697 | 1.00 | 11.90 |

FIGURE 3 (cont.)

| A | B | C | D | E | F | G | H | I | J |
|---|---|---|---|---|---|---|---|---|---|
| 3973 | CB | ARG | A | 273 | -11.881 | 13.097 | 14.830 | 1.00 | 11.99 |
| 3976 | CG | ARG | A | 273 | -12.475 | 11.991 | 15.640 | 1.00 | 11.46 |
| 3979 | CD | ARG | A | 273 | -11.762 | 10.657 | 15.526 | 1.00 | 11.09 |
| 3982 | NE | ARG | A | 273 | -11.980 | 9.902 | 16.767 | 1.00 | 9.70 |
| 3984 | CZ | ARG | A | 273 | -11.256 | 8.861 | 17.148 | 1.00 | 9.95 |
| 3985 | NH1 | ARG | A | 273 | -10.316 | 8.378 | 16.366 | 1.00 | 9.89 |
| 3988 | NH2 | ARG | A | 273 | -11.483 | 8.314 | 18.321 | 1.00 | 10.33 |
| 3991 | C | ARG | A | 273 | -13.461 | 14.652 | 16.049 | 1.00 | 12.29 |
| 3992 | O | ARG | A | 273 | -14.641 | 14.399 | 16.232 | 1.00 | 11.23 |
| 3993 | N | LYS | A | 274 | -12.712 | 15.206 | 16.994 | 1.00 | 13.15 |
| 3995 | CA | LYS | A | 274 | -13.276 | 15.476 | 18.318 | 1.00 | 14.18 |
| 3997 | CB | LYS | A | 274 | -12.195 | 15.840 | 19.347 | 1.00 | 15.51 |
| 4000 | CG | LYS | A | 274 | -11.587 | 14.602 | 20.043 | 1.00 | 19.22 |
| 4003 | CD | LYS | A | 274 | -12.529 | 13.934 | 21.064 | 1.00 | 23.59 |
| 4006 | CE | LYS | A | 274 | -12.715 | 14.754 | 22.349 | 1.00 | 26.53 |
| 4009 | NZ | LYS | A | 274 | -11.450 | 15.070 | 23.056 | 1.00 | 29.55 |
| 4013 | C | LYS | A | 274 | -14.349 | 16.566 | 18.238 | 1.00 | 13.43 |
| 4014 | O | LYS | A | 274 | -15.331 | 16.505 | 18.959 | 1.00 | 13.79 |
| 4015 | N | ILE | A | 275 | -14.170 | 17.531 | 17.341 | 1.00 | 12.90 |
| 4017 | CA | ILE | A | 275 | -15.179 | 18.569 | 17.120 | 1.00 | 12.53 |
| 4019 | CB | ILE | A | 275 | -14.676 | 19.649 | 16.129 | 1.00 | 13.20 |
| 4021 | CG1 | ILE | A | 275 | -13.619 | 20.505 | 16.827 | 1.00 | 14.01 |
| 4024 | CD1 | ILE | A | 275 | -12.753 | 21.320 | 15.876 | 1.00 | 14.59 |
| 4028 | CG2 | ILE | A | 275 | -15.841 | 20.530 | 15.635 | 1.00 | 13.51 |
| 4032 | C | ILE | A | 275 | -16.485 | 17.949 | 16.643 | 1.00 | 12.40 |
| 4033 | O | ILE | A | 275 | -17.547 | 18.253 | 17.186 | 1.00 | 11.97 |
| 4034 | N | LEU | A | 276 | -16.408 | 17.084 | 15.638 | 1.00 | 11.93 |
| 4036 | CA | LEU | A | 276 | -17.606 | 16.459 | 15.099 | 1.00 | 12.46 |
| 4038 | CB | LEU | A | 276 | -17.296 | 15.720 | 13.804 | 1.00 | 13.18 |
| 4041 | CG | LEU | A | 276 | -16.908 | 16.625 | 12.636 | 1.00 | 15.33 |
| 4043 | CD1 | LEU | A | 276 | -16.447 | 15.767 | 11.453 | 1.00 | 17.19 |
| 4047 | CD2 | LEU | A | 276 | -18.057 | 17.527 | 12.230 | 1.00 | 16.58 |
| 4051 | C | LEU | A | 276 | -18.252 | 15.529 | 16.115 | 1.00 | 11.71 |
| 4052 | O | LEU | A | 276 | -19.473 | 15.491 | 16.220 | 1.00 | 12.57 |
| 4053 | N | GLU | A | 277 | -17.451 | 14.796 | 16.881 | 1.00 | 11.42 |
| 4055 | CA | GLU | A | 277 | -18.011 | 13.963 | 17.941 | 1.00 | 11.20 |
| 4057 | CB | GLU | A | 277 | -16.933 | 13.172 | 18.678 | 1.00 | 11.21 |
| 4060 | CG | GLU | A | 277 | -16.283 | 12.100 | 17.818 | 1.00 | 10.62 |
| 4063 | CD | GLU | A | 277 | -15.046 | 11.474 | 18.436 | 1.00 | 11.45 |
| 4064 | OE1 | GLU | A | 277 | -14.485 | 10.547 | 17.821 | 1.00 | 10.82 |
| 4065 | OE2 | GLU | A | 277 | -14.594 | 11.890 | 19.531 | 1.00 | 13.35 |
| 4066 | C | GLU | A | 277 | -18.805 | 14.818 | 18.920 | 1.00 | 11.99 |
| 4067 | O | GLU | A | 277 | -19.901 | 14.453 | 19.318 | 1.00 | 12.45 |
| 4068 | N | PHE | A | 278 | -18.271 | 15.981 | 19.265 | 1.00 | 12.15 |
| 4070 | CA | PHE | A | 278 | -18.962 | 16.883 | 20.177 | 1.00 | 12.91 |
| 4072 | CB | PHE | A | 278 | -18.035 | 18.014 | 20.619 | 1.00 | 13.16 |
| 4075 | CG | PHE | A | 278 | -18.741 | 19.104 | 21.367 | 1.00 | 16.16 |
| 4076 | CD1 | PHE | A | 278 | -19.067 | 18.946 | 22.707 | 1.00 | 18.86 |
| 4078 | CE1 | PHE | A | 278 | -19.743 | 19.953 | 23.398 | 1.00 | 20.15 |

FIGURE 3 (cont.)

| A | B | C | D | E | F | G | H | I | J |
|---|---|---|---|---|---|---|---|---|---|
| 4080 | CZ | PHE | A | 278 | -20.100 | 21.115 | 22.743 | 1.00 | 20.75 |
| 4082 | CE2 | PHE | A | 278 | -19.790 | 21.280 | 21.397 | 1.00 | 19.66 |
| 4084 | CD2 | PHE | A | 278 | -19.109 | 20.268 | 20.717 | 1.00 | 18.31 |
| 4086 | C | PHE | A | 278 | -20.247 | 17.436 | 19.559 | 1.00 | 12.91 |
| 4087 | O | PHE | A | 278 | -21.299 | 17.443 | 20.207 | 1.00 | 12.84 |
| 4088 | N | LEU | A | 279 | -20.170 | 17.881 | 18.305 | 1.00 | 13.02 |
| 4090 | CA | LEU | A | 279 | -21.320 | 18.473 | 17.626 | 1.00 | 13.85 |
| 4092 | CB | LEU | A | 279 | -20.904 | 19.092 | 16.294 | 1.00 | 13.50 |
| 4095 | CG | LEU | A | 279 | -20.063 | 20.361 | 16.453 | 1.00 | 13.69 |
| 4097 | CD1 | LEU | A | 279 | -19.497 | 20.792 | 15.115 | 1.00 | 13.87 |
| 4101 | CD2 | LEU | A | 279 | -20.866 | 21.492 | 17.087 | 1.00 | 14.19 |
| 4105 | C | LEU | A | 279 | -22.418 | 17.434 | 17.418 | 1.00 | 15.13 |
| 4106 | O | LEU | A | 279 | -23.612 | 17.754 | 17.490 | 1.00 | 14.67 |
| 4107 | N | TYR | A | 280 | -22.009 | 16.187 | 17.206 | 1.00 | 17.39 |
| 4109 | CA | TYR | A | 280 | -22.956 | 15.098 | 16.952 | 1.00 | 18.83 |
| 4111 | CB | TYR | A | 280 | -22.263 | 13.922 | 16.248 | 1.00 | 18.64 |
| 4114 | CG | TYR | A | 280 | -21.829 | 14.138 | 14.812 | 1.00 | 17.60 |
| 4115 | CD1 | TYR | A | 280 | -21.223 | 13.107 | 14.108 | 1.00 | 16.54 |
| 4117 | CE1 | TYR | A | 280 | -20.829 | 13.255 | 12.805 | 1.00 | 17.67 |
| 4119 | CZ | TYR | A | 280 | -20.983 | 14.465 | 12.177 | 1.00 | 16.80 |
| 4120 | OH | TYR | A | 280 | -20.580 | 14.601 | 10.870 | 1.00 | 19.36 |
| 4122 | CE2 | TYR | A | 280 | -21.584 | 15.517 | 12.844 | 1.00 | 16.35 |
| 4124 | CD2 | TYR | A | 280 | -22.003 | 15.351 | 14.163 | 1.00 | 16.97 |
| 4126 | C | TYR | A | 280 | -23.625 | 14.583 | 18.236 | 1.00 | 20.92 |
| 4127 | O | TYR | A | 280 | -24.668 | 13.909 | 18.160 | 1.00 | 22.66 |
| 4128 | N | SER | A | 281 | -23.053 | 14.909 | 19.393 | 1.00 | 22.74 |
| 4130 | CA | SER | A | 281 | -23.441 | 14.319 | 20.679 | 1.00 | 24.99 |
| 4132 | CB | SER | A | 281 | -22.385 | 14.609 | 21.742 | 1.00 | 25.16 |
| 4135 | OG | SER | A | 281 | -22.373 | 15.981 | 22.104 | 1.00 | 24.47 |
| 4137 | C | SER | A | 281 | -24.806 | 14.743 | 21.222 | 1.00 | 27.70 |
| 4138 | O | SER | A | 281 | -25.362 | 14.054 | 22.089 | 1.00 | 28.32 |
| 4139 | N | THR | A | 282 | -25.330 | 15.867 | 20.748 | 1.00 | 30.09 |
| 4141 | CA | THR | A | 282 | -26.631 | 16.359 | 21.220 | 1.00 | 32.53 |
| 4143 | CB | THR | A | 282 | -26.808 | 17.861 | 20.901 | 1.00 | 32.60 |
| 4145 | OG1 | THR | A | 282 | -26.678 | 18.084 | 19.490 | 1.00 | 34.49 |
| 4147 | CG2 | THR | A | 282 | -25.699 | 18.699 | 21.521 | 1.00 | 34.08 |
| 4151 | C | THR | A | 282 | -27.795 | 15.586 | 20.609 | 1.00 | 33.55 |
| 4152 | O | THR | A | 282 | -28.919 | 15.684 | 21.096 | 1.00 | 33.93 |
| 4153 | N | SER | A | 283 | -27.519 | 14.815 | 19.555 | 1.00 | 34.90 |
| 4155 | CA | SER | A | 283 | -28.562 | 14.185 | 18.748 | 1.00 | 35.89 |
| 4157 | CB | SER | A | 283 | -28.139 | 14.181 | 17.273 | 1.00 | 35.89 |
| 4160 | OG | SER | A | 283 | -28.175 | 15.496 | 16.740 | 1.00 | 37.27 |
| 4162 | C | SER | A | 283 | -28.970 | 12.770 | 19.189 | 1.00 | 36.40 |
| 4163 | O | SER | A | 283 | -29.809 | 12.149 | 18.535 | 1.00 | 37.07 |
| 4164 | N | TYR | A | 284 | -28.410 | 12.250 | 20.282 | 1.00 | 37.17 |
| 4166 | CA | TYR | A | 284 | -28.940 | 10.995 | 20.839 | 1.00 | 37.25 |
| 4168 | CB | BTYR | A | 284 | -27.988 | 9.804 | 20.643 | 0.35 | 37.05 |
| 4169 | CB | ATYR | A | 284 | -28.006 | 9.802 | 20.558 | 0.65 | 37.18 |
| 4174 | CG | BTYR | A | 284 | -26.677 | 10.145 | 19.995 | 0.35 | 35.02 |

FIGURE 3 (cont.)

| A | B | C | D | E | F | G | H | I | J |
|---|---|---|---|---|---|---|---|---|---|
| 4175 | CG | A | TYR | A 284 | -26.519 | 10.087 | 20.631 | 0.65 | 35.41 |
| 4176 | CD1 | B | TYR | A 284 | -26.531 | 10.078 | 18.617 | 0.35 | 33.54 |
| 4177 | CD1 | A | TYR | A 284 | -25.709 | 10.016 | 19.495 | 0.65 | 34.19 |
| 4180 | CE1 | B | TYR | A 284 | -25.339 | 10.385 | 18.013 | 0.35 | 32.28 |
| 4181 | CE1 | A | TYR | A 284 | -24.334 | 10.270 | 19.576 | 0.65 | 33.47 |
| 4184 | CZ | B | TYR | A 284 | -24.264 | 10.772 | 18.785 | 0.35 | 31.47 |
| 4185 | CZ | A | TYR | A 284 | -23.774 | 10.592 | 20.800 | 0.65 | 32.46 |
| 4186 | OH | B | TYR | A 284 | -23.086 | 11.080 | 18.172 | 0.35 | 30.12 |
| 4187 | OH | A | TYR | A 284 | -22.428 | 10.845 | 20.910 | 0.65 | 31.11 |
| 4190 | CE2 | B | TYR | A 284 | -24.374 | 10.846 | 20.161 | 0.35 | 31.97 |
| 4191 | CE2 | A | TYR | A 284 | -24.562 | 10.664 | 21.930 | 0.65 | 33.01 |
| 4194 | CD2 | B | TYR | A 284 | -25.580 | 10.531 | 20.760 | 0.35 | 33.31 |
| 4195 | CD2 | A | TYR | A 284 | -25.921 | 10.411 | 21.839 | 0.65 | 33.91 |
| 4198 | C | | TYR | A 284 | -29.307 | 11.115 | 22.319 | 1.00 | 38.54 |
| 4199 | O | | TYR | A 284 | -28.651 | 11.823 | 23.089 | 1.00 | 39.00 |
| 4200 | N | | ASN | A 285 | -30.371 | 10.404 | 22.683 | 1.00 | 39.93 |
| 4202 | CA | | ASN | A 285 | -31.023 | 10.518 | 23.979 | 1.00 | 41.06 |
| 4204 | CB | | ASN | A 285 | -32.547 | 10.472 | 23.792 | 1.00 | 41.26 |
| 4207 | CG | | ASN | A 285 | -33.325 | 10.766 | 25.074 | 1.00 | 42.39 |
| 4208 | OD1 | | ASN | A 285 | -34.551 | 10.913 | 25.039 | 1.00 | 43.71 |
| 4209 | ND2 | | ASN | A 285 | -32.626 | 10.842 | 26.203 | 1.00 | 43.32 |
| 4212 | C | | ASN | A 285 | -30.557 | 9.363 | 24.852 | 1.00 | 41.84 |
| 4213 | O | | ASN | A 285 | -30.951 | 8.211 | 24.635 | 1.00 | 41.55 |
| 4214 | N | | MET | A 286 | -29.717 | 9.681 | 25.835 | 1.00 | 43.04 |
| 4216 | CA | | MET | A 286 | -29.148 | 8.662 | 26.719 | 1.00 | 43.94 |
| 4218 | CB | | MET | A 286 | -27.654 | 8.322 | 26.524 | 1.00 | 44.34 |
| 4221 | CG | | MET | A 286 | -26.829 | 9.341 | 25.747 | 1.00 | 45.83 |
| 4224 | SD | | MET | A 286 | -25.780 | 8.554 | 24.522 | 1.00 | 49.97 |
| 4225 | CE | | MET | A 286 | -24.522 | 7.957 | 25.487 | 1.00 | 48.62 |
| 4229 | C | | MET | A 286 | -29.820 | 8.056 | 27.966 | 1.00 | 44.23 |
| 4230 | O | | MET | A 286 | -29.294 | 7.130 | 28.584 | 1.00 | 44.03 |
| 4231 | N | | ASP | A 287 | -30.963 | 8.648 | 28.327 | 1.00 | 44.71 |
| 4233 | CA | | ASP | A 287 | -31.698 | 8.327 | 29.557 | 1.00 | 45.18 |
| 4235 | CB | | ASP | A 287 | -33.059 | 9.048 | 29.574 | 1.00 | 45.46 |
| 4238 | CG | | ASP | A 287 | -32.983 | 10.457 | 30.157 | 1.00 | 46.78 |
| 4239 | OD1 | | ASP | A 287 | -31.896 | 10.876 | 30.622 | 1.00 | 48.76 |
| 4240 | OD2 | | ASP | A 287 | -33.976 | 11.219 | 30.196 | 1.00 | 48.42 |
| 4241 | C | | ASP | A 287 | -31.924 | 6.832 | 29.722 | 1.00 | 45.05 |
| 4242 | O | | ASP | A 287 | -31.774 | 6.290 | 30.818 | 1.00 | 45.16 |
| 4243 | N | | ARG | A 288 | -32.305 | 6.190 | 28.621 | 1.00 | 44.98 |
| 4245 | CA | | ARG | A 288 | -32.384 | 4.733 | 28.511 | 1.00 | 45.09 |
| 4247 | CB | | ARG | A 288 | -32.289 | 4.344 | 27.029 | 1.00 | 45.17 |
| 4250 | CG | | ARG | A 288 | -33.171 | 3.189 | 26.602 | 1.00 | 45.72 |
| 4253 | CD | | ARG | A 288 | -34.168 | 3.567 | 25.523 | 1.00 | 45.90 |
| 4256 | NE | | ARG | A 288 | -34.313 | 2.539 | 24.499 | 1.00 | 46.47 |
| 4258 | CZ | | ARG | A 288 | -35.102 | 2.654 | 23.438 | 1.00 | 46.36 |
| 4259 | NH1 | | ARG | A 288 | -35.822 | 3.755 | 23.253 | 1.00 | 46.20 |
| 4262 | NH2 | | ARG | A 288 | -35.177 | 1.664 | 22.558 | 1.00 | 46.85 |
| 4265 | C | | ARG | A 288 | -31.259 | 4.017 | 29.265 | 1.00 | 45.02 |

FIGURE 3 (cont.)

| A | B | C | D | E | F | G | H | I | J |
|---|---|---|---|---|---|---|---|---|---|
| 4266 | O | ARG | A | 288 | -31.488 | 3.024 | 29.958 | 1.00 | 44.94 |
| 4267 | N | PHE | A | 289 | -30.042 | 4.527 | 29.088 | 1.00 | 44.85 |
| 4269 | CA | PHE | A | 289 | -28.837 | 3.962 | 29.681 | 1.00 | 44.69 |
| 4271 | CB | PHE | A | 289 | -27.821 | 3.652 | 28.579 | 1.00 | 44.59 |
| 4274 | CG | PHE | A | 289 | -28.433 | 3.138 | 27.301 | 1.00 | 44.14 |
| 4275 | CD1 | PHE | A | 289 | -28.731 | 4.004 | 26.258 | 1.00 | 44.11 |
| 4277 | CE1 | PHE | A | 289 | -29.285 | 3.526 | 25.065 | 1.00 | 43.59 |
| 4279 | CZ | PHE | A | 289 | -29.538 | 2.173 | 24.914 | 1.00 | 43.54 |
| 4281 | CE2 | PHE | A | 289 | -29.238 | 1.298 | 25.949 | 1.00 | 43.76 |
| 4283 | CD2 | PHE | A | 289 | -28.686 | 1.784 | 27.133 | 1.00 | 43.87 |
| 4285 | C | PHE | A | 289 | -28.210 | 4.930 | 30.684 | 1.00 | 44.78 |
| 4286 | O | PHE | A | 289 | -28.774 | 5.212 | 31.741 | 1.00 | 44.82 |
| 4287 | N | GLN | B | 20 | -5.719 | 3.636 | -4.824 | 1.00 | 36.45 |
| 4289 | CA | GLN | B | 20 | -5.585 | 3.373 | -6.276 | 1.00 | 35.95 |
| 4291 | CB | GLN | B | 20 | -6.503 | 2.214 | -6.665 | 1.00 | 35.41 |
| 4294 | CG | GLN | B | 20 | -7.985 | 2.459 | -6.412 | 1.00 | 31.81 |
| 4297 | CD | GLN | B | 20 | -8.514 | 1.877 | -5.103 | 1.00 | 27.25 |
| 4298 | OE1 | GLN | B | 20 | -7.843 | 1.105 | -4.393 | 1.00 | 18.76 |
| 4299 | NE2 | GLN | B | 20 | -9.742 | 2.243 | -4.794 | 1.00 | 25.21 |
| 4302 | C | GLN | B | 20 | -5.913 | 4.671 | -7.010 | 1.00 | 36.44 |
| 4303 | O | GLN | B | 20 | -5.929 | 5.728 | -6.386 | 1.00 | 37.25 |
| 4307 | N | GLN | B | 21 | -6.149 | 4.624 | -8.317 | 1.00 | 36.71 |
| 4309 | CA | GLN | B | 21 | -6.707 | 5.800 | -8.986 | 1.00 | 36.79 |
| 4311 | CB | GLN | B | 21 | -5.705 | 6.439 | -9.962 | 1.00 | 37.03 |
| 4314 | CG | GLN | B | 21 | -4.639 | 7.334 | -9.262 | 1.00 | 37.91 |
| 4317 | CD | GLN | B | 21 | -5.064 | 8.800 | -9.068 | 1.00 | 38.95 |
| 4318 | OE1 | GLN | B | 21 | -6.116 | 9.233 | -9.551 | 1.00 | 40.45 |
| 4319 | NE2 | GLN | B | 21 | -4.236 | 9.560 | -8.355 | 1.00 | 39.76 |
| 4322 | C | GLN | B | 21 | -8.040 | 5.450 | -9.653 | 1.00 | 36.53 |
| 4323 | O | GLN | B | 21 | -8.166 | 4.408 | -10.313 | 1.00 | 36.40 |
| 4324 | N | PRO | B | 22 | -9.047 | 6.304 | -9.464 | 1.00 | 36.31 |
| 4325 | CA | PRO | B | 22 | -10.382 | 6.008 | -9.979 | 1.00 | 36.04 |
| 4327 | CB | PRO | B | 22 | -11.271 | 7.093 | -9.346 | 1.00 | 36.07 |
| 4330 | CG | PRO | B | 22 | -10.423 | 7.815 | -8.380 | 1.00 | 36.23 |
| 4333 | CD | PRO | B | 22 | -9.005 | 7.615 | -8.789 | 1.00 | 36.26 |
| 4336 | C | PRO | B | 22 | -10.424 | 6.113 | -11.494 | 1.00 | 35.90 |
| 4337 | O | PRO | B | 22 | -9.489 | 6.637 | -12.106 | 1.00 | 36.05 |
| 4338 | N | LEU | B | 23 | -11.492 | 5.599 | -12.089 | 1.00 | 35.54 |
| 4340 | CA | LEU | B | 23 | -11.746 | 5.803 | -13.504 | 1.00 | 35.33 |
| 4342 | CB | LEU | B | 23 | -12.823 | 4.837 | -13.998 | 1.00 | 35.28 |
| 4345 | CG | LEU | B | 23 | -12.541 | 3.346 | -13.789 | 1.00 | 35.36 |
| 4347 | CD1 | LEU | B | 23 | -13.675 | 2.517 | -14.372 | 1.00 | 35.32 |
| 4351 | CD2 | LEU | B | 23 | -11.199 | 2.949 | -14.403 | 1.00 | 35.65 |
| 4355 | C | LEU | B | 23 | -12.202 | 7.247 | -13.685 | 1.00 | 35.19 |
| 4356 | O | LEU | B | 23 | -13.131 | 7.692 | -13.008 | 1.00 | 35.21 |
| 4357 | N | ASN | B | 24 | -11.529 | 7.978 | -14.572 | 1.00 | 34.72 |
| 4359 | CA | ASN | B | 24 | -11.889 | 9.357 | -14.884 | 1.00 | 34.51 |
| 4361 | CB | ASN | B | 24 | -10.658 | 10.134 | -15.375 | 1.00 | 34.65 |
| 4364 | CG | ASN | B | 24 | -10.893 | 11.639 | -15.443 | 1.00 | 35.54 |

FIGURE 3 (cont.)

| A | B | C | D | E | F | G | H | I | J |
|---|---|---|---|---|---|---|---|---|---|
| 4365 | OD1 | ASN | B | 24 | -11.928 | 12.146 | -15.004 | 1.00 | 37.54 |
| 4366 | ND2 | ASN | B | 24 | -9.920 | 12.360 | -15.994 | 1.00 | 36.15 |
| 4369 | C | ASN | B | 24 | -13.011 | 9.376 | -15.920 | 1.00 | 33.84 |
| 4370 | O | ASN | B | 24 | -12.798 | 9.658 | -17.101 | 1.00 | 33.82 |
| 4371 | N | GLU | B | 25 | -14.210 | 9.053 | -15.454 | 1.00 | 32.91 |
| 4373 | CA | GLU | B | 25 | -15.400 | 9.027 | -16.294 | 1.00 | 32.15 |
| 4375 | CB | GLU | B | 25 | -15.363 | 7.853 | -17.287 | 1.00 | 32.64 |
| 4378 | CG | GLU | B | 25 | -14.912 | 6.522 | -16.697 | 1.00 | 33.98 |
| 4381 | CD | GLU | B | 25 | -15.039 | 5.353 | -17.665 | 1.00 | 36.09 |
| 4382 | OE1 | GLU | B | 25 | -14.328 | 4.344 | -17.468 | 1.00 | 37.86 |
| 4383 | OE2 | GLU | B | 25 | -15.853 | 5.424 | -18.614 | 1.00 | 38.09 |
| 4384 | C | GLU | B | 25 | -16.637 | 8.943 | -15.405 | 1.00 | 30.71 |
| 4385 | O | GLU | B | 25 | -16.546 | 8.590 | -14.225 | 1.00 | 30.59 |
| 4386 | N | GLU | B | 26 | -17.786 | 9.295 | -15.969 | 1.00 | 28.93 |
| 4388 | CA | GLU | B | 26 | -19.037 | 9.228 | -15.239 | 1.00 | 27.75 |
| 4390 | CB | GLU | B | 26 | -20.111 | 10.094 | -15.905 | 1.00 | 28.26 |
| 4393 | CG | GLU | B | 26 | -21.115 | 10.688 | -14.923 | 1.00 | 30.31 |
| 4396 | CD | GLU | B | 26 | -21.800 | 11.930 | -15.464 | 1.00 | 33.30 |
| 4397 | OE1 | GLU | B | 26 | -23.048 | 11.928 | -15.556 | 1.00 | 34.92 |
| 4398 | OE2 | GLU | B | 26 | -21.090 | 12.905 | -15.801 | 1.00 | 35.14 |
| 4399 | C | GLU | B | 26 | -19.492 | 7.776 | -15.181 | 1.00 | 25.74 |
| 4400 | O | GLU | B | 26 | -19.273 | 7.004 | -16.115 | 1.00 | 25.10 |
| 4401 | N | PHE | B | 27 | -20.125 | 7.413 | -14.075 | 1.00 | 23.65 |
| 4403 | CA | PHE | B | 27 | -20.710 | 6.094 | -13.949 | 1.00 | 22.47 |
| 4405 | CB | PHE | B | 27 | -21.360 | 5.910 | -12.580 | 1.00 | 21.78 |
| 4408 | CG | PHE | B | 27 | -22.025 | 4.579 | -12.420 | 1.00 | 20.51 |
| 4409 | CD1 | PHE | B | 27 | -21.272 | 3.454 | -12.130 | 1.00 | 18.84 |
| 4411 | CE1 | PHE | B | 27 | -21.867 | 2.223 | -12.003 | 1.00 | 18.82 |
| 4413 | CZ | PHE | B | 27 | -23.242 | 2.095 | -12.161 | 1.00 | 18.47 |
| 4415 | CE2 | PHE | B | 27 | -24.003 | 3.202 | -12.459 | 1.00 | 19.59 |
| 4417 | CD2 | PHE | B | 27 | -23.400 | 4.440 | -12.591 | 1.00 | 19.83 |
| 4419 | C | PHE | B | 27 | -21.774 | 5.896 | -15.017 | 1.00 | 22.16 |
| 4420 | O | PHE | B | 27 | -22.550 | 6.809 | -15.310 | 1.00 | 22.26 |
| 4421 | N | ARG | B | 28 | -21.798 | 4.704 | -15.596 | 1.00 | 21.83 |
| 4423 | CA | ARG | B | 28 | -22.934 | 4.271 | -16.397 | 1.00 | 22.27 |
| 4425 | CB | ARG | B | 28 | -22.643 | 4.362 | -17.898 | 1.00 | 22.85 |
| 4428 | CG | ARG | B | 28 | -21.399 | 3.644 | -18.368 | 1.00 | 25.70 |
| 4431 | CD | ARG | B | 28 | -20.797 | 4.201 | -19.666 | 1.00 | 29.30 |
| 4434 | NE | ARG | B | 28 | -19.436 | 3.695 | -19.846 | 1.00 | 32.02 |
| 4436 | CZ | ARG | B | 28 | -19.125 | 2.505 | -20.363 | 1.00 | 34.35 |
| 4437 | NH1 | ARG | B | 28 | -20.072 | 1.673 | -20.793 | 1.00 | 35.52 |
| 4440 | NH2 | ARG | B | 28 | -17.848 | 2.144 | -20.459 | 1.00 | 35.35 |
| 4443 | C | ARG | B | 28 | -23.286 | 2.849 | -15.994 | 1.00 | 21.49 |
| 4444 | O | ARG | B | 28 | -22.394 | 2.047 | -15.725 | 1.00 | 20.35 |
| 4445 | N | PRO | B | 29 | -24.577 | 2.530 | -15.924 | 1.00 | 21.49 |
| 4446 | CA | PRO | B | 29 | -25.000 | 1.189 | -15.491 | 1.00 | 21.35 |
| 4448 | CB | PRO | B | 29 | -26.533 | 1.242 | -15.563 | 1.00 | 21.45 |
| 4451 | CG | PRO | B | 29 | -26.878 | 2.477 | -16.305 | 1.00 | 22.07 |
| 4454 | CD | PRO | B | 29 | -25.721 | 3.415 | -16.213 | 1.00 | 21.83 |

FIGURE 3 (cont.)

| A | B | C | D | E | F | G | H | I | J |
|---|---|---|---|---|---|---|---|---|---|
| 4457 | C | PRO | B | 29 | -24.432 | 0.039 | -16.334 | 1.00 | 20.88 |
| 4458 | O | PRO | B | 29 | -24.280 | -1.057 | -15.804 | 1.00 | 20.83 |
| 4459 | N | GLU | B | 30 | -24.076 | 0.289 | -17.593 | 1.00 | 20.54 |
| 4461 | CA | GLU | B | 30 | -23.489 | -0.753 | -18.439 | 1.00 | 20.88 |
| 4463 | CB | GLU | B | 30 | -23.369 | -0.290 | -19.891 | 1.00 | 21.30 |
| 4466 | CG | GLU | B | 30 | -24.670 | 0.226 | -20.480 | 1.00 | 24.00 |
| 4469 | CD | GLU | B | 30 | -24.699 | 1.741 | -20.540 | 1.00 | 27.46 |
| 4470 | OE1 | GLU | B | 30 | -25.159 | 2.369 | -19.560 | 1.00 | 27.28 |
| 4471 | OE2 | GLU | B | 30 | -24.234 | 2.303 | -21.562 | 1.00 | 30.43 |
| 4472 | C | GLU | B | 30 | -22.126 | -1.226 | -17.937 | 1.00 | 19.67 |
| 4473 | O | GLU | B | 30 | -21.675 | -2.297 | -18.310 | 1.00 | 19.61 |
| 4474 | N | MET | B | 31 | -21.475 | -0.425 | -17.092 | 1.00 | 19.18 |
| 4476 | CA | MET | B | 31 | -20.247 | -0.840 | -16.408 | 1.00 | 18.72 |
| 4478 | CB | MET | B | 31 | -19.775 | 0.251 | -15.451 | 1.00 | 18.80 |
| 4481 | CG | MET | B | 31 | -19.242 | 1.484 | -16.145 | 1.00 | 19.60 |
| 4484 | SD | MET | B | 31 | -18.784 | 2.784 | -14.992 | 1.00 | 19.64 |
| 4485 | CE | MET | B | 31 | -17.796 | 3.811 | -16.068 | 1.00 | 20.33 |
| 4489 | C | MET | B | 31 | -20.405 | -2.143 | -15.608 | 1.00 | 17.99 |
| 4490 | O | MET | B | 31 | -19.422 | -2.834 | -15.360 | 1.00 | 18.01 |
| 4491 | N | LEU | B | 32 | -21.629 | -2.463 | -15.191 | 1.00 | 17.19 |
| 4493 | CA | LEU | B | 32 | -21.883 | -3.684 | -14.419 | 1.00 | 16.71 |
| 4495 | CB | LEU | B | 32 | -22.773 | -3.383 | -13.205 | 1.00 | 17.00 |
| 4498 | CG | LEU | B | 32 | -22.084 | -2.882 | -11.928 | 1.00 | 18.30 |
| 4500 | CD1 | LEU | B | 32 | -21.044 | -3.883 | -11.441 | 1.00 | 18.08 |
| 4504 | CD2 | LEU | B | 32 | -21.464 | -1.517 | -12.159 | 1.00 | 18.86 |
| 4508 | C | LEU | B | 32 | -22.512 | -4.814 | -15.240 | 1.00 | 16.13 |
| 4509 | O | LEU | B | 32 | -22.620 | -5.934 | -14.756 | 1.00 | 14.69 |
| 4510 | N | GLN | B | 33 | -22.926 | -4.528 | -16.469 | 1.00 | 15.72 |
| 4512 | CA | GLN | B | 33 | -23.521 | -5.551 | -17.332 | 1.00 | 16.16 |
| 4514 | CB | GLN | B | 33 | -23.896 | -4.951 | -18.685 | 1.00 | 16.69 |
| 4517 | CG | GLN | B | 33 | -24.773 | -5.824 | -19.541 | 1.00 | 18.87 |
| 4520 | CD | GLN | B | 33 | -25.350 | -5.052 | -20.707 | 1.00 | 22.92 |
| 4521 | OE1 | GLN | B | 33 | -26.393 | -4.410 | -20.575 | 1.00 | 27.06 |
| 4522 | NE2 | GLN | B | 33 | -24.666 | -5.094 | -21.843 | 1.00 | 25.66 |
| 4525 | C | GLN | B | 33 | -22.567 | -6.722 | -17.542 | 1.00 | 15.74 |
| 4526 | O | GLN | B | 33 | -21.430 | -6.533 | -17.980 | 1.00 | 16.35 |
| 4527 | N | GLY | B | 34 | -23.023 | -7.926 | -17.209 | 1.00 | 14.59 |
| 4529 | CA | GLY | B | 34 | -22.210 | -9.122 | -17.354 | 1.00 | 14.57 |
| 4532 | C | GLY | B | 34 | -21.118 | -9.320 | -16.309 | 1.00 | 14.56 |
| 4533 | O | GLY | B | 34 | -20.411 | -10.330 | -16.341 | 1.00 | 15.11 |
| 4534 | N | LYS | B | 35 | -20.965 | -8.374 | -15.385 | 1.00 | 13.95 |
| 4536 | CA | LYS | B | 35 | -19.950 | -8.486 | -14.346 | 1.00 | 14.32 |
| 4538 | CB | LYS | B | 35 | -19.647 | -7.130 | -13.703 | 1.00 | 14.03 |
| 4541 | CG | LYS | B | 35 | -19.049 | -6.106 | -14.674 | 1.00 | 16.08 |
| 4544 | CD | LYS | B | 35 | -17.652 | -6.486 | -15.139 | 1.00 | 18.35 |
| 4547 | CE | LYS | B | 35 | -17.178 | -5.575 | -16.275 | 1.00 | 20.67 |
| 4550 | NZ | LYS | B | 35 | -15.715 | -5.720 | -16.509 | 1.00 | 22.25 |
| 4554 | C | LYS | B | 35 | -20.388 | -9.486 | -13.303 | 1.00 | 14.06 |
| 4555 | O | LYS | B | 35 | -21.572 | -9.706 | -13.108 | 1.00 | 14.30 |

FIGURE 3 (cont.)

| A | B | C | D | E | F | G | H | I | J |
|---|---|---|---|---|---|---|---|---|---|
| 4556 | N | LYS | B | 36 | -19.411 | -10.112 | -12.662 | 1.00 | 13.32 |
| 4558 | CA | LYS | B | 36 | -19.635 | -11.213 | -11.743 | 1.00 | 13.15 |
| 4560 | CB | LYS | B | 36 | -18.679 | -12.364 | -12.075 | 1.00 | 13.62 |
| 4563 | CG | LYS | B | 36 | -18.984 | -12.986 | -13.432 | 1.00 | 15.14 |
| 4566 | CD | LYS | B | 36 | -17.868 | -13.860 | -13.973 | 1.00 | 18.88 |
| 4569 | CE | LYS | B | 36 | -18.182 | -14.205 | -15.429 | 1.00 | 20.40 |
| 4572 | NZ | LYS | B | 36 | -17.391 | -15.346 | -15.955 | 1.00 | 21.94 |
| 4576 | C | LYS | B | 36 | -19.431 | -10.707 | -10.320 | 1.00 | 12.69 |
| 4577 | O | LYS | B | 36 | -18.317 | -10.362 | -9.937 | 1.00 | 12.18 |
| 4578 | N | VAL | B | 37 | -20.512 | -10.651 | -9.539 | 1.00 | 11.50 |
| 4580 | CA | VAL | B | 37 | -20.479 | -9.945 | -8.266 | 1.00 | 11.19 |
| 4582 | CB | VAL | B | 37 | -21.275 | -8.617 | -8.352 | 1.00 | 10.89 |
| 4584 | CG1 | VAL | B | 37 | -21.053 | -7.772 | -7.100 | 1.00 | 11.91 |
| 4588 | CG2 | VAL | B | 37 | -20.882 | -7.853 | -9.627 | 1.00 | 11.17 |
| 4592 | C | VAL | B | 37 | -21.003 | -10.788 | -7.118 | 1.00 | 11.28 |
| 4593 | O | VAL | B | 37 | -22.047 | -11.420 | -7.238 | 1.00 | 11.91 |
| 4594 | N | ILE | B | 38 | -20.245 | -10.811 | -6.025 | 1.00 | 11.11 |
| 4596 | CA | ILE | B | 38 | -20.697 | -11.350 | -4.743 | 1.00 | 11.28 |
| 4598 | CB | ILE | B | 38 | -19.535 | -12.065 | -4.019 | 1.00 | 11.56 |
| 4600 | CG1 | ILE | B | 38 | -19.256 | -13.419 | -4.672 | 1.00 | 12.32 |
| 4603 | CD1 | ILE | B | 38 | -17.990 | -14.080 | -4.186 | 1.00 | 12.03 |
| 4607 | CG2 | ILE | B | 38 | -19.795 | -12.190 | -2.502 | 1.00 | 11.25 |
| 4611 | C | ILE | B | 38 | -21.200 | -10.192 | -3.890 | 1.00 | 11.21 |
| 4612 | O | ILE | B | 38 | -20.535 | -9.157 | -3.788 | 1.00 | 10.09 |
| 4613 | N | VAL | B | 39 | -22.340 | -10.386 | -3.232 | 1.00 | 10.84 |
| 4615 | CA | VAL | B | 39 | -22.801 | -9.463 | -2.205 | 1.00 | 11.17 |
| 4617 | CB | VAL | B | 39 | -24.083 | -8.692 | -2.609 | 1.00 | 11.06 |
| 4619 | CG1 | VAL | B | 39 | -24.330 | -7.544 | -1.633 | 1.00 | 11.93 |
| 4623 | CG2 | VAL | B | 39 | -23.991 | -8.167 | -4.041 | 1.00 | 12.80 |
| 4627 | C | VAL | B | 39 | -23.086 | -10.263 | -0.948 | 1.00 | 10.67 |
| 4628 | O | VAL | B | 39 | -23.924 | -11.165 | -0.961 | 1.00 | 10.68 |
| 4629 | N | THR | B | 40 | -22.377 | -9.959 | 0.132 | 1.00 | 10.45 |
| 4631 | CA | THR | B | 40 | -22.686 | -10.569 | 1.416 | 1.00 | 10.33 |
| 4633 | CB | THR | B | 40 | -21.437 | -10.870 | 2.246 | 1.00 | 10.35 |
| 4635 | OG1 | THR | B | 40 | -20.872 | -9.645 | 2.756 | 1.00 | 11.62 |
| 4637 | CG2 | THR | B | 40 | -20.321 | -11.525 | 1.419 | 1.00 | 10.86 |
| 4641 | C | THR | B | 40 | -23.661 | -9.713 | 2.211 | 1.00 | 10.47 |
| 4642 | O | THR | B | 40 | -23.885 | -8.546 | 1.918 | 1.00 | 11.01 |
| 4643 | N | GLY | B | 41 | -24.269 | -10.331 | 3.212 | 1.00 | 10.59 |
| 4645 | CA | GLY | B | 41 | -25.315 | -9.686 | 3.980 | 1.00 | 10.74 |
| 4648 | C | GLY | B | 41 | -26.423 | -9.163 | 3.092 | 1.00 | 11.18 |
| 4649 | O | GLY | B | 41 | -26.892 | -8.039 | 3.266 | 1.00 | 10.32 |
| 4650 | N | ALA | B | 42 | -26.859 | -9.992 | 2.138 | 1.00 | 11.14 |
| 4652 | CA | ALA | B | 42 | -27.712 | -9.499 | 1.054 | 1.00 | 10.96 |
| 4654 | CB | ALA | B | 42 | -27.064 | -9.819 | -0.287 | 1.00 | 11.72 |
| 4658 | C | ALA | B | 42 | -29.164 | -9.972 | 1.094 | 1.00 | 11.56 |
| 4659 | O | ALA | B | 42 | -29.892 | -9.834 | 0.106 | 1.00 | 12.32 |
| 4660 | N | SER | B | 43 | -29.599 | -10.461 | 2.247 | 1.00 | 11.19 |
| 4662 | CA | SER | B | 43 | -30.968 | -10.948 | 2.405 | 1.00 | 11.28 |

FIGURE 3 (cont.)

| A | B | C | D | E | F | G | H | I | J |
|---|---|---|---|---|---|---|---|---|---|
| 4664 | CB | SER | B | 43 | -31.034 | -12.021 | 3.492 | 1.00 | 11.43 |
| 4667 | OG | SER | B | 43 | -30.663 | -11.501 | 4.763 | 1.00 | 11.82 |
| 4669 | C | SER | B | 43 | -31.921 | -9.823 | 2.751 | 1.00 | 10.78 |
| 4670 | O | SER | B | 43 | -33.129 | -9.955 | 2.603 | 1.00 | 10.88 |
| 4671 | N | LYS | B | 44 | -31.365 | -8.714 | 3.237 | 1.00 | 10.94 |
| 4673 | CA | LYS | B | 44 | -32.156 | -7.551 | 3.606 | 1.00 | 10.46 |
| 4675 | CB | LYS | B | 44 | -32.811 | -7.742 | 4.970 | 1.00 | 11.62 |
| 4678 | CG | LYS | B | 44 | -31.868 | -8.011 | 6.083 | 1.00 | 12.64 |
| 4681 | CD | LYS | B | 44 | -32.632 | -8.418 | 7.348 | 1.00 | 15.79 |
| 4684 | CE | LYS | B | 44 | -31.707 | -8.666 | 8.530 | 1.00 | 17.74 |
| 4687 | NZ | LYS | B | 44 | -32.515 | -8.929 | 9.774 | 1.00 | 18.83 |
| 4691 | C | LYS | B | 44 | -31.278 | -6.304 | 3.603 | 1.00 | 10.34 |
| 4692 | O | LYS | B | 44 | -30.098 | -6.365 | 3.266 | 1.00 | 10.13 |
| 4693 | N | GLY | B | 45 | -31.872 | -5.170 | 3.956 | 1.00 | 10.24 |
| 4695 | CA | GLY | B | 45 | -31.121 | -3.936 | 4.129 | 1.00 | 9.78 |
| 4698 | C | GLY | B | 45 | -30.421 | -3.471 | 2.864 | 1.00 | 9.92 |
| 4699 | O | GLY | B | 45 | -30.920 | -3.642 | 1.766 | 1.00 | 9.73 |
| 4700 | N | ILE | B | 46 | -29.260 | -2.847 | 3.051 | 1.00 | 9.83 |
| 4702 | CA | ILE | B | 46 | -28.482 | -2.284 | 1.967 | 1.00 | 10.71 |
| 4704 | CB | ILE | B | 46 | -27.310 | -1.427 | 2.560 | 1.00 | 10.90 |
| 4706 | CG1 | ILE | B | 46 | -27.860 | -0.274 | 3.417 | 1.00 | 11.85 |
| 4709 | CD1 | ILE | B | 46 | -26.916 | 0.187 | 4.490 | 1.00 | 12.01 |
| 4713 | CG2 | ILE | B | 46 | -26.430 | -0.898 | 1.460 | 1.00 | 11.89 |
| 4717 | C | ILE | B | 46 | -27.977 | -3.367 | 1.008 | 1.00 | 10.36 |
| 4718 | O | ILE | B | 46 | -27.950 | -3.158 | -0.198 | 1.00 | 10.94 |
| 4719 | N | GLY | B | 47 | -27.585 | -4.522 | 1.547 | 1.00 | 10.39 |
| 4721 | CA | GLY | B | 47 | -27.108 | -5.631 | 0.737 | 1.00 | 10.40 |
| 4724 | C | GLY | B | 47 | -28.163 | -6.101 | -0.252 | 1.00 | 10.58 |
| 4725 | O | GLY | B | 47 | -27.870 | -6.321 | -1.422 | 1.00 | 10.10 |
| 4726 | N | ARG | B | 48 | -29.390 | -6.268 | 0.215 | 1.00 | 10.36 |
| 4728 | CA | ARG | B | 48 | -30.495 | -6.643 | -0.669 | 1.00 | 10.85 |
| 4730 | CB | ARG | B | 48 | -31.804 | -6.838 | 0.116 | 1.00 | 10.81 |
| 4733 | CG | ARG | B | 48 | -33.065 | -6.998 | -0.755 | 1.00 | 12.26 |
| 4736 | CD | ARG | B | 48 | -34.283 | -7.475 | 0.020 | 1.00 | 13.95 |
| 4739 | NE | ARG | B | 48 | -34.603 | -6.543 | 1.096 | 1.00 | 15.81 |
| 4741 | CZ | ARG | B | 48 | -35.534 | -6.735 | 2.029 | 1.00 | 18.10 |
| 4742 | NH1 | ARG | B | 48 | -36.298 | -7.823 | 2.020 | 1.00 | 18.81 |
| 4745 | NH2 | ARG | B | 48 | -35.720 | -5.820 | 2.971 | 1.00 | 18.46 |
| 4748 | C | ARG | B | 48 | -30.680 | -5.594 | -1.767 | 1.00 | 10.59 |
| 4749 | O | ARG | B | 48 | -30.843 | -5.937 | -2.929 | 1.00 | 10.42 |
| 4750 | N | GLU | B | 49 | -30.627 | -4.313 | -1.410 | 1.00 | 10.73 |
| 4752 | CA | GLU | B | 49 | -30.780 | -3.266 | -2.417 | 1.00 | 10.56 |
| 4754 | CB | GLU | B | 49 | -30.895 | -1.889 | -1.775 | 1.00 | 11.33 |
| 4757 | CG | GLU | B | 49 | -32.095 | -1.721 | -0.847 | 1.00 | 11.49 |
| 4760 | CD | GLU | B | 49 | -33.433 | -2.050 | -1.499 | 1.00 | 16.05 |
| 4761 | OE1 | GLU | B | 49 | -34.297 | -2.645 | -0.814 | 1.00 | 16.08 |
| 4762 | OE2 | GLU | B | 49 | -33.633 | -1.713 | -2.694 | 1.00 | 18.16 |
| 4763 | C | GLU | B | 49 | -29.634 | -3.275 | -3.414 | 1.00 | 10.64 |
| 4764 | O | GLU | B | 49 | -29.848 | -3.010 | -4.588 | 1.00 | 11.13 |

FIGURE 3 (cont.)

| A | B | C | D | E | F | G | H | I | J |
|---|---|---|---|---|---|---|---|---|---|
| 4765 | N | MET | B | 50 | -28.428 | -3.585 | -2.958 | 1.00 | 10.44 |
| 4767 | CA | MET | B | 50 | -27.299 | -3.700 | -3.876 | 1.00 | 10.75 |
| 4769 | CB | MET | B | 50 | -25.982 | -3.888 | -3.118 | 1.00 | 10.94 |
| 4772 | CG | MET | B | 50 | -25.500 | -2.599 | -2.496 | 1.00 | 11.45 |
| 4775 | SD | MET | B | 50 | -23.833 | -2.637 | -1.809 | 1.00 | 12.29 |
| 4776 | CE | MET | B | 50 | -24.061 | -3.638 | -0.349 | 1.00 | 11.44 |
| 4780 | C | MET | B | 50 | -27.528 | -4.833 | -4.877 | 1.00 | 11.28 |
| 4781 | O | MET | B | 50 | -27.306 | -4.658 | -6.072 | 1.00 | 11.30 |
| 4782 | N | ALA | B | 51 | -27.994 | -5.980 | -4.401 | 1.00 | 11.40 |
| 4784 | CA | ALA | B | 51 | -28.326 | -7.096 | -5.284 | 1.00 | 11.74 |
| 4786 | CB | ALA | B | 51 | -28.836 | -8.277 | -4.479 | 1.00 | 11.64 |
| 4790 | C | ALA | B | 51 | -29.352 | -6.677 | -6.334 | 1.00 | 11.49 |
| 4791 | O | ALA | B | 51 | -29.209 | -6.998 | -7.507 | 1.00 | 11.83 |
| 4792 | N | TYR | B | 52 | -30.366 | -5.927 | -5.923 | 1.00 | 11.06 |
| 4794 | CA | TYR | B | 52 | -31.413 | -5.496 | -6.840 | 1.00 | 11.42 |
| 4796 | CB | TYR | B | 52 | -32.560 | -4.833 | -6.078 | 1.00 | 11.42 |
| 4799 | CG | TYR | B | 52 | -33.399 | -5.774 | -5.236 | 1.00 | 12.30 |
| 4800 | CD1 | TYR | B | 52 | -33.282 | -7.162 | -5.342 | 1.00 | 12.93 |
| 4802 | CE1 | TYR | B | 52 | -34.069 | -8.006 | -4.560 | 1.00 | 13.87 |
| 4804 | CZ | TYR | B | 52 | -34.975 | -7.467 | -3.676 | 1.00 | 14.55 |
| 4805 | OH | TYR | B | 52 | -35.756 | -8.313 | -2.908 | 1.00 | 17.23 |
| 4807 | CE2 | TYR | B | 52 | -35.101 | -6.110 | -3.548 | 1.00 | 14.56 |
| 4809 | CD2 | TYR | B | 52 | -34.314 | -5.266 | -4.327 | 1.00 | 14.92 |
| 4811 | C | TYR | B | 52 | -30.883 | -4.549 | -7.905 | 1.00 | 11.61 |
| 4812 | O | TYR | B | 52 | -31.247 | -4.680 | -9.066 | 1.00 | 12.01 |
| 4813 | N | HIS | B | 53 | -30.021 | -3.600 | -7.528 | 1.00 | 11.20 |
| 4815 | CA | HIS | B | 53 | -29.437 | -2.693 | -8.515 | 1.00 | 11.41 |
| 4817 | CB | HIS | B | 53 | -28.589 | -1.621 | -7.839 | 1.00 | 11.43 |
| 4820 | CG | HIS | B | 53 | -29.379 | -0.476 | -7.303 | 1.00 | 11.70 |
| 4821 | ND1 | HIS | B | 53 | -30.181 | 0.313 | -8.098 | 1.00 | 14.86 |
| 4823 | CE1 | HIS | B | 53 | -30.743 | 1.248 | -7.354 | 1.00 | 14.75 |
| 4825 | NE2 | HIS | B | 53 | -30.341 | 1.087 | -6.109 | 1.00 | 13.92 |
| 4827 | CD2 | HIS | B | 53 | -29.480 | 0.024 | -6.050 | 1.00 | 13.65 |
| 4829 | C | HIS | B | 53 | -28.560 | -3.451 | -9.497 | 1.00 | 11.22 |
| 4830 | O | HIS | B | 53 | -28.610 | -3.200 | -10.695 | 1.00 | 12.07 |
| 4831 | N | LEU | B | 54 | -27.754 | -4.372 | -8.980 | 1.00 | 11.26 |
| 4833 | CA | LEU | B | 54 | -26.889 | -5.180 | -9.823 | 1.00 | 11.80 |
| 4835 | CB | LEU | B | 54 | -26.003 | -6.090 | -8.977 | 1.00 | 11.35 |
| 4838 | CG | LEU | B | 54 | -24.920 | -5.357 | -8.182 | 1.00 | 11.68 |
| 4840 | CD1 | LEU | B | 54 | -24.424 | -6.229 | -7.039 | 1.00 | 11.98 |
| 4844 | CD2 | LEU | B | 54 | -23.764 | -4.906 | -9.092 | 1.00 | 12.69 |
| 4848 | C | LEU | B | 54 | -27.722 | -5.983 | -10.816 | 1.00 | 11.95 |
| 4849 | O | LEU | B | 54 | -27.373 | -6.073 | -11.991 | 1.00 | 12.30 |
| 4850 | N | ALA | B | 55 | -28.835 | -6.540 | -10.348 | 1.00 | 12.23 |
| 4852 | CA | ALA | B | 55 | -29.738 | -7.299 | -11.204 | 1.00 | 12.51 |
| 4854 | CB | ALA | B | 55 | -30.878 | -7.867 | -10.382 | 1.00 | 12.61 |
| 4858 | C | ALA | B | 55 | -30.282 | -6.429 | -12.343 | 1.00 | 13.29 |
| 4859 | O | ALA | B | 55 | -30.268 | -6.825 | -13.511 | 1.00 | 12.82 |
| 4860 | N | LYS | B | 56 | -30.753 | -5.240 | -12.000 | 1.00 | 13.47 |

FIGURE 3 (cont.)

| A | B | C | D | E | F | G | H | I | J |
|---|---|---|---|---|---|---|---|---|---|
| 4862 | CA | LYS | B | 56 | -31.265 | -4.302 | -12.997 | 1.00 | 14.78 |
| 4864 | CB | LYS | B | 56 | -31.794 | -3.045 | -12.320 | 1.00 | 15.21 |
| 4867 | CG | LYS | B | 56 | -33.150 | -3.214 | -11.665 | 1.00 | 18.77 |
| 4870 | CD | LYS | B | 56 | -33.802 | -1.864 | -11.341 | 1.00 | 21.92 |
| 4873 | CE | LYS | B | 56 | -33.504 | -1.411 | -9.912 | 1.00 | 24.95 |
| 4876 | NZ | LYS | B | 56 | -34.617 | -0.581 | -9.354 | 1.00 | 25.95 |
| 4880 | C | LYS | B | 56 | -30.202 | -3.930 | -14.046 | 1.00 | 14.64 |
| 4881 | O | LYS | B | 56 | -30.541 | -3.667 | -15.203 | 1.00 | 15.61 |
| 4882 | N | MET | B | 57 | -28.930 | -3.924 | -13.640 | 1.00 | 14.23 |
| 4884 | CA | MET | B | 57 | -27.812 | -3.617 | -14.529 | 1.00 | 14.34 |
| 4886 | CB | MET | B | 57 | -26.634 | -3.084 | -13.710 | 1.00 | 14.23 |
| 4889 | CG | MET | B | 57 | -26.908 | -1.759 | -13.031 | 1.00 | 16.36 |
| 4892 | SD | MET | B | 57 | -25.547 | -1.291 | -11.913 | 1.00 | 21.40 |
| 4893 | CE | MET | B | 57 | -26.338 | -0.108 | -10.855 | 1.00 | 20.93 |
| 4897 | C | MET | B | 57 | -27.358 | -4.826 | -15.359 | 1.00 | 13.43 |
| 4898 | O | MET | B | 57 | -26.489 | -4.704 | -16.224 | 1.00 | 13.77 |
| 4899 | N | GLY | B | 58 | -27.929 | -5.995 | -15.092 | 1.00 | 12.87 |
| 4901 | CA | GLY | B | 58 | -27.622 | -7.198 | -15.840 | 1.00 | 12.60 |
| 4904 | C | GLY | B | 58 | -26.355 | -7.904 | -15.412 | 1.00 | 12.64 |
| 4905 | O | GLY | B | 58 | -25.724 | -8.601 | -16.222 | 1.00 | 12.60 |
| 4906 | N | ALA | B | 59 | -25.976 | -7.729 | -14.149 | 1.00 | 12.67 |
| 4908 | CA | ALA | B | 59 | -24.853 | -8.450 | -13.579 | 1.00 | 12.49 |
| 4910 | CB | ALA | B | 59 | -24.352 | -7.744 | -12.318 | 1.00 | 13.04 |
| 4914 | C | ALA | B | 59 | -25.215 | -9.892 | -13.249 | 1.00 | 13.02 |
| 4915 | O | ALA | B | 59 | -26.388 | -10.239 | -13.127 | 1.00 | 12.97 |
| 4916 | N | HIS | B | 60 | -24.194 | -10.731 | -13.122 | 1.00 | 12.99 |
| 4918 | CA | HIS | B | 60 | -24.330 | -12.015 | -12.441 | 1.00 | 13.22 |
| 4920 | CB | HIS | B | 60 | -23.277 | -13.007 | -12.914 | 1.00 | 13.72 |
| 4923 | CG | HIS | B | 60 | -23.336 | -13.325 | -14.374 | 1.00 | 13.97 |
| 4924 | ND1 | HIS | B | 60 | -24.021 | -14.413 | -14.867 | 1.00 | 14.72 |
| 4926 | CE1 | HIS | B | 60 | -23.862 | -14.472 | -16.178 | 1.00 | 16.58 |
| 4928 | NE2 | HIS | B | 60 | -23.095 | -13.462 | -16.553 | 1.00 | 15.42 |
| 4930 | CD2 | HIS | B | 60 | -22.748 | -12.733 | -15.441 | 1.00 | 14.82 |
| 4932 | C | HIS | B | 60 | -24.122 | -11.754 | -10.962 | 1.00 | 13.22 |
| 4933 | O | HIS | B | 60 | -23.175 | -11.064 | -10.592 | 1.00 | 12.64 |
| 4934 | N | VAL | B | 61 | -24.978 | -12.313 | -10.114 | 1.00 | 13.18 |
| 4936 | CA | VAL | B | 61 | -24.894 | -12.069 | -8.674 | 1.00 | 13.14 |
| 4938 | CB | BVAL | B | 61 | -25.986 | -11.093 | -8.136 | 0.35 | 12.98 |
| 4939 | CB | AVAL | B | 61 | -26.028 | -11.118 | -8.199 | 0.65 | 13.49 |
| 4942 | CG1 | BVAL | B | 61 | -25.700 | -9.668 | -8.572 | 0.35 | 12.81 |
| 4943 | CG1 | AVAL | B | 61 | -25.784 | -10.644 | -6.786 | 0.65 | 14.74 |
| 4950 | CG2 | BVAL | B | 61 | -27.397 | -11.534 | -8.549 | 0.35 | 12.59 |
| 4951 | CG2 | AVAL | B | 61 | -26.188 | -9.941 | -9.155 | 0.65 | 13.97 |
| 4958 | C | VAL | B | 61 | -24.974 | -13.364 | -7.891 | 1.00 | 12.92 |
| 4959 | O | VAL | B | 61 | -25.766 | -14.252 | -8.213 | 1.00 | 12.38 |
| 4960 | N | VAL | B | 62 | -24.145 | -13.466 | -6.861 | 1.00 | 12.25 |
| 4962 | CA | VAL | B | 62 | -24.303 | -14.499 | -5.857 | 1.00 | 12.23 |
| 4964 | CB | VAL | B | 62 | -23.119 | -15.481 | -5.824 | 1.00 | 12.33 |
| 4966 | CG1 | VAL | B | 62 | -23.301 | -16.504 | -4.717 | 1.00 | 13.22 |

FIGURE 3 (cont.)

| A | B | C | D | E | F | G | H | I | J |
|---|---|---|---|---|---|---|---|---|---|
| 4970 | CG2 | VAL | B | 62 | -22.962 | -16.171 | -7.181 | 1.00 | 13.64 |
| 4974 | C | VAL | B | 62 | -24.452 | -13.776 | -4.530 | 1.00 | 12.12 |
| 4975 | O | VAL | B | 62 | -23.599 | -12.970 | -4.155 | 1.00 | 12.10 |
| 4976 | N | VAL | B | 63 | -25.548 | -14.054 | -3.837 | 1.00 | 11.41 |
| 4978 | CA | VAL | B | 63 | -25.850 | -13.434 | -2.559 | 1.00 | 11.23 |
| 4980 | CB | VAL | B | 63 | -27.268 | -12.801 | -2.536 | 1.00 | 11.45 |
| 4982 | CG1 | VAL | B | 63 | -28.369 | -13.810 | -2.845 | 1.00 | 12.29 |
| 4986 | CG2 | VAL | B | 63 | -27.341 | -11.610 | -3.490 | 1.00 | 12.95 |
| 4990 | C | VAL | B | 63 | -25.716 | -14.428 | -1.421 | 1.00 | 11.27 |
| 4991 | O | VAL | B | 63 | -25.950 | -15.624 | -1.599 | 1.00 | 11.43 |
| 4992 | N | THR | B | 64 | -25.345 | -13.928 | -0.251 | 1.00 | 11.16 |
| 4994 | CA | THR | B | 64 | -25.289 | -14.742 | 0.941 | 1.00 | 10.94 |
| 4996 | CB | THR | B | 64 | -23.881 | -15.367 | 1.092 | 1.00 | 11.01 |
| 4998 | OG1 | THR | B | 64 | -23.873 | -16.336 | 2.151 | 1.00 | 11.55 |
| 5000 | CG2 | THR | B | 64 | -22.810 | -14.327 | 1.455 | 1.00 | 10.73 |
| 5004 | C | THR | B | 64 | -25.743 | -14.004 | 2.202 | 1.00 | 11.00 |
| 5005 | O | THR | B | 64 | -25.799 | -12.767 | 2.240 | 1.00 | 10.83 |
| 5006 | N | ALA | B | 65 | -26.082 | -14.821 | 3.188 | 1.00 | 10.69 |
| 5008 | CA | ALA | B | 65 | -26.584 | -14.488 | 4.527 | 1.00 | 10.22 |
| 5010 | CB | ALA | B | 65 | -27.824 | -13.624 | 4.480 | 1.00 | 10.27 |
| 5014 | C | ALA | B | 65 | -26.890 | -15.844 | 5.171 | 1.00 | 10.61 |
| 5015 | O | ALA | B | 65 | -26.720 | -16.885 | 4.541 | 1.00 | 10.78 |
| 5016 | N | ARG | B | 66 | -27.373 | -15.862 | 6.407 | 1.00 | 11.87 |
| 5018 | CA | ARG | B | 66 | -27.688 | -17.139 | 7.050 | 1.00 | 12.24 |
| 5020 | CB | ARG | B | 66 | -27.682 | -17.001 | 8.573 | 1.00 | 11.88 |
| 5023 | CG | ARG | B | 66 | -26.308 | -16.697 | 9.161 | 1.00 | 10.67 |
| 5026 | CD | ARG | B | 66 | -26.333 | -16.321 | 10.626 | 1.00 | 10.36 |
| 5029 | NE | ARG | B | 66 | -27.156 | -15.139 | 10.856 | 1.00 | 11.69 |
| 5031 | CZ | ARG | B | 66 | -27.501 | -14.685 | 12.049 | 1.00 | 13.13 |
| 5032 | NH1 | ARG | B | 66 | -28.268 | -13.612 | 12.149 | 1.00 | 14.08 |
| 5035 | NH2 | ARG | B | 66 | -27.085 | -15.292 | 13.150 | 1.00 | 16.68 |
| 5038 | C | ARG | B | 66 | -29.026 | -17.729 | 6.590 | 1.00 | 13.55 |
| 5039 | O | ARG | B | 66 | -29.167 | -18.958 | 6.519 | 1.00 | 14.49 |
| 5040 | N | SER | B | 67 | -29.994 | -16.868 | 6.278 | 1.00 | 14.61 |
| 5042 | CA | SER | B | 67 | -31.380 | -17.315 | 6.057 | 1.00 | 15.17 |
| 5044 | CB | BSER | B | 67 | -32.348 | -16.251 | 6.568 | 0.35 | 15.27 |
| 5045 | CB | ASER | B | 67 | -32.378 | -16.274 | 6.552 | 0.65 | 15.48 |
| 5050 | OG | BSER | B | 67 | -31.936 | -15.747 | 7.829 | 0.35 | 15.23 |
| 5051 | OG | ASER | B | 67 | -33.718 | -16.653 | 6.243 | 0.65 | 16.23 |
| 5054 | C | SER | B | 67 | -31.676 | -17.641 | 4.596 | 1.00 | 15.57 |
| 5055 | O | SER | B | 67 | -31.746 | -16.751 | 3.757 | 1.00 | 15.08 |
| 5056 | N | LYS | B | 68 | -31.879 | -18.921 | 4.306 | 1.00 | 16.31 |
| 5058 | CA | LYS | B | 68 | -32.209 | -19.356 | 2.948 | 1.00 | 16.94 |
| 5060 | CB | LYS | B | 68 | -32.230 | -20.887 | 2.853 | 1.00 | 17.69 |
| 5063 | CG | LYS | B | 68 | -33.262 | -21.557 | 3.738 | 1.00 | 20.27 |
| 5066 | CD | LYS | B | 68 | -33.168 | -23.071 | 3.671 | 1.00 | 23.39 |
| 5069 | CE | LYS | B | 68 | -34.158 | -23.700 | 4.631 | 1.00 | 25.32 |
| 5072 | NZ | LYS | B | 68 | -35.566 | -23.319 | 4.295 | 1.00 | 26.88 |
| 5076 | C | LYS | B | 68 | -33.544 | -18.766 | 2.482 | 1.00 | 17.00 |

FIGURE 3 (cont.)

| A | B | C | D | E | F | G | H | I | J |
|---|---|---|---|---|---|---|---|---|---|
| 5077 | O | LYS | B | 68 | -33.697 | -18.424 | 1.321 | 1.00 | 16.21 |
| 5078 | N | GLU | B | 69 | -34.506 | -18.646 | 3.394 | 1.00 | 17.16 |
| 5080 | CA | GLU | B | 69 | -35.846 | -18.171 | 3.036 | 1.00 | 18.03 |
| 5082 | CB | GLU | B | 69 | -36.781 | -18.309 | 4.246 | 1.00 | 19.01 |
| 5085 | CG | GLU | B | 69 | -38.074 | -17.512 | 4.186 | 1.00 | 22.91 |
| 5088 | CD | GLU | B | 69 | -38.962 | -17.761 | 5.395 | 1.00 | 27.61 |
| 5089 | OE1 | GLU | B | 69 | -38.646 | -18.679 | 6.180 | 1.00 | 29.79 |
| 5090 | OE2 | GLU | B | 69 | -39.970 | -17.032 | 5.562 | 1.00 | 31.63 |
| 5091 | C | GLU | B | 69 | -35.831 | -16.738 | 2.491 | 1.00 | 16.82 |
| 5092 | O | GLU | B | 69 | -36.443 | -16.448 | 1.464 | 1.00 | 16.76 |
| 5093 | N | THR | B | 70 | -35.110 | -15.851 | 3.170 | 1.00 | 15.59 |
| 5095 | CA | THR | B | 70 | -35.016 | -14.462 | 2.743 | 1.00 | 14.70 |
| 5097 | CB | THR | B | 70 | -34.575 | -13.560 | 3.920 | 1.00 | 15.40 |
| 5099 | OG1 | THR | B | 70 | -33.385 | -14.074 | 4.513 | 1.00 | 15.62 |
| 5101 | CG2 | THR | B | 70 | -35.596 | -13.629 | 5.048 | 1.00 | 16.12 |
| 5105 | C | THR | B | 70 | -34.088 | -14.317 | 1.536 | 1.00 | 13.87 |
| 5106 | O | THR | B | 70 | -34.341 | -13.493 | 0.665 | 1.00 | 13.80 |
| 5107 | N | LEU | B | 71 | -33.018 | -15.106 | 1.483 | 1.00 | 12.53 |
| 5109 | CA | LEU | B | 71 | -32.147 | -15.108 | 0.303 | 1.00 | 12.28 |
| 5111 | CB | LEU | B | 71 | -30.931 | -16.017 | 0.507 | 1.00 | 12.21 |
| 5114 | CG | LEU | B | 71 | -29.894 | -15.505 | 1.494 | 1.00 | 12.18 |
| 5116 | CD1 | LEU | B | 71 | -28.896 | -16.600 | 1.831 | 1.00 | 12.74 |
| 5120 | CD2 | LEU | B | 71 | -29.176 | -14.298 | 0.915 | 1.00 | 13.61 |
| 5124 | C | LEU | B | 71 | -32.906 | -15.541 | -0.946 | 1.00 | 12.33 |
| 5125 | O | LEU | B | 71 | -32.691 | -14.998 | -2.024 | 1.00 | 11.70 |
| 5126 | N | GLN | B | 72 | -33.799 | -16.513 | -0.788 | 1.00 | 12.93 |
| 5128 | CA | GLN | B | 72 | -34.564 | -17.053 | -1.915 | 1.00 | 13.12 |
| 5130 | CB | BGLN | B | 72 | -35.428 | -18.239 | -1.487 | 0.35 | 13.30 |
| 5131 | CB | AGLN | B | 72 | -35.443 | -18.234 | -1.462 | 0.65 | 13.85 |
| 5136 | CG | BGLN | B | 72 | -36.414 | -18.681 | -2.560 | 0.35 | 13.02 |
| 5137 | CG | AGLN | B | 72 | -34.684 | -19.551 | -1.322 | 0.65 | 15.06 |
| 5142 | CD | BGLN | B | 72 | -36.784 | -20.145 | -2.467 | 0.35 | 14.03 |
| 5143 | CD | AGLN | B | 72 | -35.483 | -20.691 | -0.665 | 0.65 | 17.70 |
| 5144 | OE1BGLN | | B | 72 | -36.967 | -20.681 | -1.371 | 0.35 | 15.69 |
| 5145 | OE1AGLN | | B | 72 | -36.410 | -20.467 | 0.127 | 0.65 | 19.97 |
| 5146 | NE2BGLN | | B | 72 | -36.896 | -20.796 | -3.617 | 0.35 | 12.09 |
| 5147 | NE2AGLN | | B | 72 | -35.100 | -21.918 | -0.985 | 0.65 | 20.50 |
| 5152 | C | GLN | B | 72 | -35.434 | -15.955 | -2.527 | 1.00 | 13.02 |
| 5153 | O | GLN | B | 72 | -35.541 | -15.830 | -3.752 | 1.00 | 12.87 |
| 5154 | N | LYS | B | 73 | -36.032 | -15.142 | -1.671 | 1.00 | 12.47 |
| 5156 | CA | LYS | B | 73 | -36.858 | -14.031 | -2.126 | 1.00 | 13.29 |
| 5158 | CB | LYS | B | 73 | -37.586 | -13.385 | -0.944 | 1.00 | 14.34 |
| 5161 | CG | LYS | B | 73 | -38.643 | -14.289 | -0.330 | 1.00 | 17.96 |
| 5164 | CD | LYS | B | 73 | -39.199 | -13.727 | 0.985 | 1.00 | 22.72 |
| 5167 | CE | LYS | B | 73 | -40.199 | -14.683 | 1.628 | 1.00 | 24.89 |
| 5170 | NZ | LYS | B | 73 | -41.579 | -14.514 | 1.087 | 1.00 | 27.34 |
| 5174 | C | LYS | B | 73 | -36.037 | -13.007 | -2.894 | 1.00 | 12.55 |
| 5175 | O | LYS | B | 73 | -36.473 | -12.498 | -3.930 | 1.00 | 12.96 |
| 5176 | N | VAL | B | 74 | -34.828 | -12.733 | -2.411 | 1.00 | 12.04 |

FIGURE 3 (cont.)

| A | B | C | D | E | F | G | H | I | J |
|---|---|---|---|---|---|---|---|---|---|
| 5178 | CA | VAL | B | 74 | -33.949 | -11.792 | -3.096 | 1.00 | 11.38 |
| 5180 | CB | VAL | B | 74 | -32.681 | -11.462 | -2.263 | 1.00 | 11.18 |
| 5182 | CG1 | VAL | B | 74 | -31.667 | -10.639 | -3.067 | 1.00 | 10.96 |
| 5186 | CG2 | VAL | B | 74 | -33.089 | -10.700 | -1.012 | 1.00 | 12.21 |
| 5190 | C | VAL | B | 74 | -33.597 | -12.332 | -4.480 | 1.00 | 11.57 |
| 5191 | O | VAL | B | 74 | -33.693 | -11.606 | -5.459 | 1.00 | 11.53 |
| 5192 | N | VAL | B | 75 | -33.243 | -13.610 | -4.561 | 1.00 | 11.67 |
| 5194 | CA | VAL | B | 75 | -32.883 | -14.209 | -5.848 | 1.00 | 12.29 |
| 5196 | CB | VAL | B | 75 | -32.376 | -15.647 | -5.695 | 1.00 | 12.69 |
| 5198 | CG1 | VAL | B | 75 | -31.018 | -15.665 | -5.005 | 1.00 | 12.85 |
| 5202 | CG2 | VAL | B | 75 | -32.297 | -16.350 | -7.052 | 1.00 | 13.10 |
| 5206 | C | VAL | B | 75 | -34.068 | -14.131 | -6.813 | 1.00 | 12.56 |
| 5207 | O | VAL | B | 75 | -33.894 | -13.792 | -7.989 | 1.00 | 12.16 |
| 5208 | N | SER | B | 76 | -35.274 | -14.413 | -6.319 | 1.00 | 12.75 |
| 5210 | CA | SER | B | 76 | -36.467 | -14.358 | -7.177 | 1.00 | 13.14 |
| 5212 | CB | SER | B | 76 | -37.723 | -14.746 | -6.397 | 1.00 | 13.73 |
| 5215 | OG | SER | B | 76 | -37.693 | -16.123 | -6.099 | 1.00 | 15.89 |
| 5217 | C | SER | B | 76 | -36.650 | -12.986 | -7.803 | 1.00 | 13.16 |
| 5218 | O | SER | B | 76 | -36.930 | -12.873 | -9.003 | 1.00 | 12.89 |
| 5219 | N | HIS | B | 77 | -36.469 | -11.939 | -7.002 | 1.00 | 12.59 |
| 5221 | CA | HIS | B | 77 | -36.637 | -10.578 | -7.493 | 1.00 | 13.20 |
| 5223 | CB | HIS | B | 77 | -36.757 | -9.581 | -6.333 | 1.00 | 13.55 |
| 5226 | CG | HIS | B | 77 | -37.289 | -8.239 | -6.740 | 1.00 | 17.44 |
| 5227 | ND1 | HIS | B | 77 | -38.485 | -8.080 | -7.409 | 1.00 | 21.59 |
| 5229 | CE1 | HIS | B | 77 | -38.690 | -6.795 | -7.642 | 1.00 | 22.70 |
| 5231 | NE2 | HIS | B | 77 | -37.679 | -6.112 | -7.136 | 1.00 | 21.19 |
| 5233 | CD2 | HIS | B | 77 | -36.788 | -6.991 | -6.571 | 1.00 | 21.20 |
| 5235 | C | HIS | B | 77 | -35.498 | -10.197 | -8.436 | 1.00 | 12.76 |
| 5236 | O | HIS | B | 77 | -35.735 | -9.549 | -9.448 | 1.00 | 12.83 |
| 5237 | N | CYS | B | 78 | -34.275 | -10.618 | -8.123 | 1.00 | 12.54 |
| 5239 | CA | CYS | B | 78 | -33.136 | -10.370 | -9.011 | 1.00 | 12.18 |
| 5241 | CB | CYS | B | 78 | -31.841 | -10.939 | -8.418 | 1.00 | 11.72 |
| 5244 | SG | CYS | B | 78 | -31.144 | -10.004 | -7.018 | 1.00 | 12.23 |
| 5245 | C | CYS | B | 78 | -33.352 | -10.976 | -10.402 | 1.00 | 12.35 |
| 5246 | O | CYS | B | 78 | -33.025 | -10.360 | -11.404 | 1.00 | 12.28 |
| 5247 | N | LEU | B | 79 | -33.887 | -12.192 | -10.458 | 1.00 | 12.57 |
| 5249 | CA | LEU | B | 79 | -34.106 | -12.868 | -11.732 | 1.00 | 12.97 |
| 5251 | CB | LEU | B | 79 | -34.547 | -14.317 | -11.504 | 1.00 | 12.73 |
| 5254 | CG | LEU | B | 79 | -33.460 | -15.222 | -10.909 | 1.00 | 12.61 |
| 5256 | CD1 | LEU | B | 79 | -32.236 | -15.360 | -11.821 | 1.00 | 12.90 |
| 5260 | CD2 | LEU | B | 79 | -34.040 | -16.594 | -10.574 | 1.00 | 12.64 |
| 5264 | C | LEU | B | 79 | -35.142 | -12.102 | -12.544 | 1.00 | 13.48 |
| 5265 | O | LEU | B | 79 | -34.977 | -11.908 | -13.742 | 1.00 | 14.04 |
| 5266 | N | GLU | B | 80 | -36.180 | -11.623 | -11.867 | 1.00 | 14.29 |
| 5268 | CA | GLU | B | 80 | -37.233 | -10.859 | -12.523 | 1.00 | 15.56 |
| 5270 | CB | GLU | B | 80 | -38.426 | -10.673 | -11.589 | 1.00 | 16.58 |
| 5273 | CG | GLU | B | 80 | -39.625 | -10.069 | -12.297 | 1.00 | 19.55 |
| 5276 | CD | GLU | B | 80 | -40.962 | -10.478 | -11.716 | 1.00 | 22.06 |
| 5277 | OE1 | GLU | B | 80 | -41.016 | -11.336 | -10.799 | 1.00 | 22.99 |

FIGURE 3 (cont.)

| A | B | C | D | E | F | G | H | I | J |
|---|---|---|---|---|---|---|---|---|---|
| 5278 | OE2 | GLU | B | 80 | -41.968 | -9.919 | -12.193 | 1.00 | 25.64 |
| 5279 | C | GLU | B | 80 | -36.732 | -9.501 | -13.023 | 1.00 | 15.11 |
| 5280 | O | GLU | B | 80 | -37.161 | -9.038 | -14.084 | 1.00 | 14.85 |
| 5281 | N | LEU | B | 81 | -35.808 | -8.898 | -12.276 | 1.00 | 14.72 |
| 5283 | CA | LEU | B | 81 | -35.281 | -7.570 | -12.579 | 1.00 | 14.99 |
| 5285 | CB | LEU | B | 81 | -34.556 | -6.976 | -11.369 | 1.00 | 15.34 |
| 5288 | CG | LEU | B | 81 | -35.436 | -6.452 | -10.234 | 1.00 | 15.75 |
| 5290 | CD1 | LEU | B | 81 | -34.580 | -6.181 | -9.005 | 1.00 | 17.29 |
| 5294 | CD2 | LEU | B | 81 | -36.201 | -5.208 | -10.669 | 1.00 | 17.29 |
| 5298 | C | LEU | B | 81 | -34.320 | -7.586 | -13.757 | 1.00 | 14.85 |
| 5299 | O | LEU | B | 81 | -34.040 | -6.527 | -14.342 | 1.00 | 15.16 |
| 5300 | N | GLY | B | 82 | -33.797 | -8.762 | -14.087 | 1.00 | 14.15 |
| 5302 | CA | GLY | B | 82 | -32.937 | -8.930 | -15.249 | 1.00 | 14.12 |
| 5305 | C | GLY | B | 82 | -31.481 | -9.276 | -14.993 | 1.00 | 14.28 |
| 5306 | O | GLY | B | 82 | -30.624 | -9.005 | -15.837 | 1.00 | 14.31 |
| 5307 | N | ALA | B | 83 | -31.184 | -9.869 | -13.837 | 1.00 | 13.95 |
| 5309 | CA | ALA | B | 83 | -29.846 | -10.376 | -13.565 | 1.00 | 14.20 |
| 5311 | CB | ALA | B | 83 | -29.814 | -11.043 | -12.204 | 1.00 | 14.07 |
| 5315 | C | ALA | B | 83 | -29.460 | -11.370 | -14.657 | 1.00 | 14.38 |
| 5316 | O | ALA | B | 83 | -30.309 | -12.146 | -15.104 | 1.00 | 13.64 |
| 5317 | N | ALA | B | 84 | -28.211 | -11.323 | -15.130 | 1.00 | 14.52 |
| 5319 | CA | ALA | B | 84 | -27.700 | -12.346 | -16.055 | 1.00 | 14.86 |
| 5321 | CB | ALA | B | 84 | -26.265 | -12.075 | -16.409 | 1.00 | 14.96 |
| 5325 | C | ALA | B | 84 | -27.836 | -13.743 | -15.451 | 1.00 | 14.79 |
| 5326 | O | ALA | B | 84 | -28.164 | -14.706 | -16.143 | 1.00 | 15.68 |
| 5327 | N | SER | B | 85 | -27.558 | -13.832 | -14.156 | 1.00 | 14.98 |
| 5329 | CA | SER | B | 85 | -27.836 | -15.012 | -13.341 | 1.00 | 14.41 |
| 5331 | CB | SER | B | 85 | -26.764 | -16.091 | -13.517 | 1.00 | 15.07 |
| 5334 | OG | SER | B | 85 | -25.506 | -15.693 | -12.983 | 1.00 | 15.95 |
| 5336 | C | SER | B | 85 | -27.899 | -14.553 | -11.889 | 1.00 | 14.07 |
| 5337 | O | SER | B | 85 | -27.366 | -13.505 | -11.535 | 1.00 | 13.09 |
| 5338 | N | ALA | B | 86 | -28.576 | -15.318 | -11.048 | 1.00 | 13.23 |
| 5340 | CA | ALA | B | 86 | -28.638 | -15.009 | -9.627 | 1.00 | 13.31 |
| 5342 | CB | ALA | B | 86 | -29.792 | -14.073 | -9.330 | 1.00 | 13.39 |
| 5346 | C | ALA | B | 86 | -28.758 | -16.295 | -8.828 | 1.00 | 13.75 |
| 5347 | O | ALA | B | 86 | -29.591 | -17.150 | -9.133 | 1.00 | 13.98 |
| 5348 | N | HIS | B | 87 | -27.873 | -16.451 | -7.844 | 1.00 | 13.70 |
| 5350 | CA | HIS | B | 87 | -27.847 | -17.615 | -6.973 | 1.00 | 13.32 |
| 5352 | CB | HIS | B | 87 | -26.664 | -18.525 | -7.323 | 1.00 | 14.02 |
| 5355 | CG | HIS | B | 87 | -26.683 | -19.056 | -8.722 | 1.00 | 16.44 |
| 5356 | ND1 | HIS | B | 87 | -27.212 | -20.287 | -9.048 | 1.00 | 20.96 |
| 5358 | CE1 | HIS | B | 87 | -27.062 | -20.497 | -10.345 | 1.00 | 20.56 |
| 5360 | NE2 | HIS | B | 87 | -26.422 | -19.464 | -10.864 | 1.00 | 21.18 |
| 5362 | CD2 | HIS | B | 87 | -26.167 | -18.555 | -9.867 | 1.00 | 18.86 |
| 5364 | C | HIS | B | 87 | -27.672 | -17.152 | -5.539 | 1.00 | 13.09 |
| 5365 | O | HIS | B | 87 | -27.132 | -16.056 | -5.289 | 1.00 | 11.68 |
| 5366 | N | TYR | B | 88 | -28.090 | -17.989 | -4.597 | 1.00 | 12.65 |
| 5368 | CA | TYR | B | 88 | -27.758 | -17.786 | -3.198 | 1.00 | 13.20 |
| 5370 | CB | TYR | B | 88 | -29.010 | -17.452 | -2.385 | 1.00 | 13.05 |

FIGURE 3 (cont.)

| A | B | C | D | E | F | G | H | I | J |
|---|---|---|---|---|---|---|---|---|---|
| 5373 | CG | TYR | B | 88 | -29.932 | -18.627 | -2.142 | 1.00 | 15.19 |
| 5374 | CD1 | TYR | B | 88 | -29.806 | -19.405 | -0.994 | 1.00 | 19.13 |
| 5376 | CE1 | TYR | B | 88 | -30.648 | -20.481 | -0.762 | 1.00 | 20.55 |
| 5378 | CZ | TYR | B | 88 | -31.632 | -20.776 | -1.682 | 1.00 | 21.35 |
| 5379 | OH | TYR | B | 88 | -32.483 | -21.841 | -1.455 | 1.00 | 25.30 |
| 5381 | CE2 | TYR | B | 88 | -31.780 | -20.011 | -2.830 | 1.00 | 20.23 |
| 5383 | CD2 | TYR | B | 88 | -30.931 | -18.941 | -3.049 | 1.00 | 18.92 |
| 5385 | C | TYR | B | 88 | -27.059 | -18.994 | -2.592 | 1.00 | 13.17 |
| 5386 | O | TYR | B | 88 | -27.248 | -20.136 | -3.030 | 1.00 | 13.72 |
| 5387 | N | ILE | B | 89 | -26.259 | -18.725 | -1.569 | 1.00 | 13.13 |
| 5389 | CA | ILE | B | 89 | -25.644 | -19.747 | -0.740 | 1.00 | 13.40 |
| 5391 | CB | ILE | B | 89 | -24.164 | -19.954 | -1.114 | 1.00 | 13.47 |
| 5393 | CG1 | ILE | B | 89 | -24.003 | -20.295 | -2.599 | 1.00 | 14.51 |
| 5396 | CD1 | ILE | B | 89 | -22.569 | -20.256 | -3.077 | 1.00 | 16.49 |
| 5400 | CG2 | ILE | B | 89 | -23.535 | -21.033 | -0.237 | 1.00 | 14.36 |
| 5404 | C | ILE | B | 89 | -25.774 | -19.270 | 0.698 | 1.00 | 13.60 |
| 5405 | O | ILE | B | 89 | -25.276 | -18.203 | 1.042 | 1.00 | 13.98 |
| 5406 | N | ALA | B | 90 | -26.434 | -20.059 | 1.531 | 1.00 | 13.19 |
| 5408 | CA | ALA | B | 90 | -26.672 | -19.695 | 2.927 | 1.00 | 12.87 |
| 5410 | CB | ALA | B | 90 | -28.039 | -20.166 | 3.368 | 1.00 | 12.71 |
| 5414 | C | ALA | B | 90 | -25.611 | -20.254 | 3.858 | 1.00 | 12.96 |
| 5415 | O | ALA | B | 90 | -25.173 | -21.403 | 3.718 | 1.00 | 13.49 |
| 5416 | N | GLY | B | 91 | -25.206 | -19.430 | 4.822 | 1.00 | 12.42 |
| 5418 | CA | GLY | B | 91 | -24.297 | -19.860 | 5.861 | 1.00 | 11.92 |
| 5421 | C | GLY | B | 91 | -23.919 | -18.719 | 6.766 | 1.00 | 11.99 |
| 5422 | O | GLY | B | 91 | -24.307 | -17.572 | 6.528 | 1.00 | 11.49 |
| 5423 | N | THR | B | 92 | -23.198 | -19.035 | 7.833 | 1.00 | 11.98 |
| 5425 | CA | THR | B | 92 | -22.797 | -18.019 | 8.786 | 1.00 | 12.58 |
| 5427 | CB | THR | B | 92 | -23.081 | -18.430 | 10.238 | 1.00 | 12.35 |
| 5429 | OG1 | THR | B | 92 | -22.528 | -17.430 | 11.104 | 1.00 | 12.85 |
| 5431 | CG2 | THR | B | 92 | -22.345 | -19.723 | 10.629 | 1.00 | 13.17 |
| 5435 | C | THR | B | 92 | -21.336 | -17.659 | 8.616 | 1.00 | 12.55 |
| 5436 | O | THR | B | 92 | -20.474 | -18.537 | 8.479 | 1.00 | 13.03 |
| 5437 | N | MET | B | 93 | -21.059 | -16.364 | 8.647 | 1.00 | 12.38 |
| 5439 | CA | MET | B | 93 | -19.698 | -15.854 | 8.500 | 1.00 | 12.98 |
| 5441 | CB | MET | B | 93 | -19.718 | -14.435 | 7.915 | 1.00 | 12.86 |
| 5444 | CG | MET | B | 93 | -20.148 | -14.410 | 6.455 | 1.00 | 12.81 |
| 5447 | SD | MET | B | 93 | -19.054 | -15.248 | 5.320 | 1.00 | 13.60 |
| 5448 | CE | MET | B | 93 | -19.954 | -15.003 | 3.766 | 1.00 | 14.79 |
| 5452 | C | MET | B | 93 | -18.934 | -15.907 | 9.819 | 1.00 | 13.78 |
| 5453 | O | MET | B | 93 | -17.817 | -15.407 | 9.910 | 1.00 | 14.29 |
| 5454 | N | GLU | B | 94 | -19.547 | -16.499 | 10.844 | 1.00 | 14.48 |
| 5456 | CA | GLU | B | 94 | -18.845 | -16.902 | 12.060 | 1.00 | 15.20 |
| 5458 | CB | GLU | B | 94 | -19.813 | -17.381 | 13.133 | 1.00 | 15.81 |
| 5461 | CG | GLU | B | 94 | -20.832 | -16.384 | 13.627 | 1.00 | 17.81 |
| 5464 | CD | GLU | B | 94 | -21.932 | -17.095 | 14.383 | 1.00 | 21.28 |
| 5465 | OE1 | GLU | B | 94 | -22.884 | -17.600 | 13.734 | 1.00 | 22.16 |
| 5466 | OE2 | GLU | B | 94 | -21.820 | -17.194 | 15.627 | 1.00 | 24.40 |
| 5467 | C | GLU | B | 94 | -17.916 | -18.064 | 11.772 | 1.00 | 15.25 |

FIGURE 3 (cont.)

| A | B | C | D | E | F | G | H | I | J |
|---|---|---|---|---|---|---|---|---|---|
| 5468 | O | GLU | B | 94 | -16.982 | -18.305 | 12.529 | 1.00 | 15.57 |
| 5469 | N | ASP | B | 95 | -18.205 | -18.783 | 10.688 | 1.00 | 14.82 |
| 5471 | CA | ASP | B | 95 | -17.494 | -20.002 | 10.299 | 1.00 | 15.53 |
| 5473 | CB | ASP | B | 95 | -18.518 | -21.063 | 9.881 | 1.00 | 15.98 |
| 5476 | CG | ASP | B | 95 | -17.896 | -22.393 | 9.528 | 1.00 | 16.87 |
| 5477 | OD1 | ASP | B | 95 | -16.657 | -22.469 | 9.399 | 1.00 | 18.17 |
| 5478 | OD2 | ASP | B | 95 | -18.582 | -23.420 | 9.352 | 1.00 | 19.28 |
| 5479 | C | ASP | B | 95 | -16.561 | -19.648 | 9.160 | 1.00 | 15.28 |
| 5480 | O | ASP | B | 95 | -16.995 | -19.439 | 8.037 | 1.00 | 14.72 |
| 5481 | N | MET | B | 96 | -15.267 | -19.555 | 9.455 | 1.00 | 15.51 |
| 5483 | CA | MET | B | 96 | -14.296 | -19.126 | 8.459 | 1.00 | 15.54 |
| 5485 | CB | MET | B | 96 | -12.930 | -18.854 | 9.093 | 1.00 | 15.89 |
| 5488 | CG | MET | B | 96 | -12.911 | -17.797 | 10.179 | 1.00 | 16.96 |
| 5491 | SD | MET | B | 96 | -13.574 | -16.194 | 9.700 | 1.00 | 19.45 |
| 5492 | CE | MET | B | 96 | -14.684 | -15.854 | 11.010 | 1.00 | 19.14 |
| 5496 | C | MET | B | 96 | -14.143 | -20.150 | 7.342 | 1.00 | 15.09 |
| 5497 | O | MET | B | 96 | -13.740 | -19.798 | 6.238 | 1.00 | 14.82 |
| 5498 | N | THR | B | 97 | -14.456 | -21.413 | 7.628 | 1.00 | 15.60 |
| 5500 | CA | THR | B | 97 | -14.465 | -22.455 | 6.607 | 1.00 | 15.99 |
| 5502 | CB | THR | B | 97 | -14.562 | -23.845 | 7.253 | 1.00 | 16.62 |
| 5504 | OG1 | THR | B | 97 | -13.473 | -24.014 | 8.170 | 1.00 | 18.56 |
| 5506 | CG2 | THR | B | 97 | -14.360 | -24.934 | 6.218 | 1.00 | 17.61 |
| 5510 | C | THR | B | 97 | -15.586 | -22.239 | 5.594 | 1.00 | 15.64 |
| 5511 | O | THR | B | 97 | -15.371 | -22.379 | 4.388 | 1.00 | 15.56 |
| 5512 | N | PHE | B | 98 | -16.769 | -21.877 | 6.079 | 1.00 | 15.35 |
| 5514 | CA | PHE | B | 98 | -17.846 | -21.489 | 5.188 | 1.00 | 14.97 |
| 5516 | CB | PHE | B | 98 | -19.134 | -21.144 | 5.941 | 1.00 | 15.19 |
| 5519 | CG | PHE | B | 98 | -20.178 | -20.537 | 5.051 | 1.00 | 14.81 |
| 5520 | CD1 | PHE | B | 98 | -20.880 | -21.335 | 4.156 | 1.00 | 15.21 |
| 5522 | CE1 | PHE | B | 98 | -21.824 | -20.792 | 3.308 | 1.00 | 16.09 |
| 5524 | CZ | PHE | B | 98 | -22.070 | -19.426 | 3.331 | 1.00 | 16.70 |
| 5526 | CE2 | PHE | B | 98 | -21.371 | -18.616 | 4.199 | 1.00 | 15.71 |
| 5528 | CD2 | PHE | B | 98 | -20.420 | -19.167 | 5.055 | 1.00 | 15.07 |
| 5530 | C | PHE | B | 98 | -17.433 | -20.296 | 4.338 | 1.00 | 14.76 |
| 5531 | O | PHE | B | 98 | -17.681 | -20.276 | 3.140 | 1.00 | 14.57 |
| 5532 | N | ALA | B | 99 | -16.804 | -19.301 | 4.957 | 1.00 | 14.68 |
| 5534 | CA | ALA | B | 99 | -16.424 | -18.096 | 4.217 | 1.00 | 14.57 |
| 5536 | CB | ALA | B | 99 | -15.730 | -17.091 | 5.134 | 1.00 | 14.75 |
| 5540 | C | ALA | B | 99 | -15.542 | -18.438 | 3.015 | 1.00 | 15.11 |
| 5541 | O | ALA | B | 99 | -15.810 | -18.017 | 1.891 | 1.00 | 14.86 |
| 5542 | N | GLU | B | 100 | -14.505 | -19.231 | 3.255 | 1.00 | 15.41 |
| 5544 | CA | GLU | B | 100 | -13.580 | -19.628 | 2.203 | 1.00 | 16.52 |
| 5546 | CB | GLU | B | 100 | -12.418 | -20.437 | 2.793 | 1.00 | 17.00 |
| 5549 | CG | GLU | B | 100 | -11.436 | -20.930 | 1.735 | 1.00 | 20.05 |
| 5552 | CD | GLU | B | 100 | -10.193 | -21.577 | 2.315 | 1.00 | 23.96 |
| 5553 | OE1 | GLU | B | 100 | -9.298 | -21.933 | 1.520 | 1.00 | 27.94 |
| 5554 | OE2 | GLU | B | 100 | -10.105 | -21.742 | 3.551 | 1.00 | 26.14 |
| 5555 | C | GLU | B | 100 | -14.284 | -20.439 | 1.121 | 1.00 | 16.30 |
| 5556 | O | GLU | B | 100 | -14.115 | -20.184 | -0.074 | 1.00 | 16.61 |

FIGURE 3 (cont.)

| A | B | C | D | E | F | G | H | I | J |
|---|---|---|---|---|---|---|---|---|---|
| 5557 | N | GLN | B | 101 | -15.075 | -21.419 | 1.539 | 1.00 | 16.35 |
| 5559 | CA | GLN | B | 101 | -15.732 | -22.317 | 0.597 | 1.00 | 16.40 |
| 5561 | CB | GLN | B | 101 | -16.288 | -23.532 | 1.341 | 1.00 | 17.14 |
| 5564 | CG | GLN | B | 101 | -15.183 | -24.467 | 1.836 | 1.00 | 19.00 |
| 5567 | CD | GLN | B | 101 | -15.712 | -25.647 | 2.660 | 1.00 | 21.91 |
| 5568 | OE1 | GLN | B | 101 | -16.894 | -25.706 | 2.993 | 1.00 | 25.14 |
| 5569 | NE2 | GLN | B | 101 | -14.822 | -26.583 | 2.994 | 1.00 | 25.16 |
| 5572 | C | GLN | B | 101 | -16.829 | -21.609 | -0.183 | 1.00 | 15.19 |
| 5573 | O | GLN | B | 101 | -17.079 | -21.927 | -1.336 | 1.00 | 15.71 |
| 5574 | N | PHE | B | 102 | -17.461 | -20.624 | 0.444 | 1.00 | 14.16 |
| 5576 | CA | PHE | B | 102 | -18.476 | -19.827 | -0.226 | 1.00 | 13.43 |
| 5578 | CB | PHE | B | 102 | -19.079 | -18.788 | 0.720 | 1.00 | 13.06 |
| 5581 | CG | PHE | B | 102 | -19.796 | -17.694 | -0.001 | 1.00 | 13.20 |
| 5582 | CD1 | PHE | B | 102 | -21.010 | -17.944 | -0.624 | 1.00 | 13.03 |
| 5584 | CE1 | PHE | B | 102 | -21.667 | -16.943 | -1.322 | 1.00 | 14.54 |
| 5586 | CZ | PHE | B | 102 | -21.112 | -15.673 | -1.389 | 1.00 | 14.17 |
| 5588 | CE2 | PHE | B | 102 | -19.913 | -15.419 | -0.778 | 1.00 | 13.73 |
| 5590 | CD2 | PHE | B | 102 | -19.252 | -16.424 | -0.084 | 1.00 | 12.25 |
| 5592 | C | PHE | B | 102 | -17.922 | -19.123 | -1.457 | 1.00 | 13.24 |
| 5593 | O | PHE | B | 102 | -18.512 | -19.156 | -2.524 | 1.00 | 13.06 |
| 5594 | N | VAL | B | 103 | -16.781 | -18.465 | -1.299 | 1.00 | 13.03 |
| 5596 | CA | VAL | B | 103 | -16.202 | -17.714 | -2.401 | 1.00 | 12.67 |
| 5598 | CB | VAL | B | 103 | -14.979 | -16.901 | -1.942 | 1.00 | 12.83 |
| 5600 | CG1 | VAL | B | 103 | -14.271 | -16.259 | -3.123 | 1.00 | 12.54 |
| 5604 | CG2 | VAL | B | 103 | -15.421 | -15.845 | -0.960 | 1.00 | 12.79 |
| 5608 | C | VAL | B | 103 | -15.847 | -18.648 | -3.547 | 1.00 | 12.79 |
| 5609 | O | VAL | B | 103 | -16.055 | -18.306 | -4.708 | 1.00 | 12.97 |
| 5610 | N | ALA | B | 104 | -15.332 | -19.829 | -3.216 | 1.00 | 12.92 |
| 5612 | CA | ALA | B | 104 | -14.948 | -20.790 | -4.250 | 1.00 | 13.56 |
| 5614 | CB | ALA | B | 104 | -14.254 | -21.970 | -3.636 | 1.00 | 13.73 |
| 5618 | C | ALA | B | 104 | -16.172 | -21.241 | -5.040 | 1.00 | 13.78 |
| 5619 | O | ALA | B | 104 | -16.152 | -21.272 | -6.276 | 1.00 | 14.08 |
| 5620 | N | GLN | B | 105 | -17.243 | -21.560 | -4.324 | 1.00 | 14.35 |
| 5622 | CA | GLN | B | 105 | -18.481 | -21.996 | -4.964 | 1.00 | 15.10 |
| 5624 | CB BGLN | | B | 105 | -19.472 | -22.606 | -3.964 | 0.35 | 14.88 |
| 5625 | CB AGLN | | B | 105 | -19.439 | -22.504 | -3.882 | 0.65 | 15.24 |
| 5630 | CG BGLN | | B | 105 | -20.529 | -23.568 | -4.585 | 0.35 | 15.60 |
| 5631 | CG AGLN | | B | 105 | -20.797 | -22.994 | -4.369 | 0.65 | 17.83 |
| 5636 | CD BGLN | | B | 105 | -20.104 | -24.229 | -5.905 | 0.35 | 15.35 |
| 5637 | CD AGLN | | B | 105 | -21.615 | -23.651 | -3.256 | 0.65 | 20.47 |
| 5638 | OE1BGLN | | B | 105 | -20.607 | -23.872 | -6.975 | 0.35 | 15.81 |
| 5639 | OE1AGLN | | B | 105 | -22.763 | -24.046 | -3.475 | 0.65 | 24.49 |
| 5640 | NE2BGLN | | B | 105 | -19.191 | -25.194 | -5.828 | 0.35 | 15.06 |
| 5641 | NE2AGLN | | B | 105 | -21.027 | -23.761 | -2.062 | 0.65 | 22.35 |
| 5646 | C | GLN | B | 105 | -19.134 | -20.873 | -5.780 | 1.00 | 14.89 |
| 5647 | O | GLN | B | 105 | -19.625 | -21.113 | -6.877 | 1.00 | 14.74 |
| 5648 | N | ALA | B | 106 | -19.114 | -19.644 | -5.257 | 1.00 | 14.81 |
| 5650 | CA | ALA | B | 106 | -19.672 | -18.503 | -5.972 | 1.00 | 14.58 |
| 5652 | CB | ALA | B | 106 | -19.631 | -17.245 | -5.089 | 1.00 | 14.32 |

FIGURE 3 (cont.)

| A | B | C | D | E | F | G | H | I | J |
|---|---|---|---|---|---|---|---|---|---|
| 5656 | C | ALA | B | 106 | -18.904 | -18.272 | -7.277 | 1.00 | 15.23 |
| 5657 | O | ALA | B | 106 | -19.491 | -17.996 | -8.320 | 1.00 | 15.22 |
| 5658 | N | GLY | B | 107 | -17.585 | -18.401 | -7.204 | 1.00 | 15.51 |
| 5660 | CA | GLY | B | 107 | -16.720 | -18.266 | -8.365 | 1.00 | 16.19 |
| 5663 | C | GLY | B | 107 | -17.008 | -19.324 | -9.414 | 1.00 | 17.13 |
| 5664 | O | GLY | B | 107 | -17.044 | -19.034 | -10.606 | 1.00 | 17.74 |
| 5665 | N | LYS | B | 108 | -17.248 | -20.548 | -8.966 | 1.00 | 17.91 |
| 5667 | CA | LYS | B | 108 | -17.591 | -21.645 | -9.866 | 1.00 | 18.66 |
| 5669 | CB | LYS | B | 108 | -17.625 | -22.965 | -9.093 | 1.00 | 19.19 |
| 5672 | CG | LYS | B | 108 | -17.783 | -24.216 | -9.959 | 1.00 | 21.83 |
| 5675 | CD | LYS | B | 108 | -16.619 | -25.192 | -9.744 | 1.00 | 25.20 |
| 5678 | CE | LYS | B | 108 | -16.485 | -26.196 | -10.884 | 1.00 | 26.60 |
| 5681 | NZ | LYS | B | 108 | -16.774 | -27.581 | -10.424 | 1.00 | 28.82 |
| 5685 | C | LYS | B | 108 | -18.945 | -21.412 | -10.546 | 1.00 | 18.46 |
| 5686 | O | LYS | B | 108 | -19.109 | -21.708 | -11.731 | 1.00 | 18.82 |
| 5687 | N | LEU | B | 109 | -19.909 | -20.885 | -9.797 | 1.00 | 17.88 |
| 5689 | CA | LEU | B | 109 | -21.250 | -20.639 | -10.329 | 1.00 | 18.03 |
| 5691 | CB | LEU | B | 109 | -22.219 | -20.191 | -9.229 | 1.00 | 17.95 |
| 5694 | CG | LEU | B | 109 | -22.707 | -21.232 | -8.224 | 1.00 | 18.69 |
| 5696 | CD1 | LEU | B | 109 | -23.375 | -20.555 | -7.030 | 1.00 | 19.02 |
| 5700 | CD2 | LEU | B | 109 | -23.672 | -22.227 | -8.883 | 1.00 | 20.30 |
| 5704 | C | LEU | B | 109 | -21.235 | -19.592 | -11.435 | 1.00 | 17.79 |
| 5705 | O | LEU | B | 109 | -21.975 | -19.717 | -12.404 | 1.00 | 18.70 |
| 5706 | N | MET | B | 110 | -20.396 | -18.568 | -11.286 | 1.00 | 17.06 |
| 5708 | CA | MET | B | 110 | -20.343 | -17.454 | -12.231 | 1.00 | 16.65 |
| 5710 | CB | MET | B | 110 | -20.186 | -16.135 | -11.461 | 1.00 | 15.97 |
| 5713 | CG | MET | B | 110 | -21.390 | -15.788 | -10.585 | 1.00 | 15.39 |
| 5716 | SD | MET | B | 110 | -21.342 | -14.125 | -9.889 | 1.00 | 14.67 |
| 5717 | CE | MET | B | 110 | -20.028 | -14.328 | -8.692 | 1.00 | 15.38 |
| 5721 | C | MET | B | 110 | -19.230 | -17.570 | -13.281 | 1.00 | 16.48 |
| 5722 | O | MET | B | 110 | -19.227 | -16.830 | -14.263 | 1.00 | 17.05 |
| 5723 | N | GLY | B | 111 | -18.291 | -18.491 | -13.090 | 1.00 | 16.70 |
| 5725 | CA | GLY | B | 111 | -17.129 | -18.590 | -13.962 | 1.00 | 16.57 |
| 5728 | C | GLY | B | 111 | -16.127 | -17.459 | -13.777 | 1.00 | 16.53 |
| 5729 | O | GLY | B | 111 | -15.483 | -17.015 | -14.734 | 1.00 | 17.27 |
| 5730 | N | GLY | B | 112 | -15.993 | -17.003 | -12.536 | 1.00 | 15.78 |
| 5732 | CA | GLY | B | 112 | -15.059 | -15.950 | -12.185 | 1.00 | 15.20 |
| 5735 | C | GLY | B | 112 | -15.656 | -14.946 | -11.233 | 1.00 | 14.82 |
| 5736 | O | GLY | B | 112 | -16.744 | -15.146 | -10.716 | 1.00 | 14.76 |
| 5737 | N | LEU | B | 113 | -14.928 | -13.860 | -11.008 | 1.00 | 14.04 |
| 5739 | CA | LEU | B | 113 | -15.356 | -12.826 | -10.070 | 1.00 | 13.57 |
| 5741 | CB | LEU | B | 113 | -14.963 | -13.212 | -8.644 | 1.00 | 13.54 |
| 5744 | CG | LEU | B | 113 | -15.448 | -12.269 | -7.542 | 1.00 | 13.59 |
| 5746 | CD1 | LEU | B | 113 | -16.952 | -12.366 | -7.379 | 1.00 | 12.89 |
| 5750 | CD2 | LEU | B | 113 | -14.776 | -12.605 | -6.233 | 1.00 | 13.85 |
| 5754 | C | LEU | B | 113 | -14.749 | -11.475 | -10.431 | 1.00 | 13.12 |
| 5755 | O | LEU | B | 113 | -13.542 | -11.364 | -10.600 | 1.00 | 13.65 |
| 5756 | N | ASP | B | 114 | -15.604 | -10.464 | -10.553 | 1.00 | 12.50 |
| 5758 | CA | ASP | B | 114 | -15.203 | -9.094 | -10.858 | 1.00 | 12.77 |

FIGURE 3 (cont.)

| A | B | C | D | E | F | G | H | I | J |
|---|---|---|---|---|---|---|---|---|---|
| 5760 | CB | ASP | B | 114 | -16.082 | -8.528 | -11.967 | 1.00 | 12.87 |
| 5763 | CG | ASP | B | 114 | -15.914 | -9.263 | -13.263 | 1.00 | 13.64 |
| 5764 | OD1 | ASP | B | 114 | -14.780 | -9.246 | -13.794 | 1.00 | 15.61 |
| 5765 | OD2 | ASP | B | 114 | -16.837 | -9.903 | -13.817 | 1.00 | 15.44 |
| 5766 | C | ASP | B | 114 | -15.272 | -8.156 | -9.659 | 1.00 | 12.61 |
| 5767 | O | ASP | B | 114 | -14.484 | -7.214 | -9.562 | 1.00 | 12.13 |
| 5768 | N | MET | B | 115 | -16.226 | -8.388 | -8.761 | 1.00 | 12.27 |
| 5770 | CA | MET | B | 115 | -16.427 | -7.512 | -7.611 | 1.00 | 11.81 |
| 5772 | CB | MET | B | 115 | -17.443 | -6.413 | -7.941 | 1.00 | 12.41 |
| 5775 | CG | MET | B | 115 | -17.616 | -5.388 | -6.835 | 1.00 | 13.00 |
| 5778 | SD | MET | B | 115 | -18.762 | -4.058 | -7.281 | 1.00 | 17.87 |
| 5779 | CE | MET | B | 115 | -17.742 | -3.072 | -8.317 | 1.00 | 18.65 |
| 5783 | C | MET | B | 115 | -16.884 | -8.313 | -6.391 | 1.00 | 11.51 |
| 5784 | O | MET | B | 115 | -17.794 | -9.148 | -6.484 | 1.00 | 11.58 |
| 5785 | N | LEU | B | 116 | -16.227 | -8.052 | -5.267 | 1.00 | 11.34 |
| 5787 | CA | LEU | B | 116 | -16.539 | -8.645 | -3.971 | 1.00 | 11.05 |
| 5789 | CB | LEU | B | 116 | -15.265 | -9.238 | -3.362 | 1.00 | 11.36 |
| 5792 | CG | LEU | B | 116 | -15.378 | -9.882 | -1.980 | 1.00 | 11.17 |
| 5794 | CD1 | LEU | B | 116 | -16.226 | -11.139 | -2.061 | 1.00 | 12.97 |
| 5798 | CD2 | LEU | B | 116 | -14.015 | -10.203 | -1.395 | 1.00 | 13.15 |
| 5802 | C | LEU | B | 116 | -17.082 | -7.546 | -3.060 | 1.00 | 11.06 |
| 5803 | O | LEU | B | 116 | -16.335 | -6.641 | -2.692 | 1.00 | 10.73 |
| 5804 | N | ILE | B | 117 | -18.373 | -7.588 | -2.733 | 1.00 | 10.99 |
| 5806 | CA | ILE | B | 117 | -18.991 | -6.577 | -1.861 | 1.00 | 10.67 |
| 5808 | CB | ILE | B | 117 | -20.316 | -6.002 | -2.456 | 1.00 | 10.54 |
| 5810 | CG1 | ILE | B | 117 | -20.081 | -5.440 | -3.860 | 1.00 | 10.94 |
| 5813 | CD1 | ILE | B | 117 | -21.333 | -4.840 | -4.493 | 1.00 | 11.34 |
| 5817 | CG2 | ILE | B | 117 | -20.911 | -4.931 | -1.532 | 1.00 | 11.14 |
| 5821 | C | ILE | B | 117 | -19.229 | -7.203 | -0.485 | 1.00 | 10.86 |
| 5822 | O | ILE | B | 117 | -20.038 | -8.126 | -0.331 | 1.00 | 10.96 |
| 5823 | N | LEU | B | 118 | -18.502 | -6.688 | 0.501 | 1.00 | 10.96 |
| 5825 | CA | LEU | B | 118 | -18.451 | -7.211 | 1.859 | 1.00 | 10.82 |
| 5827 | CB | LEU | B | 118 | -17.000 | -7.307 | 2.336 | 1.00 | 11.35 |
| 5830 | CG | LEU | B | 118 | -16.075 | -8.144 | 1.455 | 1.00 | 11.47 |
| 5832 | CD1 | LEU | B | 118 | -14.612 | -8.009 | 1.873 | 1.00 | 13.66 |
| 5836 | CD2 | LEU | B | 118 | -16.514 | -9.611 | 1.502 | 1.00 | 12.89 |
| 5840 | C | LEU | B | 118 | -19.273 | -6.264 | 2.724 | 1.00 | 10.94 |
| 5841 | O | LEU | B | 118 | -18.898 | -5.111 | 2.951 | 1.00 | 10.70 |
| 5842 | N | ASN | B | 119 | -20.422 | -6.758 | 3.166 | 1.00 | 10.94 |
| 5844 | CA | ASN | B | 119 | -21.453 | -5.914 | 3.746 | 1.00 | 10.66 |
| 5846 | CB | ASN | B | 119 | -22.485 | -5.681 | 2.637 | 1.00 | 10.88 |
| 5849 | CG | ASN | B | 119 | -23.783 | -5.129 | 3.131 | 1.00 | 11.09 |
| 5850 | OD1 | ASN | B | 119 | -24.763 | -5.875 | 3.295 | 1.00 | 13.12 |
| 5851 | ND2 | ASN | B | 119 | -23.839 | -3.834 | 3.327 | 1.00 | 8.03 |
| 5854 | C | ASN | B | 119 | -22.077 | -6.467 | 5.037 | 1.00 | 10.34 |
| 5855 | O | ASN | B | 119 | -22.600 | -5.695 | 5.847 | 1.00 | 9.93 |
| 5856 | N | HIS | B | 120 | -22.024 | -7.783 | 5.245 | 1.00 | 9.85 |
| 5858 | CA | HIS | B | 120 | -22.611 | -8.383 | 6.448 | 1.00 | 10.13 |
| 5860 | CB | HIS | B | 120 | -22.518 | -9.923 | 6.396 | 1.00 | 10.03 |

FIGURE 3 (cont.)

| A | B | C | D | E | F | G | H | I | J |
|---|---|---|---|---|---|---|---|---|---|
| 5863 | CG | HIS | B | 120 | -21.111 | -10.435 | 6.349 | 1.00 | 10.52 |
| 5864 | ND1 | HIS | B | 120 | -20.355 | -10.688 | 7.469 | 1.00 | 13.78 |
| 5866 | CE1 | HIS | B | 120 | -19.158 | -11.108 | 7.102 | 1.00 | 9.73 |
| 5868 | NE2 | HIS | B | 120 | -19.099 | -11.109 | 5.787 | 1.00 | 13.10 |
| 5870 | CD2 | HIS | B | 120 | -20.301 | -10.673 | 5.295 | 1.00 | 9.94 |
| 5872 | C | HIS | B | 120 | -22.004 | -7.865 | 7.763 | 1.00 | 10.37 |
| 5873 | O | HIS | B | 120 | -20.838 | -7.495 | 7.849 | 1.00 | 10.29 |
| 5874 | N | ILE | B | 121 | -22.820 | -7.901 | 8.807 | 1.00 | 10.61 |
| 5876 | CA | ILE | B | 121 | -22.386 | -7.677 | 10.183 | 1.00 | 11.08 |
| 5878 | CB | ILE | B | 121 | -22.633 | -6.213 | 10.652 | 1.00 | 11.23 |
| 5880 | CG1 | ILE | B | 121 | -24.077 | -5.787 | 10.391 | 1.00 | 11.88 |
| 5883 | CD1 | ILE | B | 121 | -24.471 | -4.492 | 11.084 | 1.00 | 13.43 |
| 5887 | CG2 | ILE | B | 121 | -21.647 | -5.266 | 9.988 | 1.00 | 12.03 |
| 5891 | C | ILE | B | 121 | -23.145 | -8.621 | 11.095 | 1.00 | 11.00 |
| 5892 | O | ILE | B | 121 | -24.208 | -9.112 | 10.729 | 1.00 | 11.76 |
| 5893 | N | THR | B | 122 | -22.602 | -8.867 | 12.274 | 1.00 | 11.26 |
| 5895 | CA | THR | B | 122 | -23.337 | -9.597 | 13.298 | 1.00 | 12.09 |
| 5897 | CB | THR | B | 122 | -22.363 | -10.191 | 14.358 | 1.00 | 12.73 |
| 5899 | OG1 | THR | B | 122 | -23.048 | -11.147 | 15.179 | 1.00 | 13.75 |
| 5901 | CG2 | THR | B | 122 | -21.834 | -9.133 | 15.314 | 1.00 | 12.70 |
| 5905 | C | THR | B | 122 | -24.389 | -8.670 | 13.906 | 1.00 | 13.10 |
| 5906 | O | THR | B | 122 | -24.240 | -7.453 | 13.908 | 1.00 | 12.73 |
| 5907 | N | ASN | B | 123 | -25.465 | -9.248 | 14.417 | 1.00 | 14.53 |
| 5909 | CA | ASN | B | 123 | -26.531 | -8.439 | 14.986 | 1.00 | 15.80 |
| 5911 | CB | ASN | B | 123 | -27.645 | -9.315 | 15.552 | 1.00 | 16.12 |
| 5914 | CG | ASN | B | 123 | -28.479 | -10.012 | 14.474 | 1.00 | 17.74 |
| 5915 | OD1 | ASN | B | 123 | -28.181 | -9.961 | 13.283 | 1.00 | 18.99 |
| 5916 | ND2 | ASN | B | 123 | -29.537 | -10.690 | 14.913 | 1.00 | 22.15 |
| 5919 | C | ASN | B | 123 | -25.950 | -7.526 | 16.078 | 1.00 | 17.12 |
| 5920 | O | ASN | B | 123 | -25.249 | -7.988 | 16.985 | 1.00 | 16.93 |
| 5921 | N | THR | B | 124 | -26.231 | -6.231 | 15.955 | 1.00 | 18.33 |
| 5923 | CA | THR | B | 124 | -25.738 | -5.203 | 16.871 | 1.00 | 20.06 |
| 5925 | CB | THR | B | 124 | -24.552 | -4.392 | 16.242 | 1.00 | 20.66 |
| 5927 | OG1 | THR | B | 124 | -24.357 | -3.131 | 16.908 | 1.00 | 23.44 |
| 5929 | CG2 | THR | B | 124 | -24.799 | -3.988 | 14.807 | 1.00 | 20.74 |
| 5933 | C | THR | B | 124 | -26.906 | -4.293 | 17.272 | 1.00 | 20.70 |
| 5934 | O | THR | B | 124 | -27.655 | -3.832 | 16.413 | 1.00 | 21.01 |
| 5935 | N | SER | B | 125 | -27.066 | -4.069 | 18.572 | 1.00 | 20.93 |
| 5937 | CA | SER | B | 125 | -27.957 | -3.025 | 19.072 | 1.00 | 21.01 |
| 5939 | CB | SER | B | 125 | -29.121 | -3.649 | 19.849 | 1.00 | 21.06 |
| 5942 | OG | SER | B | 125 | -28.691 | -4.291 | 21.018 | 1.00 | 22.26 |
| 5944 | C | SER | B | 125 | -27.215 | -1.997 | 19.936 | 1.00 | 20.65 |
| 5945 | O | SER | B | 125 | -26.071 | -2.205 | 20.350 | 1.00 | 21.40 |
| 5946 | N | LEU | B | 126 | -27.878 | -0.879 | 20.210 | 1.00 | 19.36 |
| 5948 | CA | LEU | B | 126 | -27.280 | 0.163 | 21.025 | 1.00 | 18.80 |
| 5950 | CB | LEU | B | 126 | -28.030 | 1.476 | 20.820 | 1.00 | 18.76 |
| 5953 | CG | LEU | B | 126 | -28.061 | 1.969 | 19.373 | 1.00 | 18.94 |
| 5955 | CD1 | LEU | B | 126 | -28.846 | 3.267 | 19.250 | 1.00 | 19.67 |
| 5959 | CD2 | LEU | B | 126 | -26.626 | 2.148 | 18.870 | 1.00 | 19.43 |

FIGURE 3 (cont.)

| A | B | C | D | E | F | G | H | I | J |
|---|---|---|---|---|---|---|---|---|---|
| 5963 | C | LEU | B | 126 | -27.324 | -0.263 | 22.494 | 1.00 | 18.36 |
| 5964 | O | LEU | B | 126 | -28.399 | -0.481 | 23.032 | 1.00 | 18.29 |
| 5965 | N | ASN | B | 127 | -26.161 | -0.415 | 23.125 | 1.00 | 17.62 |
| 5967 | CA | ASN | B | 127 | -26.077 | -0.689 | 24.572 | 1.00 | 17.83 |
| 5969 | CB | ASN | B | 127 | -26.203 | -2.190 | 24.894 | 1.00 | 18.62 |
| 5972 | CG | ASN | B | 127 | -27.400 | -2.854 | 24.245 | 1.00 | 21.83 |
| 5973 | OD1 | ASN | B | 127 | -28.505 | -2.846 | 24.794 | 1.00 | 26.41 |
| 5974 | ND2 | ASN | B | 127 | -27.183 | -3.456 | 23.076 | 1.00 | 27.58 |
| 5977 | C | ASN | B | 127 | -24.742 | -0.228 | 25.139 | 1.00 | 16.87 |
| 5978 | O | ASN | B | 127 | -23.733 | -0.239 | 24.425 | 1.00 | 15.83 |
| 5979 | N | LEU | B | 128 | -24.727 | 0.132 | 26.423 | 1.00 | 16.44 |
| 5981 | CA | LEU | B | 128 | -23.471 | 0.360 | 27.144 | 1.00 | 17.29 |
| 5983 | CB | LEU | B | 128 | -23.728 | 0.800 | 28.588 | 1.00 | 17.69 |
| 5986 | CG | LEU | B | 128 | -24.210 | 2.227 | 28.853 | 1.00 | 20.16 |
| 5988 | CD1 | LEU | B | 128 | -24.829 | 2.299 | 30.237 | 1.00 | 21.49 |
| 5992 | CD2 | LEU | B | 128 | -23.068 | 3.208 | 28.743 | 1.00 | 21.98 |
| 5996 | C | LEU | B | 128 | -22.673 | -0.938 | 27.174 | 1.00 | 17.09 |
| 5997 | O | LEU | B | 128 | -23.246 | -2.026 | 27.233 | 1.00 | 17.14 |
| 5998 | N | PHE | B | 129 | -21.352 | -0.820 | 27.106 | 1.00 | 16.64 |
| 6000 | CA | PHE | B | 129 | -20.467 | -1.969 | 27.271 | 1.00 | 17.36 |
| 6002 | CB | PHE | B | 129 | -19.106 | -1.722 | 26.622 | 1.00 | 16.86 |
| 6005 | CG | PHE | B | 129 | -18.132 | -2.850 | 26.848 | 1.00 | 15.42 |
| 6006 | CD1 | PHE | B | 129 | -18.223 | -4.010 | 26.109 | 1.00 | 14.33 |
| 6008 | CE1 | PHE | B | 129 | -17.337 | -5.070 | 26.341 | 1.00 | 13.92 |
| 6010 | CZ | PHE | B | 129 | -16.377 | -4.960 | 27.303 | 1.00 | 13.02 |
| 6012 | CE2 | PHE | B | 129 | -16.278 | -3.817 | 28.058 | 1.00 | 13.91 |
| 6014 | CD2 | PHE | B | 129 | -17.164 | -2.763 | 27.840 | 1.00 | 14.78 |
| 6016 | C | PHE | B | 129 | -20.230 | -2.265 | 28.753 | 1.00 | 18.60 |
| 6017 | O | PHE | B | 129 | -19.845 | -1.380 | 29.517 | 1.00 | 18.70 |
| 6018 | N | HIS | B | 130 | -20.415 | -3.516 | 29.147 | 1.00 | 20.30 |
| 6020 | CA | HIS | B | 130 | -20.118 | -3.929 | 30.517 | 1.00 | 21.64 |
| 6022 | CB | HIS | B | 130 | -21.410 | -4.358 | 31.221 | 1.00 | 22.50 |
| 6025 | CG | HIS | B | 130 | -22.346 | -3.221 | 31.483 | 1.00 | 24.61 |
| 6026 | ND1 | HIS | B | 130 | -23.671 | -3.238 | 31.098 | 1.00 | 28.31 |
| 6028 | CE1 | HIS | B | 130 | -24.244 | -2.102 | 31.457 | 1.00 | 28.73 |
| 6030 | NE2 | HIS | B | 130 | -23.337 | -1.345 | 32.048 | 1.00 | 28.00 |
| 6032 | CD2 | HIS | B | 130 | -22.142 | -2.022 | 32.079 | 1.00 | 26.84 |
| 6034 | C | HIS | B | 130 | -19.044 | -5.021 | 30.564 | 1.00 | 22.13 |
| 6035 | O | HIS | B | 130 | -17.893 | -4.769 | 30.961 | 1.00 | 22.42 |
| 6036 | N | ASP | B | 131 | -19.403 | -6.226 | 30.151 | 1.00 | 22.71 |
| 6038 | CA | ASP | B | 131 | -18.478 | -7.345 | 30.238 | 1.00 | 23.07 |
| 6040 | CB | ASP | B | 131 | -18.506 | -7.939 | 31.659 | 1.00 | 23.40 |
| 6043 | CG | ASP | B | 131 | -19.825 | -8.628 | 31.996 | 1.00 | 25.28 |
| 6044 | OD1 | ASP | B | 131 | -20.804 | -8.498 | 31.227 | 1.00 | 28.06 |
| 6045 | OD2 | ASP | B | 131 | -19.978 | -9.326 | 33.030 | 1.00 | 28.76 |
| 6046 | C | ASP | B | 131 | -18.730 | -8.425 | 29.197 | 1.00 | 22.74 |
| 6047 | O | ASP | B | 131 | -18.331 | -9.568 | 29.390 | 1.00 | 23.32 |
| 6048 | N | ASP | B | 132 | -19.354 | -8.057 | 28.080 | 1.00 | 22.36 |
| 6050 | CA | ASP | B | 132 | -19.740 | -9.031 | 27.070 | 1.00 | 21.77 |

FIGURE 3 (cont.)

| A | B | C | D | E | F | G | H | I | J |
|---|---|---|---|---|---|---|---|---|---|
| 6052 | CB | ASP | B | 132 | -21.028 | -8.603 | 26.346 | 1.00 | 22.13 |
| 6055 | CG | ASP | B | 132 | -21.705 | -9.746 | 25.621 | 1.00 | 23.22 |
| 6056 | OD1 | ASP | B | 132 | -21.065 | -10.797 | 25.401 | 1.00 | 23.84 |
| 6057 | OD2 | ASP | B | 132 | -22.899 | -9.693 | 25.247 | 1.00 | 25.19 |
| 6058 | C | ASP | B | 132 | -18.592 | -9.175 | 26.096 | 1.00 | 21.19 |
| 6059 | O | ASP | B | 132 | -18.657 | -8.674 | 24.971 | 1.00 | 19.49 |
| 6060 | N | ILE | B | 133 | -17.552 | -9.873 | 26.551 | 1.00 | 20.63 |
| 6062 | CA | ILE | B | 133 | -16.379 | -10.172 | 25.740 | 1.00 | 20.34 |
| 6064 | CB | ILE | B | 133 | -15.278 | -10.853 | 26.599 | 1.00 | 20.78 |
| 6066 | CG1 | ILE | B | 133 | -14.840 | -9.926 | 27.745 | 1.00 | 22.22 |
| 6069 | CD1 | ILE | B | 133 | -14.234 | -10.631 | 28.925 | 1.00 | 24.20 |
| 6073 | CG2 | ILE | B | 133 | -14.073 | -11.237 | 25.737 | 1.00 | 21.05 |
| 6077 | C | ILE | B | 133 | -16.808 | -11.089 | 24.597 | 1.00 | 20.10 |
| 6078 | O | ILE | B | 133 | -16.230 | -11.066 | 23.518 | 1.00 | 18.59 |
| 6079 | N | HIS | B | 134 | -17.838 | -11.893 | 24.830 | 1.00 | 19.66 |
| 6081 | CA | HIS | B | 134 | -18.331 | -12.775 | 23.781 | 1.00 | 20.01 |
| 6083 | CB | BHIS | B | 134 | -19.438 | -13.691 | 24.321 | 0.35 | 20.05 |
| 6084 | CB | AHIS | B | 134 | -19.371 | -13.733 | 24.340 | 0.65 | 20.50 |
| 6089 | CG | BHIS | B | 134 | -20.072 | -14.555 | 23.274 | 0.35 | 20.99 |
| 6090 | CG | AHIS | B | 134 | -18.820 | -14.628 | 25.405 | 0.65 | 22.79 |
| 6091 | ND1BHIS | | B | 134 | -21.020 | -14.080 | 22.395 | 0.35 | 21.74 |
| 6092 | ND1AHIS | | B | 134 | -18.008 | -15.705 | 25.123 | 0.65 | 25.14 |
| 6095 | CE1BHIS | | B | 134 | -21.392 | -15.053 | 21.584 | 0.35 | 21.86 |
| 6096 | CE1AHIS | | B | 134 | -17.654 | -16.294 | 26.251 | 0.65 | 25.52 |
| 6099 | NE2BHIS | | B | 134 | -20.717 | -16.142 | 21.902 | 0.35 | 21.70 |
| 6100 | NE2AHIS | | B | 134 | -18.190 | -15.624 | 27.256 | 0.65 | 26.30 |
| 6103 | CD2BHIS | | B | 134 | -19.885 | -15.858 | 22.958 | 0.35 | 22.10 |
| 6104 | CD2AHIS | | B | 134 | -18.915 | -14.571 | 26.754 | 0.65 | 25.17 |
| 6107 | C | HIS | B | 134 | -18.844 | -11.982 | 22.581 | 1.00 | 18.88 |
| 6108 | O | HIS | B | 134 | -18.563 | -12.348 | 21.444 | 1.00 | 18.66 |
| 6109 | N | HIS | B | 135 | -19.558 | -10.889 | 22.831 | 1.00 | 18.30 |
| 6111 | CA | HIS | B | 135 | -20.036 | -10.022 | 21.760 | 1.00 | 17.67 |
| 6113 | CB | HIS | B | 135 | -21.039 | -8.997 | 22.280 | 1.00 | 18.39 |
| 6116 | CG | HIS | B | 135 | -21.486 | -7.998 | 21.254 | 1.00 | 19.37 |
| 6117 | ND1 | HIS | B | 135 | -22.439 | -8.279 | 20.298 | 1.00 | 22.62 |
| 6119 | CE1 | HIS | B | 135 | -22.639 | -7.210 | 19.552 | 1.00 | 22.52 |
| 6121 | NE2 | HIS | B | 135 | -21.847 | -6.246 | 19.983 | 1.00 | 23.50 |
| 6123 | CD2 | HIS | B | 135 | -21.109 | -6.717 | 21.040 | 1.00 | 21.59 |
| 6125 | C | HIS | B | 135 | -18.871 | -9.307 | 21.096 | 1.00 | 16.64 |
| 6126 | O | HIS | B | 135 | -18.876 | -9.103 | 19.889 | 1.00 | 16.39 |
| 6127 | N | VAL | B | 136 | -17.877 | -8.919 | 21.886 | 1.00 | 15.10 |
| 6129 | CA | VAL | B | 136 | -16.706 | -8.260 | 21.322 | 1.00 | 13.90 |
| 6131 | CB | VAL | B | 136 | -15.744 | -7.758 | 22.412 | 1.00 | 13.67 |
| 6133 | CG1 | VAL | B | 136 | -14.516 | -7.129 | 21.776 | 1.00 | 13.30 |
| 6137 | CG2 | VAL | B | 136 | -16.429 | -6.746 | 23.289 | 1.00 | 14.14 |
| 6141 | C | VAL | B | 136 | -15.984 | -9.214 | 20.366 | 1.00 | 13.19 |
| 6142 | O | VAL | B | 136 | -15.653 | -8.829 | 19.241 | 1.00 | 11.72 |
| 6143 | N | ARG | B | 137 | -15.749 | -10.449 | 20.804 | 1.00 | 13.24 |
| 6145 | CA | ARG | B | 137 | -15.091 | -11.436 | 19.960 | 1.00 | 13.70 |

FIGURE 3 (cont.)

| A | B | C | D | E | F | G | H | I | J |
|---|---|---|---|---|---|---|---|---|---|
| 6147 | CB | ARG | B | 137 | -14.782 | -12.738 | 20.703 | 1.00 | 14.75 |
| 6150 | CG | ARG | B | 137 | -13.868 | -13.624 | 19.877 | 1.00 | 16.93 |
| 6153 | CD | ARG | B | 137 | -13.649 | -15.005 | 20.405 | 1.00 | 21.23 |
| 6156 | NE | ARG | B | 137 | -12.360 | -15.128 | 21.070 | 1.00 | 25.07 |
| 6158 | CZ | ARG | B | 137 | -12.189 | -15.046 | 22.379 | 1.00 | 28.33 |
| 6159 | NH1 | ARG | B | 137 | -13.226 | -14.816 | 23.185 | 1.00 | 29.36 |
| 6162 | NH2 | ARG | B | 137 | -10.973 | -15.193 | 22.893 | 1.00 | 28.26 |
| 6165 | C | ARG | B | 137 | -15.907 | -11.733 | 18.709 | 1.00 | 13.13 |
| 6166 | O | ARG | B | 137 | -15.362 | -11.777 | 17.611 | 1.00 | 12.08 |
| 6167 | N | LYS | B | 138 | -17.212 | -11.920 | 18.872 | 1.00 | 13.25 |
| 6169 | CA | LYS | B | 138 | -18.061 | -12.268 | 17.740 | 1.00 | 13.63 |
| 6171 | CB | LYS | B | 138 | -19.475 | -12.622 | 18.202 | 1.00 | 14.03 |
| 6174 | CG | LYS | B | 138 | -20.354 | -13.165 | 17.079 | 1.00 | 16.95 |
| 6177 | CD | LYS | B | 138 | -21.750 | -13.472 | 17.571 | 1.00 | 19.47 |
| 6180 | CE | LYS | B | 138 | -21.821 | -14.813 | 18.233 | 1.00 | 22.59 |
| 6183 | NZ | LYS | B | 138 | -23.212 | -15.073 | 18.710 | 1.00 | 25.93 |
| 6187 | C | LYS | B | 138 | -18.109 | -11.131 | 16.733 | 1.00 | 13.03 |
| 6188 | O | LYS | B | 138 | -18.111 | -11.366 | 15.524 | 1.00 | 13.21 |
| 6189 | N | SER | B | 139 | -18.118 | -9.902 | 17.228 | 1.00 | 12.83 |
| 6191 | CA | SER | B | 139 | -18.080 | -8.741 | 16.349 | 1.00 | 12.66 |
| 6193 | CB | SER | B | 139 | -18.203 | -7.447 | 17.154 | 1.00 | 13.29 |
| 6196 | OG | SER | B | 139 | -19.492 | -7.350 | 17.746 | 1.00 | 14.95 |
| 6198 | C | SER | B | 139 | -16.792 | -8.734 | 15.552 | 1.00 | 12.54 |
| 6199 | O | SER | B | 139 | -16.803 | -8.484 | 14.338 | 1.00 | 12.28 |
| 6200 | N | MET | B | 140 | -15.680 | -9.005 | 16.225 | 1.00 | 12.60 |
| 6202 | CA | MET | B | 140 | -14.395 | -8.978 | 15.556 | 1.00 | 12.80 |
| 6204 | CB | MET | B | 140 | -13.235 | -9.057 | 16.554 | 1.00 | 13.25 |
| 6207 | CG | MET | B | 140 | -13.012 | -7.828 | 17.434 | 1.00 | 16.23 |
| 6210 | SD | MET | B | 140 | -12.919 | -6.194 | 16.580 | 1.00 | 21.70 |
| 6211 | CE | MET | B | 140 | -12.095 | -6.717 | 15.058 | 1.00 | 14.36 |
| 6215 | C | MET | B | 140 | -14.325 | -10.107 | 14.526 | 1.00 | 12.58 |
| 6216 | O | MET | B | 140 | -13.812 | -9.919 | 13.424 | 1.00 | 12.83 |
| 6217 | N | GLU | B | 141 | -14.903 | -11.267 | 14.844 | 1.00 | 12.10 |
| 6219 | CA | GLU | B | 141 | -14.819 | -12.415 | 13.940 | 1.00 | 12.43 |
| 6221 | CB | GLU | B | 141 | -15.151 | -13.719 | 14.675 | 1.00 | 12.80 |
| 6224 | CG | GLU | B | 141 | -14.069 | -14.185 | 15.646 | 1.00 | 15.61 |
| 6227 | CD | GLU | B | 141 | -12.943 | -14.945 | 14.970 | 1.00 | 21.48 |
| 6228 | OE1 | GLU | B | 141 | -11.782 | -14.827 | 15.422 | 1.00 | 25.76 |
| 6229 | OE2 | GLU | B | 141 | -13.209 | -15.684 | 13.997 | 1.00 | 26.71 |
| 6230 | C | GLU | B | 141 | -15.724 | -12.234 | 12.719 | 1.00 | 11.67 |
| 6231 | O | GLU | B | 141 | -15.301 | -12.417 | 11.583 | 1.00 | 12.21 |
| 6232 | N | VAL | B | 142 | -16.974 | -11.836 | 12.947 | 1.00 | 11.25 |
| 6234 | CA | VAL | B | 142 | -17.927 | -11.713 | 11.855 | 1.00 | 11.22 |
| 6236 | CB | VAL | B | 142 | -19.370 | -11.773 | 12.364 | 1.00 | 10.62 |
| 6238 | CG1 | VAL | B | 142 | -20.358 | -11.520 | 11.249 | 1.00 | 11.29 |
| 6242 | CG2 | VAL | B | 142 | -19.635 | -13.128 | 13.015 | 1.00 | 11.47 |
| 6246 | C | VAL | B | 142 | -17.720 | -10.436 | 11.048 | 1.00 | 10.72 |
| 6247 | O | VAL | B | 142 | -17.721 | -10.472 | 9.816 | 1.00 | 11.69 |
| 6248 | N | ASN | B | 143 | -17.534 | -9.313 | 11.723 | 1.00 | 10.27 |

FIGURE 3 (cont.)

| A | B | C | D | E | F | G | H | I | J |
|---|---|---|---|---|---|---|---|---|---|
| 6250 | CA | ASN | B | 143 | -17.486 | -8.021 | 11.036 | 1.00 | 9.98 |
| 6252 | CB | ASN | B | 143 | -17.788 | -6.873 | 11.986 | 1.00 | 9.71 |
| 6255 | CG | ASN | B | 143 | -19.150 | -6.948 | 12.603 | 1.00 | 10.65 |
| 6256 | OD1 | ASN | B | 143 | -19.964 | -7.839 | 12.300 | 1.00 | 9.89 |
| 6257 | ND2 | ASN | B | 143 | -19.407 | -6.012 | 13.522 | 1.00 | 11.96 |
| 6260 | C | ASN | B | 143 | -16.134 | -7.709 | 10.401 | 1.00 | 9.99 |
| 6261 | O | ASN | B | 143 | -16.068 | -6.870 | 9.497 | 1.00 | 11.03 |
| 6262 | N | PHE | B | 144 | -15.068 | -8.350 | 10.903 | 1.00 | 10.09 |
| 6264 | CA | PHE | B | 144 | -13.698 | -8.033 | 10.484 | 1.00 | 10.06 |
| 6266 | CB | PHE | B | 144 | -12.880 | -7.377 | 11.606 | 1.00 | 9.97 |
| 6269 | CG | PHE | B | 144 | -11.420 | -7.287 | 11.283 | 1.00 | 10.21 |
| 6270 | CD1 | PHE | B | 144 | -11.003 | -6.484 | 10.249 | 1.00 | 11.64 |
| 6272 | CE1 | PHE | B | 144 | -9.673 | -6.420 | 9.899 | 1.00 | 12.65 |
| 6274 | CZ | PHE | B | 144 | -8.749 | -7.186 | 10.559 | 1.00 | 11.94 |
| 6276 | CE2 | PHE | B | 144 | -9.135 | -8.002 | 11.584 | 1.00 | 11.08 |
| 6278 | CD2 | PHE | B | 144 | -10.490 | -8.069 | 11.941 | 1.00 | 10.76 |
| 6280 | C | PHE | B | 144 | -12.966 | -9.265 | 9.946 | 1.00 | 10.00 |
| 6281 | O | PHE | B | 144 | -12.627 | -9.299 | 8.773 | 1.00 | 10.10 |
| 6282 | N | LEU | B | 145 | -12.744 | -10.285 | 10.767 | 1.00 | 10.14 |
| 6284 | CA | LEU | B | 145 | -11.915 | -11.411 | 10.309 | 1.00 | 10.57 |
| 6286 | CB BLEU | | B | 145 | -11.636 | -12.402 | 11.446 | 0.35 | 10.78 |
| 6287 | CB ALEU | | B | 145 | -11.663 | -12.396 | 11.456 | 0.65 | 10.84 |
| 6292 | CG BLEU | | B | 145 | -10.504 | -11.991 | 12.390 | 0.35 | 11.79 |
| 6293 | CG ALEU | | B | 145 | -10.559 | -13.423 | 11.214 | 0.65 | 12.14 |
| 6296 | CD1BLEU | | B | 145 | -10.429 | -12.962 | 13.541 | 0.35 | 13.06 |
| 6297 | CD1ALEU | | B | 145 | -9.201 | -12.766 | 11.048 | 0.65 | 12.48 |
| 6304 | CD2BLEU | | B | 145 | -9.168 | -11.911 | 11.672 | 0.35 | 12.39 |
| 6305 | CD2ALEU | | B | 145 | -10.553 | -14.386 | 12.373 | 0.65 | 12.74 |
| 6312 | C | LEU | B | 145 | -12.518 | -12.132 | 9.102 | 1.00 | 10.24 |
| 6313 | O | LEU | B | 145 | -11.792 | -12.502 | 8.173 | 1.00 | 10.28 |
| 6314 | N | SER | B | 146 | -13.842 | -12.300 | 9.064 | 1.00 | 9.84 |
| 6316 | CA | SER | B | 146 | -14.450 | -12.956 | 7.915 | 1.00 | 9.89 |
| 6318 | CB | SER | B | 146 | -15.934 | -13.267 | 8.129 | 1.00 | 9.62 |
| 6321 | OG | SER | B | 146 | -16.725 | -12.091 | 8.059 | 1.00 | 10.58 |
| 6323 | C | SER | B | 146 | -14.231 | -12.157 | 6.638 | 1.00 | 9.60 |
| 6324 | O | SER | B | 146 | -14.111 | -12.743 | 5.568 | 1.00 | 10.67 |
| 6325 | N | TYR | B | 147 | -14.175 | -10.825 | 6.728 | 1.00 | 9.77 |
| 6327 | CA | TYR | B | 147 | -13.891 | -10.018 | 5.543 | 1.00 | 10.01 |
| 6329 | CB | TYR | B | 147 | -13.990 | -8.512 | 5.818 | 1.00 | 10.11 |
| 6332 | CG | TYR | B | 147 | -15.404 | -7.920 | 5.917 | 1.00 | 9.31 |
| 6333 | CD1 | TYR | B | 147 | -16.484 | -8.637 | 6.450 | 1.00 | 10.54 |
| 6335 | CE1 | TYR | B | 147 | -17.755 | -8.058 | 6.544 | 1.00 | 10.91 |
| 6337 | CZ | TYR | B | 147 | -17.958 | -6.771 | 6.091 | 1.00 | 10.19 |
| 6338 | OH | TYR | B | 147 | -19.214 | -6.196 | 6.192 | 1.00 | 11.05 |
| 6340 | CE2 | TYR | B | 147 | -16.899 | -6.047 | 5.553 | 1.00 | 9.46 |
| 6342 | CD2 | TYR | B | 147 | -15.646 | -6.622 | 5.474 | 1.00 | 9.21 |
| 6344 | C | TYR | B | 147 | -12.500 | -10.332 | 5.009 | 1.00 | 10.15 |
| 6345 | O | TYR | B | 147 | -12.297 | -10.370 | 3.810 | 1.00 | 10.88 |
| 6346 | N | VAL | B | 148 | -11.546 | -10.541 | 5.912 | 1.00 | 10.24 |

FIGURE 3 (cont.)

| A | B | C | D | E | F | G | H | I | J |
|---|---|---|---|---|---|---|---|---|---|
| 6348 | CA | VAL | B | 148 | -10.179 | -10.882 | 5.512 | 1.00 | 10.73 |
| 6350 | CB | VAL | B | 148 | -9.204 | -10.789 | 6.705 | 1.00 | 10.37 |
| 6352 | CG1 | VAL | B | 148 | -9.247 | -9.396 | 7.318 | 1.00 | 11.74 |
| 6356 | CG2 | VAL | B | 148 | -7.782 | -11.137 | 6.260 | 1.00 | 11.68 |
| 6360 | C | VAL | B | 148 | -10.150 | -12.260 | 4.843 | 1.00 | 10.43 |
| 6361 | O | VAL | B | 148 | -9.545 | -12.437 | 3.782 | 1.00 | 10.90 |
| 6362 | N | VAL | B | 149 | -10.839 | -13.226 | 5.441 | 1.00 | 10.89 |
| 6364 | CA | VAL | B | 149 | -10.904 | -14.567 | 4.882 | 1.00 | 11.04 |
| 6366 | CB | VAL | B | 149 | -11.670 | -15.522 | 5.808 | 1.00 | 11.48 |
| 6368 | CG1 | VAL | B | 149 | -11.877 | -16.876 | 5.131 | 1.00 | 11.08 |
| 6372 | CG2 | VAL | B | 149 | -10.946 | -15.687 | 7.131 | 1.00 | 12.02 |
| 6376 | C | VAL | B | 149 | -11.531 | -14.541 | 3.487 | 1.00 | 11.11 |
| 6377 | O | VAL | B | 149 | -11.040 | -15.203 | 2.566 | 1.00 | 11.58 |
| 6378 | N | LEU | B | 150 | -12.625 | -13.794 | 3.332 | 1.00 | 10.60 |
| 6380 | CA | LEU | B | 150 | -13.305 | -13.692 | 2.052 | 1.00 | 10.56 |
| 6382 | CB | LEU | B | 150 | -14.597 | -12.880 | 2.215 | 1.00 | 10.24 |
| 6385 | CG | LEU | B | 150 | -15.686 | -13.601 | 2.996 | 1.00 | 11.43 |
| 6387 | CD1 | LEU | B | 150 | -16.712 | -12.580 | 3.499 | 1.00 | 10.46 |
| 6391 | CD2 | LEU | B | 150 | -16.367 | -14.699 | 2.188 | 1.00 | 12.15 |
| 6395 | C | LEU | B | 150 | -12.403 | -13.070 | 0.998 | 1.00 | 10.64 |
| 6396 | O | LEU | B | 150 | -12.373 | -13.501 | -0.153 | 1.00 | 10.72 |
| 6397 | N | THR | B | 151 | -11.671 | -12.042 | 1.402 | 1.00 | 11.03 |
| 6399 | CA | THR | B | 151 | -10.739 | -11.368 | 0.517 | 1.00 | 11.66 |
| 6401 | CB | THR | B | 151 | -10.164 | -10.133 | 1.222 | 1.00 | 11.70 |
| 6403 | OG1 | THR | B | 151 | -11.212 | -9.169 | 1.415 | 1.00 | 12.53 |
| 6405 | CG2 | THR | B | 151 | -9.128 | -9.416 | 0.347 | 1.00 | 13.92 |
| 6409 | C | THR | B | 151 | -9.637 | -12.308 | 0.052 | 1.00 | 11.60 |
| 6410 | O | THR | B | 151 | -9.321 | -12.349 | -1.133 | 1.00 | 12.25 |
| 6411 | N | VAL | B | 152 | -9.063 | -13.072 | 0.967 | 1.00 | 10.91 |
| 6413 | CA | VAL | B | 152 | -8.004 | -14.014 | 0.607 | 1.00 | 11.09 |
| 6415 | CB | VAL | B | 152 | -7.458 | -14.710 | 1.874 | 1.00 | 11.31 |
| 6417 | CG1 | VAL | B | 152 | -6.630 | -15.919 | 1.514 | 1.00 | 12.41 |
| 6421 | CG2 | VAL | B | 152 | -6.639 | -13.724 | 2.702 | 1.00 | 11.67 |
| 6425 | C | VAL | B | 152 | -8.512 | -15.037 | -0.413 | 1.00 | 11.04 |
| 6426 | O | VAL | B | 152 | -7.826 | -15.349 | -1.402 | 1.00 | 12.04 |
| 6427 | N | ALA | B | 153 | -9.716 | -15.537 | -0.179 | 1.00 | 11.23 |
| 6429 | CA | ALA | B | 153 | -10.354 | -16.507 | -1.070 | 1.00 | 11.42 |
| 6431 | CB | ALA | B | 153 | -11.635 | -17.013 | -0.444 | 1.00 | 11.88 |
| 6435 | C | ALA | B | 153 | -10.633 | -15.917 | -2.449 | 1.00 | 11.72 |
| 6436 | O | ALA | B | 153 | -10.584 | -16.626 | -3.448 | 1.00 | 12.33 |
| 6437 | N | ALA | B | 154 | -10.974 | -14.637 | -2.500 | 1.00 | 11.17 |
| 6439 | CA | ALA | B | 154 | -11.416 | -13.997 | -3.738 | 1.00 | 11.57 |
| 6441 | CB | ALA | B | 154 | -12.382 | -12.869 | -3.422 | 1.00 | 12.27 |
| 6445 | C | ALA | B | 154 | -10.265 | -13.447 | -4.565 | 1.00 | 11.52 |
| 6446 | O | ALA | B | 154 | -10.415 | -13.209 | -5.766 | 1.00 | 11.61 |
| 6447 | N | LEU | B | 155 | -9.133 | -13.189 | -3.928 | 1.00 | 12.01 |
| 6449 | CA | LEU | B | 155 | -8.102 | -12.383 | -4.579 | 1.00 | 12.40 |
| 6451 | CB | LEU | B | 155 | -6.957 | -12.017 | -3.623 | 1.00 | 12.53 |
| 6454 | CG | LEU | B | 155 | -6.019 | -10.910 | -4.122 | 1.00 | 15.17 |

FIGURE 3 (cont.)

| A | B | C | D | E | F | G | H | I | J |
|---|---|---|---|---|---|---|---|---|---|
| 6456 | CD1 | LEU | B | 155 | -4.872 | -10.735 | -3.139 | 1.00 | 17.34 |
| 6460 | CD2 | LEU | B | 155 | -6.727 | -9.588 | -4.376 | 1.00 | 16.49 |
| 6464 | C | LEU | B | 155 | -7.575 | -12.982 | -5.891 | 1.00 | 12.20 |
| 6465 | O | LEU | B | 155 | -7.423 | -12.236 | -6.856 | 1.00 | 11.65 |
| 6466 | N | PRO | B | 156 | -7.287 | -14.283 | -5.971 | 1.00 | 12.56 |
| 6467 | CA | PRO | B | 156 | -6.824 | -14.838 | -7.250 | 1.00 | 12.74 |
| 6469 | CB | PRO | B | 156 | -6.681 | -16.331 | -6.956 | 1.00 | 12.66 |
| 6472 | CG | PRO | B | 156 | -6.418 | -16.378 | -5.513 | 1.00 | 12.78 |
| 6475 | CD | PRO | B | 156 | -7.302 | -15.312 | -4.917 | 1.00 | 13.15 |
| 6478 | C | PRO | B | 156 | -7.780 | -14.555 | -8.416 | 1.00 | 12.90 |
| 6479 | O | PRO | B | 156 | -7.310 | -14.172 | -9.491 | 1.00 | 13.46 |
| 6480 | N | MET | B | 157 | -9.085 | -14.698 | -8.195 | 1.00 | 12.50 |
| 6482 | CA | MET | B | 157 | -10.079 | -14.383 | -9.215 | 1.00 | 12.50 |
| 6484 | CB | MET | B | 157 | -11.473 | -14.878 | -8.799 | 1.00 | 12.82 |
| 6487 | CG | MET | B | 157 | -11.661 | -16.369 | -8.979 | 1.00 | 13.70 |
| 6490 | SD | MET | B | 157 | -13.345 | -16.928 | -8.707 | 1.00 | 16.97 |
| 6491 | CE | MET | B | 157 | -13.494 | -16.728 | -6.948 | 1.00 | 15.98 |
| 6495 | C | MET | B | 157 | -10.126 | -12.892 | -9.538 | 1.00 | 12.28 |
| 6496 | O | MET | B | 157 | -10.277 | -12.513 | -10.699 | 1.00 | 12.48 |
| 6497 | N | LEU | B | 158 | -10.012 | -12.046 | -8.516 | 1.00 | 12.06 |
| 6499 | CA | LEU | B | 158 | -9.988 | -10.600 | -8.723 | 1.00 | 11.94 |
| 6501 | CB | LEU | B | 158 | -10.151 | -9.856 | -7.402 | 1.00 | 11.86 |
| 6504 | CG | LEU | B | 158 | -11.477 | -10.107 | -6.670 | 1.00 | 11.77 |
| 6506 | CD1 | LEU | B | 158 | -11.428 | -9.484 | -5.268 | 1.00 | 13.32 |
| 6510 | CD2 | LEU | B | 158 | -12.655 | -9.578 | -7.466 | 1.00 | 12.74 |
| 6514 | C | LEU | B | 158 | -8.719 | -10.139 | -9.450 | 1.00 | 12.20 |
| 6515 | O | LEU | B | 158 | -8.781 | -9.212 | -10.230 | 1.00 | 12.72 |
| 6516 | N | LYS | B | 159 | -7.592 | -10.801 | -9.224 | 1.00 | 12.72 |
| 6518 | CA | LYS | B | 159 | -6.366 | -10.459 | -9.949 | 1.00 | 13.55 |
| 6520 | CB | LYS | B | 159 | -5.150 | -11.160 | -9.338 | 1.00 | 13.65 |
| 6523 | CG | LYS | B | 159 | -4.675 | -10.532 | -8.046 | 1.00 | 14.07 |
| 6526 | CD | LYS | B | 159 | -3.698 | -11.422 | -7.300 | 1.00 | 15.40 |
| 6529 | CE | LYS | B | 159 | -2.983 | -10.659 | -6.207 | 1.00 | 16.67 |
| 6532 | NZ | LYS | B | 159 | -2.057 | -11.539 | -5.405 | 1.00 | 19.28 |
| 6536 | C | LYS | B | 159 | -6.537 | -10.814 | -11.423 | 1.00 | 14.46 |
| 6537 | O | LYS | B | 159 | -6.063 | -10.092 | -12.310 | 1.00 | 15.16 |
| 6538 | N | GLN | B | 160 | -7.236 | -11.912 | -11.696 | 1.00 | 15.28 |
| 6540 | CA | GLN | B | 160 | -7.489 | -12.331 | -13.072 | 1.00 | 16.39 |
| 6542 | CB | GLN | B | 160 | -8.185 | -13.695 | -13.098 | 1.00 | 16.89 |
| 6545 | CG | GLN | B | 160 | -7.328 | -14.858 | -12.668 | 1.00 | 20.04 |
| 6548 | CD | GLN | B | 160 | -8.105 | -16.166 | -12.691 | 1.00 | 23.99 |
| 6549 | OE1 | GLN | B | 160 | -8.376 | -16.708 | -13.765 | 1.00 | 29.36 |
| 6550 | NE2 | GLN | B | 160 | -8.491 | -16.662 | -11.515 | 1.00 | 25.62 |
| 6553 | C | GLN | B | 160 | -8.331 | -11.316 | -13.834 | 1.00 | 16.16 |
| 6554 | O | GLN | B | 160 | -8.092 | -11.066 | -15.016 | 1.00 | 17.01 |
| 6555 | N | SER | B | 161 | -9.291 | -10.703 | -13.143 | 1.00 | 15.38 |
| 6557 | CA | SER | B | 161 | -10.235 | -9.781 | -13.769 | 1.00 | 14.97 |
| 6559 | CB | SER | B | 161 | -11.631 | -10.046 | -13.221 | 1.00 | 15.47 |
| 6562 | OG | SER | B | 161 | -11.666 | -9.816 | -11.826 | 1.00 | 14.66 |

FIGURE 3 (cont.)

| A | B | C | D | E | F | G | H | I | J |
|---|---|---|---|---|---|---|---|---|---|
| 6564 | C | SER | B | 161 | -9.907 | -8.301 | -13.563 | 1.00 | 14.44 |
| 6565 | O | SER | B | 161 | -10.672 | -7.436 | -14.011 | 1.00 | 14.01 |
| 6566 | N | ASN | B | 162 | -8.787 | -8.005 | -12.899 | 1.00 | 14.05 |
| 6568 | CA | ASN | B | 162 | -8.493 | -6.629 | -12.458 | 1.00 | 14.12 |
| 6570 | CB | ASN | B | 162 | -8.111 | -5.731 | -13.631 | 1.00 | 14.73 |
| 6573 | CG | ASN | B | 162 | -6.944 | -6.280 | -14.425 | 1.00 | 17.47 |
| 6574 | OD1 | ASN | B | 162 | -5.858 | -6.471 | -13.889 | 1.00 | 20.39 |
| 6575 | ND2 | ASN | B | 162 | -7.166 | -6.533 | -15.713 | 1.00 | 22.34 |
| 6578 | C | ASN | B | 162 | -9.700 | -6.040 | -11.744 | 1.00 | 13.54 |
| 6579 | O | ASN | B | 162 | -10.167 | -4.941 | -12.066 | 1.00 | 13.29 |
| 6580 | N | GLY | B | 163 | -10.200 | -6.800 | -10.776 | 1.00 | 12.77 |
| 6582 | CA | GLY | B | 163 | -11.468 | -6.533 | -10.140 | 1.00 | 12.40 |
| 6585 | C | GLY | B | 163 | -11.394 | -5.588 | -8.962 | 1.00 | 12.14 |
| 6586 | O | GLY | B | 163 | -10.469 | -4.799 | -8.833 | 1.00 | 10.92 |
| 6587 | N | SER | B | 164 | -12.386 | -5.709 | -8.088 | 1.00 | 12.40 |
| 6589 | CA | SER | B | 164 | -12.657 | -4.716 | -7.063 | 1.00 | 12.29 |
| 6591 | CB | SER | B | 164 | -13.675 | -3.711 | -7.604 | 1.00 | 12.63 |
| 6594 | OG | SER | B | 164 | -13.190 | -3.090 | -8.783 | 1.00 | 15.53 |
| 6596 | C | SER | B | 164 | -13.209 | -5.337 | -5.795 | 1.00 | 11.77 |
| 6597 | O | SER | B | 164 | -14.020 | -6.263 | -5.845 | 1.00 | 12.29 |
| 6598 | N | ILE | B | 165 | -12.760 | -4.804 | -4.669 | 1.00 | 10.79 |
| 6600 | CA | ILE | B | 165 | -13.257 | -5.136 | -3.348 | 1.00 | 10.81 |
| 6602 | CB | ILE | B | 165 | -12.103 | -5.536 | -2.422 | 1.00 | 11.35 |
| 6604 | CG1 | ILE | B | 165 | -11.351 | -6.735 | -2.983 | 1.00 | 12.49 |
| 6607 | CD1 | ILE | B | 165 | -9.968 | -6.920 | -2.362 | 1.00 | 15.04 |
| 6611 | CG2 | ILE | B | 165 | -12.641 | -5.827 | -1.025 | 1.00 | 12.62 |
| 6615 | C | ILE | B | 165 | -13.950 | -3.907 | -2.788 | 1.00 | 10.55 |
| 6616 | O | ILE | B | 165 | -13.384 | -2.818 | -2.788 | 1.00 | 10.14 |
| 6617 | N | VAL | B | 166 | -15.170 | -4.088 | -2.298 | 1.00 | 10.31 |
| 6619 | CA | VAL | B | 166 | -15.942 | -3.021 | -1.693 | 1.00 | 10.44 |
| 6621 | CB | VAL | B | 166 | -17.271 | -2.772 | -2.437 | 1.00 | 10.79 |
| 6623 | CG1 | VAL | B | 166 | -18.079 | -1.672 | -1.749 | 1.00 | 12.71 |
| 6627 | CG2 | VAL | B | 166 | -16.992 | -2.419 | -3.881 | 1.00 | 11.11 |
| 6631 | C | VAL | B | 166 | -16.214 | -3.433 | -0.263 | 1.00 | 10.36 |
| 6632 | O | VAL | B | 166 | -16.777 | -4.509 | -0.012 | 1.00 | 10.73 |
| 6633 | N | VAL | B | 167 | -15.770 | -2.606 | 0.670 | 1.00 | 10.27 |
| 6635 | CA | VAL | B | 167 | -15.926 | -2.849 | 2.104 | 1.00 | 10.60 |
| 6637 | CB | VAL | B | 167 | -14.555 | -2.767 | 2.832 | 1.00 | 10.54 |
| 6639 | CG1 | VAL | B | 167 | -14.724 | -2.936 | 4.339 | 1.00 | 11.91 |
| 6643 | CG2 | VAL | B | 167 | -13.599 | -3.811 | 2.281 | 1.00 | 13.18 |
| 6647 | C | VAL | B | 167 | -16.885 | -1.813 | 2.690 | 1.00 | 10.88 |
| 6648 | O | VAL | B | 167 | -16.612 | -0.621 | 2.651 | 1.00 | 10.80 |
| 6649 | N | VAL | B | 168 | -18.010 | -2.284 | 3.230 | 1.00 | 10.31 |
| 6651 | CA | VAL | B | 168 | -19.035 | -1.400 | 3.781 | 1.00 | 10.54 |
| 6653 | CB | VAL | B | 168 | -20.475 | -1.944 | 3.575 | 1.00 | 10.54 |
| 6655 | CG1 | VAL | B | 168 | -21.500 | -0.928 | 4.056 | 1.00 | 10.55 |
| 6659 | CG2 | VAL | B | 168 | -20.715 | -2.249 | 2.108 | 1.00 | 10.42 |
| 6663 | C | VAL | B | 168 | -18.738 | -1.129 | 5.257 | 1.00 | 10.84 |
| 6664 | O | VAL | B | 168 | -18.599 | -2.046 | 6.066 | 1.00 | 11.28 |

FIGURE 3 (cont.)

| A | B | C | D | E | F | G | H | I | J |
|---|---|---|---|---|---|---|---|---|---|
| 6665 | N | SER | B | 169 | -18.620 | 0.154 | 5.567 | 1.00 | 10.80 |
| 6667 | CA | SER | B | 169 | -18.340 | 0.634 | 6.912 | 1.00 | 10.94 |
| 6669 | CB | SER | B | 169 | -16.866 | 1.013 | 7.062 | 1.00 | 10.92 |
| 6672 | OG | SER | B | 169 | -16.539 | 1.221 | 8.434 | 1.00 | 12.02 |
| 6674 | C | SER | B | 169 | -19.276 | 1.802 | 7.242 | 1.00 | 11.06 |
| 6675 | O | SER | B | 169 | -20.375 | 1.906 | 6.695 | 1.00 | 11.35 |
| 6676 | N | SER | B | 170 | -18.841 | 2.680 | 8.133 | 1.00 | 10.47 |
| 6678 | CA | SER | B | 170 | -19.768 | 3.360 | 9.033 | 1.00 | 10.20 |
| 6680 | CB | SER | B | 170 | -20.057 | 2.457 | 10.245 | 1.00 | 10.68 |
| 6683 | OG | SER | B | 170 | -20.316 | 1.135 | 9.837 | 1.00 | 11.35 |
| 6685 | C | SER | B | 170 | -19.177 | 4.643 | 9.554 | 1.00 | 9.92 |
| 6686 | O | SER | B | 170 | -17.965 | 4.741 | 9.722 | 1.00 | 10.64 |
| 6687 | N | LEU | B | 171 | -20.024 | 5.613 | 9.880 | 1.00 | 9.43 |
| 6689 | CA | LEU | B | 171 | -19.539 | 6.765 | 10.646 | 1.00 | 9.32 |
| 6691 | CB | LEU | B | 171 | -20.683 | 7.709 | 11.036 | 1.00 | 9.63 |
| 6694 | CG | LEU | B | 171 | -21.317 | 8.485 | 9.875 | 1.00 | 10.60 |
| 6696 | CD1 | LEU | B | 171 | -20.317 | 9.408 | 9.182 | 1.00 | 13.36 |
| 6700 | CD2 | LEU | B | 171 | -22.482 | 9.277 | 10.404 | 1.00 | 10.91 |
| 6704 | C | LEU | B | 171 | -18.800 | 6.307 | 11.904 | 1.00 | 9.27 |
| 6705 | O | LEU | B | 171 | -17.779 | 6.886 | 12.258 | 1.00 | 9.16 |
| 6706 | N | ALA | B | 172 | -19.305 | 5.269 | 12.573 | 1.00 | 9.43 |
| 6708 | CA | ALA | B | 172 | -18.681 | 4.742 | 13.792 | 1.00 | 9.90 |
| 6710 | CB | ALA | B | 172 | -19.697 | 3.930 | 14.604 | 1.00 | 10.25 |
| 6714 | C | ALA | B | 172 | -17.427 | 3.904 | 13.489 | 1.00 | 10.34 |
| 6715 | O | ALA | B | 172 | -16.815 | 3.345 | 14.401 | 1.00 | 10.61 |
| 6716 | N | GLY | B | 173 | -17.054 | 3.841 | 12.208 | 1.00 | 9.97 |
| 6718 | CA | GLY | B | 173 | -15.771 | 3.333 | 11.764 | 1.00 | 10.16 |
| 6721 | C | GLY | B | 173 | -14.752 | 4.415 | 11.424 | 1.00 | 10.15 |
| 6722 | O | GLY | B | 173 | -13.647 | 4.095 | 10.973 | 1.00 | 9.80 |
| 6723 | N | LYS | B | 174 | -15.117 | 5.679 | 11.655 | 1.00 | 9.63 |
| 6725 | CA | LYS | B | 174 | -14.239 | 6.838 | 11.411 | 1.00 | 10.00 |
| 6727 | CB | LYS | B | 174 | -14.716 | 7.637 | 10.180 | 1.00 | 9.93 |
| 6730 | CG | LYS | B | 174 | -14.516 | 6.920 | 8.855 | 1.00 | 10.50 |
| 6733 | CD | LYS | B | 174 | -13.044 | 6.724 | 8.522 | 1.00 | 10.16 |
| 6736 | CE | LYS | B | 174 | -12.829 | 6.393 | 7.066 | 1.00 | 10.53 |
| 6739 | NZ | LYS | B | 174 | -11.360 | 6.286 | 6.773 | 1.00 | 10.87 |
| 6743 | C | LYS | B | 174 | -14.143 | 7.768 | 12.619 | 1.00 | 10.23 |
| 6744 | O | LYS | B | 174 | -13.119 | 8.440 | 12.811 | 1.00 | 10.55 |
| 6745 | N | VAL | B | 175 | -15.214 | 7.862 | 13.392 | 1.00 | 10.53 |
| 6747 | CA | VAL | B | 175 | -15.215 | 8.602 | 14.651 | 1.00 | 10.47 |
| 6749 | CB | VAL | B | 175 | -15.903 | 9.971 | 14.523 | 1.00 | 10.86 |
| 6751 | CG1 | VAL | B | 175 | -17.403 | 9.829 | 14.318 | 1.00 | 12.39 |
| 6755 | CG2 | VAL | B | 175 | -15.250 | 10.768 | 13.384 | 1.00 | 10.43 |
| 6759 | C | VAL | B | 175 | -15.868 | 7.752 | 15.734 | 1.00 | 10.34 |
| 6760 | O | VAL | B | 175 | -16.515 | 6.728 | 15.444 | 1.00 | 10.95 |
| 6761 | N | ALA | B | 176 | -15.690 | 8.169 | 16.975 | 1.00 | 11.24 |
| 6763 | CA | ALA | B | 176 | -16.190 | 7.405 | 18.118 | 1.00 | 11.39 |
| 6765 | CB | ALA | B | 176 | -15.226 | 7.500 | 19.273 | 1.00 | 11.50 |
| 6769 | C | ALA | B | 176 | -17.588 | 7.806 | 18.577 | 1.00 | 11.40 |

FIGURE 3 (cont.)

| A | B | C | D | E | F | G | H | I | J |
|---|---|---|---|---|---|---|---|---|---|
| 6770 | O | ALA | B | 176 | -17.942 | 8.986 | 18.620 | 1.00 | 12.07 |
| 6771 | N | TYR | B | 177 | -18.374 | 6.794 | 18.944 | 1.00 | 10.95 |
| 6773 | CA | TYR | B | 177 | -19.714 | 6.977 | 19.490 | 1.00 | 11.62 |
| 6775 | CB | TYR | B | 177 | -20.766 | 6.506 | 18.487 | 1.00 | 11.73 |
| 6778 | CG | TYR | B | 177 | -20.956 | 7.363 | 17.270 | 1.00 | 10.76 |
| 6779 | CD1 | TYR | B | 177 | -20.118 | 7.228 | 16.175 | 1.00 | 11.13 |
| 6781 | CE1 | TYR | B | 177 | -20.288 | 7.991 | 15.042 | 1.00 | 11.25 |
| 6783 | CZ | TYR | B | 177 | -21.311 | 8.916 | 14.991 | 1.00 | 10.66 |
| 6784 | OH | TYR | B | 177 | -21.472 | 9.665 | 13.852 | 1.00 | 11.56 |
| 6786 | CE2 | TYR | B | 177 | -22.158 | 9.074 | 16.056 | 1.00 | 11.13 |
| 6788 | CD2 | TYR | B | 177 | -21.986 | 8.289 | 17.194 | 1.00 | 11.28 |
| 6790 | C | TYR | B | 177 | -19.876 | 6.077 | 20.702 | 1.00 | 11.37 |
| 6791 | O | TYR | B | 177 | -19.401 | 4.944 | 20.684 | 1.00 | 11.93 |
| 6792 | N | PRO | B | 178 | -20.626 | 6.507 | 21.704 | 1.00 | 11.55 |
| 6793 | CA | PRO | B | 178 | -21.017 | 5.587 | 22.772 | 1.00 | 11.93 |
| 6795 | CB | PRO | B | 178 | -21.627 | 6.504 | 23.825 | 1.00 | 11.95 |
| 6798 | CG | PRO | B | 178 | -22.167 | 7.653 | 23.042 | 1.00 | 11.98 |
| 6801 | CD | PRO | B | 178 | -21.254 | 7.831 | 21.861 | 1.00 | 11.86 |
| 6804 | C | PRO | B | 178 | -22.062 | 4.594 | 22.248 | 1.00 | 11.98 |
| 6805 | O | PRO | B | 178 | -22.723 | 4.847 | 21.248 | 1.00 | 12.48 |
| 6806 | N | MET | B | 179 | -22.188 | 3.473 | 22.947 | 1.00 | 12.17 |
| 6808 | CA | MET | B | 179 | -23.224 | 2.444 | 22.757 | 1.00 | 12.36 |
| 6810 | CB | BMET | B | 179 | -24.633 | 3.029 | 22.495 | 0.35 | 12.42 |
| 6811 | CB | AMET | B | 179 | -24.630 | 3.067 | 22.664 | 0.65 | 13.16 |
| 6816 | CG | BMET | B | 179 | -25.055 | 4.271 | 23.253 | 0.35 | 12.59 |
| 6817 | CG | AMET | B | 179 | -24.956 | 4.066 | 23.789 | 0.65 | 15.42 |
| 6822 | SD | BMET | B | 179 | -26.674 | 4.858 | 22.660 | 0.35 | 12.77 |
| 6823 | SD | AMET | B | 179 | -24.457 | 3.555 | 25.461 | 0.65 | 20.19 |
| 6824 | CE | BMET | B | 179 | -27.213 | 5.684 | 24.020 | 0.35 | 14.60 |
| 6825 | CE | AMET | B | 179 | -24.896 | 4.938 | 26.456 | 0.65 | 21.28 |
| 6832 | C | MET | B | 179 | -22.944 | 1.461 | 21.613 | 1.00 | 11.78 |
| 6833 | O | MET | B | 179 | -23.747 | 0.559 | 21.368 | 1.00 | 12.41 |
| 6834 | N | VAL | B | 180 | -21.817 | 1.636 | 20.917 | 1.00 | 10.61 |
| 6836 | CA | VAL | B | 180 | -21.448 | 0.772 | 19.800 | 1.00 | 10.87 |
| 6838 | CB | VAL | B | 180 | -21.767 | 1.429 | 18.426 | 1.00 | 11.08 |
| 6840 | CG1 | VAL | B | 180 | -23.269 | 1.474 | 18.191 | 1.00 | 12.20 |
| 6844 | CG2 | VAL | B | 180 | -21.140 | 2.809 | 18.315 | 1.00 | 12.39 |
| 6848 | C | VAL | B | 180 | -19.959 | 0.382 | 19.869 | 1.00 | 10.10 |
| 6849 | O | VAL | B | 180 | -19.294 | 0.270 | 18.844 | 1.00 | 11.08 |
| 6850 | N | ALA | B | 181 | -19.436 | 0.158 | 21.067 | 1.00 | 10.18 |
| 6852 | CA | ALA | B | 181 | -17.978 | -0.030 | 21.247 | 1.00 | 10.20 |
| 6854 | CB | ALA | B | 181 | -17.621 | -0.135 | 22.729 | 1.00 | 10.67 |
| 6858 | C | ALA | B | 181 | -17.418 | -1.225 | 20.471 | 1.00 | 9.89 |
| 6859 | O | ALA | B | 181 | -16.440 | -1.077 | 19.740 | 1.00 | 9.82 |
| 6860 | N | ALA | B | 182 | -18.022 | -2.404 | 20.633 | 1.00 | 9.30 |
| 6862 | CA | ALA | B | 182 | -17.560 | -3.607 | 19.925 | 1.00 | 9.47 |
| 6864 | CB | ALA | B | 182 | -18.362 | -4.798 | 20.362 | 1.00 | 9.82 |
| 6868 | C | ALA | B | 182 | -17.661 | -3.449 | 18.413 | 1.00 | 9.76 |
| 6869 | O | ALA | B | 182 | -16.763 | -3.840 | 17.667 | 1.00 | 10.64 |

FIGURE 3 (cont.)

| A | B | C | D | E | F | G | H | I | J |
|---|---|---|---|---|---|---|---|---|---|
| 6870 | N | TYR | B | 183 | -18.766 | -2.875 | 17.946 | 1.00 | 9.09 |
| 6872 | CA | TYR | B | 183 | -18.970 | -2.653 | 16.521 | 1.00 | 9.39 |
| 6874 | CB | TYR | B | 183 | -20.362 | -2.091 | 16.307 | 1.00 | 9.89 |
| 6877 | CG | TYR | B | 183 | -20.697 | -1.582 | 14.930 | 1.00 | 9.36 |
| 6878 | CD1 | TYR | B | 183 | -21.250 | -2.421 | 13.973 | 1.00 | 8.46 |
| 6880 | CE1 | TYR | B | 183 | -21.595 | -1.955 | 12.721 | 1.00 | 8.81 |
| 6882 | CZ | TYR | B | 183 | -21.437 | -0.621 | 12.415 | 1.00 | 9.45 |
| 6883 | OH | TYR | B | 183 | -21.833 | -0.136 | 11.192 | 1.00 | 11.31 |
| 6885 | CE2 | TYR | B | 183 | -20.872 | 0.237 | 13.346 | 1.00 | 10.50 |
| 6887 | CD2 | TYR | B | 183 | -20.515 | -0.240 | 14.595 | 1.00 | 8.78 |
| 6889 | C | TYR | B | 183 | -17.949 | -1.678 | 15.977 | 1.00 | 9.38 |
| 6890 | O | TYR | B | 183 | -17.369 | -1.905 | 14.919 | 1.00 | 9.47 |
| 6891 | N | SER | B | 184 | -17.754 | -0.580 | 16.689 | 1.00 | 9.95 |
| 6893 | CA | SER | B | 184 | -16.801 | 0.435 | 16.267 | 1.00 | 10.14 |
| 6895 | CB | SER | B | 184 | -16.824 | 1.622 | 17.220 | 1.00 | 11.38 |
| 6898 | OG | SER | B | 184 | -15.894 | 2.602 | 16.828 | 1.00 | 16.20 |
| 6900 | C | SER | B | 184 | -15.394 | -0.148 | 16.170 | 1.00 | 9.89 |
| 6901 | O | SER | B | 184 | -14.698 | 0.133 | 15.217 | 1.00 | 9.45 |
| 6902 | N | ALA | B | 185 | -15.006 | -0.978 | 17.132 | 1.00 | 9.56 |
| 6904 | CA | ALA | B | 185 | -13.696 | -1.643 | 17.060 | 1.00 | 9.45 |
| 6906 | CB | ALA | B | 185 | -13.475 | -2.551 | 18.215 | 1.00 | 9.09 |
| 6910 | C | ALA | B | 185 | -13.567 | -2.403 | 15.761 | 1.00 | 9.17 |
| 6911 | O | ALA | B | 185 | -12.531 | -2.304 | 15.090 | 1.00 | 8.89 |
| 6912 | N | SER | B | 186 | -14.605 | -3.149 | 15.383 | 1.00 | 8.39 |
| 6914 | CA | SER | B | 186 | -14.534 | -3.955 | 14.168 | 1.00 | 8.65 |
| 6916 | CB | SER | B | 186 | -15.677 | -4.965 | 14.094 | 1.00 | 8.65 |
| 6919 | OG | SER | B | 186 | -16.932 | -4.356 | 13.840 | 1.00 | 9.10 |
| 6921 | C | SER | B | 186 | -14.454 | -3.115 | 12.904 | 1.00 | 8.69 |
| 6922 | O | SER | B | 186 | -13.738 | -3.474 | 11.969 | 1.00 | 9.00 |
| 6923 | N | LYS | B | 187 | -15.171 | -1.995 | 12.860 | 1.00 | 8.31 |
| 6925 | CA | LYS | B | 187 | -15.178 | -1.150 | 11.665 | 1.00 | 8.18 |
| 6927 | CB | LYS | B | 187 | -16.413 | -0.241 | 11.645 | 1.00 | 8.67 |
| 6930 | CG | LYS | B | 187 | -17.749 | -0.998 | 11.530 | 1.00 | 8.98 |
| 6933 | CD | LYS | B | 187 | -17.837 | -1.815 | 10.238 | 1.00 | 8.83 |
| 6936 | CE | LYS | B | 187 | -19.274 | -2.175 | 9.865 | 1.00 | 10.34 |
| 6939 | NZ | LYS | B | 187 | -19.399 | -2.928 | 8.581 | 1.00 | 8.88 |
| 6943 | C | LYS | B | 187 | -13.881 | -0.330 | 11.552 | 1.00 | 7.85 |
| 6944 | O | LYS | B | 187 | -13.358 | -0.128 | 10.460 | 1.00 | 8.40 |
| 6945 | N | PHE | B | 188 | -13.382 | 0.161 | 12.672 | 1.00 | 8.19 |
| 6947 | CA | PHE | B | 188 | -12.053 | 0.764 | 12.709 | 1.00 | 7.78 |
| 6949 | CB | PHE | B | 188 | -11.692 | 1.235 | 14.122 | 1.00 | 7.54 |
| 6952 | CG | PHE | B | 188 | -12.081 | 2.669 | 14.429 | 1.00 | 7.84 |
| 6953 | CD1 | PHE | B | 188 | -11.101 | 3.626 | 14.630 | 1.00 | 8.16 |
| 6955 | CE1 | PHE | B | 188 | -11.433 | 4.943 | 14.941 | 1.00 | 8.44 |
| 6957 | CZ | PHE | B | 188 | -12.742 | 5.322 | 15.056 | 1.00 | 8.30 |
| 6959 | CE2 | PHE | B | 188 | -13.752 | 4.352 | 14.876 | 1.00 | 7.99 |
| 6961 | CD2 | PHE | B | 188 | -13.408 | 3.044 | 14.560 | 1.00 | 8.33 |
| 6963 | C | PHE | B | 188 | -11.011 | -0.247 | 12.195 | 1.00 | 7.71 |
| 6964 | O | PHE | B | 188 | -10.138 | 0.120 | 11.394 | 1.00 | 8.02 |

FIGURE 3 (cont.)

| A | B | C | D | E | F | G | H | I | J |
|---|---|---|---|---|---|---|---|---|---|
| 6965 | N | ALA | B | 189 | -11.112 | -1.509 | 12.617 | 1.00 | 7.76 |
| 6967 | CA | ALA | B | 189 | -10.165 | -2.544 | 12.178 | 1.00 | 8.36 |
| 6969 | CB | ALA | B | 189 | -10.462 | -3.851 | 12.849 | 1.00 | 8.12 |
| 6973 | C | ALA | B | 189 | -10.187 | -2.710 | 10.659 | 1.00 | 8.84 |
| 6974 | O | ALA | B | 189 | -9.140 | -2.831 | 10.044 | 1.00 | 8.96 |
| 6975 | N | LEU | B | 190 | -11.377 | -2.691 | 10.058 | 1.00 | 8.73 |
| 6977 | CA | LEU | B | 190 | -11.505 | -2.771 | 8.607 | 1.00 | 9.25 |
| 6979 | CB | LEU | B | 190 | -12.982 | -2.718 | 8.193 | 1.00 | 9.20 |
| 6982 | CG | LEU | B | 190 | -13.817 | -3.958 | 8.470 | 1.00 | 10.50 |
| 6984 | CD1 | LEU | B | 190 | -15.268 | -3.629 | 8.170 | 1.00 | 11.23 |
| 6988 | CD2 | LEU | B | 190 | -13.330 | -5.138 | 7.637 | 1.00 | 10.76 |
| 6992 | C | LEU | B | 190 | -10.750 | -1.642 | 7.907 | 1.00 | 9.46 |
| 6993 | O | LEU | B | 190 | -10.103 | -1.864 | 6.891 | 1.00 | 9.36 |
| 6994 | N | ASP | B | 191 | -10.834 | -0.433 | 8.440 | 1.00 | 9.39 |
| 6996 | CA | ASP | B | 191 | -10.131 | 0.706 | 7.852 | 1.00 | 9.69 |
| 6998 | CB | ASP | B | 191 | -10.544 | 1.972 | 8.583 | 1.00 | 9.68 |
| 7001 | CG | ASP | B | 191 | -10.029 | 3.233 | 7.948 | 1.00 | 10.57 |
| 7002 | OD1 | ASP | B | 191 | -9.398 | 3.195 | 6.869 | 1.00 | 11.55 |
| 7003 | OD2 | ASP | B | 191 | -10.235 | 4.331 | 8.493 | 1.00 | 11.12 |
| 7004 | C | ASP | B | 191 | -8.618 | 0.467 | 7.920 | 1.00 | 9.64 |
| 7005 | O | ASP | B | 191 | -7.911 | 0.572 | 6.921 | 1.00 | 10.14 |
| 7006 | N | GLY | B | 192 | -8.121 | 0.129 | 9.104 | 1.00 | 10.15 |
| 7008 | CA | GLY | B | 192 | -6.708 | -0.122 | 9.289 | 1.00 | 10.31 |
| 7011 | C | GLY | B | 192 | -6.208 | -1.203 | 8.358 | 1.00 | 10.56 |
| 7012 | O | GLY | B | 192 | -5.215 | -1.020 | 7.668 | 1.00 | 10.85 |
| 7013 | N | PHE | B | 193 | -6.923 | -2.321 | 8.300 | 1.00 | 9.70 |
| 7015 | CA | PHE | B | 193 | -6.484 | -3.443 | 7.490 | 1.00 | 9.67 |
| 7017 | CB | PHE | B | 193 | -7.295 | -4.700 | 7.780 | 1.00 | 9.24 |
| 7020 | CG | PHE | B | 193 | -6.740 | -5.916 | 7.118 | 1.00 | 9.60 |
| 7021 | CD1 | PHE | B | 193 | -7.239 | -6.357 | 5.893 | 1.00 | 11.05 |
| 7023 | CE1 | PHE | B | 193 | -6.695 | -7.469 | 5.271 | 1.00 | 11.40 |
| 7025 | CZ | PHE | B | 193 | -5.645 | -8.139 | 5.865 | 1.00 | 11.63 |
| 7027 | CE2 | PHE | B | 193 | -5.138 | -7.704 | 7.063 | 1.00 | 11.22 |
| 7029 | CD2 | PHE | B | 193 | -5.681 | -6.599 | 7.690 | 1.00 | 10.48 |
| 7031 | C | PHE | B | 193 | -6.551 | -3.148 | 5.992 | 1.00 | 9.36 |
| 7032 | O | PHE | B | 193 | -5.561 | -3.303 | 5.262 | 1.00 | 9.24 |
| 7033 | N | PHE | B | 194 | -7.733 | -2.794 | 5.510 | 1.00 | 9.11 |
| 7035 | CA | PHE | B | 194 | -7.931 | -2.616 | 4.074 | 1.00 | 9.13 |
| 7037 | CB | PHE | B | 194 | -9.418 | -2.649 | 3.712 | 1.00 | 9.54 |
| 7040 | CG | PHE | B | 194 | -9.976 | -4.038 | 3.726 | 1.00 | 9.84 |
| 7041 | CD1 | PHE | B | 194 | -10.542 | -4.562 | 4.878 | 1.00 | 9.76 |
| 7043 | CE1 | PHE | B | 194 | -11.018 | -5.872 | 4.890 | 1.00 | 10.82 |
| 7045 | CZ | PHE | B | 194 | -10.895 | -6.663 | 3.766 | 1.00 | 11.13 |
| 7047 | CE2 | PHE | B | 194 | -10.312 | -6.154 | 2.625 | 1.00 | 12.24 |
| 7049 | CD2 | PHE | B | 194 | -9.838 | -4.858 | 2.616 | 1.00 | 11.28 |
| 7051 | C | PHE | B | 194 | -7.214 | -1.397 | 3.508 | 1.00 | 9.90 |
| 7052 | O | PHE | B | 194 | -6.800 | -1.421 | 2.351 | 1.00 | 9.84 |
| 7053 | N | SER | B | 195 | -7.059 | -0.341 | 4.301 | 1.00 | 9.93 |
| 7055 | CA | SER | B | 195 | -6.256 | 0.801 | 3.867 | 1.00 | 10.52 |

FIGURE 3 (cont.)

| A | B | C | D | E | F | G | H | I | J |
|---|---|---|---|---|---|---|---|---|---|
| 7057 | CB | SER | B | 195 | -6.444 | 1.997 | 4.789 | 1.00 | 10.59 |
| 7060 | OG | SER | B | 195 | -7.804 | 2.384 | 4.784 | 1.00 | 10.33 |
| 7062 | C | SER | B | 195 | -4.787 | 0.431 | 3.757 | 1.00 | 10.42 |
| 7063 | O | SER | B | 195 | -4.088 | 0.955 | 2.902 | 1.00 | 10.61 |
| 7064 | N | SER | B | 196 | -4.311 | -0.460 | 4.628 | 1.00 | 9.86 |
| 7066 | CA | SER | B | 196 | -2.935 | -0.952 | 4.566 | 1.00 | 10.09 |
| 7068 | CB | BSER | B | 196 | -2.584 | -1.731 | 5.834 | 0.35 | 10.28 |
| 7069 | CB | ASER | B | 196 | -2.565 | -1.771 | 5.809 | 0.65 | 10.07 |
| 7074 | OG | BSER | B | 196 | -2.265 | -0.836 | 6.880 | 0.35 | 12.07 |
| 7075 | OG | ASER | B | 196 | -1.287 | -2.387 | 5.642 | 0.65 | 8.68 |
| 7078 | C | SER | B | 196 | -2.736 | -1.816 | 3.336 | 1.00 | 9.89 |
| 7079 | O | SER | B | 196 | -1.767 | -1.647 | 2.617 | 1.00 | 10.28 |
| 7080 | N | ILE | B | 197 | -3.655 | -2.753 | 3.086 | 1.00 | 9.77 |
| 7082 | CA | ILE | B | 197 | -3.527 | -3.592 | 1.903 | 1.00 | 10.76 |
| 7084 | CB | BILE | B | 197 | -4.697 | -4.632 | 1.902 | 0.35 | 10.20 |
| 7085 | CB | AILE | B | 197 | -4.335 | -4.923 | 1.915 | 0.65 | 11.84 |
| 7088 | CG1 | BILE | B | 197 | -4.608 | -5.587 | 3.097 | 0.35 | 9.52 |
| 7089 | CG1 | AILE | B | 197 | -5.831 | -4.730 | 1.986 | 0.65 | 13.67 |
| 7094 | CD1 | BILE | B | 197 | -3.445 | -6.572 | 3.017 | 0.35 | 8.96 |
| 7095 | CD1 | AILE | B | 197 | -6.584 | -5.960 | 1.472 | 0.65 | 14.81 |
| 7102 | CG2 | BILE | B | 197 | -4.762 | -5.399 | 0.589 | 0.35 | 8.96 |
| 7103 | CG2 | AILE | B | 197 | -3.835 | -5.842 | 3.060 | 0.65 | 12.75 |
| 7110 | C | ILE | B | 197 | -3.636 | -2.767 | 0.616 | 1.00 | 10.72 |
| 7111 | O | ILE | B | 197 | -2.950 | -3.079 | -0.347 | 1.00 | 11.23 |
| 7112 | N | ARG | B | 198 | -4.437 | -1.701 | 0.601 | 1.00 | 11.00 |
| 7114 | CA | ARG | B | 198 | -4.497 | -0.857 | -0.584 | 1.00 | 11.27 |
| 7116 | CB | ARG | B | 198 | -5.489 | 0.291 | -0.411 | 1.00 | 11.44 |
| 7119 | CG | ARG | B | 198 | -5.691 | 1.087 | -1.697 | 1.00 | 12.03 |
| 7122 | CD | ARG | B | 198 | -6.503 | 2.344 | -1.531 | 1.00 | 12.79 |
| 7125 | NE | ARG | B | 198 | -7.891 | 2.097 | -1.143 | 1.00 | 13.14 |
| 7127 | CZ | ARG | B | 198 | -8.430 | 2.422 | 0.034 | 1.00 | 13.41 |
| 7128 | NH1 | ARG | B | 198 | -7.696 | 2.948 | 1.005 | 1.00 | 14.44 |
| 7131 | NH2 | ARG | B | 198 | -9.718 | 2.210 | 0.254 | 1.00 | 13.48 |
| 7134 | C | ARG | B | 198 | -3.109 | -0.306 | -0.910 | 1.00 | 11.51 |
| 7135 | O | ARG | B | 198 | -2.693 | -0.293 | -2.070 | 1.00 | 11.80 |
| 7136 | N | LYS | B | 199 | -2.392 | 0.132 | 0.120 | 1.00 | 11.68 |
| 7138 | CA | LYS | B | 199 | -1.028 | 0.622 | -0.056 | 1.00 | 11.98 |
| 7140 | CB | LYS | B | 199 | -0.539 | 1.293 | 1.222 | 1.00 | 12.64 |
| 7143 | CG | LYS | B | 199 | -1.269 | 2.613 | 1.442 | 1.00 | 13.65 |
| 7146 | CD | LYS | B | 199 | -0.943 | 3.257 | 2.741 | 1.00 | 16.59 |
| 7149 | CE | LYS | B | 199 | -1.843 | 4.455 | 2.955 | 1.00 | 16.60 |
| 7152 | NZ | LYS | B | 199 | -1.851 | 5.467 | 1.862 | 1.00 | 17.18 |
| 7156 | C | LYS | B | 199 | -0.079 | -0.479 | -0.530 | 1.00 | 11.97 |
| 7157 | O | LYS | B | 199 | 0.770 | -0.246 | -1.375 | 1.00 | 12.47 |
| 7158 | N | GLU | B | 200 | -0.258 | -1.689 | -0.015 | 1.00 | 11.75 |
| 7160 | CA | GLU | B | 200 | 0.550 | -2.821 | -0.447 | 1.00 | 11.92 |
| 7162 | CB | GLU | B | 200 | 0.275 | -4.041 | 0.430 | 1.00 | 11.83 |
| 7165 | CG | GLU | B | 200 | 0.717 | -3.805 | 1.862 | 1.00 | 11.98 |
| 7168 | CD | GLU | B | 200 | 0.612 | -5.024 | 2.756 | 1.00 | 13.26 |

FIGURE 3 (cont.)

| A | B | C | D | E | F | G | H | I | J |
|---|---|---|---|---|---|---|---|---|---|
| 7169 | OE1 | GLU | B | 200 | 0.872 | -4.850 | 3.967 | 1.00 | 13.29 |
| 7170 | OE2 | GLU | B | 200 | 0.261 | -6.129 | 2.280 | 1.00 | 11.54 |
| 7171 | C | GLU | B | 200 | 0.286 | -3.159 | -1.898 | 1.00 | 12.45 |
| 7172 | O | GLU | B | 200 | 1.205 | -3.514 | -2.613 | 1.00 | 13.09 |
| 7173 | N | TYR | B | 201 | -0.969 | -3.080 | -2.337 | 1.00 | 12.52 |
| 7175 | CA | TYR | B | 201 | -1.283 | -3.370 | -3.734 | 1.00 | 13.50 |
| 7177 | CB | TYR | B | 201 | -2.788 | -3.450 | -3.998 | 1.00 | 12.95 |
| 7180 | CG | TYR | B | 201 | -3.491 | -4.638 | -3.373 | 1.00 | 13.96 |
| 7181 | CD1 | TYR | B | 201 | -2.784 | -5.624 | -2.680 | 1.00 | 15.84 |
| 7183 | CE1 | TYR | B | 201 | -3.443 | -6.706 | -2.107 | 1.00 | 17.27 |
| 7185 | CZ | TYR | B | 201 | -4.807 | -6.811 | -2.227 | 1.00 | 18.05 |
| 7186 | OH | TYR | B | 201 | -5.480 | -7.865 | -1.653 | 1.00 | 23.09 |
| 7188 | CE2 | TYR | B | 201 | -5.529 | -5.859 | -2.912 | 1.00 | 16.69 |
| 7190 | CD2 | TYR | B | 201 | -4.871 | -4.779 | -3.488 | 1.00 | 14.83 |
| 7192 | C | TYR | B | 201 | -0.653 | -2.327 | -4.643 | 1.00 | 14.54 |
| 7193 | O | TYR | B | 201 | -0.263 | -2.651 | -5.758 | 1.00 | 14.82 |
| 7194 | N | SER | B | 202 | -0.541 | -1.084 | -4.176 | 1.00 | 15.83 |
| 7196 | CA | SER | B | 202 | 0.124 | -0.047 | -4.977 | 1.00 | 17.14 |
| 7198 | CB | BSER | B | 202 | -0.048 | 1.333 | -4.337 | 0.35 | 17.06 |
| 7199 | CB | ASER | B | 202 | -0.038 | 1.329 | -4.331 | 0.65 | 17.29 |
| 7204 | OG | BSER | B | 202 | 0.618 | 2.332 | -5.093 | 0.35 | 16.87 |
| 7205 | OG | ASER | B | 202 | -1.398 | 1.621 | -4.078 | 0.65 | 18.68 |
| 7208 | C | SER | B | 202 | 1.607 | -0.361 | -5.184 | 1.00 | 17.90 |
| 7209 | O | SER | B | 202 | 2.108 | -0.259 | -6.309 | 1.00 | 18.61 |
| 7210 | N | VAL | B | 203 | 2.311 | -0.760 | -4.120 | 1.00 | 18.56 |
| 7212 | CA | VAL | B | 203 | 3.750 | -1.047 | -4.246 | 1.00 | 18.86 |
| 7214 | CB | BVAL | B | 203 | 4.527 | -0.999 | -2.873 | 0.35 | 19.08 |
| 7215 | CB | AVAL | B | 203 | 4.505 | -0.939 | -2.892 | 0.65 | 19.42 |
| 7218 | CG1 | BVAL | B | 203 | 3.900 | -0.011 | -1.893 | 0.35 | 18.74 |
| 7219 | CG1 | AVAL | B | 203 | 4.543 | 0.511 | -2.431 | 0.65 | 19.82 |
| 7226 | CG2 | BVAL | B | 203 | 4.655 | -2.386 | -2.231 | 0.35 | 19.17 |
| 7227 | CG2 | AVAL | B | 203 | 3.887 | -1.817 | -1.832 | 0.65 | 19.25 |
| 7234 | C | VAL | B | 203 | 4.019 | -2.386 | -4.952 | 1.00 | 18.83 |
| 7235 | O | VAL | B | 203 | 5.032 | -2.517 | -5.642 | 1.00 | 19.05 |
| 7236 | N | SER | B | 204 | 3.115 | -3.357 | -4.804 | 1.00 | 17.91 |
| 7238 | CA | SER | B | 204 | 3.263 | -4.669 | -5.443 | 1.00 | 17.77 |
| 7240 | CB | BSER | B | 204 | 2.727 | -5.793 | -4.544 | 0.35 | 17.81 |
| 7241 | CB | ASER | B | 204 | 2.627 | -5.770 | -4.586 | 0.65 | 18.25 |
| 7246 | OG | BSER | B | 204 | 1.379 | -5.583 | -4.171 | 0.35 | 17.15 |
| 7247 | OG | ASER | B | 204 | 3.309 | -5.945 | -3.366 | 0.65 | 20.23 |
| 7250 | C | SER | B | 204 | 2.613 | -4.708 | -6.835 | 1.00 | 17.20 |
| 7251 | O | SER | B | 204 | 2.649 | -5.737 | -7.495 | 1.00 | 16.75 |
| 7252 | N | ARG | B | 205 | 2.023 | -3.594 | -7.269 | 1.00 | 16.27 |
| 7254 | CA | ARG | B | 205 | 1.372 | -3.502 | -8.585 | 1.00 | 16.65 |
| 7256 | CB | ARG | B | 205 | 2.426 | -3.524 | -9.697 | 1.00 | 17.54 |
| 7259 | CG | ARG | B | 205 | 3.446 | -2.426 | -9.518 | 1.00 | 20.28 |
| 7262 | CD | ARG | B | 205 | 4.084 | -1.945 | -10.808 | 1.00 | 24.36 |
| 7265 | NE | ARG | B | 205 | 5.080 | -2.895 | -11.297 | 1.00 | 27.85 |
| 7267 | CZ | ARG | B | 205 | 6.201 | -2.570 | -11.950 | 1.00 | 30.37 |

FIGURE 3 (cont.)

| A | B | C | D | E | F | G | H | I | J |
|---|---|---|---|---|---|---|---|---|---|
| 7268 | NH1 | ARG | B | 205 | 6.503 | -1.299 | -12.217 | 1.00 | 31.90 |
| 7271 | NH2 | ARG | B | 205 | 7.033 | -3.529 | -12.343 | 1.00 | 32.06 |
| 7274 | C | ARG | B | 205 | 0.280 | -4.549 | -8.800 | 1.00 | 16.17 |
| 7275 | O | ARG | B | 205 | 0.195 | -5.208 | -9.842 | 1.00 | 16.15 |
| 7276 | N | VAL | B | 206 | -0.561 | -4.695 | -7.787 | 1.00 | 14.89 |
| 7278 | CA | VAL | B | 206 | -1.745 | -5.534 | -7.880 | 1.00 | 14.33 |
| 7280 | CB | VAL | B | 206 | -2.058 | -6.212 | -6.538 | 1.00 | 14.18 |
| 7282 | CG1 | VAL | B | 206 | -3.390 | -6.954 | -6.601 | 1.00 | 14.04 |
| 7286 | CG2 | VAL | B | 206 | -0.930 | -7.167 | -6.146 | 1.00 | 13.98 |
| 7290 | C | VAL | B | 206 | -2.903 | -4.639 | -8.303 | 1.00 | 14.42 |
| 7291 | O | VAL | B | 206 | -3.248 | -3.693 | -7.597 | 1.00 | 14.75 |
| 7292 | N | ASN | B | 207 | -3.510 | -4.953 | -9.446 | 1.00 | 14.06 |
| 7294 | CA | ASN | B | 207 | -4.534 | -4.103 | -10.049 | 1.00 | 14.20 |
| 7296 | CB | ASN | B | 207 | -4.430 | -4.165 | -11.585 | 1.00 | 14.73 |
| 7299 | CG | ASN | B | 207 | -5.192 | -3.038 | -12.270 | 1.00 | 17.92 |
| 7300 | OD1 | ASN | B | 207 | -5.525 | -2.028 | -11.641 | 1.00 | 22.61 |
| 7301 | ND2 | ASN | B | 207 | -5.457 | -3.198 | -13.565 | 1.00 | 21.33 |
| 7304 | C | ASN | B | 207 | -5.943 | -4.488 | -9.586 | 1.00 | 13.25 |
| 7305 | O | ASN | B | 207 | -6.827 | -4.775 | -10.393 | 1.00 | 13.76 |
| 7306 | N | VAL | B | 208 | -6.124 | -4.498 | -8.266 | 1.00 | 12.11 |
| 7308 | CA | VAL | B | 208 | -7.402 | -4.762 | -7.622 | 1.00 | 11.71 |
| 7310 | CB | VAL | B | 208 | -7.328 | -6.036 | -6.763 | 1.00 | 11.42 |
| 7312 | CG1 | VAL | B | 208 | -8.621 | -6.226 | -5.916 | 1.00 | 12.16 |
| 7316 | CG2 | VAL | B | 208 | -7.055 | -7.259 | -7.638 | 1.00 | 12.23 |
| 7320 | C | VAL | B | 208 | -7.721 | -3.550 | -6.751 | 1.00 | 11.16 |
| 7321 | O | VAL | B | 208 | -6.914 | -3.163 | -5.902 | 1.00 | 11.33 |
| 7322 | N | SER | B | 209 | -8.866 | -2.923 | -6.990 | 1.00 | 10.70 |
| 7324 | CA | SER | B | 209 | -9.242 | -1.720 | -6.247 | 1.00 | 10.48 |
| 7326 | CB | SER | B | 209 | -10.145 | -0.814 | -7.077 | 1.00 | 10.69 |
| 7329 | OG | SER | B | 209 | -11.373 | -1.440 | -7.399 | 1.00 | 11.75 |
| 7331 | C | SER | B | 209 | -9.908 | -2.093 | -4.922 | 1.00 | 10.01 |
| 7332 | O | SER | B | 209 | -10.499 | -3.157 | -4.798 | 1.00 | 9.89 |
| 7333 | N | ILE | B | 210 | -9.767 | -1.210 | -3.944 | 1.00 | 10.03 |
| 7335 | CA | ILE | B | 210 | -10.419 | -1.331 | -2.644 | 1.00 | 10.61 |
| 7337 | CB | ILE | B | 210 | -9.390 | -1.631 | -1.525 | 1.00 | 10.69 |
| 7339 | CG1 | ILE | B | 210 | -8.725 | -2.994 | -1.744 | 1.00 | 11.41 |
| 7342 | CD1 | ILE | B | 210 | -7.526 | -3.250 | -0.867 | 1.00 | 12.15 |
| 7346 | CG2 | ILE | B | 210 | -10.058 | -1.610 | -0.156 | 1.00 | 11.69 |
| 7350 | C | ILE | B | 210 | -11.162 | -0.028 | -2.354 | 1.00 | 10.96 |
| 7351 | O | ILE | B | 210 | -10.561 | 1.049 | -2.341 | 1.00 | 10.99 |
| 7352 | N | THR | B | 211 | -12.466 | -0.139 | -2.109 | 1.00 | 11.44 |
| 7354 | CA | THR | B | 211 | -13.334 | 0.992 | -1.831 | 1.00 | 11.79 |
| 7356 | CB | THR | B | 211 | -14.484 | 1.016 | -2.853 | 1.00 | 11.55 |
| 7358 | OG1 | THR | B | 211 | -13.961 | 1.133 | -4.192 | 1.00 | 12.06 |
| 7360 | CG2 | THR | B | 211 | -15.353 | 2.230 | -2.670 | 1.00 | 11.79 |
| 7364 | C | THR | B | 211 | -13.910 | 0.802 | -0.447 | 1.00 | 11.64 |
| 7365 | O | THR | B | 211 | -14.583 | -0.203 | -0.206 | 1.00 | 12.36 |
| 7366 | N | LEU | B | 212 | -13.650 | 1.739 | 0.453 | 1.00 | 11.05 |
| 7368 | CA | LEU | B | 212 | -14.239 | 1.733 | 1.789 | 1.00 | 11.17 |

FIGURE 3 (cont.)

| A | B | C | D | E | F | G | H | I | J |
|---|---|---|---|---|---|---|---|---|---|
| 7370 | CB | LEU | B | 212 | -13.198 | 2.137 | 2.835 | 1.00 | 11.04 |
| 7373 | CG | LEU | B | 212 | -13.637 | 2.124 | 4.308 | 1.00 | 11.93 |
| 7375 | CD1 | LEU | B | 212 | -12.576 | 2.789 | 5.160 | 1.00 | 14.69 |
| 7379 | CD2 | LEU | B | 212 | -13.886 | 0.711 | 4.774 | 1.00 | 13.42 |
| 7383 | C | LEU | B | 212 | -15.409 | 2.702 | 1.824 | 1.00 | 11.32 |
| 7384 | O | LEU | B | 212 | -15.252 | 3.866 | 1.471 | 1.00 | 12.08 |
| 7385 | N | CYS | B | 213 | -16.576 | 2.228 | 2.264 | 1.00 | 11.29 |
| 7387 | CA | CYS | B | 213 | -17.805 | 3.022 | 2.259 | 1.00 | 11.65 |
| 7389 | CB | CYS | B | 213 | -18.952 | 2.188 | 1.707 | 1.00 | 12.12 |
| 7392 | SG | CYS | B | 213 | -18.577 | 1.572 | 0.069 | 1.00 | 15.40 |
| 7393 | C | CYS | B | 213 | -18.097 | 3.442 | 3.678 | 1.00 | 11.82 |
| 7394 | O | CYS | B | 213 | -17.989 | 2.632 | 4.591 | 1.00 | 13.43 |
| 7395 | N | VAL | B | 214 | -18.416 | 4.709 | 3.882 | 1.00 | 10.75 |
| 7397 | CA | VAL | B | 214 | -18.670 | 5.237 | 5.220 | 1.00 | 10.92 |
| 7399 | CB | VAL | B | 214 | -17.675 | 6.364 | 5.546 | 1.00 | 10.83 |
| 7401 | CG1 | VAL | B | 214 | -18.003 | 7.019 | 6.892 | 1.00 | 12.07 |
| 7405 | CG2 | VAL | B | 214 | -16.254 | 5.835 | 5.548 | 1.00 | 12.08 |
| 7409 | C | VAL | B | 214 | -20.098 | 5.766 | 5.251 | 1.00 | 10.89 |
| 7410 | O | VAL | B | 214 | -20.418 | 6.762 | 4.590 | 1.00 | 11.66 |
| 7411 | N | LEU | B | 215 | -20.965 | 5.081 | 5.990 | 1.00 | 10.35 |
| 7413 | CA | LEU | B | 215 | -22.406 | 5.356 | 5.946 | 1.00 | 10.42 |
| 7415 | CB | LEU | B | 215 | -23.176 | 4.058 | 5.697 | 1.00 | 10.13 |
| 7418 | CG | LEU | B | 215 | -22.726 | 3.218 | 4.497 | 1.00 | 10.67 |
| 7420 | CD1 | LEU | B | 215 | -23.642 | 2.025 | 4.347 | 1.00 | 11.48 |
| 7424 | CD2 | LEU | B | 215 | -22.626 | 4.010 | 3.204 | 1.00 | 12.21 |
| 7428 | C | LEU | B | 215 | -22.945 | 5.997 | 7.201 | 1.00 | 9.79 |
| 7429 | O | LEU | B | 215 | -22.640 | 5.575 | 8.309 | 1.00 | 10.80 |
| 7430 | N | GLY | B | 216 | -23.798 | 7.001 | 7.019 | 1.00 | 10.34 |
| 7432 | CA | GLY | B | 216 | -24.593 | 7.546 | 8.102 | 1.00 | 10.49 |
| 7435 | C | GLY | B | 216 | -25.844 | 6.719 | 8.304 | 1.00 | 10.54 |
| 7436 | O | GLY | B | 216 | -25.877 | 5.530 | 7.967 | 1.00 | 11.01 |
| 7437 | N | LEU | B | 217 | -26.870 | 7.336 | 8.872 | 1.00 | 10.50 |
| 7439 | CA | LEU | B | 217 | -28.108 | 6.619 | 9.158 | 1.00 | 10.52 |
| 7441 | CB | LEU | B | 217 | -28.999 | 7.438 | 10.098 | 1.00 | 10.86 |
| 7444 | CG | LEU | B | 217 | -30.328 | 6.795 | 10.519 | 1.00 | 11.32 |
| 7446 | CD1 | LEU | B | 217 | -30.094 | 5.482 | 11.240 | 1.00 | 11.10 |
| 7450 | CD2 | LEU | B | 217 | -31.134 | 7.748 | 11.389 | 1.00 | 11.10 |
| 7454 | C | LEU | B | 217 | -28.860 | 6.300 | 7.868 | 1.00 | 10.61 |
| 7455 | O | LEU | B | 217 | -29.216 | 7.201 | 7.117 | 1.00 | 10.95 |
| 7456 | N | ILE | B | 218 | -29.119 | 5.015 | 7.651 | 1.00 | 10.23 |
| 7458 | CA | ILE | B | 218 | -29.802 | 4.516 | 6.460 | 1.00 | 10.15 |
| 7460 | CB | ILE | B | 218 | -28.908 | 3.508 | 5.674 | 1.00 | 10.76 |
| 7462 | CG1 | ILE | B | 218 | -27.460 | 4.007 | 5.535 | 1.00 | 10.83 |
| 7465 | CD1 | ILE | B | 218 | -27.284 | 5.362 | 4.823 | 1.00 | 12.05 |
| 7469 | CG2 | ILE | B | 218 | -29.521 | 3.200 | 4.305 | 1.00 | 10.95 |
| 7473 | C | ILE | B | 218 | -31.056 | 3.796 | 6.931 | 1.00 | 10.66 |
| 7474 | O | ILE | B | 218 | -31.014 | 3.060 | 7.911 | 1.00 | 10.02 |
| 7475 | N | ASP | B | 219 | -32.156 | 3.984 | 6.213 | 1.00 | 10.31 |
| 7477 | CA | ASP | B | 219 | -33.483 | 3.516 | 6.665 | 1.00 | 10.38 |

FIGURE 3 (cont.)

| A | B | C | D | E | F | G | H | I | J |
|---|---|---|---|---|---|---|---|---|---|
| 7479 | CB | ASP | B | 219 | -34.583 | 4.320 | 5.956 | 1.00 | 10.41 |
| 7482 | CG | ASP | B | 219 | -34.662 | 4.043 | 4.478 | 1.00 | 11.92 |
| 7483 | OD1 | ASP | B | 219 | -35.546 | 4.640 | 3.808 | 1.00 | 13.77 |
| 7484 | OD2 | ASP | B | 219 | -33.900 | 3.237 | 3.885 | 1.00 | 11.88 |
| 7485 | C | ASP | B | 219 | -33.765 | 2.007 | 6.543 | 1.00 | 10.34 |
| 7486 | O | ASP | B | 219 | -34.900 | 1.594 | 6.264 | 1.00 | 10.76 |
| 7487 | N | THR | B | 220 | -32.752 | 1.175 | 6.769 | 1.00 | 10.14 |
| 7489 | CA | THR | B | 220 | -32.982 | -0.268 | 6.839 | 1.00 | 9.80 |
| 7491 | CB | THR | B | 220 | -31.648 | -1.052 | 6.884 | 1.00 | 9.33 |
| 7493 | OG1 | THR | B | 220 | -30.935 | -0.774 | 8.097 | 1.00 | 10.11 |
| 7495 | CG2 | THR | B | 220 | -30.720 | -0.670 | 5.743 | 1.00 | 10.26 |
| 7499 | C | THR | B | 220 | -33.815 | -0.615 | 8.063 | 1.00 | 9.87 |
| 7500 | O | THR | B | 220 | -33.816 | 0.111 | 9.049 | 1.00 | 9.67 |
| 7501 | N | GLU | B | 221 | -34.526 | -1.738 | 8.007 | 1.00 | 10.11 |
| 7503 | CA | GLU | B | 221 | -35.305 | -2.168 | 9.161 | 1.00 | 11.25 |
| 7505 | CB | GLU | B | 221 | -36.022 | -3.482 | 8.869 | 1.00 | 11.92 |
| 7508 | CG | GLU | B | 221 | -37.062 | -3.401 | 7.768 | 1.00 | 13.84 |
| 7511 | CD | GLU | B | 221 | -38.004 | -2.217 | 7.918 | 1.00 | 17.41 |
| 7512 | OE1 | GLU | B | 221 | -38.028 | -1.383 | 6.994 | 1.00 | 20.81 |
| 7513 | OE2 | GLU | B | 221 | -38.718 | -2.129 | 8.945 | 1.00 | 18.79 |
| 7514 | C | GLU | B | 221 | -34.436 | -2.293 | 10.412 | 1.00 | 10.67 |
| 7515 | O | GLU | B | 221 | -34.815 | -1.874 | 11.479 | 1.00 | 10.38 |
| 7516 | N | THR | B | 222 | -33.240 | -2.845 | 10.274 | 1.00 | 10.92 |
| 7518 | CA | THR | B | 222 | -32.344 | -2.988 | 11.411 | 1.00 | 11.04 |
| 7520 | CB | THR | B | 222 | -31.051 | -3.638 | 10.938 | 1.00 | 11.25 |
| 7522 | OG1 | THR | B | 222 | -31.319 | -5.005 | 10.606 | 1.00 | 10.97 |
| 7524 | CG2 | THR | B | 222 | -29.996 | -3.661 | 12.043 | 1.00 | 11.76 |
| 7528 | C | THR | B | 222 | -32.052 | -1.646 | 12.076 | 1.00 | 10.99 |
| 7529 | O | THR | B | 222 | -32.153 | -1.509 | 13.283 | 1.00 | 11.01 |
| 7530 | N | ALA | B | 223 | -31.691 | -0.651 | 11.268 | 1.00 | 10.76 |
| 7532 | CA | ALA | B | 223 | -31.325 | 0.646 | 11.807 | 1.00 | 10.99 |
| 7534 | CB | ALA | B | 223 | -30.714 | 1.517 | 10.728 | 1.00 | 10.70 |
| 7538 | C | ALA | B | 223 | -32.530 | 1.335 | 12.426 | 1.00 | 10.95 |
| 7539 | O | ALA | B | 223 | -32.433 | 1.917 | 13.494 | 1.00 | 11.55 |
| 7540 | N | MET | B | 224 | -33.670 | 1.236 | 11.759 | 1.00 | 11.07 |
| 7542 | CA | MET | B | 224 | -34.856 | 1.963 | 12.187 | 1.00 | 11.99 |
| 7544 | CB | MET | B | 224 | -35.893 | 1.928 | 11.074 | 1.00 | 11.67 |
| 7547 | CG | MET | B | 224 | -35.448 | 2.641 | 9.795 | 1.00 | 12.08 |
| 7550 | SD | MET | B | 224 | -35.230 | 4.426 | 10.001 | 1.00 | 14.55 |
| 7551 | CE | MET | B | 224 | -33.504 | 4.544 | 10.420 | 1.00 | 13.47 |
| 7555 | C | MET | B | 224 | -35.377 | 1.406 | 13.507 | 1.00 | 12.29 |
| 7556 | O | MET | B | 224 | -35.805 | 2.164 | 14.387 | 1.00 | 12.73 |
| 7557 | N | LYS | B | 225 | -35.306 | 0.083 | 13.672 | 1.00 | 12.69 |
| 7559 | CA | LYS | B | 225 | -35.637 | -0.546 | 14.948 | 1.00 | 13.43 |
| 7561 | CB | LYS | B | 225 | -35.691 | -2.075 | 14.807 | 1.00 | 13.90 |
| 7564 | CG | LYS | B | 225 | -36.898 | -2.604 | 14.075 | 1.00 | 17.24 |
| 7567 | CD | LYS | B | 225 | -36.872 | -4.139 | 14.104 | 1.00 | 20.63 |
| 7570 | CE | LYS | B | 225 | -38.089 | -4.779 | 13.501 | 1.00 | 24.77 |
| 7573 | NZ | LYS | B | 225 | -37.768 | -5.669 | 12.332 | 1.00 | 26.89 |

FIGURE 3 (cont.)

| A | B | C | D | E | F | G | H | I | J |
|---|---|---|---|---|---|---|---|---|---|
| 7577 | C | LYS | B | 225 | -34.637 | -0.171 | 16.042 | 1.00 | 13.77 |
| 7578 | O | LYS | B | 225 | -35.011 | 0.112 | 17.183 | 1.00 | 14.16 |
| 7579 | N | ALA | B | 226 | -33.357 | -0.155 | 15.688 | 1.00 | 13.62 |
| 7581 | CA | ALA | B | 226 | -32.300 | 0.051 | 16.662 | 1.00 | 14.17 |
| 7583 | CB | ALA | B | 226 | -30.944 | -0.234 | 16.017 | 1.00 | 14.38 |
| 7587 | C | ALA | B | 226 | -32.302 | 1.443 | 17.270 | 1.00 | 14.61 |
| 7588 | O | ALA | B | 226 | -32.004 | 1.601 | 18.451 | 1.00 | 14.97 |
| 7589 | N | VAL | B | 227 | -32.655 | 2.449 | 16.480 | 1.00 | 14.63 |
| 7591 | CA | VAL | B | 227 | -32.522 | 3.830 | 16.922 | 1.00 | 15.33 |
| 7593 | CB | VAL | B | 227 | -31.989 | 4.748 | 15.796 | 1.00 | 15.02 |
| 7595 | CG1 | VAL | B | 227 | -30.652 | 4.244 | 15.283 | 1.00 | 14.46 |
| 7599 | CG2 | VAL | B | 227 | -32.993 | 4.920 | 14.659 | 1.00 | 14.68 |
| 7603 | C | VAL | B | 227 | -33.821 | 4.399 | 17.474 | 1.00 | 16.76 |
| 7604 | O | VAL | B | 227 | -33.840 | 5.525 | 17.955 | 1.00 | 17.18 |
| 7605 | N | SER | B | 228 | -34.887 | 3.603 | 17.406 | 1.00 | 18.11 |
| 7607 | CA | SER | B | 228 | -36.210 | 4.006 | 17.882 | 1.00 | 19.66 |
| 7609 | CB | SER | B | 228 | -37.165 | 2.813 | 17.783 | 1.00 | 19.87 |
| 7612 | OG | SER | B | 228 | -38.378 | 3.064 | 18.459 | 1.00 | 21.76 |
| 7614 | C | SER | B | 228 | -36.140 | 4.514 | 19.317 | 1.00 | 20.25 |
| 7615 | O | SER | B | 228 | -35.707 | 3.790 | 20.219 | 1.00 | 21.00 |
| 7616 | N | GLY | B | 229 | -36.527 | 5.773 | 19.512 | 1.00 | 21.33 |
| 7618 | CA | GLY | B | 229 | -36.507 | 6.409 | 20.823 | 1.00 | 21.68 |
| 7621 | C | GLY | B | 229 | -35.190 | 7.041 | 21.245 | 1.00 | 22.30 |
| 7622 | O | GLY | B | 229 | -35.160 | 7.824 | 22.194 | 1.00 | 22.20 |
| 7623 | N | ILE | B | 230 | -34.104 | 6.707 | 20.551 | 1.00 | 22.47 |
| 7625 | CA | ILE | B | 230 | -32.766 | 7.217 | 20.874 | 1.00 | 23.46 |
| 7627 | CB | ILE | B | 230 | -31.690 | 6.120 | 20.659 | 1.00 | 23.53 |
| 7629 | CG1 | ILE | B | 230 | -32.110 | 4.787 | 21.277 | 1.00 | 25.04 |
| 7632 | CD1 | ILE | B | 230 | -32.563 | 4.885 | 22.700 | 1.00 | 26.14 |
| 7636 | CG2 | ILE | B | 230 | -30.335 | 6.591 | 21.199 | 1.00 | 23.50 |
| 7640 | C | ILE | B | 230 | -32.388 | 8.400 | 20.000 | 1.00 | 23.86 |
| 7641 | O | ILE | B | 230 | -31.793 | 9.370 | 20.464 | 1.00 | 23.99 |
| 7642 | N | VAL | B | 231 | -32.705 | 8.289 | 18.719 | 1.00 | 24.75 |
| 7644 | CA | VAL | B | 231 | -32.311 | 9.267 | 17.728 | 1.00 | 25.51 |
| 7646 | CB | VAL | B | 231 | -31.362 | 8.607 | 16.708 | 1.00 | 26.00 |
| 7648 | CG1 | VAL | B | 231 | -31.216 | 9.438 | 15.465 | 1.00 | 27.56 |
| 7652 | CG2 | VAL | B | 231 | -30.011 | 8.347 | 17.350 | 1.00 | 26.14 |
| 7656 | C | VAL | B | 231 | -33.534 | 9.832 | 17.013 | 1.00 | 25.49 |
| 7657 | O | VAL | B | 231 | -34.522 | 9.134 | 16.776 | 1.00 | 25.73 |
| 7658 | N | HIS | B | 232 | -33.456 | 11.117 | 16.698 | 1.00 | 25.39 |
| 7660 | CA | HIS | B | 232 | -34.427 | 11.791 | 15.858 | 1.00 | 25.54 |
| 7662 | CB | HIS | B | 232 | -35.320 | 12.708 | 16.692 | 1.00 | 26.04 |
| 7665 | CG | HIS | B | 232 | -36.147 | 11.989 | 17.707 | 1.00 | 28.51 |
| 7666 | ND1 | HIS | B | 232 | -36.130 | 12.318 | 19.046 | 1.00 | 31.50 |
| 7668 | CE1 | HIS | B | 232 | -36.961 | 11.527 | 19.701 | 1.00 | 32.45 |
| 7670 | NE2 | HIS | B | 232 | -37.518 | 10.698 | 18.836 | 1.00 | 32.18 |
| 7672 | CD2 | HIS | B | 232 | -37.028 | 10.969 | 17.581 | 1.00 | 31.04 |
| 7674 | C | HIS | B | 232 | -33.633 | 12.600 | 14.840 | 1.00 | 24.42 |
| 7675 | O | HIS | B | 232 | -33.300 | 13.760 | 15.068 | 1.00 | 25.65 |

FIGURE 3 (cont.)

| A | B | C | D | E | F | G | H | I | J |
|---|---|---|---|---|---|---|---|---|---|
| 7676 | N | MET | B | 233 | -33.254 | 11.945 | 13.752 | 1.00 | 22.60 |
| 7678 | CA | MET | B | 233 | -32.650 | 12.628 | 12.611 | 1.00 | 20.79 |
| 7680 | CB | MET | B | 233 | -31.120 | 12.612 | 12.706 | 1.00 | 20.37 |
| 7683 | CG | MET | B | 233 | -30.513 | 11.236 | 12.626 | 1.00 | 19.21 |
| 7686 | SD | MET | B | 233 | -28.739 | 11.251 | 12.892 | 1.00 | 18.15 |
| 7687 | CE | MET | B | 233 | -28.637 | 11.470 | 14.653 | 1.00 | 16.65 |
| 7691 | C | MET | B | 233 | -33.129 | 11.980 | 11.319 | 1.00 | 19.81 |
| 7692 | O | MET | B | 233 | -33.839 | 10.976 | 11.343 | 1.00 | 19.44 |
| 7693 | N | GLN | B | 234 | -32.766 | 12.570 | 10.188 | 1.00 | 18.67 |
| 7695 | CA | GLN | B | 234 | -33.193 | 12.041 | 8.899 | 1.00 | 18.42 |
| 7697 | CB | GLN | B | 234 | -32.908 | 13.034 | 7.777 | 1.00 | 19.13 |
| 7700 | CG | GLN | B | 234 | -33.747 | 14.303 | 7.857 | 1.00 | 22.36 |
| 7703 | CD | GLN | B | 234 | -35.212 | 14.057 | 7.545 | 1.00 | 26.30 |
| 7704 | OE1 | GLN | B | 234 | -36.083 | 14.285 | 8.392 | 1.00 | 30.03 |
| 7705 | NE2 | GLN | B | 234 | -35.490 | 13.584 | 6.335 | 1.00 | 29.20 |
| 7708 | C | GLN | B | 234 | -32.479 | 10.729 | 8.623 | 1.00 | 17.16 |
| 7709 | O | GLN | B | 234 | -31.328 | 10.559 | 8.989 | 1.00 | 16.54 |
| 7710 | N | ALA | B | 235 | -33.184 | 9.791 | 8.006 | 1.00 | 15.84 |
| 7712 | CA | ALA | B | 235 | -32.563 | 8.553 | 7.546 | 1.00 | 15.29 |
| 7714 | CB | ALA | B | 235 | -33.332 | 7.370 | 8.066 | 1.00 | 14.89 |
| 7718 | C | ALA | B | 235 | -32.551 | 8.554 | 6.026 | 1.00 | 14.93 |
| 7719 | O | ALA | B | 235 | -33.580 | 8.845 | 5.392 | 1.00 | 15.91 |
| 7720 | N | ALA | B | 236 | -31.402 | 8.230 | 5.438 | 1.00 | 13.69 |
| 7722 | CA | ALA | B | 236 | -31.253 | 8.205 | 3.984 | 1.00 | 13.16 |
| 7724 | CB | ALA | B | 236 | -29.796 | 8.314 | 3.612 | 1.00 | 12.83 |
| 7728 | C | ALA | B | 236 | -31.862 | 6.934 | 3.390 | 1.00 | 13.10 |
| 7729 | O | ALA | B | 236 | -31.887 | 5.890 | 4.048 | 1.00 | 13.11 |
| 7730 | N | PRO | B | 237 | -32.341 | 7.007 | 2.155 | 1.00 | 12.79 |
| 7731 | CA | PRO | B | 237 | -32.955 | 5.839 | 1.516 | 1.00 | 12.55 |
| 7733 | CB | PRO | B | 237 | -33.619 | 6.412 | 0.255 | 1.00 | 13.14 |
| 7736 | CG | PRO | B | 237 | -32.968 | 7.715 | 0.010 | 1.00 | 13.89 |
| 7739 | CD | PRO | B | 237 | -32.363 | 8.200 | 1.289 | 1.00 | 13.35 |
| 7742 | C | PRO | B | 237 | -31.936 | 4.750 | 1.169 | 1.00 | 12.24 |
| 7743 | O | PRO | B | 237 | -30.916 | 5.002 | 0.525 | 1.00 | 12.31 |
| 7744 | N | LYS | B | 238 | -32.241 | 3.535 | 1.596 | 1.00 | 11.92 |
| 7746 | CA | LYS | B | 238 | -31.364 | 2.391 | 1.386 | 1.00 | 12.01 |
| 7748 | CB | LYS | B | 238 | -31.930 | 1.153 | 2.096 | 1.00 | 11.80 |
| 7751 | CG | LYS | B | 238 | -33.354 | 0.767 | 1.716 | 1.00 | 12.22 |
| 7754 | CD | LYS | B | 238 | -33.823 | -0.377 | 2.569 | 1.00 | 13.37 |
| 7757 | CE | LYS | B | 238 | -35.179 | -0.898 | 2.108 | 1.00 | 13.68 |
| 7760 | NZ | LYS | B | 238 | -35.716 | -1.960 | 3.028 | 1.00 | 14.84 |
| 7764 | C | LYS | B | 238 | -31.110 | 2.090 | -0.094 | 1.00 | 12.18 |
| 7765 | O | LYS | B | 238 | -30.037 | 1.618 | -0.466 | 1.00 | 12.12 |
| 7766 | N | GLU | B | 239 | -32.098 | 2.361 | -0.939 | 1.00 | 12.75 |
| 7768 | CA | GLU | B | 239 | -31.968 | 2.139 | -2.369 | 1.00 | 13.85 |
| 7770 | CB | GLU | B | 239 | -33.316 | 2.389 | -3.053 | 1.00 | 14.87 |
| 7773 | CG | GLU | B | 239 | -34.424 | 1.440 | -2.595 | 1.00 | 17.43 |
| 7776 | CD | GLU | B | 239 | -35.236 | 1.905 | -1.372 | 1.00 | 20.25 |
| 7777 | OE1 | GLU | B | 239 | -34.949 | 2.982 | -0.759 | 1.00 | 17.06 |

FIGURE 3 (cont.)

| A | B | C | D | E | F | G | H | I | J |
|---|---|---|---|---|---|---|---|---|---|
| 7778 | OE2 | GLU | B | 239 | -36.195 | 1.154 | -1.022 | 1.00 | 23.38 |
| 7779 | C | GLU | B | 239 | -30.883 | 3.046 | -2.956 | 1.00 | 13.21 |
| 7780 | O | GLU | B | 239 | -30.034 | 2.593 | -3.722 | 1.00 | 12.93 |
| 7781 | N | GLU | B | 240 | -30.897 | 4.318 | -2.569 | 1.00 | 13.33 |
| 7783 | CA | GLU | B | 240 | -29.906 | 5.280 | -3.064 | 1.00 | 13.65 |
| 7785 | CB | GLU | B | 240 | -30.299 | 6.712 | -2.721 | 1.00 | 14.49 |
| 7788 | CG | GLU | B | 240 | -29.317 | 7.738 | -3.263 | 1.00 | 18.44 |
| 7791 | CD | GLU | B | 240 | -29.781 | 9.168 | -3.067 | 1.00 | 22.98 |
| 7792 | OE1 | GLU | B | 240 | -30.281 | 9.775 | -4.047 | 1.00 | 29.75 |
| 7793 | OE2 | GLU | B | 240 | -29.650 | 9.693 | -1.942 | 1.00 | 24.99 |
| 7794 | C | GLU | B | 240 | -28.531 | 4.967 | -2.487 | 1.00 | 12.54 |
| 7795 | O | GLU | B | 240 | -27.527 | 5.048 | -3.192 | 1.00 | 11.92 |
| 7796 | N | CYS | B | 241 | -28.496 | 4.593 | -1.214 | 1.00 | 11.78 |
| 7798 | CA | CYS | B | 241 | -27.248 | 4.217 | -0.552 | 1.00 | 11.84 |
| 7800 | CB | CYS | B | 241 | -27.530 | 3.771 | 0.876 | 1.00 | 11.72 |
| 7803 | SG | CYS | B | 241 | -26.079 | 3.283 | 1.817 | 1.00 | 13.87 |
| 7804 | C | CYS | B | 241 | -26.551 | 3.096 | -1.318 | 1.00 | 11.36 |
| 7805 | O | CYS | B | 241 | -25.362 | 3.178 | -1.618 | 1.00 | 12.56 |
| 7806 | N | ALA | B | 242 | -27.309 | 2.043 | -1.613 | 1.00 | 11.13 |
| 7808 | CA | ALA | B | 242 | -26.800 | 0.881 | -2.325 | 1.00 | 11.03 |
| 7810 | CB | ALA | B | 242 | -27.915 | -0.140 | -2.495 | 1.00 | 11.07 |
| 7814 | C | ALA | B | 242 | -26.237 | 1.269 | -3.688 | 1.00 | 11.62 |
| 7815 | O | ALA | B | 242 | -25.198 | 0.755 | -4.099 | 1.00 | 12.12 |
| 7816 | N | LEU | B | 243 | -26.919 | 2.171 | -4.392 | 1.00 | 11.85 |
| 7818 | CA | LEU | B | 243 | -26.452 | 2.574 | -5.714 | 1.00 | 12.49 |
| 7820 | CB | LEU | B | 243 | -27.499 | 3.396 | -6.455 | 1.00 | 12.70 |
| 7823 | CG | LEU | B | 243 | -27.135 | 3.809 | -7.886 | 1.00 | 13.71 |
| 7825 | CD1 | LEU | B | 243 | -26.846 | 2.596 | -8.752 | 1.00 | 15.54 |
| 7829 | CD2 | LEU | B | 243 | -28.262 | 4.634 | -8.468 | 1.00 | 16.34 |
| 7833 | C | LEU | B | 243 | -25.146 | 3.355 | -5.612 | 1.00 | 12.60 |
| 7834 | O | LEU | B | 243 | -24.238 | 3.138 | -6.408 | 1.00 | 13.22 |
| 7835 | N | GLU | B | 244 | -25.026 | 4.238 | -4.629 | 1.00 | 13.13 |
| 7837 | CA | GLU | B | 244 | -23.783 | 5.002 | -4.472 | 1.00 | 13.43 |
| 7839 | CB | GLU | B | 244 | -23.949 | 6.121 | -3.437 | 1.00 | 13.78 |
| 7842 | CG | GLU | B | 244 | -24.878 | 7.250 | -3.863 | 1.00 | 16.59 |
| 7845 | CD | GLU | B | 244 | -24.495 | 7.916 | -5.182 | 1.00 | 20.36 |
| 7846 | OE1 | GLU | B | 244 | -25.411 | 8.279 | -5.948 | 1.00 | 23.95 |
| 7847 | OE2 | GLU | B | 244 | -23.290 | 8.085 | -5.456 | 1.00 | 22.51 |
| 7848 | C | GLU | B | 244 | -22.590 | 4.108 | -4.112 | 1.00 | 13.06 |
| 7849 | O | GLU | B | 244 | -21.463 | 4.371 | -4.526 | 1.00 | 13.45 |
| 7850 | N | ILE | B | 245 | -22.839 | 3.030 | -3.375 | 1.00 | 12.16 |
| 7852 | CA | ILE | B | 245 | -21.787 | 2.069 | -3.064 | 1.00 | 12.01 |
| 7854 | CB | ILE | B | 245 | -22.265 | 1.037 | -2.018 | 1.00 | 11.84 |
| 7856 | CG1 | ILE | B | 245 | -22.450 | 1.733 | -0.655 | 1.00 | 12.13 |
| 7859 | CD1 | ILE | B | 245 | -23.201 | 0.894 | 0.379 | 1.00 | 12.63 |
| 7863 | CG2 | ILE | B | 245 | -21.289 | -0.153 | -1.940 | 1.00 | 11.58 |
| 7867 | C | ILE | B | 245 | -21.313 | 1.375 | -4.340 | 1.00 | 12.44 |
| 7868 | O | ILE | B | 245 | -20.115 | 1.281 | -4.578 | 1.00 | 11.98 |
| 7869 | N | ILE | B | 246 | -22.253 | 0.884 | -5.150 | 1.00 | 12.81 |

FIGURE 3 (cont.)

| A | B | C | D | E | F | G | H | I | J |
|---|---|---|---|---|---|---|---|---|---|
| 7871 | CA | ILE | B | 246 | -21.908 | 0.231 | -6.420 | 1.00 | 12.90 |
| 7873 | CB | ILE | B | 246 | -23.163 | -0.309 | -7.120 | 1.00 | 12.91 |
| 7875 | CG1 | ILE | B | 246 | -23.754 | -1.460 | -6.290 | 1.00 | 12.60 |
| 7878 | CD1 | ILE | B | 246 | -25.192 | -1.745 | -6.606 | 1.00 | 13.67 |
| 7882 | CG2 | ILE | B | 246 | -22.836 | -0.776 | -8.545 | 1.00 | 13.68 |
| 7886 | C | ILE | B | 246 | -21.148 | 1.181 | -7.343 | 1.00 | 13.52 |
| 7887 | O | ILE | B | 246 | -20.140 | 0.791 | -7.927 | 1.00 | 13.62 |
| 7888 | N | LYS | B | 247 | -21.625 | 2.416 | -7.468 | 1.00 | 14.06 |
| 7890 | CA | LYS | B | 247 | -20.970 | 3.405 | -8.326 | 1.00 | 14.69 |
| 7892 | CB | LYS | B | 247 | -21.711 | 4.747 | -8.294 | 1.00 | 15.04 |
| 7895 | CG | LYS | B | 247 | -23.047 | 4.752 | -8.988 | 1.00 | 18.01 |
| 7898 | CD | LYS | B | 247 | -23.706 | 6.116 | -8.871 | 1.00 | 22.58 |
| 7901 | CE | LYS | B | 247 | -24.882 | 6.269 | -9.818 | 1.00 | 25.17 |
| 7904 | NZ | LYS | B | 247 | -25.505 | 7.616 | -9.665 | 1.00 | 27.36 |
| 7908 | C | LYS | B | 247 | -19.529 | 3.624 | -7.885 | 1.00 | 14.43 |
| 7909 | O | LYS | B | 247 | -18.623 | 3.653 | -8.713 | 1.00 | 14.95 |
| 7910 | N | GLY | B | 248 | -19.322 | 3.790 | -6.585 | 1.00 | 14.40 |
| 7912 | CA | GLY | B | 248 | -17.991 | 4.001 | -6.049 | 1.00 | 14.38 |
| 7915 | C | GLY | B | 248 | -17.059 | 2.834 | -6.327 | 1.00 | 14.08 |
| 7916 | O | GLY | B | 248 | -15.911 | 3.034 | -6.692 | 1.00 | 14.30 |
| 7917 | N | GLY | B | 249 | -17.554 | 1.612 | -6.167 | 1.00 | 14.32 |
| 7919 | CA | GLY | B | 249 | -16.776 | 0.423 | -6.456 | 1.00 | 13.50 |
| 7922 | C | GLY | B | 249 | -16.446 | 0.292 | -7.936 | 1.00 | 13.82 |
| 7923 | O | GLY | B | 249 | -15.315 | -0.032 | -8.297 | 1.00 | 14.64 |
| 7924 | N | ALA | B | 250 | -17.438 | 0.551 | -8.781 | 1.00 | 13.68 |
| 7926 | CA | ALA | B | 250 | -17.290 | 0.469 | -10.229 | 1.00 | 13.73 |
| 7928 | CB | ALA | B | 250 | -18.622 | 0.701 | -10.900 | 1.00 | 14.09 |
| 7932 | C | ALA | B | 250 | -16.268 | 1.479 | -10.733 | 1.00 | 13.57 |
| 7933 | O | ALA | B | 250 | -15.508 | 1.193 | -11.669 | 1.00 | 14.50 |
| 7934 | N | LEU | B | 251 | -16.241 | 2.652 | -10.106 | 1.00 | 12.96 |
| 7936 | CA | LEU | B | 251 | -15.302 | 3.713 | -10.482 | 1.00 | 12.56 |
| 7938 | CB | LEU | B | 251 | -15.924 | 5.087 | -10.235 | 1.00 | 12.83 |
| 7941 | CG | LEU | B | 251 | -17.179 | 5.400 | -11.053 | 1.00 | 13.10 |
| 7943 | CD1 | LEU | B | 251 | -17.735 | 6.738 | -10.624 | 1.00 | 13.88 |
| 7947 | CD2 | LEU | B | 251 | -16.877 | 5.383 | -12.549 | 1.00 | 13.61 |
| 7951 | C | LEU | B | 251 | -13.966 | 3.609 | -9.746 | 1.00 | 12.78 |
| 7952 | O | LEU | B | 251 | -13.102 | 4.476 | -9.902 | 1.00 | 12.57 |
| 7953 | N | ARG | B | 252 | -13.807 | 2.563 | -8.934 | 1.00 | 12.68 |
| 7955 | CA | ARG | B | 252 | -12.542 | 2.278 | -8.252 | 1.00 | 12.81 |
| 7957 | CB | ARG | B | 252 | -11.450 | 1.936 | -9.278 | 1.00 | 12.72 |
| 7960 | CG | ARG | B | 252 | -11.848 | 0.854 | -10.265 | 1.00 | 12.91 |
| 7963 | CD | ARG | B | 252 | -10.786 | 0.559 | -11.324 | 1.00 | 13.85 |
| 7966 | NE | ARG | B | 252 | -9.750 | -0.370 | -10.865 | 1.00 | 12.37 |
| 7968 | CZ | ARG | B | 252 | -9.898 | -1.692 | -10.776 | 1.00 | 13.56 |
| 7969 | NH1 | ARG | B | 252 | -11.039 | -2.280 | -11.103 | 1.00 | 13.88 |
| 7972 | NH2 | ARG | B | 252 | -8.877 | -2.437 | -10.376 | 1.00 | 14.94 |
| 7975 | C | ARG | B | 252 | -12.095 | 3.411 | -7.329 | 1.00 | 13.09 |
| 7976 | O | ARG | B | 252 | -10.904 | 3.671 | -7.160 | 1.00 | 12.90 |
| 7977 | N | GLN | B | 253 | -13.068 | 4.075 | -6.713 | 1.00 | 13.58 |

FIGURE 3 (cont.)

| A | B | C | D | E | F | G | H | I | J |
|---|---|---|---|---|---|---|---|---|---|
| 7979 | CA | GLN | B | 253 | -12.800 | 5.125 | -5.749 | 1.00 | 14.02 |
| 7981 | CB | GLN | B | 253 | -14.078 | 5.916 | -5.466 | 1.00 | 14.80 |
| 7984 | CG | GLN | B | 253 | -14.597 | 6.721 | -6.639 | 1.00 | 17.82 |
| 7987 | CD | GLN | B | 253 | -15.978 | 7.300 | -6.376 | 1.00 | 18.47 |
| 7988 | OE1 | GLN | B | 253 | -16.456 | 7.295 | -5.240 | 1.00 | 25.71 |
| 7989 | NE2 | GLN | B | 253 | -16.619 | 7.791 | -7.420 | 1.00 | 24.02 |
| 7992 | C | GLN | B | 253 | -12.289 | 4.529 | -4.436 | 1.00 | 14.01 |
| 7993 | O | GLN | B | 253 | -12.682 | 3.425 | -4.049 | 1.00 | 14.04 |
| 7994 | N | GLU | B | 254 | -11.425 | 5.257 | -3.741 | 1.00 | 13.56 |
| 7996 | CA | GLU | B | 254 | -10.901 | 4.769 | -2.467 | 1.00 | 14.26 |
| 7998 | CB | GLU | B | 254 | -9.674 | 5.564 | -2.024 | 1.00 | 14.78 |
| 8001 | CG | GLU | B | 254 | -8.525 | 5.380 | -3.004 | 1.00 | 17.36 |
| 8004 | CD | GLU | B | 254 | -7.171 | 5.816 | -2.476 | 1.00 | 22.30 |
| 8005 | OE1 | GLU | B | 254 | -6.212 | 5.795 | -3.275 | 1.00 | 26.53 |
| 8006 | OE2 | GLU | B | 254 | -7.054 | 6.160 | -1.287 | 1.00 | 25.82 |
| 8007 | C | GLU | B | 254 | -11.963 | 4.770 | -1.378 | 1.00 | 13.94 |
| 8008 | O | GLU | B | 254 | -12.055 | 3.819 | -0.618 | 1.00 | 12.66 |
| 8009 | N | GLU | B | 255 | -12.762 | 5.831 | -1.320 | 1.00 | 15.01 |
| 8011 | CA | GLU | B | 255 | -13.770 | 5.973 | -0.272 | 1.00 | 15.77 |
| 8013 | CB | GLU | B | 255 | -13.210 | 6.800 | 0.914 | 1.00 | 16.30 |
| 8016 | CG | GLU | B | 255 | -12.044 | 6.103 | 1.645 | 1.00 | 18.53 |
| 8019 | CD | GLU | B | 255 | -11.679 | 6.677 | 3.029 | 1.00 | 22.66 |
| 8020 | OE1 | GLU | B | 255 | -11.018 | 5.969 | 3.839 | 1.00 | 23.75 |
| 8021 | OE2 | GLU | B | 255 | -12.019 | 7.834 | 3.316 | 1.00 | 23.84 |
| 8022 | C | GLU | B | 255 | -15.090 | 6.519 | -0.836 | 1.00 | 15.86 |
| 8023 | O | GLU | B | 255 | -15.098 | 7.320 | -1.777 | 1.00 | 17.19 |
| 8024 | N | VAL | B | 256 | -16.194 | 6.001 | -0.309 | 1.00 | 14.66 |
| 8026 | CA | VAL | B | 256 | -17.542 | 6.496 | -0.590 | 1.00 | 14.63 |
| 8028 | CB | VAL | B | 256 | -18.456 | 5.394 | -1.156 | 1.00 | 15.32 |
| 8030 | CG1 | VAL | B | 256 | -19.919 | 5.868 | -1.217 | 1.00 | 16.33 |
| 8034 | CG2 | VAL | B | 256 | -17.963 | 4.946 | -2.518 | 1.00 | 16.42 |
| 8038 | C | VAL | B | 256 | -18.112 | 6.956 | 0.732 | 1.00 | 13.96 |
| 8039 | O | VAL | B | 256 | -18.065 | 6.223 | 1.719 | 1.00 | 14.84 |
| 8040 | N | TYR | B | 257 | -18.624 | 8.177 | 0.770 | 1.00 | 13.12 |
| 8042 | CA | TYR | B | 257 | -19.294 | 8.707 | 1.948 | 1.00 | 13.09 |
| 8044 | CB | TYR | B | 257 | -18.633 | 10.027 | 2.393 | 1.00 | 13.44 |
| 8047 | CG | TYR | B | 257 | -17.256 | 9.812 | 2.977 | 1.00 | 13.61 |
| 8048 | CD1 | TYR | B | 257 | -16.133 | 9.792 | 2.176 | 1.00 | 17.63 |
| 8050 | CE1 | TYR | B | 257 | -14.858 | 9.558 | 2.733 | 1.00 | 17.29 |
| 8052 | CZ | TYR | B | 257 | -14.740 | 9.338 | 4.091 | 1.00 | 18.07 |
| 8053 | OH | TYR | B | 257 | -13.502 | 9.104 | 4.672 | 1.00 | 19.81 |
| 8055 | CE2 | TYR | B | 257 | -15.848 | 9.356 | 4.889 | 1.00 | 17.24 |
| 8057 | CD2 | TYR | B | 257 | -17.095 | 9.586 | 4.337 | 1.00 | 16.04 |
| 8059 | C | TYR | B | 257 | -20.746 | 8.948 | 1.559 | 1.00 | 13.03 |
| 8060 | O | TYR | B | 257 | -21.011 | 9.593 | 0.544 | 1.00 | 13.29 |
| 8061 | N | TYR | B | 258 | -21.677 | 8.436 | 2.358 | 1.00 | 12.26 |
| 8063 | CA | TYR | B | 258 | -23.099 | 8.572 | 2.069 | 1.00 | 12.22 |
| 8065 | CB | TYR | B | 258 | -23.639 | 7.335 | 1.346 | 1.00 | 12.46 |
| 8068 | CG | TYR | B | 258 | -25.074 | 7.518 | 0.952 | 1.00 | 13.55 |

FIGURE 3 (cont.)

| A | B | C | D | E | F | G | H | I | J |
|---|---|---|---|---|---|---|---|---|---|
| 8069 | CD1 | TYR | B | 258 | -26.098 | 7.040 | 1.751 | 1.00 | 14.03 |
| 8071 | CE1 | TYR | B | 258 | -27.416 | 7.232 | 1.418 | 1.00 | 15.60 |
| 8073 | CZ | TYR | B | 258 | -27.738 | 7.934 | 0.280 | 1.00 | 15.83 |
| 8074 | OH | TYR | B | 258 | -29.057 | 8.150 | -0.046 | 1.00 | 19.89 |
| 8076 | CE2 | TYR | B | 258 | -26.745 | 8.437 | -0.531 | 1.00 | 15.50 |
| 8078 | CD2 | TYR | B | 258 | -25.410 | 8.231 | -0.184 | 1.00 | 14.89 |
| 8080 | C | TYR | B | 258 | -23.913 | 8.839 | 3.331 | 1.00 | 12.18 |
| 8081 | O | TYR | B | 258 | -23.773 | 8.149 | 4.329 | 1.00 | 12.00 |
| 8082 | N | ASP | B | 259 | -24.787 | 9.837 | 3.239 | 1.00 | 11.60 |
| 8084 | CA | ASP | B | 259 | -25.586 | 10.315 | 4.354 | 1.00 | 11.80 |
| 8086 | CB | ASP | B | 259 | -24.737 | 11.192 | 5.287 | 1.00 | 12.13 |
| 8089 | CG | ASP | B | 259 | -25.414 | 11.471 | 6.626 | 1.00 | 12.82 |
| 8090 | OD1 | ASP | B | 259 | -25.925 | 12.603 | 6.835 | 1.00 | 13.38 |
| 8091 | OD2 | ASP | B | 259 | -25.460 | 10.638 | 7.545 | 1.00 | 15.84 |
| 8092 | C | ASP | B | 259 | -26.733 | 11.155 | 3.792 | 1.00 | 12.11 |
| 8093 | O | ASP | B | 259 | -26.710 | 11.585 | 2.634 | 1.00 | 13.32 |
| 8094 | N | SER | B | 260 | -27.716 | 11.406 | 4.636 | 1.00 | 12.17 |
| 8096 | CA | SER | B | 260 | -28.806 | 12.319 | 4.307 | 1.00 | 12.73 |
| 8098 | CB | SER | B | 260 | -29.797 | 12.378 | 5.471 | 1.00 | 12.53 |
| 8101 | OG | SER | B | 260 | -30.616 | 11.212 | 5.513 | 1.00 | 15.25 |
| 8103 | C | SER | B | 260 | -28.305 | 13.733 | 4.020 | 1.00 | 13.30 |
| 8104 | O | SER | B | 260 | -28.916 | 14.457 | 3.231 | 1.00 | 13.95 |
| 8105 | N | SER | B | 261 | -27.210 | 14.118 | 4.673 | 1.00 | 13.17 |
| 8107 | CA | SER | B | 261 | -26.730 | 15.497 | 4.676 | 1.00 | 13.51 |
| 8109 | CB | SER | B | 261 | -26.766 | 16.051 | 6.096 | 1.00 | 13.96 |
| 8112 | OG | SER | B | 261 | -26.317 | 17.396 | 6.123 | 1.00 | 15.44 |
| 8114 | C | SER | B | 261 | -25.307 | 15.614 | 4.129 | 1.00 | 13.16 |
| 8115 | O | SER | B | 261 | -24.430 | 14.833 | 4.485 | 1.00 | 12.66 |
| 8116 | N | LEU | B | 262 | -25.104 | 16.596 | 3.259 | 1.00 | 13.32 |
| 8118 | CA | LEU | B | 262 | -23.778 | 16.957 | 2.779 | 1.00 | 13.40 |
| 8120 | CB | LEU | B | 262 | -23.871 | 18.007 | 1.663 | 1.00 | 13.97 |
| 8123 | CG | LEU | B | 262 | -24.346 | 17.431 | 0.326 | 1.00 | 16.35 |
| 8125 | CD1 | LEU | B | 262 | -24.687 | 18.515 | -0.665 | 1.00 | 18.16 |
| 8129 | CD2 | LEU | B | 262 | -23.302 | 16.480 | -0.262 | 1.00 | 19.16 |
| 8133 | C | LEU | B | 262 | -22.899 | 17.482 | 3.908 | 1.00 | 12.51 |
| 8134 | O | LEU | B | 262 | -21.678 | 17.421 | 3.815 | 1.00 | 11.68 |
| 8135 | N | TRP | B | 263 | -23.505 | 17.989 | 4.981 | 1.00 | 11.84 |
| 8137 | CA | TRP | B | 263 | -22.730 | 18.386 | 6.155 | 1.00 | 11.33 |
| 8139 | CB | TRP | B | 263 | -23.630 | 18.952 | 7.262 | 1.00 | 11.33 |
| 8142 | CG | TRP | B | 263 | -24.111 | 20.331 | 6.992 | 1.00 | 10.42 |
| 8143 | CD1 | TRP | B | 263 | -25.155 | 20.701 | 6.189 | 1.00 | 11.81 |
| 8145 | NE1 | TRP | B | 263 | -25.285 | 22.069 | 6.176 | 1.00 | 13.12 |
| 8147 | CE2 | TRP | B | 263 | -24.326 | 22.613 | 6.990 | 1.00 | 10.72 |
| 8148 | CD2 | TRP | B | 263 | -23.564 | 21.549 | 7.514 | 1.00 | 10.82 |
| 8149 | CE3 | TRP | B | 263 | -22.509 | 21.846 | 8.381 | 1.00 | 11.14 |
| 8151 | CZ3 | TRP | B | 263 | -22.246 | 23.174 | 8.681 | 1.00 | 11.04 |
| 8153 | CH2 | TRP | B | 263 | -23.018 | 24.201 | 8.139 | 1.00 | 11.20 |
| 8155 | CZ2 | TRP | B | 263 | -24.060 | 23.940 | 7.293 | 1.00 | 11.38 |
| 8157 | C | TRP | B | 263 | -21.949 | 17.190 | 6.689 | 1.00 | 11.26 |

FIGURE 3 (cont.)

| A | B | C | D | E | F | G | H | I | J |
|---|---|---|---|---|---|---|---|---|---|
| 8158 | O | TRP | B | 263 | -20.805 | 17.310 | 7.089 | 1.00 | 12.27 |
| 8159 | N | THR | B | 264 | -22.577 | 16.024 | 6.687 | 1.00 | 10.81 |
| 8161 | CA | THR | B | 264 | -21.925 | 14.824 | 7.159 | 1.00 | 11.18 |
| 8163 | CB | THR | B | 264 | -22.955 | 13.727 | 7.376 | 1.00 | 11.47 |
| 8165 | OG1 | THR | B | 264 | -23.962 | 14.192 | 8.279 | 1.00 | 12.43 |
| 8167 | CG2 | THR | B | 264 | -22.295 | 12.504 | 8.049 | 1.00 | 11.97 |
| 8171 | C | THR | B | 264 | -20.884 | 14.323 | 6.181 | 1.00 | 11.34 |
| 8172 | O | THR | B | 264 | -19.744 | 14.111 | 6.563 | 1.00 | 12.15 |
| 8173 | N | THR | B | 265 | -21.272 | 14.127 | 4.930 | 1.00 | 11.82 |
| 8175 | CA | THR | B | 265 | -20.367 | 13.483 | 3.983 | 1.00 | 12.54 |
| 8177 | CB | THR | B | 265 | -21.047 | 13.141 | 2.660 | 1.00 | 12.86 |
| 8179 | OG1 | THR | B | 265 | -21.584 | 14.326 | 2.063 | 1.00 | 13.86 |
| 8181 | CG2 | THR | B | 265 | -22.235 | 12.223 | 2.866 | 1.00 | 13.40 |
| 8185 | C | THR | B | 265 | -19.145 | 14.338 | 3.703 | 1.00 | 12.85 |
| 8186 | O | THR | B | 265 | -18.068 | 13.794 | 3.491 | 1.00 | 12.62 |
| 8187 | N | LEU | B | 266 | -19.301 | 15.662 | 3.686 | 1.00 | 12.49 |
| 8189 | CA | LEU | B | 266 | -18.165 | 16.531 | 3.385 | 1.00 | 12.87 |
| 8191 | CB | LEU | B | 266 | -18.637 | 17.874 | 2.811 | 1.00 | 12.67 |
| 8194 | CG | LEU | B | 266 | -19.380 | 17.761 | 1.470 | 1.00 | 14.14 |
| 8196 | CD1 | LEU | B | 266 | -19.884 | 19.109 | 0.995 | 1.00 | 14.67 |
| 8200 | CD2 | LEU | B | 266 | -18.480 | 17.130 | 0.405 | 1.00 | 16.43 |
| 8204 | C | LEU | B | 266 | -17.247 | 16.734 | 4.594 | 1.00 | 12.76 |
| 8205 | O | LEU | B | 266 | -16.029 | 16.787 | 4.443 | 1.00 | 13.82 |
| 8206 | N | LEU | B | 267 | -17.808 | 16.840 | 5.793 | 1.00 | 12.75 |
| 8208 | CA | LEU | B | 267 | -16.995 | 17.126 | 6.973 | 1.00 | 13.15 |
| 8210 | CB | LEU | B | 267 | -17.809 | 17.871 | 8.051 | 1.00 | 13.10 |
| 8213 | CG | LEU | B | 267 | -18.244 | 19.300 | 7.685 | 1.00 | 14.02 |
| 8215 | CD1 | LEU | B | 267 | -19.246 | 19.818 | 8.700 | 1.00 | 14.09 |
| 8219 | CD2 | LEU | B | 267 | -17.055 | 20.245 | 7.583 | 1.00 | 15.58 |
| 8223 | C | LEU | B | 267 | -16.326 | 15.901 | 7.582 | 1.00 | 13.40 |
| 8224 | O | LEU | B | 267 | -15.281 | 16.039 | 8.210 | 1.00 | 14.20 |
| 8225 | N | ILE | B | 268 | -16.907 | 14.713 | 7.399 | 1.00 | 14.15 |
| 8227 | CA | ILE | B | 268 | -16.326 | 13.485 | 7.946 | 1.00 | 15.57 |
| 8229 | CB | ILE | B | 268 | -17.370 | 12.323 | 7.960 | 1.00 | 16.26 |
| 8231 | CG1 | ILE | B | 268 | -16.872 | 11.152 | 8.801 | 1.00 | 18.86 |
| 8234 | CD1 | ILE | B | 268 | -17.039 | 11.367 | 10.259 | 1.00 | 21.64 |
| 8238 | CG2 | ILE | B | 268 | -17.633 | 11.828 | 6.563 | 1.00 | 17.50 |
| 8242 | C | ILE | B | 268 | -15.085 | 13.047 | 7.175 | 1.00 | 16.30 |
| 8243 | O | ILE | B | 268 | -14.234 | 12.332 | 7.706 | 1.00 | 15.96 |
| 8244 | N | ARG | B | 269 | -14.966 | 13.456 | 5.919 | 1.00 | 17.45 |
| 8246 | CA | ARG | B | 269 | -13.778 | 13.069 | 5.176 | 1.00 | 18.43 |
| 8248 | CB | ARG | B | 269 | -13.946 | 13.293 | 3.670 | 1.00 | 19.93 |
| 8251 | CG | ARG | B | 269 | -13.635 | 14.661 | 3.181 | 1.00 | 23.73 |
| 8254 | CD | ARG | B | 269 | -14.071 | 14.881 | 1.733 | 1.00 | 28.73 |
| 8257 | NE | ARG | B | 269 | -15.463 | 14.475 | 1.550 | 1.00 | 32.05 |
| 8259 | CZ | ARG | B | 269 | -15.929 | 13.681 | 0.586 | 1.00 | 34.04 |
| 8260 | NH1 | ARG | B | 269 | -17.223 | 13.394 | 0.556 | 1.00 | 34.03 |
| 8263 | NH2 | ARG | B | 269 | -15.128 | 13.180 | -0.355 | 1.00 | 35.66 |
| 8266 | C | ARG | B | 269 | -12.564 | 13.784 | 5.763 | 1.00 | 17.41 |

FIGURE 3 (cont.)

| A | B | C | D | E | F | G | H | I | J |
|---|---|---|---|---|---|---|---|---|---|
| 8267 | O | ARG | B | 269 | -12.664 | 14.883 | 6.320 | 1.00 | 17.41 |
| 8268 | N | ASN | B | 270 | -11.425 | 13.106 | 5.677 | 1.00 | 16.66 |
| 8270 | CA | ASN | B | 270 | -10.193 | 13.521 | 6.326 | 1.00 | 15.94 |
| 8272 | CB | ASN | B | 270 | -9.897 | 12.545 | 7.489 | 1.00 | 15.91 |
| 8275 | CG | ASN | B | 270 | -8.634 | 12.881 | 8.283 | 1.00 | 15.90 |
| 8276 | OD1 | ASN | B | 270 | -8.224 | 12.104 | 9.166 | 1.00 | 16.27 |
| 8277 | ND2 | ASN | B | 270 | -8.028 | 14.017 | 8.006 | 1.00 | 14.28 |
| 8280 | C | ASN | B | 270 | -9.079 | 13.526 | 5.286 | 1.00 | 15.83 |
| 8281 | O | ASN | B | 270 | -8.212 | 12.640 | 5.285 | 1.00 | 15.02 |
| 8282 | N | PRO | B | 271 | -9.088 | 14.511 | 4.380 | 1.00 | 15.13 |
| 8283 | CA | PRO | B | 271 | -8.068 | 14.560 | 3.323 | 1.00 | 14.80 |
| 8285 | CB | PRO | B | 271 | -8.475 | 15.776 | 2.490 | 1.00 | 15.03 |
| 8288 | CG | PRO | B | 271 | -9.275 | 16.600 | 3.396 | 1.00 | 15.15 |
| 8291 | CD | PRO | B | 271 | -10.030 | 15.637 | 4.271 | 1.00 | 15.28 |
| 8294 | C | PRO | B | 271 | -6.655 | 14.719 | 3.860 | 1.00 | 14.35 |
| 8295 | O | PRO | B | 271 | -5.725 | 14.306 | 3.177 | 1.00 | 14.29 |
| 8296 | N | SER | B | 272 | -6.496 | 15.301 | 5.044 | 1.00 | 13.66 |
| 8298 | CA | SER | B | 272 | -5.184 | 15.443 | 5.653 | 1.00 | 13.66 |
| 8300 | CB | SER | B | 272 | -5.269 | 16.281 | 6.930 | 1.00 | 14.30 |
| 8303 | OG | SER | B | 272 | -5.549 | 17.637 | 6.602 | 1.00 | 17.01 |
| 8305 | C | SER | B | 272 | -4.523 | 14.104 | 5.931 | 1.00 | 13.18 |
| 8306 | O | SER | B | 272 | -3.322 | 13.968 | 5.782 | 1.00 | 13.09 |
| 8307 | N | ARG | B | 273 | -5.307 | 13.103 | 6.327 | 1.00 | 12.74 |
| 8309 | CA | ARG | B | 273 | -4.743 | 11.783 | 6.544 | 1.00 | 12.80 |
| 8311 | CB | ARG | B | 273 | -5.798 | 10.807 | 7.082 | 1.00 | 12.19 |
| 8314 | CG | ARG | B | 273 | -5.382 | 9.356 | 6.958 | 1.00 | 12.13 |
| 8317 | CD | ARG | B | 273 | -6.307 | 8.346 | 7.673 | 1.00 | 11.21 |
| 8320 | NE | ARG | B | 273 | -6.277 | 7.071 | 6.964 | 1.00 | 9.98 |
| 8322 | CZ | ARG | B | 273 | -7.137 | 6.083 | 7.157 | 1.00 | 10.46 |
| 8323 | NH1 | ARG | B | 273 | -8.058 | 6.177 | 8.101 | 1.00 | 10.65 |
| 8326 | NH2 | ARG | B | 273 | -7.061 | 4.997 | 6.404 | 1.00 | 12.09 |
| 8329 | C | ARG | B | 273 | -4.134 | 11.239 | 5.259 | 1.00 | 13.07 |
| 8330 | O | ARG | B | 273 | -3.026 | 10.717 | 5.280 | 1.00 | 12.90 |
| 8331 | N | LYS | B | 274 | -4.867 | 11.343 | 4.151 | 1.00 | 13.99 |
| 8333 | CA | LYS | B | 274 | -4.402 | 10.802 | 2.873 | 1.00 | 14.94 |
| 8335 | CB | LYS | B | 274 | -5.486 | 10.923 | 1.794 | 1.00 | 16.35 |
| 8338 | CG | LYS | B | 274 | -6.712 | 10.068 | 2.018 | 1.00 | 20.16 |
| 8341 | CD | LYS | B | 274 | -7.383 | 9.742 | 0.686 | 1.00 | 24.62 |
| 8344 | CE | LYS | B | 274 | -8.895 | 9.715 | 0.789 | 1.00 | 26.67 |
| 8347 | NZ | LYS | B | 274 | -9.498 | 9.117 | -0.447 | 1.00 | 27.18 |
| 8351 | C | LYS | B | 274 | -3.142 | 11.536 | 2.416 | 1.00 | 14.45 |
| 8352 | O | LYS | B | 274 | -2.232 | 10.931 | 1.863 | 1.00 | 13.70 |
| 8353 | N | ILE | B | 275 | -3.095 | 12.841 | 2.655 | 1.00 | 13.49 |
| 8355 | CA | ILE | B | 275 | -1.941 | 13.650 | 2.282 | 1.00 | 13.22 |
| 8357 | CB | ILE | B | 275 | -2.264 | 15.167 | 2.426 | 1.00 | 13.26 |
| 8359 | CG1 | ILE | B | 275 | -3.091 | 15.610 | 1.214 | 1.00 | 14.51 |
| 8362 | CD1 | ILE | B | 275 | -3.862 | 16.896 | 1.422 | 1.00 | 16.05 |
| 8366 | CG2 | ILE | B | 275 | -0.981 | 15.986 | 2.585 | 1.00 | 12.85 |
| 8370 | C | ILE | B | 275 | -0.712 | 13.241 | 3.096 | 1.00 | 13.24 |

FIGURE 3 (cont.)

| A | B | C | D | E | F | G | H | I | J |
|---|---|---|---|---|---|---|---|---|---|
| 8371 | O | ILE | B | 275 | 0.355 | 13.070 | 2.532 | 1.00 | 12.67 |
| 8372 | N | LEU | B | 276 | -0.853 | 13.067 | 4.407 | 1.00 | 13.15 |
| 8374 | CA | LEU | B | 276 | 0.285 | 12.656 | 5.237 | 1.00 | 13.49 |
| 8376 | CB | LEU | B | 276 | -0.054 | 12.684 | 6.724 | 1.00 | 14.39 |
| 8379 | CG | LEU | B | 276 | -0.126 | 14.011 | 7.449 | 1.00 | 16.17 |
| 8381 | CD1 | LEU | B | 276 | -0.511 | 13.716 | 8.892 | 1.00 | 17.23 |
| 8385 | CD2 | LEU | B | 276 | 1.185 | 14.776 | 7.372 | 1.00 | 16.43 |
| 8389 | C | LEU | B | 276 | 0.771 | 11.250 | 4.884 | 1.00 | 13.17 |
| 8390 | O | LEU | B | 276 | 1.963 | 10.991 | 4.870 | 1.00 | 12.63 |
| 8391 | N | GLU | B | 277 | -0.153 | 10.340 | 4.594 | 1.00 | 12.96 |
| 8393 | CA | GLU | B | 277 | 0.246 | 9.002 | 4.169 | 1.00 | 12.89 |
| 8395 | CB | GLU | B | 277 | -0.978 | 8.129 | 3.895 | 1.00 | 12.80 |
| 8398 | CG | GLU | B | 277 | -1.724 | 7.735 | 5.151 | 1.00 | 12.57 |
| 8401 | CD | GLU | B | 277 | -3.085 | 7.117 | 4.888 | 1.00 | 13.04 |
| 8402 | OE1 | GLU | B | 277 | -3.760 | 6.743 | 5.863 | 1.00 | 12.09 |
| 8403 | OE2 | GLU | B | 277 | -3.504 | 7.003 | 3.716 | 1.00 | 14.22 |
| 8404 | C | GLU | B | 277 | 1.103 | 9.097 | 2.920 | 1.00 | 13.20 |
| 8405 | O | GLU | B | 277 | 2.126 | 8.422 | 2.806 | 1.00 | 13.71 |
| 8406 | N | PHE | B | 278 | 0.686 | 9.939 | 1.981 | 1.00 | 13.73 |
| 8408 | CA | PHE | B | 278 | 1.447 | 10.105 | 0.748 | 1.00 | 14.82 |
| 8410 | CB | PHE | B | 278 | 0.710 | 10.985 | -0.259 | 1.00 | 14.65 |
| 8413 | CG | PHE | B | 278 | 1.571 | 11.385 | -1.420 | 1.00 | 16.88 |
| 8414 | CD1 | PHE | B | 278 | 1.828 | 10.487 | -2.444 | 1.00 | 20.02 |
| 8416 | CE1 | PHE | B | 278 | 2.651 | 10.850 | -3.513 | 1.00 | 20.53 |
| 8418 | CZ | PHE | B | 278 | 3.226 | 12.106 | -3.545 | 1.00 | 20.84 |
| 8420 | CE2 | PHE | B | 278 | 2.986 | 13.010 | -2.504 | 1.00 | 19.97 |
| 8422 | CD2 | PHE | B | 278 | 2.166 | 12.634 | -1.449 | 1.00 | 17.67 |
| 8424 | C | PHE | B | 278 | 2.820 | 10.697 | 1.035 | 1.00 | 14.55 |
| 8425 | O | PHE | B | 278 | 3.836 | 10.194 | 0.557 | 1.00 | 15.16 |
| 8426 | N | LEU | B | 279 | 2.864 | 11.773 | 1.817 | 1.00 | 14.35 |
| 8428 | CA | LEU | B | 279 | 4.125 | 12.428 | 2.117 | 1.00 | 14.35 |
| 8430 | CB | LEU | B | 279 | 3.905 | 13.707 | 2.919 | 1.00 | 13.89 |
| 8433 | CG | LEU | B | 279 | 3.207 | 14.816 | 2.139 | 1.00 | 13.96 |
| 8435 | CD1 | LEU | B | 279 | 2.774 | 15.941 | 3.080 | 1.00 | 12.96 |
| 8439 | CD2 | LEU | B | 279 | 4.108 | 15.360 | 1.029 | 1.00 | 12.84 |
| 8443 | C | LEU | B | 279 | 5.075 | 11.502 | 2.860 | 1.00 | 15.30 |
| 8444 | O | LEU | B | 279 | 6.283 | 11.517 | 2.605 | 1.00 | 15.01 |
| 8445 | N | TYR | B | 280 | 4.529 | 10.679 | 3.751 | 1.00 | 16.26 |
| 8447 | CA | TYR | B | 280 | 5.336 | 9.750 | 4.528 | 1.00 | 17.66 |
| 8449 | CB | TYR | B | 280 | 4.521 | 9.118 | 5.666 | 1.00 | 17.55 |
| 8452 | CG | TYR | B | 280 | 4.191 | 10.046 | 6.827 | 1.00 | 15.50 |
| 8453 | CD1 | TYR | B | 280 | 3.484 | 9.575 | 7.924 | 1.00 | 14.31 |
| 8455 | CE1 | TYR | B | 280 | 3.163 | 10.399 | 8.984 | 1.00 | 13.88 |
| 8457 | CZ | TYR | B | 280 | 3.534 | 11.726 | 8.963 | 1.00 | 14.03 |
| 8458 | OH | TYR | B | 280 | 3.213 | 12.546 | 10.026 | 1.00 | 16.74 |
| 8460 | CE2 | TYR | B | 280 | 4.229 | 12.227 | 7.880 | 1.00 | 13.43 |
| 8462 | CD2 | TYR | B | 280 | 4.556 | 11.395 | 6.829 | 1.00 | 14.11 |
| 8464 | C | TYR | B | 280 | 5.936 | 8.686 | 3.613 | 1.00 | 20.05 |
| 8465 | O | TYR | B | 280 | 7.074 | 8.281 | 3.825 | 1.00 | 20.38 |

FIGURE 3 (cont.)

| A | B | C | D | E | F | G | H | I | J |
|---|---|---|---|---|---|---|---|---|---|
| 8466 | N | SER | B | 281 | 5.196 | 8.294 | 2.578 | 1.00 | 22.76 |
| 8468 | CA | SER | B | 281 | 5.606 | 7.222 | 1.666 | 1.00 | 25.12 |
| 8470 | CB | SER | B | 281 | 4.435 | 6.780 | 0.777 | 1.00 | 25.24 |
| 8473 | OG | SER | B | 281 | 4.240 | 7.651 | -0.329 | 1.00 | 25.80 |
| 8475 | C | SER | B | 281 | 6.786 | 7.627 | 0.797 | 1.00 | 27.46 |
| 8476 | O | SER | B | 281 | 7.565 | 6.773 | 0.382 | 1.00 | 28.13 |
| 8477 | N | THR | B | 282 | 6.919 | 8.927 | 0.534 | 1.00 | 30.00 |
| 8479 | CA | THR | B | 282 | 8.041 | 9.442 | -0.255 | 1.00 | 31.75 |
| 8481 | CB | THR | B | 282 | 7.786 | 10.914 | -0.715 | 1.00 | 31.78 |
| 8483 | OG1 | THR | B | 282 | 7.706 | 11.795 | 0.414 | 1.00 | 33.17 |
| 8485 | CG2 | THR | B | 282 | 6.437 | 11.068 | -1.410 | 1.00 | 32.34 |
| 8489 | C | THR | B | 282 | 9.379 | 9.340 | 0.490 | 1.00 | 32.84 |
| 8490 | O | THR | B | 282 | 10.434 | 9.494 | -0.121 | 1.00 | 33.74 |
| 8491 | N | SER | B | 283 | 9.333 | 9.071 | 1.797 | 1.00 | 33.83 |
| 8493 | CA | SER | B | 283 | 10.531 | 8.957 | 2.630 | 1.00 | 34.45 |
| 8495 | CB | SER | B | 283 | 10.234 | 9.404 | 4.070 | 1.00 | 34.79 |
| 8498 | OG | SER | B | 283 | 11.039 | 10.506 | 4.437 | 1.00 | 36.40 |
| 8500 | C | SER | B | 283 | 11.112 | 7.556 | 2.700 | 1.00 | 34.09 |
| 8501 | O | SER | B | 283 | 12.291 | 7.397 | 3.006 | 1.00 | 35.02 |
| 8502 | N | TYR | B | 284 | 10.295 | 6.534 | 2.457 | 1.00 | 33.59 |
| 8504 | CA | TYR | B | 284 | 10.726 | 5.156 | 2.689 | 1.00 | 32.95 |
| 8506 | CB | TYR | B | 284 | 9.797 | 4.474 | 3.694 | 1.00 | 32.12 |
| 8509 | CG | TYR | B | 284 | 9.654 | 5.238 | 4.993 | 1.00 | 28.73 |
| 8510 | CD1 | TYR | B | 284 | 8.521 | 5.994 | 5.255 | 1.00 | 26.22 |
| 8512 | CE1 | TYR | B | 284 | 8.385 | 6.700 | 6.448 | 1.00 | 24.33 |
| 8514 | CZ | TYR | B | 284 | 9.398 | 6.650 | 7.388 | 1.00 | 23.63 |
| 8515 | OH | TYR | B | 284 | 9.288 | 7.335 | 8.566 | 1.00 | 21.11 |
| 8517 | CE2 | TYR | B | 284 | 10.536 | 5.909 | 7.150 | 1.00 | 24.98 |
| 8519 | CD2 | TYR | B | 284 | 10.658 | 5.207 | 5.955 | 1.00 | 26.04 |
| 8521 | C | TYR | B | 284 | 10.793 | 4.339 | 1.405 | 1.00 | 33.85 |
| 8522 | O | TYR | B | 284 | 10.024 | 4.569 | 0.469 | 1.00 | 34.22 |
| 8523 | N | ASN | B | 285 | 11.716 | 3.378 | 1.387 | 1.00 | 34.62 |
| 8525 | CA | ASN | B | 285 | 11.962 | 2.521 | 0.233 | 1.00 | 35.16 |
| 8527 | CB | ASN | B | 285 | 13.474 | 2.393 | -0.002 | 1.00 | 35.69 |
| 8530 | CG | ASN | B | 285 | 13.821 | 1.773 | -1.353 | 1.00 | 36.74 |
| 8531 | OD1 | ASN | B | 285 | 12.946 | 1.372 | -2.118 | 1.00 | 38.95 |
| 8532 | ND2 | ASN | B | 285 | 15.117 | 1.697 | -1.648 | 1.00 | 39.65 |
| 8535 | C | ASN | B | 285 | 11.343 | 1.144 | 0.459 | 1.00 | 35.32 |
| 8536 | O | ASN | B | 285 | 11.760 | 0.410 | 1.359 | 1.00 | 35.16 |
| 8537 | N | MET | B | 286 | 10.355 | 0.799 | -0.366 | 1.00 | 35.43 |
| 8539 | CA | MET | B | 286 | 9.591 | -0.438 | -0.207 | 1.00 | 35.68 |
| 8541 | CB | MET | B | 286 | 8.128 | -0.219 | -0.626 | 1.00 | 35.78 |
| 8544 | CG | MET | B | 286 | 7.395 | 0.860 | 0.153 | 1.00 | 36.06 |
| 8547 | SD | MET | B | 286 | 7.077 | 0.401 | 1.873 | 1.00 | 38.05 |
| 8548 | CE | MET | B | 286 | 8.096 | 1.588 | 2.710 | 1.00 | 38.26 |
| 8552 | C | MET | B | 286 | 10.153 | -1.622 | -1.002 | 1.00 | 35.73 |
| 8553 | O | MET | B | 286 | 9.575 | -2.705 | -0.958 | 1.00 | 35.88 |
| 8554 | N | ASP | B | 287 | 11.260 | -1.424 | -1.723 | 1.00 | 36.01 |
| 8556 | CA | ASP | B | 287 | 11.855 | -2.484 | -2.556 | 1.00 | 36.13 |

FIGURE 3 (cont.)

| A | B | C | D | E | F | G | H | I | J |
|---|---|---|---|---|---|---|---|---|---|
| 8558 | CB | ASP | B | 287 | 13.152 | -1.991 | -3.222 | 1.00 | 36.54 |
| 8561 | CG | ASP | B | 287 | 12.899 | -1.090 | -4.422 | 1.00 | 38.05 |
| 8562 | OD1 | ASP | B | 287 | 11.727 | -0.934 | -4.836 | 1.00 | 39.91 |
| 8563 | OD2 | ASP | B | 287 | 13.824 | -0.494 | -5.021 | 1.00 | 40.92 |
| 8564 | C | ASP | B | 287 | 12.149 | -3.745 | -1.748 | 1.00 | 35.73 |
| 8565 | O | ASP | B | 287 | 11.867 | -4.856 | -2.188 | 1.00 | 35.62 |
| 8566 | N | ARG | B | 288 | 12.726 | -3.538 | -0.567 | 1.00 | 35.51 |
| 8568 | CA | ARG | B | 288 | 12.943 | -4.559 | 0.466 | 1.00 | 35.62 |
| 8570 | CB | ARG | B | 288 | 13.124 | -3.814 | 1.808 | 1.00 | 36.14 |
| 8573 | CG | ARG | B | 288 | 13.509 | -4.633 | 3.022 | 1.00 | 37.85 |
| 8576 | CD | ARG | B | 288 | 13.464 | -3.837 | 4.336 | 1.00 | 39.97 |
| 8579 | NE | ARG | B | 288 | 13.307 | -4.721 | 5.495 | 1.00 | 41.73 |
| 8581 | CZ | ARG | B | 288 | 12.940 | -4.335 | 6.715 | 1.00 | 43.08 |
| 8582 | NH1 | ARG | B | 288 | 12.668 | -3.058 | 6.982 | 1.00 | 41.03 |
| 8585 | NH2 | ARG | B | 288 | 12.840 | -5.250 | 7.680 | 1.00 | 44.66 |
| 8588 | C | ARG | B | 288 | 11.800 | -5.585 | 0.589 | 1.00 | 34.78 |
| 8589 | O | ARG | B | 288 | 12.039 | -6.786 | 0.741 | 1.00 | 34.29 |
| 8590 | N | PHE | B | 289 | 10.561 | -5.100 | 0.529 | 1.00 | 33.96 |
| 8592 | CA | PHE | B | 289 | 9.376 | -5.929 | 0.784 | 1.00 | 33.49 |
| 8594 | CB | PHE | B | 289 | 8.284 | -5.078 | 1.437 | 1.00 | 33.18 |
| 8597 | CG | PHE | B | 289 | 8.754 | -4.338 | 2.651 | 1.00 | 32.18 |
| 8598 | CD1 | PHE | B | 289 | 8.938 | -2.964 | 2.615 | 1.00 | 31.36 |
| 8600 | CE1 | PHE | B | 289 | 9.385 | -2.276 | 3.737 | 1.00 | 31.08 |
| 8602 | CZ | PHE | B | 289 | 9.659 | -2.966 | 4.908 | 1.00 | 30.78 |
| 8604 | CE2 | PHE | B | 289 | 9.484 | -4.340 | 4.952 | 1.00 | 31.52 |
| 8606 | CD2 | PHE | B | 289 | 9.034 | -5.021 | 3.824 | 1.00 | 31.95 |
| 8608 | C | PHE | B | 289 | 8.815 | -6.593 | -0.463 | 1.00 | 33.46 |
| 8609 | O | PHE | B | 289 | 8.064 | -7.567 | -0.350 | 1.00 | 33.70 |
| 8610 | N | GLN | C | 20 | -58.294 | -40.530 | -19.881 | 1.00 | 34.74 |
| 8612 | CA | GLN | C | 20 | -58.716 | -40.474 | -21.311 | 1.00 | 33.92 |
| 8614 | CB | GLN | C | 20 | -58.639 | -39.069 | -21.940 | 1.00 | 33.64 |
| 8617 | CG | GLN | C | 20 | -57.233 | -38.613 | -22.240 | 1.00 | 30.56 |
| 8620 | CD | GLN | C | 20 | -56.449 | -38.272 | -20.994 | 1.00 | 26.16 |
| 8621 | OE1 | GLN | C | 20 | -56.998 | -37.722 | -20.037 | 1.00 | 19.55 |
| 8622 | NE2 | GLN | C | 20 | -55.161 | -38.569 | -21.015 | 1.00 | 23.79 |
| 8625 | C | GLN | C | 20 | -58.703 | -41.693 | -22.286 | 1.00 | 34.23 |
| 8626 | O | GLN | C | 20 | -58.210 | -42.768 | -21.949 | 1.00 | 35.14 |
| 8630 | N | GLN | C | 21 | -59.251 | -41.476 | -23.479 | 1.00 | 34.08 |
| 8632 | CA | GLN | C | 21 | -58.974 | -42.319 | -24.633 | 1.00 | 34.04 |
| 8634 | CB | GLN | C | 21 | -60.177 | -42.369 | -25.578 | 1.00 | 34.40 |
| 8637 | CG | GLN | C | 21 | -61.117 | -43.536 | -25.320 | 1.00 | 35.52 |
| 8640 | CD | GLN | C | 21 | -62.431 | -43.395 | -26.062 | 1.00 | 37.46 |
| 8641 | OE1 | GLN | C | 21 | -62.518 | -43.721 | -27.248 | 1.00 | 38.85 |
| 8642 | NE2 | GLN | C | 21 | -63.457 | -42.904 | -25.370 | 1.00 | 38.76 |
| 8645 | C | GLN | C | 21 | -57.769 | -41.711 | -25.354 | 1.00 | 33.63 |
| 8646 | O | GLN | C | 21 | -57.858 | -40.597 | -25.884 | 1.00 | 33.46 |
| 8647 | N | PRO | C | 22 | -56.643 | -42.422 | -25.369 | 1.00 | 32.92 |
| 8648 | CA | PRO | C | 22 | -55.456 | -41.927 | -26.068 | 1.00 | 32.63 |
| 8650 | CB | PRO | C | 22 | -54.325 | -42.796 | -25.510 | 1.00 | 32.47 |

FIGURE 3 (cont.)

| A | B | C | D | E | F | G | H | I | J |
|---|---|---|---|---|---|---|---|---|---|
| 8653 | CG | PRO | C | 22 | -54.981 | -44.065 | -25.062 | 1.00 | 32.96 |
| 8656 | CD | PRO | C | 22 | -56.414 | -43.745 | -24.763 | 1.00 | 32.97 |
| 8659 | C | PRO | C | 22 | -55.623 | -42.118 | -27.572 | 1.00 | 32.44 |
| 8660 | O | PRO | C | 22 | -56.507 | -42.869 | -27.998 | 1.00 | 32.00 |
| 8661 | N | LEU | C | 23 | -54.809 | -41.425 | -28.360 | 1.00 | 32.07 |
| 8663 | CA | LEU | C | 23 | -54.842 | -41.563 | -29.810 | 1.00 | 32.03 |
| 8665 | CB | LEU | C | 23 | -54.134 | -40.381 | -30.482 | 1.00 | 31.96 |
| 8668 | CG | LEU | C | 23 | -54.591 | -38.974 | -30.085 | 1.00 | 32.00 |
| 8670 | CD1 | LEU | C | 23 | -53.811 | -37.925 | -30.871 | 1.00 | 32.25 |
| 8674 | CD2 | LEU | C | 23 | -56.094 | -38.805 | -30.294 | 1.00 | 32.10 |
| 8678 | C | LEU | C | 23 | -54.153 | -42.866 | -30.189 | 1.00 | 32.18 |
| 8679 | O | LEU | C | 23 | -53.012 | -43.096 | -29.785 | 1.00 | 32.36 |
| 8680 | N | ASN | C | 24 | -54.855 | -43.722 | -30.935 | 1.00 | 32.33 |
| 8682 | CA | ASN | C | 24 | -54.269 | -44.956 | -31.465 | 1.00 | 32.45 |
| 8684 | CB | ASN | C | 24 | -55.354 | -46.008 | -31.764 | 1.00 | 32.89 |
| 8687 | CG | ASN | C | 24 | -55.890 | -46.687 | -30.499 | 1.00 | 34.04 |
| 8688 | OD1 | ASN | C | 24 | -55.579 | -46.285 | -29.375 | 1.00 | 36.84 |
| 8689 | ND2 | ASN | C | 24 | -56.705 | -47.723 | -30.685 | 1.00 | 35.96 |
| 8692 | C | ASN | C | 24 | -53.460 | -44.617 | -32.722 | 1.00 | 31.90 |
| 8693 | O | ASN | C | 24 | -53.883 | -44.884 | -33.854 | 1.00 | 31.87 |
| 8694 | N | GLU | C | 25 | -52.295 | -44.008 | -32.496 | 1.00 | 31.12 |
| 8696 | CA | GLU | C | 25 | -51.475 | -43.413 | -33.555 | 1.00 | 30.47 |
| 8698 | CB | GLU | C | 25 | -51.908 | -41.963 | -33.808 | 1.00 | 30.75 |
| 8701 | CG | GLU | C | 25 | -53.368 | -41.775 | -34.195 | 1.00 | 32.21 |
| 8704 | CD | GLU | C | 25 | -53.754 | -40.319 | -34.374 | 1.00 | 33.97 |
| 8705 | OE1 | GLU | C | 25 | -54.904 | -39.968 | -34.033 | 1.00 | 35.70 |
| 8706 | OE2 | GLU | C | 25 | -52.921 | -39.525 | -34.860 | 1.00 | 35.50 |
| 8707 | C | GLU | C | 25 | -49.992 | -43.403 | -33.174 | 1.00 | 29.30 |
| 8708 | O | GLU | C | 25 | -49.638 | -43.395 | -31.993 | 1.00 | 29.30 |
| 8709 | N | GLU | C | 26 | -49.129 | -43.396 | -34.186 | 1.00 | 27.68 |
| 8711 | CA | GLU | C | 26 | -47.704 | -43.169 | -33.985 | 1.00 | 26.35 |
| 8713 | CB | GLU | C | 26 | -46.908 | -43.657 | -35.203 | 1.00 | 26.79 |
| 8716 | CG | GLU | C | 26 | -45.414 | -43.844 | -34.954 | 1.00 | 29.24 |
| 8719 | CD | GLU | C | 26 | -44.667 | -44.403 | -36.161 | 1.00 | 32.01 |
| 8720 | OE1 | GLU | C | 26 | -43.503 | -43.995 | -36.386 | 1.00 | 34.80 |
| 8721 | OE2 | GLU | C | 26 | -45.231 | -45.251 | -36.889 | 1.00 | 34.16 |
| 8722 | C | GLU | C | 26 | -47.515 | -41.667 | -33.798 | 1.00 | 24.05 |
| 8723 | O | GLU | C | 26 | -48.145 | -40.876 | -34.501 | 1.00 | 23.56 |
| 8724 | N | PHE | C | 27 | -46.672 | -41.270 | -32.847 | 1.00 | 21.62 |
| 8726 | CA | PHE | C | 27 | -46.326 | -39.860 | -32.700 | 1.00 | 19.65 |
| 8728 | CB | PHE | C | 27 | -45.439 | -39.592 | -31.475 | 1.00 | 19.28 |
| 8731 | CG | PHE | C | 27 | -44.962 | -38.164 | -31.393 | 1.00 | 16.57 |
| 8732 | CD1 | PHE | C | 27 | -43.707 | -37.798 | -31.863 | 1.00 | 15.23 |
| 8734 | CE1 | PHE | C | 27 | -43.292 | -36.476 | -31.823 | 1.00 | 14.65 |
| 8736 | CZ | PHE | C | 27 | -44.134 | -35.498 | -31.316 | 1.00 | 14.61 |
| 8738 | CE2 | PHE | C | 27 | -45.384 | -35.848 | -30.861 | 1.00 | 14.24 |
| 8740 | CD2 | PHE | C | 27 | -45.799 | -37.171 | -30.903 | 1.00 | 14.62 |
| 8742 | C | PHE | C | 27 | -45.582 | -39.391 | -33.940 | 1.00 | 18.77 |
| 8743 | O | PHE | C | 27 | -44.716 | -40.095 | -34.455 | 1.00 | 18.59 |

FIGURE 3 (cont.)

| A | B | C | D | E | F | G | H | I | J |
|---|---|---|---|---|---|---|---|---|---|
| 8744 | N | ARG | C | 28 | -45.919 | -38.198 | -34.418 | 1.00 | 17.61 |
| 8746 | CA | ARG | C | 28 | -45.074 | -37.503 | -35.379 | 1.00 | 17.40 |
| 8748 | CB | ARG | C | 28 | -45.621 | -37.622 | -36.805 | 1.00 | 18.04 |
| 8751 | CG B | ARG | C | 28 | -46.908 | -36.841 | -37.052 | 0.35 | 19.02 |
| 8752 | CG A | ARG | C | 28 | -46.898 | -36.858 | -37.058 | 0.65 | 20.07 |
| 8757 | CD B | ARG | C | 28 | -47.652 | -37.222 | -38.327 | 0.35 | 20.33 |
| 8758 | CD A | ARG | C | 28 | -47.769 | -37.475 | -38.132 | 0.65 | 22.53 |
| 8763 | NE B | ARG | C | 28 | -49.069 | -37.494 | -38.069 | 0.35 | 20.89 |
| 8764 | NE A | ARG | C | 28 | -48.263 | -38.791 | -37.722 | 0.65 | 23.73 |
| 8767 | CZ B | ARG | C | 28 | -50.050 | -36.595 | -38.124 | 0.35 | 21.86 |
| 8768 | CZ A | ARG | C | 28 | -49.494 | -39.052 | -37.290 | 0.65 | 24.81 |
| 8769 | NH1B | ARG | C | 28 | -51.296 | -36.974 | -37.871 | 0.35 | 22.22 |
| 8770 | NH1A | ARG | C | 28 | -50.417 | -38.094 | -37.201 | 0.65 | 25.76 |
| 8775 | NH2B | ARG | C | 28 | -49.808 | -35.323 | -38.424 | 0.35 | 22.88 |
| 8776 | NH2A | ARG | C | 28 | -49.811 | -40.297 | -36.951 | 0.65 | 25.62 |
| 8781 | C | ARG | C | 28 | -44.968 | -36.046 | -34.960 | 1.00 | 16.08 |
| 8782 | O | ARG | C | 28 | -45.919 | -35.509 | -34.387 | 1.00 | 14.94 |
| 8783 | N | PRO | C | 29 | -43.824 | -35.411 | -35.219 | 1.00 | 15.89 |
| 8784 | CA | PRO | C | 29 | -43.629 | -34.021 | -34.791 | 1.00 | 15.52 |
| 8786 | CB | PRO | C | 29 | -42.209 | -33.697 | -35.250 | 1.00 | 15.90 |
| 8789 | CG | PRO | C | 29 | -41.884 | -34.705 | -36.265 | 1.00 | 16.44 |
| 8792 | CD | PRO | C | 29 | -42.629 | -35.944 | -35.892 | 1.00 | 15.85 |
| 8795 | C | PRO | C | 29 | -44.622 | -33.044 | -35.396 | 1.00 | 15.17 |
| 8796 | O | PRO | C | 29 | -44.833 | -31.989 | -34.818 | 1.00 | 14.21 |
| 8797 | N | GLU | C | 30 | -45.220 | -33.388 | -36.534 | 1.00 | 14.88 |
| 8799 | CA | GLU | C | 30 | -46.200 | -32.516 | -37.180 | 1.00 | 14.90 |
| 8801 | CB | GLU | C | 30 | -46.507 | -33.005 | -38.606 | 1.00 | 15.12 |
| 8804 | CG | GLU | C | 30 | -45.343 | -32.842 | -39.573 | 1.00 | 16.80 |
| 8807 | CD | GLU | C | 30 | -44.191 | -33.810 | -39.349 | 1.00 | 17.15 |
| 8808 | OE1 | GLU | C | 30 | -43.039 | -33.422 | -39.635 | 1.00 | 18.60 |
| 8809 | OE2 | GLU | C | 30 | -44.413 | -34.954 | -38.883 | 1.00 | 19.19 |
| 8810 | C | GLU | C | 30 | -47.488 | -32.384 | -36.372 | 1.00 | 14.30 |
| 8811 | O | GLU | C | 30 | -48.276 | -31.480 | -36.610 | 1.00 | 14.68 |
| 8812 | N | MET | C | 31 | -47.691 | -33.272 | -35.401 | 1.00 | 13.87 |
| 8814 | CA | MET | C | 31 | -48.788 | -33.137 | -34.445 | 1.00 | 13.81 |
| 8816 | CB | MET | C | 31 | -48.771 | -34.310 | -33.460 | 1.00 | 13.99 |
| 8819 | CG | MET | C | 31 | -49.217 | -35.622 | -34.067 | 1.00 | 14.31 |
| 8822 | SD | MET | C | 31 | -49.025 | -36.994 | -32.932 | 1.00 | 16.13 |
| 8823 | CE | MET | C | 31 | -50.136 | -38.189 | -33.639 | 1.00 | 16.41 |
| 8827 | C | MET | C | 31 | -48.760 | -31.817 | -33.663 | 1.00 | 13.62 |
| 8828 | O | MET | C | 31 | -49.797 | -31.361 | -33.157 | 1.00 | 14.44 |
| 8829 | N | LEU | C | 32 | -47.582 | -31.212 | -33.542 | 1.00 | 12.84 |
| 8831 | CA | LEU | C | 32 | -47.429 | -29.967 | -32.793 | 1.00 | 12.41 |
| 8833 | CB | LEU | C | 32 | -46.208 | -30.045 | -31.867 | 1.00 | 12.16 |
| 8836 | CG | LEU | C | 32 | -46.390 | -30.739 | -30.510 | 1.00 | 13.21 |
| 8838 | CD1 | LEU | C | 32 | -46.715 | -32.207 | -30.703 | 1.00 | 14.47 |
| 8842 | CD2 | LEU | C | 32 | -47.451 | -30.037 | -29.675 | 1.00 | 13.75 |
| 8846 | C | LEU | C | 32 | -47.311 | -28.749 | -33.705 | 1.00 | 12.13 |
| 8847 | O | LEU | C | 32 | -47.226 | -27.628 | -33.238 | 1.00 | 12.23 |

FIGURE 3 (cont.)

| A | B | C | D | E | F | G | H | I | J |
|---|---|---|---|---|---|---|---|---|---|
| 8848 | N | GLN | C | 33 | -47.292 | -28.977 | -35.010 | 1.00 | 11.56 |
| 8850 | CA | GLN | C | 33 | -47.152 | -27.888 | -35.972 | 1.00 | 12.02 |
| 8852 | CB | GLN | C | 33 | -47.065 | -28.474 | -37.374 | 1.00 | 12.50 |
| 8855 | CG | GLN | C | 33 | -46.679 | -27.489 | -38.445 | 1.00 | 13.47 |
| 8858 | CD | GLN | C | 33 | -46.534 | -28.171 | -39.802 | 1.00 | 15.42 |
| 8859 | OE1 | GLN | C | 33 | -45.630 | -28.979 | -39.994 | 1.00 | 17.41 |
| 8860 | NE2 | GLN | C | 33 | -47.428 | -27.856 | -40.729 | 1.00 | 15.74 |
| 8863 | C | GLN | C | 33 | -48.319 | -26.908 | -35.888 | 1.00 | 11.74 |
| 8864 | O | GLN | C | 33 | -49.475 | -27.297 | -36.047 | 1.00 | 12.39 |
| 8865 | N | GLY | C | 34 | -48.014 | -25.643 | -35.605 | 1.00 | 11.29 |
| 8867 | CA | GLY | C | 34 | -49.024 | -24.608 | -35.459 | 1.00 | 11.07 |
| 8870 | C | GLY | C | 34 | -49.833 | -24.662 | -34.173 | 1.00 | 10.89 |
| 8871 | O | GLY | C | 34 | -50.736 | -23.847 | -33.969 | 1.00 | 11.58 |
| 8872 | N | LYS | C | 35 | -49.515 | -25.605 | -33.297 | 1.00 | 11.09 |
| 8874 | CA | LYS | C | 35 | -50.224 | -25.719 | -32.033 | 1.00 | 11.12 |
| 8876 | CB | LYS | C | 35 | -50.042 | -27.105 | -31.416 | 1.00 | 11.33 |
| 8879 | CG | LYS | C | 35 | -50.649 | -28.260 | -32.222 | 1.00 | 13.18 |
| 8882 | CD | LYS | C | 35 | -52.160 | -28.163 | -32.298 | 1.00 | 15.59 |
| 8885 | CE | LYS | C | 35 | -52.774 | -29.389 | -32.993 | 1.00 | 18.26 |
| 8888 | NZ | LYS | C | 35 | -54.264 | -29.302 | -33.053 | 1.00 | 22.35 |
| 8892 | C | LYS | C | 35 | -49.718 | -24.645 | -31.094 | 1.00 | 10.85 |
| 8893 | O | LYS | C | 35 | -48.576 | -24.212 | -31.185 | 1.00 | 11.64 |
| 8894 | N | LYS | C | 36 | -50.579 | -24.222 | -30.180 | 1.00 | 10.28 |
| 8896 | CA | LYS | C | 36 | -50.316 | -23.095 | -29.288 | 1.00 | 10.30 |
| 8898 | CB | LYS | C | 36 | -51.523 | -22.148 | -29.324 | 1.00 | 10.46 |
| 8901 | CG | LYS | C | 36 | -51.745 | -21.593 | -30.724 | 1.00 | 11.20 |
| 8904 | CD | LYS | C | 36 | -53.107 | -21.004 | -30.941 | 1.00 | 13.10 |
| 8907 | CE | LYS | C | 36 | -53.188 | -20.561 | -32.409 | 1.00 | 15.63 |
| 8910 | NZ | LYS | C | 36 | -54.478 | -19.927 | -32.742 | 1.00 | 18.66 |
| 8914 | C | LYS | C | 36 | -50.057 | -23.664 | -27.898 | 1.00 | 10.34 |
| 8915 | O | LYS | C | 36 | -50.935 | -24.236 | -27.281 | 1.00 | 10.38 |
| 8916 | N | VAL | C | 37 | -48.820 | -23.538 | -27.438 | 1.00 | 9.90 |
| 8918 | CA | VAL | C | 37 | -48.351 | -24.266 | -26.262 | 1.00 | 9.42 |
| 8920 | CB | VAL | C | 37 | -47.325 | -25.366 | -26.648 | 1.00 | 9.26 |
| 8922 | CG1 | VAL | C | 37 | -46.985 | -26.231 | -25.432 | 1.00 | 9.38 |
| 8926 | CG2 | VAL | C | 37 | -47.849 | -26.206 | -27.795 | 1.00 | 10.02 |
| 8930 | C | VAL | C | 37 | -47.701 | -23.342 | -25.231 | 1.00 | 9.79 |
| 8931 | O | VAL | C | 37 | -46.835 | -22.529 | -25.563 | 1.00 | 10.00 |
| 8932 | N | ILE | C | 38 | -48.154 | -23.449 | -23.988 | 1.00 | 9.17 |
| 8934 | CA | ILE | C | 38 | -47.484 | -22.853 | -22.839 | 1.00 | 9.27 |
| 8936 | CB | ILE | C | 38 | -48.513 | -22.426 | -21.769 | 1.00 | 9.39 |
| 8938 | CG1 | ILE | C | 38 | -49.227 | -21.147 | -22.203 | 1.00 | 9.78 |
| 8941 | CD1 | ILE | C | 38 | -50.414 | -20.801 | -21.363 | 1.00 | 11.02 |
| 8945 | CG2 | ILE | C | 38 | -47.882 | -22.292 | -20.357 | 1.00 | 9.47 |
| 8949 | C | ILE | C | 38 | -46.525 | -23.869 | -22.256 | 1.00 | 9.61 |
| 8950 | O | ILE | C | 38 | -46.899 | -25.022 | -22.052 | 1.00 | 9.66 |
| 8951 | N | VAL | C | 39 | -45.294 | -23.445 | -21.978 | 1.00 | 9.16 |
| 8953 | CA | VAL | C | 39 | -44.377 | -24.251 | -21.176 | 1.00 | 9.38 |
| 8955 | CB | VAL | C | 39 | -43.123 | -24.705 | -21.946 | 1.00 | 9.89 |

FIGURE 3 (cont.)

| A | B | C | D | E | F | G | H | I | J |
|---|---|---|---|---|---|---|---|---|---|
| 8957 | CG1 | VAL | C | 39 | -42.354 | -25.735 | -21.137 | 1.00 | 10.83 |
| 8961 | CG2 | VAL | C | 39 | -43.488 | -25.241 | -23.312 | 1.00 | 11.16 |
| 8965 | C | VAL | C | 39 | -43.941 | -23.450 | -19.954 | 1.00 | 9.46 |
| 8966 | O | VAL | C | 39 | -43.358 | -22.379 | -20.094 | 1.00 | 9.23 |
| 8967 | N | THR | C | 40 | -44.224 | -23.956 | -18.758 | 1.00 | 8.93 |
| 8969 | CA | THR | C | 40 | -43.726 | -23.314 | -17.534 | 1.00 | 9.10 |
| 8971 | CB | THR | C | 40 | -44.756 | -23.322 | -16.376 | 1.00 | 9.12 |
| 8973 | OG1 | THR | C | 40 | -44.857 | -24.633 | -15.785 | 1.00 | 10.21 |
| 8975 | CG2 | THR | C | 40 | -46.151 | -22.930 | -16.852 | 1.00 | 9.30 |
| 8979 | C | THR | C | 40 | -42.409 | -23.939 | -17.082 | 1.00 | 8.88 |
| 8980 | O | THR | C | 40 | -42.033 | -25.023 | -17.543 | 1.00 | 9.42 |
| 8981 | N | GLY | C | 41 | -41.674 | -23.220 | -16.243 | 1.00 | 8.58 |
| 8983 | CA | GLY | C | 41 | -40.349 | -23.649 | -15.835 | 1.00 | 8.78 |
| 8986 | C | GLY | C | 41 | -39.460 | -23.901 | -17.038 | 1.00 | 9.70 |
| 8987 | O | GLY | C | 41 | -38.798 | -24.933 | -17.124 | 1.00 | 9.56 |
| 8988 | N | ALA | C | 42 | -39.419 | -22.935 | -17.949 | 1.00 | 9.58 |
| 8990 | CA | ALA | C | 42 | -38.818 | -23.146 | -19.269 | 1.00 | 10.14 |
| 8992 | CB | ALA | C | 42 | -39.841 | -22.817 | -20.353 | 1.00 | 10.78 |
| 8996 | C | ALA | C | 42 | -37.525 | -22.374 | -19.491 | 1.00 | 10.71 |
| 8997 | O | ALA | C | 42 | -36.999 | -22.341 | -20.622 | 1.00 | 11.74 |
| 8998 | N | SER | C | 43 | -36.974 | -21.787 | -18.435 | 1.00 | 11.03 |
| 9000 | CA | SER | C | 43 | -35.695 | -21.080 | -18.549 | 1.00 | 11.33 |
| 9002 | CB | SER | C | 43 | -35.524 | -20.045 | -17.435 | 1.00 | 11.39 |
| 9005 | OG | SER | C | 43 | -35.562 | -20.642 | -16.158 | 1.00 | 11.36 |
| 9007 | C | SER | C | 43 | -34.499 | -22.035 | -18.544 | 1.00 | 12.10 |
| 9008 | O | SER | C | 43 | -33.426 | -21.692 | -19.028 | 1.00 | 12.13 |
| 9009 | N | LYS | C | 44 | -34.674 | -23.220 | -17.980 | 1.00 | 11.92 |
| 9011 | CA | LYS | C | 44 | -33.599 | -24.215 | -17.933 | 1.00 | 12.09 |
| 9013 | CB | LYS | C | 44 | -32.651 | -23.905 | -16.781 | 1.00 | 13.06 |
| 9016 | CG | LYS | C | 44 | -33.288 | -23.932 | -15.419 | 1.00 | 13.91 |
| 9019 | CD | LYS | C | 44 | -32.326 | -23.440 | -14.337 | 1.00 | 16.38 |
| 9022 | CE | LYS | C | 44 | -32.944 | -23.533 | -12.945 | 1.00 | 17.60 |
| 9025 | NZ | LYS | C | 44 | -31.966 | -23.049 | -11.895 | 1.00 | 18.30 |
| 9029 | C | LYS | C | 44 | -34.180 | -25.610 | -17.788 | 1.00 | 11.80 |
| 9030 | O | LYS | C | 44 | -35.390 | -25.787 | -17.799 | 1.00 | 11.61 |
| 9031 | N | GLY | C | 45 | -33.307 | -26.600 | -17.678 | 1.00 | 11.96 |
| 9033 | CA | GLY | C | 45 | -33.736 | -27.960 | -17.417 | 1.00 | 11.30 |
| 9036 | C | GLY | C | 45 | -34.611 | -28.561 | -18.496 | 1.00 | 11.07 |
| 9037 | O | GLY | C | 45 | -34.506 | -28.221 | -19.685 | 1.00 | 10.93 |
| 9038 | N | ILE | C | 46 | -35.514 | -29.434 | -18.066 | 1.00 | 10.70 |
| 9040 | CA | ILE | C | 46 | -36.425 | -30.131 | -18.964 | 1.00 | 10.28 |
| 9042 | CB | ILE | C | 46 | -37.210 | -31.205 | -18.181 | 1.00 | 10.39 |
| 9044 | CG1 | ILE | C | 46 | -36.266 | -32.274 | -17.605 | 1.00 | 11.07 |
| 9047 | CD1 | ILE | C | 46 | -36.799 | -32.947 | -16.344 | 1.00 | 12.06 |
| 9051 | CG2 | ILE | C | 46 | -38.248 | -31.872 | -19.070 | 1.00 | 12.00 |
| 9055 | C | ILE | C | 46 | -37.370 | -29.154 | -19.696 | 1.00 | 10.06 |
| 9056 | O | ILE | C | 46 | -37.671 | -29.328 | -20.869 | 1.00 | 10.64 |
| 9057 | N | GLY | C | 47 | -37.826 | -28.121 | -19.003 | 1.00 | 9.73 |
| 9059 | CA | GLY | C | 47 | -38.747 | -27.166 | -19.597 | 1.00 | 9.86 |

FIGURE 3 (cont.)

| A | B | C | D | E | F | G | H | I | J |
|---|---|---|---|---|---|---|---|---|---|
| 9062 | C | GLY | C | 47 | -38.144 | -26.442 | -20.779 | 1.00 | 9.83 |
| 9063 | O | GLY | C | 47 | -38.806 | -26.245 | -21.784 | 1.00 | 9.75 |
| 9064 | N | ARG | C | 48 | -36.892 | -26.020 | -20.636 | 1.00 | 9.89 |
| 9066 | CA | ARG | C | 48 | -36.186 | -25.372 | -21.735 | 1.00 | 10.00 |
| 9068 | CB | ARG | C | 48 | -34.784 | -24.919 | -21.307 | 1.00 | 10.57 |
| 9071 | CG | ARG | C | 48 | -33.968 | -24.327 | -22.462 | 1.00 | 12.41 |
| 9074 | CD | ARG | C | 48 | -32.694 | -23.612 | -22.012 | 1.00 | 15.48 |
| 9077 | NE | ARG | C | 48 | -31.799 | -24.489 | -21.279 | 1.00 | 19.90 |
| 9079 | CZ | ARG | C | 48 | -30.885 | -24.081 | -20.390 | 1.00 | 21.69 |
| 9080 | NH1 | ARG | C | 48 | -30.726 | -22.785 | -20.081 | 1.00 | 22.79 |
| 9083 | NH2 | ARG | C | 48 | -30.134 | -24.983 | -19.782 | 1.00 | 22.98 |
| 9086 | C | ARG | C | 48 | -36.088 | -26.333 | -22.913 | 1.00 | 10.04 |
| 9087 | O | ARG | C | 48 | -36.324 | -25.955 | -24.055 | 1.00 | 9.50 |
| 9088 | N | GLU | C | 49 | -35.749 | -27.586 | -22.640 | 1.00 | 9.52 |
| 9090 | CA | GLU | C | 49 | -35.648 | -28.567 | -23.712 | 1.00 | 10.42 |
| 9092 | CB | GLU | C | 49 | -35.050 | -29.880 | -23.202 | 1.00 | 10.62 |
| 9095 | CG | GLU | C | 49 | -33.621 | -29.754 | -22.658 | 1.00 | 13.07 |
| 9098 | CD | GLU | C | 49 | -32.648 | -29.075 | -23.622 | 1.00 | 16.89 |
| 9099 | OE1 | GLU | C | 49 | -31.837 | -28.222 | -23.173 | 1.00 | 19.30 |
| 9100 | OE2 | GLU | C | 49 | -32.681 | -29.384 | -24.842 | 1.00 | 19.75 |
| 9101 | C | GLU | C | 49 | -36.988 | -28.801 | -24.398 | 1.00 | 10.05 |
| 9102 | O | GLU | C | 49 | -37.044 | -29.018 | -25.601 | 1.00 | 10.17 |
| 9103 | N | MET | C | 50 | -38.078 | -28.750 | -23.644 | 1.00 | 9.36 |
| 9105 | CA | MET | C | 50 | -39.406 | -28.896 | -24.243 | 1.00 | 9.62 |
| 9107 | CB | MET | C | 50 | -40.492 | -29.042 | -23.162 | 1.00 | 9.98 |
| 9110 | CG | MET | C | 50 | -40.469 | -30.405 | -22.496 | 1.00 | 10.30 |
| 9113 | SD | MET | C | 50 | -41.882 | -30.737 | -21.419 | 1.00 | 11.40 |
| 9114 | CE | MET | C | 50 | -41.552 | -29.666 | -20.060 | 1.00 | 11.95 |
| 9118 | C | MET | C | 50 | -39.717 | -27.721 | -25.172 | 1.00 | 9.95 |
| 9119 | O | MET | C | 50 | -40.227 | -27.918 | -26.264 | 1.00 | 10.16 |
| 9120 | N | ALA | C | 51 | -39.396 | -26.506 | -24.733 | 1.00 | 10.28 |
| 9122 | CA | ALA | C | 51 | -39.552 | -25.318 | -25.576 | 1.00 | 10.22 |
| 9124 | CB | ALA | C | 51 | -39.086 | -24.072 | -24.852 | 1.00 | 10.32 |
| 9128 | C | ALA | C | 51 | -38.810 | -25.484 | -26.898 | 1.00 | 10.37 |
| 9129 | O | ALA | C | 51 | -39.368 | -25.214 | -27.953 | 1.00 | 10.15 |
| 9130 | N | TYR | C | 52 | -37.566 | -25.947 | -26.842 | 1.00 | 10.10 |
| 9132 | CA | TYR | C | 52 | -36.773 | -26.146 | -28.052 | 1.00 | 10.14 |
| 9134 | CB | TYR | C | 52 | -35.322 | -26.452 | -27.682 | 1.00 | 10.18 |
| 9137 | CG | TYR | C | 52 | -34.545 | -25.310 | -27.060 | 1.00 | 10.31 |
| 9138 | CD1 | TYR | C | 52 | -35.020 | -24.000 | -27.072 | 1.00 | 10.91 |
| 9140 | CE1 | TYR | C | 52 | -34.289 | -22.964 | -26.514 | 1.00 | 12.38 |
| 9142 | CZ | TYR | C | 52 | -33.090 | -23.223 | -25.920 | 1.00 | 13.51 |
| 9143 | OH | TYR | C | 52 | -32.376 | -22.170 | -25.370 | 1.00 | 17.22 |
| 9145 | CE2 | TYR | C | 52 | -32.592 | -24.502 | -25.881 | 1.00 | 12.99 |
| 9147 | CD2 | TYR | C | 52 | -33.319 | -25.545 | -26.448 | 1.00 | 12.38 |
| 9149 | C | TYR | C | 52 | -37.347 | -27.214 | -28.983 | 1.00 | 10.50 |
| 9150 | O | TYR | C | 52 | -37.388 | -27.012 | -30.198 | 1.00 | 10.63 |
| 9151 | N | HIS | C | 53 | -37.804 | -28.338 | -28.439 | 1.00 | 10.28 |
| 9153 | CA | HIS | C | 53 | -38.446 | -29.365 | -29.259 | 1.00 | 10.56 |

FIGURE 3 (cont.)

| A | B | C | D | E | F | G | H | I | J |
|---|---|---|---|---|---|---|---|---|---|
| 9155 | CB | HIS | C | 53 | -38.830 | -30.595 | -28.450 | 1.00 | 11.10 |
| 9158 | CG | HIS | C | 53 | -37.703 | -31.537 | -28.189 | 1.00 | 11.49 |
| 9159 | ND1 | HIS | C | 53 | -36.989 | -32.148 | -29.201 | 1.00 | 13.66 |
| 9161 | CE1 | HIS | C | 53 | -36.082 | -32.946 | -28.665 | 1.00 | 13.86 |
| 9163 | NE2 | HIS | C | 53 | -36.190 | -32.882 | -27.351 | 1.00 | 14.64 |
| 9165 | CD2 | HIS | C | 53 | -37.203 | -32.017 | -27.027 | 1.00 | 13.26 |
| 9167 | C | HIS | C | 53 | -39.697 | -28.812 | -29.936 | 1.00 | 10.34 |
| 9168 | O | HIS | C | 53 | -39.898 | -29.031 | -31.125 | 1.00 | 10.57 |
| 9169 | N | LEU | C | 54 | -40.528 | -28.098 | -29.184 | 1.00 | 9.83 |
| 9171 | CA | LEU | C | 54 | -41.743 | -27.505 | -29.722 | 1.00 | 9.97 |
| 9173 | CB | LEU | C | 54 | -42.542 | -26.819 | -28.609 | 1.00 | 10.09 |
| 9176 | CG | LEU | C | 54 | -43.180 | -27.801 | -27.624 | 1.00 | 10.41 |
| 9178 | CD1 | LEU | C | 54 | -43.573 | -27.108 | -26.349 | 1.00 | 10.61 |
| 9182 | CD2 | LEU | C | 54 | -44.366 | -28.525 | -28.244 | 1.00 | 11.32 |
| 9186 | C | LEU | C | 54 | -41.425 | -26.515 | -30.840 | 1.00 | 10.00 |
| 9187 | O | LEU | C | 54 | -42.104 | -26.469 | -31.869 | 1.00 | 10.01 |
| 9188 | N | ALA | C | 55 | -40.372 | -25.740 | -30.640 | 1.00 | 10.04 |
| 9190 | CA | ALA | C | 55 | -39.931 | -24.776 | -31.634 | 1.00 | 9.96 |
| 9192 | CB | ALA | C | 55 | -38.780 | -23.945 | -31.085 | 1.00 | 10.11 |
| 9196 | C | ALA | C | 55 | -39.525 | -25.482 | -32.930 | 1.00 | 10.21 |
| 9197 | O | ALA | C | 55 | -39.957 | -25.096 | -34.010 | 1.00 | 10.50 |
| 9198 | N | LYS | C | 56 | -38.746 | -26.552 | -32.815 | 1.00 | 10.86 |
| 9200 | CA | LYS | C | 56 | -38.371 | -27.358 | -33.974 | 1.00 | 12.10 |
| 9202 | CB | LYS | C | 56 | -37.400 | -28.466 | -33.571 | 1.00 | 13.15 |
| 9205 | CG | LYS | C | 56 | -36.026 | -27.987 | -33.176 | 1.00 | 17.15 |
| 9208 | CD | LYS | C | 56 | -35.086 | -29.152 | -32.868 | 1.00 | 21.41 |
| 9211 | CE | LYS | C | 56 | -34.119 | -28.830 | -31.731 | 1.00 | 24.71 |
| 9214 | NZ | LYS | C | 56 | -34.636 | -29.204 | -30.384 | 1.00 | 27.93 |
| 9218 | C | LYS | C | 56 | -39.578 | -27.952 | -34.707 | 1.00 | 11.97 |
| 9219 | O | LYS | C | 56 | -39.547 | -28.104 | -35.941 | 1.00 | 12.71 |
| 9220 | N | MET | C | 57 | -40.639 | -28.277 | -33.966 | 1.00 | 11.66 |
| 9222 | CA | MET | C | 57 | -41.874 | -28.797 | -34.545 | 1.00 | 11.34 |
| 9224 | CB | MET | C | 57 | -42.659 | -29.592 | -33.497 | 1.00 | 11.80 |
| 9227 | CG | MET | C | 57 | -41.920 | -30.812 | -32.956 | 1.00 | 12.52 |
| 9230 | SD | MET | C | 57 | -42.761 | -31.490 | -31.494 | 1.00 | 16.13 |
| 9231 | CE | MET | C | 57 | -41.557 | -32.632 | -30.857 | 1.00 | 16.25 |
| 9235 | C | MET | C | 57 | -42.777 | -27.721 | -35.163 | 1.00 | 10.82 |
| 9236 | O | MET | C | 57 | -43.803 | -28.043 | -35.754 | 1.00 | 11.20 |
| 9237 | N | GLY | C | 58 | -42.419 | -26.453 | -35.015 | 1.00 | 10.40 |
| 9239 | CA | GLY | C | 58 | -43.187 | -25.375 | -35.601 | 1.00 | 10.33 |
| 9242 | C | GLY | C | 58 | -44.387 | -24.942 | -34.779 | 1.00 | 10.39 |
| 9243 | O | GLY | C | 58 | -45.353 | -24.418 | -35.329 | 1.00 | 10.94 |
| 9244 | N | ALA | C | 59 | -44.338 | -25.188 | -33.477 | 1.00 | 10.05 |
| 9246 | CA | ALA | C | 59 | -45.376 | -24.706 | -32.575 | 1.00 | 10.08 |
| 9248 | CB | ALA | C | 59 | -45.350 | -25.477 | -31.268 | 1.00 | 10.26 |
| 9252 | C | ALA | C | 59 | -45.237 | -23.216 | -32.308 | 1.00 | 9.86 |
| 9253 | O | ALA | C | 59 | -44.166 | -22.628 | -32.497 | 1.00 | 9.56 |
| 9254 | N | HIS | C | 60 | -46.345 | -22.616 | -31.869 | 1.00 | 9.96 |
| 9256 | CA | HIS | C | 60 | -46.341 | -21.334 | -31.170 | 1.00 | 10.37 |

FIGURE 3 (cont.)

| A | B | C | D | E | F | G | H | I | J |
|---|---|---|---|---|---|---|---|---|---|
| 9258 | CB | HIS | C | 60 | -47.703 | -20.657 | -31.253 | 1.00 | 10.97 |
| 9261 | CG | HIS | C | 60 | -48.114 | -20.262 | -32.637 | 1.00 | 11.54 |
| 9262 | ND1 | HIS | C | 60 | -47.765 | -19.051 | -33.194 | 1.00 | 10.89 |
| 9264 | CE1 | HIS | C | 60 | -48.290 | -18.961 | -34.405 | 1.00 | 11.52 |
| 9266 | NE2 | HIS | C | 60 | -48.976 | -20.065 | -34.649 | 1.00 | 11.71 |
| 9268 | CD2 | HIS | C | 60 | -48.896 | -20.887 | -33.550 | 1.00 | 11.20 |
| 9270 | C | HIS | C | 60 | -46.059 | -21.635 | -29.714 | 1.00 | 10.75 |
| 9271 | O | HIS | C | 60 | -46.682 | -22.521 | -29.155 | 1.00 | 10.58 |
| 9272 | N | VAL | C | 61 | -45.124 | -20.912 | -29.103 | 1.00 | 10.62 |
| 9274 | CA | VAL | C | 61 | -44.782 | -21.152 | -27.698 | 1.00 | 11.59 |
| 9276 | CB | VAL | C | 61 | -43.422 | -21.872 | -27.536 | 1.00 | 12.02 |
| 9278 | CG1 | VAL | C | 61 | -43.413 | -23.172 | -28.306 | 1.00 | 13.77 |
| 9282 | CG2 | VAL | C | 61 | -42.272 | -20.992 | -27.965 | 1.00 | 13.73 |
| 9286 | C | VAL | C | 61 | -44.770 | -19.885 | -26.876 | 1.00 | 11.39 |
| 9287 | O | VAL | C | 61 | -44.349 | -18.826 | -27.350 | 1.00 | 11.45 |
| 9288 | N | VAL | C | 62 | -45.284 | -19.981 | -25.649 | 1.00 | 10.43 |
| 9290 | CA | VAL | C | 62 | -45.062 | -18.966 | -24.637 | 1.00 | 10.88 |
| 9292 | CB | VAL | C | 62 | -46.368 | -18.272 | -24.196 | 1.00 | 10.32 |
| 9294 | CG1 | VAL | C | 62 | -46.098 | -17.223 | -23.120 | 1.00 | 11.49 |
| 9298 | CG2 | VAL | C | 62 | -47.036 | -17.621 | -25.388 | 1.00 | 11.11 |
| 9302 | C | VAL | C | 62 | -44.403 | -19.667 | -23.466 | 1.00 | 10.82 |
| 9303 | O | VAL | C | 62 | -44.950 | -20.628 | -22.933 | 1.00 | 11.68 |
| 9304 | N | VAL | C | 63 | -43.232 | -19.172 | -23.088 | 1.00 | 10.56 |
| 9306 | CA | VAL | C | 63 | -42.441 | -19.746 | -22.010 | 1.00 | 10.42 |
| 9308 | CB | VAL | C | 63 | -40.979 | -20.024 | -22.441 | 1.00 | 10.74 |
| 9310 | CG1 | VAL | C | 63 | -40.297 | -18.787 | -23.008 | 1.00 | 10.69 |
| 9314 | CG2 | VAL | C | 63 | -40.962 | -21.154 | -23.448 | 1.00 | 11.36 |
| 9318 | C | VAL | C | 63 | -42.483 | -18.822 | -20.796 | 1.00 | 10.47 |
| 9319 | O | VAL | C | 63 | -42.628 | -17.607 | -20.922 | 1.00 | 10.36 |
| 9320 | N | THR | C | 64 | -42.387 | -19.408 | -19.609 | 1.00 | 9.23 |
| 9322 | CA | THR | C | 64 | -42.310 | -18.624 | -18.392 | 1.00 | 9.70 |
| 9324 | CB | THR | C | 64 | -43.726 | -18.332 | -17.835 | 1.00 | 9.90 |
| 9326 | OG1 | THR | C | 64 | -43.650 | -17.466 | -16.701 | 1.00 | 10.69 |
| 9328 | CG2 | THR | C | 64 | -44.431 | -19.590 | -17.362 | 1.00 | 10.15 |
| 9332 | C | THR | C | 64 | -41.394 | -19.291 | -17.381 | 1.00 | 9.61 |
| 9333 | O | THR | C | 64 | -41.122 | -20.492 | -17.464 | 1.00 | 10.11 |
| 9334 | N | ALA | C | 65 | -40.888 | -18.447 | -16.488 | 1.00 | 9.43 |
| 9336 | CA | ALA | C | 65 | -40.030 | -18.763 | -15.341 | 1.00 | 9.33 |
| 9338 | CB | ALA | C | 65 | -38.748 | -19.466 | -15.790 | 1.00 | 9.95 |
| 9342 | C | ALA | C | 65 | -39.741 | -17.386 | -14.705 | 1.00 | 9.61 |
| 9343 | O | ALA | C | 65 | -40.263 | -16.375 | -15.175 | 1.00 | 9.33 |
| 9344 | N | ARG | C | 66 | -38.920 | -17.327 | -13.662 | 1.00 | 9.34 |
| 9346 | CA | ARG | C | 66 | -38.539 | -16.032 | -13.093 | 1.00 | 9.67 |
| 9348 | CB | ARG | C | 66 | -38.040 | -16.192 | -11.667 | 1.00 | 9.72 |
| 9351 | CG | ARG | C | 66 | -39.074 | -16.779 | -10.709 | 1.00 | 10.29 |
| 9354 | CD | ARG | C | 66 | -38.483 | -17.237 | -9.401 | 1.00 | 11.04 |
| 9357 | NE | ARG | C | 66 | -37.459 | -18.247 | -9.633 | 1.00 | 12.29 |
| 9359 | CZ | ARG | C | 66 | -36.557 | -18.633 | -8.743 | 1.00 | 13.19 |
| 9360 | NH1 | ARG | C | 66 | -35.660 | -19.538 | -9.075 | 1.00 | 13.27 |

FIGURE 3 (cont.)

| A | B | C | D | E | F | G | H | I | J |
|---|---|---|---|---|---|---|---|---|---|
| 9363 | NH2 | ARG | C | 66 | -36.544 | -18.124 | -7.518 | 1.00 | 15.60 |
| 9366 | C | ARG | C | 66 | -37.468 | -15.298 | -13.909 | 1.00 | 10.07 |
| 9367 | O | ARG | C | 66 | -37.443 | -14.075 | -13.892 | 1.00 | 10.35 |
| 9368 | N | SER | C | 67 | -36.610 | -16.044 | -14.607 | 1.00 | 9.93 |
| 9370 | CA | SER | C | 67 | -35.374 | -15.502 | -15.179 | 1.00 | 10.92 |
| 9372 | CB | SER | C | 67 | -34.346 | -16.617 | -15.399 | 1.00 | 10.67 |
| 9375 | OG | SER | C | 67 | -33.928 | -17.196 | -14.174 | 1.00 | 12.25 |
| 9377 | C | SER | C | 67 | -35.615 | -14.776 | -16.497 | 1.00 | 11.10 |
| 9378 | O | SER | C | 67 | -35.568 | -15.383 | -17.557 | 1.00 | 11.90 |
| 9379 | N | LYS | C | 68 | -35.868 | -13.476 | -16.424 | 1.00 | 12.46 |
| 9381 | CA | LYS | C | 68 | -36.099 | -12.651 | -17.605 | 1.00 | 12.89 |
| 9383 | CB | LYS | C | 68 | -36.218 | -11.179 | -17.189 | 1.00 | 14.02 |
| 9386 | CG | LYS | C | 68 | -36.426 | -10.209 | -18.328 | 1.00 | 15.12 |
| 9389 | CD | LYS | C | 68 | -36.332 | -8.769 | -17.850 | 1.00 | 15.81 |
| 9392 | CE | LYS | C | 68 | -36.418 | -7.809 | -19.014 | 1.00 | 17.58 |
| 9395 | NZ | LYS | C | 68 | -36.115 | -6.399 | -18.628 | 1.00 | 18.58 |
| 9399 | C | LYS | C | 68 | -35.008 | -12.808 | -18.676 | 1.00 | 12.97 |
| 9400 | O | LYS | C | 68 | -35.310 | -13.064 | -19.844 | 1.00 | 12.95 |
| 9401 | N | GLU | C | 69 | -33.742 | -12.623 | -18.303 | 1.00 | 13.10 |
| 9403 | CA | GLU | C | 69 | -32.678 | -12.596 | -19.305 | 1.00 | 14.14 |
| 9405 | CB | GLU | C | 69 | -31.345 | -12.082 | -18.725 | 1.00 | 14.61 |
| 9408 | CG | BGLU | C | 69 | -30.505 | -11.331 | -19.756 | 0.35 | 15.94 |
| 9409 | CG | AGLU | C | 69 | -30.543 | -11.221 | -19.693 | 0.65 | 18.10 |
| 9414 | CD | BGLU | C | 69 | -29.297 | -10.613 | -19.182 | 0.35 | 15.79 |
| 9415 | CD | AGLU | C | 69 | -30.963 | -9.753 | -19.693 | 0.65 | 18.95 |
| 9416 | OE1 | BGLU | C | 69 | -28.161 | -11.066 | -19.436 | 0.35 | 14.97 |
| 9417 | OE1 | AGLU | C | 69 | -32.171 | -9.437 | -19.823 | 0.65 | 20.31 |
| 9418 | OE2 | BGLU | C | 69 | -29.481 | -9.582 | -18.503 | 0.35 | 17.12 |
| 9419 | OE2 | AGLU | C | 69 | -30.070 | -8.893 | -19.530 | 0.65 | 23.66 |
| 9420 | C | GLU | C | 69 | -32.500 | -13.963 | -19.974 | 1.00 | 13.34 |
| 9421 | O | GLU | C | 69 | -32.335 | -14.037 | -21.191 | 1.00 | 13.45 |
| 9422 | N | THR | C | 70 | -32.577 | -15.039 | -19.202 | 1.00 | 12.85 |
| 9424 | CA | THR | C | 70 | -32.444 | -16.376 | -19.782 | 1.00 | 12.93 |
| 9426 | CB | THR | C | 70 | -32.235 | -17.424 | -18.683 | 1.00 | 13.24 |
| 9428 | OG1 | THR | C | 70 | -30.969 | -17.178 | -18.039 | 1.00 | 15.98 |
| 9430 | CG2 | THR | C | 70 | -32.096 | -18.819 | -19.282 | 1.00 | 14.25 |
| 9434 | C | THR | C | 70 | -33.657 | -16.715 | -20.652 | 1.00 | 12.07 |
| 9435 | O | THR | C | 70 | -33.528 | -17.341 | -21.700 | 1.00 | 11.58 |
| 9436 | N | LEU | C | 71 | -34.836 | -16.286 | -20.231 | 1.00 | 11.41 |
| 9438 | CA | LEU | C | 71 | -36.038 | -16.509 | -21.030 | 1.00 | 11.28 |
| 9440 | CB | LEU | C | 71 | -37.290 | -16.022 | -20.299 | 1.00 | 11.13 |
| 9443 | CG | LEU | C | 71 | -37.771 | -16.938 | -19.175 | 1.00 | 11.58 |
| 9445 | CD1 | LEU | C | 71 | -38.785 | -16.187 | -18.345 | 1.00 | 11.73 |
| 9449 | CD2 | LEU | C | 71 | -38.351 | -18.254 | -19.679 | 1.00 | 11.28 |
| 9453 | C | LEU | C | 71 | -35.929 | -15.830 | -22.384 | 1.00 | 11.10 |
| 9454 | O | LEU | C | 71 | -36.337 | -16.392 | -23.383 | 1.00 | 11.02 |
| 9455 | N | GLN | C | 72 | -35.356 | -14.634 | -22.431 | 1.00 | 11.25 |
| 9457 | CA | GLN | C | 72 | -35.185 | -13.959 | -23.710 | 1.00 | 11.42 |
| 9459 | CB | GLN | C | 72 | -34.620 | -12.536 | -23.520 | 1.00 | 11.62 |

FIGURE 3 (cont.)

| A | B | C | D | E | F | G | H | I | J |
|---|---|---|---|---|---|---|---|---|---|
| 9462 | CG | GLN | C | 72 | -34.302 | -11.835 | -24.834 | 1.00 | 12.95 |
| 9465 | CD | GLN | C | 72 | -35.524 | -11.602 | -25.711 | 1.00 | 14.15 |
| 9466 | OE1 | GLN | C | 72 | -35.743 | -12.326 | -26.701 | 1.00 | 18.98 |
| 9467 | NE2 | GLN | C | 72 | -36.300 | -10.584 | -25.379 | 1.00 | 13.78 |
| 9470 | C | GLN | C | 72 | -34.277 | -14.783 | -24.618 | 1.00 | 11.45 |
| 9471 | O | GLN | C | 72 | -34.541 | -14.900 | -25.819 | 1.00 | 11.46 |
| 9472 | N | LYS | C | 73 | -33.213 | -15.364 | -24.059 | 1.00 | 11.62 |
| 9474 | CA | LYS | C | 73 | -32.305 | -16.195 | -24.843 | 1.00 | 12.27 |
| 9476 | CB | LYS | C | 73 | -31.047 | -16.542 | -24.050 | 1.00 | 12.53 |
| 9479 | CG | LYS | C | 73 | -30.197 | -15.326 | -23.702 | 1.00 | 15.49 |
| 9482 | CD | LYS | C | 73 | -29.023 | -15.740 | -22.829 | 1.00 | 19.38 |
| 9485 | CE | LYS | C | 73 | -28.051 | -14.607 | -22.591 | 1.00 | 21.70 |
| 9488 | NZ | LYS | C | 73 | -26.915 | -15.100 | -21.778 | 1.00 | 25.05 |
| 9492 | C | LYS | C | 73 | -33.013 | -17.458 | -25.336 | 1.00 | 11.58 |
| 9493 | O | LYS | C | 73 | -32.810 | -17.864 | -26.475 | 1.00 | 11.76 |
| 9494 | N | VAL | C | 74 | -33.875 | -18.045 | -24.501 | 1.00 | 11.32 |
| 9496 | CA | VAL | C | 74 | -34.642 | -19.223 | -24.899 | 1.00 | 10.74 |
| 9498 | CB | VAL | C | 74 | -35.436 | -19.812 | -23.696 | 1.00 | 10.92 |
| 9500 | CG1 | VAL | C | 74 | -36.476 | -20.831 | -24.134 | 1.00 | 10.72 |
| 9504 | CG2 | VAL | C | 74 | -34.488 | -20.432 | -22.699 | 1.00 | 10.97 |
| 9508 | C | VAL | C | 74 | -35.569 | -18.879 | -26.063 | 1.00 | 10.41 |
| 9509 | O | VAL | C | 74 | -35.632 | -19.614 | -27.045 | 1.00 | 10.95 |
| 9510 | N | VAL | C | 75 | -36.236 | -17.741 | -25.968 | 1.00 | 10.61 |
| 9512 | CA | VAL | C | 75 | -37.153 | -17.285 | -27.010 | 1.00 | 10.51 |
| 9514 | CB | VAL | C | 75 | -37.881 | -15.991 | -26.585 | 1.00 | 10.44 |
| 9516 | CG1 | VAL | C | 75 | -38.982 | -16.328 | -25.569 | 1.00 | 11.03 |
| 9520 | CG2 | VAL | C | 75 | -38.469 | -15.244 | -27.769 | 1.00 | 11.93 |
| 9524 | C | VAL | C | 75 | -36.407 | -17.086 | -28.325 | 1.00 | 10.54 |
| 9525 | O | VAL | C | 75 | -36.863 | -17.528 | -29.362 | 1.00 | 10.92 |
| 9526 | N | SER | C | 76 | -35.253 | -16.435 | -28.267 | 1.00 | 10.96 |
| 9528 | CA | SER | C | 76 | -34.495 | -16.165 | -29.475 | 1.00 | 11.67 |
| 9530 | CB | SER | C | 76 | -33.285 | -15.290 | -29.151 | 1.00 | 11.99 |
| 9533 | OG | SER | C | 76 | -33.754 | -13.994 | -28.794 | 1.00 | 14.79 |
| 9535 | C | SER | C | 76 | -34.077 | -17.455 | -30.151 | 1.00 | 11.70 |
| 9536 | O | SER | C | 76 | -34.151 | -17.567 | -31.372 | 1.00 | 12.66 |
| 9537 | N | HIS | C | 77 | -33.655 | -18.439 | -29.364 | 1.00 | 11.16 |
| 9539 | CA | HIS | C | 77 | -33.272 | -19.735 | -29.917 | 1.00 | 11.51 |
| 9541 | CB | HIS | C | 77 | -32.540 | -20.580 | -28.883 | 1.00 | 11.86 |
| 9544 | CG | HIS | C | 77 | -31.878 | -21.786 | -29.468 | 1.00 | 13.66 |
| 9545 | ND1 | HIS | C | 77 | -30.896 | -21.694 | -30.433 | 1.00 | 17.29 |
| 9547 | CE1 | HIS | C | 77 | -30.496 | -22.909 | -30.765 | 1.00 | 17.57 |
| 9549 | NE2 | HIS | C | 77 | -31.198 | -23.785 | -30.071 | 1.00 | 17.33 |
| 9551 | CD2 | HIS | C | 77 | -32.079 | -23.107 | -29.261 | 1.00 | 16.44 |
| 9553 | C | HIS | C | 77 | -34.482 | -20.489 | -30.501 | 1.00 | 11.30 |
| 9554 | O | HIS | C | 77 | -34.366 | -21.157 | -31.537 | 1.00 | 10.83 |
| 9555 | N | CYS | C | 78 | -35.636 | -20.391 | -29.837 | 1.00 | 11.00 |
| 9557 | CA | CYS | C | 78 | -36.873 | -20.999 | -30.342 | 1.00 | 11.06 |
| 9559 | CB | CYS | C | 78 | -38.040 | -20.744 | -29.385 | 1.00 | 10.77 |
| 9562 | SG | CYS | C | 78 | -38.031 | -21.772 | -27.904 | 1.00 | 11.67 |

FIGURE 3 (cont.)

| A | B | C | D | E | F | G | H | I | J |
|---|---|---|---|---|---|---|---|---|---|
| 9563 | C | CYS | C | 78 | -37.208 | -20.429 | -31.729 | 1.00 | 11.12 |
| 9564 | O | CYS | C | 78 | -37.577 | -21.167 | -32.638 | 1.00 | 10.85 |
| 9565 | N | LEU | C | 79 | -37.045 | -19.122 | -31.905 | 1.00 | 11.29 |
| 9567 | CA | LEU | C | 79 | -37.296 | -18.516 | -33.207 | 1.00 | 11.68 |
| 9569 | CB | LEU | C | 79 | -37.239 | -16.984 | -33.133 | 1.00 | 11.95 |
| 9572 | CG | LEU | C | 79 | -38.341 | -16.350 | -32.266 | 1.00 | 12.31 |
| 9574 | CD1 | LEU | C | 79 | -39.728 | -16.672 | -32.783 | 1.00 | 13.03 |
| 9578 | CD2 | LEU | C | 79 | -38.145 | -14.845 | -32.145 | 1.00 | 14.85 |
| 9582 | C | LEU | C | 79 | -36.306 | -19.067 | -34.247 | 1.00 | 12.25 |
| 9583 | O | LEU | C | 79 | -36.710 | -19.412 | -35.354 | 1.00 | 11.91 |
| 9584 | N | GLU | C | 80 | -35.027 | -19.187 | -33.878 | 1.00 | 12.83 |
| 9586 | CA | GLU | C | 80 | -34.002 | -19.730 | -34.783 | 1.00 | 13.65 |
| 9588 | CB | GLU | C | 80 | -32.614 | -19.729 | -34.112 | 1.00 | 14.43 |
| 9591 | CG | GLU | C | 80 | -32.013 | -18.372 | -33.770 | 1.00 | 19.06 |
| 9594 | CD | GLU | C | 80 | -30.662 | -18.500 | -33.065 | 1.00 | 23.60 |
| 9595 | OE1 | GLU | C | 80 | -30.443 | -19.482 | -32.307 | 1.00 | 27.14 |
| 9596 | OE2 | GLU | C | 80 | -29.804 | -17.611 | -33.260 | 1.00 | 27.59 |
| 9597 | C | GLU | C | 80 | -34.328 | -21.160 | -35.214 | 1.00 | 12.95 |
| 9598 | O | GLU | C | 80 | -34.103 | -21.551 | -36.368 | 1.00 | 13.12 |
| 9599 | N | LEU | C | 81 | -34.861 | -21.941 | -34.278 | 1.00 | 12.08 |
| 9601 | CA | LEU | C | 81 | -35.196 | -23.338 | -34.514 | 1.00 | 11.72 |
| 9603 | CB | LEU | C | 81 | -35.397 | -24.074 | -33.177 | 1.00 | 12.04 |
| 9606 | CG | LEU | C | 81 | -34.149 | -24.299 | -32.334 | 1.00 | 12.68 |
| 9608 | CD1 | LEU | C | 81 | -34.523 | -24.806 | -30.955 | 1.00 | 13.46 |
| 9612 | CD2 | LEU | C | 81 | -33.209 | -25.277 | -33.025 | 1.00 | 13.08 |
| 9616 | C | LEU | C | 81 | -36.441 | -23.546 | -35.371 | 1.00 | 11.61 |
| 9617 | O | LEU | C | 81 | -36.663 | -24.655 | -35.835 | 1.00 | 12.71 |
| 9618 | N | GLY | C | 82 | -37.245 | -22.497 | -35.557 | 1.00 | 11.32 |
| 9620 | CA | GLY | C | 82 | -38.409 | -22.544 | -36.424 | 1.00 | 11.36 |
| 9623 | C | GLY | C | 82 | -39.765 | -22.453 | -35.753 | 1.00 | 11.12 |
| 9624 | O | GLY | C | 82 | -40.774 | -22.818 | -36.371 | 1.00 | 10.81 |
| 9625 | N | ALA | C | 83 | -39.818 | -21.944 | -34.519 | 1.00 | 10.96 |
| 9627 | CA | ALA | C | 83 | -41.103 | -21.719 | -33.859 | 1.00 | 10.61 |
| 9629 | CB | ALA | C | 83 | -40.924 | -21.092 | -32.487 | 1.00 | 10.78 |
| 9633 | C | ALA | C | 83 | -41.982 | -20.835 | -34.721 | 1.00 | 10.78 |
| 9634 | O | ALA | C | 83 | -41.506 | -19.896 | -35.346 | 1.00 | 10.50 |
| 9635 | N | ALA | C | 84 | -43.263 | -21.172 | -34.790 | 1.00 | 10.06 |
| 9637 | CA | ALA | C | 84 | -44.223 | -20.308 | -35.468 | 1.00 | 10.19 |
| 9639 | CB | ALA | C | 84 | -45.597 | -20.904 | -35.412 | 1.00 | 10.24 |
| 9643 | C | ALA | C | 84 | -44.217 | -18.919 | -34.855 | 1.00 | 9.82 |
| 9644 | O | ALA | C | 84 | -44.379 | -17.920 | -35.559 | 1.00 | 10.50 |
| 9645 | N | SER | C | 85 | -44.076 | -18.891 | -33.530 | 1.00 | 10.08 |
| 9647 | CA | SER | C | 85 | -43.855 | -17.678 | -32.750 | 1.00 | 10.63 |
| 9649 | CB | SER | C | 85 | -45.127 | -16.846 | -32.601 | 1.00 | 11.36 |
| 9652 | OG | SER | C | 85 | -46.115 | -17.487 | -31.792 | 1.00 | 13.29 |
| 9654 | C | SER | C | 85 | -43.350 | -18.100 | -31.370 | 1.00 | 10.36 |
| 9655 | O | SER | C | 85 | -43.522 | -19.246 | -30.957 | 1.00 | 10.45 |
| 9656 | N | ALA | C | 86 | -42.710 | -17.174 | -30.678 | 1.00 | 10.36 |
| 9658 | CA | ALA | C | 86 | -42.191 | -17.445 | -29.341 | 1.00 | 10.21 |

FIGURE 3 (cont.)

| A | B | C | D | E | F | G | H | I | J |
|---|---|---|---|---|---|---|---|---|---|
| 9660 | CB | ALA | C | 86 | -40.825 | -18.087 | -29.410 | 1.00 | 10.25 |
| 9664 | C | ALA | C | 86 | -42.134 | -16.147 | -28.534 | 1.00 | 10.14 |
| 9665 | O | ALA | C | 86 | -41.638 | -15.136 | -29.009 | 1.00 | 9.59 |
| 9666 | N | HIS | C | 87 | -42.673 | -16.194 | -27.317 | 1.00 | 9.93 |
| 9668 | CA | HIS | C | 87 | -42.656 | -15.079 | -26.373 | 1.00 | 10.62 |
| 9670 | CB | HIS | C | 87 | -44.001 | -14.352 | -26.350 | 1.00 | 10.72 |
| 9673 | CG | HIS | C | 87 | -44.411 | -13.831 | -27.683 | 1.00 | 13.45 |
| 9674 | ND1 | HIS | C | 87 | -43.930 | -12.650 | -28.205 | 1.00 | 16.20 |
| 9676 | CE1 | HIS | C | 87 | -44.431 | -12.471 | -29.413 | 1.00 | 14.34 |
| 9678 | NE2 | HIS | C | 87 | -45.224 | -13.486 | -29.688 | 1.00 | 17.69 |
| 9680 | CD2 | HIS | C | 87 | -45.229 | -14.352 | -28.622 | 1.00 | 13.92 |
| 9682 | C | HIS | C | 87 | -42.390 | -15.627 | -24.982 | 1.00 | 10.03 |
| 9683 | O | HIS | C | 87 | -42.629 | -16.804 | -24.715 | 1.00 | 10.03 |
| 9684 | N | TYR | C | 88 | -41.875 | -14.767 | -24.115 | 1.00 | 10.50 |
| 9686 | CA | TYR | C | 88 | -41.756 | -15.081 | -22.699 | 1.00 | 10.47 |
| 9688 | CB | TYR | C | 88 | -40.287 | -15.144 | -22.243 | 1.00 | 10.56 |
| 9691 | CG | TYR | C | 88 | -39.648 | -13.793 | -22.020 | 1.00 | 10.93 |
| 9692 | CD1 | TYR | C | 88 | -39.806 | -13.116 | -20.815 | 1.00 | 12.28 |
| 9694 | CE1 | TYR | C | 88 | -39.242 | -11.861 | -20.618 | 1.00 | 13.12 |
| 9696 | CZ | TYR | C | 88 | -38.508 | -11.284 | -21.623 | 1.00 | 13.73 |
| 9697 | OH | TYR | C | 88 | -37.944 | -10.033 | -21.437 | 1.00 | 15.02 |
| 9699 | CE2 | TYR | C | 88 | -38.324 | -11.948 | -22.819 | 1.00 | 11.86 |
| 9701 | CD2 | TYR | C | 88 | -38.904 | -13.189 | -23.016 | 1.00 | 12.50 |
| 9703 | C | TYR | C | 88 | -42.518 | -14.074 | -21.872 | 1.00 | 10.92 |
| 9704 | O | TYR | C | 88 | -42.740 | -12.927 | -22.281 | 1.00 | 10.95 |
| 9705 | N | ILE | C | 89 | -42.908 | -14.526 | -20.687 | 1.00 | 10.32 |
| 9707 | CA | ILE | C | 89 | -43.421 | -13.662 | -19.633 | 1.00 | 11.13 |
| 9709 | CB | ILE | C | 89 | -44.951 | -13.786 | -19.529 | 1.00 | 11.03 |
| 9711 | CG1 | ILE | C | 89 | -45.632 | -13.369 | -20.845 | 1.00 | 12.20 |
| 9714 | CD1 | ILE | C | 89 | -47.114 | -13.657 | -20.893 | 1.00 | 13.25 |
| 9718 | CG2 | ILE | C | 89 | -45.468 | -12.927 | -18.386 | 1.00 | 11.68 |
| 9722 | C | ILE | C | 89 | -42.757 | -14.138 | -18.350 | 1.00 | 11.21 |
| 9723 | O | ILE | C | 89 | -42.842 | -15.311 | -18.011 | 1.00 | 11.66 |
| 9724 | N | ALA | C | 90 | -42.073 | -13.235 | -17.653 | 1.00 | 11.07 |
| 9726 | CA | ALA | C | 90 | -41.313 | -13.593 | -16.456 | 1.00 | 11.45 |
| 9728 | CB | ALA | C | 90 | -40.004 | -12.836 | -16.395 | 1.00 | 11.59 |
| 9732 | C | ALA | C | 90 | -42.135 | -13.312 | -15.217 | 1.00 | 11.90 |
| 9733 | O | ALA | C | 90 | -42.825 | -12.290 | -15.123 | 1.00 | 12.14 |
| 9734 | N | GLY | C | 91 | -42.059 | -14.226 | -14.263 | 1.00 | 11.45 |
| 9736 | CA | GLY | C | 91 | -42.694 | -14.025 | -12.977 | 1.00 | 11.43 |
| 9739 | C | GLY | C | 91 | -42.545 | -15.235 | -12.092 | 1.00 | 11.15 |
| 9740 | O | GLY | C | 91 | -42.062 | -16.293 | -12.521 | 1.00 | 11.42 |
| 9741 | N | THR | C | 92 | -42.950 | -15.074 | -10.839 | 1.00 | 10.96 |
| 9743 | CA | THR | C | 92 | -42.914 | -16.186 | -9.899 | 1.00 | 10.73 |
| 9745 | CB | THR | C | 92 | -42.310 | -15.787 | -8.540 | 1.00 | 11.32 |
| 9747 | OG1 | THR | C | 92 | -42.439 | -16.897 | -7.639 | 1.00 | 11.27 |
| 9749 | CG2 | THR | C | 92 | -43.089 | -14.648 | -7.878 | 1.00 | 12.24 |
| 9753 | C | THR | C | 92 | -44.295 | -16.788 | -9.710 | 1.00 | 10.61 |
| 9754 | O | THR | C | 92 | -45.278 | -16.082 | -9.522 | 1.00 | 10.35 |

FIGURE 3 (cont.)

| A | B | C | D | E | F | G | H | I | J |
|---|---|---|---|---|---|---|---|---|---|
| 9755 | N | MET | C | 93 | -44.341 | -18.116 | -9.747 | 1.00 | 10.55 |
| 9757 | CA | MET | C | 93 | -45.568 | -18.869 | -9.598 | 1.00 | 11.21 |
| 9759 | CB | MET | C | 93 | -45.447 | -20.230 | -10.301 | 1.00 | 10.93 |
| 9762 | CG | MET | C | 93 | -45.403 | -20.125 | -11.808 | 1.00 | 10.86 |
| 9765 | SD | MET | C | 93 | -46.979 | -19.547 | -12.465 | 1.00 | 12.03 |
| 9766 | CE | MET | C | 93 | -46.585 | -19.480 | -14.210 | 1.00 | 13.53 |
| 9770 | C | MET | C | 93 | -45.967 | -19.024 | -8.127 | 1.00 | 12.30 |
| 9771 | O | MET | C | 93 | -46.930 | -19.716 | -7.822 | 1.00 | 13.81 |
| 9772 | N | GLU | C | 94 | -45.228 | -18.372 | -7.237 | 1.00 | 12.60 |
| 9774 | CA | GLU | C | 94 | -45.681 | -18.142 | -5.855 | 1.00 | 13.42 |
| 9776 | CB | GLU | C | 94 | -44.561 | -17.541 | -4.993 | 1.00 | 14.22 |
| 9779 | CG | GLU | C | 94 | -43.221 | -18.264 | -4.964 | 1.00 | 17.38 |
| 9782 | CD | GLU | C | 94 | -42.097 | -17.360 | -4.450 | 1.00 | 21.80 |
| 9783 | OE1 | GLU | C | 94 | -41.471 | -16.601 | -5.245 | 1.00 | 22.26 |
| 9784 | OE2 | GLU | C | 94 | -41.854 | -17.393 | -3.222 | 1.00 | 25.46 |
| 9785 | C | GLU | C | 94 | -46.849 | -17.144 | -5.849 | 1.00 | 13.33 |
| 9786 | O | GLU | C | 94 | -47.639 | -17.106 | -4.912 | 1.00 | 14.06 |
| 9787 | N | ASP | C | 95 | -46.932 | -16.327 | -6.891 | 1.00 | 13.30 |
| 9789 | CA | ASP | C | 95 | -47.931 | -15.264 | -7.004 | 1.00 | 13.37 |
| 9791 | CB | ASP | C | 95 | -47.258 | -14.040 | -7.621 | 1.00 | 13.79 |
| 9794 | CG | ASP | C | 95 | -48.166 | -12.843 | -7.732 | 1.00 | 15.27 |
| 9795 | OD1 | ASP | C | 95 | -49.405 | -12.981 | -7.673 | 1.00 | 16.12 |
| 9796 | OD2 | ASP | C | 95 | -47.702 | -11.698 | -7.877 | 1.00 | 18.74 |
| 9797 | C | ASP | C | 95 | -49.099 | -15.764 | -7.850 | 1.00 | 13.24 |
| 9798 | O | ASP | C | 95 | -48.979 | -15.902 | -9.071 | 1.00 | 12.96 |
| 9799 | N | MET | C | 96 | -50.220 | -16.067 | -7.204 | 1.00 | 13.39 |
| 9801 | CA | MET | C | 96 | -51.362 | -16.660 | -7.910 | 1.00 | 13.65 |
| 9803 | CB | MET | C | 96 | -52.406 | -17.203 | -6.924 | 1.00 | 14.47 |
| 9806 | CG | MET | C | 96 | -51.901 | -18.298 | -5.979 | 1.00 | 15.32 |
| 9809 | SD | MET | C | 96 | -51.228 | -19.753 | -6.817 | 1.00 | 17.26 |
| 9810 | CE | MET | C | 96 | -49.705 | -20.017 | -5.948 | 1.00 | 16.93 |
| 9814 | C | MET | C | 96 | -52.009 | -15.661 | -8.881 | 1.00 | 13.50 |
| 9815 | O | MET | C | 96 | -52.616 | -16.058 | -9.876 | 1.00 | 13.25 |
| 9816 | N | THR | C | 97 | -51.907 | -14.369 | -8.593 | 1.00 | 13.11 |
| 9818 | CA | THR | C | 97 | -52.396 | -13.370 | -9.541 | 1.00 | 13.69 |
| 9820 | CB | THR | C | 97 | -52.387 | -11.981 | -8.926 | 1.00 | 14.13 |
| 9822 | OG1 | THR | C | 97 | -53.233 | -11.993 | -7.776 | 1.00 | 15.04 |
| 9824 | CG2 | THR | C | 97 | -53.020 | -10.965 | -9.874 | 1.00 | 15.45 |
| 9828 | C | THR | C | 97 | -51.558 | -13.395 | -10.801 | 1.00 | 13.08 |
| 9829 | O | THR | C | 97 | -52.093 | -13.319 | -11.903 | 1.00 | 13.47 |
| 9830 | N | PHE | C | 98 | -50.243 | -13.501 | -10.643 | 1.00 | 12.85 |
| 9832 | CA | PHE | C | 98 | -49.366 | -13.620 | -11.806 | 1.00 | 12.31 |
| 9834 | CB | PHE | C | 98 | -47.886 | -13.719 | -11.427 | 1.00 | 12.66 |
| 9837 | CG | PHE | C | 98 | -47.022 | -14.112 | -12.594 | 1.00 | 12.26 |
| 9838 | CD1 | PHE | C | 98 | -46.781 | -13.204 | -13.609 | 1.00 | 13.75 |
| 9840 | CE1 | PHE | C | 98 | -46.035 | -13.558 | -14.720 | 1.00 | 13.31 |
| 9842 | CZ | PHE | C | 98 | -45.540 | -14.841 | -14.838 | 1.00 | 13.65 |
| 9844 | CE2 | PHE | C | 98 | -45.787 | -15.767 | -13.842 | 1.00 | 12.88 |
| 9846 | CD2 | PHE | C | 98 | -46.537 | -15.399 | -12.723 | 1.00 | 14.35 |

FIGURE 3 (cont.)

| A | B | C | D | E | F | G | H | I | J |
|---|---|---|---|---|---|---|---|---|---|
| 9848 | C | PHE | C | 98 | -49.768 | -14.832 | -12.636 | 1.00 | 12.27 |
| 9849 | O | PHE | C | 98 | -49.851 | -14.755 | -13.857 | 1.00 | 12.04 |
| 9850 | N | ALA | C | 99 | -50.004 | -15.962 | -11.980 | 1.00 | 11.95 |
| 9852 | CA | ALA | C | 99 | -50.390 | -17.180 | -12.690 | 1.00 | 12.34 |
| 9854 | CB | ALA | C | 99 | -50.588 | -18.316 | -11.718 | 1.00 | 12.81 |
| 9858 | C | ALA | C | 99 | -51.640 | -16.966 | -13.547 | 1.00 | 12.68 |
| 9859 | O | ALA | C | 99 | -51.650 | -17.293 | -14.736 | 1.00 | 12.01 |
| 9860 | N | GLU | C | 100 | -52.682 | -16.394 | -12.946 | 1.00 | 13.19 |
| 9862 | CA | GLU | C | 100 | -53.921 | -16.063 | -13.656 | 1.00 | 14.53 |
| 9864 | CB | GLU | C | 100 | -54.874 | -15.307 | -12.737 | 1.00 | 15.69 |
| 9867 | CG | GLU | C | 100 | -55.456 | -16.092 | -11.593 | 1.00 | 19.04 |
| 9870 | CD | GLU | C | 100 | -56.334 | -15.220 | -10.702 | 1.00 | 23.74 |
| 9871 | OE1 | GLU | C | 100 | -57.237 | -15.772 | -10.055 | 1.00 | 27.43 |
| 9872 | OE2 | GLU | C | 100 | -56.119 | -13.980 | -10.640 | 1.00 | 27.05 |
| 9873 | C | GLU | C | 100 | -53.679 | -15.160 | -14.858 | 1.00 | 13.87 |
| 9874 | O | GLU | C | 100 | -54.128 | -15.445 | -15.982 | 1.00 | 14.88 |
| 9875 | N | GLN | C | 101 | -52.963 | -14.070 | -14.615 | 1.00 | 13.12 |
| 9877 | CA | GLN | C | 101 | -52.725 | -13.058 | -15.636 | 1.00 | 13.26 |
| 9879 | CB | GLN | C | 101 | -52.100 | -11.804 | -15.022 | 1.00 | 13.37 |
| 9882 | CG | GLN | C | 101 | -53.044 | -11.055 | -14.068 | 1.00 | 16.52 |
| 9885 | CD | GLN | C | 101 | -52.430 | -9.780 | -13.512 | 1.00 | 19.64 |
| 9886 | OE1 | GLN | C | 101 | -51.244 | -9.521 | -13.701 | 1.00 | 23.65 |
| 9887 | NE2 | GLN | C | 101 | -53.238 | -8.984 | -12.824 | 1.00 | 22.00 |
| 9890 | C | GLN | C | 101 | -51.833 | -13.595 | -16.748 | 1.00 | 12.72 |
| 9891 | O | GLN | C | 101 | -51.995 | -13.233 | -17.918 | 1.00 | 13.99 |
| 9892 | N | PHE | C | 102 | -50.905 | -14.474 | -16.387 | 1.00 | 11.29 |
| 9894 | CA | PHE | C | 102 | -49.990 | -15.077 | -17.344 | 1.00 | 10.48 |
| 9896 | CB | PHE | C | 102 | -49.000 | -16.013 | -16.631 | 1.00 | 10.52 |
| 9899 | CG | PHE | C | 102 | -48.303 | -16.931 | -17.562 | 1.00 | 10.45 |
| 9900 | CD1 | PHE | C | 102 | -47.356 | -16.433 | -18.424 | 1.00 | 9.23 |
| 9902 | CE1 | PHE | C | 102 | -46.735 | -17.262 | -19.353 | 1.00 | 11.22 |
| 9904 | CZ | PHE | C | 102 | -47.080 | -18.593 | -19.416 | 1.00 | 10.65 |
| 9906 | CE2 | PHE | C | 102 | -48.035 | -19.088 | -18.559 | 1.00 | 11.41 |
| 9908 | CD2 | PHE | C | 102 | -48.645 | -18.268 | -17.645 | 1.00 | 11.66 |
| 9910 | C | PHE | C | 102 | -50.744 | -15.854 | -18.412 | 1.00 | 10.11 |
| 9911 | O | PHE | C | 102 | -50.466 | -15.721 | -19.608 | 1.00 | 9.83 |
| 9912 | N | VAL | C | 103 | -51.688 | -16.682 | -17.995 | 1.00 | 10.41 |
| 9914 | CA | VAL | C | 103 | -52.415 | -17.509 | -18.952 | 1.00 | 10.86 |
| 9916 | CB | VAL | C | 103 | -53.333 | -18.534 | -18.243 | 1.00 | 10.82 |
| 9918 | CG1 | VAL | C | 103 | -54.222 | -19.259 | -19.238 | 1.00 | 12.10 |
| 9922 | CG2 | VAL | C | 103 | -52.492 | -19.540 | -17.473 | 1.00 | 11.88 |
| 9926 | C | VAL | C | 103 | -53.237 | -16.642 | -19.901 | 1.00 | 10.74 |
| 9927 | O | VAL | C | 103 | -53.276 | -16.906 | -21.103 | 1.00 | 10.87 |
| 9928 | N | ALA | C | 104 | -53.863 | -15.595 | -19.369 | 1.00 | 11.18 |
| 9930 | CA | ALA | C | 104 | -54.683 | -14.704 | -20.182 | 1.00 | 11.65 |
| 9932 | CB | ALA | C | 104 | -55.394 | -13.679 | -19.325 | 1.00 | 11.89 |
| 9936 | C | ALA | C | 104 | -53.810 | -14.025 | -21.227 | 1.00 | 11.62 |
| 9937 | O | ALA | C | 104 | -54.191 | -13.938 | -22.392 | 1.00 | 12.71 |
| 9938 | N | GLN | C | 105 | -52.629 | -13.574 | -20.823 | 1.00 | 11.78 |

FIGURE 3 (cont.)

| A | B | C | D | E | F | G | H | I | J |
|---|---|---|---|---|---|---|---|---|---|
| 9940 | CA | GLN | C | 105 | -51.735 | -12.903 | -21.774 | 1.00 | 11.48 |
| 9942 | CB | GLN | C | 105 | -50.637 | -12.130 | -21.054 | 1.00 | 11.87 |
| 9945 | CG | GLN | C | 105 | -49.714 | -11.329 | -21.976 | 1.00 | 13.85 |
| 9948 | CD | GLN | C | 105 | -50.388 | -10.160 | -22.707 | 1.00 | 16.20 |
| 9949 | OE1 | GLN | C | 105 | -51.535 | -9.790 | -22.432 | 1.00 | 17.95 |
| 9950 | NE2 | GLN | C | 105 | -49.653 | -9.569 | -23.634 | 1.00 | 19.10 |
| 9953 | C | GLN | C | 105 | -51.150 | -13.879 | -22.775 | 1.00 | 11.40 |
| 9954 | O | GLN | C | 105 | -51.061 | -13.562 | -23.957 | 1.00 | 11.34 |
| 9955 | N | ALA | C | 106 | -50.770 | -15.074 | -22.328 | 1.00 | 10.66 |
| 9957 | CA | ALA | C | 106 | -50.238 | -16.081 | -23.245 | 1.00 | 11.05 |
| 9959 | CB | ALA | C | 106 | -49.813 | -17.320 | -22.494 | 1.00 | 10.68 |
| 9963 | C | ALA | C | 106 | -51.264 | -16.434 | -24.325 | 1.00 | 10.96 |
| 9964 | O | ALA | C | 106 | -50.916 | -16.580 | -25.503 | 1.00 | 11.06 |
| 9965 | N | GLY | C | 107 | -52.527 | -16.541 | -23.927 | 1.00 | 11.32 |
| 9967 | CA | GLY | C | 107 | -53.619 | -16.825 | -24.842 | 1.00 | 11.85 |
| 9970 | C | GLY | C | 107 | -53.770 | -15.737 | -25.885 | 1.00 | 12.19 |
| 9971 | O | GLY | C | 107 | -54.005 | -16.027 | -27.057 | 1.00 | 12.87 |
| 9972 | N | LYS | C | 108 | -53.603 | -14.483 | -25.472 | 1.00 | 12.13 |
| 9974 | CA | LYS | C | 108 | -53.690 | -13.360 | -26.405 | 1.00 | 11.90 |
| 9976 | CB | LYS | C | 108 | -53.778 | -12.041 | -25.652 | 1.00 | 12.00 |
| 9979 | CG | LYS | C | 108 | -55.099 | -11.828 | -24.978 | 1.00 | 13.13 |
| 9982 | CD | LYS | C | 108 | -55.061 | -10.604 | -24.114 | 1.00 | 16.74 |
| 9985 | CE | LYS | C | 108 | -56.325 | -10.440 | -23.309 | 1.00 | 18.83 |
| 9988 | NZ | LYS | C | 108 | -56.137 | -9.316 | -22.351 | 1.00 | 20.85 |
| 9992 | C | LYS | C | 108 | -52.508 | -13.339 | -27.360 | 1.00 | 11.60 |
| 9993 | O | LYS | C | 108 | -52.648 | -12.965 | -28.535 | 1.00 | 11.38 |
| 9994 | N | LEU | C | 109 | -51.333 | -13.712 | -26.859 | 1.00 | 11.21 |
| 9996 | CA | LEU | C | 109 | -50.136 | -13.743 | -27.690 | 1.00 | 11.45 |
| 9998 | CB | LEU | C | 109 | -48.892 | -14.021 | -26.846 | 1.00 | 10.99 |
| 10001 | CG | LEU | C | 109 | -48.435 | -12.832 | -26.001 | 1.00 | 11.40 |
| 10003 | CD1 | LEU | C | 109 | -47.465 | -13.265 | -24.921 | 1.00 | 11.64 |
| 10007 | CD2 | LEU | C | 109 | -47.809 | -11.750 | -26.878 | 1.00 | 11.41 |
| 10011 | C | LEU | C | 109 | -50.232 | -14.771 | -28.805 | 1.00 | 11.60 |
| 10012 | O | LEU | C | 109 | -49.680 | -14.563 | -29.891 | 1.00 | 13.02 |
| 10013 | N | MET | C | 110 | -50.913 | -15.887 | -28.546 | 1.00 | 11.68 |
| 10015 | CA | MET | C | 110 | -51.011 | -16.982 | -29.514 | 1.00 | 11.43 |
| 10017 | CB | MET | C | 110 | -50.707 | -18.317 | -28.826 | 1.00 | 11.22 |
| 10020 | CG | MET | C | 110 | -49.320 | -18.358 | -28.203 | 1.00 | 11.11 |
| 10023 | SD | MET | C | 110 | -48.806 | -19.991 | -27.682 | 1.00 | 11.22 |
| 10024 | CE | MET | C | 110 | -49.733 | -20.156 | -26.217 | 1.00 | 11.83 |
| 10028 | C | MET | C | 110 | -52.367 | -17.092 | -30.216 | 1.00 | 11.79 |
| 10029 | O | MET | C | 110 | -52.489 | -17.833 | -31.195 | 1.00 | 12.14 |
| 10030 | N | GLY | C | 111 | -53.371 | -16.364 | -29.742 | 1.00 | 11.94 |
| 10032 | CA | GLY | C | 111 | -54.726 | -16.503 | -30.262 | 1.00 | 12.21 |
| 10035 | C | GLY | C | 111 | -55.390 | -17.812 | -29.890 | 1.00 | 12.63 |
| 10036 | O | GLY | C | 111 | -56.146 | -18.384 | -30.678 | 1.00 | 13.55 |
| 10037 | N | GLY | C | 112 | -55.132 | -18.275 | -28.674 | 1.00 | 11.86 |
| 10039 | CA | GLY | C | 112 | -55.694 | -19.522 | -28.193 | 1.00 | 11.30 |
| 10042 | C | GLY | C | 112 | -54.677 | -20.368 | -27.462 | 1.00 | 10.88 |

FIGURE 3 (cont.)

| A | B | C | D | E | F | G | H | I | J |
|---|---|---|---|---|---|---|---|---|---|
| 10043 | O | GLY | C | 112 | -53.559 | -19.938 | -27.206 | 1.00 | 10.98 |
| 10044 | N | LEU | C | 113 | -55.078 | -21.592 | -27.141 | 1.00 | 10.04 |
| 10046 | CA | LEU | C | 113 | -54.238 | -22.519 | -26.407 | 1.00 | 10.43 |
| 10048 | CB | LEU | C | 113 | -54.342 | -22.250 | -24.897 | 1.00 | 10.59 |
| 10051 | CG | LEU | C | 113 | -53.380 | -23.040 | -24.013 | 1.00 | 10.78 |
| 10053 | CD1 | LEU | C | 113 | -51.932 | -22.619 | -24.262 | 1.00 | 11.54 |
| 10057 | CD2 | LEU | C | 113 | -53.724 | -22.851 | -22.550 | 1.00 | 11.09 |
| 10061 | C | LEU | C | 113 | -54.647 | -23.956 | -26.700 | 1.00 | 10.54 |
| 10062 | O | LEU | C | 113 | -55.813 | -24.326 | -26.520 | 1.00 | 11.26 |
| 10063 | N | ASP | C | 114 | -53.680 | -24.756 | -27.147 | 1.00 | 10.61 |
| 10065 | CA | ASP | C | 114 | -53.872 | -26.176 | -27.405 | 1.00 | 10.85 |
| 10067 | CB | ASP | C | 114 | -53.228 | -26.563 | -28.736 | 1.00 | 10.89 |
| 10070 | CG | ASP | C | 114 | -53.853 | -25.860 | -29.906 | 1.00 | 12.73 |
| 10071 | OD1 | ASP | C | 114 | -55.052 | -26.117 | -30.193 | 1.00 | 15.70 |
| 10072 | OD2 | ASP | C | 114 | -53.218 | -25.053 | -30.618 | 1.00 | 12.90 |
| 10073 | C | ASP | C | 114 | -53.288 | -27.076 | -26.331 | 1.00 | 10.75 |
| 10074 | O | ASP | C | 114 | -53.790 | -28.164 | -26.118 | 1.00 | 11.16 |
| 10075 | N | MET | C | 115 | -52.213 | -26.643 | -25.679 | 1.00 | 10.45 |
| 10077 | CA | MET | C | 115 | -51.507 | -27.489 | -24.719 | 1.00 | 10.74 |
| 10079 | CB | MET | C | 115 | -50.417 | -28.305 | -25.402 | 1.00 | 11.23 |
| 10082 | CG | MET | C | 115 | -49.751 | -29.324 | -24.485 | 1.00 | 11.94 |
| 10085 | SD | MET | C | 115 | -48.491 | -30.360 | -25.284 | 1.00 | 15.8 |
| 10086 | CE | MET | C | 115 | -49.523 | -31.663 | -25.938 | 1.00 | 17.69 |
| 10090 | C | MET | C | 115 | -50.894 | -26.643 | -23.621 | 1.00 | 10.76 |
| 10091 | O | MET | C | 115 | -50.205 | -25.668 | -23.891 | 1.00 | 10.73 |
| 10092 | N | LEU | C | 116 | -51.123 | -27.059 | -22.386 | 1.00 | 10.32 |
| 10094 | CA | LEU | C | 116 | -50.601 | -26.400 | -21.211 | 1.00 | 10.64 |
| 10096 | CB | LEU | C | 116 | -51.751 | -26.087 | -20.268 | 1.00 | 10.39 |
| 10099 | CG | LEU | C | 116 | -51.387 | -25.485 | -18.926 | 1.00 | 11.20 |
| 10101 | CD1 | LEU | C | 116 | -50.827 | -24.088 | -19.093 | 1.00 | 11.89 |
| 10105 | CD2 | LEU | C | 116 | -52.607 | -25.480 | -18.048 | 1.00 | 11.84 |
| 10109 | C | LEU | C | 116 | -49.627 | -27.378 | -20.549 | 1.00 | 10.31 |
| 10110 | O | LEU | C | 116 | -50.043 | -28.406 | -20.018 | 1.00 | 11.38 |
| 10111 | N | ILE | C | 117 | -48.337 | -27.067 | -20.586 | 1.00 | 9.60 |
| 10113 | CA | ILE | C | 117 | -47.328 | -27.923 | -19.980 | 1.00 | 9.58 |
| 10115 | CB | ILE | C | 117 | -46.127 | -28.149 | -20.926 | 1.00 | 9.64 |
| 10117 | CG1 | ILE | C | 117 | -46.594 | -28.770 | -22.248 | 1.00 | 10.29 |
| 10120 | CD1 | ILE | C | 117 | -45.487 | -29.065 | -23.271 | 1.00 | 11.58 |
| 10124 | CG2 | ILE | C | 117 | -45.104 | -29.054 | -20.246 | 1.00 | 10.50 |
| 10128 | C | ILE | C | 117 | -46.871 | -27.285 | -18.681 | 1.00 | 9.81 |
| 10129 | O | ILE | C | 117 | -46.233 | -26.227 | -18.661 | 1.00 | 9.40 |
| 10130 | N | LEU | C | 118 | -47.254 | -27.933 | -17.586 | 1.00 | 9.04 |
| 10132 | CA | LEU | C | 118 | -46.979 | -27.482 | -16.242 | 1.00 | 9.06 |
| 10134 | CB | LEU | C | 118 | -48.214 | -27.724 | -15.382 | 1.00 | 9.37 |
| 10137 | CG | LEU | C | 118 | -49.481 | -27.078 | -15.926 | 1.00 | 10.39 |
| 10139 | CD1 | LEU | C | 118 | -50.675 | -27.486 | -15.098 | 1.00 | 11.51 |
| 10143 | CD2 | LEU | C | 118 | -49.352 | -25.555 | -15.952 | 1.00 | 11.76 |
| 10147 | C | LEU | C | 118 | -45.768 | -28.237 | -15.701 | 1.00 | 9.53 |
| 10148 | O | LEU | C | 118 | -45.832 | -29.428 | -15.442 | 1.00 | 9.57 |

FIGURE 3 (cont.)

| A | B | C | D | E | F | G | H | I | J |
|---|---|---|---|---|---|---|---|---|---|
| 10149 | N | ASN | C | 119 | -44.666 | -27.520 | -15.525 | 1.00 | 9.00 |
| 10151 | CA | ASN | C | 119 | -43.383 | -28.159 | -15.276 | 1.00 | 9.50 |
| 10153 | CB | ASN | C | 119 | -42.627 | -28.174 | -16.615 | 1.00 | 9.91 |
| 10156 | CG | ASN | C | 119 | -41.147 | -28.419 | -16.477 | 1.00 | 10.58 |
| 10157 | OD1 | ASN | C | 119 | -40.338 | -27.457 | -16.459 | 1.00 | 13.51 |
| 10158 | ND2 | ASN | C | 119 | -40.762 | -29.673 | -16.405 | 1.00 | 7.46 |
| 10161 | C | ASN | C | 119 | -42.559 | -27.535 | -14.141 | 1.00 | 9.42 |
| 10162 | O | ASN | C | 119 | -41.707 | -28.196 | -13.562 | 1.00 | 10.26 |
| 10163 | N | HIS | C | 120 | -42.788 | -26.263 | -13.826 | 1.00 | 9.55 |
| 10165 | CA | HIS | C | 120 | -42.003 | -25.586 | -12.805 | 1.00 | 9.10 |
| 10167 | CB | HIS | C | 120 | -42.412 | -24.123 | -12.710 | 1.00 | 9.31 |
| 10170 | CG | HIS | C | 120 | -43.833 | -23.919 | -12.303 | 1.00 | 10.66 |
| 10171 | ND1 | HIS | C | 120 | -44.863 | -23.853 | -13.213 | 1.00 | 11.17 |
| 10173 | CE1 | HIS | C | 120 | -45.999 | -23.655 | -12.569 | 1.00 | 11.17 |
| 10175 | NE2 | HIS | C | 120 | -45.747 | -23.617 | -11.272 | 1.00 | 10.80 |
| 10177 | CD2 | HIS | C | 120 | -44.401 | -23.797 | -11.079 | 1.00 | 10.69 |
| 10179 | C | HIS | C | 120 | -42.138 | -26.207 | -11.405 | 1.00 | 9.58 |
| 10180 | O | HIS | C | 120 | -43.158 | -26.804 | -11.056 | 1.00 | 9.29 |
| 10181 | N | ILE | C | 121 | -41.088 | -26.033 | -10.621 | 1.00 | 9.72 |
| 10183 | CA | ILE | C | 121 | -41.097 | -26.336 | -9.192 | 1.00 | 9.66 |
| 10185 | CB | ILE | C | 121 | -40.481 | -27.730 | -8.871 | 1.00 | 9.69 |
| 10187 | CG1 | ILE | C | 121 | -39.077 | -27.851 | -9.465 | 1.00 | 11.66 |
| 10190 | CD1 | ILE | C | 121 | -38.329 | -29.099 | -8.981 | 1.00 | 13.48 |
| 10194 | CG2 | ILE | C | 121 | -41.391 | -28.830 | -9.342 | 1.00 | 9.04 |
| 10198 | C | ILE | C | 121 | -40.301 | -25.279 | -8.465 | 1.00 | 10.04 |
| 10199 | O | ILE | C | 121 | -39.454 | -24.598 | -9.060 | 1.00 | 10.46 |
| 10200 | N | THR | C | 122 | -40.550 | -25.164 | -7.175 | 1.00 | 9.95 |
| 10202 | CA | THR | C | 122 | -39.726 | -24.308 | -6.330 | 1.00 | 11.42 |
| 10204 | CB | THR | C | 122 | -40.517 | -23.903 | -5.087 | 1.00 | 11.76 |
| 10206 | OG1 | THR | C | 122 | -39.838 | -22.832 | -4.412 | 1.00 | 11.76 |
| 10208 | CG2 | THR | C | 122 | -40.604 | -25.026 | -4.071 | 1.00 | 12.14 |
| 10212 | C | THR | C | 122 | -38.423 | -25.016 | -5.963 | 1.00 | 12.88 |
| 10213 | O | THR | C | 122 | -38.339 | -26.239 | -6.024 | 1.00 | 13.41 |
| 10214 | N | ASN | C | 123 | -37.407 | -24.248 | -5.571 | 1.00 | 14.51 |
| 10216 | CA | ASN | C | 123 | -36.109 | -24.828 | -5.234 | 1.00 | 16.88 |
| 10218 | CB | ASN | C | 123 | -35.170 | -23.770 | -4.665 | 1.00 | 17.35 |
| 10221 | CG | ASN | C | 123 | -33.804 | -24.335 | -4.328 | 1.00 | 21.50 |
| 10222 | OD1 | ASN | C | 123 | -33.467 | -24.518 | -3.161 | 1.00 | 27.20 |
| 10223 | ND2 | ASN | C | 123 | -33.022 | -24.649 | -5.358 | 1.00 | 26.81 |
| 10226 | C | ASN | C | 123 | -36.246 | -25.957 | -4.227 | 1.00 | 16.95 |
| 10227 | O | ASN | C | 123 | -36.828 | -25.777 | -3.174 | 1.00 | 16.58 |
| 10228 | N | THR | C | 124 | -35.690 | -27.111 | -4.587 | 1.00 | 18.02 |
| 10230 | CA | THR | C | 124 | -35.783 | -28.339 | -3.818 | 1.00 | 18.77 |
| 10232 | CB | THR | C | 124 | -36.777 | -29.282 | -4.513 | 1.00 | 19.02 |
| 10234 | OG1 | THR | C | 124 | -38.070 | -28.665 | -4.514 | 1.00 | 20.80 |
| 10236 | CG2 | THR | C | 124 | -36.965 | -30.563 | -3.727 | 1.00 | 18.30 |
| 10240 | C | THR | C | 124 | -34.404 | -28.988 | -3.780 | 1.00 | 19.65 |
| 10241 | O | THR | C | 124 | -33.784 | -29.168 | -4.827 | 1.00 | 20.22 |
| 10242 | N | SER | C | 125 | -33.924 | -29.297 | -2.582 | 1.00 | 19.97 |

FIGURE 3 (cont.)

| A | B | C | D | E | F | G | H | I | J |
|---|---|---|---|---|---|---|---|---|---|
| 10244 | CA | SER | C | 125 | -32.731 | -30.127 | -2.417 | 1.00 | 20.51 |
| 10246 | CB | SER | C | 125 | -31.539 | -29.260 | -2.003 | 1.00 | 20.74 |
| 10249 | OG | SER | C | 125 | -31.800 | -28.570 | -0.794 | 1.00 | 22.53 |
| 10251 | C | SER | C | 125 | -32.992 | -31.250 | -1.401 | 1.00 | 20.25 |
| 10252 | O | SER | C | 125 | -34.048 | -31.302 | -0.754 | 1.00 | 20.81 |
| 10253 | N | LEU | C | 126 | -32.039 | -32.165 | -1.273 | 1.00 | 19.17 |
| 10255 | CA | LEU | C | 126 | -32.186 | -33.295 | -0.366 | 1.00 | 18.81 |
| 10257 | CB | LEU | C | 126 | -31.322 | -34.470 | -0.829 | 1.00 | 18.81 |
| 10260 | CG | LEU | C | 126 | -31.601 | -34.931 | -2.265 | 1.00 | 19.10 |
| 10262 | CD1 | LEU | C | 126 | -30.680 | -36.082 | -2.646 | 1.00 | 20.60 |
| 10266 | CD2 | LEU | C | 126 | -33.052 | -35.336 | -2.424 | 1.00 | 19.16 |
| 10270 | C | LEU | C | 126 | -31.826 | -32.883 | 1.060 | 1.00 | 18.46 |
| 10271 | O | LEU | C | 126 | -30.671 | -32.562 | 1.349 | 1.00 | 18.15 |
| 10272 | N | ASN | C | 127 | -32.826 | -32.872 | 1.940 | 1.00 | 17.75 |
| 10274 | CA | ASN | C | 127 | -32.619 | -32.609 | 3.365 | 1.00 | 18.29 |
| 10276 | CB BASN | C | 127 | -32.658 | -31.100 | 3.652 | 0.35 | 18.44 |
| 10277 | CB AASN | C | 127 | -32.661 | -31.108 | 3.646 | 0.65 | 19.02 |
| 10282 | CG BASN | C | 127 | -31.963 | -30.268 | 2.578 | 0.35 | 18.55 |
| 10283 | CG AASN | C | 127 | -31.294 | -30.446 | 3.534 | 0.65 | 20.64 |
| 10284 | OD1BASN | C | 127 | -32.609 | -29.734 | 1.674 | 0.35 | 19.74 |
| 10285 | OD1AASN | C | 127 | -30.300 | -30.932 | 4.084 | 0.65 | 24.10 |
| 10286 | ND2BASN | C | 127 | -30.639 | -30.163 | 2.672 | 0.35 | 18.96 |
| 10287 | ND2AASN | C | 127 | -31.244 | -29.322 | 2.824 | 0.65 | 22.89 |
| 10292 | C | ASN | C | 127 | -33.688 | -33.311 | 4.191 | 1.00 | 18.03 |
| 10293 | O | ASN | C | 127 | -34.808 | -33.488 | 3.729 | 1.00 | 17.44 |
| 10294 | N | LEU | C | 128 | -33.358 | -33.681 | 5.422 | 1.00 | 18.13 |
| 10296 | CA | LEU | C | 128 | -34.354 | -34.195 | 6.349 | 1.00 | 18.63 |
| 10298 | CB | LEU | C | 128 | -33.708 | -34.668 | 7.650 | 1.00 | 19.11 |
| 10301 | CG | LEU | C | 128 | -32.840 | -35.931 | 7.596 | 1.00 | 19.91 |
| 10303 | CD1 | LEU | C | 128 | -31.916 | -36.009 | 8.796 | 1.00 | 20.83 |
| 10307 | CD2 | LEU | C | 128 | -33.698 | -37.177 | 7.532 | 1.00 | 20.96 |
| 10311 | C | LEU | C | 128 | -35.362 | -33.091 | 6.658 | 1.00 | 18.94 |
| 10312 | O | LEU | C | 128 | -35.025 | -31.901 | 6.631 | 1.00 | 19.50 |
| 10313 | N | PHE | C | 129 | -36.599 | -33.492 | 6.924 | 1.00 | 18.66 |
| 10315 | CA | PHE | C | 129 | -37.621 | -32.590 | 7.418 | 1.00 | 19.13 |
| 10317 | CB | PHE | C | 129 | -39.020 | -33.154 | 7.231 | 1.00 | 18.55 |
| 10320 | CG | PHE | C | 129 | -40.091 | -32.242 | 7.746 | 1.00 | 16.44 |
| 10321 | CD1 | PHE | C | 129 | -40.433 | -31.107 | 7.042 | 1.00 | 15.38 |
| 10323 | CE1 | PHE | C | 129 | -41.409 | -30.244 | 7.524 | 1.00 | 14.43 |
| 10325 | CZ | PHE | C | 129 | -42.031 | -30.511 | 8.710 | 1.00 | 14.56 |
| 10327 | CE2 | PHE | C | 129 | -41.698 | -31.641 | 9.430 | 1.00 | 15.64 |
| 10329 | CD2 | PHE | C | 129 | -40.720 | -32.492 | 8.954 | 1.00 | 16.18 |
| 10331 | C | PHE | C | 129 | -37.421 | -32.344 | 8.909 | 1.00 | 20.90 |
| 10332 | O | PHE | C | 129 | -37.716 | -33.215 | 9.745 | 1.00 | 21.20 |
| 10333 | N | HIS | C | 130 | -36.908 | -31.166 | 9.224 | 1.00 | 22.26 |
| 10335 | CA | HIS | C | 130 | -36.928 | -30.639 | 10.579 | 1.00 | 23.53 |
| 10337 | CB | HIS | C | 130 | -35.506 | -30.509 | 11.114 | 1.00 | 24.17 |
| 10340 | CG | HIS | C | 130 | -34.889 | -31.816 | 11.513 | 1.00 | 27.59 |
| 10341 | ND1 | HIS | C | 130 | -34.203 | -32.620 | 10.626 | 1.00 | 31.35 |

FIGURE 3 (cont.)

| A | B | C | D | E | F | G | H | I | J |
|---|---|---|---|---|---|---|---|---|---|
| 10343 | CE1 | HIS | C | 130 | -33.768 | -33.697 | 11.256 | 1.00 | 31.35 |
| 10345 | NE2 | HIS | C | 130 | -34.154 | -33.627 | 12.516 | 1.00 | 31.40 |
| 10347 | CD2 | HIS | C | 130 | -34.856 | -32.460 | 12.703 | 1.00 | 30.03 |
| 10349 | C | HIS | C | 130 | -37.641 | -29.286 | 10.619 | 1.00 | 23.20 |
| 10350 | O | HIS | C | 130 | -37.050 | -28.240 | 10.333 | 1.00 | 22.94 |
| 10351 | N | ASP | C | 131 | -38.927 | -29.336 | 10.942 | 1.00 | 22.72 |
| 10353 | CA | ASP | C | 131 | -39.711 | -28.173 | 11.365 | 1.00 | 23.04 |
| 10355 | CB | ASP | C | 131 | -39.154 | -27.584 | 12.700 | 1.00 | 23.56 |
| 10358 | CG | ASP | C | 131 | -38.313 | -26.297 | 12.535 | 1.00 | 25.77 |
| 10359 | OD1 | ASP | C | 131 | -37.727 | -26.031 | 11.457 | 1.00 | 30.38 |
| 10360 | OD2 | ASP | C | 131 | -38.157 | -25.480 | 13.476 | 1.00 | 29.41 |
| 10361 | C | ASP | C | 131 | -39.951 | -27.110 | 10.282 | 1.00 | 21.78 |
| 10362 | O | ASP | C | 131 | -40.475 | -26.042 | 10.576 | 1.00 | 22.74 |
| 10363 | N | ASP | C | 132 | -39.619 | -27.420 | 9.030 | 1.00 | 20.50 |
| 10365 | CA | ASP | C | 132 | -39.647 | -26.410 | 7.975 | 1.00 | 19.51 |
| 10367 | CB | ASP | C | 132 | -38.555 | -26.664 | 6.928 | 1.00 | 20.02 |
| 10370 | CG | ASP | C | 132 | -38.201 | -25.411 | 6.141 | 1.00 | 20.05 |
| 10371 | OD1 | ASP | C | 132 | -38.958 | -24.421 | 6.200 | 1.00 | 20.20 |
| 10372 | OD2 | ASP | C | 132 | -37.161 | -25.308 | 5.455 | 1.00 | 22.26 |
| 10373 | C | ASP | C | 132 | -41.022 | -26.306 | 7.320 | 1.00 | 18.47 |
| 10374 | O | ASP | C | 132 | -41.199 | -26.625 | 6.142 | 1.00 | 17.67 |
| 10375 | N | ILE | C | 133 | -41.982 | -25.809 | 8.090 | 1.00 | 17.52 |
| 10377 | CA | ILE | C | 133 | -43.346 | -25.639 | 7.611 | 1.00 | 17.21 |
| 10379 | CB | ILE | C | 133 | -44.276 | -25.219 | 8.770 | 1.00 | 17.52 |
| 10381 | CG1 | ILE | C | 133 | -44.299 | -26.306 | 9.862 | 1.00 | 19.82 |
| 10384 | CD1 | ILE | C | 133 | -44.714 | -25.806 | 11.232 | 1.00 | 22.45 |
| 10388 | CG2 | ILE | C | 133 | -45.690 | -24.974 | 8.274 | 1.00 | 17.69 |
| 10392 | C | ILE | C | 133 | -43.373 | -24.615 | 6.465 | 1.00 | 16.32 |
| 10393 | O | ILE | C | 133 | -44.190 | -24.713 | 5.562 | 1.00 | 15.00 |
| 10394 | N | HIS | C | 134 | -42.459 | -23.648 | 6.486 | 1.00 | 15.88 |
| 10396 | CA | HIS | C | 134 | -42.390 | -22.654 | 5.410 | 1.00 | 16.32 |
| 10398 | CB | BHIS | C | 134 | -41.380 | -21.548 | 5.745 | 0.35 | 16.05 |
| 10399 | CB | AHIS | C | 134 | -41.309 | -21.599 | 5.707 | 0.65 | 16.79 |
| 10404 | CG | BHIS | C | 134 | -41.828 | -20.645 | 6.858 | 0.35 | 16.23 |
| 10405 | CG | AHIS | C | 134 | -40.939 | -20.751 | 4.527 | 0.65 | 20.03 |
| 10406 | ND1 | BHIS | C | 134 | -43.111 | -20.660 | 7.362 | 0.35 | 16.25 |
| 10407 | ND1 | AHIS | C | 134 | -39.866 | -21.037 | 3.709 | 0.65 | 23.89 |
| 10410 | CE1 | BHIS | C | 134 | -43.214 | -19.768 | 8.331 | 0.35 | 16.83 |
| 10411 | CE1 | AHIS | C | 134 | -39.785 | -20.126 | 2.755 | 0.65 | 23.82 |
| 10414 | NE2 | BHIS | C | 134 | -42.046 | -19.169 | 8.471 | 0.35 | 16.98 |
| 10415 | NE2 | AHIS | C | 134 | -40.772 | -19.264 | 2.919 | 0.65 | 23.25 |
| 10418 | CD2 | BHIS | C | 134 | -41.162 | -19.699 | 7.562 | 0.35 | 16.68 |
| 10419 | CD2 | AHIS | C | 134 | -41.504 | -19.628 | 4.024 | 0.65 | 23.08 |
| 10422 | C | HIS | C | 134 | -42.103 | -23.318 | 4.059 | 1.00 | 15.27 |
| 10423 | O | HIS | C | 134 | -42.728 | -22.958 | 3.064 | 1.00 | 14.85 |
| 10424 | N | HIS | C | 135 | -41.178 | -24.280 | 4.024 | 1.00 | 14.87 |
| 10426 | CA | HIS | C | 135 | -40.857 | -25.012 | 2.789 | 1.00 | 14.49 |
| 10428 | CB | HIS | C | 135 | -39.597 | -25.879 | 2.944 | 1.00 | 15.13 |
| 10431 | CG | HIS | C | 135 | -39.206 | -26.589 | 1.685 | 1.00 | 15.71 |

FIGURE 3 (cont.)

| A | B | C | D | E | F | G | H | I | J |
|---|---|---|---|---|---|---|---|---|---|
| 10432 | ND1 | HIS | C | 135 | -39.121 | -27.961 | 1.582 | 1.00 | 18.56 |
| 10434 | CE1 | HIS | C | 135 | -38.769 | -28.286 | 0.350 | 1.00 | 17.75 |
| 10436 | NE2 | HIS | C | 135 | -38.621 | -27.175 | -0.347 | 1.00 | 18.30 |
| 10438 | CD2 | HIS | C | 135 | -38.887 | -26.103 | 0.464 | 1.00 | 15.10 |
| 10440 | C | HIS | C | 135 | -42.007 | -25.906 | 2.363 | 1.00 | 13.90 |
| 10441 | O | HIS | C | 135 | -42.263 | -26.077 | 1.172 | 1.00 | 13.64 |
| 10442 | N | VAL | C | 136 | -42.713 | -26.481 | 3.332 | 1.00 | 12.43 |
| 10444 | CA | VAL | C | 136 | -43.875 | -27.298 | 3.006 | 1.00 | 12.03 |
| 10446 | CB | VAL | C | 136 | -44.471 | -27.987 | 4.247 | 1.00 | 11.77 |
| 10448 | CG1 | VAL | C | 136 | -45.745 | -28.715 | 3.876 | 1.00 | 12.54 |
| 10452 | CG2 | VAL | C | 136 | -43.451 | -28.962 | 4.850 | 1.00 | 13.22 |
| 10456 | C | VAL | C | 136 | -44.931 | -26.433 | 2.336 | 1.00 | 11.72 |
| 10457 | O | VAL | C | 136 | -45.488 | -26.816 | 1.308 | 1.00 | 11.73 |
| 10458 | N | ARG | C | 137 | -45.188 | -25.261 | 2.903 | 1.00 | 11.52 |
| 10460 | CA | ARG | C | 137 | -46.192 | -24.363 | 2.355 | 1.00 | 11.78 |
| 10462 | CB | ARG | C | 137 | -46.445 | -23.178 | 3.284 | 1.00 | 12.53 |
| 10465 | CG | ARG | C | 137 | -47.480 | -22.226 | 2.726 | 1.00 | 16.74 |
| 10468 | CD | ARG | C | 137 | -47.687 | -20.990 | 3.554 | 1.00 | 22.35 |
| 10471 | NE | ARG | C | 137 | -48.901 | -21.068 | 4.356 | 1.00 | 27.23 |
| 10473 | CZ | ARG | C | 137 | -48.987 | -21.570 | 5.577 | 1.00 | 29.79 |
| 10474 | NH1 | ARG | C | 137 | -47.922 | -22.078 | 6.189 | 1.00 | 31.32 |
| 10477 | NH2 | ARG | C | 137 | -50.164 | -21.572 | 6.198 | 1.00 | 31.88 |
| 10480 | C | ARG | C | 137 | -45.785 | -23.855 | 0.980 | 1.00 | 11.68 |
| 10481 | O | ARG | C | 137 | -46.595 | -23.839 | 0.058 | 1.00 | 10.65 |
| 10482 | N | LYS | C | 138 | -44.521 | -23.470 | 0.838 | 1.00 | 11.55 |
| 10484 | CA | LYS | C | 138 | -44.048 | -22.911 | -0.428 | 1.00 | 12.05 |
| 10486 | CB | LYS | C | 138 | -42.644 | -22.303 | -0.283 | 1.00 | 12.70 |
| 10489 | CG | LYS | C | 138 | -42.201 | -21.476 | -1.495 | 1.00 | 15.14 |
| 10492 | CD | LYS | C | 138 | -40.767 | -21.047 | -1.340 | 1.00 | 19.51 |
| 10495 | CE | LYS | C | 138 | -40.347 | -20.072 | -2.422 | 1.00 | 21.97 |
| 10498 | NZ | LYS | C | 138 | -39.683 | -18.881 | -1.838 | 1.00 | 23.87 |
| 10502 | C | LYS | C | 138 | -44.083 | -23.972 | -1.516 | 1.00 | 11.56 |
| 10503 | O | LYS | C | 138 | -44.482 | -23.694 | -2.644 | 1.00 | 11.32 |
| 10504 | N | SER | C | 139 | -43.689 | -25.201 | -1.174 | 1.00 | 11.25 |
| 10506 | CA | SER | C | 139 | -43.748 | -26.306 | -2.119 | 1.00 | 10.87 |
| 10508 | CB | SER | C | 139 | -43.153 | -27.573 | -1.502 | 1.00 | 10.63 |
| 10511 | OG | SER | C | 139 | -41.777 | -27.404 | -1.226 | 1.00 | 13.04 |
| 10513 | C | SER | C | 139 | -45.194 | -26.570 | -2.552 | 1.00 | 11.08 |
| 10514 | O | SER | C | 139 | -45.474 | -26.757 | -3.732 | 1.00 | 11.24 |
| 10515 | N | MET | C | 140 | -46.119 | -26.553 | -1.603 | 1.00 | 11.24 |
| 10517 | CA | MET | C | 140 | -47.527 | -26.766 | -1.943 | 1.00 | 11.89 |
| 10519 | CB | MET | C | 140 | -48.388 | -26.910 | -0.696 | 1.00 | 12.74 |
| 10522 | CG | MET | C | 140 | -49.713 | -27.599 | -0.967 | 1.00 | 16.16 |
| 10525 | SD | MET | C | 140 | -49.542 | -29.206 | -1.819 | 1.00 | 21.15 |
| 10526 | CE | MET | C | 140 | -48.255 | -29.937 | -0.846 | 1.00 | 9.85 |
| 10530 | C | MET | C | 140 | -48.059 | -25.636 | -2.823 | 1.00 | 11.41 |
| 10531 | O | MET | C | 140 | -48.823 | -25.889 | -3.744 | 1.00 | 11.04 |
| 10532 | N | GLU | C | 141 | -47.638 | -24.395 | -2.574 | 1.00 | 10.66 |
| 10534 | CA | GLU | C | 141 | -48.147 | -23.255 | -3.340 | 1.00 | 11.39 |

FIGURE 3 (cont.)

| A | B | C | D | E | F | G | H | I | J |
|---|---|---|---|---|---|---|---|---|---|
| 10536 | CB | GLU | C | 141 | -47.757 | -21.937 | -2.671 | 1.00 | 12.34 |
| 10539 | CG | GLU | C | 141 | -48.496 | -21.654 | -1.374 | 1.00 | 16.25 |
| 10542 | CD | GLU | C | 141 | -49.861 | -21.009 | -1.558 | 1.00 | 21.15 |
| 10543 | OE1 | GLU | C | 141 | -50.738 | -21.270 | -0.709 | 1.00 | 26.97 |
| 10544 | OE2 | GLU | C | 141 | -50.062 | -20.225 | -2.517 | 1.00 | 25.27 |
| 10545 | C | GLU | C | 141 | -47.594 | -23.279 | -4.758 | 1.00 | 10.61 |
| 10546 | O | GLU | C | 141 | -48.354 | -23.180 | -5.717 | 1.00 | 10.81 |
| 10547 | N | VAL | C | 142 | -46.279 | -23.421 | -4.892 | 1.00 | 10.06 |
| 10549 | CA | VAL | C | 142 | -45.641 | -23.324 | -6.204 | 1.00 | 9.90 |
| 10551 | CB | VAL | C | 142 | -44.118 | -23.008 | -6.097 | 1.00 | 9.92 |
| 10553 | CG1 | VAL | C | 142 | -43.453 | -23.014 | -7.468 | 1.00 | 9.87 |
| 10557 | CG2 | VAL | C | 142 | -43.890 | -21.669 | -5.407 | 1.00 | 10.73 |
| 10561 | C | VAL | C | 142 | -45.848 | -24.600 | -7.017 | 1.00 | 10.12 |
| 10562 | O | VAL | C | 142 | -46.123 | -24.544 | -8.217 | 1.00 | 10.04 |
| 10563 | N | ASN | C | 143 | -45.646 | -25.753 | -6.381 | 1.00 | 9.30 |
| 10565 | CA | ASN | C | 143 | -45.619 | -27.016 | -7.110 | 1.00 | 9.26 |
| 10567 | CB | ASN | C | 143 | -44.850 | -28.094 | -6.344 | 1.00 | 8.54 |
| 10570 | CG | ASN | C | 143 | -43.393 | -27.748 | -6.073 | 1.00 | 9.98 |
| 10571 | OD1 | ASN | C | 143 | -42.867 | -26.710 | -6.491 | 1.00 | 9.50 |
| 10572 | ND2 | ASN | C | 143 | -42.739 | -28.626 | -5.308 | 1.00 | 11.56 |
| 10575 | C | ASN | C | 143 | -47.005 | -27.593 | -7.379 | 1.00 | 9.79 |
| 10576 | O | ASN | C | 143 | -47.178 | -28.405 | -8.299 | 1.00 | 10.10 |
| 10577 | N | PHE | C | 144 | -47.986 | -27.199 | -6.565 | 1.00 | 9.50 |
| 10579 | CA | PHE | C | 144 | -49.329 | -27.747 | -6.659 | 1.00 | 9.25 |
| 10581 | CB | PHE | C | 144 | -49.690 | -28.577 | -5.418 | 1.00 | 9.31 |
| 10584 | CG | PHE | C | 144 | -51.143 | -28.925 | -5.364 | 1.00 | 9.66 |
| 10585 | CD1 | PHE | C | 144 | -51.662 | -29.838 | -6.262 | 1.00 | 10.31 |
| 10587 | CE1 | PHE | C | 144 | -53.005 | -30.128 | -6.279 | 1.00 | 11.30 |
| 10589 | CZ | PHE | C | 144 | -53.853 | -29.510 | -5.370 | 1.00 | 11.77 |
| 10591 | CE2 | PHE | C | 144 | -53.340 | -28.600 | -4.470 | 1.00 | 10.72 |
| 10593 | CD2 | PHE | C | 144 | -52.001 | -28.298 | -4.474 | 1.00 | 11.84 |
| 10595 | C | PHE | C | 144 | -50.390 | -26.670 | -6.917 | 1.00 | 9.51 |
| 10596 | O | PHE | C | 144 | -51.059 | -26.705 | -7.939 | 1.00 | 9.70 |
| 10597 | N | LEU | C | 145 | -50.562 | -25.717 | -6.005 | 1.00 | 9.54 |
| 10599 | CA | LEU | C | 145 | -51.674 | -24.781 | -6.138 | 1.00 | 10.24 |
| 10601 | CB | LEU | C | 145 | -51.764 | -23.827 | -4.941 | 1.00 | 11.13 |
| 10604 | CG | LEU | C | 145 | -53.035 | -22.978 | -4.915 | 1.00 | 15.42 |
| 10606 | CD1 | LEU | C | 145 | -54.281 | -23.835 | -4.900 | 1.00 | 18.11 |
| 10610 | CD2 | LEU | C | 145 | -52.986 | -22.049 | -3.725 | 1.00 | 17.85 |
| 10614 | C | LEU | C | 145 | -51.573 | -23.969 | -7.422 | 1.00 | 9.65 |
| 10615 | O | LEU | C | 145 | -52.574 | -23.745 | -8.095 | 1.00 | 9.94 |
| 10616 | N | SER | C | 146 | -50.372 | -23.518 | -7.761 | 1.00 | 9.33 |
| 10618 | CA | SER | C | 146 | -50.209 | -22.741 | -8.995 | 1.00 | 9.53 |
| 10620 | CB | SER | C | 146 | -48.800 | -22.177 | -9.133 | 1.00 | 9.57 |
| 10623 | OG | SER | C | 146 | -47.884 | -23.177 | -9.512 | 1.00 | 9.52 |
| 10625 | C | SER | C | 146 | -50.604 | -23.538 | -10.240 | 1.00 | 9.49 |
| 10626 | O | SER | C | 146 | -51.140 | -22.967 | -11.183 | 1.00 | 9.66 |
| 10627 | N | TYR | C | 147 | -50.385 | -24.856 | -10.231 | 1.00 | 9.39 |
| 10629 | CA | TYR | C | 147 | -50.812 | -25.701 | -11.343 | 1.00 | 9.19 |

FIGURE 3 (cont.)

| A | B | C | D | E | F | G | H | I | J |
|---|---|---|---|---|---|---|---|---|---|
| 10631 | CB | TYR | C | 147 | -50.334 | -27.151 | -11.181 | 1.00 | 9.12 |
| 10634 | CG | TYR | C | 147 | -48.881 | -27.436 | -11.480 | 1.00 | 9.26 |
| 10635 | CD1 | TYR | C | 147 | -47.867 | -26.518 | -11.196 | 1.00 | 10.97 |
| 10637 | CE1 | TYR | C | 147 | -46.535 | -26.818 | -11.464 | 1.00 | 10.28 |
| 10639 | CZ | TYR | C | 147 | -46.206 | -28.051 | -12.024 | 1.00 | 9.77 |
| 10640 | OH | TYR | C | 147 | -44.890 | -28.382 | -12.294 | 1.00 | 10.98 |
| 10642 | CE2 | TYR | C | 147 | -47.199 | -28.962 | -12.304 | 1.00 | 10.13 |
| 10644 | CD2 | TYR | C | 147 | -48.514 | -28.655 | -12.035 | 1.00 | 9.75 |
| 10646 | C | TYR | C | 147 | -52.340 | -25.695 | -11.472 | 1.00 | 9.26 |
| 10647 | O | TYR | C | 147 | -52.872 | -25.682 | -12.578 | 1.00 | 9.37 |
| 10648 | N | VAL | C | 148 | -53.043 | -25.727 | -10.342 | 1.00 | 9.23 |
| 10650 | CA | VAL | C | 148 | -54.501 | -25.675 | -10.351 | 1.00 | 9.66 |
| 10652 | CB | VAL | C | 148 | -55.083 | -26.009 | -8.948 | 1.00 | 9.79 |
| 10654 | CG1 | VAL | C | 148 | -54.640 | -27.391 | -8.499 | 1.00 | 10.65 |
| 10658 | CG2 | VAL | C | 148 | -56.609 | -25.937 | -8.973 | 1.00 | 10.40 |
| 10662 | C | VAL | C | 148 | -54.994 | -24.314 | -10.861 | 1.00 | 9.64 |
| 10663 | O | VAL | C | 148 | -55.930 | -24.243 | -11.658 | 1.00 | 10.08 |
| 10664 | N | VAL | C | 149 | -54.359 | -23.238 | -10.411 | 1.00 | 9.45 |
| 10666 | CA | VAL | C | 149 | -54.740 | -21.891 | -10.817 | 1.00 | 9.55 |
| 10668 | CB | VAL | C | 149 | -53.965 | -20.833 | -10.011 | 1.00 | 9.47 |
| 10670 | CG1 | VAL | C | 149 | -54.120 | -19.443 | -10.612 | 1.00 | 10.83 |
| 10674 | CG2 | VAL | C | 149 | -54.420 | -20.861 | -8.543 | 1.00 | 9.60 |
| 10678 | C | VAL | C | 149 | -54.521 | -21.709 | -12.327 | 1.00 | 9.64 |
| 10679 | O | VAL | C | 149 | -55.368 | -21.146 | -13.029 | 1.00 | 9.66 |
| 10680 | N | LEU | C | 150 | -53.396 | -22.200 | -12.816 | 1.00 | 9.80 |
| 10682 | CA | LEU | C | 150 | -53.084 | -22.129 | -14.242 | 1.00 | 9.82 |
| 10684 | CB | LEU | C | 150 | -51.663 | -22.647 | -14.506 | 1.00 | 10.08 |
| 10687 | CG | LEU | C | 150 | -50.550 | -21.736 | -13.979 | 1.00 | 10.13 |
| 10689 | CD1 | LEU | C | 150 | -49.245 | -22.515 | -13.836 | 1.00 | 11.23 |
| 10693 | CD2 | LEU | C | 150 | -50.352 | -20.536 | -14.870 | 1.00 | 9.96 |
| 10697 | C | LEU | C | 150 | -54.116 | -22.918 | -15.059 | 1.00 | 10.66 |
| 10698 | O | LEU | C | 150 | -54.557 | -22.481 | -16.124 | 1.00 | 10.53 |
| 10699 | N | THR | C | 151 | -54.486 | -24.090 | -14.566 | 1.00 | 10.13 |
| 10701 | CA | THR | C | 151 | -55.443 | -24.950 | -15.243 | 1.00 | 10.89 |
| 10703 | CB | THR | C | 151 | -55.556 | -26.292 | -14.497 | 1.00 | 11.27 |
| 10705 | OG1 | THR | C | 151 | -54.338 | -27.031 | -14.658 | 1.00 | 11.70 |
| 10707 | CG2 | THR | C | 151 | -56.627 | -27.186 | -15.106 | 1.00 | 12.94 |
| 10711 | C | THR | C | 151 | -56.801 | -24.278 | -15.328 | 1.00 | 10.70 |
| 10712 | O | THR | C | 151 | -57.430 | -24.265 | -16.384 | 1.00 | 10.80 |
| 10713 | N | VAL | C | 152 | -57.265 | -23.720 | -14.211 | 1.00 | 10.58 |
| 10715 | CA | VAL | C | 152 | -58.558 | -23.039 | -14.192 | 1.00 | 11.10 |
| 10717 | CB | VAL | C | 152 | -58.908 | -22.559 | -12.775 | 1.00 | 11.01 |
| 10719 | CG1 | VAL | C | 152 | -60.053 | -21.560 | -12.796 | 1.00 | 11.13 |
| 10723 | CG2 | VAL | C | 152 | -59.258 | -23.745 | -11.888 | 1.00 | 12.30 |
| 10727 | C | VAL | C | 152 | -58.563 | -21.883 | -15.198 | 1.00 | 11.12 |
| 10728 | O | VAL | C | 152 | -59.536 | -21.705 | -15.945 | 1.00 | 11.53 |
| 10729 | N | ALA | C | 153 | -57.471 | -21.123 | -15.243 | 1.00 | 11.17 |
| 10731 | CA | ALA | C | 153 | -57.356 | -20.001 | -16.169 | 1.00 | 11.11 |
| 10733 | CB | ALA | C | 153 | -56.117 | -19.195 | -15.857 | 1.00 | 11.65 |

FIGURE 3 (cont.)

| A | B | C | D | E | F | G | H | I | J |
|---|---|---|---|---|---|---|---|---|---|
| 10737 | C | ALA | C | 153 | -57.312 | -20.454 | -17.639 | 1.00 | 11.26 |
| 10738 | O | ALA | C | 153 | -57.774 | -19.741 | -18.521 | 1.00 | 11.86 |
| 10739 | N | ALA | C | 154 | -56.748 | -21.631 | -17.882 | 1.00 | 10.68 |
| 10741 | CA | ALA | C | 154 | -56.537 | -22.143 | -19.234 | 1.00 | 10.86 |
| 10743 | CB | ALA | C | 154 | -55.318 | -23.041 | -19.246 | 1.00 | 11.09 |
| 10747 | C | ALA | C | 154 | -57.724 | -22.920 | -19.774 | 1.00 | 11.00 |
| 10748 | O | ALA | C | 154 | -57.841 | -23.112 | -20.979 | 1.00 | 10.98 |
| 10749 | N | LEU | C | 155 | -58.593 | -23.393 | -18.888 | 1.00 | 11.32 |
| 10751 | CA | LEU | C | 155 | -59.573 | -24.386 | -19.301 | 1.00 | 12.69 |
| 10753 | CB | LEU | C | 155 | -60.326 | -24.975 | -18.095 | 1.00 | 13.05 |
| 10756 | CG | LEU | C | 155 | -61.032 | -26.308 | -18.380 | 1.00 | 16.34 |
| 10758 | CD1 | LEU | C | 155 | -61.870 | -26.680 | -17.184 | 1.00 | 17.18 |
| 10762 | CD2 | LEU | C | 155 | -60.049 | -27.426 | -18.721 | 1.00 | 16.43 |
| 10766 | C | LEU | C | 155 | -60.537 | -23.890 | -20.389 | 1.00 | 12.29 |
| 10767 | O | LEU | C | 155 | -60.828 | -24.645 | -21.303 | 1.00 | 12.59 |
| 10768 | N | PRO | C | 156 | -61.040 | -22.660 | -20.325 | 1.00 | 12.60 |
| 10769 | CA | PRO | C | 156 | -61.903 | -22.175 | -21.413 | 1.00 | 12.23 |
| 10771 | CB | PRO | C | 156 | -62.179 | -20.722 | -21.029 | 1.00 | 12.07 |
| 10774 | CG | PRO | C | 156 | -62.097 | -20.743 | -19.525 | 1.00 | 12.49 |
| 10777 | CD | PRO | C | 156 | -60.948 | -21.681 | -19.233 | 1.00 | 12.50 |
| 10780 | C | PRO | C | 156 | -61.263 | -22.301 | -22.799 | 1.00 | 12.23 |
| 10781 | O | PRO | C | 156 | -61.921 | -22.804 | -23.708 | 1.00 | 12.31 |
| 10782 | N | MET | C | 157 | -60.007 | -21.886 | -22.934 | 1.00 | 11.80 |
| 10784 | CA | MET | C | 157 | -59.287 | -22.017 | -24.202 | 1.00 | 11.75 |
| 10786 | CB | MET | C | 157 | -57.948 | -21.281 | -24.164 | 1.00 | 11.83 |
| 10789 | CG | MET | C | 157 | -58.075 | -19.782 | -24.274 | 1.00 | 12.01 |
| 10792 | SD | MET | C | 157 | -56.503 | -18.933 | -24.344 | 1.00 | 13.15 |
| 10793 | CE | MET | C | 157 | -55.976 | -19.071 | -22.645 | 1.00 | 14.30 |
| 10797 | C | MET | C | 157 | -59.064 | -23.478 | -24.575 | 1.00 | 11.63 |
| 10798 | O | MET | C | 157 | -59.162 | -23.835 | -25.737 | 1.00 | 11.83 |
| 10799 | N | LEU | C | 158 | -58.726 | -24.319 | -23.600 | 1.00 | 11.15 |
| 10801 | CA | LEU | C | 158 | -58.465 | -25.732 | -23.884 | 1.00 | 11.34 |
| 10803 | CB | LEU | C | 158 | -57.804 | -26.427 | -22.691 | 1.00 | 11.54 |
| 10806 | CG | LEU | C | 158 | -56.426 | -25.914 | -22.286 | 1.00 | 11.46 |
| 10808 | CD1 | LEU | C | 158 | -56.052 | -26.464 | -20.916 | 1.00 | 12.53 |
| 10812 | CD2 | LEU | C | 158 | -55.394 | -26.290 | -23.352 | 1.00 | 10.93 |
| 10816 | C | LEU | C | 158 | -59.757 | -26.455 | -24.290 | 1.00 | 11.70 |
| 10817 | O | LEU | C | 158 | -59.732 | -27.348 | -25.126 | 1.00 | 11.73 |
| 10818 | N | LYS | C | 159 | -60.884 | -26.039 | -23.726 | 1.00 | 12.44 |
| 10820 | CA | LYS | C | 159 | -62.170 | -26.614 | -24.114 | 1.00 | 13.17 |
| 10822 | CB | LYS | C | 159 | -63.279 | -26.159 | -23.171 | 1.00 | 13.26 |
| 10825 | CG | LYS | C | 159 | -63.266 | -26.899 | -21.843 | 1.00 | 14.05 |
| 10828 | CD | LYS | C | 159 | -64.204 | -26.251 | -20.837 | 1.00 | 15.54 |
| 10831 | CE | LYS | C | 159 | -64.426 | -27.133 | -19.607 | 1.00 | 17.54 |
| 10834 | NZ | LYS | C | 159 | -65.087 | -26.391 | -18.494 | 1.00 | 19.85 |
| 10838 | C | LYS | C | 159 | -62.481 | -26.240 | -25.560 | 1.00 | 13.82 |
| 10839 | O | LYS | C | 159 | -62.982 | -27.073 | -26.324 | 1.00 | 13.83 |
| 10840 | N | GLN | C | 160 | -62.138 | -25.009 | -25.946 | 1.00 | 14.43 |
| 10842 | CA | GLN | C | 160 | -62.353 | -24.547 | -27.319 | 1.00 | 15.11 |

FIGURE 3 (cont.)

| A | B | C | D | E | F | G | H | I | J |
|---|---|---|---|---|---|---|---|---|---|
| 10844 | CB | GLN | C | 160 | -61.981 | -23.060 | -27.458 | 1.00 | 15.75 |
| 10847 | CG | GLN | C | 160 | -62.338 | -22.422 | -28.784 | 1.00 | 19.69 |
| 10850 | CD | GLN | C | 160 | -63.744 | -21.857 | -28.793 | 1.00 | 24.32 |
| 10851 | OE1 | GLN | C | 160 | -63.931 | -20.637 | -28.716 | 1.00 | 29.90 |
| 10852 | NE2 | GLN | C | 160 | -64.732 | -22.733 | -28.861 | 1.00 | 26.30 |
| 10855 | C | GLN | C | 160 | -61.560 | -25.373 | -28.331 | 1.00 | 14.82 |
| 10856 | O | GLN | C | 160 | -62.043 | -25.660 | -29.429 | 1.00 | 15.00 |
| 10857 | N | SER | C | 161 | -60.348 | -25.768 | -27.958 | 1.00 | 13.58 |
| 10859 | CA | SER | C | 161 | -59.432 | -26.442 | -28.871 | 1.00 | 13.34 |
| 10861 | CB | SER | C | 161 | -58.009 | -25.905 | -28.663 | 1.00 | 13.59 |
| 10864 | OG | SER | C | 161 | -57.547 | -26.233 | -27.369 | 1.00 | 14.26 |
| 10866 | C | SER | C | 161 | -59.405 | -27.955 | -28.701 | 1.00 | 13.20 |
| 10867 | O | SER | C | 161 | -58.660 | -28.636 | -29.404 | 1.00 | 12.81 |
| 10868 | N | ASN | C | 162 | -60.197 | -28.488 | -27.770 | 1.00 | 13.25 |
| 10870 | CA | ASN | C | 162 | -60.086 | -29.892 | -27.384 | 1.00 | 13.42 |
| 10872 | CB | ASN | C | 162 | -60.640 | -30.815 | -28.477 | 1.00 | 14.20 |
| 10875 | CG | ASN | C | 162 | -62.074 | -30.484 | -28.852 | 1.00 | 16.23 |
| 10876 | OD1 | ASN | C | 162 | -62.950 | -30.438 | -28.002 | 1.00 | 19.16 |
| 10877 | ND2 | ASN | C | 162 | -62.307 | -30.220 | -30.135 | 1.00 | 22.21 |
| 10880 | C | ASN | C | 162 | -58.636 | -30.244 | -27.061 | 1.00 | 12.44 |
| 10881 | O | ASN | C | 162 | -58.084 | -31.227 | -27.562 | 1.00 | 11.76 |
| 10882 | N | GLY | C | 163 | -58.034 | -29.409 | -26.216 | 1.00 | 11.67 |
| 10884 | CA | GLY | C | 163 | -56.622 | -29.446 | -25.933 | 1.00 | 11.43 |
| 10887 | C | GLY | C | 163 | -56.204 | -30.406 | -24.842 | 1.00 | 11.08 |
| 10888 | O | GLY | C | 163 | -56.880 | -31.401 | -24.557 | 1.00 | 10.37 |
| 10889 | N | SER | C | 164 | -55.060 | -30.098 | -24.245 | 1.00 | 10.76 |
| 10891 | CA | SER | C | 164 | -54.332 | -31.044 | -23.410 | 1.00 | 11.11 |
| 10893 | CB | BSER | C | 164 | -53.332 | -31.820 | -24.283 | 0.35 | 11.22 |
| 10894 | CB | ASER | C | 164 | -53.337 | -31.830 | -24.247 | 0.65 | 10.93 |
| 10899 | OG | BSER | C | 164 | -52.125 | -32.162 | -23.610 | 0.35 | 12.99 |
| 10900 | OG | ASER | C | 164 | -53.977 | -32.490 | -25.332 | 0.65 | 10.55 |
| 10903 | C | SER | C | 164 | -53.604 | -30.317 | -22.286 | 1.00 | 11.07 |
| 10904 | O | SER | C | 164 | -53.043 | -29.222 | -22.477 | 1.00 | 11.12 |
| 10905 | N | ILE | C | 165 | -53.614 | -30.940 | -21.116 | 1.00 | 11.02 |
| 10907 | CA | ILE | C | 165 | -52.832 | -30.510 | -19.971 | 1.00 | 10.80 |
| 10909 | CB | ILE | C | 165 | -53.726 | -30.350 | -18.743 | 1.00 | 11.30 |
| 10911 | CG1 | ILE | C | 165 | -54.849 | -29.336 | -19.019 | 1.00 | 11.60 |
| 10914 | CD1 | ILE | C | 165 | -55.933 | -29.326 | -17.987 | 1.00 | 13.37 |
| 10918 | CG2 | ILE | C | 165 | -52.896 | -29.949 | -17.519 | 1.00 | 12.80 |
| 10922 | C | ILE | C | 165 | -51.781 | -31.576 | -19.697 | 1.00 | 11.02 |
| 10923 | O | ILE | C | 165 | -52.106 | -32.749 | -19.615 | 1.00 | 11.76 |
| 10924 | N | VAL | C | 166 | -50.526 | -31.156 | -19.569 | 1.00 | 9.66 |
| 10926 | CA | VAL | C | 166 | -49.421 | -32.043 | -19.251 | 1.00 | 10.51 |
| 10928 | CB | VAL | C | 166 | -48.359 | -31.984 | -20.369 | 1.00 | 10.67 |
| 10930 | CG1 | VAL | C | 166 | -47.215 | -32.939 | -20.077 | 1.00 | 11.96 |
| 10934 | CG2 | VAL | C | 166 | -49.003 | -32.321 | -21.698 | 1.00 | 12.13 |
| 10938 | C | VAL | C | 166 | -48.854 | -31.608 | -17.901 | 1.00 | 10.66 |
| 10939 | O | VAL | C | 166 | -48.458 | -30.451 | -17.724 | 1.00 | 10.78 |
| 10940 | N | VAL | C | 167 | -48.838 | -32.530 | -16.947 | 1.00 | 10.45 |

FIGURE 3 (cont.)

| A | B | C | D | E | F | G | H | I | J |
|---|---|---|---|---|---|---|---|---|---|
| 10942 | CA | VAL | C | 167 | -48.376 | -32.259 | -15.601 | 1.00 | 10.11 |
| 10944 | CB | VAL | C | 167 | -49.436 | -32.668 | -14.570 | 1.00 | 10.54 |
| 10946 | CG1 | VAL | C | 167 | -48.916 | -32.462 | -13.150 | 1.00 | 11.06 |
| 10950 | CG2 | VAL | C | 167 | -50.727 | -31.894 | -14.819 | 1.00 | 10.24 |
| 10954 | C | VAL | C | 167 | -47.107 | -33.059 | -15.364 | 1.00 | 9.95 |
| 10955 | O | VAL | C | 167 | -47.121 | -34.284 | -15.419 | 1.00 | 11.18 |
| 10956 | N | VAL | C | 168 | -46.011 | -32.375 | -15.087 | 1.00 | 9.74 |
| 10958 | CA | VAL | C | 168 | -44.733 | -33.055 | -14.887 | 1.00 | 9.53 |
| 10960 | CB | VAL | C | 168 | -43.544 | -32.234 | -15.412 | 1.00 | 9.85 |
| 10962 | CG1 | VAL | C | 168 | -42.247 | -33.007 | -15.232 | 1.00 | 10.20 |
| 10966 | CG2 | VAL | C | 168 | -43.741 | -31.871 | -16.878 | 1.00 | 9.78 |
| 10970 | C | VAL | C | 168 | -44.576 | -33.420 | -13.408 | 1.00 | 10.22 |
| 10971 | O | VAL | C | 168 | -44.708 | -32.589 | -12.520 | 1.00 | 10.39 |
| 10972 | N | SER | C | 169 | -44.336 | -34.700 | -13.166 | 1.00 | 10.11 |
| 10974 | CA | SER | C | 169 | -44.179 | -35.238 | -11.824 | 1.00 | 10.92 |
| 10976 | CB | SER | C | 169 | -45.449 | -35.944 | -11.387 | 1.00 | 11.42 |
| 10979 | OG | SER | C | 169 | -45.409 | -36.251 | -10.001 | 1.00 | 11.77 |
| 10981 | C | SER | C | 169 | -42.967 | -36.159 | -11.789 | 1.00 | 10.65 |
| 10982 | O | SER | C | 169 | -42.052 | -36.010 | -12.586 | 1.00 | 11.33 |
| 10983 | N | SER | C | 170 | -42.969 | -37.134 | -10.897 | 1.00 | 10.80 |
| 10985 | CA | SER | C | 170 | -41.735 | -37.637 | -10.322 | 1.00 | 10.54 |
| 10987 | CB | SER | C | 170 | -41.365 | -36.729 | -9.155 | 1.00 | 11.04 |
| 10990 | OG | SER | C | 170 | -41.518 | -35.369 | -9.508 | 1.00 | 11.64 |
| 10992 | C | SER | C | 170 | -41.909 | -39.018 | -9.746 | 1.00 | 10.49 |
| 10993 | O | SER | C | 170 | -42.999 | -39.369 | -9.313 | 1.00 | 10.35 |
| 10994 | N | LEU | C | 171 | -40.828 | -39.790 | -9.684 | 1.00 | 9.63 |
| 10996 | CA | LEU | C | 171 | -40.871 | -41.033 | -8.913 | 1.00 | 9.86 |
| 10998 | CB | LEU | C | 171 | -39.511 | -41.726 | -8.867 | 1.00 | 9.95 |
| 11001 | CG | LEU | C | 171 | -39.010 | -42.313 | -10.185 | 1.00 | 10.79 |
| 11003 | CD1 | LEU | C | 171 | -39.924 | -43.383 | -10.703 | 1.00 | 12.00 |
| 11007 | CD2 | LEU | C | 171 | -37.609 | -42.864 | -10.006 | 1.00 | 10.79 |
| 11011 | C | LEU | C | 171 | -41.354 | -40.765 | -7.480 | 1.00 | 9.64 |
| 11012 | O | LEU | C | 171 | -42.133 | -41.540 | -6.936 | 1.00 | 10.13 |
| 11013 | N | ALA | C | 172 | -40.892 | -39.665 | -6.885 | 1.00 | 9.61 |
| 11015 | CA | ALA | C | 172 | -41.286 | -39.285 | -5.521 | 1.00 | 9.96 |
| 11017 | CB | ALA | C | 172 | -40.298 | -38.278 | -4.956 | 1.00 | 10.57 |
| 11021 | C | ALA | C | 172 | -42.732 | -38.740 | -5.445 | 1.00 | 9.81 |
| 11022 | O | ALA | C | 172 | -43.203 | -38.331 | -4.372 | 1.00 | 10.31 |
| 11023 | N | GLY | C | 173 | -43.429 | -38.746 | -6.580 | 1.00 | 10.12 |
| 11025 | CA | GLY | C | 173 | -44.848 | -38.454 | -6.648 | 1.00 | 10.07 |
| 11028 | C | GLY | C | 173 | -45.703 | -39.704 | -6.792 | 1.00 | 10.08 |
| 11029 | O | GLY | C | 173 | -46.924 | -39.602 | -6.924 | 1.00 | 10.02 |
| 11030 | N | LYS | C | 174 | -45.055 | -40.872 | -6.767 | 1.00 | 10.13 |
| 11032 | CA | LYS | C | 174 | -45.723 | -42.179 | -6.880 | 1.00 | 10.29 |
| 11034 | CB | LYS | C | 174 | -45.403 | -42.838 | -8.227 | 1.00 | 10.55 |
| 11037 | CG | LYS | C | 174 | -46.083 | -42.184 | -9.412 | 1.00 | 10.70 |
| 11040 | CD | LYS | C | 174 | -47.591 | -42.356 | -9.381 | 1.00 | 9.89 |
| 11043 | CE | LYS | C | 174 | -48.213 | -41.984 | -10.704 | 1.00 | 10.64 |
| 11046 | NZ | LYS | C | 174 | -49.689 | -42.236 | -10.689 | 1.00 | 10.05 |

FIGURE 3 (cont.)

| A | B | C | D | E | F | G | H | I | J |
|---|---|---|---|---|---|---|---|---|---|
| 11050 | C | LYS | C | 174 | -45.353 | -43.143 | -5.747 | 1.00 | 10.58 |
| 11051 | O | LYS | C | 174 | -46.158 | -44.004 | -5.371 | 1.00 | 11.41 |
| 11052 | N | VAL | C | 175 | -44.130 | -43.025 | -5.246 | 1.00 | 11.20 |
| 11054 | CA | VAL | C | 175 | -43.653 | -43.780 | -4.103 | 1.00 | 11.43 |
| 11056 | CB | VAL | C | 175 | -42.750 | -44.980 | -4.507 | 1.00 | 11.37 |
| 11058 | CG1 | VAL | C | 175 | -41.413 | -44.531 | -5.080 | 1.00 | 12.55 |
| 11062 | CG2 | VAL | C | 175 | -43.483 | -45.898 | -5.481 | 1.00 | 11.65 |
| 11066 | C | VAL | C | 175 | -42.903 | -42.838 | -3.163 | 1.00 | 11.93 |
| 11067 | O | VAL | C | 175 | -42.562 | -41.716 | -3.534 | 1.00 | 11.71 |
| 11068 | N | ALA | C | 176 | -42.671 | -43.302 | -1.944 | 1.00 | 11.71 |
| 11070 | CA | ALA | C | 176 | -42.078 | -42.471 | -0.901 | 1.00 | 12.00 |
| 11072 | CB | ALA | C | 176 | -42.707 | -42.808 | 0.454 | 1.00 | 12.06 |
| 11076 | C | ALA | C | 176 | -40.560 | -42.589 | -0.815 | 1.00 | 12.14 |
| 11077 | O | ALA | C | 176 | -39.989 | -43.687 | -0.876 | 1.00 | 13.06 |
| 11078 | N | TYR | C | 177 | -39.918 | -41.437 | -0.640 | 1.00 | 12.24 |
| 11080 | CA | TYR | C | 177 | -38.492 | -41.336 | -0.418 | 1.00 | 11.81 |
| 11082 | CB | TYR | C | 177 | -37.805 | -40.651 | -1.599 | 1.00 | 12.39 |
| 11085 | CG | TYR | C | 177 | -37.756 | -41.426 | -2.873 | 1.00 | 11.35 |
| 11086 | CD1 | TYR | C | 177 | -38.829 | -41.431 | -3.738 | 1.00 | 11.90 |
| 11088 | CE1 | TYR | C | 177 | -38.787 | -42.114 | -4.924 | 1.00 | 11.56 |
| 11090 | CZ | TYR | C | 177 | -37.645 | -42.808 | -5.264 | 1.00 | 11.78 |
| 11091 | OH | TYR | C | 177 | -37.602 | -43.470 | -6.450 | 1.00 | 13.49 |
| 11093 | CE2 | TYR | C | 177 | -36.551 | -42.812 | -4.437 | 1.00 | 11.67 |
| 11095 | CD2 | TYR | C | 177 | -36.609 | -42.117 | -3.239 | 1.00 | 11.55 |
| 11097 | C | TYR | C | 177 | -38.223 | -40.450 | 0.779 | 1.00 | 11.91 |
| 11098 | O | TYR | C | 177 | -38.912 | -39.451 | 0.955 | 1.00 | 12.34 |
| 11099 | N | PRO | C | 178 | -37.164 | -40.726 | 1.531 | 1.00 | 12.35 |
| 11100 | CA | PRO | C | 178 | -36.708 | -39.769 | 2.536 | 1.00 | 12.78 |
| 11102 | CB | PRO | C | 178 | -35.653 | -40.558 | 3.326 | 1.00 | 12.91 |
| 11105 | CG | PRO | C | 178 | -35.109 | -41.519 | 2.351 | 1.00 | 13.31 |
| 11108 | CD | PRO | C | 178 | -36.267 | -41.896 | 1.448 | 1.00 | 12.22 |
| 11111 | C | PRO | C | 178 | -36.069 | -38.581 | 1.831 | 1.00 | 12.83 |
| 11112 | O | PRO | C | 178 | -35.661 | -38.707 | 0.681 | 1.00 | 12.97 |
| 11113 | N | MET | C | 179 | -35.982 | -37.459 | 2.535 | 1.00 | 12.85 |
| 11115 | CA | MET | C | 179 | -35.233 | -36.265 | 2.122 | 1.00 | 13.13 |
| 11117 | CB | MET | C | 179 | -33.834 | -36.608 | 1.569 | 1.00 | 13.65 |
| 11120 | CG | MET | C | 179 | -33.048 | -37.602 | 2.398 | 1.00 | 16.60 |
| 11123 | SD | MET | C | 179 | -32.943 | -37.180 | 4.133 | 1.00 | 23.62 |
| 11124 | CE | MET | C | 179 | -31.984 | -38.595 | 4.760 | 1.00 | 24.08 |
| 11128 | C | MET | C | 179 | -35.955 | -35.344 | 1.140 | 1.00 | 12.42 |
| 11129 | O | MET | C | 179 | -35.417 | -34.298 | 0.780 | 1.00 | 12.54 |
| 11130 | N | VAL | C | 180 | -37.180 | -35.706 | 0.754 | 1.00 | 11.55 |
| 11132 | CA | VAL | C | 180 | -37.981 | -34.904 | -0.173 | 1.00 | 11.53 |
| 11134 | CB | VAL | C | 180 | -37.859 | -35.450 | -1.621 | 1.00 | 11.42 |
| 11136 | CG1 | VAL | C | 180 | -36.467 | -35.217 | -2.159 | 1.00 | 13.39 |
| 11140 | CG2 | VAL | C | 180 | -38.215 | -36.936 | -1.675 | 1.00 | 13.07 |
| 11144 | C | VAL | C | 180 | -39.449 | -34.851 | 0.284 | 1.00 | 11.28 |
| 11145 | O | VAL | C | 180 | -40.371 | -34.893 | -0.522 | 1.00 | 11.27 |
| 11146 | N | ALA | C | 181 | -39.663 | -34.742 | 1.589 | 1.00 | 10.97 |

FIGURE 3 (cont.)

| A | B | C | D | E | F | G | H | I | J |
|---|---|---|---|---|---|---|---|---|---|
| 11148 | CA | ALA | C | 181 | -41.022 | -34.858 | 2.131 | 1.00 | 10.45 |
| 11150 | CB | ALA | C | 181 | -41.005 | -34.829 | 3.650 | 1.00 | 10.76 |
| 11154 | C | ALA | C | 181 | -41.990 | -33.804 | 1.583 | 1.00 | 9.89 |
| 11155 | O | ALA | C | 181 | -43.087 | -34.140 | 1.154 | 1.00 | 10.31 |
| 11156 | N | ALA | C | 182 | -41.585 | -32.545 | 1.609 | 1.00 | 9.08 |
| 11158 | CA | ALA | C | 182 | -42.436 | -31.454 | 1.155 | 1.00 | 9.39 |
| 11160 | CB | ALA | C | 182 | -41.798 | -30.126 | 1.482 | 1.00 | 9.89 |
| 11164 | C | ALA | C | 182 | -42.714 | -31.553 | -0.340 | 1.00 | 9.11 |
| 11165 | O | ALA | C | 182 | -43.837 | -31.345 | -0.806 | 1.00 | 9.95 |
| 11166 | N | TYR | C | 183 | -41.680 | -31.873 | -1.104 | 1.00 | 9.19 |
| 11168 | CA | TYR | C | 183 | -41.821 | -32.048 | -2.526 | 1.00 | 8.92 |
| 11170 | CB | TYR | C | 183 | -40.437 | -32.315 | -3.093 | 1.00 | 8.98 |
| 11173 | CG | TYR | C | 183 | -40.351 | -32.700 | -4.541 | 1.00 | 9.20 |
| 11174 | CD1 | TYR | C | 183 | -40.212 | -31.731 | -5.529 | 1.00 | 8.55 |
| 11176 | CE1 | TYR | C | 183 | -40.089 | -32.084 | -6.851 | 1.00 | 9.04 |
| 11178 | CZ | TYR | C | 183 | -40.080 | -33.427 | -7.208 | 1.00 | 8.86 |
| 11179 | OH | TYR | C | 183 | -39.897 | -33.800 | -8.510 | 1.00 | 10.98 |
| 11181 | CE2 | TYR | C | 183 | -40.213 | -34.402 | -6.251 | 1.00 | 9.82 |
| 11183 | CD2 | TYR | C | 183 | -40.344 | -34.032 | -4.917 | 1.00 | 9.84 |
| 11185 | C | TYR | C | 183 | -42.759 | -33.197 | -2.844 | 1.00 | 8.97 |
| 11186 | O | TYR | C | 183 | -43.642 | -33.080 | -3.682 | 1.00 | 8.82 |
| 11187 | N | SER | C | 184 | -42.553 | -34.320 | -2.171 | 1.00 | 9.22 |
| 11189 | CA | SER | C | 184 | -43.375 | -35.498 | -2.397 | 1.00 | 9.36 |
| 11191 | CB | BSER | C | 184 | -42.914 | -36.652 | -1.517 | 0.35 | 9.51 |
| 11192 | CB | ASER | C | 184 | -42.869 | -36.647 | -1.517 | 0.65 | 9.80 |
| 11197 | OG | BSER | C | 184 | -41.639 | -37.084 | -1.922 | 0.35 | 10.14 |
| 11198 | OG | ASER | C | 184 | -43.608 | -37.836 | -1.728 | 0.65 | 12.37 |
| 11201 | C | SER | C | 184 | -44.838 | -35.189 | -2.107 | 1.00 | 9.21 |
| 11202 | O | SER | C | 184 | -45.715 | -35.583 | -2.859 | 1.00 | 9.01 |
| 11203 | N | ALA | C | 185 | -45.100 | -34.477 | -1.023 | 1.00 | 9.21 |
| 11205 | CA | ALA | C | 185 | -46.471 | -34.071 | -0.713 | 1.00 | 9.21 |
| 11207 | CB | ALA | C | 185 | -46.510 | -33.180 | 0.524 | 1.00 | 8.89 |
| 11211 | C | ALA | C | 185 | -47.108 | -33.353 | -1.894 | 1.00 | 9.11 |
| 11212 | O | ALA | C | 185 | -48.246 | -33.626 | -2.289 | 1.00 | 9.42 |
| 11213 | N | SER | C | 186 | -46.358 | -32.436 | -2.486 | 1.00 | 9.15 |
| 11215 | CA | SER | C | 186 | -46.883 | -31.635 | -3.570 | 1.00 | 9.23 |
| 11217 | CB | SER | C | 186 | -45.992 | -30.404 | -3.818 | 1.00 | 10.04 |
| 11220 | OG | SER | C | 186 | -44.786 | -30.733 | -4.452 | 1.00 | 10.67 |
| 11222 | C | SER | C | 186 | -47.108 | -32.452 | -4.835 | 1.00 | 8.44 |
| 11223 | O | SER | C | 186 | -48.066 | -32.220 | -5.537 | 1.00 | 8.67 |
| 11224 | N | LYS | C | 187 | -46.237 | -33.425 | -5.108 | 1.00 | 8.52 |
| 11226 | CA | LYS | C | 187 | -46.357 | -34.217 | -6.320 | 1.00 | 8.63 |
| 11228 | CB | LYS | C | 187 | -45.015 | -34.819 | -6.710 | 1.00 | 8.62 |
| 11231 | CG | LYS | C | 187 | -43.977 | -33.790 | -7.088 | 1.00 | 9.99 |
| 11234 | CD | LYS | C | 187 | -44.350 | -32.999 | -8.329 | 1.00 | 10.38 |
| 11237 | CE | LYS | C | 187 | -43.120 | -32.404 | -8.989 | 1.00 | 12.16 |
| 11240 | NZ | LYS | C | 187 | -43.432 | -31.591 | -10.202 | 1.00 | 10.43 |
| 11244 | C | LYS | C | 187 | -47.444 | -35.280 | -6.183 | 1.00 | 8.09 |
| 11245 | O | LYS | C | 187 | -48.162 | -35.546 | -7.137 | 1.00 | 8.21 |

FIGURE 3 (cont.)

| A | B | C | D | E | F | G | H | I | J |
|---|---|---|---|---|---|---|---|---|---|
| 11246 | N | PHE | C | 188 | -47.548 | -35.896 | -5.011 | 1.00 | 8.80 |
| 11248 | CA | PHE | C | 188 | -48.694 | -36.746 | -4.711 | 1.00 | 8.21 |
| 11250 | CB | PHE | C | 188 | -48.608 | -37.337 | -3.285 | 1.00 | 8.23 |
| 11253 | CG | PHE | C | 188 | -47.864 | -38.658 | -3.171 | 1.00 | 8.88 |
| 11254 | CD1 | PHE | C | 188 | -48.544 | -39.816 | -2.781 | 1.00 | 9.22 |
| 11256 | CE1 | PHE | C | 188 | -47.874 | -41.036 | -2.665 | 1.00 | 9.48 |
| 11258 | CZ | PHE | C | 188 | -46.518 | -41.100 | -2.883 | 1.00 | 10.66 |
| 11260 | CE2 | PHE | C | 188 | -45.822 | -39.960 | -3.242 | 1.00 | 9.38 |
| 11262 | CD2 | PHE | C | 188 | -46.491 | -38.742 | -3.383 | 1.00 | 8.92 |
| 11264 | C | PHE | C | 188 | -50.005 | -35.941 | -4.886 | 1.00 | 8.46 |
| 11265 | O | PHE | C | 188 | -50.969 | -36.432 | -5.470 | 1.00 | 7.98 |
| 11266 | N | ALA | C | 189 | -50.059 | -34.710 | -4.378 | 1.00 | 8.38 |
| 11268 | CA | ALA | C | 189 | -51.255 | -33.879 | -4.509 | 1.00 | 8.54 |
| 11270 | CB | ALA | C | 189 | -51.072 | -32.538 | -3.814 | 1.00 | 9.41 |
| 11274 | C | ALA | C | 189 | -51.661 | -33.680 | -5.966 | 1.00 | 8.74 |
| 11275 | O | ALA | C | 189 | -52.856 | -33.699 | -6.296 | 1.00 | 9.40 |
| 11276 | N | LEU | C | 190 | -50.678 | -33.473 | -6.840 | 1.00 | 8.78 |
| 11278 | CA | LEU | C | 190 | -50.961 | -33.356 | -8.261 | 1.00 | 8.89 |
| 11280 | CB | LEU | C | 190 | -49.687 | -33.103 | -9.059 | 1.00 | 8.62 |
| 11283 | CG | LEU | C | 190 | -49.028 | -31.740 | -8.902 | 1.00 | 9.75 |
| 11285 | CD1 | LEU | C | 190 | -47.653 | -31.762 | -9.583 | 1.00 | 9.93 |
| 11289 | CD2 | LEU | C | 190 | -49.888 | -30.632 | -9.466 | 1.00 | 9.62 |
| 11293 | C | LEU | C | 190 | -51.652 | -34.598 | -8.804 | 1.00 | 8.31 |
| 11294 | O | LEU | C | 190 | -52.555 | -34.492 | -9.604 | 1.00 | 8.80 |
| 11295 | N | ASP | C | 191 | -51.182 | -35.776 | -8.400 | 1.00 | 8.74 |
| 11297 | CA | ASP | C | 191 | -51.750 | -37.032 | -8.879 | 1.00 | 9.15 |
| 11299 | CB | ASP | C | 191 | -50.912 | -38.202 | -8.362 | 1.00 | 8.59 |
| 11302 | CG | ASP | C | 191 | -51.275 | -39.537 | -8.978 | 1.00 | 10.40 |
| 11303 | OD1 | ASP | C | 191 | -52.113 | -39.608 | -9.897 | 1.00 | 11.97 |
| 11304 | OD2 | ASP | C | 191 | -50.719 | -40.581 | -8.575 | 1.00 | 11.31 |
| 11305 | C | ASP | C | 191 | -53.185 | -37.115 | -8.428 | 1.00 | 9.63 |
| 11306 | O | ASP | C | 191 | -54.089 | -37.341 | -9.228 | 1.00 | 10.09 |
| 11307 | N | GLY | C | 192 | -53.420 | -36.890 | -7.137 | 1.00 | 9.36 |
| 11309 | CA | GLY | C | 192 | -54.774 | -36.925 | -6.626 | 1.00 | 10.23 |
| 11312 | C | GLY | C | 192 | -55.701 | -35.959 | -7.346 | 1.00 | 9.90 |
| 11313 | O | GLY | C | 192 | -56.786 | -36.335 | -7.787 | 1.00 | 10.69 |
| 11314 | N | PHE | C | 193 | -55.280 | -34.705 | -7.468 | 1.00 | 9.49 |
| 11316 | CA | PHE | C | 193 | -56.127 | -33.683 | -8.055 | 1.00 | 9.00 |
| 11318 | CB | PHE | C | 193 | -55.520 | -32.276 | -7.931 | 1.00 | 8.70 |
| 11321 | CG | PHE | C | 193 | -56.433 | -31.212 | -8.436 | 1.00 | 9.06 |
| 11322 | CD1 | PHE | C | 193 | -56.265 | -30.673 | -9.705 | 1.00 | 11.25 |
| 11324 | CE1 | PHE | C | 193 | -57.153 | -29.713 | -10.190 | 1.00 | 11.83 |
| 11326 | CZ | PHE | C | 193 | -58.207 | -29.296 | -9.409 | 1.00 | 11.61 |
| 11328 | CE2 | PHE | C | 193 | -58.403 | -29.834 | -8.152 | 1.00 | 11.48 |
| 11330 | CD2 | PHE | C | 193 | -57.521 | -30.802 | -7.670 | 1.00 | 11.03 |
| 11332 | C | PHE | C | 193 | -56.391 | -33.946 | -9.524 | 1.00 | 8.94 |
| 11333 | O | PHE | C | 193 | -57.528 | -33.995 | -9.962 | 1.00 | 9.05 |
| 11334 | N | PHE | C | 194 | -55.334 | -34.076 | -10.304 | 1.00 | 9.12 |
| 11336 | CA | PHE | C | 194 | -55.485 | -34.206 | -11.751 | 1.00 | 9.24 |

FIGURE 3 (cont.)

| A | B | C | D | E | F | G | H | I | J |
|---|---|---|---|---|---|---|---|---|---|
| 11338 | CB | PHE | C | 194 | -54.164 | -33.877 | -12.461 | 1.00 | 9.39 |
| 11341 | CG | PHE | C | 194 | -53.896 | -32.403 | -12.523 | 1.00 | 9.84 |
| 11342 | CD1 | PHE | C | 194 | -53.071 | -31.787 | -11.594 | 1.00 | 10.52 |
| 11344 | CE1 | PHE | C | 194 | -52.870 | -30.406 | -11.631 | 1.00 | 10.34 |
| 11346 | CZ | PHE | C | 194 | -53.486 | -29.649 | -12.617 | 1.00 | 11.68 |
| 11348 | CE2 | PHE | C | 194 | -54.317 | -30.257 | -13.538 | 1.00 | 10.85 |
| 11350 | CD2 | PHE | C | 194 | -54.528 | -31.621 | -13.477 | 1.00 | 10.84 |
| 11352 | C | PHE | C | 194 | -56.071 | -35.535 | -12.190 | 1.00 | 9.64 |
| 11353 | O | PHE | C | 194 | -56.743 | -35.603 | -13.223 | 1.00 | 9.99 |
| 11354 | N | SER | C | 195 | -55.832 | -36.592 | -11.420 | 1.00 | 9.87 |
| 11356 | CA | SER | C | 195 | -56.431 | -37.886 | -11.759 | 1.00 | 9.68 |
| 11358 | CB | SER | C | 195 | -55.732 | -39.037 | -11.053 | 1.00 | 10.48 |
| 11361 | OG | SER | C | 195 | -54.361 | -39.094 | -11.422 | 1.00 | 10.88 |
| 11363 | C | SER | C | 195 | -57.932 | -37.864 | -11.450 | 1.00 | 10.15 |
| 11364 | O | SER | C | 195 | -58.725 | -38.504 | -12.135 | 1.00 | 9.84 |
| 11365 | N | SER | C | 196 | -58.329 | -37.115 | -10.431 | 1.00 | 10.68 |
| 11367 | CA | SER | C | 196 | -59.753 | -36.937 | -10.129 | 1.00 | 11.00 |
| 11369 | CB | BSER | C | 196 | -59.922 | -36.276 | -8.763 | 0.35 | 11.16 |
| 11370 | CB | ASER | C | 196 | -59.951 | -36.264 | -8.760 | 0.65 | 10.98 |
| 11375 | OG | BSER | C | 196 | -59.388 | -37.109 | -7.755 | 0.35 | 13.05 |
| 11376 | OG | ASER | C | 196 | -61.329 | -35.968 | -8.526 | 0.65 | 10.88 |
| 11379 | C | SER | C | 196 | -60.453 | -36.129 | -11.210 | 1.00 | 11.18 |
| 11380 | O | SER | C | 196 | -61.511 | -36.538 | -11.711 | 1.00 | 10.91 |
| 11381 | N | ILE | C | 197 | -59.882 | -34.992 | -11.609 | 1.00 | 11.70 |
| 11383 | CA | ILE | C | 197 | -60.540 | -34.212 | -12.643 | 1.00 | 12.40 |
| 11385 | CB | BILE | C | 197 | -59.829 | -32.832 | -12.820 | 0.35 | 12.66 |
| 11386 | CB | AILE | C | 197 | -60.082 | -32.734 | -12.757 | 0.65 | 13.05 |
| 11389 | CG1 | BILE | C | 197 | -60.366 | -31.818 | -11.808 | 0.35 | 14.42 |
| 11390 | CG1 | AILE | C | 197 | -58.606 | -32.605 | -13.058 | 0.65 | 13.34 |
| 11395 | CD1 | BILE | C | 197 | -59.681 | -31.905 | -10.522 | 0.35 | 15.75 |
| 11396 | CD1 | AILE | C | 197 | -58.240 | -31.268 | -13.672 | 0.65 | 14.02 |
| 11403 | CG2 | BILE | C | 197 | -60.020 | -32.284 | -14.212 | 0.35 | 12.73 |
| 11404 | CG2 | AILE | C | 197 | -60.484 | -31.950 | -11.468 | 0.65 | 13.92 |
| 11411 | C | ILE | C | 197 | -60.532 | -34.980 | -13.972 | 1.00 | 11.80 |
| 11412 | O | ILE | C | 197 | -61.447 | -34.830 | -14.750 | 1.00 | 11.83 |
| 11413 | N | ARG | C | 198 | -59.539 | -35.834 | -14.210 | 1.00 | 11.75 |
| 11415 | CA | ARG | C | 198 | -59.571 | -36.668 | -15.414 | 1.00 | 11.78 |
| 11417 | CB | ARG | C | 198 | -58.309 | -37.541 | -15.544 | 1.00 | 11.81 |
| 11420 | CG | ARG | C | 198 | -58.173 | -38.177 | -16.916 | 1.00 | 12.68 |
| 11423 | CD | ARG | C | 198 | -57.122 | -39.245 | -17.006 | 1.00 | 13.32 |
| 11426 | NE | ARG | C | 198 | -55.764 | -38.721 | -16.913 | 1.00 | 13.11 |
| 11428 | CZ | ARG | C | 198 | -54.905 | -38.954 | -15.915 | 1.00 | 13.98 |
| 11429 | NH1 | ARG | C | 198 | -55.263 | -39.649 | -14.843 | 1.00 | 13.66 |
| 11432 | NH2 | ARG | C | 198 | -53.675 | -38.454 | -15.963 | 1.00 | 14.46 |
| 11435 | C | ARG | C | 198 | -60.838 | -37.529 | -15.420 | 1.00 | 12.00 |
| 11436 | O | ARG | C | 198 | -61.513 | -37.637 | -16.441 | 1.00 | 12.93 |
| 11437 | N | LYS | C | 199 | -61.159 | -38.127 | -14.280 | 1.00 | 11.67 |
| 11439 | CA | LYS | C | 199 | -62.376 | -38.940 | -14.169 | 1.00 | 12.09 |
| 11441 | CB | LYS | C | 199 | -62.518 | -39.591 | -12.788 | 1.00 | 11.99 |

FIGURE 3 (cont.)

| A | B | C | D | E | F | G | H | I | J |
|---|---|---|---|---|---|---|---|---|---|
| 11444 | CG | LYS | C | 199 | -61.418 | -40.532 | -12.345 | 1.00 | 14.00 |
| 11447 | CD | LYS | C | 199 | -61.115 | -41.620 | -13.316 | 1.00 | 14.50 |
| 11450 | CE | LYS | C | 199 | -60.216 | -42.660 | -12.662 | 1.00 | 14.92 |
| 11453 | NZ | LYS | C | 199 | -59.894 | -43.821 | -13.526 | 1.00 | 14.90 |
| 11457 | C | LYS | C | 199 | -63.610 | -38.064 | -14.423 | 1.00 | 12.29 |
| 11458 | O | LYS | C | 199 | -64.555 | -38.476 | -15.103 | 1.00 | 12.67 |
| 11459 | N | GLU | C | 200 | -63.606 | -36.856 | -13.873 | 1.00 | 12.47 |
| 11461 | CA | GLU | C | 200 | -64.723 | -35.928 | -14.059 | 1.00 | 13.12 |
| 11463 | CB | GLU | C | 200 | -64.537 | -34.670 | -13.214 | 1.00 | 13.30 |
| 11466 | CG | GLU | C | 200 | -64.588 | -34.948 | -11.724 | 1.00 | 14.11 |
| 11469 | CD | GLU | C | 200 | -64.475 | -33.707 | -10.865 | 1.00 | 13.83 |
| 11470 | OE1 | GLU | C | 200 | -64.379 | -33.867 | -9.635 | 1.00 | 15.72 |
| 11471 | OE2 | GLU | C | 200 | -64.507 | -32.575 | -11.398 | 1.00 | 14.40 |
| 11472 | C | GLU | C | 200 | -64.913 | -35.541 | -15.518 | 1.00 | 14.02 |
| 11473 | O | GLU | C | 200 | -66.040 | -35.456 | -15.993 | 1.00 | 13.78 |
| 11474 | N | TYR | C | 201 | -63.811 | -35.291 | -16.223 | 1.00 | 14.32 |
| 11476 | CA | TYR | C | 201 | -63.893 | -34.882 | -17.623 | 1.00 | 15.45 |
| 11478 | CB | TYR | C | 201 | -62.545 | -34.359 | -18.136 | 1.00 | 15.63 |
| 11481 | CG | TYR | C | 201 | -62.103 | -33.025 | -17.548 | 1.00 | 15.54 |
| 11482 | CD1 | TYR | C | 201 | -62.899 | -32.329 | -16.634 | 1.00 | 16.11 |
| 11484 | CE1 | TYR | C | 201 | -62.500 | -31.124 | -16.102 | 1.00 | 17.36 |
| 11486 | CZ | TYR | C | 201 | -61.287 | -30.587 | -16.467 | 1.00 | 17.96 |
| 11487 | OH | TYR | C | 201 | -60.896 | -29.390 | -15.910 | 1.00 | 21.51 |
| 11489 | CE2 | TYR | C | 201 | -60.465 | -31.252 | -17.367 | 1.00 | 17.82 |
| 11491 | CD2 | TYR | C | 201 | -60.881 | -32.465 | -17.903 | 1.00 | 17.27 |
| 11493 | C | TYR | C | 201 | -64.398 | -36.046 | -18.470 | 1.00 | 16.52 |
| 11494 | O | TYR | C | 201 | -65.107 | -35.831 | -19.450 | 1.00 | 16.68 |
| 11495 | N | SER | C | 202 | -64.069 | -37.278 | -18.082 | 1.00 | 17.99 |
| 11497 | CA | SER | C | 202 | -64.595 | -38.444 | -18.795 | 1.00 | 19.38 |
| 11499 | CB | BSER | C | 202 | -63.963 | -39.742 | -18.285 | 0.35 | 19.36 |
| 11500 | CB | ASER | C | 202 | -63.939 | -39.730 | -18.304 | 0.65 | 19.51 |
| 11505 | OG | BSER | C | 202 | -64.650 | -40.873 | -18.798 | 0.35 | 19.55 |
| 11506 | OG | ASER | C | 202 | -62.588 | -39.761 | -18.714 | 0.65 | 20.60 |
| 11509 | C | SER | C | 202 | -66.107 | -38.529 | -18.675 | 1.00 | 20.30 |
| 11510 | O | SER | C | 202 | -66.800 | -38.684 | -19.688 | 1.00 | 21.51 |
| 11511 | N | VAL | C | 203 | -66.631 | -38.410 | -17.457 | 1.00 | 21.13 |
| 11513 | CA | VAL | C | 203 | -68.080 | -38.534 | -17.247 | 1.00 | 21.71 |
| 11515 | CB | VAL | C | 203 | -68.447 | -38.819 | -15.762 | 1.00 | 21.98 |
| 11517 | CG1 | VAL | C | 203 | -67.726 | -40.053 | -15.260 | 1.00 | 23.19 |
| 11521 | CG2 | VAL | C | 203 | -68.150 | -37.632 | -14.862 | 1.00 | 22.59 |
| 11525 | C | VAL | C | 203 | -68.870 | -37.324 | -17.761 | 1.00 | 21.49 |
| 11526 | O | VAL | C | 203 | -70.019 | -37.462 | -18.182 | 1.00 | 21.51 |
| 11527 | N | SER | C | 204 | -68.260 | -36.142 | -17.748 | 1.00 | 21.18 |
| 11529 | CA | SER | C | 204 | -68.932 | -34.934 | -18.222 | 1.00 | 21.40 |
| 11531 | CB | SER | C | 204 | -68.566 | -33.733 | -17.344 | 1.00 | 21.60 |
| 11534 | OG | SER | C | 204 | -67.215 | -33.344 | -17.502 | 1.00 | 23.00 |
| 11536 | C | SER | C | 204 | -68.641 | -34.650 | -19.704 | 1.00 | 21.14 |
| 11537 | O | SER | C | 204 | -69.092 | -33.642 | -20.241 | 1.00 | 21.54 |
| 11538 | N | ARG | C | 205 | -67.902 | -35.550 | -20.354 | 1.00 | 20.92 |

FIGURE 3 (cont.)

| A | B | C | D | E | F | G | H | I | J |
|---|---|---|---|---|---|---|---|---|---|
| 11540 | CA | ARG | C | 205 | -67.552 | -35.430 | -21.774 | 1.00 | 21.11 |
| 11542 | CB | ARG | C | 205 | -68.787 | -35.675 | -22.649 | 1.00 | 21.64 |
| 11545 | CG | ARG | C | 205 | -69.402 | -37.042 | -22.437 | 1.00 | 24.83 |
| 11548 | CD | ARG | C | 205 | -68.577 | -38.204 | -22.999 | 1.00 | 28.80 |
| 11551 | NE | ARG | C | 205 | -68.857 | -38.461 | -24.415 | 1.00 | 32.01 |
| 11553 | CZ | ARG | C | 205 | -69.936 | -39.087 | -24.887 | 1.00 | 34.42 |
| 11554 | NH1 | ARG | C | 205 | -70.073 | -39.261 | -26.199 | 1.00 | 35.76 |
| 11557 | NH2 | ARG | C | 205 | -70.880 | -39.542 | -24.064 | 1.00 | 35.77 |
| 11560 | C | ARG | C | 205 | -66.849 | -34.113 | -22.133 | 1.00 | 20.20 |
| 11561 | O | ARG | C | 205 | -67.114 | -33.498 | -23.176 | 1.00 | 20.96 |
| 11562 | N | VAL | C | 206 | -65.947 | -33.686 | -21.250 | 1.00 | 18.39 |
| 11564 | CA | VAL | C | 206 | -65.039 | -32.579 | -21.517 | 1.00 | 17.38 |
| 11566 | CB | VAL | C | 206 | -64.593 | -31.899 | -20.213 | 1.00 | 17.01 |
| 11568 | CG1 | VAL | C | 206 | -63.527 | -30.848 | -20.473 | 1.00 | 16.97 |
| 11572 | CG2 | VAL | C | 206 | -65.788 | -31.280 | -19.488 | 1.00 | 17.54 |
| 11576 | C | VAL | C | 206 | -63.827 | -33.154 | -22.256 | 1.00 | 16.25 |
| 11577 | O | VAL | C | 206 | -63.126 | -34.018 | -21.733 | 1.00 | 15.77 |
| 11578 | N | ASN | C | 207 | -63.582 | -32.669 | -23.469 | 1.00 | 15.36 |
| 11580 | CA | ASN | C | 207 | -62.583 | -33.268 | -24.353 | 1.00 | 15.03 |
| 11582 | CB BASN | | C | 207 | -63.064 | -33.243 | -25.812 | 0.35 | 14.94 |
| 11583 | CB AASN | | C | 207 | -63.074 | -33.231 | -25.802 | 0.65 | 15.52 |
| 11588 | CG BASN | | C | 207 | -62.217 | -34.121 | -26.728 | 0.35 | 15.15 |
| 11589 | CG AASN | | C | 207 | -64.321 | -34.061 | -26.003 | 0.65 | 17.58 |
| 11590 | OD1BASN | | C | 207 | -61.505 | -35.016 | -26.272 | 0.35 | 15.96 |
| 11591 | OD1AASN | | C | 207 | -64.289 | -35.284 | -25.856 | 0.65 | 21.70 |
| 11592 | ND2BASN | | C | 207 | -62.284 | -33.853 | -28.028 | 0.35 | 15.46 |
| 11593 | ND2AASN | | C | 207 | -65.435 | -33.404 | -26.327 | 0.65 | 21.32 |
| 11598 | C | ASN | C | 207 | -61.213 | -32.590 | -24.213 | 1.00 | 13.96 |
| 11599 | O | ASN | C | 207 | -60.612 | -32.131 | -25.187 | 1.00 | 14.42 |
| 11600 | N | VAL | C | 208 | -60.743 | -32.553 | -22.971 | 1.00 | 12.84 |
| 11602 | CA | VAL | C | 208 | -59.425 | -32.053 | -22.602 | 1.00 | 12.45 |
| 11604 | CB | VAL | C | 208 | -59.520 | -30.840 | -21.656 | 1.00 | 12.09 |
| 11606 | CG1 | VAL | C | 208 | -58.139 | -30.397 | -21.200 | 1.00 | 12.54 |
| 11610 | CG2 | VAL | C | 208 | -60.273 | -29.675 | -22.338 | 1.00 | 12.27 |
| 11614 | C | VAL | C | 208 | -58.673 | -33.200 | -21.929 | 1.00 | 11.94 |
| 11615 | O | VAL | C | 208 | -59.130 | -33.761 | -20.907 | 1.00 | 12.96 |
| 11616 | N | SER | C | 209 | -57.547 | -33.581 | -22.517 | 1.00 | 11.04 |
| 11618 | CA | SER | C | 209 | -56.753 | -34.678 | -21.996 | 1.00 | 10.80 |
| 11620 | CB | SER | C | 209 | -55.973 | -35.349 | -23.123 | 1.00 | 10.79 |
| 11623 | OG | SER | C | 209 | -55.001 | -34.475 | -23.651 | 1.00 | 11.51 |
| 11625 | C | SER | C | 209 | -55.834 | -34.201 | -20.872 | 1.00 | 11.00 |
| 11626 | O | SER | C | 209 | -55.453 | -33.041 | -20.820 | 1.00 | 10.64 |
| 11627 | N | ILE | C | 210 | -55.508 | -35.123 | -19.966 | 1.00 | 10.67 |
| 11629 | CA | ILE | C | 210 | -54.622 | -34.874 | -18.840 | 1.00 | 10.64 |
| 11631 | CB | ILE | C | 210 | -55.406 | -34.842 | -17.510 | 1.00 | 10.99 |
| 11633 | CG1 | ILE | C | 210 | -56.335 | -33.633 | -17.515 | 1.00 | 12.38 |
| 11636 | CD1 | ILE | C | 210 | -57.320 | -33.597 | -16.371 | 1.00 | 14.25 |
| 11640 | CG2 | ILE | C | 210 | -54.444 | -34.779 | -16.318 | 1.00 | 12.39 |
| 11644 | C | ILE | C | 210 | -53.574 | -35.970 | -18.815 | 1.00 | 10.42 |

FIGURE 3 (cont.)

| A | B | C | D | E | F | G | H | I | J |
|---|---|---|---|---|---|---|---|---|---|
| 11645 | O | ILE | C | 210 | -53.893 | -37.147 | -18.690 | 1.00 | 10.52 |
| 11646 | N | THR | C | 211 | -52.318 | -35.563 | -18.932 | 1.00 | 10.85 |
| 11648 | CA | THR | C | 211 | -51.185 | -36.470 | -18.954 | 1.00 | 10.87 |
| 11650 | CB | THR | C | 211 | -50.371 | -36.267 | -20.245 | 1.00 | 11.03 |
| 11652 | OG1 | THR | C | 211 | -51.191 | -36.536 | -21.395 | 1.00 | 12.04 |
| 11654 | CG2 | THR | C | 211 | -49.237 | -37.257 | -20.322 | 1.00 | 12.58 |
| 11658 | C | THR | C | 211 | -50.301 | -36.180 | -17.743 | 1.00 | 11.25 |
| 11659 | O | THR | C | 211 | -49.804 | -35.062 | -17.600 | 1.00 | 11.86 |
| 11660 | N | LEU | C | 212 | -50.088 | -37.176 | -16.891 | 1.00 | 10.98 |
| 11662 | CA | LEU | C | 212 | -49.179 | -37.060 | -15.751 | 1.00 | 11.24 |
| 11664 | CB | LEU | C | 212 | -49.826 | -37.696 | -14.508 | 1.00 | 11.53 |
| 11667 | CG | LEU | C | 212 | -49.049 | -37.596 | -13.190 | 1.00 | 12.33 |
| 11669 | CD1 | LEU | C | 212 | -49.656 | -38.530 | -12.126 | 1.00 | 13.66 |
| 11673 | CD2 | LEU | C | 212 | -49.026 | -36.156 | -12.719 | 1.00 | 13.88 |
| 11677 | C | LEU | C | 212 | -47.870 | -37.777 | -16.092 | 1.00 | 11.11 |
| 11678 | O | LEU | C | 212 | -47.883 | -38.947 | -16.476 | 1.00 | 11.80 |
| 11679 | N | CYS | C | 213 | -46.745 | -37.089 | -15.943 | 1.00 | 11.36 |
| 11681 | CA | CYS | C | 213 | -45.438 | -37.642 | -16.285 | 1.00 | 12.04 |
| 11683 | CB | CYS | C | 213 | -44.654 | -36.647 | -17.128 | 1.00 | 12.06 |
| 11686 | SG | CYS | C | 213 | -45.567 | -36.107 | -18.590 | 1.00 | 15.58 |
| 11687 | C | CYS | C | 213 | -44.674 | -37.982 | -15.018 | 1.00 | 12.03 |
| 11688 | O | CYS | C | 213 | -44.601 | -37.180 | -14.102 | 1.00 | 13.42 |
| 11689 | N | VAL | C | 214 | -44.099 | -39.173 | -14.972 | 1.00 | 11.13 |
| 11691 | CA | VAL | C | 214 | -43.405 | -39.682 | -13.801 | 1.00 | 11.15 |
| 11693 | CB | VAL | C | 214 | -44.032 | -41.010 | -13.341 | 1.00 | 11.37 |
| 11695 | CG1 | VAL | C | 214 | -43.284 | -41.597 | -12.148 | 1.00 | 11.36 |
| 11699 | CG2 | VAL | C | 214 | -45.500 | -40.783 | -13.025 | 1.00 | 12.19 |
| 11703 | C | VAL | C | 214 | -41.941 | -39.887 | -14.190 | 1.00 | 11.10 |
| 11704 | O | VAL | C | 214 | -41.614 | -40.792 | -14.949 | 1.00 | 11.55 |
| 11705 | N | LEU | C | 215 | -41.072 | -39.026 | -13.673 | 1.00 | 11.10 |
| 11707 | CA | LEU | C | 215 | -39.668 | -38.979 | -14.094 | 1.00 | 10.76 |
| 11709 | CB | LEU | C | 215 | -39.277 | -37.532 | -14.413 | 1.00 | 11.03 |
| 11712 | CG | LEU | C | 215 | -40.113 | -36.777 | -15.444 | 1.00 | 11.45 |
| 11714 | CD1 | LEU | C | 215 | -39.478 | -35.401 | -15.705 | 1.00 | 11.15 |
| 11718 | CD2 | LEU | C | 215 | -40.293 | -37.563 | -16.715 | 1.00 | 13.08 |
| 11722 | C | LEU | C | 215 | -38.690 | -39.502 | -13.055 | 1.00 | 10.94 |
| 11723 | O | LEU | C | 215 | -38.762 | -39.144 | -11.870 | 1.00 | 10.54 |
| 11724 | N | GLY | C | 216 | -37.748 | -40.318 | -13.527 | 1.00 | 10.24 |
| 11726 | CA | GLY | C | 216 | -36.578 | -40.690 | -12.761 | 1.00 | 10.40 |
| 11729 | C | GLY | C | 216 | -35.527 | -39.597 | -12.799 | 1.00 | 10.80 |
| 11730 | O | GLY | C | 216 | -35.834 | -38.443 | -13.054 | 1.00 | 10.94 |
| 11731 | N | LEU | C | 217 | -34.279 | -39.970 | -12.549 | 1.00 | 10.40 |
| 11733 | CA | LEU | C | 217 | -33.170 | -39.017 | -12.544 | 1.00 | 10.31 |
| 11735 | CB | LEU | C | 217 | -31.925 | -39.654 | -11.939 | 1.00 | 10.26 |
| 11738 | CG | LEU | C | 217 | -30.696 | -38.742 | -11.917 | 1.00 | 11.04 |
| 11740 | CD1 | LEU | C | 217 | -30.907 | -37.484 | -11.083 | 1.00 | 11.91 |
| 11744 | CD2 | LEU | C | 217 | -29.505 | -39.511 | -11.389 | 1.00 | 11.15 |
| 11748 | C | LEU | C | 217 | -32.864 | -38.525 | -13.950 | 1.00 | 10.26 |
| 11749 | O | LEU | C | 217 | -32.544 | -39.316 | -14.836 | 1.00 | 10.40 |

FIGURE 3 (cont.)

| A | B | C | D | E | F | G | H | I | J |
|---|---|---|---|---|---|---|---|---|---|
| 11750 | N | ILE | C | 218 | -32.992 | -37.211 | -14.139 | 1.00 | 10.47 |
| 11752 | CA | ILE | C | 218 | -32.748 | -36.545 | -15.410 | 1.00 | 10.15 |
| 11754 | CB | ILE | C | 218 | -34.009 | -35.772 | -15.897 | 1.00 | 10.34 |
| 11756 | CG1 | ILE | C | 218 | -35.283 | -36.607 | -15.720 | 1.00 | 10.79 |
| 11759 | CD1 | ILE | C | 218 | -35.315 | -37.938 | -16.450 | 1.00 | 12.88 |
| 11763 | CG2 | ILE | C | 218 | -33.839 | -35.343 | -17.351 | 1.00 | 10.17 |
| 11767 | C | ILE | C | 218 | -31.575 | -35.587 | -15.205 | 1.00 | 11.25 |
| 11768 | O | ILE | C | 218 | -31.506 | -34.911 | -14.180 | 1.00 | 11.27 |
| 11769 | N | ASP | C | 219 | -30.678 | -35.516 | -16.195 | 1.00 | 11.41 |
| 11771 | CA | ASP | C | 219 | -29.396 | -34.806 | -16.065 | 1.00 | 12.13 |
| 11773 | CB | ASP | C | 219 | -28.362 | -35.378 | -17.057 | 1.00 | 12.25 |
| 11776 | CG | ASP | C | 219 | -28.669 | -35.039 | -18.486 | 1.00 | 14.46 |
| 11777 | OD1 | ASP | C | 219 | -27.884 | -35.450 | -19.376 | 1.00 | 18.63 |
| 11778 | OD2 | ASP | C | 219 | -29.667 | -34.372 | -18.819 | 1.00 | 15.36 |
| 11779 | C | ASP | C | 219 | -29.432 | -33.275 | -16.155 | 1.00 | 12.14 |
| 11780 | O | ASP | C | 219 | -28.507 | -32.650 | -16.689 | 1.00 | 13.04 |
| 11781 | N | THR | C | 220 | -30.465 | -32.653 | -15.598 | 1.00 | 12.34 |
| 11783 | CA | THR | C | 220 | -30.496 | -31.202 | -15.489 | 1.00 | 12.12 |
| 11785 | CB | THR | C | 220 | -31.898 | -30.714 | -15.071 | 1.00 | 11.34 |
| 11787 | OG1 | THR | C | 220 | -32.221 | -31.168 | -13.736 | 1.00 | 10.94 |
| 11789 | CG2 | THR | C | 220 | -32.983 | -31.289 | -15.990 | 1.00 | 11.15 |
| 11793 | C | THR | C | 220 | -29.448 | -30.734 | -14.487 | 1.00 | 12.50 |
| 11794 | O | THR | C | 220 | -29.048 | -31.487 | -13.595 | 1.00 | 12.84 |
| 11795 | N | GLU | C | 221 | -29.005 | -29.491 | -14.624 | 1.00 | 13.49 |
| 11797 | CA | GLU | C | 221 | -28.019 | -28.936 | -13.696 | 1.00 | 14.50 |
| 11799 | CB | GLU | C | 221 | -27.656 | -27.500 | -14.075 | 1.00 | 15.68 |
| 11802 | CG | GLU | C | 221 | -26.714 | -27.401 | -15.267 | 1.00 | 20.55 |
| 11805 | CD | GLU | C | 221 | -25.246 | -27.512 | -14.885 | 1.00 | 25.80 |
| 11806 | OE1 | GLU | C | 221 | -24.840 | -28.565 | -14.341 | 1.00 | 30.39 |
| 11807 | OE2 | GLU | C | 221 | -24.488 | -26.540 | -15.129 | 1.00 | 32.37 |
| 11808 | C | GLU | C | 221 | -28.523 | -29.009 | -12.254 | 1.00 | 14.20 |
| 11809 | O | GLU | C | 221 | -27.784 | -29.370 | -11.339 | 1.00 | 13.80 |
| 11810 | N | THR | C | 222 | -29.807 | -28.718 | -12.070 | 1.00 | 13.18 |
| 11812 | CA | THR | C | 222 | -30.445 | -28.808 | -10.762 | 1.00 | 12.90 |
| 11814 | CB | THR | C | 222 | -31.934 | -28.445 | -10.879 | 1.00 | 12.97 |
| 11816 | OG1 | THR | C | 222 | -32.050 | -27.033 | -11.103 | 1.00 | 13.26 |
| 11818 | CG2 | THR | C | 222 | -32.671 | -28.687 | -9.583 | 1.00 | 13.56 |
| 11822 | C | THR | C | 222 | -30.278 | -30.189 | -10.157 | 1.00 | 12.67 |
| 11823 | O | THR | C | 222 | -29.849 | -30.314 | -9.023 | 1.00 | 13.04 |
| 11824 | N | ALA | C | 223 | -30.609 | -31.226 | -10.919 | 1.00 | 12.33 |
| 11826 | CA | ALA | C | 223 | -30.535 | -32.581 | -10.385 | 1.00 | 12.40 |
| 11828 | CB | ALA | C | 223 | -31.207 | -33.562 | -11.322 | 1.00 | 12.00 |
| 11832 | C | ALA | C | 223 | -29.101 | -33.017 | -10.110 | 1.00 | 13.18 |
| 11833 | O | ALA | C | 223 | -28.825 | -33.611 | -9.079 | 1.00 | 13.22 |
| 11834 | N | MET | C | 224 | -28.193 | -32.703 | -11.023 | 1.00 | 14.67 |
| 11836 | CA | MET | C | 224 | -26.810 | -33.150 | -10.885 | 1.00 | 15.66 |
| 11838 | CB | MET | C | 224 | -26.025 | -32.858 | -12.157 | 1.00 | 16.02 |
| 11841 | CG | MET | C | 224 | -26.544 | -33.583 | -13.382 | 1.00 | 18.03 |
| 11844 | SD | MET | C | 224 | -26.776 | -35.368 | -13.191 | 1.00 | 23.43 |

FIGURE 3 (cont.)

| A | B | C | D | E | F | G | H | I | J |
|---|---|---|---|---|---|---|---|---|---|
| 11845 | CE | MET | C | 224 | -28.250 | -35.565 | -12.482 | 1.00 | 24.53 |
| 11849 | C | MET | C | 224 | -26.144 | -32.521 | -9.672 | 1.00 | 16.27 |
| 11850 | O | MET | C | 224 | -25.335 | -33.169 | -8.994 | 1.00 | 16.17 |
| 11851 | N | LYS | C | 225 | -26.500 | -31.278 | -9.370 | 1.00 | 16.66 |
| 11853 | CA | LYS | C | 225 | -25.987 | -30.626 | -8.171 | 1.00 | 17.61 |
| 11855 | CB | LYS | C | 225 | -26.170 | -29.113 | -8.281 | 1.00 | 18.39 |
| 11858 | CG | LYS | C | 225 | -25.185 | -28.501 | -9.275 | 1.00 | 21.20 |
| 11861 | CD | LYS | C | 225 | -25.611 | -27.144 | -9.805 | 1.00 | 25.11 |
| 11864 | CE | LYS | C | 225 | -24.397 | -26.346 | -10.296 | 1.00 | 26.80 |
| 11867 | NZ | LYS | C | 225 | -24.729 | -24.945 | -10.663 | 1.00 | 29.27 |
| 11871 | C | LYS | C | 225 | -26.637 | -31.202 | -6.912 | 1.00 | 17.40 |
| 11872 | O | LYS | C | 225 | -25.986 | -31.403 | -5.888 | 1.00 | 16.91 |
| 11873 | N | ALA | C | 226 | -27.919 | -31.524 | -7.005 | 1.00 | 16.84 |
| 11875 | CA | ALA | C | 226 | -28.650 | -32.083 | -5.876 | 1.00 | 17.21 |
| 11877 | CB | ALA | C | 226 | -30.130 | -32.127 | -6.203 | 1.00 | 16.94 |
| 11881 | C | ALA | C | 226 | -28.177 | -33.479 | -5.459 | 1.00 | 17.65 |
| 11882 | O | ALA | C | 226 | -28.246 | -33.831 | -4.276 | 1.00 | 17.84 |
| 11883 | N | VAL | C | 227 | -27.701 | -34.273 | -6.412 | 1.00 | 18.15 |
| 11885 | CA | VAL | C | 227 | -27.323 | -35.658 | -6.127 | 1.00 | 19.01 |
| 11887 | CB | VAL | C | 227 | -27.946 | -36.667 | -7.137 | 1.00 | 18.72 |
| 11889 | CG1 | VAL | C | 227 | -29.464 | -36.517 | -7.194 | 1.00 | 18.64 |
| 11893 | CG2 | VAL | C | 227 | -27.323 | -36.527 | -8.528 | 1.00 | 18.71 |
| 11897 | C | VAL | C | 227 | -25.807 | -35.851 | -6.098 | 1.00 | 20.43 |
| 11898 | O | VAL | C | 227 | -25.323 | -36.982 | -6.088 | 1.00 | 21.02 |
| 11899 | N | SER | C | 228 | -25.057 | -34.754 | -6.085 | 1.00 | 21.60 |
| 11901 | CA | SER | C | 228 | -23.590 | -34.849 | -6.109 | 1.00 | 23.41 |
| 11903 | CB | SER | C | 228 | -22.961 | -33.456 | -6.189 | 1.00 | 23.50 |
| 11906 | OG | SER | C | 228 | -23.339 | -32.670 | -5.075 | 1.00 | 25.53 |
| 11908 | C | SER | C | 228 | -23.013 | -35.619 | -4.914 | 1.00 | 24.37 |
| 11909 | O | SER | C | 228 | -21.969 | -36.264 | -5.037 | 1.00 | 25.17 |
| 11910 | N | GLY | C | 229 | -23.681 | -35.542 | -3.767 | 1.00 | 25.54 |
| 11912 | CA | GLY | C | 229 | -23.243 | -36.235 | -2.559 | 1.00 | 26.50 |
| 11915 | C | GLY | C | 229 | -23.842 | -37.616 | -2.348 | 1.00 | 27.29 |
| 11916 | O | GLY | C | 229 | -23.679 | -38.202 | -1.273 | 1.00 | 27.35 |
| 11917 | N | ILE | C | 230 | -24.555 | -38.120 | -3.355 | 1.00 | 28.25 |
| 11919 | CA | ILE | C | 230 | -25.022 | -39.507 | -3.390 | 1.00 | 29.37 |
| 11921 | CB | ILE | C | 230 | -26.544 | -39.602 | -3.121 | 1.00 | 29.53 |
| 11923 | CG1 | ILE | C | 230 | -27.352 | -38.919 | -4.231 | 1.00 | 30.02 |
| 11926 | CD1 | ILE | C | 230 | -28.719 | -39.552 | -4.476 | 1.00 | 29.92 |
| 11930 | CG2 | ILE | C | 230 | -26.885 | -38.990 | -1.764 | 1.00 | 30.30 |
| 11934 | C | ILE | C | 230 | -24.669 | -40.128 | -4.744 | 1.00 | 29.62 |
| 11935 | O | ILE | C | 230 | -24.208 | -41.265 | -4.804 | 1.00 | 31.08 |
| 11936 | N | ALA | C | 235 | -27.850 | -40.788 | -14.960 | 1.00 | 15.59 |
| 11938 | CA | ALA | C | 235 | -28.919 | -39.824 | -15.235 | 1.00 | 14.65 |
| 11940 | CB | ALA | C | 235 | -28.465 | -38.410 | -14.887 | 1.00 | 14.99 |
| 11944 | C | ALA | C | 235 | -29.317 | -39.891 | -16.701 | 1.00 | 14.89 |
| 11945 | O | ALA | C | 235 | -28.460 | -39.972 | -17.583 | 1.00 | 15.68 |
| 11946 | N | ALA | C | 236 | -30.619 | -39.824 | -16.965 | 1.00 | 14.03 |
| 11948 | CA | ALA | C | 236 | -31.125 | -39.859 | -18.321 | 1.00 | 13.49 |

FIGURE 3 (cont.)

| A | B | C | D | E | F | G | H | I | J |
|---|---|---|---|---|---|---|---|---|---|
| 11950 | CB | ALA | C | 236 | -32.552 | -40.346 | -18.334 | 1.00 | 13.29 |
| 11954 | C | ALA | C | 236 | -31.012 | -38.478 | -18.977 | 1.00 | 13.32 |
| 11955 | O | ALA | C | 236 | -31.017 | -37.451 | -18.292 | 1.00 | 12.80 |
| 11956 | N | PRO | C | 237 | -30.886 | -38.438 | -20.298 | 1.00 | 13.16 |
| 11957 | CA | PRO | C | 237 | -30.702 | -37.160 | -20.988 | 1.00 | 12.90 |
| 11959 | CB | PRO | C | 237 | -30.288 | -37.564 | -22.406 | 1.00 | 13.19 |
| 11962 | CG | PRO | C | 237 | -30.549 | -39.003 | -22.537 | 1.00 | 14.25 |
| 11965 | CD | PRO | C | 237 | -30.897 | -39.586 | -21.225 | 1.00 | 13.46 |
| 11968 | C | PRO | C | 237 | -31.948 | -36.281 | -21.008 | 1.00 | 13.01 |
| 11969 | O | PRO | C | 237 | -33.036 | -36.746 | -21.366 | 1.00 | 13.06 |
| 11970 | N | LYS | C | 238 | -31.771 | -35.018 | -20.638 | 1.00 | 12.36 |
| 11972 | CA | LYS | C | 238 | -32.895 | -34.085 | -20.538 | 1.00 | 12.40 |
| 11974 | CB | LYS | C | 238 | -32.469 | -32.768 | -19.875 | 1.00 | 12.37 |
| 11977 | CG | LYS | C | 238 | -31.353 | -32.003 | -20.575 | 1.00 | 13.16 |
| 11980 | CD | LYS | C | 238 | -30.933 | -30.777 | -19.797 | 1.00 | 14.89 |
| 11983 | CE | LYS | C | 238 | -29.845 | -30.009 | -20.527 | 1.00 | 15.48 |
| 11986 | NZ | LYS | C | 238 | -29.391 | -28.779 | -19.809 | 1.00 | 18.83 |
| 11990 | C | LYS | C | 238 | -33.575 | -33.831 | -21.882 | 1.00 | 12.76 |
| 11991 | O | LYS | C | 238 | -34.787 | -33.627 | -21.922 | 1.00 | 12.67 |
| 11992 | N | GLU | C | 239 | -32.817 | -33.879 | -22.985 | 1.00 | 13.42 |
| 11994 | CA | GLU | C | 239 | -33.411 | -33.666 | -24.303 | 1.00 | 14.33 |
| 11996 | CB | GLU | C | 239 | -32.339 | -33.580 | -25.397 | 1.00 | 15.64 |
| 11999 | CG | GLU | C | 239 | -32.891 | -33.217 | -26.772 | 1.00 | 20.08 |
| 12002 | CD | GLU | C | 239 | -31.823 | -33.076 | -27.845 | 1.00 | 25.16 |
| 12003 | OE1 | GLU | C | 239 | -32.189 | -33.077 | -29.045 | 1.00 | 28.77 |
| 12004 | OE2 | GLU | C | 239 | -30.627 | -32.960 | -27.502 | 1.00 | 30.13 |
| 12005 | C | GLU | C | 239 | -34.399 | -34.778 | -24.633 | 1.00 | 13.73 |
| 12006 | O | GLU | C | 239 | -35.477 | -34.517 | -25.155 | 1.00 | 12.94 |
| 12007 | N | GLU | C | 240 | -34.031 | -36.020 | -24.338 | 1.00 | 13.83 |
| 12009 | CA | GLU | C | 240 | -34.915 | -37.152 | -24.640 | 1.00 | 13.97 |
| 12011 | CB | GLU | C | 240 | -34.173 | -38.487 | -24.532 | 1.00 | 14.80 |
| 12014 | CG | GLU | C | 240 | -35.045 | -39.698 | -24.842 | 1.00 | 18.44 |
| 12017 | CD | GLU | C | 240 | -34.277 | -41.011 | -24.846 | 1.00 | 23.31 |
| 12018 | OE1 | GLU | C | 240 | -33.969 | -41.547 | -23.758 | 1.00 | 24.72 |
| 12019 | OE2 | GLU | C | 240 | -33.986 | -41.519 | -25.952 | 1.00 | 27.48 |
| 12020 | C | GLU | C | 240 | -36.124 | -37.151 | -23.710 | 1.00 | 13.03 |
| 12021 | O | GLU | C | 240 | -37.238 | -37.451 | -24.136 | 1.00 | 12.63 |
| 12022 | N | CYS | C | 241 | -35.890 | -36.836 | -22.441 | 1.00 | 12.26 |
| 12024 | CA | CYS | C | 241 | -36.963 | -36.737 | -21.457 | 1.00 | 12.13 |
| 12026 | CB | CYS | C | 241 | -36.392 | -36.230 | -20.132 | 1.00 | 12.21 |
| 12029 | SG | CYS | C | 241 | -37.622 | -36.092 | -18.819 | 1.00 | 12.92 |
| 12030 | C | CYS | C | 241 | -38.032 | -35.766 | -21.952 | 1.00 | 11.54 |
| 12031 | O | CYS | C | 241 | -39.220 | -36.070 | -21.956 | 1.00 | 11.42 |
| 12032 | N | ALA | C | 242 | -37.588 | -34.585 | -22.354 | 1.00 | 11.14 |
| 12034 | CA | ALA | C | 242 | -38.478 | -33.533 | -22.820 | 1.00 | 10.68 |
| 12036 | CB | ALA | C | 242 | -37.664 | -32.300 | -23.182 | 1.00 | 11.33 |
| 12040 | C | ALA | C | 242 | -39.311 | -34.010 | -24.011 | 1.00 | 11.02 |
| 12041 | O | ALA | C | 242 | -40.508 | -33.735 | -24.095 | 1.00 | 10.47 |
| 12042 | N | LEU | C | 243 | -38.691 | -34.742 | -24.935 | 1.00 | 11.46 |

FIGURE 3 (cont.)

| A | B | C | D | E | F | G | H | I | J |
|---|---|---|---|---|---|---|---|---|---|
| 12044 | CA | LEU | C | 243 | -39.415 | -35.218 | -26.098 | 1.00 | 12.20 |
| 12046 | CB | LEU | C | 243 | -38.459 | -35.808 | -27.135 | 1.00 | 12.99 |
| 12049 | CG | LEU | C | 243 | -39.123 | -36.281 | -28.423 | 1.00 | 14.19 |
| 12051 | CD1 | LEU | C | 243 | -39.909 | -35.153 | -29.077 | 1.00 | 14.92 |
| 12055 | CD2 | LEU | C | 243 | -38.075 | -36.848 | -29.373 | 1.00 | 15.95 |
| 12059 | C | LEU | C | 243 | -40.476 | -36.236 | -25.698 | 1.00 | 12.29 |
| 12060 | O | LEU | C | 243 | -41.580 | -36.192 | -26.204 | 1.00 | 12.28 |
| 12061 | N | GLU | C | 244 | -40.165 | -37.128 | -24.763 | 1.00 | 12.61 |
| 12063 | CA | GLU | C | 244 | -41.139 | -38.140 | -24.359 | 1.00 | 12.79 |
| 12065 | CB | GLU | C | 244 | -40.481 | -39.215 | -23.493 | 1.00 | 13.07 |
| 12068 | CG | GLU | C | 244 | -39.460 | -40.062 | -24.238 | 1.00 | 15.24 |
| 12071 | CD | GLU | C | 244 | -40.019 | -40.742 | -25.481 | 1.00 | 19.30 |
| 12072 | OE1 | GLU | C | 244 | -39.317 | -40.734 | -26.519 | 1.00 | 21.69 |
| 12073 | OE2 | GLU | C | 244 | -41.158 | -41.257 | -25.427 | 1.00 | 20.80 |
| 12074 | C | GLU | C | 244 | -42.341 | -37.532 | -23.650 | 1.00 | 12.17 |
| 12075 | O | GLU | C | 244 | -43.460 | -38.036 | -23.774 | 1.00 | 12.48 |
| 12076 | N | ILE | C | 245 | -42.125 | -36.448 | -22.906 | 1.00 | 11.79 |
| 12078 | CA | ILE | C | 245 | -43.231 | -35.739 | -22.267 | 1.00 | 11.17 |
| 12080 | CB | ILE | C | 245 | -42.710 | -34.617 | -21.356 | 1.00 | 11.19 |
| 12082 | CG1 | ILE | C | 245 | -41.996 | -35.194 | -20.122 | 1.00 | 10.84 |
| 12085 | CD1 | ILE | C | 245 | -41.195 | -34.156 | -19.336 | 1.00 | 10.48 |
| 12089 | CG2 | ILE | C | 245 | -43.867 | -33.710 | -20.939 | 1.00 | 11.40 |
| 12093 | C | ILE | C | 245 | -44.164 | -35.173 | -23.336 | 1.00 | 11.48 |
| 12094 | O | ILE | C | 245 | -45.370 | -35.346 | -23.263 | 1.00 | 11.59 |
| 12095 | N | ILE | C | 246 | -43.598 | -34.494 | -24.330 | 1.00 | 11.41 |
| 12097 | CA | ILE | C | 246 | -44.388 | -33.923 | -25.420 | 1.00 | 11.80 |
| 12099 | CB | ILE | C | 246 | -43.494 | -33.127 | -26.399 | 1.00 | 11.94 |
| 12101 | CG1 | ILE | C | 246 | -42.957 | -31.862 | -25.717 | 1.00 | 12.20 |
| 12104 | CD1 | ILE | C | 246 | -41.738 | -31.301 | -26.365 | 1.00 | 12.71 |
| 12108 | CG2 | ILE | C | 246 | -44.253 | -32.759 | -27.670 | 1.00 | 12.43 |
| 12112 | C | ILE | C | 246 | -45.165 | -35.010 | -26.159 | 1.00 | 12.06 |
| 12113 | O | ILE | C | 246 | -46.335 | -34.823 | -26.478 | 1.00 | 12.63 |
| 12114 | N | LYS | C | 247 | -44.506 | -36.133 | -26.431 | 1.00 | 12.28 |
| 12116 | CA | LYS | C | 247 | -45.114 | -37.221 | -27.190 | 1.00 | 13.13 |
| 12118 | CB | LYS | C | 247 | -44.121 | -38.368 | -27.402 | 1.00 | 13.19 |
| 12121 | CG | LYS | C | 247 | -42.983 | -38.123 | -28.371 | 1.00 | 16.39 |
| 12124 | CD | LYS | C | 247 | -42.235 | -39.445 | -28.601 | 1.00 | 18.33 |
| 12127 | CE | LYS | C | 247 | -41.095 | -39.338 | -29.581 | 1.00 | 21.36 |
| 12130 | NZ | LYS | C | 247 | -40.239 | -40.570 | -29.497 | 1.00 | 22.66 |
| 12134 | C | LYS | C | 247 | -46.319 | -37.744 | -26.434 | 1.00 | 13.16 |
| 12135 | O | LYS | C | 247 | -47.371 | -37.964 | -27.014 | 1.00 | 13.27 |
| 12136 | N | GLY | C | 248 | -46.164 | -37.933 | -25.123 | 1.00 | 13.15 |
| 12138 | CA | GLY | C | 248 | -47.251 | -38.404 | -24.292 | 1.00 | 13.13 |
| 12141 | C | GLY | C | 248 | -48.447 | -37.484 | -24.289 | 1.00 | 12.70 |
| 12142 | O | GLY | C | 248 | -49.584 | -37.937 | -24.384 | 1.00 | 13.09 |
| 12143 | N | GLY | C | 249 | -48.203 | -36.184 | -24.162 | 1.00 | 12.55 |
| 12145 | CA | GLY | C | 249 | -49.259 | -35.187 | -24.204 | 1.00 | 12.63 |
| 12148 | C | GLY | C | 249 | -49.962 | -35.144 | -25.545 | 1.00 | 12.79 |
| 12149 | O | GLY | C | 249 | -51.187 | -35.059 | -25.606 | 1.00 | 13.00 |

FIGURE 3 (cont.)

| A | B | C | D | E | F | G | H | I | J |
|---|---|---|---|---|---|---|---|---|---|
| 12150 | N | ALA | C | 250 | -49.181 | -35.206 | -26.621 | 1.00 | 12.39 |
| 12152 | CA | ALA | C | 250 | -49.719 | -35.150 | -27.982 | 1.00 | 12.27 |
| 12154 | CB | ALA | C | 250 | -48.601 | -35.081 | -28.990 | 1.00 | 12.75 |
| 12158 | C | ALA | C | 250 | -50.605 | -36.351 | -28.268 | 1.00 | 12.07 |
| 12159 | O | ALA | C | 250 | -51.627 | -36.214 | -28.931 | 1.00 | 13.44 |
| 12160 | N | LEU | C | 251 | -50.210 | -37.512 | -27.750 | 1.00 | 11.77 |
| 12162 | CA | LEU | C | 251 | -50.968 | -38.757 | -27.916 | 1.00 | 11.68 |
| 12164 | CB | LEU | C | 251 | -50.025 | -39.953 | -27.845 | 1.00 | 11.90 |
| 12167 | CG | LEU | C | 251 | -49.059 | -40.076 | -29.033 | 1.00 | 13.00 |
| 12169 | CD1 | LEU | C | 251 | -48.107 | -41.240 | -28.818 | 1.00 | 14.12 |
| 12173 | CD2 | LEU | C | 251 | -49.808 | -40.207 | -30.341 | 1.00 | 13.94 |
| 12177 | C | LEU | C | 251 | -52.092 | -38.910 | -26.885 | 1.00 | 11.97 |
| 12178 | O | LEU | C | 251 | -52.818 | -39.909 | -26.899 | 1.00 | 12.23 |
| 12179 | N | ARG | C | 252 | -52.230 | -37.926 | -26.000 | 1.00 | 12.03 |
| 12181 | CA | ARG | C | 252 | -53.304 | -37.886 | -25.000 | 1.00 | 12.27 |
| 12183 | CB | ARG | C | 252 | -54.678 | -37.736 | -25.671 | 1.00 | 12.40 |
| 12186 | CG | ARG | C | 252 | -54.761 | -36.562 | -26.625 | 1.00 | 13.25 |
| 12189 | CD | ARG | C | 252 | -56.091 | -36.454 | -27.343 | 1.00 | 12.65 |
| 12192 | NE | ARG | C | 252 | -57.130 | -35.762 | -26.588 | 1.00 | 13.17 |
| 12194 | CZ | ARG | C | 252 | -57.264 | -34.443 | -26.497 | 1.00 | 12.51 |
| 12195 | NH1 | ARG | C | 252 | -56.405 | -33.625 | -27.079 | 1.00 | 12.96 |
| 12198 | NH2 | ARG | C | 252 | -58.272 | -33.925 | -25.808 | 1.00 | 12.62 |
| 12201 | C | ARG | C | 252 | -53.264 | -39.092 | -24.063 | 1.00 | 12.06 |
| 12202 | O | ARG | C | 252 | -54.299 | -39.610 | -23.648 | 1.00 | 12.00 |
| 12203 | N | GLN | C | 253 | -52.056 | -39.534 | -23.730 | 1.00 | 12.30 |
| 12205 | CA | GLN | C | 253 | -51.856 | -40.656 | -22.818 | 1.00 | 12.53 |
| 12207 | CB | GLN | C | 253 | -50.400 | -41.140 | -22.885 | 1.00 | 13.27 |
| 12210 | CG | GLN | C | 253 | -50.010 | -41.784 | -24.193 | 1.00 | 15.78 |
| 12213 | CD | GLN | C | 253 | -48.520 | -42.133 | -24.255 | 1.00 | 17.39 |
| 12214 | OE1 | GLN | C | 253 | -47.810 | -42.089 | -23.242 | 1.00 | 23.39 |
| 12215 | NE2 | GLN | C | 253 | -48.056 | -42.497 | -25.433 | 1.00 | 23.94 |
| 12218 | C | GLN | C | 253 | -52.152 | -40.206 | -21.390 | 1.00 | 12.57 |
| 12219 | O | GLN | C | 253 | -51.904 | -39.054 | -21.039 | 1.00 | 12.59 |
| 12220 | N | GLU | C | 254 | -52.668 | -41.107 | -20.561 | 1.00 | 12.68 |
| 12222 | CA | GLU | C | 254 | -52.905 | -40.763 | -19.155 | 1.00 | 12.99 |
| 12224 | CB | GLU | C | 254 | -53.726 | -41.842 | -18.440 | 1.00 | 13.57 |
| 12227 | CG | GLU | C | 254 | -55.188 | -41.885 | -18.868 | 1.00 | 16.45 |
| 12230 | CD | GLU | C | 254 | -56.106 | -42.603 | -17.879 | 1.00 | 20.30 |
| 12231 | OE1 | GLU | C | 254 | -57.265 | -42.878 | -18.247 | 1.00 | 26.45 |
| 12232 | OE2 | GLU | C | 254 | -55.698 | -42.886 | -16.739 | 1.00 | 25.89 |
| 12233 | C | GLU | C | 254 | -51.612 | -40.511 | -18.399 | 1.00 | 12.99 |
| 12234 | O | GLU | C | 254 | -51.515 | -39.548 | -17.640 | 1.00 | 12.12 |
| 12235 | N | GLU | C | 255 | -50.620 | -41.373 | -18.602 | 1.00 | 13.42 |
| 12237 | CA | GLU | C | 255 | -49.348 | -41.265 | -17.891 | 1.00 | 14.07 |
| 12239 | CB | GLU | C | 255 | -49.344 | -42.171 | -16.640 | 1.00 | 15.08 |
| 12242 | CG | GLU | C | 255 | -50.429 | -41.781 | -15.638 | 1.00 | 15.86 |
| 12245 | CD | GLU | C | 255 | -50.358 | -42.485 | -14.288 | 1.00 | 19.79 |
| 12246 | OE1 | GLU | C | 255 | -50.838 | -41.887 | -13.298 | 1.00 | 19.00 |
| 12247 | OE2 | GLU | C | 255 | -49.865 | -43.635 | -14.213 | 1.00 | 21.69 |

FIGURE 3 (cont.)

| A | B | C | D | E | F | G | H | I | J |
|---|---|---|---|---|---|---|---|---|---|
| 12248 | C | GLU | C | 255 | -48.167 | -41.561 | -18.811 | 1.00 | 14.54 |
| 12249 | O | GLU | C | 255 | -48.289 | -42.320 | -19.783 | 1.00 | 15.85 |
| 12250 | N | VAL | C | 256 | -47.043 | -40.916 | -18.518 | 1.00 | 13.79 |
| 12252 | CA | VAL | C | 256 | -45.763 | -41.163 | -19.174 | 1.00 | 14.05 |
| 12254 | CB | VAL | C | 256 | -45.231 | -39.901 | -19.878 | 1.00 | 14.24 |
| 12256 | CG1 | VAL | C | 256 | -43.779 | -40.084 | -20.369 | 1.00 | 15.45 |
| 12260 | CG2 | VAL | C | 256 | -46.154 | -39.462 | -21.009 | 1.00 | 15.91 |
| 12264 | C | VAL | C | 256 | -44.783 | -41.511 | -18.073 | 1.00 | 13.66 |
| 12265 | O | VAL | C | 256 | -44.728 | -40.812 | -17.072 | 1.00 | 13.87 |
| 12266 | N | TYR | C | 257 | -44.015 | -42.580 | -18.263 | 1.00 | 12.64 |
| 12268 | CA | TYR | C | 257 | -42.942 | -42.966 | -17.341 | 1.00 | 12.61 |
| 12270 | CB | TYR | C | 257 | -43.192 | -44.374 | -16.789 | 1.00 | 12.98 |
| 12273 | CG | TYR | C | 257 | -44.389 | -44.438 | -15.867 | 1.00 | 13.54 |
| 12274 | CD1 | TYR | C | 257 | -45.671 | -44.561 | -16.372 | 1.00 | 16.99 |
| 12276 | CE1 | TYR | C | 257 | -46.778 | -44.592 | -15.522 | 1.00 | 16.68 |
| 12278 | CZ | TYR | C | 257 | -46.589 | -44.491 | -14.162 | 1.00 | 16.74 |
| 12279 | OH | TYR | C | 257 | -47.684 | -44.541 | -13.314 | 1.00 | 18.08 |
| 12281 | CE2 | TYR | C | 257 | -45.317 | -44.376 | -13.641 | 1.00 | 16.63 |
| 12283 | CD2 | TYR | C | 257 | -44.232 | -44.338 | -14.493 | 1.00 | 15.20 |
| 12285 | C | TYR | C | 257 | -41.611 | -42.898 | -18.090 | 1.00 | 12.31 |
| 12286 | O | TYR | C | 257 | -41.459 | -43.476 | -19.177 | 1.00 | 12.69 |
| 12287 | N | TYR | C | 258 | -40.653 | -42.164 | -17.536 | 1.00 | 11.52 |
| 12289 | CA | TYR | C | 258 | -39.366 | -41.988 | -18.194 | 1.00 | 11.61 |
| 12291 | CB | TYR | C | 258 | -39.301 | -40.641 | -18.941 | 1.00 | 11.76 |
| 12294 | CG | TYR | C | 258 | -38.003 | -40.489 | -19.681 | 1.00 | 12.60 |
| 12295 | CD1 | TYR | C | 258 | -36.944 | -39.800 | -19.119 | 1.00 | 13.41 |
| 12297 | CE1 | TYR | C | 258 | -35.737 | -39.693 | -19.774 | 1.00 | 14.57 |
| 12299 | CZ | TYR | C | 258 | -35.571 | -40.271 | -21.006 | 1.00 | 15.50 |
| 12300 | OH | TYR | C | 258 | -34.354 | -40.155 | -21.640 | 1.00 | 18.37 |
| 12302 | CE2 | TYR | C | 258 | -36.606 | -40.971 | -21.594 | 1.00 | 15.20 |
| 12304 | CD2 | TYR | C | 258 | -37.822 | -41.068 | -20.928 | 1.00 | 15.06 |
| 12306 | C | TYR | C | 258 | -38.233 | -42.098 | -17.190 | 1.00 | 11.75 |
| 12307 | O | TYR | C | 258 | -38.245 | -41.454 | -16.134 | 1.00 | 11.72 |
| 12308 | N | ASP | C | 259 | -37.264 | -42.946 | -17.521 | 1.00 | 11.55 |
| 12310 | CA | ASP | C | 259 | -36.098 | -43.218 | -16.688 | 1.00 | 12.47 |
| 12312 | CB | ASP | C | 259 | -36.444 | -44.209 | -15.578 | 1.00 | 12.44 |
| 12315 | CG | ASP | C | 259 | -35.344 | -44.328 | -14.538 | 1.00 | 13.61 |
| 12316 | OD1 | ASP | C | 259 | -34.579 | -45.335 | -14.508 | 1.00 | 13.32 |
| 12317 | OD2 | ASP | C | 259 | -35.178 | -43.439 | -13.698 | 1.00 | 15.07 |
| 12318 | C | ASP | C | 259 | -35.007 | -43.834 | -17.574 | 1.00 | 13.04 |
| 12319 | O | ASP | C | 259 | -35.299 | -44.365 | -18.645 | 1.00 | 14.14 |
| 12320 | N | SER | C | 260 | -33.770 | -43.806 | -17.096 | 1.00 | 13.75 |
| 12322 | CA | SER | C | 260 | -32.660 | -44.475 | -17.785 | 1.00 | 14.36 |
| 12324 | CB | SER | C | 260 | -31.336 | -44.241 | -17.048 | 1.00 | 14.73 |
| 12327 | OG | SER | C | 260 | -30.898 | -42.903 | -17.163 | 1.00 | 18.81 |
| 12329 | C | SER | C | 260 | -32.869 | -45.981 | -17.908 | 1.00 | 14.41 |
| 12330 | O | SER | C | 260 | -32.357 | -46.597 | -18.842 | 1.00 | 15.00 |
| 12331 | N | SER | C | 261 | -33.603 | -46.572 | -16.970 | 1.00 | 14.01 |
| 12333 | CA | SER | C | 261 | -33.740 | -48.025 | -16.894 | 1.00 | 13.87 |

FIGURE 3 (cont.)

| A | B | C | D | E | F | G | H | I | J |
|---|---|---|---|---|---|---|---|---|---|
| 12335 | CB | SER | C | 261 | -33.253 | -48.514 | -15.543 | 1.00 | 14.49 |
| 12338 | OG | SER | C | 261 | -33.361 | -49.932 | -15.455 | 1.00 | 15.84 |
| 12340 | C | SER | C | 261 | -35.180 | -48.483 | -17.087 | 1.00 | 13.53 |
| 12341 | O | SER | C | 261 | -36.104 | -47.920 | -16.487 | 1.00 | 12.62 |
| 12342 | N | LEU | C | 262 | -35.355 | -49.525 | -17.896 | 1.00 | 13.00 |
| 12344 | CA | LEU | C | 262 | -36.642 | -50.212 | -18.006 | 1.00 | 13.34 |
| 12346 | CB | LEU | C | 262 | -36.623 | -51.231 | -19.154 | 1.00 | 13.85 |
| 12349 | CG | LEU | C | 262 | -36.748 | -50.638 | -20.563 | 1.00 | 15.75 |
| 12351 | CD1 | LEU | C | 262 | -36.296 | -51.629 | -21.632 | 1.00 | 17.50 |
| 12355 | CD2 | LEU | C | 262 | -38.183 | -50.196 | -20.829 | 1.00 | 17.92 |
| 12359 | C | LEU | C | 262 | -37.055 | -50.903 | -16.704 | 1.00 | 13.03 |
| 12360 | O | LEU | C | 262 | -38.243 | -51.147 | -16.491 | 1.00 | 12.35 |
| 12361 | N | TRP | C | 263 | -36.106 | -51.245 | -15.830 | 1.00 | 12.74 |
| 12363 | CA | TRP | C | 263 | -36.481 | -51.756 | -14.508 | 1.00 | 12.55 |
| 12365 | CB | TRP | C | 263 | -35.256 | -52.068 | -13.646 | 1.00 | 12.84 |
| 12368 | CG | TRP | C | 263 | -34.510 | -53.295 | -14.100 | 1.00 | 12.36 |
| 12369 | CD1 | TRP | C | 263 | -33.638 | -53.389 | -15.139 | 1.00 | 13.05 |
| 12371 | NE1 | TRP | C | 263 | -33.161 | -54.671 | -15.244 | 1.00 | 11.54 |
| 12373 | CE2 | TRP | C | 263 | -33.727 | -55.438 | -14.263 | 1.00 | 11.98 |
| 12374 | CD2 | TRP | C | 263 | -34.583 | -54.605 | -13.523 | 1.00 | 12.40 |
| 12375 | CE3 | TRP | C | 263 | -35.291 | -55.160 | -12.449 | 1.00 | 13.26 |
| 12377 | CZ3 | TRP | C | 263 | -35.115 | -56.506 | -12.157 | 1.00 | 13.17 |
| 12379 | CH2 | TRP | C | 263 | -34.256 | -57.298 | -12.911 | 1.00 | 12.56 |
| 12381 | CZ2 | TRP | C | 263 | -33.559 | -56.789 | -13.968 | 1.00 | 11.95 |
| 12383 | C | TRP | C | 263 | -37.374 | -50.747 | -13.794 | 1.00 | 12.35 |
| 12384 | O | TRP | C | 263 | -38.355 | -51.122 | -13.192 | 1.00 | 12.64 |
| 12385 | N | THR | C | 264 | -37.022 | -49.469 | -13.894 | 1.00 | 11.86 |
| 12387 | CA | THR | C | 264 | -37.807 | -48.413 | -13.274 | 1.00 | 11.60 |
| 12389 | CB | THR | C | 264 | -37.024 | -47.096 | -13.293 | 1.00 | 11.77 |
| 12391 | OG1 | THR | C | 264 | -35.732 | -47.279 | -12.693 | 1.00 | 12.80 |
| 12393 | CG2 | THR | C | 264 | -37.718 | -46.041 | -12.450 | 1.00 | 11.94 |
| 12397 | C | THR | C | 264 | -39.139 | -48.217 | -13.968 | 1.00 | 11.37 |
| 12398 | O | THR | C | 264 | -40.174 | -48.249 | -13.319 | 1.00 | 11.86 |
| 12399 | N | THR | C | 265 | -39.130 | -47.998 | -15.280 | 1.00 | 11.28 |
| 12401 | CA | THR | C | 265 | -40.368 | -47.602 | -15.950 | 1.00 | 11.73 |
| 12403 | CB | THR | C | 265 | -40.135 | -47.039 | -17.361 | 1.00 | 11.94 |
| 12405 | OG1 | THR | C | 265 | -39.498 | -48.015 | -18.182 | 1.00 | 12.80 |
| 12407 | CG2 | THR | C | 265 | -39.170 | -45.865 | -17.326 | 1.00 | 12.88 |
| 12411 | C | THR | C | 265 | -41.398 | -48.728 | -15.994 | 1.00 | 12.33 |
| 12412 | O | THR | C | 265 | -42.597 | -48.461 | -15.936 | 1.00 | 13.36 |
| 12413 | N | LEU | C | 266 | -40.940 | -49.973 | -16.056 | 1.00 | 12.18 |
| 12415 | CA | LEU | C | 266 | -41.865 | -51.104 | -16.103 | 1.00 | 12.10 |
| 12417 | CB | LEU | C | 266 | -41.212 | -52.335 | -16.751 | 1.00 | 12.70 |
| 12420 | CG | LEU | C | 266 | -40.830 | -52.222 | -18.233 | 1.00 | 12.88 |
| 12422 | CD1 | LEU | C | 266 | -40.131 | -53.496 | -18.728 | 1.00 | 14.06 |
| 12426 | CD2 | LEU | C | 266 | -42.064 | -51.924 | -19.085 | 1.00 | 15.54 |
| 12430 | C | LEU | C | 266 | -42.410 | -51.438 | -14.711 | 1.00 | 12.64 |
| 12431 | O | LEU | C | 266 | -43.595 | -51.750 | -14.570 | 1.00 | 13.23 |
| 12432 | N | LEU | C | 267 | -41.565 | -51.391 | -13.684 | 1.00 | 12.34 |

FIGURE 3 (cont.)

| A | B | C | D | E | F | G | H | I | J |
|---|---|---|---|---|---|---|---|---|---|
| 12434 | CA | LEU | C | 267 | -42.001 | -51.818 | -12.342 | 1.00 | 13.06 |
| 12436 | CB | LEU | C | 267 | -40.828 | -52.378 | -11.527 | 1.00 | 13.18 |
| 12439 | CG | LEU | C | 267 | -40.198 | -53.656 | -12.083 | 1.00 | 14.62 |
| 12441 | CD1 | LEU | C | 267 | -38.906 | -53.953 | -11.365 | 1.00 | 15.80 |
| 12445 | CD2 | LEU | C | 267 | -41.172 | -54.848 | -12.003 | 1.00 | 16.24 |
| 12449 | C | LEU | C | 267 | -42.744 | -50.763 | -11.531 | 1.00 | 13.48 |
| 12450 | O | LEU | C | 267 | -43.542 | -51.114 | -10.677 | 1.00 | 12.93 |
| 12451 | N | ILE | C | 268 | -42.480 | -49.484 | -11.784 | 1.00 | 14.13 |
| 12453 | CA | ILE | C | 268 | -43.139 | -48.401 | -11.047 | 1.00 | 14.75 |
| 12455 | CB | ILE | C | 268 | -42.415 | -47.054 | -11.288 | 1.00 | 14.94 |
| 12457 | CG1 | ILE | C | 268 | -42.883 | -45.980 | -10.293 | 1.00 | 18.07 |
| 12460 | CD1 | ILE | C | 268 | -42.227 | -46.069 | -8.978 | 1.00 | 20.18 |
| 12464 | CG2 | ILE | C | 268 | -42.655 | -46.565 | -12.688 | 1.00 | 16.47 |
| 12468 | C | ILE | C | 268 | -44.619 | -48.283 | -11.421 | 1.00 | 14.81 |
| 12469 | O | ILE | C | 268 | -45.409 | -47.721 | -10.666 | 1.00 | 14.87 |
| 12470 | N | ARG | C | 269 | -44.991 | -48.806 | -12.588 | 1.00 | 14.93 |
| 12472 | CA | ARG | C | 269 | -46.384 | -48.753 | -13.020 | 1.00 | 15.70 |
| 12474 | CB | ARG | C | 269 | -46.524 | -49.279 | -14.446 | 1.00 | 16.47 |
| 12477 | CG | ARG | C | 269 | -46.020 | -48.269 | -15.468 | 1.00 | 19.82 |
| 12480 | CD | ARG | C | 269 | -45.925 | -48.799 | -16.894 | 1.00 | 25.74 |
| 12483 | NE | ARG | C | 269 | -46.030 | -47.721 | -17.884 | 1.00 | 29.72 |
| 12485 | CZ | ARG | C | 269 | -47.152 | -47.076 | -18.203 | 1.00 | 32.58 |
| 12486 | NH1 | ARG | C | 269 | -47.121 | -46.110 | -19.118 | 1.00 | 34.25 |
| 12489 | NH2 | ARG | C | 269 | -48.312 | -47.381 | -17.621 | 1.00 | 35.19 |
| 12492 | C | ARG | C | 269 | -47.246 | -49.564 | -12.066 | 1.00 | 14.74 |
| 12493 | O | ARG | C | 269 | -46.844 | -50.628 | -11.600 | 1.00 | 14.91 |
| 12494 | N | ASN | C | 270 | -48.431 | -49.035 | -11.766 | 1.00 | 14.52 |
| 12496 | CA | ASN | C | 270 | -49.393 | -49.684 | -10.882 | 1.00 | 13.63 |
| 12498 | CB | ASN | C | 270 | -49.614 | -48.776 | -9.653 | 1.00 | 13.49 |
| 12501 | CG | ASN | C | 270 | -50.562 | -49.361 | -8.619 | 1.00 | 13.92 |
| 12502 | OD1 | ASN | C | 270 | -51.013 | -48.652 | -7.701 | 1.00 | 15.25 |
| 12503 | ND2 | ASN | C | 270 | -50.856 | -50.636 | -8.744 | 1.00 | 12.89 |
| 12506 | C | ASN | C | 270 | -50.704 | -49.929 | -11.655 | 1.00 | 13.37 |
| 12507 | O | ASN | C | 270 | -51.695 | -49.217 | -11.448 | 1.00 | 12.45 |
| 12508 | N | PRO | C | 271 | -50.724 | -50.901 | -12.572 | 1.00 | 13.12 |
| 12509 | CA | PRO | C | 271 | -51.937 | -51.165 | -13.357 | 1.00 | 12.95 |
| 12511 | CB | PRO | C | 271 | -51.543 | -52.340 | -14.265 | 1.00 | 13.18 |
| 12514 | CG | PRO | C | 271 | -50.332 | -52.932 | -13.650 | 1.00 | 13.46 |
| 12517 | CD | PRO | C | 271 | -49.628 | -51.812 | -12.944 | 1.00 | 13.41 |
| 12520 | C | PRO | C | 271 | -53.136 | -51.533 | -12.509 | 1.00 | 12.78 |
| 12521 | O | PRO | C | 271 | -54.260 | -51.289 | -12.937 | 1.00 | 12.71 |
| 12522 | N | SER | C | 272 | -52.908 | -52.117 | -11.341 | 1.00 | 12.01 |
| 12524 | CA | SER | C | 272 | -54.002 | -52.507 | -10.460 | 1.00 | 11.99 |
| 12526 | CB | SER | C | 272 | -53.470 | -53.246 | -9.231 | 1.00 | 12.81 |
| 12529 | OG | SER | C | 272 | -52.989 | -54.534 | -9.597 | 1.00 | 14.99 |
| 12531 | C | SER | C | 272 | -54.841 | -51.319 | -10.014 | 1.00 | 11.35 |
| 12532 | O | SER | C | 272 | -56.058 | -51.439 | -9.875 | 1.00 | 11.41 |
| 12533 | N | ARG | C | 273 | -54.207 | -50.174 | -9.781 | 1.00 | 10.61 |
| 12535 | CA | ARG | C | 273 | -54.970 | -48.965 | -9.443 | 1.00 | 10.56 |

FIGURE 3 (cont.)

| A | B | C | D | E | F | G | H | I | J |
|---|---|---|---|---|---|---|---|---|---|
| 12537 | CB | ARG | C | 273 | -54.043 | -47.774 | -9.165 | 1.00 | 10.09 |
| 12540 | CG | ARG | C | 273 | -54.736 | -46.418 | -9.209 | 1.00 | 9.69 |
| 12543 | CD | ARG | C | 273 | -53.908 | -45.238 | -8.678 | 1.00 | 10.35 |
| 12546 | NE | ARG | C | 273 | -54.400 | -43.988 | -9.241 | 1.00 | 11.05 |
| 12548 | CZ | ARG | C | 273 | -53.748 | -42.840 | -9.198 | 1.00 | 10.78 |
| 12549 | NH1 | ARG | C | 273 | -52.597 | -42.745 | -8.556 | 1.00 | 11.38 |
| 12552 | NH2 | ARG | C | 273 | -54.260 | -41.784 | -9.804 | 1.00 | 11.11 |
| 12555 | C | ARG | C | 273 | -55.989 | -48.612 | -10.528 | 1.00 | 11.27 |
| 12556 | O | ARG | C | 273 | -57.159 | -48.355 | -10.229 | 1.00 | 10.92 |
| 12557 | N | LYS | C | 274 | -55.562 | -48.609 | -11.790 | 1.00 | 12.16 |
| 12559 | CA | LYS | C | 274 | -56.445 | -48.218 | -12.890 | 1.00 | 13.62 |
| 12561 | CB | LYS | C | 274 | -55.659 | -48.054 | -14.198 | 1.00 | 14.83 |
| 12564 | CG | LYS | C | 274 | -54.447 | -47.103 | -14.118 | 1.00 | 18.31 |
| 12567 | CD | LYS | C | 274 | -54.810 | -45.619 | -13.969 | 1.00 | 22.54 |
| 12570 | CE | LYS | C | 274 | -53.569 | -44.722 | -13.797 | 1.00 | 24.36 |
| 12573 | NZ | LYS | C | 274 | -53.846 | -43.320 | -13.308 | 1.00 | 25.56 |
| 12577 | C | LYS | C | 274 | -57.574 | -49.241 | -13.058 | 1.00 | 13.93 |
| 12578 | O | LYS | C | 274 | -58.709 | -48.893 | -13.372 | 1.00 | 13.23 |
| 12579 | N | ILE | C | 275 | -57.252 | -50.505 | -12.833 | 1.00 | 15.40 |
| 12581 | CA | ILE | C | 275 | -58.246 | -51.574 | -12.898 | 1.00 | 16.26 |
| 12583 | CB | ILE | C | 275 | -57.555 | -52.942 | -12.792 | 1.00 | 16.49 |
| 12585 | CG1 | ILE | C | 275 | -56.826 | -53.257 | -14.110 | 1.00 | 17.58 |
| 12588 | CD1 | ILE | C | 275 | -55.759 | -54.334 | -13.987 | 1.00 | 19.28 |
| 12592 | CG2 | ILE | C | 275 | -58.558 | -54.044 | -12.453 | 1.00 | 17.69 |
| 12596 | C | ILE | C | 275 | -59.313 | -51.385 | -11.806 | 1.00 | 16.51 |
| 12597 | O | ILE | C | 275 | -60.507 | -51.477 | -12.079 | 1.00 | 16.64 |
| 12598 | N | LEU | C | 276 | -58.892 | -51.123 | -10.574 | 1.00 | 16.80 |
| 12600 | CA | LEU | C | 276 | -59.847 | -50.918 | -9.481 | 1.00 | 17.40 |
| 12602 | CB | LEU | C | 276 | -59.154 | -50.846 | -8.129 | 1.00 | 17.71 |
| 12605 | CG | LEU | C | 276 | -58.562 | -52.175 | -7.665 | 1.00 | 20.24 |
| 12607 | CD1 | LEU | C | 276 | -57.740 | -51.993 | -6.400 | 1.00 | 22.08 |
| 12611 | CD2 | LEU | C | 276 | -59.668 | -53.217 | -7.446 | 1.00 | 20.01 |
| 12615 | C | LEU | C | 276 | -60.709 | -49.677 | -9.717 | 1.00 | 17.22 |
| 12616 | O | LEU | C | 276 | -61.913 | -49.722 | -9.529 | 1.00 | 17.27 |
| 12617 | N | GLU | C | 277 | -60.108 | -48.584 | -10.175 | 1.00 | 16.44 |
| 12619 | CA | GLU | C | 277 | -60.890 | -47.395 | -10.523 | 1.00 | 16.53 |
| 12621 | CB | GLU | C | 277 | -59.990 | -46.275 | -11.055 | 1.00 | 16.41 |
| 12624 | CG | GLU | C | 277 | -59.058 | -45.718 | -9.993 | 1.00 | 15.89 |
| 12627 | CD | GLU | C | 277 | -57.953 | -44.850 | -10.553 | 1.00 | 16.14 |
| 12628 | OE1 | GLU | C | 277 | -57.153 | -44.323 | -9.747 | 1.00 | 16.19 |
| 12629 | OE2 | GLU | C | 277 | -57.877 | -44.673 | -11.780 | 1.00 | 17.26 |
| 12630 | C | GLU | C | 277 | -61.992 | -47.744 | -11.527 | 1.00 | 17.38 |
| 12631 | O | GLU | C | 277 | -63.137 | -47.319 | -11.369 | 1.00 | 18.10 |
| 12632 | N | PHE | C | 278 | -61.657 | -48.528 | -12.548 | 1.00 | 17.85 |
| 12634 | CA | PHE | C | 278 | -62.648 | -48.916 | -13.550 | 1.00 | 18.72 |
| 12636 | CB | PHE | C | 278 | -61.980 | -49.637 | -14.714 | 1.00 | 19.52 |
| 12639 | CG | PHE | C | 278 | -62.956 | -50.301 | -15.631 | 1.00 | 21.01 |
| 12640 | CD1 | PHE | C | 278 | -63.693 | -49.546 | -16.529 | 1.00 | 24.55 |
| 12642 | CE1 | PHE | C | 278 | -64.620 | -50.160 | -17.365 | 1.00 | 25.63 |

FIGURE 3 (cont.)

| A | B | C | D | E | F | G | H | I | J |
|---|---|---|---|---|---|---|---|---|---|
| 12644 | CZ | PHE | C | 278 | -64.826 | -51.524 | -17.279 | 1.00 | 26.02 |
| 12646 | CE2 | PHE | C | 278 | -64.111 | -52.277 | -16.371 | 1.00 | 25.07 |
| 12648 | CD2 | PHE | C | 278 | -63.185 | -51.666 | -15.550 | 1.00 | 23.74 |
| 12650 | C | PHE | C | 278 | -63.742 | -49.801 | -12.936 | 1.00 | 19.15 |
| 12651 | O | PHE | C | 278 | -64.941 | -49.550 | -13.115 | 1.00 | 19.58 |
| 12652 | N | LEU | C | 279 | -63.330 | -50.814 | -12.192 | 1.00 | 19.14 |
| 12654 | CA | LEU | C | 279 | -64.281 | -51.784 | -11.636 | 1.00 | 19.72 |
| 12656 | CB | LEU | C | 279 | -63.547 | -52.953 | -10.976 | 1.00 | 19.69 |
| 12659 | CG | LEU | C | 279 | -62.866 | -53.928 | -11.935 | 1.00 | 19.83 |
| 12661 | CD1 | LEU | C | 279 | -61.983 | -54.880 | -11.142 | 1.00 | 20.16 |
| 12665 | CD2 | LEU | C | 279 | -63.873 | -54.675 | -12.809 | 1.00 | 19.87 |
| 12669 | C | LEU | C | 279 | -65.229 | -51.117 | -10.641 | 1.00 | 20.77 |
| 12670 | O | LEU | C | 279 | -66.420 | -51.440 | -10.596 | 1.00 | 21.85 |
| 12671 | N | TYR | C | 280 | -64.710 | -50.166 | -9.874 | 1.00 | 21.78 |
| 12673 | CA | TYR | C | 280 | -65.509 | -49.460 | -8.875 | 1.00 | 22.98 |
| 12675 | CB | TYR | C | 280 | -64.604 | -48.657 | -7.948 | 1.00 | 22.85 |
| 12678 | CG | TYR | C | 280 | -63.756 | -49.469 | -6.979 | 1.00 | 20.88 |
| 12679 | CD1 | TYR | C | 280 | -62.941 | -48.813 | -6.057 | 1.00 | 20.74 |
| 12681 | CE1 | TYR | C | 280 | -62.160 | -49.511 | -5.172 | 1.00 | 21.12 |
| 12683 | CZ | TYR | C | 280 | -62.167 | -50.891 | -5.178 | 1.00 | 21.71 |
| 12684 | OH | TYR | C | 280 | -61.379 | -51.564 | -4.271 | 1.00 | 22.84 |
| 12686 | CE2 | TYR | C | 280 | -62.970 | -51.584 | -6.078 | 1.00 | 21.29 |
| 12688 | CD2 | TYR | C | 280 | -63.751 | -50.872 | -6.976 | 1.00 | 21.28 |
| 12690 | C | TYR | C | 280 | -66.534 | -48.536 | -9.527 | 1.00 | 24.51 |
| 12691 | O | TYR | C | 280 | -67.636 | -48.375 | -9.007 | 1.00 | 26.24 |
| 12692 | N | SER | C | 281 | -66.185 | -47.967 | -10.674 | 1.00 | 25.25 |
| 12694 | CA | SER | C | 281 | -67.055 | -47.034 | -11.383 | 1.00 | 26.30 |
| 12696 | CB | SER | C | 281 | -66.296 | -46.377 | -12.543 | 1.00 | 26.33 |
| 12699 | OG | SER | C | 281 | -66.134 | -47.264 | -13.640 | 1.00 | 27.98 |
| 12701 | C | SER | C | 281 | -68.321 | -47.730 | -11.892 | 1.00 | 27.08 |
| 12702 | O | SER | C | 281 | -69.340 | -47.070 | -12.125 | 1.00 | 28.82 |
| 12703 | N | GLN | D | 20 | -43.213 | -49.029 | 9.812 | 1.00 | 35.53 |
| 12705 | CA | GLN | D | 20 | -41.978 | -49.181 | 10.621 | 1.00 | 34.93 |
| 12707 | CB | GLN | D | 20 | -42.035 | -48.238 | 11.830 | 1.00 | 34.67 |
| 12710 | CG | GLN | D | 20 | -43.417 | -48.133 | 12.450 | 1.00 | 32.05 |
| 12713 | CD | GLN | D | 20 | -44.329 | -47.149 | 11.730 | 1.00 | 28.53 |
| 12714 | OE1 | GLN | D | 20 | -43.888 | -46.079 | 11.296 | 1.00 | 21.34 |
| 12715 | NE2 | GLN | D | 20 | -45.610 | -47.500 | 11.624 | 1.00 | 26.91 |
| 12718 | C | GLN | D | 20 | -41.884 | -50.664 | 10.992 | 1.00 | 35.29 |
| 12719 | O | GLN | D | 20 | -42.195 | -51.506 | 10.147 | 1.00 | 36.37 |
| 12723 | N | GLN | D | 21 | -41.461 | -51.004 | 12.209 | 1.00 | 35.37 |
| 12725 | CA | GLN | D | 21 | -41.618 | -52.379 | 12.691 | 1.00 | 35.30 |
| 12727 | CB | GLN | D | 21 | -40.360 | -52.881 | 13.419 | 1.00 | 35.55 |
| 12730 | CG | GLN | D | 21 | -39.264 | -53.490 | 12.512 | 1.00 | 36.15 |
| 12733 | CD | GLN | D | 21 | -39.799 | -54.154 | 11.237 | 1.00 | 37.29 |
| 12734 | OE1 | GLN | D | 21 | -40.534 | -55.144 | 11.301 | 1.00 | 38.87 |
| 12735 | NE2 | GLN | D | 21 | -39.427 | -53.610 | 10.083 | 1.00 | 37.34 |
| 12738 | C | GLN | D | 21 | -42.852 | -52.468 | 13.596 | 1.00 | 34.93 |
| 12739 | O | GLN | D | 21 | -42.872 | -51.893 | 14.688 | 1.00 | 34.87 |

FIGURE 3 (cont.)

| A | B | C | D | E | F | G | H | I | J |
|---|---|---|---|---|---|---|---|---|---|
| 12740 | N | PRO | D | 22 | -43.882 | -53.182 | 13.142 | 1.00 | 34.50 |
| 12741 | CA | PRO | D | 22 | -45.117 | -53.318 | 13.919 | 1.00 | 34.20 |
| 12743 | CB | PRO | D | 22 | -46.113 | -53.885 | 12.899 | 1.00 | 34.39 |
| 12746 | CG | PRO | D | 22 | -45.277 | -54.629 | 11.907 | 1.00 | 34.47 |
| 12749 | CD | PRO | D | 22 | -43.940 | -53.944 | 11.878 | 1.00 | 34.59 |
| 12752 | C | PRO | D | 22 | -44.918 | -54.284 | 15.084 | 1.00 | 33.99 |
| 12753 | O | PRO | D | 22 | -44.163 | -55.248 | 14.943 | 1.00 | 33.57 |
| 12754 | N | LEU | D | 23 | -45.562 | -54.014 | 16.215 | 1.00 | 33.52 |
| 12756 | CA | LEU | D | 23 | -45.477 | -54.887 | 17.379 | 1.00 | 33.55 |
| 12758 | CB | LEU | D | 23 | -46.300 | -54.320 | 18.543 | 1.00 | 33.47 |
| 12761 | CG | LEU | D | 23 | -45.854 | -52.979 | 19.139 | 1.00 | 33.62 |
| 12763 | CD1 | LEU | D | 23 | -46.713 | -52.638 | 20.354 | 1.00 | 33.83 |
| 12767 | CD2 | LEU | D | 23 | -44.373 | -52.988 | 19.510 | 1.00 | 33.97 |
| 12771 | C | LEU | D | 23 | -45.981 | -56.282 | 17.023 | 1.00 | 33.51 |
| 12772 | O | LEU | D | 23 | -47.090 | -56.429 | 16.503 | 1.00 | 33.57 |
| 12773 | N | ASN | D | 24 | -45.159 | -57.294 | 17.300 | 1.00 | 33.61 |
| 12775 | CA | ASN | D | 24 | -45.513 | -58.686 | 17.024 | 1.00 | 33.72 |
| 12777 | CB | ASN | D | 24 | -44.250 | -59.513 | 16.748 | 1.00 | 33.80 |
| 12780 | CG | ASN | D | 24 | -44.561 | -60.944 | 16.332 | 1.00 | 34.30 |
| 12781 | OD1 | ASN | D | 24 | -45.577 | -61.216 | 15.686 | 1.00 | 35.34 |
| 12782 | ND2 | ASN | D | 24 | -43.685 | -61.868 | 16.707 | 1.00 | 34.97 |
| 12785 | C | ASN | D | 24 | -46.319 | -59.280 | 18.181 | 1.00 | 33.42 |
| 12786 | O | ASN | D | 24 | -45.826 | -60.102 | 18.951 | 1.00 | 33.61 |
| 12787 | N | GLU | D | 25 | -47.568 | -58.842 | 18.291 | 1.00 | 33.03 |
| 12789 | CA | GLU | D | 25 | -48.471 | -59.299 | 19.342 | 1.00 | 32.66 |
| 12791 | CB | GLU | D | 25 | -48.037 | -58.756 | 20.711 | 1.00 | 32.96 |
| 12794 | CG | GLU | D | 25 | -47.907 | -57.242 | 20.786 | 1.00 | 34.33 |
| 12797 | CD | GLU | D | 25 | -47.061 | -56.784 | 21.962 | 1.00 | 36.12 |
| 12798 | OE1 | GLU | D | 25 | -46.065 | -56.059 | 21.747 | 1.00 | 38.25 |
| 12799 | OE2 | GLU | D | 25 | -47.388 | -57.148 | 23.108 | 1.00 | 38.35 |
| 12800 | C | GLU | D | 25 | -49.903 | -58.868 | 19.029 | 1.00 | 31.73 |
| 12801 | O | GLU | D | 25 | -50.124 | -57.905 | 18.294 | 1.00 | 31.53 |
| 12802 | N | GLU | D | 26 | -50.874 | -59.589 | 19.579 | 1.00 | 30.53 |
| 12804 | CA | GLU | D | 26 | -52.275 | -59.235 | 19.382 | 1.00 | 29.77 |
| 12806 | CB | GLU | D | 26 | -53.200 | -60.407 | 19.747 | 1.00 | 30.39 |
| 12809 | CG | GLU | D | 26 | -53.310 | -61.477 | 18.665 | 1.00 | 32.33 |
| 12812 | CD | GLU | D | 26 | -54.023 | -60.988 | 17.412 | 1.00 | 35.21 |
| 12813 | OE1 | GLU | D | 26 | -55.215 | -60.611 | 17.502 | 1.00 | 36.80 |
| 12814 | OE2 | GLU | D | 26 | -53.390 | -60.975 | 16.329 | 1.00 | 37.60 |
| 12815 | C | GLU | D | 26 | -52.610 | -57.995 | 20.210 | 1.00 | 28.32 |
| 12816 | O | GLU | D | 26 | -52.026 | -57.762 | 21.274 | 1.00 | 27.63 |
| 12817 | N | PHE | D | 27 | -53.536 | -57.188 | 19.704 | 1.00 | 26.58 |
| 12819 | CA | PHE | D | 27 | -53.969 | -55.991 | 20.406 | 1.00 | 25.53 |
| 12821 | CB | PHE | D | 27 | -54.939 | -55.173 | 19.556 | 1.00 | 25.06 |
| 12824 | CG | PHE | D | 27 | -55.487 | -53.963 | 20.265 | 1.00 | 23.00 |
| 12825 | CD1 | PHE | D | 27 | -54.723 | -52.808 | 20.377 | 1.00 | 21.55 |
| 12827 | CE1 | PHE | D | 27 | -55.213 | -51.692 | 21.031 | 1.00 | 20.67 |
| 12829 | CZ | PHE | D | 27 | -56.486 | -51.720 | 21.589 | 1.00 | 21.35 |
| 12831 | CE2 | PHE | D | 27 | -57.253 | -52.867 | 21.492 | 1.00 | 22.05 |

FIGURE 3 (cont.)

| A | B | C | D | E | F | G | H | I | J |
|---|---|---|---|---|---|---|---|---|---|
| 12833 | CD2 | PHE | D | 27 | -56.755 | -53.984 | 20.839 | 1.00 | 22.19 |
| 12835 | C | PHE | D | 27 | -54.663 | -56.366 | 21.704 | 1.00 | 25.18 |
| 12836 | O | PHE | D | 27 | -55.423 | -57.338 | 21.755 | 1.00 | 24.81 |
| 12837 | N | ARG | D | 28 | -54.383 | -55.589 | 22.743 | 1.00 | 24.90 |
| 12839 | CA | ARG | D | 28 | -55.113 | -55.654 | 24.004 | 1.00 | 24.81 |
| 12841 | CB | ARG | D | 28 | -54.241 | -56.255 | 25.102 | 1.00 | 24.97 |
| 12844 | CG | ARG | D | 28 | -53.614 | -57.600 | 24.744 | 1.00 | 26.25 |
| 12847 | CD | ARG | D | 28 | -52.670 | -58.146 | 25.807 | 1.00 | 27.58 |
| 12850 | NE BARG | D | 28 | -51.515 | -57.265 | 26.015 | 0.35 | 27.81 |
| 12851 | NE AARG | D | 28 | -51.546 | -57.244 | 26.064 | 0.65 | 28.63 |
| 12854 | CZ BARG | D | 28 | -51.260 | -56.560 | 27.120 | 0.35 | 27.67 |
| 12855 | CZ AARG | D | 28 | -50.467 | -57.126 | 25.291 | 0.65 | 28.72 |
| 12856 | NH1BARG | D | 28 | -52.070 | -56.602 | 28.177 | 0.35 | 27.83 |
| 12857 | NH1AARG | D | 28 | -50.330 | -57.859 | 24.186 | 0.65 | 29.18 |
| 12862 | NH2BARG | D | 28 | -50.172 | -55.799 | 27.170 | 0.35 | 27.42 |
| 12863 | NH2AARG | D | 28 | -49.513 | -56.267 | 25.628 | 0.65 | 29.24 |
| 12868 | C | ARG | D | 28 | -55.513 | -54.226 | 24.376 | 1.00 | 24.36 |
| 12869 | O | ARG | D | 28 | -54.708 | -53.308 | 24.211 | 1.00 | 23.52 |
| 12870 | N | PRO | D | 29 | -56.736 | -54.027 | 24.869 | 1.00 | 24.25 |
| 12871 | CA | PRO | D | 29 | -57.178 | -52.683 | 25.275 | 1.00 | 24.18 |
| 12873 | CB | PRO | D | 29 | -58.615 | -52.903 | 25.774 | 1.00 | 24.40 |
| 12876 | CG | PRO | D | 29 | -58.769 | -54.372 | 25.968 | 1.00 | 24.63 |
| 12879 | CD | PRO | D | 29 | -57.792 | -55.040 | 25.061 | 1.00 | 24.44 |
| 12882 | C | PRO | D | 29 | -56.300 | -52.034 | 26.355 | 1.00 | 23.87 |
| 12883 | O | PRO | D | 29 | -56.269 | -50.804 | 26.443 | 1.00 | 23.79 |
| 12884 | N | GLU | D | 30 | -55.585 | -52.848 | 27.134 | 1.00 | 23.67 |
| 12886 | CA | GLU | D | 30 | -54.693 | -52.361 | 28.188 | 1.00 | 23.57 |
| 12888 | CB | GLU | D | 30 | -54.186 | -53.529 | 29.045 | 1.00 | 23.93 |
| 12891 | CG | GLU | D | 30 | -55.229 | -54.118 | 29.984 | 1.00 | 25.91 |
| 12894 | CD | GLU | D | 30 | -56.134 | -55.163 | 29.346 | 1.00 | 27.74 |
| 12895 | OE1 | GLU | D | 30 | -57.090 | -55.595 | 30.034 | 1.00 | 30.26 |
| 12896 | OE2 | GLU | D | 30 | -55.906 | -55.562 | 28.180 | 1.00 | 26.91 |
| 12897 | C | GLU | D | 30 | -53.497 | -51.587 | 27.635 | 1.00 | 22.81 |
| 12898 | O | GLU | D | 30 | -52.860 | -50.834 | 28.363 | 1.00 | 22.79 |
| 12899 | N | MET | D | 31 | -53.200 | -51.782 | 26.351 | 1.00 | 22.23 |
| 12901 | CA | MET | D | 31 | -52.141 | -51.047 | 25.661 | 1.00 | 21.45 |
| 12903 | CB | MET | D | 31 | -52.022 | -51.525 | 24.210 | 1.00 | 21.52 |
| 12906 | CG | MET | D | 31 | -51.484 | -52.934 | 24.050 | 1.00 | 21.00 |
| 12909 | SD | MET | D | 31 | -51.453 | -53.400 | 22.306 | 1.00 | 20.72 |
| 12910 | CE | MET | D | 31 | -50.291 | -54.786 | 22.343 | 1.00 | 21.39 |
| 12914 | C | MET | D | 31 | -52.370 | -49.533 | 25.656 | 1.00 | 20.96 |
| 12915 | O | MET | D | 31 | -51.422 | -48.769 | 25.498 | 1.00 | 21.26 |
| 12916 | N | LEU | D | 32 | -53.625 | -49.112 | 25.792 | 1.00 | 20.36 |
| 12918 | CA | LEU | D | 32 | -53.978 | -47.692 | 25.806 | 1.00 | 20.12 |
| 12920 | CB | LEU | D | 32 | -55.245 | -47.447 | 24.969 | 1.00 | 20.35 |
| 12923 | CG | LEU | D | 32 | -55.058 | -47.222 | 23.458 | 1.00 | 20.52 |
| 12925 | CD1 | LEU | D | 32 | -54.493 | -48.472 | 22.793 | 1.00 | 21.37 |
| 12929 | CD2 | LEU | D | 32 | -54.178 | -46.008 | 23.181 | 1.00 | 21.68 |
| 12933 | C | LEU | D | 32 | -54.197 | -47.167 | 27.224 | 1.00 | 19.78 |

FIGURE 3 (cont.)

| A | B | C | D | E | F | G | H | I | J |
|---|---|---|---|---|---|---|---|---|---|
| 12934 | O | LEU | D | 32 | -54.412 | -45.982 | 27.417 | 1.00 | 19.56 |
| 12935 | N | GLN | D | 33 | -54.152 | -48.047 | 28.219 | 1.00 | 19.69 |
| 12937 | CA | GLN | D | 33 | -54.401 | -47.637 | 29.596 | 1.00 | 19.88 |
| 12939 | CB | GLN | D | 33 | -54.389 | -48.861 | 30.509 | 1.00 | 20.14 |
| 12942 | CG | GLN | D | 33 | -55.053 | -48.665 | 31.834 | 1.00 | 22.57 |
| 12945 | CD | GLN | D | 33 | -55.217 | -49.984 | 32.561 | 1.00 | 25.03 |
| 12946 | OE1 | GLN | D | 33 | -56.333 | -50.485 | 32.711 | 1.00 | 27.96 |
| 12947 | NE2 | GLN | D | 33 | -54.101 | -50.568 | 32.983 | 1.00 | 27.57 |
| 12950 | C | GLN | D | 33 | -53.353 | -46.630 | 30.060 | 1.00 | 19.21 |
| 12951 | O | GLN | D | 33 | -52.160 | -46.901 | 30.000 | 1.00 | 19.74 |
| 12952 | N | GLY | D | 34 | -53.802 | -45.451 | 30.480 | 1.00 | 18.80 |
| 12954 | CA | GLY | D | 34 | -52.910 | -44.407 | 30.958 | 1.00 | 18.55 |
| 12957 | C | GLY | D | 34 | -52.144 | -43.667 | 29.878 | 1.00 | 18.12 |
| 12958 | O | GLY | D | 34 | -51.325 | -42.801 | 30.185 | 1.00 | 18.38 |
| 12959 | N | LYS | D | 35 | -52.401 | -44.000 | 28.615 | 1.00 | 17.40 |
| 12961 | CA | LYS | D | 35 | -51.736 | -43.330 | 27.504 | 1.00 | 17.08 |
| 12963 | CB | LYS | D | 35 | -51.801 | -44.179 | 26.231 | 1.00 | 17.28 |
| 12966 | CG | LYS | D | 35 | -51.079 | -45.515 | 26.337 | 1.00 | 18.28 |
| 12969 | CD | LYS | D | 35 | -49.587 | -45.340 | 26.554 | 1.00 | 20.33 |
| 12972 | CE | LYS | D | 35 | -48.887 | -46.665 | 26.760 | 1.00 | 22.38 |
| 12975 | NZ | LYS | D | 35 | -47.484 | -46.443 | 27.215 | 1.00 | 24.78 |
| 12979 | C | LYS | D | 35 | -52.372 | -41.969 | 27.269 | 1.00 | 16.45 |
| 12980 | O | LYS | D | 35 | -53.555 | -41.771 | 27.520 | 1.00 | 17.02 |
| 12981 | N | LYS | D | 36 | -51.568 | -41.042 | 26.765 | 1.00 | 15.85 |
| 12983 | CA | LYS | D | 36 | -51.960 | -39.653 | 26.608 | 1.00 | 15.43 |
| 12985 | CB | LYS | D | 36 | -50.847 | -38.748 | 27.139 | 1.00 | 15.49 |
| 12988 | CG | LYS | D | 36 | -50.626 | -38.925 | 28.653 | 1.00 | 16.39 |
| 12991 | CD | LYS | D | 36 | -49.262 | -38.453 | 29.106 | 1.00 | 18.44 |
| 12994 | CE | LYS | D | 36 | -49.045 | -38.837 | 30.566 | 1.00 | 20.24 |
| 12997 | NZ | LYS | D | 36 | -47.824 | -38.208 | 31.135 | 1.00 | 22.80 |
| 13001 | C | LYS | D | 36 | -52.214 | -39.414 | 25.138 | 1.00 | 15.40 |
| 13002 | O | LYS | D | 36 | -51.291 | -39.487 | 24.347 | 1.00 | 15.35 |
| 13003 | N | VAL | D | 37 | -53.465 | -39.159 | 24.779 | 1.00 | 14.89 |
| 13005 | CA | VAL | D | 37 | -53.872 | -39.149 | 23.376 | 1.00 | 14.49 |
| 13007 | CB | VAL | D | 37 | -54.729 | -40.385 | 23.037 | 1.00 | 14.54 |
| 13009 | CG1 | VAL | D | 37 | -54.947 | -40.490 | 21.524 | 1.00 | 15.16 |
| 13013 | CG2 | VAL | D | 37 | -54.083 | -41.655 | 23.578 | 1.00 | 15.88 |
| 13017 | C | VAL | D | 37 | -54.650 | -37.895 | 22.983 | 1.00 | 14.45 |
| 13018 | O | VAL | D | 37 | -55.582 | -37.485 | 23.671 | 1.00 | 14.07 |
| 13019 | N | ILE | D | 38 | -54.246 | -37.293 | 21.867 | 1.00 | 14.15 |
| 13021 | CA | ILE | D | 38 | -54.984 | -36.213 | 21.219 | 1.00 | 14.29 |
| 13023 | CB | ILE | D | 38 | -54.008 | -35.189 | 20.602 | 1.00 | 14.22 |
| 13025 | CG1 | ILE | D | 38 | -53.410 | -34.294 | 21.692 | 1.00 | 14.47 |
| 13028 | CD1 | ILE | D | 38 | -52.240 | -33.464 | 21.208 | 1.00 | 13.47 |
| 13032 | CG2 | ILE | D | 38 | -54.694 | -34.353 | 19.479 | 1.00 | 13.72 |
| 13036 | C | ILE | D | 38 | -55.823 | -36.835 | 20.119 | 1.00 | 14.66 |
| 13037 | O | ILE | D | 38 | -55.313 | -37.652 | 19.346 | 1.00 | 14.40 |
| 13038 | N | VAL | D | 39 | -57.093 | -36.446 | 20.043 | 1.00 | 14.41 |
| 13040 | CA | VAL | D | 39 | -57.940 | -36.792 | 18.901 | 1.00 | 14.71 |

FIGURE 3 (cont.)

| A | B | C | D | E | F | G | H | I | J |
|---|---|---|---|---|---|---|---|---|---|
| 13042 | CB | VAL | D | 39 | -59.115 | -37.704 | 19.289 | 1.00 | 14.96 |
| 13044 | CG1 | VAL | D | 39 | -59.796 | -38.237 | 18.030 | 1.00 | 15.66 |
| 13048 | CG2 | VAL | D | 39 | -58.638 | -38.832 | 20.178 | 1.00 | 15.63 |
| 13052 | C | VAL | D | 39 | -58.490 | -35.502 | 18.309 | 1.00 | 14.26 |
| 13053 | O | VAL | D | 39 | -59.143 | -34.727 | 19.001 | 1.00 | 14.39 |
| 13054 | N | THR | D | 40 | -58.216 | -35.250 | 17.032 | 1.00 | 13.79 |
| 13056 | CA | THR | D | 40 | -58.815 | -34.097 | 16.374 | 1.00 | 13.70 |
| 13058 | CB | THR | D | 40 | -57.830 | -33.372 | 15.443 | 1.00 | 13.33 |
| 13060 | OG1 | THR | D | 40 | -57.631 | -34.126 | 14.240 | 1.00 | 14.34 |
| 13062 | CG2 | THR | D | 40 | -56.455 | -33.245 | 16.047 | 1.00 | 13.29 |
| 13066 | C | THR | D | 40 | -60.057 | -34.532 | 15.609 | 1.00 | 13.41 |
| 13067 | O | THR | D | 40 | -60.292 | -35.722 | 15.390 | 1.00 | 13.63 |
| 13068 | N | GLY | D | 41 | -60.853 | -33.556 | 15.210 | 1.00 | 13.42 |
| 13070 | CA | GLY | D | 41 | -62.152 | -33.813 | 14.620 | 1.00 | 14.27 |
| 13073 | C | GLY | D | 41 | -62.972 | -34.779 | 15.449 | 1.00 | 14.75 |
| 13074 | O | GLY | D | 41 | -63.550 | -35.712 | 14.906 | 1.00 | 15.02 |
| 13075 | N | ALA | D | 42 | -63.043 | -34.527 | 16.759 | 1.00 | 15.40 |
| 13077 | CA | ALA | D | 42 | -63.594 | -35.478 | 17.729 | 1.00 | 15.81 |
| 13079 | CB | ALA | D | 42 | -62.605 | -35.659 | 18.855 | 1.00 | 16.55 |
| 13083 | C | ALA | D | 42 | -64.981 | -35.129 | 18.295 | 1.00 | 16.04 |
| 13084 | O | ALA | D | 42 | -65.448 | -35.773 | 19.239 | 1.00 | 16.36 |
| 13085 | N | SER | D | 43 | -65.640 | -34.128 | 17.726 | 1.00 | 16.06 |
| 13087 | CA | SER | D | 43 | -66.986 | -33.747 | 18.165 | 1.00 | 16.28 |
| 13089 | CB | SER | D | 43 | -67.280 | -32.308 | 17.765 | 1.00 | 16.60 |
| 13092 | OG | SER | D | 43 | -67.218 | -32.140 | 16.361 | 1.00 | 16.23 |
| 13094 | C | SER | D | 43 | -68.083 | -34.661 | 17.605 | 1.00 | 16.50 |
| 13095 | O | SER | D | 43 | -69.197 | -34.711 | 18.143 | 1.00 | 16.79 |
| 13096 | N | LYS | D | 44 | -67.788 | -35.339 | 16.498 | 1.00 | 15.89 |
| 13098 | CA | LYS | D | 44 | -68.731 | -36.259 | 15.868 | 1.00 | 15.95 |
| 13100 | CB | LYS | D | 44 | -69.754 | -35.486 | 15.032 | 1.00 | 16.60 |
| 13103 | CG | LYS | D | 44 | -69.176 | -34.691 | 13.867 | 1.00 | 17.76 |
| 13106 | CD | LYS | D | 44 | -70.256 | -33.846 | 13.187 | 1.00 | 19.81 |
| 13109 | CE | LYS | D | 44 | -69.735 | -33.132 | 11.949 | 1.00 | 21.72 |
| 13112 | NZ | LYS | D | 44 | -70.765 | -32.221 | 11.366 | 1.00 | 23.31 |
| 13116 | C | LYS | D | 44 | -67.987 | -37.287 | 15.006 | 1.00 | 15.31 |
| 13117 | O | LYS | D | 44 | -66.756 | -37.295 | 14.979 | 1.00 | 14.54 |
| 13118 | N | GLY | D | 45 | -68.739 | -38.174 | 14.356 | 1.00 | 15.02 |
| 13120 | CA | GLY | D | 45 | -68.172 | -39.125 | 13.405 | 1.00 | 15.06 |
| 13123 | C | GLY | D | 45 | -67.183 | -40.094 | 14.024 | 1.00 | 14.94 |
| 13124 | O | GLY | D | 45 | -67.291 | -40.477 | 15.197 | 1.00 | 15.10 |
| 13125 | N | ILE | D | 46 | -66.205 | -40.497 | 13.223 | 1.00 | 14.50 |
| 13127 | CA | ILE | D | 46 | -65.190 | -41.444 | 13.651 | 1.00 | 14.49 |
| 13129 | CB | ILE | D | 46 | -64.298 | -41.834 | 12.440 | 1.00 | 14.34 |
| 13131 | CG1 | ILE | D | 46 | -65.152 | -42.521 | 11.369 | 1.00 | 14.52 |
| 13134 | CD1 | ILE | D | 46 | -64.619 | -42.340 | 9.962 | 1.00 | 15.30 |
| 13138 | CG2 | ILE | D | 46 | -63.172 | -42.759 | 12.854 | 1.00 | 15.39 |
| 13142 | C | ILE | D | 46 | -64.362 | -40.902 | 14.819 | 1.00 | 14.22 |
| 13143 | O | ILE | D | 46 | -64.015 | -41.648 | 15.725 | 1.00 | 14.26 |
| 13144 | N | GLY | D | 47 | -64.062 | -39.605 | 14.798 | 1.00 | 14.29 |

FIGURE 3 (cont.)

| A | B | C | D | E | F | G | H | I | J |
|---|---|---|---|---|---|---|---|---|---|
| 13146 | CA | GLY | D | 47 | -63.269 | -38.971 | 15.836 | 1.00 | 14.10 |
| 13149 | C | GLY | D | 47 | -63.913 | -39.107 | 17.209 | 1.00 | 14.14 |
| 13150 | O | GLY | D | 47 | -63.254 | -39.467 | 18.178 | 1.00 | 14.08 |
| 13151 | N | ARG | D | 48 | -65.207 | -38.816 | 17.277 | 1.00 | 14.17 |
| 13153 | CA | ARG | D | 48 | -65.954 | -38.994 | 18.528 | 1.00 | 14.45 |
| 13155 | CB | ARG | D | 48 | -67.413 | -38.587 | 18.337 | 1.00 | 14.52 |
| 13158 | CG | ARG | D | 48 | -68.269 | -38.703 | 19.591 | 1.00 | 16.48 |
| 13161 | CD | ARG | D | 48 | -69.612 | -38.029 | 19.458 | 1.00 | 18.45 |
| 13164 | NE | ARG | D | 48 | -70.364 | -38.565 | 18.326 | 1.00 | 21.04 |
| 13166 | CZ | ARG | D | 48 | -71.458 | -38.012 | 17.815 | 1.00 | 23.54 |
| 13167 | NH1 | ARG | D | 48 | -71.977 | -36.909 | 18.349 | 1.00 | 25.29 |
| 13170 | NH2 | ARG | D | 48 | -72.052 | -38.574 | 16.766 | 1.00 | 24.30 |
| 13173 | C | ARG | D | 48 | -65.885 | -40.443 | 19.002 | 1.00 | 14.84 |
| 13174 | O | ARG | D | 48 | -65.648 | -40.695 | 20.184 | 1.00 | 15.19 |
| 13175 | N | GLU | D | 49 | -66.110 | -41.387 | 18.093 | 1.00 | 14.91 |
| 13177 | CA | GLU | D | 49 | -66.038 | -42.811 | 18.438 | 1.00 | 15.16 |
| 13179 | CB | GLU | D | 49 | -66.484 | -43.696 | 17.268 | 1.00 | 15.73 |
| 13182 | CG | GLU | D | 49 | -67.925 | -43.500 | 16.802 | 1.00 | 17.94 |
| 13185 | CD | GLU | D | 49 | -68.955 | -43.646 | 17.908 | 1.00 | 21.21 |
| 13186 | OE1 | GLU | D | 49 | -69.940 | -42.870 | 17.923 | 1.00 | 22.92 |
| 13187 | OE2 | GLU | D | 49 | -68.790 | -44.539 | 18.759 | 1.00 | 23.86 |
| 13188 | C | GLU | D | 49 | -64.651 | -43.242 | 18.910 | 1.00 | 14.85 |
| 13189 | O | GLU | D | 49 | -64.539 | -44.119 | 19.758 | 1.00 | 14.65 |
| 13190 | N | MET | D | 50 | -63.596 | -42.638 | 18.362 | 1.00 | 14.23 |
| 13192 | CA | MET | D | 50 | -62.235 | -42.926 | 18.815 | 1.00 | 14.22 |
| 13194 | CB | MET | D | 50 | -61.187 | -42.342 | 17.864 | 1.00 | 14.64 |
| 13197 | CG | MET | D | 50 | -61.053 | -43.142 | 16.593 | 1.00 | 14.82 |
| 13200 | SD | MET | D | 50 | -59.683 | -42.626 | 15.549 | 1.00 | 15.26 |
| 13201 | CE | MET | D | 50 | -60.229 | -41.022 | 15.048 | 1.00 | 16.09 |
| 13205 | C | MET | D | 50 | -62.045 | -42.408 | 20.244 | 1.00 | 14.35 |
| 13206 | O | MET | D | 50 | -61.486 | -43.108 | 21.083 | 1.00 | 13.96 |
| 13207 | N | ALA | D | 51 | -62.522 | -41.199 | 20.524 | 1.00 | 14.65 |
| 13209 | CA | ALA | D | 51 | -62.464 | -40.661 | 21.888 | 1.00 | 14.97 |
| 13211 | CB | ALA | D | 51 | -63.086 | -39.281 | 21.950 | 1.00 | 15.27 |
| 13215 | C | ALA | D | 51 | -63.147 | -41.588 | 22.877 | 1.00 | 14.95 |
| 13216 | O | ALA | D | 51 | -62.615 | -41.853 | 23.947 | 1.00 | 15.58 |
| 13217 | N | TYR | D | 52 | -64.313 | -42.095 | 22.506 | 1.00 | 14.90 |
| 13219 | CA | TYR | D | 52 | -65.067 | -42.984 | 23.389 | 1.00 | 14.93 |
| 13221 | CB | TYR | D | 52 | -66.468 | -43.222 | 22.829 | 1.00 | 15.14 |
| 13224 | CG | TYR | D | 52 | -67.398 | -42.019 | 22.889 | 1.00 | 15.78 |
| 13225 | CD1 | TYR | D | 52 | -67.058 | -40.863 | 23.590 | 1.00 | 15.69 |
| 13227 | CE1 | TYR | D | 52 | -67.913 | -39.769 | 23.625 | 1.00 | 17.43 |
| 13229 | CZ | TYR | D | 52 | -69.115 | -39.822 | 22.970 | 1.00 | 16.96 |
| 13230 | OH | TYR | D | 52 | -69.959 | -38.734 | 23.036 | 1.00 | 21.07 |
| 13232 | CE2 | TYR | D | 52 | -69.485 | -40.957 | 22.278 | 1.00 | 17.19 |
| 13234 | CD2 | TYR | D | 52 | -68.622 | -42.044 | 22.235 | 1.00 | 17.16 |
| 13236 | C | TYR | D | 52 | -64.348 | -44.313 | 23.627 | 1.00 | 15.41 |
| 13237 | O | TYR | D | 52 | -64.324 | -44.805 | 24.750 | 1.00 | 15.63 |
| 13238 | N | HIS | D | 53 | -63.760 | -44.896 | 22.585 | 1.00 | 15.29 |

FIGURE 3 (cont.)

| A | B | C | D | E | F | G | H | I | J |
|---|---|---|---|---|---|---|---|---|---|
| 13240 | CA  | HIS | D | 53 | -63.002 | -46.135 | 22.742 | 1.00 | 15.88 |
| 13242 | CB  | HIS | D | 53 | -62.509 | -46.666 | 21.388 | 1.00 | 15.92 |
| 13245 | CG  | HIS | D | 53 | -63.524 | -47.470 | 20.647 | 1.00 | 17.59 |
| 13246 | ND1 | HIS | D | 53 | -64.079 | -48.625 | 21.157 | 1.00 | 19.23 |
| 13248 | CE1 | HIS | D | 53 | -64.932 | -49.123 | 20.280 | 1.00 | 19.57 |
| 13250 | NE2 | HIS | D | 53 | -64.947 | -48.338 | 19.220 | 1.00 | 19.83 |
| 13252 | CD2 | HIS | D | 53 | -64.077 | -47.296 | 19.423 | 1.00 | 19.48 |
| 13254 | C   | HIS | D | 53 | -61.808 | -45.913 | 23.656 | 1.00 | 15.70 |
| 13255 | O   | HIS | D | 53 | -61.502 | -46.751 | 24.496 | 1.00 | 15.89 |
| 13256 | N   | LEU | D | 54 | -61.131 | -44.781 | 23.486 | 1.00 | 15.83 |
| 13258 | CA  | LEU | D | 54 | -59.958 | -44.464 | 24.280 | 1.00 | 15.68 |
| 13260 | CB  | LEU | D | 54 | -59.278 | -43.194 | 23.771 | 1.00 | 15.77 |
| 13263 | CG  | LEU | D | 54 | -58.540 | -43.418 | 22.452 | 1.00 | 15.44 |
| 13265 | CD1 | LEU | D | 54 | -58.229 | -42.078 | 21.791 | 1.00 | 15.31 |
| 13269 | CD2 | LEU | D | 54 | -57.262 | -44.231 | 22.679 | 1.00 | 16.16 |
| 13273 | C   | LEU | D | 54 | -60.373 | -44.290 | 25.730 | 1.00 | 15.87 |
| 13274 | O   | LEU | D | 54 | -59.678 | -44.742 | 26.639 | 1.00 | 16.62 |
| 13275 | N   | ALA | D | 55 | -61.533 | -43.678 | 25.919 | 1.00 | 16.59 |
| 13277 | CA  | ALA | D | 55 | -62.096 | -43.451 | 27.249 | 1.00 | 17.08 |
| 13279 | CB  | ALA | D | 55 | -63.383 | -42.650 | 27.148 | 1.00 | 17.31 |
| 13283 | C   | ALA | D | 55 | -62.351 | -44.787 | 27.948 | 1.00 | 17.76 |
| 13284 | O   | ALA | D | 55 | -61.937 | -44.978 | 29.086 | 1.00 | 17.71 |
| 13285 | N   | LYS | D | 56 | -62.996 | -45.718 | 27.245 | 1.00 | 18.33 |
| 13287 | CA  | LYS | D | 56 | -63.267 | -47.063 | 27.769 | 1.00 | 19.06 |
| 13289 | CB  | LYS | D | 56 | -64.063 | -47.881 | 26.748 | 1.00 | 19.43 |
| 13292 | CG  | LYS | D | 56 | -65.515 | -47.470 | 26.606 | 1.00 | 22.17 |
| 13295 | CD  | LYS | D | 56 | -66.254 | -48.340 | 25.588 | 1.00 | 25.20 |
| 13298 | CE  | LYS | D | 56 | -67.682 | -47.836 | 25.388 | 1.00 | 27.07 |
| 13301 | NZ  | LYS | D | 56 | -68.540 | -48.779 | 24.609 | 1.00 | 28.97 |
| 13305 | C   | LYS | D | 56 | -61.988 | -47.825 | 28.131 | 1.00 | 19.01 |
| 13306 | O   | LYS | D | 56 | -61.987 | -48.648 | 29.049 | 1.00 | 19.09 |
| 13307 | N   | MET | D | 57 | -60.906 | -47.553 | 27.405 | 1.00 | 18.87 |
| 13309 | CA  | MET | D | 57 | -59.606 | -48.174 | 27.663 | 1.00 | 18.94 |
| 13311 | CB  | MET | D | 57 | -58.767 | -48.195 | 26.380 | 1.00 | 19.22 |
| 13314 | CG  | MET | D | 57 | -59.347 | -49.060 | 25.285 | 1.00 | 20.67 |
| 13317 | SD  | MET | D | 57 | -58.430 | -48.919 | 23.737 | 1.00 | 25.77 |
| 13318 | CE  | MET | D | 57 | -59.684 | -49.364 | 22.550 | 1.00 | 25.96 |
| 13322 | C   | MET | D | 57 | -58.813 | -47.489 | 28.788 | 1.00 | 18.40 |
| 13323 | O   | MET | D | 57 | -57.730 | -47.941 | 29.149 | 1.00 | 18.23 |
| 13324 | N   | GLY | D | 58 | -59.337 | -46.393 | 29.331 | 1.00 | 17.89 |
| 13326 | CA  | GLY | D | 58 | -58.696 | -45.709 | 30.444 | 1.00 | 17.48 |
| 13329 | C   | GLY | D | 58 | -57.554 | -44.804 | 30.031 | 1.00 | 17.04 |
| 13330 | O   | GLY | D | 58 | -56.611 | -44.593 | 30.792 | 1.00 | 16.65 |
| 13331 | N   | ALA | D | 59 | -57.632 | -44.269 | 28.815 | 1.00 | 16.84 |
| 13333 | CA  | ALA | D | 59 | -56.649 | -43.308 | 28.348 | 1.00 | 16.40 |
| 13335 | CB  | ALA | D | 59 | -56.627 | -43.276 | 26.821 | 1.00 | 16.37 |
| 13339 | C   | ALA | D | 59 | -56.951 | -41.915 | 28.885 | 1.00 | 16.52 |
| 13340 | O   | ALA | D | 59 | -58.061 | -41.638 | 29.345 | 1.00 | 16.65 |
| 13341 | N   | HIS | D | 60 | -55.935 | -41.059 | 28.841 | 1.00 | 16.33 |

FIGURE 3 (cont.)

| A | B | C | D | E | F | G | H | I | J |
|---|---|---|---|---|---|---|---|---|---|
| 13343 | CA  | HIS | D | 60 | -56.117 | -39.622 | 28.970 | 1.00 | 16.43 |
| 13345 | CB  | HIS | D | 60 | -54.853 | -38.962 | 29.493 | 1.00 | 16.81 |
| 13348 | CG  | HIS | D | 60 | -54.433 | -39.419 | 30.851 | 1.00 | 17.95 |
| 13349 | ND1 | HIS | D | 60 | -54.571 | -38.627 | 31.969 | 1.00 | 20.59 |
| 13351 | CE1 | HIS | D | 60 | -54.094 | -39.268 | 33.019 | 1.00 | 20.83 |
| 13353 | NE2 | HIS | D | 60 | -53.653 | -40.449 | 32.626 | 1.00 | 21.30 |
| 13355 | CD2 | HIS | D | 60 | -53.846 | -40.564 | 31.269 | 1.00 | 19.18 |
| 13357 | C   | HIS | D | 60 | -56.374 | -39.082 | 27.577 | 1.00 | 16.45 |
| 13358 | O   | HIS | D | 60 | -55.618 | -39.398 | 26.656 | 1.00 | 15.81 |
| 13359 | N   | VAL | D | 61 | -57.416 | -38.278 | 27.412 | 1.00 | 16.32 |
| 13361 | CA  | VAL | D | 61 | -57.748 | -37.751 | 26.090 | 1.00 | 16.73 |
| 13363 | CB  | VAL | D | 61 | -59.011 | -38.418 | 25.476 | 1.00 | 17.29 |
| 13365 | CG1 | VAL | D | 61 | -58.870 | -39.942 | 25.475 | 1.00 | 18.64 |
| 13369 | CG2 | VAL | D | 61 | -60.268 | -38.012 | 26.200 | 1.00 | 17.82 |
| 13373 | C   | VAL | D | 61 | -57.914 | -36.246 | 26.114 | 1.00 | 16.32 |
| 13374 | O   | VAL | D | 61 | -58.416 | -35.681 | 27.078 | 1.00 | 15.58 |
| 13375 | N   | VAL | D | 62 | -57.435 | -35.603 | 25.057 | 1.00 | 15.37 |
| 13377 | CA  | VAL | D | 62 | -57.749 | -34.214 | 24.758 | 1.00 | 15.64 |
| 13379 | CB  | VAL | D | 62 | -56.513 | -33.296 | 24.819 | 1.00 | 15.33 |
| 13381 | CG1 | VAL | D | 62 | -56.881 | -31.873 | 24.407 | 1.00 | 15.18 |
| 13385 | CG2 | VAL | D | 62 | -55.901 | -33.297 | 26.227 | 1.00 | 16.56 |
| 13389 | C   | VAL | D | 62 | -58.350 | -34.204 | 23.359 | 1.00 | 15.53 |
| 13390 | O   | VAL | D | 62 | -57.717 | -34.655 | 22.391 | 1.00 | 16.35 |
| 13391 | N   | VAL | D | 63 | -59.584 | -33.723 | 23.268 | 1.00 | 15.31 |
| 13393 | CA  | VAL | D | 63 | -60.319 | -33.693 | 22.016 | 1.00 | 15.13 |
| 13395 | CB  | VAL | D | 63 | -61.727 | -34.322 | 22.157 | 1.00 | 15.50 |
| 13397 | CG1 | VAL | D | 63 | -62.531 | -33.647 | 23.253 | 1.00 | 16.05 |
| 13401 | CG2 | VAL | D | 63 | -61.622 | -35.820 | 22.417 | 1.00 | 15.61 |
| 13405 | C   | VAL | D | 63 | -60.407 | -32.265 | 21.509 | 1.00 | 15.30 |
| 13406 | O   | VAL | D | 63 | -60.385 | -31.306 | 22.289 | 1.00 | 15.00 |
| 13407 | N   | THR | D | 64 | -60.486 | -32.124 | 20.193 | 1.00 | 14.80 |
| 13409 | CA  | THR | D | 64 | -60.665 | -30.820 | 19.584 | 1.00 | 14.93 |
| 13411 | CB  | THR | D | 64 | -59.286 | -30.148 | 19.304 | 1.00 | 15.17 |
| 13413 | OG1 | THR | D | 64 | -59.465 | -28.805 | 18.826 | 1.00 | 14.85 |
| 13415 | CG2 | THR | D | 64 | -58.520 | -30.860 | 18.199 | 1.00 | 14.72 |
| 13419 | C   | THR | D | 64 | -61.560 | -30.910 | 18.350 | 1.00 | 15.11 |
| 13420 | O   | THR | D | 64 | -61.747 | -31.987 | 17.765 | 1.00 | 15.38 |
| 13421 | N   | ALA | D | 65 | -62.139 | -29.755 | 18.035 | 1.00 | 14.88 |
| 13423 | CA  | ALA | D | 65 | -63.042 | -29.487 | 16.912 | 1.00 | 15.56 |
| 13425 | CB  | ALA | D | 65 | -64.260 | -30.383 | 16.933 | 1.00 | 15.43 |
| 13429 | C   | ALA | D | 65 | -63.436 | -28.022 | 17.119 | 1.00 | 16.24 |
| 13430 | O   | ALA | D | 65 | -62.909 | -27.378 | 18.017 | 1.00 | 16.32 |
| 13431 | N   | ARG | D | 66 | -64.360 | -27.495 | 16.328 | 1.00 | 17.07 |
| 13433 | CA  | ARG | D | 66 | -64.681 | -26.068 | 16.427 | 1.00 | 18.47 |
| 13435 | CB  | ARG | D | 66 | -65.158 | -25.510 | 15.092 | 1.00 | 18.10 |
| 13438 | CG  | ARG | D | 66 | -64.067 | -25.449 | 14.028 | 1.00 | 17.70 |
| 13441 | CD  | ARG | D | 66 | -64.594 | -25.105 | 12.649 | 1.00 | 18.24 |
| 13444 | NE  | ARG | D | 66 | -65.542 | -26.119 | 12.192 | 1.00 | 18.56 |
| 13446 | CZ  | ARG | D | 66 | -66.310 | -26.010 | 11.120 | 1.00 | 18.54 |

FIGURE 3 (cont.)

| A | B | C | D | E | F | G | H | I | J |
|---|---|---|---|---|---|---|---|---|---|
| 13447 | NH1 | ARG | D | 66 | -67.146 | -26.994 | 10.819 | 1.00 | 19.00 |
| 13450 | NH2 | ARG | D | 66 | -66.234 | -24.944 | 10.328 | 1.00 | 20.56 |
| 13453 | C | ARG | D | 66 | -65.735 | -25.782 | 17.488 | 1.00 | 20.21 |
| 13454 | O | ARG | D | 66 | -65.750 | -24.686 | 18.057 | 1.00 | 20.65 |
| 13455 | N | SER | D | 67 | -66.607 | -26.758 | 17.737 | 1.00 | 22.28 |
| 13457 | CA | SER | D | 67 | -67.815 | -26.541 | 18.541 | 1.00 | 24.10 |
| 13459 | CB | SER | D | 67 | -68.975 | -27.341 | 17.947 | 1.00 | 24.32 |
| 13462 | OG | SER | D | 67 | -70.126 | -27.269 | 18.768 | 1.00 | 26.98 |
| 13464 | C | SER | D | 67 | -67.616 | -26.925 | 20.005 | 1.00 | 25.02 |
| 13465 | O | SER | D | 67 | -67.574 | -28.104 | 20.338 | 1.00 | 25.05 |
| 13466 | N | LYS | D | 68 | -67.507 | -25.922 | 20.872 | 1.00 | 25.92 |
| 13468 | CA | LYS | D | 68 | -67.275 | -26.153 | 22.297 | 1.00 | 26.88 |
| 13470 | CB | LYS | D | 68 | -66.959 | -24.837 | 23.027 | 1.00 | 27.37 |
| 13473 | CG | LYS | D | 68 | -68.146 | -23.895 | 23.209 | 1.00 | 29.09 |
| 13476 | CD | LYS | D | 68 | -67.703 | -22.453 | 23.458 | 1.00 | 30.27 |
| 13479 | CE | LYS | D | 68 | -68.730 | -21.445 | 22.932 | 1.00 | 31.55 |
| 13482 | NZ | LYS | D | 68 | -68.798 | -20.217 | 23.778 | 1.00 | 31.94 |
| 13486 | C | LYS | D | 68 | -68.444 | -26.875 | 22.969 | 1.00 | 26.67 |
| 13487 | O | LYS | D | 68 | -68.230 | -27.670 | 23.876 | 1.00 | 26.79 |
| 13488 | N | GLU | D | 69 | -69.666 | -26.613 | 22.511 | 1.00 | 26.67 |
| 13490 | CA | GLU | D | 69 | -70.856 | -27.231 | 23.095 | 1.00 | 26.60 |
| 13492 | CB | GLU | D | 69 | -72.136 | -26.647 | 22.480 | 1.00 | 27.13 |
| 13495 | CG | GLU | D | 69 | -72.463 | -25.228 | 22.933 | 1.00 | 28.84 |
| 13498 | CD | GLU | D | 69 | -71.828 | -24.141 | 22.079 | 1.00 | 30.87 |
| 13499 | OE1 | GLU | D | 69 | -72.010 | -22.951 | 22.421 | 1.00 | 32.20 |
| 13500 | OE2 | GLU | D | 69 | -71.148 | -24.460 | 21.072 | 1.00 | 32.91 |
| 13501 | C | GLU | D | 69 | -70.843 | -28.744 | 22.900 | 1.00 | 26.03 |
| 13502 | O | GLU | D | 69 | -71.096 | -29.503 | 23.845 | 1.00 | 25.84 |
| 13503 | N | THR | D | 70 | -70.552 | -29.170 | 21.672 | 1.00 | 24.98 |
| 13505 | CA | THR | D | 70 | -70.530 | -30.591 | 21.333 | 1.00 | 24.44 |
| 13507 | CB | THR | D | 70 | -70.556 | -30.818 | 19.803 | 1.00 | 24.55 |
| 13509 | OG1 | THR | D | 70 | -69.490 | -30.099 | 19.163 | 1.00 | 26.54 |
| 13511 | CG2 | THR | D | 70 | -71.821 | -30.240 | 19.190 | 1.00 | 23.88 |
| 13515 | C | THR | D | 70 | -69.323 | -31.270 | 21.958 | 1.00 | 23.28 |
| 13516 | O | THR | D | 70 | -69.424 | -32.402 | 22.405 | 1.00 | 23.33 |
| 13517 | N | LEU | D | 71 | -68.192 | -30.568 | 22.007 | 1.00 | 21.87 |
| 13519 | CA | LEU | D | 71 | -66.982 | -31.107 | 22.623 | 1.00 | 21.18 |
| 13521 | CB | LEU | D | 71 | -65.787 | -30.171 | 22.412 | 1.00 | 20.87 |
| 13524 | CG | LEU | D | 71 | -65.157 | -30.163 | 21.014 | 1.00 | 20.02 |
| 13526 | CD1 | LEU | D | 71 | -64.173 | -29.013 | 20.898 | 1.00 | 19.62 |
| 13530 | CD2 | LEU | D | 71 | -64.466 | -31.501 | 20.710 | 1.00 | 19.65 |
| 13534 | C | LEU | D | 71 | -67.171 | -31.342 | 24.118 | 1.00 | 21.23 |
| 13535 | O | LEU | D | 71 | -66.643 | -32.302 | 24.662 | 1.00 | 20.60 |
| 13536 | N | GLN | D | 72 | -67.908 | -30.452 | 24.780 | 1.00 | 21.21 |
| 13538 | CA | GLN | D | 72 | -68.179 | -30.609 | 26.206 | 1.00 | 21.75 |
| 13540 | CB | GLN | D | 72 | -68.926 | -29.390 | 26.764 | 1.00 | 22.00 |
| 13543 | CG | GLN | D | 72 | -69.338 | -29.524 | 28.231 | 1.00 | 23.59 |
| 13546 | CD | GLN | D | 72 | -68.156 | -29.781 | 29.152 | 1.00 | 25.57 |
| 13547 | OE1 | GLN | D | 72 | -67.368 | -28.871 | 29.414 | 1.00 | 28.46 |

FIGURE 3 (cont.)

| A | B | C | D | E | F | G | H | I | J |
|---|---|---|---|---|---|---|---|---|---|
| 13548 | NE2 | GLN | D | 72 | -68.030 | -31.016 | 29.646 | 1.00 | 26.08 |
| 13551 | C | GLN | D | 72 | -68.984 | -31.882 | 26.453 | 1.00 | 21.39 |
| 13552 | O | GLN | D | 72 | -68.756 | -32.575 | 27.445 | 1.00 | 21.80 |
| 13553 | N | LYS | D | 73 | -69.923 | -32.179 | 25.554 | 1.00 | 21.16 |
| 13555 | CA | LYS | D | 73 | -70.725 | -33.396 | 25.653 | 1.00 | 21.14 |
| 13557 | CB | LYS | D | 73 | -71.868 | -33.393 | 24.633 | 1.00 | 21.82 |
| 13560 | CG | LYS | D | 73 | -72.862 | -32.248 | 24.819 | 1.00 | 23.90 |
| 13563 | CD | LYS | D | 73 | -74.236 | -32.595 | 24.263 | 1.00 | 26.55 |
| 13566 | CE | LYS | D | 73 | -75.224 | -31.462 | 24.461 | 1.00 | 27.92 |
| 13569 | NZ | LYS | D | 73 | -76.606 | -31.980 | 24.674 | 1.00 | 29.70 |
| 13573 | C | LYS | D | 73 | -69.857 | -34.638 | 25.463 | 1.00 | 20.40 |
| 13574 | O | LYS | D | 73 | -70.064 | -35.647 | 26.133 | 1.00 | 20.36 |
| 13575 | N | VAL | D | 74 | -68.879 | -34.558 | 24.560 | 1.00 | 19.26 |
| 13577 | CA | VAL | D | 74 | -67.978 | -35.675 | 24.328 | 1.00 | 18.61 |
| 13579 | CB | VAL | D | 74 | -67.115 | -35.463 | 23.049 | 1.00 | 18.14 |
| 13581 | CG1 | VAL | D | 74 | -65.993 | -36.494 | 22.958 | 1.00 | 18.71 |
| 13585 | CG2 | VAL | D | 74 | -68.010 | -35.543 | 21.833 | 1.00 | 18.61 |
| 13589 | C | VAL | D | 74 | -67.099 | -35.901 | 25.550 | 1.00 | 18.35 |
| 13590 | O | VAL | D | 74 | -66.912 | -37.039 | 25.967 | 1.00 | 18.87 |
| 13591 | N | VAL | D | 75 | -66.576 | -34.823 | 26.129 | 1.00 | 18.41 |
| 13593 | CA | VAL | D | 75 | -65.720 | -34.922 | 27.309 | 1.00 | 18.43 |
| 13595 | CB | VAL | D | 75 | -65.123 | -33.543 | 27.721 | 1.00 | 18.32 |
| 13597 | CG1 | VAL | D | 75 | -64.061 | -33.105 | 26.710 | 1.00 | 18.96 |
| 13601 | CG2 | VAL | D | 75 | -64.512 | -33.586 | 29.114 | 1.00 | 18.56 |
| 13605 | C | VAL | D | 75 | -66.502 | -35.557 | 28.460 | 1.00 | 18.60 |
| 13606 | O | VAL | D | 75 | -65.998 | -36.451 | 29.124 | 1.00 | 17.68 |
| 13607 | N | SER | D | 76 | -67.744 | -35.126 | 28.658 | 1.00 | 19.64 |
| 13609 | CA | SER | D | 76 | -68.556 | -35.640 | 29.767 | 1.00 | 19.94 |
| 13611 | CB | BSER | D | 76 | -69.884 | -34.882 | 29.867 | 0.35 | 19.93 |
| 13612 | CB | ASER | D | 76 | -69.878 | -34.875 | 29.896 | 0.65 | 20.22 |
| 13617 | OG | BSER | D | 76 | -69.673 | -33.529 | 30.218 | 0.35 | 19.26 |
| 13618 | OG | ASER | D | 76 | -70.597 | -35.319 | 31.036 | 0.65 | 21.86 |
| 13621 | C | SER | D | 76 | -68.826 | -37.137 | 29.602 | 1.00 | 20.12 |
| 13622 | O | SER | D | 76 | -68.837 | -37.882 | 30.586 | 1.00 | 20.15 |
| 13623 | N | HIS | D | 77 | -69.035 | -37.582 | 28.365 | 1.00 | 20.16 |
| 13625 | CA | HIS | D | 77 | -69.263 | -38.998 | 28.113 | 1.00 | 20.05 |
| 13627 | CB | HIS | D | 77 | -69.866 | -39.247 | 26.730 | 1.00 | 20.07 |
| 13630 | CG | HIS | D | 77 | -70.517 | -40.591 | 26.595 | 1.00 | 21.08 |
| 13631 | ND1 | HIS | D | 77 | -70.131 | -41.521 | 25.652 | 1.00 | 23.13 |
| 13633 | CE1 | HIS | D | 77 | -70.878 | -42.604 | 25.770 | 1.00 | 23.08 |
| 13635 | NE2 | HIS | D | 77 | -71.729 | -42.415 | 26.763 | 1.00 | 23.44 |
| 13637 | CD2 | HIS | D | 77 | -71.520 | -41.168 | 27.298 | 1.00 | 22.18 |
| 13639 | C | HIS | D | 77 | -67.977 | -39.798 | 28.292 | 1.00 | 19.84 |
| 13640 | O | HIS | D | 77 | -68.013 | -40.899 | 28.819 | 1.00 | 19.65 |
| 13641 | N | CYS | D | 78 | -66.845 | -39.241 | 27.858 | 1.00 | 19.41 |
| 13643 | CA | CYS | D | 78 | -65.544 | -39.882 | 28.059 | 1.00 | 19.28 |
| 13645 | CB | CYS | D | 78 | -64.411 | -39.024 | 27.486 | 1.00 | 19.16 |
| 13648 | SG | CYS | D | 78 | -64.314 | -39.059 | 25.677 | 1.00 | 19.2 |
| 13649 | C | CYS | D | 78 | -65.292 | -40.161 | 29.547 | 1.00 | 19.56 |

FIGURE 3 (cont.)

| A | B | C | D | E | F | G | H | I | J |
|---|---|---|---|---|---|---|---|---|---|
| 13650 | O | CYS | D | 78 | -64.892 | -41.253 | 29.913 | 1.00 | 19.33 |
| 13651 | N | LEU | D | 79 | -65.559 | -39.182 | 30.406 | 1.00 | 19.85 |
| 13653 | CA | LEU | D | 79 | -65.372 | -39.373 | 31.844 | 1.00 | 20.34 |
| 13655 | CB | LEU | D | 79 | -65.592 | -38.058 | 32.598 | 1.00 | 20.46 |
| 13658 | CG | LEU | D | 79 | -64.540 | -36.971 | 32.320 | 1.00 | 20.52 |
| 13660 | CD1 | LEU | D | 79 | -63.167 | -37.388 | 32.834 | 1.00 | 20.72 |
| 13664 | CD2 | LEU | D | 79 | -64.958 | -35.637 | 32.929 | 1.00 | 21.91 |
| 13668 | C | LEU | D | 79 | -66.287 | -40.485 | 32.372 | 1.00 | 20.60 |
| 13669 | O | LEU | D | 79 | -65.846 | -41.321 | 33.162 | 1.00 | 20.51 |
| 13670 | N | GLU | D | 80 | -67.538 | -40.515 | 31.909 | 1.00 | 21.00 |
| 13672 | CA | GLU | D | 80 | -68.493 | -41.562 | 32.306 | 1.00 | 21.67 |
| 13674 | CB | GLU | D | 80 | -69.864 | -41.317 | 31.665 | 1.00 | 22.31 |
| 13677 | CG | GLU | D | 80 | -70.690 | -40.210 | 32.291 | 1.00 | 24.78 |
| 13680 | CD | GLU | D | 80 | -72.018 | -39.991 | 31.577 | 1.00 | 27.49 |
| 13681 | OE1 | GLU | D | 80 | -72.041 | -39.968 | 30.325 | 1.00 | 29.83 |
| 13682 | OE2 | GLU | D | 80 | -73.050 | -39.837 | 32.267 | 1.00 | 30.43 |
| 13683 | C | GLU | D | 80 | -68.022 | -42.962 | 31.899 | 1.00 | 21.34 |
| 13684 | O | GLU | D | 80 | -68.232 | -43.934 | 32.617 | 1.00 | 21.40 |
| 13685 | N | LEU | D | 81 | -67.384 | -43.048 | 30.735 | 1.00 | 20.60 |
| 13687 | CA | LEU | D | 81 | -66.927 | -44.313 | 30.167 | 1.00 | 20.28 |
| 13689 | CB | LEU | D | 81 | -66.653 | -44.147 | 28.668 | 1.00 | 20.07 |
| 13692 | CG | LEU | D | 81 | -67.862 | -44.055 | 27.743 | 1.00 | 20.59 |
| 13694 | CD1 | LEU | D | 81 | -67.412 | -43.691 | 26.324 | 1.00 | 21.10 |
| 13698 | CD2 | LEU | D | 81 | -68.651 | -45.353 | 27.744 | 1.00 | 21.07 |
| 13702 | C | LEU | D | 81 | -65.668 | -44.855 | 30.827 | 1.00 | 19.71 |
| 13703 | O | LEU | D | 81 | -65.320 | -46.011 | 30.616 | 1.00 | 19.37 |
| 13704 | N | GLY | D | 82 | -64.965 | -44.006 | 31.577 | 1.00 | 19.28 |
| 13706 | CA | GLY | D | 82 | -63.777 | -44.417 | 32.296 | 1.00 | 19.12 |
| 13709 | C | GLY | D | 82 | -62.462 | -43.778 | 31.892 | 1.00 | 18.68 |
| 13710 | O | GLY | D | 82 | -61.418 | -44.306 | 32.242 | 1.00 | 18.69 |
| 13711 | N | ALA | D | 83 | -62.490 | -42.640 | 31.198 | 1.00 | 18.38 |
| 13713 | CA | ALA | D | 83 | -61.251 | -41.955 | 30.840 | 1.00 | 18.46 |
| 13715 | CB | ALA | D | 83 | -61.546 | -40.735 | 29.975 | 1.00 | 18.46 |
| 13719 | C | ALA | D | 83 | -60.465 | -41.552 | 32.095 | 1.00 | 18.79 |
| 13720 | O | ALA | D | 83 | -61.050 | -41.106 | 33.092 | 1.00 | 18.75 |
| 13721 | N | ALA | D | 84 | -59.148 | -41.742 | 32.048 | 1.00 | 18.64 |
| 13723 | CA | ALA | D | 84 | -58.246 | -41.319 | 33.122 | 1.00 | 18.68 |
| 13725 | CB | ALA | D | 84 | -56.822 | -41.714 | 32.800 | 1.00 | 18.67 |
| 13729 | C | ALA | D | 84 | -58.325 | -39.818 | 33.351 | 1.00 | 18.61 |
| 13730 | O | ALA | D | 84 | -58.211 | -39.346 | 34.483 | 1.00 | 18.08 |
| 13731 | N | SER | D | 85 | -58.465 | -39.088 | 32.251 | 1.00 | 18.01 |
| 13733 | CA | SER | D | 85 | -58.838 | -37.675 | 32.245 | 1.00 | 18.23 |
| 13735 | CB | SER | D | 85 | -57.655 | -36.768 | 32.614 | 1.00 | 18.54 |
| 13738 | OG | SER | D | 85 | -56.655 | -36.750 | 31.613 | 1.00 | 18.84 |
| 13740 | C | SER | D | 85 | -59.367 | -37.320 | 30.855 | 1.00 | 17.98 |
| 13741 | O | SER | D | 85 | -59.109 | -38.037 | 29.884 | 1.00 | 17.85 |
| 13742 | N | ALA | D | 86 | -60.127 | -36.234 | 30.762 | 1.00 | 17.77 |
| 13744 | CA | ALA | D | 86 | -60.647 | -35.776 | 29.477 | 1.00 | 17.26 |
| 13746 | CB | ALA | D | 86 | -61.979 | -36.443 | 29.172 | 1.00 | 17.29 |

FIGURE 3 (cont.)

| A | B | C | D | E | F | G | H | I | J |
|---|---|---|---|---|---|---|---|---|---|
| 13750 | C | ALA | D | 86 | -60.800 | -34.261 | 29.482 | 1.00 | 17.29 |
| 13751 | O | ALA | D | 86 | -61.365 | -33.696 | 30.413 | 1.00 | 17.23 |
| 13752 | N | HIS | D | 87 | -60.268 | -33.611 | 28.450 | 1.00 | 16.78 |
| 13754 | CA | HIS | D | 87 | -60.387 | -32.167 | 28.270 | 1.00 | 16.80 |
| 13756 | CB | HIS | D | 87 | -59.075 | -31.462 | 28.627 | 1.00 | 16.59 |
| 13759 | CG | HIS | D | 87 | -58.650 | -31.645 | 30.048 | 1.00 | 18.73 |
| 13760 | ND1 | HIS | D | 87 | -57.992 | -32.774 | 30.491 | 1.00 | 19.97 |
| 13762 | CE1 | HIS | D | 87 | -57.757 | -32.662 | 31.787 | 1.00 | 22.31 |
| 13764 | NE2 | HIS | D | 87 | -58.227 | -31.500 | 32.198 | 1.00 | 22.08 |
| 13766 | CD2 | HIS | D | 87 | -58.797 | -30.845 | 31.132 | 1.00 | 20.34 |
| 13768 | C | HIS | D | 87 | -60.705 | -31.887 | 26.808 | 1.00 | 16.76 |
| 13769 | O | HIS | D | 87 | -60.474 | -32.731 | 25.946 | 1.00 | 16.32 |
| 13770 | N | TYR | D | 88 | -61.243 | -30.707 | 26.537 | 1.00 | 16.44 |
| 13772 | CA | TYR | D | 88 | -61.379 | -30.227 | 25.167 | 1.00 | 16.99 |
| 13774 | CB | TYR | D | 88 | -62.845 | -30.187 | 24.735 | 1.00 | 17.08 |
| 13777 | CG | TYR | D | 88 | -63.632 | -29.017 | 25.296 | 1.00 | 18.69 |
| 13778 | CD1 | TYR | D | 88 | -63.718 | -27.811 | 24.601 | 1.00 | 20.27 |
| 13780 | CE1 | TYR | D | 88 | -64.447 | -26.736 | 25.107 | 1.00 | 22.08 |
| 13782 | CZ | TYR | D | 88 | -65.097 | -26.872 | 26.317 | 1.00 | 22.48 |
| 13783 | OH | TYR | D | 88 | -65.814 | -25.806 | 26.818 | 1.00 | 23.79 |
| 13785 | CE2 | TYR | D | 88 | -65.023 | -28.056 | 27.025 | 1.00 | 21.58 |
| 13787 | CD2 | TYR | D | 88 | -64.297 | -29.125 | 26.510 | 1.00 | 20.81 |
| 13789 | C | TYR | D | 88 | -60.743 | -28.851 | 25.014 | 1.00 | 17.05 |
| 13790 | O | TYR | D | 88 | -60.649 | -28.078 | 25.964 | 1.00 | 17.08 |
| 13791 | N | ILE | D | 89 | -60.276 | -28.570 | 23.803 | 1.00 | 17.08 |
| 13793 | CA | ILE | D | 89 | -59.863 | -27.241 | 23.404 | 1.00 | 17.19 |
| 13795 | CB | ILE | D | 89 | -58.328 | -27.153 | 23.309 | 1.00 | 17.53 |
| 13797 | CG1 | ILE | D | 89 | -57.679 | -27.575 | 24.628 | 1.00 | 18.25 |
| 13800 | CD1 | ILE | D | 89 | -56.176 | -27.649 | 24.589 | 1.00 | 18.53 |
| 13804 | CG2 | ILE | D | 89 | -57.892 | -25.737 | 22.929 | 1.00 | 18.48 |
| 13808 | C | ILE | D | 89 | -60.516 | -27.003 | 22.047 | 1.00 | 17.51 |
| 13809 | O | ILE | D | 89 | -60.326 | -27.793 | 21.116 | 1.00 | 17.53 |
| 13810 | N | ALA | D | 90 | -61.322 | -25.950 | 21.953 | 1.00 | 17.35 |
| 13812 | CA | ALA | D | 90 | -62.054 | -25.652 | 20.730 | 1.00 | 17.08 |
| 13814 | CB | ALA | D | 90 | -63.434 | -25.103 | 21.045 | 1.00 | 17.49 |
| 13818 | C | ALA | D | 90 | -61.288 | -24.664 | 19.865 | 1.00 | 16.90 |
| 13819 | O | ALA | D | 90 | -60.719 | -23.684 | 20.352 | 1.00 | 16.95 |
| 13820 | N | GLY | D | 91 | -61.279 | -24.926 | 18.568 | 1.00 | 16.29 |
| 13822 | CA | GLY | D | 91 | -60.767 | -23.970 | 17.613 | 1.00 | 16.12 |
| 13825 | C | GLY | D | 91 | -60.819 | -24.514 | 16.204 | 1.00 | 15.77 |
| 13826 | O | GLY | D | 91 | -61.174 | -25.677 | 15.983 | 1.00 | 16.00 |
| 13827 | N | THR | D | 92 | -60.478 | -23.661 | 15.246 | 1.00 | 15.57 |
| 13829 | CA | THR | D | 92 | -60.435 | -24.076 | 13.853 | 1.00 | 14.94 |
| 13831 | CB | THR | D | 92 | -61.139 | -23.073 | 12.920 | 1.00 | 15.31 |
| 13833 | OG1 | THR | D | 92 | -60.926 | -23.471 | 11.559 | 1.00 | 14.35 |
| 13835 | CG2 | THR | D | 92 | -60.536 | -21.676 | 12.999 | 1.00 | 15.60 |
| 13839 | C | THR | D | 92 | -59.004 | -24.336 | 13.404 | 1.00 | 14.65 |
| 13840 | O | THR | D | 92 | -58.096 | -23.560 | 13.689 | 1.00 | 14.25 |
| 13841 | N | MET | D | 93 | -58.831 | -25.430 | 12.664 | 1.00 | 14.20 |

FIGURE 3 (cont.)

| A | B | C | D | E | F | G | H | I | J |
|---|---|---|---|---|---|---|---|---|---|
| 13843 | CA | MET | D | 93 | -57.542 | -25.839 | 12.137 | 1.00 | 14.63 |
| 13845 | CB | MET | D | 93 | -57.517 | -27.364 | 11.959 | 1.00 | 14.57 |
| 13848 | CG | MET | D | 93 | -57.577 | -28.104 | 13.301 | 1.00 | 14.89 |
| 13851 | SD | MET | D | 93 | -56.051 | -27.913 | 14.216 | 1.00 | 15.45 |
| 13852 | CE | MET | D | 93 | -56.411 | -28.935 | 15.651 | 1.00 | 16.45 |
| 13856 | C | MET | D | 93 | -57.226 | -25.097 | 10.833 | 1.00 | 14.56 |
| 13857 | O | MET | D | 93 | -56.216 | -25.353 | 10.191 | 1.00 | 15.66 |
| 13858 | N | GLU | D | 94 | -58.087 | -24.151 | 10.459 | 1.00 | 14.55 |
| 13860 | CA | GLU | D | 94 | -57.730 | -23.126 | 9.486 | 1.00 | 15.10 |
| 13862 | CB | GLU | D | 94 | -58.931 | -22.234 | 9.150 | 1.00 | 15.26 |
| 13865 | CG | GLU | D | 94 | -60.085 | -22.925 | 8.449 | 1.00 | 16.41 |
| 13868 | CD | GLU | D | 94 | -61.372 | -22.124 | 8.535 | 1.00 | 17.88 |
| 13869 | OE1 | GLU | D | 94 | -61.984 | -22.080 | 9.639 | 1.00 | 19.54 |
| 13870 | OE2 | GLU | D | 94 | -61.762 | -21.515 | 7.508 | 1.00 | 19.72 |
| 13871 | C | GLU | D | 94 | -56.646 | -22.200 | 10.043 | 1.00 | 15.57 |
| 13872 | O | GLU | D | 94 | -55.917 | -21.577 | 9.281 | 1.00 | 15.84 |
| 13873 | N | ASP | D | 95 | -56.586 | -22.086 | 11.370 | 1.00 | 15.53 |
| 13875 | CA | ASP | D | 95 | -55.692 | -21.153 | 12.057 | 1.00 | 15.74 |
| 13877 | CB | ASP | D | 95 | -56.454 | -20.537 | 13.238 | 1.00 | 15.71 |
| 13880 | CG | ASP | D | 95 | -55.626 | -19.572 | 14.063 | 1.00 | 17.06 |
| 13881 | OD1 | ASP | D | 95 | -54.406 | -19.451 | 13.844 | 1.00 | 18.02 |
| 13882 | OD2 | ASP | D | 95 | -56.150 | -18.887 | 14.962 | 1.00 | 18.47 |
| 13883 | C | ASP | D | 95 | -54.465 | -21.945 | 12.515 | 1.00 | 15.57 |
| 13884 | O | ASP | D | 95 | -54.538 | -22.712 | 13.466 | 1.00 | 15.78 |
| 13885 | N | MET | D | 96 | -53.347 | -21.769 | 11.818 | 1.00 | 15.97 |
| 13887 | CA | MET | D | 96 | -52.138 | -22.544 | 12.102 | 1.00 | 16.21 |
| 13889 | CB | MET | D | 96 | -51.086 | -22.355 | 11.009 | 1.00 | 17.18 |
| 13892 | CG | MET | D | 96 | -51.512 | -22.826 | 9.629 | 1.00 | 17.92 |
| 13895 | SD | MET | D | 96 | -51.975 | -24.554 | 9.533 | 1.00 | 20.34 |
| 13896 | CE | MET | D | 96 | -53.605 | -24.413 | 8.783 | 1.00 | 22.82 |
| 13900 | C | MET | D | 96 | -51.534 | -22.196 | 13.464 | 1.00 | 16.30 |
| 13901 | O | MET | D | 96 | -50.843 | -23.021 | 14.065 | 1.00 | 16.01 |
| 13902 | N | THR | D | 97 | -51.795 | -20.986 | 13.946 | 1.00 | 15.89 |
| 13904 | CA | THR | D | 97 | -51.385 | -20.596 | 15.297 | 1.00 | 16.04 |
| 13906 | CB | THR | D | 97 | -51.566 | -19.080 | 15.507 | 1.00 | 16.27 |
| 13908 | OG1 | THR | D | 97 | -50.646 | -18.378 | 14.661 | 1.00 | 17.37 |
| 13910 | CG2 | THR | D | 97 | -51.172 | -18.669 | 16.914 | 1.00 | 16.36 |
| 13914 | C | THR | D | 97 | -52.157 | -21.392 | 16.334 | 1.00 | 15.54 |
| 13915 | O | THR | D | 97 | -51.578 | -21.870 | 17.314 | 1.00 | 16.35 |
| 13916 | N | PHE | D | 98 | -53.459 | -21.555 | 16.123 | 1.00 | 15.63 |
| 13918 | CA | PHE | D | 98 | -54.253 | -22.409 | 16.990 | 1.00 | 15.59 |
| 13920 | CB | PHE | D | 98 | -55.733 | -22.440 | 16.597 | 1.00 | 15.65 |
| 13923 | CG | PHE | D | 98 | -56.498 | -23.500 | 17.327 | 1.00 | 14.79 |
| 13924 | CD1 | PHE | D | 98 | -56.770 | -23.349 | 18.673 | 1.00 | 15.88 |
| 13926 | CE1 | PHE | D | 98 | -57.441 | -24.334 | 19.371 | 1.00 | 15.75 |
| 13928 | CZ | PHE | D | 98 | -57.833 | -25.493 | 18.733 | 1.00 | 16.14 |
| 13930 | CE2 | PHE | D | 98 | -57.561 | -25.663 | 17.395 | 1.00 | 15.88 |
| 13932 | CD2 | PHE | D | 98 | -56.885 | -24.674 | 16.697 | 1.00 | 15.34 |
| 13934 | C | PHE | D | 98 | -53.718 | -23.841 | 17.004 | 1.00 | 16.04 |

FIGURE 3 (cont.)

| A | B | C | D | E | F | G | H | I | J |
|---|---|---|---|---|---|---|---|---|---|
| 13935 | O | PHE | D | 98 | -53.608 | -24.450 | 18.062 | 1.00 | 15.74 |
| 13936 | N | ALA | D | 99 | -53.404 | -24.383 | 15.832 | 1.00 | 16.14 |
| 13938 | CA | ALA | D | 99 | -52.918 | -25.756 | 15.748 | 1.00 | 16.27 |
| 13940 | CB | ALA | D | 99 | -52.606 | -26.131 | 14.295 | 1.00 | 16.29 |
| 13944 | C | ALA | D | 99 | -51.683 | -25.945 | 16.628 | 1.00 | 16.95 |
| 13945 | O | ALA | D | 99 | -51.624 | -26.872 | 17.438 | 1.00 | 16.41 |
| 13946 | N | GLU | D | 100 | -50.714 | -25.046 | 16.481 | 1.00 | 17.42 |
| 13948 | CA | GLU | D | 100 | -49.481 | -25.097 | 17.258 | 1.00 | 17.97 |
| 13950 | CB | GLU | D | 100 | -48.543 | -23.974 | 16.791 | 1.00 | 18.57 |
| 13953 | CG | GLU | D | 100 | -47.147 | -24.028 | 17.392 | 1.00 | 21.41 |
| 13956 | CD | GLU | D | 100 | -46.230 | -22.933 | 16.868 | 1.00 | 25.55 |
| 13957 | OE1 | GLU | D | 100 | -45.090 | -22.844 | 17.369 | 1.00 | 28.65 |
| 13958 | OE2 | GLU | D | 100 | -46.637 | -22.158 | 15.966 | 1.00 | 27.39 |
| 13959 | C | GLU | D | 100 | -49.756 | -24.992 | 18.770 | 1.00 | 17.97 |
| 13960 | O | GLU | D | 100 | -49.285 | -25.803 | 19.576 | 1.00 | 17.53 |
| 13961 | N | GLN | D | 101 | -50.557 | -24.007 | 19.152 | 1.00 | 17.22 |
| 13963 | CA | GLN | D | 101 | -50.805 | -23.731 | 20.568 | 1.00 | 17.19 |
| 13965 | CB | GLN | D | 101 | -51.462 | -22.357 | 20.736 | 1.00 | 17.57 |
| 13968 | CG | GLN | D | 101 | -50.537 | -21.212 | 20.365 | 1.00 | 20.00 |
| 13971 | CD | GLN | D | 101 | -51.154 | -19.839 | 20.562 | 1.00 | 23.21 |
| 13972 | OE1 | GLN | D | 101 | -52.359 | -19.705 | 20.782 | 1.00 | 26.17 |
| 13973 | NE2 | GLN | D | 101 | -50.321 | -18.809 | 20.476 | 1.00 | 25.62 |
| 13976 | C | GLN | D | 101 | -51.664 | -24.819 | 21.206 | 1.00 | 16.24 |
| 13977 | O | GLN | D | 101 | -51.523 | -25.111 | 22.389 | 1.00 | 16.90 |
| 13978 | N | PHE | D | 102 | -52.539 | -25.423 | 20.408 | 1.00 | 15.13 |
| 13980 | CA | PHE | D | 102 | -53.385 | -26.515 | 20.862 | 1.00 | 14.42 |
| 13982 | CB | PHE | D | 102 | -54.305 | -26.991 | 19.741 | 1.00 | 14.41 |
| 13985 | CG | PHE | D | 102 | -54.872 | -28.348 | 19.985 | 1.00 | 14.30 |
| 13986 | CD1 | PHE | D | 102 | -55.828 | -28.535 | 20.964 | 1.00 | 14.86 |
| 13988 | CE1 | PHE | D | 102 | -56.347 | -29.776 | 21.219 | 1.00 | 15.62 |
| 13990 | CZ | PHE | D | 102 | -55.894 | -30.880 | 20.492 | 1.00 | 15.17 |
| 13992 | CE2 | PHE | D | 102 | -54.929 | -30.714 | 19.521 | 1.00 | 15.21 |
| 13994 | CD2 | PHE | D | 102 | -54.414 | -29.453 | 19.270 | 1.00 | 13.96 |
| 13996 | C | PHE | D | 102 | -52.544 | -27.699 | 21.339 | 1.00 | 14.36 |
| 13997 | O | PHE | D | 102 | -52.802 | -28.250 | 22.399 | 1.00 | 14.55 |
| 13998 | N | VAL | D | 103 | -51.551 | -28.099 | 20.550 | 1.00 | 14.43 |
| 14000 | CA | VAL | D | 103 | -50.729 | -29.251 | 20.915 | 1.00 | 14.54 |
| 14002 | CB | VAL | D | 103 | -49.761 | -29.669 | 19.783 | 1.00 | 14.62 |
| 14004 | CG1 | VAL | D | 103 | -48.767 | -30.737 | 20.267 | 1.00 | 14.13 |
| 14008 | CG2 | VAL | D | 103 | -50.539 | -30.202 | 18.611 | 1.00 | 15.45 |
| 14012 | C | VAL | D | 103 | -49.949 | -28.965 | 22.200 | 1.00 | 14.89 |
| 14013 | O | VAL | D | 103 | -49.857 | -29.830 | 23.068 | 1.00 | 15.33 |
| 14014 | N | ALA | D | 104 | -49.399 | -27.756 | 22.319 | 1.00 | 15.40 |
| 14016 | CA | ALA | D | 104 | -48.673 | -27.359 | 23.532 | 1.00 | 15.59 |
| 14018 | CB | ALA | D | 104 | -48.132 | -25.945 | 23.414 | 1.00 | 15.70 |
| 14022 | C | ALA | D | 104 | -49.575 | -27.461 | 24.749 | 1.00 | 15.68 |
| 14023 | O | ALA | D | 104 | -49.167 | -28.004 | 25.780 | 1.00 | 16.65 |
| 14024 | N | GLN | D | 105 | -50.798 | -26.948 | 24.630 | 1.00 | 15.84 |
| 14026 | CA | GLN | D | 105 | -51.720 | -26.932 | 25.767 | 1.00 | 16.16 |

FIGURE 3 (cont.)

| A | B | C | D | E | F | G | H | I | J |
|---|---|---|---|---|---|---|---|---|---|
| 14028 | CB | GLN | D | 105 | -52.880 | -25.949 | 25.522 | 1.00 | 16.58 |
| 14031 | CG | GLN | D | 105 | -53.870 | -25.802 | 26.685 | 1.00 | 19.37 |
| 14034 | CD | GLN | D | 105 | -53.254 | -25.230 | 27.952 | 1.00 | 22.86 |
| 14035 | OE1 | GLN | D | 105 | -52.132 | -24.702 | 27.943 | 1.00 | 26.54 |
| 14036 | NE2 | GLN | D | 105 | -53.989 | -25.331 | 29.047 | 1.00 | 25.58 |
| 14039 | C | GLN | D | 105 | -52.237 | -28.332 | 26.105 | 1.00 | 15.93 |
| 14040 | O | GLN | D | 105 | -52.362 | -28.685 | 27.282 | 1.00 | 15.68 |
| 14041 | N | ALA | D | 106 | -52.509 | -29.142 | 25.089 | 1.00 | 15.72 |
| 14043 | CA | ALA | D | 106 | -52.943 | -30.516 | 25.304 | 1.00 | 15.69 |
| 14045 | CB | ALA | D | 106 | -53.298 | -31.184 | 23.970 | 1.00 | 15.46 |
| 14049 | C | ALA | D | 106 | -51.864 | -31.315 | 26.037 | 1.00 | 15.61 |
| 14050 | O | ALA | D | 106 | -52.159 | -32.062 | 26.968 | 1.00 | 15.52 |
| 14051 | N | GLY | D | 107 | -50.615 | -31.145 | 25.617 | 1.00 | 15.87 |
| 14053 | CA | GLY | D | 107 | -49.489 | -31.791 | 26.268 | 1.00 | 15.87 |
| 14056 | C | GLY | D | 107 | -49.305 | -31.327 | 27.696 | 1.00 | 16.47 |
| 14057 | O | GLY | D | 107 | -48.974 | -32.120 | 28.573 | 1.00 | 16.71 |
| 14058 | N | LYS | D | 108 | -49.515 | -30.040 | 27.928 | 1.00 | 16.53 |
| 14060 | CA | LYS | D | 108 | -49.420 | -29.491 | 29.280 | 1.00 | 16.99 |
| 14062 | CB | LYS | D | 108 | -49.570 | -27.975 | 29.247 | 1.00 | 17.14 |
| 14065 | CG | LYS | D | 108 | -49.506 | -27.289 | 30.622 | 1.00 | 18.57 |
| 14068 | CD | LYS | D | 108 | -49.473 | -25.775 | 30.464 | 1.00 | 20.61 |
| 14071 | CE | LYS | D | 108 | -49.082 | -25.078 | 31.745 | 1.00 | 22.00 |
| 14074 | NZ | LYS | D | 108 | -49.096 | -23.600 | 31.610 | 1.00 | 23.02 |
| 14078 | C | LYS | D | 108 | -50.482 | -30.123 | 30.176 | 1.00 | 17.02 |
| 14079 | O | LYS | D | 108 | -50.190 | -30.547 | 31.299 | 1.00 | 16.65 |
| 14080 | N | LEU | D | 109 | -51.704 | -30.210 | 29.665 | 1.00 | 17.05 |
| 14082 | CA | LEU | D | 109 | -52.822 | -30.780 | 30.412 | 1.00 | 17.17 |
| 14084 | CB | LEU | D | 109 | -54.105 | -30.736 | 29.577 | 1.00 | 17.59 |
| 14087 | CG | LEU | D | 109 | -55.195 | -29.673 | 29.761 | 1.00 | 20.18 |
| 14089 | CD1 | LEU | D | 109 | -55.686 | -29.180 | 28.413 | 1.00 | 20.71 |
| 14093 | CD2 | LEU | D | 109 | -54.825 | -28.512 | 30.697 | 1.00 | 20.62 |
| 14097 | C | LEU | D | 109 | -52.554 | -32.228 | 30.824 | 1.00 | 16.97 |
| 14098 | O | LEU | D | 109 | -52.870 | -32.623 | 31.948 | 1.00 | 16.89 |
| 14099 | N | MET | D | 110 | -51.968 | -33.010 | 29.920 | 1.00 | 16.61 |
| 14101 | CA | MET | D | 110 | -51.783 | -34.447 | 30.154 | 1.00 | 16.50 |
| 14103 | CB | MET | D | 110 | -52.004 | -35.216 | 28.847 | 1.00 | 15.95 |
| 14106 | CG | MET | D | 110 | -53.416 | -35.144 | 28.354 | 1.00 | 15.99 |
| 14109 | SD | MET | D | 110 | -53.740 | -36.261 | 26.974 | 1.00 | 16.12 |
| 14110 | CE | MET | D | 110 | -52.815 | -35.492 | 25.620 | 1.00 | 16.49 |
| 14114 | C | MET | D | 110 | -50.418 | -34.819 | 30.722 | 1.00 | 16.58 |
| 14115 | O | MET | D | 110 | -50.237 | -35.935 | 31.187 | 1.00 | 17.47 |
| 14116 | N | GLY | D | 111 | -49.461 | -33.900 | 30.667 | 1.00 | 16.66 |
| 14118 | CA | GLY | D | 111 | -48.088 | -34.189 | 31.053 | 1.00 | 16.95 |
| 14121 | C | GLY | D | 111 | -47.285 | -34.966 | 30.025 | 1.00 | 16.72 |
| 14122 | O | GLY | D | 111 | -46.437 | -35.799 | 30.383 | 1.00 | 16.85 |
| 14123 | N | GLY | D | 112 | -47.542 | -34.686 | 28.747 | 1.00 | 16.47 |
| 14125 | CA | GLY | D | 112 | -46.882 | -35.367 | 27.646 | 1.00 | 16.63 |
| 14128 | C | GLY | D | 112 | -47.887 | -35.869 | 26.617 | 1.00 | 16.27 |
| 14129 | O | GLY | D | 112 | -49.066 | -35.488 | 26.624 | 1.00 | 16.55 |

FIGURE 3 (cont.)

| A | B | C | D | E | F | G | H | I | J |
|---|---|---|---|---|---|---|---|---|---|
| 14130 | N | LEU | D | 113 | -47.414 | -36.745 | 25.734 | 1.00 | 15.67 |
| 14132 | CA | LEU | D | 113 | -48.199 | -37.204 | 24.597 | 1.00 | 15.38 |
| 14134 | CB | LEU | D | 113 | -48.138 | -36.179 | 23.460 | 1.00 | 15.44 |
| 14137 | CG | LEU | D | 113 | -49.065 | -36.457 | 22.281 | 1.00 | 15.19 |
| 14139 | CD1 | LEU | D | 113 | -50.527 | -36.434 | 22.706 | 1.00 | 14.48 |
| 14143 | CD2 | LEU | D | 113 | -48.826 | -35.479 | 21.144 | 1.00 | 15.59 |
| 14147 | C | LEU | D | 113 | -47.634 | -38.528 | 24.112 | 1.00 | 14.90 |
| 14148 | O | LEU | D | 113 | -46.440 | -38.620 | 23.849 | 1.00 | 15.04 |
| 14149 | N | ASP | D | 114 | -48.489 | -39.548 | 24.052 | 1.00 | 14.98 |
| 14151 | CA | ASP | D | 114 | -48.137 | -40.860 | 23.505 | 1.00 | 14.95 |
| 14153 | CB | ASP | D | 114 | -48.693 | -41.966 | 24.395 | 1.00 | 14.96 |
| 14156 | CG | ASP | D | 114 | -48.128 | -41.916 | 25.801 | 1.00 | 16.24 |
| 14157 | OD1 | ASP | D | 114 | -46.896 | -42.071 | 25.956 | 1.00 | 17.59 |
| 14158 | OD2 | ASP | D | 114 | -48.837 | -41.704 | 26.805 | 1.00 | 16.22 |
| 14159 | C | ASP | D | 114 | -48.650 | -41.083 | 22.084 | 1.00 | 15.08 |
| 14160 | O | ASP | D | 114 | -48.011 | -41.776 | 21.301 | 1.00 | 15.37 |
| 14161 | N | MET | D | 115 | -49.803 | -40.510 | 21.755 | 1.00 | 14.60 |
| 14163 | CA | MET | D | 115 | -50.426 | -40.732 | 20.451 | 1.00 | 14.51 |
| 14165 | CB | MET | D | 115 | -51.426 | -41.893 | 20.523 | 1.00 | 14.83 |
| 14168 | CG | MET | D | 115 | -52.043 | -42.274 | 19.174 | 1.00 | 16.13 |
| 14171 | SD | MET | D | 115 | -53.128 | -43.717 | 19.225 | 1.00 | 18.64 |
| 14172 | CE | MET | D | 115 | -51.918 | -45.030 | 19.350 | 1.00 | 19.52 |
| 14176 | C | MET | D | 115 | -51.131 | -39.472 | 19.953 | 1.00 | 14.49 |
| 14177 | O | MET | D | 115 | -51.891 | -38.842 | 20.683 | 1.00 | 14.53 |
| 14178 | N | LEU | D | 116 | -50.880 | -39.131 | 18.692 | 1.00 | 13.51 |
| 14180 | CA | LEU | D | 116 | -51.495 | -37.985 | 18.048 | 1.00 | 13.60 |
| 14182 | CB | LEU | D | 116 | -50.407 | -37.093 | 17.447 | 1.00 | 13.85 |
| 14185 | CG | LEU | D | 116 | -50.866 | -35.872 | 16.655 | 1.00 | 14.68 |
| 14187 | CD1 | LEU | D | 116 | -51.563 | -34.878 | 17.581 | 1.00 | 15.01 |
| 14191 | CD2 | LEU | D | 116 | -49.678 | -35.232 | 15.968 | 1.00 | 15.35 |
| 14195 | C | LEU | D | 116 | -52.392 | -38.527 | 16.948 | 1.00 | 13.69 |
| 14196 | O | LEU | D | 116 | -51.895 | -39.059 | 15.963 | 1.00 | 13.69 |
| 14197 | N | ILE | D | 117 | -53.704 | -38.395 | 17.113 | 1.00 | 12.97 |
| 14199 | CA | ILE | D | 117 | -54.645 | -38.878 | 16.109 | 1.00 | 13.06 |
| 14201 | CB | ILE | D | 117 | -55.780 | -39.710 | 16.731 | 1.00 | 13.04 |
| 14203 | CG1 | ILE | D | 117 | -55.203 | -40.897 | 17.516 | 1.00 | 13.59 |
| 14206 | CD1 | ILE | D | 117 | -56.268 | -41.800 | 18.169 | 1.00 | 15.10 |
| 14210 | CG2 | ILE | D | 117 | -56.721 | -40.204 | 15.635 | 1.00 | 14.23 |
| 14214 | C | ILE | D | 117 | -55.190 | -37.696 | 15.312 | 1.00 | 12.84 |
| 14215 | O | ILE | D | 117 | -55.934 | -36.854 | 15.811 | 1.00 | 12.34 |
| 14216 | N | LEU | D | 118 | -54.775 | -37.646 | 14.056 | 1.00 | 12.43 |
| 14218 | CA | LEU | D | 118 | -55.116 | -36.569 | 13.134 | 1.00 | 12.90 |
| 14220 | CB | LEU | D | 118 | -53.871 | -36.176 | 12.337 | 1.00 | 12.82 |
| 14223 | CG | LEU | D | 118 | -52.667 | -35.780 | 13.186 | 1.00 | 13.08 |
| 14225 | CD1 | LEU | D | 118 | -51.446 | -35.518 | 12.301 | 1.00 | 13.89 |
| 14229 | CD2 | LEU | D | 118 | -52.976 | -34.540 | 14.028 | 1.00 | 15.05 |
| 14233 | C | LEU | D | 118 | -56.235 | -37.032 | 12.207 | 1.00 | 12.92 |
| 14234 | O | LEU | D | 118 | -56.035 | -37.886 | 11.347 | 1.00 | 13.25 |
| 14235 | N | ASN | D | 119 | -57.411 | -36.447 | 12.388 | 1.00 | 12.53 |

FIGURE 3 (cont.)

| A | B | C | D | E | F | G | H | I | J |
|---|---|---|---|---|---|---|---|---|---|
| 14237 | CA | ASN | D | 119 | -58.659 | -36.980 | 11.842 | 1.00 | 12.35 |
| 14239 | CB | ASN | D | 119 | -59.388 | -37.713 | 12.985 | 1.00 | 12.16 |
| 14242 | CG | ASN | D | 119 | -60.821 | -38.071 | 12.661 | 1.00 | 12.71 |
| 14243 | OD1 | ASN | D | 119 | -61.776 | -37.403 | 13.139 | 1.00 | 15.78 |
| 14244 | ND2 | ASN | D | 119 | -61.005 | -39.120 | 11.880 | 1.00 | 10.86 |
| 14247 | C | ASN | D | 119 | -59.565 | -35.922 | 11.187 | 1.00 | 12.08 |
| 14248 | O | ASN | D | 119 | -60.363 | -36.249 | 10.299 | 1.00 | 12.80 |
| 14249 | N | HIS | D | 120 | -59.447 | -34.660 | 11.609 | 1.00 | 12.13 |
| 14251 | CA | HIS | D | 120 | -60.312 | -33.594 | 11.112 | 1.00 | 12.20 |
| 14253 | CB | HIS | D | 120 | -60.073 | -32.261 | 11.861 | 1.00 | 11.94 |
| 14256 | CG | HIS | D | 120 | -58.673 | -31.738 | 11.754 | 1.00 | 13.48 |
| 14257 | ND1 | HIS | D | 120 | -58.234 | -30.970 | 10.696 | 1.00 | 16.44 |
| 14259 | CE1 | HIS | D | 120 | -56.965 | -30.656 | 10.882 | 1.00 | 10.79 |
| 14261 | NE2 | HIS | D | 120 | -56.553 | -31.222 | 11.996 | 1.00 | 16.77 |
| 14263 | CD2 | HIS | D | 120 | -57.602 | -31.903 | 12.559 | 1.00 | 12.58 |
| 14265 | C | HIS | D | 120 | -60.146 | -33.355 | 9.617 | 1.00 | 12.03 |
| 14266 | O | HIS | D | 120 | -59.061 | -33.569 | 9.056 | 1.00 | 12.88 |
| 14267 | N | ILE | D | 121 | -61.236 | -32.917 | 8.993 | 1.00 | 12.24 |
| 14269 | CA | ILE | D | 121 | -61.235 | -32.420 | 7.622 | 1.00 | 12.41 |
| 14271 | CB | ILE | D | 121 | -61.679 | -33.492 | 6.607 | 1.00 | 12.53 |
| 14273 | CG1 | ILE | D | 121 | -63.041 | -34.091 | 6.968 | 1.00 | 13.26 |
| 14276 | CD1 | ILE | D | 121 | -63.656 | -34.978 | 5.872 | 1.00 | 15.56 |
| 14280 | CG2 | ILE | D | 121 | -60.624 | -34.579 | 6.469 | 1.00 | 13.46 |
| 14284 | C | ILE | D | 121 | -62.168 | -31.233 | 7.507 | 1.00 | 13.36 |
| 14285 | O | ILE | D | 121 | -63.078 | -31.067 | 8.313 | 1.00 | 13.55 |
| 14286 | N | THR | D | 122 | -61.951 | -30.407 | 6.499 | 1.00 | 13.21 |
| 14288 | CA | THR | D | 122 | -62.896 | -29.347 | 6.193 | 1.00 | 13.44 |
| 14290 | CB | THR | D | 122 | -62.239 | -28.258 | 5.357 | 1.00 | 13.46 |
| 14292 | OG1 | THR | D | 122 | -63.063 | -27.085 | 5.393 | 1.00 | 13.39 |
| 14294 | CG2 | THR | D | 122 | -62.112 | -28.641 | 3.871 | 1.00 | 13.36 |
| 14298 | C | THR | D | 122 | -64.130 | -29.926 | 5.506 | 1.00 | 14.66 |
| 14299 | O | THR | D | 122 | -64.079 | -30.995 | 4.888 | 1.00 | 14.62 |
| 14300 | N | ASN | D | 123 | -65.243 | -29.204 | 5.598 | 1.00 | 15.99 |
| 14302 | CA | ASN | D | 123 | -66.504 | -29.703 | 5.058 | 1.00 | 18.15 |
| 14304 | CB | ASN | D | 123 | -67.637 | -28.710 | 5.312 | 1.00 | 18.88 |
| 14307 | CG | ASN | D | 123 | -68.082 | -28.684 | 6.769 | 1.00 | 22.22 |
| 14308 | OD1 | ASN | D | 123 | -67.743 | -29.567 | 7.567 | 1.00 | 26.94 |
| 14309 | ND2 | ASN | D | 123 | -68.848 | -27.657 | 7.126 | 1.00 | 26.64 |
| 14312 | C | ASN | D | 123 | -66.383 | -29.981 | 3.573 | 1.00 | 18.51 |
| 14313 | O | ASN | D | 123 | -65.936 | -29.130 | 2.804 | 1.00 | 18.64 |
| 14314 | N | THR | D | 124 | -66.804 | -31.184 | 3.194 | 1.00 | 19.79 |
| 14316 | CA | THR | D | 124 | -66.600 | -31.736 | 1.864 | 1.00 | 21.01 |
| 14318 | CB | THR | D | 124 | -65.412 | -32.702 | 1.923 | 1.00 | 21.40 |
| 14320 | OG1 | THR | D | 124 | -64.230 | -31.960 | 2.260 | 1.00 | 22.36 |
| 14322 | CG2 | THR | D | 124 | -65.109 | -33.313 | 0.563 | 1.00 | 22.49 |
| 14326 | C | THR | D | 124 | -67.841 | -32.500 | 1.415 | 1.00 | 21.32 |
| 14327 | O | THR | D | 124 | -68.335 | -33.356 | 2.146 | 1.00 | 22.24 |
| 14328 | N | SER | D | 125 | -68.328 | -32.186 | 0.217 | 1.00 | 21.37 |
| 14330 | CA | SER | D | 125 | -69.424 | -32.933 | -0.399 | 1.00 | 21.33 |

FIGURE 3 (cont.)

| A | B | C | D | E | F | G | H | I | J |
|---|---|---|---|---|---|---|---|---|---|
| 14332 | CB | SER | D | 125 | -70.709 | -32.099 | -0.403 | 1.00 | 21.61 |
| 14335 | OG | SER | D | 125 | -70.544 | -30.894 | -1.116 | 1.00 | 23.48 |
| 14337 | C | SER | D | 125 | -69.039 | -33.366 | -1.813 | 1.00 | 20.58 |
| 14338 | O | SER | D | 125 | -67.969 | -33.013 | -2.315 | 1.00 | 20.88 |
| 14339 | N | LEU | D | 126 | -69.891 | -34.167 | -2.439 | 1.00 | 19.07 |
| 14341 | CA | LEU | D | 126 | -69.635 | -34.631 | -3.794 | 1.00 | 18.48 |
| 14343 | CB | LEU | D | 126 | -70.367 | -35.940 | -4.043 | 1.00 | 18.40 |
| 14346 | CG | LEU | D | 126 | -69.950 | -37.086 | -3.125 | 1.00 | 18.69 |
| 14348 | CD1 | LEU | D | 126 | -68.474 | -37.425 | -3.277 | 1.00 | 19.68 |
| 14352 | CD2 | LEU | D | 126 | -70.801 | -38.298 | -3.428 | 1.00 | 19.60 |
| 14356 | C | LEU | D | 126 | -70.059 | -33.590 | -4.820 | 1.00 | 18.25 |
| 14357 | O | LEU | D | 126 | -71.240 | -33.262 | -4.935 | 1.00 | 17.52 |
| 14358 | N | ASN | D | 127 | -69.093 | -33.067 | -5.568 | 1.00 | 17.29 |
| 14360 | CA | ASN | D | 127 | -69.390 | -32.108 | -6.618 | 1.00 | 18.27 |
| 14362 | CB | ASN | D | 127 | -69.617 | -30.709 | -6.017 | 1.00 | 18.95 |
| 14365 | CG | ASN | D | 127 | -71.103 | -30.377 | -5.810 | 1.00 | 22.44 |
| 14366 | OD1 | ASN | D | 127 | -71.901 | -30.382 | -6.757 | 1.00 | 28.21 |
| 14367 | ND2 | ASN | D | 127 | -71.475 | -30.093 | -4.568 | 1.00 | 25.68 |
| 14370 | C | ASN | D | 127 | -68.269 | -32.060 | -7.646 | 1.00 | 17.55 |
| 14371 | O | ASN | D | 127 | -67.106 | -32.258 | -7.301 | 1.00 | 16.52 |
| 14372 | N | LEU | D | 128 | -68.621 | -31.803 | -8.900 | 1.00 | 17.79 |
| 14374 | CA | LEU | D | 128 | -67.621 | -31.551 | -9.937 | 1.00 | 18.36 |
| 14376 | CB | LEU | D | 128 | -68.284 | -31.283 | -11.288 | 1.00 | 19.01 |
| 14379 | CG | LEU | D | 128 | -69.023 | -32.445 | -11.949 | 1.00 | 21.06 |
| 14381 | CD1 | LEU | D | 128 | -69.909 | -31.930 | -13.067 | 1.00 | 22.44 |
| 14385 | CD2 | LEU | D | 128 | -68.043 | -33.459 | -12.499 | 1.00 | 22.48 |
| 14389 | C | LEU | D | 128 | -66.784 | -30.347 | -9.548 | 1.00 | 18.36 |
| 14390 | O | LEU | D | 128 | -67.269 | -29.421 | -8.885 | 1.00 | 19.14 |
| 14391 | N | PHE | D | 129 | -65.509 | -30.383 | -9.923 | 1.00 | 17.60 |
| 14393 | CA | PHE | D | 129 | -64.633 | -29.241 | -9.779 | 1.00 | 17.61 |
| 14395 | CB | PHE | D | 129 | -63.158 | -29.657 | -9.780 | 1.00 | 17.01 |
| 14398 | CG | PHE | D | 129 | -62.214 | -28.490 | -9.713 | 1.00 | 14.85 |
| 14399 | CD1 | PHE | D | 129 | -61.925 | -27.887 | -8.503 | 1.00 | 15.21 |
| 14401 | CE1 | PHE | D | 129 | -61.070 | -26.790 | -8.456 | 1.00 | 13.72 |
| 14403 | CZ | PHE | D | 129 | -60.512 | -26.300 | -9.609 | 1.00 | 13.48 |
| 14405 | CE2 | PHE | D | 129 | -60.798 | -26.877 | -10.810 | 1.00 | 13.88 |
| 14407 | CD2 | PHE | D | 129 | -61.640 | -27.976 | -10.866 | 1.00 | 14.37 |
| 14409 | C | PHE | D | 129 | -64.866 | -28.296 | -10.955 | 1.00 | 18.97 |
| 14410 | O | PHE | D | 129 | -64.684 | -28.672 | -12.121 | 1.00 | 19.76 |
| 14411 | N | HIS | D | 130 | -65.278 | -27.079 | -10.636 | 1.00 | 19.67 |
| 14413 | CA | HIS | D | 130 | -65.245 | -25.971 | -11.582 | 1.00 | 21.03 |
| 14415 | CB | HIS | D | 130 | -66.593 | -25.768 | -12.272 | 1.00 | 21.47 |
| 14418 | CG | HIS | D | 130 | -66.555 | -24.737 | -13.360 | 1.00 | 24.17 |
| 14419 | ND1 | HIS | D | 130 | -66.081 | -25.009 | -14.627 | 1.00 | 26.18 |
| 14421 | CE1 | HIS | D | 130 | -66.159 | -23.917 | -15.369 | 1.00 | 26.96 |
| 14423 | NE2 | HIS | D | 130 | -66.658 | -22.944 | -14.627 | 1.00 | 26.86 |
| 14425 | CD2 | HIS | D | 130 | -66.909 | -23.429 | -13.364 | 1.00 | 26.24 |
| 14427 | C | HIS | D | 130 | -64.868 | -24.695 | -10.845 | 1.00 | 21.07 |
| 14428 | O | HIS | D | 130 | -65.633 | -24.202 | -9.997 | 1.00 | 21.31 |

FIGURE 3 (cont.)

| A | B | C | D | E | F | G | H | I | J |
|---|---|---|---|---|---|---|---|---|---|
| 14429 | N | ASP | D | 131 | -63.678 | -24.187 | -11.151 | 1.00 | 21.38 |
| 14431 | CA | ASP | D | 131 | -63.272 | -22.848 | -10.765 | 1.00 | 21.66 |
| 14433 | CB | ASP | D | 131 | -64.146 | -21.835 | -11.514 | 1.00 | 22.07 |
| 14436 | CG | ASP | D | 131 | -63.534 | -20.439 | -11.581 | 1.00 | 24.17 |
| 14437 | OD1 | ASP | D | 131 | -62.507 | -20.178 | -10.914 | 1.00 | 27.10 |
| 14438 | OD2 | ASP | D | 131 | -64.030 | -19.529 | -12.288 | 1.00 | 27.60 |
| 14439 | C | ASP | D | 131 | -63.396 | -22.666 | -9.244 | 1.00 | 20.97 |
| 14440 | O | ASP | D | 131 | -63.834 | -21.609 | -8.778 | 1.00 | 22.42 |
| 14441 | N | ASP | D | 132 | -63.089 | -23.708 | -8.477 | 1.00 | 19.90 |
| 14443 | CA | ASP | D | 132 | -63.204 | -23.627 | -7.023 | 1.00 | 18.58 |
| 14445 | CB | ASP | D | 132 | -64.163 | -24.693 | -6.480 | 1.00 | 19.09 |
| 14448 | CG | ASP | D | 132 | -64.702 | -24.344 | -5.093 | 1.00 | 20.84 |
| 14449 | OD1 | ASP | D | 132 | -64.231 | -23.355 | -4.474 | 1.00 | 20.27 |
| 14450 | OD2 | ASP | D | 132 | -65.614 | -25.005 | -4.540 | 1.00 | 23.90 |
| 14451 | C | ASP | D | 132 | -61.841 | -23.712 | -6.335 | 1.00 | 17.01 |
| 14452 | O | ASP | D | 132 | -61.594 | -24.600 | -5.514 | 1.00 | 16.21 |
| 14453 | N | ILE | D | 133 | -60.984 | -22.744 | -6.658 | 1.00 | 15.35 |
| 14455 | CA | ILE | D | 133 | -59.670 | -22.616 | -6.036 | 1.00 | 14.63 |
| 14457 | CB | ILE | D | 133 | -58.887 | -21.416 | -6.645 | 1.00 | 15.30 |
| 14459 | CG1 | ILE | D | 133 | -58.682 | -21.600 | -8.151 | 1.00 | 16.93 |
| 14462 | CD1 | ILE | D | 133 | -57.818 | -22.779 | -8.516 | 1.00 | 18.50 |
| 14466 | CG2 | ILE | D | 133 | -57.558 | -21.216 | -5.950 | 1.00 | 16.11 |
| 14470 | C | ILE | D | 133 | -59.810 | -22.465 | -4.523 | 1.00 | 13.46 |
| 14471 | O | ILE | D | 133 | -59.000 | -22.986 | -3.766 | 1.00 | 12.91 |
| 14472 | N | HIS | D | 134 | -60.864 | -21.778 | -4.079 | 1.00 | 12.05 |
| 14474 | CA | HIS | D | 134 | -61.076 | -21.591 | -2.655 | 1.00 | 11.92 |
| 14476 | CB | HIS | D | 134 | -62.356 | -20.798 | -2.399 | 1.00 | 11.73 |
| 14479 | CG | HIS | D | 134 | -62.709 | -20.713 | -0.950 | 1.00 | 13.46 |
| 14480 | ND1 | HIS | D | 134 | -62.159 | -19.770 | -0.110 | 1.00 | 16.73 |
| 14482 | CE1 | HIS | D | 134 | -62.625 | -19.951 | 1.114 | 1.00 | 17.63 |
| 14484 | NE2 | HIS | D | 134 | -63.443 | -20.989 | 1.100 | 1.00 | 17.98 |
| 14486 | CD2 | HIS | D | 134 | -63.508 | -21.487 | -0.178 | 1.00 | 15.83 |
| 14488 | C | HIS | D | 134 | -61.138 | -22.922 | -1.906 | 1.00 | 11.24 |
| 14489 | O | HIS | D | 134 | -60.493 | -23.069 | -0.866 | 1.00 | 11.16 |
| 14490 | N | HIS | D | 135 | -61.915 | -23.875 | -2.424 | 1.00 | 11.13 |
| 14492 | CA | HIS | D | 135 | -62.063 | -25.177 | -1.788 | 1.00 | 11.77 |
| 14494 | CB | HIS | D | 135 | -63.232 | -25.962 | -2.386 | 1.00 | 12.17 |
| 14497 | CG | HIS | D | 135 | -63.548 | -27.227 | -1.650 | 1.00 | 14.36 |
| 14498 | ND1 | HIS | D | 135 | -63.432 | -28.475 | -2.226 | 1.00 | 17.69 |
| 14500 | CE1 | HIS | D | 135 | -63.770 | -29.398 | -1.342 | 1.00 | 17.74 |
| 14502 | NE2 | HIS | D | 135 | -64.119 | -28.794 | -0.222 | 1.00 | 18.87 |
| 14504 | CD2 | HIS | D | 135 | -63.978 | -27.438 | -0.384 | 1.00 | 15.74 |
| 14506 | C | HIS | D | 135 | -60.785 | -25.994 | -1.877 | 1.00 | 11.52 |
| 14507 | O | HIS | D | 135 | -60.466 | -26.742 | -0.973 | 1.00 | 12.21 |
| 14508 | N | VAL | D | 136 | -60.047 | -25.834 | -2.963 | 1.00 | 10.87 |
| 14510 | CA | VAL | D | 136 | -58.761 | -26.508 | -3.082 | 1.00 | 11.39 |
| 14512 | CB | VAL | D | 136 | -58.146 | -26.343 | -4.484 | 1.00 | 11.11 |
| 14514 | CG1 | VAL | D | 136 | -56.743 | -26.964 | -4.533 | 1.00 | 12.59 |
| 14518 | CG2 | VAL | D | 136 | -59.027 | -26.986 | -5.514 | 1.00 | 12.43 |

FIGURE 3 (cont.)

| A | B | C | D | E | F | G | H | I | J |
|---|---|---|---|---|---|---|---|---|---|
| 14522 | C | VAL | D | 136 | -57.800 | -25.993 | -2.005 | 1.00 | 10.84 |
| 14523 | O | VAL | D | 136 | -57.164 | -26.775 | -1.322 | 1.00 | 11.31 |
| 14524 | N | ARG | D | 137 | -57.687 | -24.681 | -1.861 | 1.00 | 11.94 |
| 14526 | CA | ARG | D | 137 | -56.805 | -24.093 | -0.861 | 1.00 | 12.68 |
| 14528 | CB | ARG | D | 137 | -56.778 | -22.571 | -1.001 | 1.00 | 14.51 |
| 14531 | CG | ARG | D | 137 | -55.595 | -21.923 | -0.299 | 1.00 | 19.89 |
| 14534 | CD | ARG | D | 137 | -54.897 | -20.847 | -1.152 | 1.00 | 26.76 |
| 14537 | NE | ARG | D | 137 | -55.390 | -19.501 | -0.894 | 1.00 | 31.90 |
| 14539 | CZ | ARG | D | 137 | -54.983 | -18.406 | -1.543 | 1.00 | 35.19 |
| 14540 | NH1 | ARG | D | 137 | -54.067 | -18.482 | -2.510 | 1.00 | 36.43 |
| 14543 | NH2 | ARG | D | 137 | -55.495 | -17.219 | -1.221 | 1.00 | 36.67 |
| 14546 | C | ARG | D | 137 | -57.230 | -24.468 | 0.553 | 1.00 | 12.51 |
| 14547 | O | ARG | D | 137 | -56.404 | -24.823 | 1.382 | 1.00 | 12.39 |
| 14548 | N | LYS | D | 138 | -58.527 | -24.378 | 0.826 | 1.00 | 11.73 |
| 14550 | CA | LYS | D | 138 | -59.050 | -24.673 | 2.161 | 1.00 | 11.89 |
| 14552 | CB | LYS | D | 138 | -60.551 | -24.404 | 2.210 | 1.00 | 12.56 |
| 14555 | CG | LYS | D | 138 | -61.172 | -24.562 | 3.598 | 1.00 | 13.69 |
| 14558 | CD | LYS | D | 138 | -60.710 | -23.506 | 4.557 | 1.00 | 16.65 |
| 14561 | CE | LYS | D | 138 | -61.166 | -22.106 | 4.134 | 1.00 | 17.59 |
| 14564 | NZ | LYS | D | 138 | -60.637 | -21.055 | 5.055 | 1.00 | 19.86 |
| 14568 | C | LYS | D | 138 | -58.794 | -26.133 | 2.528 | 1.00 | 12.02 |
| 14569 | O | LYS | D | 138 | -58.415 | -26.451 | 3.642 | 1.00 | 11.85 |
| 14570 | N | SER | D | 139 | -59.032 | -27.014 | 1.573 | 1.00 | 12.18 |
| 14572 | CA | SER | D | 139 | -58.779 | -28.431 | 1.766 | 1.00 | 12.82 |
| 14574 | CB | SER | D | 139 | -59.211 | -29.240 | 0.545 | 1.00 | 12.88 |
| 14577 | OG | SER | D | 139 | -60.607 | -29.149 | 0.348 | 1.00 | 14.15 |
| 14579 | C | SER | D | 139 | -57.309 | -28.668 | 2.041 | 1.00 | 12.97 |
| 14580 | O | SER | D | 139 | -56.964 | -29.413 | 2.941 | 1.00 | 13.18 |
| 14581 | N | MET | D | 140 | -56.430 | -28.040 | 1.272 | 1.00 | 12.95 |
| 14583 | CA | MET | D | 140 | -55.005 | -28.233 | 1.501 | 1.00 | 13.42 |
| 14585 | CB | BMET | D | 140 | -54.178 | -27.614 | 0.373 | 0.35 | 13.09 |
| 14586 | CB | AMET | D | 140 | -54.176 | -27.579 | 0.394 | 0.65 | 14.08 |
| 14591 | CG | BMET | D | 140 | -52.804 | -28.257 | 0.194 | 0.35 | 12.23 |
| 14592 | CG | AMET | D | 140 | -54.253 | -28.253 | -0.975 | 0.65 | 16.83 |
| 14597 | SD | BMET | D | 140 | -52.797 | -30.072 | 0.251 | 0.35 | 11.20 |
| 14598 | SD | AMET | D | 140 | -53.977 | -30.062 | -1.092 | 0.65 | 22.19 |
| 14599 | CE | BMET | D | 140 | -53.121 | -30.508 | -1.461 | 0.35 | 10.51 |
| 14600 | CE | AMET | D | 140 | -52.538 | -30.219 | -0.091 | 0.65 | 21.51 |
| 14607 | C | MET | D | 140 | -54.579 | -27.685 | 2.861 | 1.00 | 13.69 |
| 14608 | O | MET | D | 140 | -53.776 | -28.312 | 3.545 | 1.00 | 13.29 |
| 14609 | N | GLU | D | 141 | -55.139 | -26.552 | 3.279 | 1.00 | 13.57 |
| 14611 | CA | GLU | D | 141 | -54.766 | -25.960 | 4.560 | 1.00 | 14.12 |
| 14613 | CB | GLU | D | 141 | -55.242 | -24.507 | 4.646 | 1.00 | 14.92 |
| 14616 | CG | BGLU | D | 141 | -54.515 | -23.549 | 3.717 | 0.35 | 15.67 |
| 14617 | CG | AGLU | D | 141 | -54.423 | -23.592 | 3.748 | 0.65 | 17.47 |
| 14622 | CD | BGLU | D | 141 | -53.184 | -23.057 | 4.261 | 0.35 | 16.71 |
| 14623 | CD | AGLU | D | 141 | -54.927 | -22.160 | 3.668 | 0.65 | 21.12 |
| 14624 | OE1 | BGLU | D | 141 | -52.340 | -22.635 | 3.444 | 0.35 | 18.75 |
| 14625 | OE1 | AGLU | D | 141 | -54.459 | -21.421 | 2.776 | 0.65 | 23.73 |

FIGURE 3 (cont.)

| A | B | C | D | E | F | G | H | I | J |
|---|---|---|---|---|---|---|---|---|---|
| 14626 | OE2B | GLU | D | 141 | -52.978 | -23.075 | 5.490 | 0.35 | 18.62 |
| 14627 | OE2A | GLU | D | 141 | -55.769 | -21.758 | 4.493 | 0.65 | 25.03 |
| 14628 | C | GLU | D | 141 | -55.282 | -26.772 | 5.756 | 1.00 | 13.38 |
| 14629 | O | GLU | D | 141 | -54.513 | -27.074 | 6.665 | 1.00 | 13.18 |
| 14630 | N | VAL | D | 142 | -56.559 | -27.152 | 5.737 | 1.00 | 12.61 |
| 14632 | CA | VAL | D | 142 | -57.178 | -27.815 | 6.886 | 1.00 | 12.28 |
| 14634 | CB | VAL | D | 142 | -58.718 | -27.650 | 6.888 | 1.00 | 12.73 |
| 14636 | CG1 | VAL | D | 142 | -59.365 | -28.445 | 8.034 | 1.00 | 12.36 |
| 14640 | CG2 | VAL | D | 142 | -59.102 | -26.161 | 6.970 | 1.00 | 12.37 |
| 14644 | C | VAL | D | 142 | -56.812 | -29.297 | 6.913 | 1.00 | 12.15 |
| 14645 | O | VAL | D | 142 | -56.454 | -29.843 | 7.954 | 1.00 | 12.83 |
| 14646 | N | ASN | D | 143 | -56.888 | -29.939 | 5.761 | 1.00 | 11.80 |
| 14648 | CA | ASN | D | 143 | -56.740 | -31.395 | 5.692 | 1.00 | 11.43 |
| 14650 | CB | ASN | D | 143 | -57.402 | -31.968 | 4.438 | 1.00 | 11.41 |
| 14653 | CG | ASN | D | 143 | -58.886 | -31.688 | 4.340 | 1.00 | 11.88 |
| 14654 | OD1 | ASN | D | 143 | -59.516 | -31.081 | 5.236 | 1.00 | 12.63 |
| 14655 | ND2 | ASN | D | 143 | -59.466 | -32.119 | 3.224 | 1.00 | 12.05 |
| 14658 | C | ASN | D | 143 | -55.286 | -31.855 | 5.675 | 1.00 | 11.74 |
| 14659 | O | ASN | D | 143 | -55.009 | -33.004 | 6.023 | 1.00 | 12.00 |
| 14660 | N | PHE | D | 144 | -54.383 | -30.986 | 5.222 | 1.00 | 11.59 |
| 14662 | CA | PHE | D | 144 | -52.983 | -31.344 | 5.071 | 1.00 | 11.27 |
| 14664 | CB | PHE | D | 144 | -52.576 | -31.334 | 3.594 | 1.00 | 11.63 |
| 14667 | CG | PHE | D | 144 | -51.108 | -31.476 | 3.397 | 1.00 | 11.99 |
| 14668 | CD1 | PHE | D | 144 | -50.495 | -32.682 | 3.661 | 1.00 | 13.53 |
| 14670 | CE1 | PHE | D | 144 | -49.126 | -32.821 | 3.531 | 1.00 | 12.93 |
| 14672 | CZ | PHE | D | 144 | -48.352 | -31.753 | 3.152 | 1.00 | 12.87 |
| 14674 | CE2 | PHE | D | 144 | -48.940 | -30.539 | 2.899 | 1.00 | 13.28 |
| 14676 | CD2 | PHE | D | 144 | -50.316 | -30.393 | 3.019 | 1.00 | 12.28 |
| 14678 | C | PHE | D | 144 | -52.031 | -30.462 | 5.880 | 1.00 | 11.43 |
| 14679 | O | PHE | D | 144 | -51.303 | -30.963 | 6.736 | 1.00 | 11.53 |
| 14680 | N | LEU | D | 145 | -52.005 | -29.157 | 5.623 | 1.00 | 11.25 |
| 14682 | CA | LEU | D | 145 | -50.991 | -28.333 | 6.275 | 1.00 | 11.21 |
| 14684 | CB B | LEU | D | 145 | -50.999 | -26.903 | 5.729 | 0.35 | 11.15 |
| 14685 | CB A | LEU | D | 145 | -50.996 | -26.902 | 5.743 | 0.65 | 11.75 |
| 14690 | CG B | LEU | D | 145 | -50.576 | -26.764 | 4.264 | 0.35 | 10.83 |
| 14691 | CG A | LEU | D | 145 | -49.767 | -26.083 | 6.136 | 0.65 | 13.29 |
| 14694 | CD1B | LEU | D | 145 | -50.851 | -25.344 | 3.785 | 0.35 | 10.69 |
| 14695 | CD1A | LEU | D | 145 | -48.498 | -26.603 | 5.467 | 0.65 | 15.75 |
| 14702 | CD2B | LEU | D | 145 | -49.109 | -27.119 | 4.073 | 0.35 | 10.66 |
| 14703 | CD2A | LEU | D | 145 | -50.019 | -24.641 | 5.782 | 0.65 | 15.29 |
| 14710 | C | LEU | D | 145 | -51.153 | -28.334 | 7.790 | 1.00 | 11.17 |
| 14711 | O | LEU | D | 145 | -50.167 | -28.365 | 8.517 | 1.00 | 11.40 |
| 14712 | N | SER | D | 146 | -52.384 | -28.321 | 8.278 | 1.00 | 11.31 |
| 14714 | CA | SER | D | 146 | -52.560 | -28.329 | 9.725 | 1.00 | 11.42 |
| 14716 | CB | SER | D | 146 | -54.007 | -28.083 | 10.145 | 1.00 | 11.66 |
| 14719 | OG | SER | D | 146 | -54.833 | -29.186 | 9.878 | 1.00 | 13.09 |
| 14721 | C | SER | D | 146 | -52.037 | -29.620 | 10.341 | 1.00 | 11.77 |
| 14722 | O | SER | D | 146 | -51.561 | -29.607 | 11.465 | 1.00 | 12.25 |
| 14723 | N | TYR | D | 147 | -52.145 | -30.734 | 9.619 | 1.00 | 11.12 |

FIGURE 3 (cont.)

| A | B | C | D | E | F | G | H | I | J |
|---|---|---|---|---|---|---|---|---|---|
| 14725 | CA | TYR | D | 147 | -51.605 | -31.999 | 10.120 | 1.00 | 11.42 |
| 14727 | CB | TYR | D | 147 | -51.934 | -33.161 | 9.171 | 1.00 | 11.36 |
| 14730 | CG | TYR | D | 147 | -53.346 | -33.717 | 9.210 | 1.00 | 11.23 |
| 14731 | CD1 | TYR | D | 147 | -54.467 | -32.916 | 9.428 | 1.00 | 12.11 |
| 14733 | CE1 | TYR | D | 147 | -55.750 | -33.467 | 9.442 | 1.00 | 12.95 |
| 14735 | CZ | TYR | D | 147 | -55.914 | -34.820 | 9.255 | 1.00 | 11.31 |
| 14736 | OH | TYR | D | 147 | -57.172 | -35.367 | 9.264 | 1.00 | 14.08 |
| 14738 | CE2 | TYR | D | 147 | -54.822 | -35.622 | 9.034 | 1.00 | 11.75 |
| 14740 | CD2 | TYR | D | 147 | -53.561 | -35.077 | 9.021 | 1.00 | 11.32 |
| 14742 | C | TYR | D | 147 | -50.092 | -31.901 | 10.282 | 1.00 | 11.59 |
| 14743 | O | TYR | D | 147 | -49.517 | -32.438 | 11.224 | 1.00 | 11.00 |
| 14744 | N | VAL | D | 148 | -49.433 | -31.237 | 9.340 | 1.00 | 11.58 |
| 14746 | CA | VAL | D | 148 | -47.996 | -31.041 | 9.432 | 1.00 | 11.67 |
| 14748 | CB | VAL | D | 148 | -47.421 | -30.453 | 8.116 | 1.00 | 11.23 |
| 14750 | CG1 | VAL | D | 148 | -47.693 | -31.404 | 6.918 | 1.00 | 11.97 |
| 14754 | CG2 | VAL | D | 148 | -45.942 | -30.180 | 8.265 | 1.00 | 13.32 |
| 14758 | C | VAL | D | 148 | -47.641 | -30.136 | 10.631 | 1.00 | 11.45 |
| 14759 | O | VAL | D | 148 | -46.741 | -30.445 | 11.396 | 1.00 | 11.78 |
| 14760 | N | VAL | D | 149 | -48.367 | -29.037 | 10.803 | 1.00 | 11.62 |
| 14762 | CA | VAL | D | 149 | -48.122 | -28.125 | 11.922 | 1.00 | 11.88 |
| 14764 | CB | VAL | D | 149 | -49.049 | -26.899 | 11.832 | 1.00 | 12.32 |
| 14766 | CG1 | VAL | D | 149 | -48.972 | -26.064 | 13.104 | 1.00 | 13.47 |
| 14770 | CG2 | VAL | D | 149 | -48.702 | -26.076 | 10.602 | 1.00 | 12.52 |
| 14774 | C | VAL | D | 149 | -48.310 | -28.852 | 13.255 | 1.00 | 12.06 |
| 14775 | O | VAL | D | 149 | -47.508 | -28.696 | 14.179 | 1.00 | 12.19 |
| 14776 | N | LEU | D | 150 | -49.375 | -29.636 | 13.357 | 1.00 | 11.92 |
| 14778 | CA | LEU | D | 150 | -49.659 | -30.389 | 14.565 | 1.00 | 12.22 |
| 14780 | CB | LEU | D | 150 | -51.017 | -31.092 | 14.465 | 1.00 | 11.92 |
| 14783 | CG | LEU | D | 150 | -52.250 | -30.193 | 14.413 | 1.00 | 12.25 |
| 14785 | CD1 | LEU | D | 150 | -53.422 | -30.951 | 13.851 | 1.00 | 12.10 |
| 14789 | CD2 | LEU | D | 150 | -52.601 | -29.653 | 15.798 | 1.00 | 12.57 |
| 14793 | C | LEU | D | 150 | -48.554 | -31.400 | 14.860 | 1.00 | 12.62 |
| 14794 | O | LEU | D | 150 | -48.148 | -31.564 | 16.010 | 1.00 | 12.61 |
| 14795 | N | THR | D | 151 | -48.044 | -32.049 | 13.815 | 1.00 | 12.12 |
| 14797 | CA | THR | D | 151 | -46.965 | -33.012 | 13.962 | 1.00 | 12.39 |
| 14799 | CB | THR | D | 151 | -46.731 | -33.732 | 12.634 | 1.00 | 12.40 |
| 14801 | OG1 | THR | D | 151 | -47.882 | -34.531 | 12.340 | 1.00 | 12.42 |
| 14803 | CG2 | THR | D | 151 | -45.587 | -34.700 | 12.744 | 1.00 | 14.70 |
| 14807 | C | THR | D | 151 | -45.672 | -32.352 | 14.434 | 1.00 | 12.44 |
| 14808 | O | THR | D | 151 | -45.022 | -32.846 | 15.342 | 1.00 | 13.11 |
| 14809 | N | VAL | D | 152 | -45.300 | -31.231 | 13.824 | 1.00 | 12.26 |
| 14811 | CA | VAL | D | 152 | -44.112 | -30.502 | 14.251 | 1.00 | 12.40 |
| 14813 | CB | VAL | D | 152 | -43.878 | -29.235 | 13.390 | 1.00 | 12.69 |
| 14815 | CG1 | VAL | D | 152 | -42.830 | -28.346 | 14.012 | 1.00 | 12.13 |
| 14819 | CG2 | VAL | D | 152 | -43.461 | -29.616 | 11.977 | 1.00 | 13.01 |
| 14823 | C | VAL | D | 152 | -44.213 | -30.123 | 15.735 | 1.00 | 12.74 |
| 14824 | O | VAL | D | 152 | -43.237 | -30.237 | 16.491 | 1.00 | 13.27 |
| 14825 | N | ALA | D | 153 | -45.397 | -29.700 | 16.156 | 1.00 | 12.87 |
| 14827 | CA | ALA | D | 153 | -45.599 | -29.267 | 17.536 | 1.00 | 13.52 |

FIGURE 3 (cont.)

| A | B | C | D | E | F | G | H | I | J |
|---|---|---|---|---|---|---|---|---|---|
| 14829 | CB | ALA | D | 153 | -46.922 | -28.571 | 17.670 | 1.00 | 13.63 |
| 14833 | C | ALA | D | 153 | -45.540 | -30.437 | 18.512 | 1.00 | 13.79 |
| 14834 | O | ALA | D | 153 | -45.119 | -30.272 | 19.665 | 1.00 | 14.50 |
| 14835 | N | ALA | D | 154 | -45.971 | -31.604 | 18.046 | 1.00 | 13.25 |
| 14837 | CA | ALA | D | 154 | -46.109 | -32.789 | 18.893 | 1.00 | 13.82 |
| 14839 | CB | ALA | D | 154 | -47.241 | -33.672 | 18.376 | 1.00 | 13.63 |
| 14843 | C | ALA | D | 154 | -44.830 | -33.604 | 18.961 | 1.00 | 13.85 |
| 14844 | O | ALA | D | 154 | -44.684 | -34.414 | 19.873 | 1.00 | 14.35 |
| 14845 | N | LEU | D | 155 | -43.916 | -33.414 | 18.012 | 1.00 | 14.42 |
| 14847 | CA | LEU | D | 155 | -42.821 | -34.371 | 17.849 | 1.00 | 15.07 |
| 14849 | CB | LEU | D | 155 | -42.026 | -34.139 | 16.552 | 1.00 | 15.84 |
| 14852 | CG | LEU | D | 155 | -41.075 | -35.282 | 16.161 | 1.00 | 17.72 |
| 14854 | CD1 | LEU | D | 155 | -40.261 | -34.887 | 14.935 | 1.00 | 18.37 |
| 14858 | CD2 | LEU | D | 155 | -41.819 | -36.602 | 15.919 | 1.00 | 18.95 |
| 14862 | C | LEU | D | 155 | -41.894 | -34.453 | 19.071 | 1.00 | 15.23 |
| 14863 | O | LEU | D | 155 | -41.534 | -35.562 | 19.456 | 1.00 | 14.88 |
| 14864 | N | PRO | D | 156 | -41.490 | -33.334 | 19.678 | 1.00 | 15.44 |
| 14865 | CA | PRO | D | 156 | -40.676 | -33.428 | 20.900 | 1.00 | 15.55 |
| 14867 | CB | PRO | D | 156 | -40.567 | -31.972 | 21.371 | 1.00 | 15.65 |
| 14870 | CG | PRO | D | 156 | -40.668 | -31.176 | 20.096 | 1.00 | 15.98 |
| 14873 | CD | PRO | D | 156 | -41.679 | -31.931 | 19.257 | 1.00 | 15.13 |
| 14876 | C | PRO | D | 156 | -41.295 | -34.350 | 21.957 | 1.00 | 15.37 |
| 14877 | O | PRO | D | 156 | -40.581 | -35.199 | 22.491 | 1.00 | 15.67 |
| 14878 | N | MET | D | 157 | -42.593 | -34.227 | 22.215 | 1.00 | 15.49 |
| 14880 | CA | MET | D | 157 | -43.256 | -35.056 | 23.224 | 1.00 | 15.30 |
| 14882 | CB | MET | D | 157 | -44.658 | -34.524 | 23.552 | 1.00 | 15.69 |
| 14885 | CG | MET | D | 157 | -44.654 | -33.294 | 24.462 | 1.00 | 15.80 |
| 14888 | SD | MET | D | 157 | -46.309 | -32.760 | 24.840 | 1.00 | 17.1 |
| 14889 | CE | MET | D | 157 | -46.889 | -32.166 | 23.246 | 1.00 | 17.42 |
| 14893 | C | MET | D | 157 | -43.349 | -36.510 | 22.779 | 1.00 | 15.21 |
| 14894 | O | MET | D | 157 | -43.202 | -37.424 | 23.584 | 1.00 | 15.64 |
| 14895 | N | LEU | D | 158 | -43.596 | -36.727 | 21.490 | 1.00 | 15.26 |
| 14897 | CA | LEU | D | 158 | -43.698 | -38.082 | 20.969 | 1.00 | 15.21 |
| 14899 | CB | LEU | D | 158 | -44.272 | -38.063 | 19.549 | 1.00 | 15.06 |
| 14902 | CG | LEU | D | 158 | -45.734 | -37.624 | 19.437 | 1.00 | 15.21 |
| 14904 | CD1 | LEU | D | 158 | -46.109 | -37.427 | 17.974 | 1.00 | 15.55 |
| 14908 | CD2 | LEU | D | 158 | -46.667 | -38.615 | 20.107 | 1.00 | 15.84 |
| 14912 | C | LEU | D | 158 | -42.341 | -38.792 | 20.990 | 1.00 | 15.75 |
| 14913 | O | LEU | D | 158 | -42.278 | -39.986 | 21.216 | 1.00 | 15.57 |
| 14914 | N | LYS | D | 159 | -41.261 | -38.053 | 20.767 | 1.00 | 16.68 |
| 14916 | CA | LYS | D | 159 | -39.918 | -38.621 | 20.838 | 1.00 | 17.77 |
| 14918 | CB | LYS | D | 159 | -38.872 | -37.625 | 20.337 | 1.00 | 18.05 |
| 14921 | CG | LYS | D | 159 | -38.860 | -37.462 | 18.820 | 1.00 | 19.21 |
| 14924 | CD | LYS | D | 159 | -37.937 | -36.337 | 18.379 | 1.00 | 21.12 |
| 14927 | CE | LYS | D | 159 | -37.630 | -36.418 | 16.890 | 1.00 | 22.31 |
| 14930 | NZ | LYS | D | 159 | -37.033 | -35.145 | 16.377 | 1.00 | 24.14 |
| 14934 | C | LYS | D | 159 | -39.609 | -39.039 | 22.272 | 1.00 | 18.27 |
| 14935 | O | LYS | D | 159 | -38.996 | -40.074 | 22.499 | 1.00 | 18.31 |
| 14936 | N | GLN | D | 160 | -40.062 | -38.237 | 23.233 | 1.00 | 18.71 |

FIGURE 3 (cont.)

| A | B | C | D | E | F | G | H | I | J |
|---|---|---|---|---|---|---|---|---|---|
| 14938 | CA | GLN | D | 160 | -39.853 | -38.535 | 24.651 | 1.00 | 19.46 |
| 14940 | CB | GLN | D | 160 | -40.383 | -37.380 | 25.510 | 1.00 | 20.06 |
| 14943 | CG | GLN | D | 160 | -39.992 | -37.443 | 26.978 | 1.00 | 23.30 |
| 14946 | CD | GLN | D | 160 | -38.724 | -36.661 | 27.278 | 1.00 | 26.68 |
| 14947 | OE1 | GLN | D | 160 | -37.635 | -37.231 | 27.304 | 1.00 | 30.11 |
| 14948 | NE2 | GLN | D | 160 | -38.863 | -35.354 | 27.503 | 1.00 | 29.35 |
| 14951 | C | GLN | D | 160 | -40.549 | -39.838 | 25.057 | 1.00 | 19.08 |
| 14952 | O | GLN | D | 160 | -40.020 | -40.606 | 25.866 | 1.00 | 19.23 |
| 14953 | N | SER | D | 161 | -41.726 | -40.084 | 24.483 | 1.00 | 18.48 |
| 14955 | CA | SER | D | 161 | -42.544 | -41.244 | 24.825 | 1.00 | 17.81 |
| 14957 | CB | SER | D | 161 | -44.017 | -40.838 | 24.883 | 1.00 | 18.04 |
| 14960 | OG | SER | D | 161 | -44.522 | -40.539 | 23.590 | 1.00 | 17.79 |
| 14962 | C | SER | D | 161 | -42.406 | -42.434 | 23.868 | 1.00 | 17.46 |
| 14963 | O | SER | D | 161 | -43.040 | -43.469 | 24.089 | 1.00 | 17.17 |
| 14964 | N | ASN | D | 162 | -41.596 | -42.289 | 22.817 | 1.00 | 17.13 |
| 14966 | CA | ASN | D | 162 | -41.529 | -43.282 | 21.739 | 1.00 | 17.07 |
| 14968 | CB | ASN | D | 162 | -40.880 | -44.595 | 22.218 | 1.00 | 17.45 |
| 14971 | CG | ASN | D | 162 | -39.460 | -44.406 | 22.719 | 1.00 | 19.25 |
| 14972 | OD1 | ASN | D | 162 | -38.670 | -43.688 | 22.121 | 1.00 | 22.06 |
| 14973 | ND2 | ASN | D | 162 | -39.129 | -45.070 | 23.819 | 1.00 | 22.61 |
| 14976 | C | ASN | D | 162 | -42.934 | -43.554 | 21.206 | 1.00 | 16.48 |
| 14977 | O | ASN | D | 162 | -43.358 | -44.702 | 21.069 | 1.00 | 16.42 |
| 14978 | N | GLY | D | 163 | -43.656 | -42.476 | 20.917 | 1.00 | 15.72 |
| 14980 | CA | GLY | D | 163 | -45.074 | -42.545 | 20.654 | 1.00 | 15.15 |
| 14983 | C | GLY | D | 163 | -45.428 | -42.747 | 19.196 | 1.00 | 15.00 |
| 14984 | O | GLY | D | 163 | -44.643 | -43.276 | 18.424 | 1.00 | 14.53 |
| 14985 | N | SER | D | 164 | -46.617 | -42.289 | 18.829 | 1.00 | 14.75 |
| 14987 | CA | SER | D | 164 | -47.241 | -42.667 | 17.569 | 1.00 | 14.91 |
| 14989 | CB | SER | D | 164 | -48.157 | -43.866 | 17.786 | 1.00 | 15.31 |
| 14992 | OG | SER | D | 164 | -47.453 | -44.968 | 18.339 | 1.00 | 16.88 |
| 14994 | C | SER | D | 164 | -48.060 | -41.527 | 16.983 | 1.00 | 14.53 |
| 14995 | O | SER | D | 164 | -48.734 | -40.802 | 17.704 | 1.00 | 14.25 |
| 14996 | N | ILE | D | 165 | -48.002 | -41.406 | 15.666 | 1.00 | 13.80 |
| 14998 | CA | ILE | D | 165 | -48.855 | -40.514 | 14.888 | 1.00 | 13.66 |
| 15000 | CB | ILE | D | 165 | -48.006 | -39.615 | 13.959 | 1.00 | 14.14 |
| 15002 | CG1 | ILE | D | 165 | -47.013 | -38.794 | 14.776 | 1.00 | 15.11 |
| 15005 | CD1 | ILE | D | 165 | -45.904 | -38.192 | 13.957 | 1.00 | 16.22 |
| 15009 | CG2 | ILE | D | 165 | -48.917 | -38.686 | 13.134 | 1.00 | 15.00 |
| 15013 | C | ILE | D | 165 | -49.796 | -41.375 | 14.053 | 1.00 | 13.20 |
| 15014 | O | ILE | D | 165 | -49.364 | -42.303 | 13.377 | 1.00 | 14.27 |
| 15015 | N | VAL | D | 166 | -51.080 | -41.061 | 14.104 | 1.00 | 13.09 |
| 15017 | CA | VAL | D | 166 | -52.097 | -41.756 | 13.339 | 1.00 | 13.33 |
| 15019 | CB | VAL | D | 166 | -53.141 | -42.417 | 14.267 | 1.00 | 13.57 |
| 15021 | CG1 | VAL | D | 166 | -54.227 | -43.086 | 13.465 | 1.00 | 14.05 |
| 15025 | CG2 | VAL | D | 166 | -52.461 | -43.384 | 15.233 | 1.00 | 15.39 |
| 15029 | C | VAL | D | 166 | -52.759 | -40.741 | 12.416 | 1.00 | 13.23 |
| 15030 | O | VAL | D | 166 | -53.308 | -39.742 | 12.878 | 1.00 | 13.96 |
| 15031 | N | VAL | D | 167 | -52.671 | -40.980 | 11.109 | 1.00 | 12.50 |
| 15033 | CA | VAL | D | 167 | -53.198 | -40.073 | 10.097 | 1.00 | 12.31 |

FIGURE 3 (cont.)

| A | B | C | D | E | F | G | H | I | J |
|---|---|---|---|---|---|---|---|---|---|
| 15035 | CB | VAL | D | 167 | -52.099 | -39.737 | 9.050 | 1.00 | 12.49 |
| 15037 | CG1 | VAL | D | 167 | -52.641 | -38.854 | 7.945 | 1.00 | 13.35 |
| 15041 | CG2 | VAL | D | 167 | -50.898 | -39.081 | 9.740 | 1.00 | 13.19 |
| 15045 | C | VAL | D | 167 | -54.387 | -40.747 | 9.419 | 1.00 | 12.53 |
| 15046 | O | VAL | D | 167 | -54.239 | -41.804 | 8.824 | 1.00 | 12.75 |
| 15047 | N | VAL | D | 168 | -55.577 | -40.152 | 9.530 | 1.00 | 12.48 |
| 15049 | CA | VAL | D | 168 | -56.761 | -40.753 | 8.938 | 1.00 | 12.98 |
| 15051 | CB | VAL | D | 168 | -58.031 | -40.456 | 9.741 | 1.00 | 13.08 |
| 15053 | CG1 | VAL | D | 168 | -59.240 | -41.168 | 9.111 | 1.00 | 14.02 |
| 15057 | CG2 | VAL | D | 168 | -57.837 | -40.895 | 11.190 | 1.00 | 14.06 |
| 15061 | C | VAL | D | 168 | -56.913 | -40.294 | 7.498 | 1.00 | 13.46 |
| 15062 | O | VAL | D | 168 | -56.934 | -39.104 | 7.211 | 1.00 | 13.66 |
| 15063 | N | SER | D | 169 | -57.010 | -41.268 | 6.607 | 1.00 | 13.29 |
| 15065 | CA | SER | D | 169 | -57.144 | -41.029 | 5.176 | 1.00 | 13.25 |
| 15067 | CB | SER | D | 169 | -55.804 | -41.227 | 4.462 | 1.00 | 13.35 |
| 15070 | OG | SER | D | 169 | -55.870 | -40.734 | 3.132 | 1.00 | 13.38 |
| 15072 | C | SER | D | 169 | -58.246 | -41.928 | 4.615 | 1.00 | 13.56 |
| 15073 | O | SER | D | 169 | -59.124 | -42.353 | 5.338 | 1.00 | 14.40 |
| 15074 | N | SER | D | 170 | -58.159 | -42.260 | 3.341 | 1.00 | 13.20 |
| 15076 | CA | SER | D | 170 | -59.340 | -42.510 | 2.542 | 1.00 | 12.90 |
| 15078 | CB | SER | D | 170 | -59.874 | -41.159 | 2.052 | 1.00 | 13.48 |
| 15081 | OG | SER | D | 170 | -59.887 | -40.186 | 3.099 | 1.00 | 15.10 |
| 15083 | C | SER | D | 170 | -59.007 | -43.334 | 1.321 | 1.00 | 12.68 |
| 15084 | O | SER | D | 170 | -57.889 | -43.254 | 0.811 | 1.00 | 12.07 |
| 15085 | N | LEU | D | 171 | -59.976 | -44.101 | 0.828 | 1.00 | 12.19 |
| 15087 | CA | LEU | D | 171 | -59.827 | -44.707 | -0.494 | 1.00 | 11.65 |
| 15089 | CB | LEU | D | 171 | -61.105 | -45.428 | -0.944 | 1.00 | 12.24 |
| 15092 | CG | LEU | D | 171 | -61.486 | -46.674 | -0.132 | 1.00 | 12.74 |
| 15094 | CD1 | LEU | D | 171 | -60.434 | -47.775 | -0.252 | 1.00 | 14.53 |
| 15098 | CD2 | LEU | D | 171 | -62.845 | -47.202 | -0.546 | 1.00 | 13.94 |
| 15102 | C | LEU | D | 171 | -59.445 | -43.653 | -1.524 | 1.00 | 12.15 |
| 15103 | O | LEU | D | 171 | -58.603 | -43.903 | -2.375 | 1.00 | 11.57 |
| 15104 | N | ALA | D | 172 | -60.058 | -42.472 | -1.447 | 1.00 | 12.42 |
| 15106 | CA | ALA | D | 172 | -59.747 | -41.384 | -2.377 | 1.00 | 12.48 |
| 15108 | CB | ALA | D | 172 | -60.864 | -40.351 | -2.370 | 1.00 | 13.25 |
| 15112 | C | ALA | D | 172 | -58.384 | -40.711 | -2.114 | 1.00 | 12.58 |
| 15113 | O | ALA | D | 172 | -57.998 | -39.780 | -2.834 | 1.00 | 12.96 |
| 15114 | N | GLY | D | 173 | -57.659 | -41.200 | -1.111 | 1.00 | 11.85 |
| 15116 | CA | GLY | D | 173 | -56.257 | -40.886 | -0.895 | 1.00 | 11.70 |
| 15119 | C | GLY | D | 173 | -55.257 | -41.920 | -1.429 | 1.00 | 11.80 |
| 15120 | O | GLY | D | 173 | -54.046 | -41.758 | -1.212 | 1.00 | 11.88 |
| 15121 | N | LYS | D | 174 | -55.758 | -42.963 | -2.096 | 1.00 | 12.00 |
| 15123 | CA | LYS | D | 174 | -54.931 | -44.027 | -2.691 | 1.00 | 11.97 |
| 15125 | CB | LYS | D | 174 | -55.116 | -45.339 | -1.920 | 1.00 | 12.05 |
| 15128 | CG | LYS | D | 174 | -54.496 | -45.343 | -0.548 | 1.00 | 11.63 |
| 15131 | CD | LYS | D | 174 | -52.975 | -45.199 | -0.600 | 1.00 | 11.12 |
| 15134 | CE | LYS | D | 174 | -52.325 | -45.517 | 0.717 | 1.00 | 12.30 |
| 15137 | NZ | LYS | D | 174 | -50.833 | -45.584 | 0.600 | 1.00 | 12.07 |
| 15141 | C | LYS | D | 174 | -55.239 | -44.279 | -4.159 | 1.00 | 11.80 |

FIGURE 3 (cont.)

| A | B | C | D | E | F | G | H | I | J |
|---|---|---|---|---|---|---|---|---|---|
| 15142 | O | LYS | D | 174 | -54.362 | -44.704 | -4.909 | 1.00 | 12.06 |
| 15143 | N | VAL | D | 175 | -56.491 | -44.050 | -4.561 | 1.00 | 11.67 |
| 15145 | CA | VAL | D | 175 | -56.905 | -44.128 | -5.960 | 1.00 | 11.71 |
| 15147 | CB | VAL | D | 175 | -57.622 | -45.466 | -6.313 | 1.00 | 12.10 |
| 15149 | CG1 | VAL | D | 175 | -58.954 | -45.595 | -5.606 | 1.00 | 12.79 |
| 15153 | CG2 | VAL | D | 175 | -56.724 | -46.645 | -5.993 | 1.00 | 11.66 |
| 15157 | C | VAL | D | 175 | -57.797 | -42.926 | -6.272 | 1.00 | 12.32 |
| 15158 | O | VAL | D | 175 | -58.206 | -42.196 | -5.361 | 1.00 | 12.76 |
| 15159 | N | ALA | D | 176 | -58.063 | -42.730 | -7.557 | 1.00 | 12.84 |
| 15161 | CA | ALA | D | 176 | -58.757 | -41.547 | -8.055 | 1.00 | 13.12 |
| 15163 | CB | ALA | D | 176 | -58.150 | -41.115 | -9.376 | 1.00 | 13.63 |
| 15167 | C | ALA | D | 176 | -60.252 | -41.773 | -8.222 | 1.00 | 13.33 |
| 15168 | O | ALA | D | 176 | -60.681 | -42.764 | -8.827 | 1.00 | 14.42 |
| 15169 | N | TYR | D | 177 | -61.029 | -40.810 | -7.714 | 1.00 | 12.82 |
| 15171 | CA | TYR | D | 177 | -62.486 | -40.765 | -7.851 | 1.00 | 12.83 |
| 15173 | CB | TYR | D | 177 | -63.194 | -40.922 | -6.499 | 1.00 | 12.82 |
| 15176 | CG | TYR | D | 177 | -63.089 | -42.274 | -5.857 | 1.00 | 12.62 |
| 15177 | CD1 | TYR | D | 177 | -61.981 | -42.619 | -5.094 | 1.00 | 13.75 |
| 15179 | CE1 | TYR | D | 177 | -61.880 | -43.852 | -4.483 | 1.00 | 12.93 |
| 15181 | CZ | TYR | D | 177 | -62.904 | -44.766 | -4.628 | 1.00 | 12.68 |
| 15182 | OH | TYR | D | 177 | -62.818 | -46.001 | -4.033 | 1.00 | 13.98 |
| 15184 | CE2 | TYR | D | 177 | -64.018 | -44.449 | -5.371 | 1.00 | 12.80 |
| 15186 | CD2 | TYR | D | 177 | -64.112 | -43.200 | -5.979 | 1.00 | 13.06 |
| 15188 | C | TYR | D | 177 | -62.890 | -39.401 | -8.378 | 1.00 | 12.76 |
| 15189 | O | TYR | D | 177 | -62.291 | -38.392 | -8.006 | 1.00 | 13.31 |
| 15190 | N | PRO | D | 178 | -63.945 | -39.344 | -9.183 | 1.00 | 13.20 |
| 15191 | CA | PRO | D | 178 | -64.533 | -38.054 | -9.554 | 1.00 | 12.52 |
| 15193 | CB | PRO | D | 178 | -65.510 | -38.420 | -10.662 | 1.00 | 12.78 |
| 15196 | CG | PRO | D | 178 | -65.894 | -39.818 | -10.371 | 1.00 | 12.91 |
| 15199 | CD | PRO | D | 178 | -64.716 | -40.471 | -9.734 | 1.00 | 12.44 |
| 15202 | C | PRO | D | 178 | -65.271 | -37.484 | -8.351 | 1.00 | 12.88 |
| 15203 | O | PRO | D | 178 | -65.625 | -38.232 | -7.445 | 1.00 | 13.12 |
| 15204 | N | MET | D | 179 | -65.480 | -36.178 | -8.364 | 1.00 | 12.98 |
| 15206 | CA | MET | D | 179 | -66.344 | -35.459 | -7.411 | 1.00 | 13.64 |
| 15208 | CB | MET | D | 179 | -67.675 | -36.199 | -7.166 | 1.00 | 14.25 |
| 15211 | CG | BMET | D | 179 | -68.422 | -36.571 | -8.440 | 0.35 | 15.21 |
| 15212 | CG | AMET | D | 179 | -68.414 | -36.637 | -8.425 | 0.65 | 16.54 |
| 15217 | SD | BMET | D | 179 | -70.166 | -36.914 | -8.144 | 0.35 | 16.87 |
| 15218 | SD | AMET | D | 179 | -68.576 | -35.360 | -9.671 | 0.65 | 20.23 |
| 15219 | CE | BMET | D | 179 | -70.821 | -35.261 | -7.929 | 0.35 | 16.68 |
| 15220 | CE | AMET | D | 179 | -69.117 | -36.347 | -11.067 | 0.65 | 20.59 |
| 15227 | C | MET | D | 179 | -65.695 | -35.119 | -6.075 | 1.00 | 13.27 |
| 15228 | O | MET | D | 179 | -66.333 | -34.495 | -5.225 | 1.00 | 13.68 |
| 15229 | N | VAL | D | 180 | -64.433 | -35.502 | -5.890 | 1.00 | 12.25 |
| 15231 | CA | VAL | D | 180 | -63.702 | -35.236 | -4.653 | 1.00 | 12.76 |
| 15233 | CB | VAL | D | 180 | -63.665 | -36.503 | -3.721 | 1.00 | 13.10 |
| 15235 | CG1 | VAL | D | 180 | -65.027 | -36.779 | -3.125 | 1.00 | 14.58 |
| 15239 | CG2 | VAL | D | 180 | -63.159 | -37.720 | -4.466 | 1.00 | 14.10 |
| 15243 | C | VAL | D | 180 | -62.276 | -34.741 | -4.944 | 1.00 | 12.06 |

FIGURE 3 (cont.)

| A | B | C | D | E | F | G | H | I | J |
|---|---|---|---|---|---|---|---|---|---|
| 15244 | O | VAL | D | 180 | -61.352 | -35.110 | -4.247 | 1.00 | 12.07 |
| 15245 | N | ALA | D | 181 | -62.087 | -33.917 | -5.974 | 1.00 | 12.35 |
| 15247 | CA | ALA | D | 181 | -60.731 | -33.571 | -6.418 | 1.00 | 11.75 |
| 15249 | CB | ALA | D | 181 | -60.780 | -32.761 | -7.692 | 1.00 | 11.91 |
| 15253 | C | ALA | D | 181 | -59.872 | -32.852 | -5.372 | 1.00 | 11.81 |
| 15254 | O | ALA | D | 181 | -58.743 | -33.250 | -5.115 | 1.00 | 11.83 |
| 15255 | N | ALA | D | 182 | -60.403 | -31.780 | -4.802 | 1.00 | 11.56 |
| 15257 | CA | ALA | D | 182 | -59.710 | -31.026 | -3.757 | 1.00 | 11.76 |
| 15259 | CB | ALA | D | 182 | -60.550 | -29.856 | -3.319 | 1.00 | 12.24 |
| 15263 | C | ALA | D | 182 | -59.371 | -31.907 | -2.560 | 1.00 | 11.43 |
| 15264 | O | ALA | D | 182 | -58.273 | -31.868 | -2.026 | 1.00 | 11.78 |
| 15265 | N | TYR | D | 183 | -60.344 | -32.691 | -2.124 | 1.00 | 11.14 |
| 15267 | CA | TYR | D | 183 | -60.155 | -33.604 | -1.015 | 1.00 | 10.76 |
| 15269 | CB | TYR | D | 183 | -61.472 | -34.303 | -0.742 | 1.00 | 11.17 |
| 15272 | CG | TYR | D | 183 | -61.456 | -35.413 | 0.262 | 1.00 | 10.91 |
| 15273 | CD1 | TYR | D | 183 | -61.651 | -35.156 | 1.618 | 1.00 | 11.30 |
| 15275 | CE1 | TYR | D | 183 | -61.685 | -36.187 | 2.533 | 1.00 | 13.47 |
| 15277 | CZ | TYR | D | 183 | -61.538 | -37.486 | 2.095 | 1.00 | 11.68 |
| 15278 | OH | TYR | D | 183 | -61.603 | -38.527 | 2.982 | 1.00 | 13.57 |
| 15280 | CE2 | TYR | D | 183 | -61.335 | -37.765 | 0.762 | 1.00 | 11.29 |
| 15282 | CD2 | TYR | D | 183 | -61.313 | -36.741 | -0.145 | 1.00 | 11.77 |
| 15284 | C | TYR | D | 183 | -59.094 | -34.637 | -1.316 | 1.00 | 10.53 |
| 15285 | O | TYR | D | 183 | -58.204 | -34.874 | -0.506 | 1.00 | 10.70 |
| 15286 | N | SER | D | 184 | -59.182 | -35.237 | -2.504 | 1.00 | 10.89 |
| 15288 | CA | SER | D | 184 | -58.221 | -36.253 | -2.906 | 1.00 | 10.79 |
| 15290 | CB | BSER | D | 184 | -58.603 | -36.848 | -4.262 | 0.35 | 11.04 |
| 15291 | CB | ASER | D | 184 | -58.565 | -36.823 | -4.280 | 0.65 | 11.45 |
| 15296 | OG | BSER | D | 184 | -57.682 | -37.848 | -4.660 | 0.35 | 11.04 |
| 15297 | OG | ASER | D | 184 | -59.818 | -37.464 | -4.283 | 0.65 | 13.47 |
| 15300 | C | SER | D | 184 | -56.811 | -35.681 | -2.947 | 1.00 | 10.83 |
| 15301 | O | SER | D | 184 | -55.870 | -36.331 | -2.496 | 1.00 | 11.04 |
| 15302 | N | ALA | D | 185 | -56.660 | -34.469 | -3.470 | 1.00 | 10.73 |
| 15304 | CA | ALA | D | 185 | -55.349 | -33.825 | -3.483 | 1.00 | 10.61 |
| 15306 | CB | ALA | D | 185 | -55.444 | -32.431 | -4.079 | 1.00 | 10.45 |
| 15310 | C | ALA | D | 185 | -54.763 | -33.779 | -2.068 | 1.00 | 10.48 |
| 15311 | O | ALA | D | 185 | -53.597 | -34.105 | -1.860 | 1.00 | 10.31 |
| 15312 | N | SER | D | 186 | -55.575 | -33.388 | -1.090 | 1.00 | 10.14 |
| 15314 | CA | SER | D | 186 | -55.101 | -33.252 | 0.273 | 1.00 | 10.60 |
| 15316 | CB | SER | D | 186 | -56.096 | -32.459 | 1.129 | 1.00 | 11.18 |
| 15319 | OG | SER | D | 186 | -57.263 | -33.205 | 1.408 | 1.00 | 10.48 |
| 15321 | C | SER | D | 186 | -54.758 | -34.592 | 0.903 | 1.00 | 10.50 |
| 15322 | O | SER | D | 186 | -53.777 | -34.695 | 1.634 | 1.00 | 10.89 |
| 15323 | N | LYS | D | 187 | -55.532 | -35.634 | 0.597 | 1.00 | 10.33 |
| 15325 | CA | LYS | D | 187 | -55.266 | -36.947 | 1.165 | 1.00 | 10.70 |
| 15327 | CB | LYS | D | 187 | -56.499 | -37.835 | 1.083 | 1.00 | 10.66 |
| 15330 | CG | LYS | D | 187 | -57.680 | -37.332 | 1.906 | 1.00 | 11.81 |
| 15333 | CD | LYS | D | 187 | -57.366 | -37.252 | 3.401 | 1.00 | 11.48 |
| 15336 | CE | LYS | D | 187 | -58.624 | -37.167 | 4.229 | 1.00 | 13.25 |
| 15339 | NZ | LYS | D | 187 | -58.384 | -37.209 | 5.713 | 1.00 | 12.84 |

FIGURE 3 (cont.)

| A | B | C | D | E | F | G | H | I | J |
|---|---|---|---|---|---|---|---|---|---|
| 15343 | C | LYS | D | 187 | -54.060 | -37.612 | 0.504 | 1.00 | 9.93 |
| 15344 | O | LYS | D | 187 | -53.281 | -38.260 | 1.178 | 1.00 | 10.69 |
| 15345 | N | PHE | D | 188 | -53.913 | -37.471 | -0.818 | 1.00 | 10.29 |
| 15347 | CA | PHE | D | 188 | -52.691 | -37.909 | -1.486 | 1.00 | 10.03 |
| 15349 | CB | PHE | D | 188 | -52.760 | -37.636 | -2.993 | 1.00 | 9.75 |
| 15352 | CG | PHE | D | 188 | -53.339 | -38.773 | -3.815 | 1.00 | 9.38 |
| 15353 | CD1 | PHE | D | 188 | -52.537 | -39.475 | -4.719 | 1.00 | 9.40 |
| 15355 | CE1 | PHE | D | 188 | -53.070 | -40.505 | -5.505 | 1.00 | 9.92 |
| 15357 | CZ | PHE | D | 188 | -54.410 | -40.836 | -5.391 | 1.00 | 9.54 |
| 15359 | CE2 | PHE | D | 188 | -55.215 | -40.139 | -4.519 | 1.00 | 10.24 |
| 15361 | CD2 | PHE | D | 188 | -54.685 | -39.104 | -3.740 | 1.00 | 9.53 |
| 15363 | C | PHE | D | 188 | -51.475 | -37.211 | -0.874 | 1.00 | 9.72 |
| 15364 | O | PHE | D | 188 | -50.461 | -37.847 | -0.596 | 1.00 | 9.85 |
| 15365 | N | ALA | D | 189 | -51.591 | -35.910 | -0.610 | 1.00 | 10.02 |
| 15367 | CA | ALA | D | 189 | -50.498 | -35.141 | -0.028 | 1.00 | 10.22 |
| 15369 | CB | ALA | D | 189 | -50.905 | -33.683 | 0.145 | 1.00 | 10.50 |
| 15373 | C | ALA | D | 189 | -50.070 | -35.732 | 1.315 | 1.00 | 10.27 |
| 15374 | O | ALA | D | 189 | -48.884 | -35.826 | 1.607 | 1.00 | 10.33 |
| 15375 | N | LEU | D | 190 | -51.037 | -36.128 | 2.137 | 1.00 | 10.50 |
| 15377 | CA | LEU | D | 190 | -50.728 | -36.764 | 3.413 | 1.00 | 10.66 |
| 15379 | CB | LEU | D | 190 | -52.008 | -37.123 | 4.177 | 1.00 | 10.95 |
| 15382 | CG | LEU | D | 190 | -52.829 | -35.979 | 4.787 | 1.00 | 11.91 |
| 15384 | CD1 | LEU | D | 190 | -54.142 | -36.518 | 5.332 | 1.00 | 12.38 |
| 15388 | CD2 | LEU | D | 190 | -52.091 | -35.246 | 5.912 | 1.00 | 11.46 |
| 15392 | C | LEU | D | 190 | -49.888 | -38.013 | 3.233 | 1.00 | 10.40 |
| 15393 | O | LEU | D | 190 | -48.952 | -38.244 | 3.988 | 1.00 | 11.16 |
| 15394 | N | ASP | D | 191 | -50.261 | -38.840 | 2.273 | 1.00 | 10.44 |
| 15396 | CA | ASP | D | 191 | -49.523 | -40.074 | 2.022 | 1.00 | 10.73 |
| 15398 | CB | ASP | D | 191 | -50.226 | -40.870 | 0.925 | 1.00 | 10.64 |
| 15401 | CG | ASP | D | 191 | -49.665 | -42.255 | 0.725 | 1.00 | 11.50 |
| 15402 | OD1 | ASP | D | 191 | -48.766 | -42.711 | 1.474 | 1.00 | 13.36 |
| 15403 | OD2 | ASP | D | 191 | -50.100 | -42.963 | -0.199 | 1.00 | 11.51 |
| 15404 | C | ASP | D | 191 | -48.089 | -39.739 | 1.638 | 1.00 | 10.97 |
| 15405 | O | ASP | D | 191 | -47.156 | -40.267 | 2.209 | 1.00 | 11.07 |
| 15406 | N | GLY | D | 192 | -47.902 | -38.859 | 0.658 | 1.00 | 11.14 |
| 15408 | CA | GLY | D | 192 | -46.571 | -38.476 | 0.262 | 1.00 | 10.94 |
| 15411 | C | GLY | D | 192 | -45.744 | -37.935 | 1.417 | 1.00 | 10.89 |
| 15412 | O | GLY | D | 192 | -44.600 | -38.341 | 1.630 | 1.00 | 11.73 |
| 15413 | N | PHE | D | 193 | -46.310 | -37.005 | 2.170 | 1.00 | 10.77 |
| 15415 | CA | PHE | D | 193 | -45.563 | -36.376 | 3.239 | 1.00 | 10.41 |
| 15417 | CB | PHE | D | 193 | -46.321 | -35.197 | 3.841 | 1.00 | 10.56 |
| 15420 | CG | PHE | D | 193 | -45.517 | -34.458 | 4.860 | 1.00 | 10.85 |
| 15421 | CD1 | PHE | D | 193 | -45.712 | -34.683 | 6.218 | 1.00 | 12.95 |
| 15423 | CE1 | PHE | D | 193 | -44.936 | -34.008 | 7.156 | 1.00 | 13.81 |
| 15425 | CZ | PHE | D | 193 | -43.960 | -33.145 | 6.732 | 1.00 | 12.26 |
| 15427 | CE2 | PHE | D | 193 | -43.760 | -32.925 | 5.388 | 1.00 | 12.93 |
| 15429 | CD2 | PHE | D | 193 | -44.523 | -33.586 | 4.466 | 1.00 | 11.71 |
| 15431 | C | PHE | D | 193 | -45.223 | -37.372 | 4.350 | 1.00 | 10.87 |
| 15432 | O | PHE | D | 193 | -44.065 | -37.537 | 4.700 | 1.00 | 10.74 |

FIGURE 3 (cont.)

| A | B | C | D | E | F | G | H | I | J |
|---|---|---|---|---|---|---|---|---|---|
| 15433 | N | PHE | D | 194 | -46.247 | -38.010 | 4.913 | 1.00 | 10.76 |
| 15435 | CA | PHE | D | 194 | -46.059 | -38.857 | 6.080 | 1.00 | 10.89 |
| 15437 | CB | PHE | D | 194 | -47.387 | -39.114 | 6.805 | 1.00 | 10.83 |
| 15440 | CG | PHE | D | 194 | -47.813 | -37.944 | 7.630 | 1.00 | 11.64 |
| 15441 | CD1 | PHE | D | 194 | -48.728 | -37.025 | 7.143 | 1.00 | 12.38 |
| 15443 | CE1 | PHE | D | 194 | -49.079 | -35.913 | 7.901 | 1.00 | 13.65 |
| 15445 | CZ | PHE | D | 194 | -48.509 | -35.715 | 9.139 | 1.00 | 14.05 |
| 15447 | CE2 | PHE | D | 194 | -47.595 | -36.610 | 9.625 | 1.00 | 13.74 |
| 15449 | CD2 | PHE | D | 194 | -47.240 | -37.718 | 8.881 | 1.00 | 12.23 |
| 15451 | C | PHE | D | 194 | -45.307 | -40.127 | 5.766 | 1.00 | 11.11 |
| 15452 | O | PHE | D | 194 | -44.544 | -40.591 | 6.601 | 1.00 | 10.96 |
| 15453 | N | SER | D | 195 | -45.468 | -40.654 | 4.561 | 1.00 | 11.27 |
| 15455 | CA | SER | D | 195 | -44.670 | -41.818 | 4.151 | 1.00 | 11.16 |
| 15457 | CB | SER | D | 195 | -45.227 | -42.477 | 2.891 | 1.00 | 11.21 |
| 15460 | OG | SER | D | 195 | -46.569 | -42.855 | 3.049 | 1.00 | 12.25 |
| 15462 | C | SER | D | 195 | -43.195 | -41.447 | 3.968 | 1.00 | 11.63 |
| 15463 | O | SER | D | 195 | -42.323 | -42.259 | 4.250 | 1.00 | 11.72 |
| 15464 | N | SER | D | 196 | -42.907 | -40.223 | 3.521 | 1.00 | 11.82 |
| 15466 | CA | SER | D | 196 | -41.528 | -39.743 | 3.417 | 1.00 | 12.68 |
| 15468 | CB | BSER | D | 196 | -41.477 | -38.473 | 2.576 | 0.35 | 12.82 |
| 15469 | CB | ASER | D | 196 | -41.445 | -38.438 | 2.605 | 0.65 | 13.01 |
| 15474 | OG | BSER | D | 196 | -41.916 | -38.768 | 1.264 | 0.35 | 13.11 |
| 15475 | OG | ASER | D | 196 | -40.159 | -37.832 | 2.726 | 0.65 | 13.50 |
| 15478 | C | SER | D | 196 | -40.897 | -39.531 | 4.785 | 1.00 | 13.16 |
| 15479 | O | SER | D | 196 | -39.767 | -39.979 | 5.006 | 1.00 | 13.27 |
| 15480 | N | ILE | D | 197 | -41.597 | -38.868 | 5.702 | 1.00 | 13.62 |
| 15482 | CA | ILE | D | 197 | -41.026 | -38.702 | 7.035 | 1.00 | 14.41 |
| 15484 | CB | ILE | D | 197 | -41.724 | -37.612 | 7.915 | 1.00 | 15.51 |
| 15486 | CG1 | ILE | D | 197 | -43.181 | -37.899 | 8.188 | 1.00 | 17.59 |
| 15489 | CD1 | ILE | D | 197 | -43.676 | -37.176 | 9.448 | 1.00 | 19.54 |
| 15493 | CG2 | ILE | D | 197 | -41.548 | -36.202 | 7.321 | 1.00 | 16.11 |
| 15497 | C | ILE | D | 197 | -40.876 | -40.055 | 7.739 | 1.00 | 13.72 |
| 15498 | O | ILE | D | 197 | -39.927 | -40.245 | 8.474 | 1.00 | 13.97 |
| 15499 | N | ARG | D | 198 | -41.753 | -41.019 | 7.465 | 1.00 | 13.47 |
| 15501 | CA | ARG | D | 198 | -41.574 | -42.360 | 8.024 | 1.00 | 13.78 |
| 15503 | CB | ARG | D | 198 | -42.695 | -43.322 | 7.605 | 1.00 | 13.72 |
| 15506 | CG | ARG | D | 198 | -42.692 | -44.612 | 8.410 | 1.00 | 14.65 |
| 15509 | CD | ARG | D | 198 | -43.605 | -45.688 | 7.880 | 1.00 | 14.61 |
| 15512 | NE | ARG | D | 198 | -45.018 | -45.394 | 8.055 | 1.00 | 14.15 |
| 15514 | CZ | ARG | D | 198 | -45.892 | -45.135 | 7.080 | 1.00 | 14.55 |
| 15515 | NH1 | ARG | D | 198 | -45.518 | -45.074 | 5.811 | 1.00 | 15.58 |
| 15518 | NH2 | ARG | D | 198 | -47.165 | -44.910 | 7.376 | 1.00 | 15.91 |
| 15521 | C | ARG | D | 198 | -40.221 | -42.926 | 7.608 | 1.00 | 13.72 |
| 15522 | O | ARG | D | 198 | -39.519 | -43.512 | 8.436 | 1.00 | 14.21 |
| 15523 | N | LYS | D | 199 | -39.853 | -42.749 | 6.338 | 1.00 | 14.06 |
| 15525 | CA | LYS | D | 199 | -38.542 | -43.211 | 5.843 | 1.00 | 13.97 |
| 15527 | CB | LYS | D | 199 | -38.355 | -42.988 | 4.331 | 1.00 | 14.36 |
| 15530 | CG | LYS | D | 199 | -39.406 | -43.561 | 3.421 | 1.00 | 15.66 |
| 15533 | CD | LYS | D | 199 | -39.556 | -45.040 | 3.560 | 1.00 | 16.81 |

FIGURE 3 (cont.)

| A | B | C | D | E | F | G | H | I | J |
|---|---|---|---|---|---|---|---|---|---|
| 15536 | CE | LYS | D | 199 | -40.237 | -45.645 | 2.334 | 1.00 | 17.11 |
| 15539 | NZ | LYS | D | 199 | -40.507 | -47.104 | 2.519 | 1.00 | 17.96 |
| 15543 | C | LYS | D | 199 | -37.421 | -42.481 | 6.585 | 1.00 | 14.43 |
| 15544 | O | LYS | D | 199 | -36.432 | -43.086 | 6.988 | 1.00 | 14.18 |
| 15545 | N | GLU | D | 200 | -37.583 | -41.181 | 6.782 | 1.00 | 14.22 |
| 15547 | CA | GLU | D | 200 | -36.583 | -40.387 | 7.473 | 1.00 | 14.56 |
| 15549 | CB | GLU | D | 200 | -36.946 | -38.903 | 7.425 | 1.00 | 14.70 |
| 15552 | CG | GLU | D | 200 | -36.863 | -38.326 | 6.024 | 1.00 | 14.97 |
| 15555 | CD | GLU | D | 200 | -37.170 | -36.845 | 5.957 | 1.00 | 15.33 |
| 15556 | OE1 | GLU | D | 200 | -37.285 | -36.335 | 4.820 | 1.00 | 15.96 |
| 15557 | OE2 | GLU | D | 200 | -37.290 | -36.202 | 7.013 | 1.00 | 16.35 |
| 15558 | C | GLU | D | 200 | -36.404 | -40.830 | 8.920 | 1.00 | 15.09 |
| 15559 | O | GLU | D | 200 | -35.285 | -40.901 | 9.407 | 1.00 | 15.03 |
| 15560 | N | TYR | D | 201 | -37.504 | -41.139 | 9.600 | 1.00 | 15.56 |
| 15562 | CA | TYR | D | 201 | -37.423 | -41.563 | 10.998 | 1.00 | 16.19 |
| 15564 | CB | TYR | D | 201 | -38.811 | -41.626 | 11.640 | 1.00 | 16.26 |
| 15567 | CG | TYR | D | 201 | -39.468 | -40.279 | 11.867 | 1.00 | 16.71 |
| 15568 | CD1 | TYR | D | 201 | -38.822 | -39.084 | 11.539 | 1.00 | 19.19 |
| 15570 | CE1 | TYR | D | 201 | -39.432 | -37.860 | 11.744 | 1.00 | 20.37 |
| 15572 | CZ | TYR | D | 201 | -40.702 | -37.807 | 12.269 | 1.00 | 21.02 |
| 15573 | OH | TYR | D | 201 | -41.301 | -36.579 | 12.466 | 1.00 | 25.67 |
| 15575 | CE2 | TYR | D | 201 | -41.363 | -38.967 | 12.613 | 1.00 | 19.75 |
| 15577 | CD2 | TYR | D | 201 | -40.741 | -40.202 | 12.414 | 1.00 | 19.14 |
| 15579 | C | TYR | D | 201 | -36.710 | -42.908 | 11.097 | 1.00 | 17.17 |
| 15580 | O | TYR | D | 201 | -36.003 | -43.164 | 12.064 | 1.00 | 16.78 |
| 15581 | N | SER | D | 202 | -36.858 | -43.751 | 10.083 | 1.00 | 18.13 |
| 15583 | CA | SER | D | 202 | -36.151 | -45.035 | 10.066 | 1.00 | 19.55 |
| 15585 | CB | BSER | D | 202 | -36.668 | -45.926 | 8.935 | 0.35 | 19.40 |
| 15586 | CB | ASER | D | 202 | -36.669 | -45.928 | 8.943 | 0.65 | 19.66 |
| 15591 | OG | BSER | D | 202 | -35.949 | -47.146 | 8.880 | 0.35 | 19.12 |
| 15592 | OG | ASER | D | 202 | -38.012 | -46.291 | 9.185 | 0.65 | 21.86 |
| 15595 | C | SER | D | 202 | -34.649 | -44.837 | 9.931 | 1.00 | 20.43 |
| 15596 | O | SER | D | 202 | -33.878 | -45.418 | 10.691 | 1.00 | 20.71 |
| 15597 | N | VAL | D | 203 | -34.229 | -44.010 | 8.978 | 1.00 | 21.46 |
| 15599 | CA | VAL | D | 203 | -32.802 | -43.764 | 8.770 | 1.00 | 22.67 |
| 15601 | CB | VAL | D | 203 | -32.506 | -43.057 | 7.417 | 1.00 | 23.02 |
| 15603 | CG1 | VAL | D | 203 | -33.081 | -43.848 | 6.255 | 1.00 | 24.57 |
| 15607 | CG2 | VAL | D | 203 | -33.036 | -41.650 | 7.395 | 1.00 | 24.24 |
| 15611 | C | VAL | D | 203 | -32.167 | -42.984 | 9.929 | 1.00 | 22.62 |
| 15612 | O | VAL | D | 203 | -30.985 | -43.170 | 10.227 | 1.00 | 22.58 |
| 15613 | N | SER | D | 204 | -32.951 | -42.137 | 10.593 | 1.00 | 22.63 |
| 15615 | CA | SER | D | 204 | -32.444 | -41.316 | 11.695 | 1.00 | 22.58 |
| 15617 | CB | BSER | D | 204 | -33.034 | -39.900 | 11.645 | 0.35 | 22.66 |
| 15618 | CB | ASER | D | 204 | -33.084 | -39.925 | 11.657 | 0.65 | 22.83 |
| 15623 | OG | BSER | D | 204 | -34.437 | -39.897 | 11.831 | 0.35 | 22.01 |
| 15624 | OG | ASER | D | 204 | -32.697 | -39.217 | 10.492 | 0.65 | 23.07 |
| 15627 | C | SER | D | 204 | -32.697 | -41.971 | 13.058 | 1.00 | 22.65 |
| 15628 | O | SER | D | 204 | -32.327 | -41.415 | 14.088 | 1.00 | 22.96 |
| 15629 | N | ARG | D | 205 | -33.317 | -43.153 | 13.050 | 1.00 | 22.36 |

FIGURE 3 (cont.)

| A | B | C | D | E | F | G | H | I | J |
|---|---|---|---|---|---|---|---|---|---|
| 15631 | CA | ARG | D | 205 | -33.592 | -43.926 | 14.265 | 1.00 | 22.65 |
| 15633 | CB | ARG | D | 205 | -32.283 | -44.423 | 14.886 | 1.00 | 23.12 |
| 15636 | CG | ARG | D | 205 | -31.334 | -45.058 | 13.871 | 1.00 | 25.75 |
| 15639 | CD | ARG | D | 205 | -31.493 | -46.563 | 13.712 | 1.00 | 29.10 |
| 15642 | NE | ARG | D | 205 | -30.393 | -47.291 | 14.348 | 1.00 | 31.47 |
| 15644 | CZ | ARG | D | 205 | -29.203 | -47.543 | 13.789 | 1.00 | 34.01 |
| 15645 | NH1 | ARG | D | 205 | -28.917 | -47.139 | 12.550 | 1.00 | 35.34 |
| 15648 | NH2 | ARG | D | 205 | -28.286 | -48.212 | 14.477 | 1.00 | 34.53 |
| 15651 | C | ARG | D | 205 | -34.436 | -43.147 | 15.281 | 1.00 | 21.76 |
| 15652 | O | ARG | D | 205 | -34.196 | -43.185 | 16.492 | 1.00 | 21.96 |
| 15653 | N | VAL | D | 206 | -35.425 | -42.427 | 14.763 | 1.00 | 20.35 |
| 15655 | CA | VAL | D | 206 | -36.440 | -41.778 | 15.578 | 1.00 | 19.41 |
| 15657 | CB | VAL | D | 206 | -37.038 | -40.562 | 14.843 | 1.00 | 19.52 |
| 15659 | CG1 | VAL | D | 206 | -38.266 | -40.022 | 15.569 | 1.00 | 18.94 |
| 15663 | CG2 | VAL | D | 206 | -35.986 | -39.481 | 14.663 | 1.00 | 20.11 |
| 15667 | C | VAL | D | 206 | -37.533 | -42.809 | 15.845 | 1.00 | 18.66 |
| 15668 | O | VAL | D | 206 | -38.142 | -43.318 | 14.910 | 1.00 | 17.53 |
| 15669 | N | ASN | D | 207 | -37.789 | -43.100 | 17.118 | 1.00 | 17.87 |
| 15671 | CA | ASN | D | 207 | -38.707 | -44.172 | 17.492 | 1.00 | 18.07 |
| 15673 | CB | BASN | D | 207 | -38.221 | -44.873 | 18.770 | 0.35 | 18.05 |
| 15674 | CB | AASN | D | 207 | -38.252 | -44.837 | 18.793 | 0.65 | 18.37 |
| 15679 | CG | BASN | D | 207 | -38.785 | -46.282 | 18.925 | 0.35 | 18.69 |
| 15680 | CG | AASN | D | 207 | -36.860 | -45.412 | 18.699 | 0.65 | 19.79 |
| 15681 | OD1 | BASN | D | 207 | -39.097 | -46.954 | 17.942 | 0.35 | 20.02 |
| 15682 | OD1 | AASN | D | 207 | -36.567 | -46.204 | 17.808 | 0.65 | 22.75 |
| 15683 | ND2 | BASN | D | 207 | -38.905 | -46.738 | 20.167 | 0.35 | 18.75 |
| 15684 | ND2 | AASN | D | 207 | -35.994 | -45.029 | 19.636 | 0.65 | 22.52 |
| 15689 | C | ASN | D | 207 | -40.145 | -43.664 | 17.648 | 1.00 | 17.20 |
| 15690 | O | ASN | D | 207 | -40.779 | -43.874 | 18.677 | 1.00 | 17.66 |
| 15691 | N | VAL | D | 208 | -40.642 | -42.989 | 16.614 | 1.00 | 16.47 |
| 15693 | CA | VAL | D | 208 | -42.025 | -42.526 | 16.561 | 1.00 | 15.54 |
| 15695 | CB | VAL | D | 208 | -42.106 | -40.986 | 16.415 | 1.00 | 15.82 |
| 15697 | CG1 | VAL | D | 208 | -43.551 | -40.522 | 16.238 | 1.00 | 14.94 |
| 15701 | CG2 | VAL | D | 208 | -41.478 | -40.294 | 17.629 | 1.00 | 16.11 |
| 15705 | C | VAL | D | 208 | -42.683 | -43.202 | 15.362 | 1.00 | 15.04 |
| 15706 | O | VAL | D | 208 | -42.204 | -43.075 | 14.233 | 1.00 | 15.24 |
| 15707 | N | SER | D | 209 | -43.763 | -43.928 | 15.601 | 1.00 | 14.11 |
| 15709 | CA | SER | D | 209 | -44.434 | -44.658 | 14.530 | 1.00 | 14.39 |
| 15711 | CB | SER | D | 209 | -45.128 | -45.914 | 15.057 | 1.00 | 14.21 |
| 15714 | OG | SER | D | 209 | -46.143 | -45.605 | 15.990 | 1.00 | 14.94 |
| 15716 | C | SER | D | 209 | -45.431 | -43.758 | 13.818 | 1.00 | 14.20 |
| 15717 | O | SER | D | 209 | -45.947 | -42.809 | 14.399 | 1.00 | 14.77 |
| 15718 | N | ILE | D | 210 | -45.666 | -44.060 | 12.542 | 1.00 | 14.11 |
| 15720 | CA | ILE | D | 210 | -46.611 | -43.341 | 11.697 | 1.00 | 14.23 |
| 15722 | CB | ILE | D | 210 | -45.873 | -42.521 | 10.613 | 1.00 | 14.43 |
| 15724 | CG1 | ILE | D | 210 | -45.091 | -41.396 | 11.282 | 1.00 | 14.25 |
| 15727 | CD1 | ILE | D | 210 | -44.229 | -40.633 | 10.357 | 1.00 | 15.80 |
| 15731 | CG2 | ILE | D | 210 | -46.850 | -41.953 | 9.572 | 1.00 | 14.89 |
| 15735 | C | ILE | D | 210 | -47.519 | -44.375 | 11.048 | 1.00 | 13.99 |

FIGURE 3 (cont.)

| A | B | C | D | E | F | G | H | I | J |
|---|---|---|---|---|---|---|---|---|---|
| 15736 | O | ILE | D | 210 | -47.054 | -45.263 | 10.318 | 1.00 | 13.56 |
| 15737 | N | THR | D | 211 | -48.812 | -44.245 | 11.309 | 1.00 | 13.21 |
| 15739 | CA | THR | D | 211 | -49.834 | -45.125 | 10.773 | 1.00 | 13.49 |
| 15741 | CB | THR | D | 211 | -50.634 | -45.743 | 11.935 | 1.00 | 13.70 |
| 15743 | OG1 | THR | D | 211 | -49.760 | -46.525 | 12.760 | 1.00 | 13.38 |
| 15745 | CG2 | THR | D | 211 | -51.696 | -46.716 | 11.433 | 1.00 | 14.76 |
| 15749 | C | THR | D | 211 | -50.772 | -44.318 | 9.882 | 1.00 | 13.64 |
| 15750 | O | THR | D | 211 | -51.378 | -43.361 | 10.339 | 1.00 | 13.82 |
| 15751 | N | LEU | D | 212 | -50.907 | -44.718 | 8.623 | 1.00 | 13.10 |
| 15753 | CA | LEU | D | 212 | -51.856 | -44.112 | 7.696 | 1.00 | 13.33 |
| 15755 | CB | LEU | D | 212 | -51.186 | -43.892 | 6.347 | 1.00 | 13.13 |
| 15758 | CG | LEU | D | 212 | -51.994 | -43.193 | 5.250 | 1.00 | 14.37 |
| 15760 | CD1 | LEU | D | 212 | -51.284 | -43.309 | 3.901 | 1.00 | 15.55 |
| 15764 | CD2 | LEU | D | 212 | -52.202 | -41.749 | 5.615 | 1.00 | 14.66 |
| 15768 | C | LEU | D | 212 | -53.059 | -45.029 | 7.533 | 1.00 | 13.73 |
| 15769 | O | LEU | D | 212 | -52.911 | -46.205 | 7.187 | 1.00 | 14.60 |
| 15770 | N | CYS | D | 213 | -54.249 | -44.491 | 7.767 | 1.00 | 14.08 |
| 15772 | CA | CYS | D | 213 | -55.476 | -45.285 | 7.727 | 1.00 | 14.92 |
| 15774 | CB | CYS | D | 213 | -56.360 | -44.952 | 8.924 | 1.00 | 15.42 |
| 15777 | SG | CYS | D | 213 | -55.502 | -45.181 | 10.483 | 1.00 | 19.33 |
| 15778 | C | CYS | D | 213 | -56.217 | -44.987 | 6.436 | 1.00 | 14.38 |
| 15779 | O | CYS | D | 213 | -56.367 | -43.832 | 6.065 | 1.00 | 15.63 |
| 15780 | N | VAL | D | 214 | -56.670 | -46.026 | 5.745 | 1.00 | 12.86 |
| 15782 | CA | VAL | D | 214 | -57.339 | -45.870 | 4.468 | 1.00 | 12.62 |
| 15784 | CB | VAL | D | 214 | -56.549 | -46.596 | 3.355 | 1.00 | 12.18 |
| 15786 | CG1 | VAL | D | 214 | -57.284 | -46.540 | 2.019 | 1.00 | 12.93 |
| 15790 | CG2 | VAL | D | 214 | -55.127 | -45.994 | 3.229 | 1.00 | 12.88 |
| 15794 | C | VAL | D | 214 | -58.746 | -46.431 | 4.622 | 1.00 | 12.42 |
| 15795 | O | VAL | D | 214 | -58.937 | -47.645 | 4.756 | 1.00 | 12.47 |
| 15796 | N | LEU | D | 215 | -59.730 | -45.531 | 4.603 | 1.00 | 12.02 |
| 15798 | CA | LEU | D | 215 | -61.112 | -45.871 | 4.929 | 1.00 | 12.50 |
| 15800 | CB | LEU | D | 215 | -61.646 | -44.900 | 5.984 | 1.00 | 12.51 |
| 15803 | CG | LEU | D | 215 | -60.810 | -44.662 | 7.233 | 1.00 | 13.93 |
| 15805 | CD1 | LEU | D | 215 | -61.567 | -43.724 | 8.150 | 1.00 | 14.49 |
| 15809 | CD2 | LEU | D | 215 | -60.428 | -45.943 | 7.935 | 1.00 | 14.92 |
| 15813 | C | LEU | D | 215 | -62.044 | -45.838 | 3.734 | 1.00 | 12.15 |
| 15814 | O | LEU | D | 215 | -62.002 | -44.910 | 2.911 | 1.00 | 11.97 |
| 15815 | N | GLY | D | 216 | -62.897 | -46.854 | 3.652 | 1.00 | 12.21 |
| 15817 | CA | GLY | D | 216 | -64.020 | -46.871 | 2.732 | 1.00 | 12.53 |
| 15820 | C | GLY | D | 216 | -65.200 | -46.140 | 3.329 | 1.00 | 12.77 |
| 15821 | O | GLY | D | 216 | -65.027 | -45.317 | 4.214 | 1.00 | 12.73 |
| 15822 | N | LEU | D | 217 | -66.400 | -46.459 | 2.857 | 1.00 | 12.66 |
| 15824 | CA | LEU | D | 217 | -67.601 | -45.761 | 3.312 | 1.00 | 13.14 |
| 15826 | CB | LEU | D | 217 | -68.787 | -46.087 | 2.407 | 1.00 | 13.31 |
| 15829 | CG | LEU | D | 217 | -70.150 | -45.504 | 2.796 | 1.00 | 13.13 |
| 15831 | CD1 | LEU | D | 217 | -70.066 | -43.993 | 2.873 | 1.00 | 14.01 |
| 15835 | CD2 | LEU | D | 217 | -71.192 | -45.934 | 1.797 | 1.00 | 13.73 |
| 15839 | C | LEU | D | 217 | -67.902 | -46.169 | 4.756 | 1.00 | 13.52 |
| 15840 | O | LEU | D | 217 | -68.069 | -47.358 | 5.057 | 1.00 | 13.32 |

FIGURE 3 (cont.)

| A | B | C | D | E | F | G | H | I | J |
|---|---|---|---|---|---|---|---|---|---|
| 15841 | N | ILE | D | 218 | -67.944 | -45.178 | 5.638 | 1.00 | 13.96 |
| 15843 | CA | ILE | D | 218 | -68.237 | -45.348 | 7.062 | 1.00 | 13.92 |
| 15845 | CB | ILE | D | 218 | -67.084 | -44.799 | 7.931 | 1.00 | 14.20 |
| 15847 | CG1 | ILE | D | 218 | -65.703 | -45.210 | 7.397 | 1.00 | 14.34 |
| 15850 | CD1 | ILE | D | 218 | -65.460 | -46.699 | 7.257 | 1.00 | 14.91 |
| 15854 | CG2 | ILE | D | 218 | -67.255 | -45.226 | 9.384 | 1.00 | 13.90 |
| 15858 | C | ILE | D | 218 | -69.511 | -44.573 | 7.394 | 1.00 | 14.22 |
| 15859 | O | ILE | D | 218 | -69.699 | -43.460 | 6.920 | 1.00 | 14.46 |
| 15860 | N | ASP | D | 219 | -70.363 | -45.142 | 8.240 | 1.00 | 14.52 |
| 15862 | CA | ASP | D | 219 | -71.723 | -44.613 | 8.417 | 1.00 | 15.08 |
| 15864 | CB | ASP | D | 219 | -72.644 | -45.738 | 8.894 | 1.00 | 15.09 |
| 15867 | CG | ASP | D | 219 | -72.327 | -46.213 | 10.302 | 1.00 | 17.19 |
| 15868 | OD1 | ASP | D | 219 | -73.049 | -47.116 | 10.792 | 1.00 | 19.09 |
| 15869 | OD2 | ASP | D | 219 | -71.402 | -45.747 | 11.000 | 1.00 | 18.74 |
| 15870 | C | ASP | D | 219 | -71.850 | -43.378 | 9.325 | 1.00 | 15.07 |
| 15871 | O | ASP | D | 219 | -72.815 | -43.257 | 10.100 | 1.00 | 15.22 |
| 15872 | N | THR | D | 220 | -70.904 | -42.450 | 9.236 | 1.00 | 14.64 |
| 15874 | CA | THR | D | 220 | -71.039 | -41.178 | 9.928 | 1.00 | 14.25 |
| 15876 | CB | THR | D | 220 | -69.729 | -40.352 | 9.895 | 1.00 | 14.12 |
| 15878 | OG1 | THR | D | 220 | -69.416 | -39.986 | 8.541 | 1.00 | 13.68 |
| 15880 | CG2 | THR | D | 220 | -68.550 | -41.173 | 10.373 | 1.00 | 14.11 |
| 15884 | C | THR | D | 220 | -72.164 | -40.368 | 9.301 | 1.00 | 14.78 |
| 15885 | O | THR | D | 220 | -72.489 | -40.532 | 8.126 | 1.00 | 14.49 |
| 15886 | N | GLU | D | 221 | -72.761 | -39.482 | 10.086 | 1.00 | 15.44 |
| 15888 | CA | GLU | D | 221 | -73.832 | -38.644 | 9.563 | 1.00 | 16.66 |
| 15890 | CB | GLU | D | 221 | -74.313 | -37.659 | 10.618 | 1.00 | 17.41 |
| 15893 | CG | GLU | D | 221 | -75.689 | -37.090 | 10.317 | 1.00 | 22.02 |
| 15896 | CD | GLU | D | 221 | -76.816 | -37.980 | 10.823 | 1.00 | 27.19 |
| 15897 | OE1 | GLU | D | 221 | -77.208 | -38.926 | 10.098 | 1.00 | 31.07 |
| 15898 | OE2 | GLU | D | 221 | -77.311 | -37.736 | 11.952 | 1.00 | 32.07 |
| 15899 | C | GLU | D | 221 | -73.397 | -37.879 | 8.322 | 1.00 | 16.07 |
| 15900 | O | GLU | D | 221 | -74.151 | -37.758 | 7.364 | 1.00 | 16.20 |
| 15901 | N | THR | D | 222 | -72.183 | -37.346 | 8.361 | 1.00 | 15.83 |
| 15903 | CA | THR | D | 222 | -71.620 | -36.625 | 7.224 | 1.00 | 15.25 |
| 15905 | CB | THR | D | 222 | -70.178 | -36.193 | 7.569 | 1.00 | 15.21 |
| 15907 | OG1 | THR | D | 222 | -70.208 | -35.109 | 8.511 | 1.00 | 15.44 |
| 15909 | CG2 | THR | D | 222 | -69.467 | -35.640 | 6.358 | 1.00 | 15.60 |
| 15913 | C | THR | D | 222 | -71.627 | -37.474 | 5.950 | 1.00 | 15.08 |
| 15914 | O | THR | D | 222 | -72.069 | -37.027 | 4.896 | 1.00 | 14.97 |
| 15915 | N | ALA | D | 223 | -71.121 | -38.694 | 6.052 | 1.00 | 14.99 |
| 15917 | CA | ALA | D | 223 | -71.031 | -39.582 | 4.900 | 1.00 | 15.06 |
| 15919 | CB | ALA | D | 223 | -70.229 | -40.819 | 5.255 | 1.00 | 15.15 |
| 15923 | C | ALA | D | 223 | -72.401 | -39.981 | 4.385 | 1.00 | 15.73 |
| 15924 | O | ALA | D | 223 | -72.640 | -39.983 | 3.181 | 1.00 | 14.76 |
| 15925 | N | MET | D | 224 | -73.307 | -40.302 | 5.300 | 1.00 | 16.17 |
| 15927 | CA | MET | D | 224 | -74.626 | -40.784 | 4.900 | 1.00 | 17.25 |
| 15929 | CB | MET | D | 224 | -75.391 | -41.333 | 6.102 | 1.00 | 17.89 |
| 15932 | CG | MET | D | 224 | -74.723 | -42.553 | 6.741 | 1.00 | 19.97 |
| 15935 | SD | MET | D | 224 | -74.384 | -43.936 | 5.612 | 1.00 | 25.84 |

FIGURE 3 (cont.)

| A | B | C | D | E | F | G | H | I | J |
|---|---|---|---|---|---|---|---|---|---|
| 15936 | CE | MET | D | 224 | -72.839 | -43.553 | 4.977 | 1.00 | 27.00 |
| 15940 | C | MET | D | 224 | -75.413 | -39.691 | 4.181 | 1.00 | 17.30 |
| 15941 | O | MET | D | 224 | -76.148 | -39.972 | 3.239 | 1.00 | 17.46 |
| 15942 | N | LYS | D | 225 | -75.226 | -38.444 | 4.597 | 1.00 | 17.77 |
| 15944 | CA | LYS | D | 225 | -75.851 | -37.316 | 3.911 | 1.00 | 18.38 |
| 15946 | CB | LYS | D | 225 | -75.774 | -36.058 | 4.768 | 1.00 | 18.96 |
| 15949 | CG | LYS | D | 225 | -76.777 | -36.054 | 5.920 | 1.00 | 21.88 |
| 15952 | CD | LYS | D | 225 | -76.804 | -34.699 | 6.601 | 1.00 | 25.58 |
| 15955 | CE | LYS | D | 225 | -77.456 | -34.743 | 7.979 | 1.00 | 27.29 |
| 15958 | NZ | LYS | D | 225 | -76.676 | -33.933 | 8.960 | 1.00 | 29.17 |
| 15962 | C | LYS | D | 225 | -75.203 | -37.080 | 2.548 | 1.00 | 18.03 |
| 15963 | O | LYS | D | 225 | -75.888 | -36.790 | 1.572 | 1.00 | 17.74 |
| 15964 | N | ALA | D | 226 | -73.885 | -37.252 | 2.472 | 1.00 | 17.80 |
| 15966 | CA | ALA | D | 226 | -73.154 | -36.949 | 1.250 | 1.00 | 17.82 |
| 15968 | CB | ALA | D | 226 | -71.658 | -36.911 | 1.535 | 1.00 | 17.65 |
| 15972 | C | ALA | D | 226 | -73.461 | -37.947 | 0.136 | 1.00 | 17.96 |
| 15973 | O | ALA | D | 226 | -73.466 | -37.577 | -1.040 | 1.00 | 18.22 |
| 15974 | N | VAL | D | 227 | -73.722 | -39.202 | 0.501 | 1.00 | 18.27 |
| 15976 | CA | VAL | D | 227 | -73.970 | -40.263 | -0.483 | 1.00 | 19.00 |
| 15978 | CB | VAL | D | 227 | -73.167 | -41.554 | -0.150 | 1.00 | 18.90 |
| 15980 | CG1 | VAL | D | 227 | -71.706 | -41.222 | 0.084 | 1.00 | 19.57 |
| 15984 | CG2 | VAL | D | 227 | -73.747 | -42.284 | 1.063 | 1.00 | 18.40 |
| 15988 | C | VAL | D | 227 | -75.452 | -40.622 | -0.633 | 1.00 | 20.12 |
| 15989 | O | VAL | D | 227 | -75.793 | -41.626 | -1.262 | 1.00 | 20.83 |
| 15990 | N | SER | D | 228 | -76.338 | -39.811 | -0.063 | 1.00 | 20.75 |
| 15992 | CA | SER | D | 228 | -77.759 | -40.155 | -0.055 | 1.00 | 21.65 |
| 15994 | CB | SER | D | 228 | -78.553 | -39.178 | 0.823 | 1.00 | 21.79 |
| 15997 | OG | SER | D | 228 | -78.616 | -37.897 | 0.231 | 1.00 | 23.95 |
| 15999 | C | SER | D | 228 | -78.343 | -40.218 | -1.465 | 1.00 | 22.24 |
| 16000 | O | SER | D | 228 | -79.305 | -40.965 | -1.695 | 1.00 | 23.25 |
| 16001 | N | MET | D | 233 | -74.403 | -48.276 | -1.613 | 1.00 | 32.20 |
| 16003 | CA | MET | D | 233 | -73.673 | -49.450 | -1.147 | 1.00 | 32.18 |
| 16005 | CB | MET | D | 233 | -72.276 | -49.484 | -1.765 | 1.00 | 32.75 |
| 16008 | CG | MET | D | 233 | -71.391 | -48.313 | -1.374 | 1.00 | 34.20 |
| 16011 | SD | MET | D | 233 | -69.887 | -48.247 | -2.359 | 1.00 | 37.48 |
| 16012 | CE | MET | D | 233 | -70.391 | -47.128 | -3.666 | 1.00 | 37.54 |
| 16016 | C | MET | D | 233 | -73.585 | -49.489 | 0.382 | 1.00 | 31.31 |
| 16017 | O | MET | D | 233 | -73.984 | -48.539 | 1.066 | 1.00 | 31.55 |
| 16018 | N | GLN | D | 234 | -73.066 | -50.595 | 0.908 | 1.00 | 30.00 |
| 16020 | CA | GLN | D | 234 | -73.044 | -50.832 | 2.349 | 1.00 | 29.13 |
| 16022 | CB | GLN | D | 234 | -72.773 | -52.315 | 2.659 | 1.00 | 29.61 |
| 16025 | CG | GLN | D | 234 | -74.046 | -53.190 | 2.690 | 1.00 | 31.73 |
| 16028 | CD | GLN | D | 234 | -74.000 | -54.386 | 1.750 | 1.00 | 33.97 |
| 16029 | OE1 | GLN | D | 234 | -73.053 | -54.546 | 0.978 | 1.00 | 36.91 |
| 16030 | NE2 | GLN | D | 234 | -75.030 | -55.229 | 1.813 | 1.00 | 35.97 |
| 16033 | C | GLN | D | 234 | -72.016 | -49.948 | 3.056 | 1.00 | 27.21 |
| 16034 | O | GLN | D | 234 | -70.882 | -49.793 | 2.590 | 1.00 | 27.17 |
| 16035 | N | ALA | D | 235 | -72.436 | -49.358 | 4.173 | 1.00 | 24.83 |
| 16037 | CA | ALA | D | 235 | -71.572 | -48.496 | 4.974 | 1.00 | 23.17 |

FIGURE 3 (cont.)

| A | B | C | D | E | F | G | H | I | J |
|---|---|---|---|---|---|---|---|---|---|
| 16039 | CB | ALA | D | 235 | -72.295 | -47.213 | 5.346 | 1.00 | 22.94 |
| 16043 | C | ALA | D | 235 | -71.139 | -49.245 | 6.224 | 1.00 | 21.92 |
| 16044 | O | ALA | D | 235 | -71.961 | -49.854 | 6.912 | 1.00 | 21.77 |
| 16045 | N | ALA | D | 236 | -69.849 | -49.190 | 6.518 | 1.00 | 20.27 |
| 16047 | CA | ALA | D | 236 | -69.296 | -49.850 | 7.692 | 1.00 | 19.25 |
| 16049 | CB | ALA | D | 236 | -67.811 | -50.012 | 7.535 | 1.00 | 19.24 |
| 16053 | C | ALA | D | 236 | -69.601 | -49.048 | 8.949 | 1.00 | 18.49 |
| 16054 | O | ALA | D | 236 | -69.701 | -47.829 | 8.891 | 1.00 | 17.77 |
| 16055 | N | PRO | D | 237 | -69.734 | -49.727 | 10.087 | 1.00 | 17.54 |
| 16056 | CA | PRO | D | 237 | -70.028 | -49.049 | 11.348 | 1.00 | 17.44 |
| 16058 | CB | PRO | D | 237 | -70.346 | -50.204 | 12.312 | 1.00 | 17.50 |
| 16061 | CG | PRO | D | 237 | -69.702 | -51.393 | 11.736 | 1.00 | 17.90 |
| 16064 | CD | PRO | D | 237 | -69.604 | -51.185 | 10.256 | 1.00 | 17.72 |
| 16067 | C | PRO | D | 237 | -68.859 | -48.213 | 11.870 | 1.00 | 17.09 |
| 16068 | O | PRO | D | 237 | -67.731 | -48.703 | 11.972 | 1.00 | 16.60 |
| 16069 | N | LYS | D | 238 | -69.157 | -46.968 | 12.224 | 1.00 | 16.87 |
| 16071 | CA | LYS | D | 238 | -68.155 | -46.019 | 12.699 | 1.00 | 16.99 |
| 16073 | CB | LYS | D | 238 | -68.766 | -44.610 | 12.819 | 1.00 | 16.81 |
| 16076 | CG | LYS | D | 238 | -69.951 | -44.499 | 13.790 | 1.00 | 17.32 |
| 16079 | CD | LYS | D | 238 | -70.707 | -43.192 | 13.617 | 1.00 | 17.30 |
| 16082 | CE | LYS | D | 238 | -71.748 | -43.001 | 14.717 | 1.00 | 19.10 |
| 16085 | NZ | LYS | D | 238 | -72.539 | -41.754 | 14.522 | 1.00 | 20.29 |
| 16089 | C | LYS | D | 238 | -67.494 | -46.440 | 14.010 | 1.00 | 16.95 |
| 16090 | O | LYS | D | 238 | -66.341 | -46.114 | 14.243 | 1.00 | 16.41 |
| 16091 | N | GLU | D | 239 | -68.213 | -47.161 | 14.873 | 1.00 | 17.55 |
| 16093 | CA | GLU | D | 239 | -67.628 | -47.645 | 16.124 | 1.00 | 18.48 |
| 16095 | CB | GLU | D | 239 | -68.686 | -48.311 | 17.016 | 1.00 | 19.09 |
| 16098 | CG | GLU | D | 239 | -68.208 | -48.592 | 18.431 | 1.00 | 22.45 |
| 16101 | CD | GLU | D | 239 | -69.274 | -49.242 | 19.303 | 1.00 | 26.03 |
| 16102 | OE1 | GLU | D | 239 | -68.997 | -50.319 | 19.871 | 1.00 | 29.18 |
| 16103 | OE2 | GLU | D | 239 | -70.389 | -48.677 | 19.431 | 1.00 | 30.49 |
| 16104 | C | GLU | D | 239 | -66.502 | -48.634 | 15.873 | 1.00 | 18.14 |
| 16105 | O | GLU | D | 239 | -65.435 | -48.533 | 16.476 | 1.00 | 18.30 |
| 16106 | N | GLU | D | 240 | -66.748 | -49.594 | 14.986 | 1.00 | 18.25 |
| 16108 | CA | GLU | D | 240 | -65.738 | -50.584 | 14.615 | 1.00 | 18.29 |
| 16110 | CB | GLU | D | 240 | -66.365 | -51.674 | 13.749 | 1.00 | 18.87 |
| 16113 | CG | GLU | D | 240 | -65.419 | -52.805 | 13.384 | 1.00 | 21.26 |
| 16116 | CD | GLU | D | 240 | -66.119 | -53.952 | 12.676 | 1.00 | 25.00 |
| 16117 | OE1 | GLU | D | 240 | -66.033 | -54.036 | 11.428 | 1.00 | 26.25 |
| 16118 | OE2 | GLU | D | 240 | -66.753 | -54.781 | 13.369 | 1.00 | 29.27 |
| 16119 | C | GLU | D | 240 | -64.561 | -49.946 | 13.868 | 1.00 | 17.26 |
| 16120 | O | GLU | D | 240 | -63.404 | -50.297 | 14.103 | 1.00 | 16.68 |
| 16121 | N | CYS | D | 241 | -64.866 | -49.020 | 12.966 | 1.00 | 16.24 |
| 16123 | CA | CYS | D | 241 | -63.839 | -48.280 | 12.226 | 1.00 | 15.92 |
| 16125 | CB | CYS | D | 241 | -64.501 | -47.211 | 11.349 | 1.00 | 16.00 |
| 16128 | SG | CYS | D | 241 | -63.317 | -46.255 | 10.384 | 1.00 | 16.10 |
| 16129 | C | CYS | D | 241 | -62.873 | -47.601 | 13.187 | 1.00 | 15.63 |
| 16130 | O | CYS | D | 241 | -61.659 | -47.713 | 13.070 | 1.00 | 14.64 |
| 16131 | N | ALA | D | 242 | -63.435 | -46.876 | 14.142 | 1.00 | 15.18 |

FIGURE 3 (cont.)

| A | B | C | D | E | F | G | H | I | J |
|---|---|---|---|---|---|---|---|---|---|
| 16133 | CA | ALA | D | 242 | -62.659 | -46.170 | 15.147 | 1.00 | 15.69 |
| 16135 | CB | ALA | D | 242 | -63.600 | -45.457 | 16.120 | 1.00 | 15.70 |
| 16139 | C | ALA | D | 242 | -61.729 | -47.110 | 15.897 | 1.00 | 15.82 |
| 16140 | O | ALA | D | 242 | -60.574 | -46.782 | 16.144 | 1.00 | 15.16 |
| 16141 | N | LEU | D | 243 | -62.243 | -48.276 | 16.280 | 1.00 | 16.06 |
| 16143 | CA | LEU | D | 243 | -61.449 | -49.227 | 17.042 | 1.00 | 16.56 |
| 16145 | CB | LEU | D | 243 | -62.301 | -50.396 | 17.534 | 1.00 | 17.39 |
| 16148 | CG | LEU | D | 243 | -61.546 | -51.427 | 18.371 | 1.00 | 18.77 |
| 16150 | CD1 | LEU | D | 243 | -60.916 | -50.797 | 19.597 | 1.00 | 19.77 |
| 16154 | CD2 | LEU | D | 243 | -62.482 | -52.558 | 18.773 | 1.00 | 20.04 |
| 16158 | C | LEU | D | 243 | -60.284 | -49.748 | 16.222 | 1.00 | 16.27 |
| 16159 | O | LEU | D | 243 | -59.200 | -49.861 | 16.741 | 1.00 | 15.92 |
| 16160 | N | GLU | D | 244 | -60.516 | -50.060 | 14.947 | 1.00 | 16.39 |
| 16162 | CA | GLU | D | 244 | -59.455 | -50.565 | 14.076 | 1.00 | 16.54 |
| 16164 | CB | GLU | D | 244 | -60.026 | -51.060 | 12.751 | 1.00 | 17.05 |
| 16167 | CG | GLU | D | 244 | -60.889 | -52.303 | 12.881 | 1.00 | 18.54 |
| 16170 | CD | GLU | D | 244 | -60.158 | -53.478 | 13.510 | 1.00 | 22.44 |
| 16171 | OE1 | GLU | D | 244 | -60.701 | -54.060 | 14.467 | 1.00 | 26.15 |
| 16172 | OE2 | GLU | D | 244 | -59.042 | -53.817 | 13.056 | 1.00 | 24.68 |
| 16173 | C | GLU | D | 244 | -58.362 | -49.541 | 13.832 | 1.00 | 15.87 |
| 16174 | O | GLU | D | 244 | -57.201 | -49.905 | 13.689 | 1.00 | 16.04 |
| 16175 | N | ILE | D | 245 | -58.721 | -48.263 | 13.826 | 1.00 | 15.56 |
| 16177 | CA | ILE | D | 245 | -57.730 | -47.190 | 13.706 | 1.00 | 15.17 |
| 16179 | CB | ILE | D | 245 | -58.418 | -45.823 | 13.501 | 1.00 | 14.93 |
| 16181 | CG1 | ILE | D | 245 | -59.069 | -45.774 | 12.114 | 1.00 | 15.36 |
| 16184 | CD1 | ILE | D | 245 | -59.999 | -44.603 | 11.897 | 1.00 | 15.56 |
| 16188 | CG2 | ILE | D | 245 | -57.416 | -44.666 | 13.682 | 1.00 | 14.25 |
| 16192 | C | ILE | D | 245 | -56.817 | -47.182 | 14.937 | 1.00 | 15.76 |
| 16193 | O | ILE | D | 245 | -55.588 | -47.157 | 14.814 | 1.00 | 15.56 |
| 16194 | N | ILE | D | 246 | -57.422 | -47.250 | 16.117 | 1.00 | 15.62 |
| 16196 | CA | ILE | D | 246 | -56.680 | -47.258 | 17.380 | 1.00 | 16.09 |
| 16198 | CB | ILE | D | 246 | -57.649 | -47.182 | 18.575 | 1.00 | 16.40 |
| 16200 | CG1 | ILE | D | 246 | -58.318 | -45.804 | 18.643 | 1.00 | 16.72 |
| 16203 | CD1 | ILE | D | 246 | -59.616 | -45.782 | 19.452 | 1.00 | 18.04 |
| 16207 | CG2 | ILE | D | 246 | -56.935 | -47.458 | 19.906 | 1.00 | 16.63 |
| 16211 | C | ILE | D | 246 | -55.791 | -48.490 | 17.486 | 1.00 | 15.95 |
| 16212 | O | ILE | D | 246 | -54.645 | -48.384 | 17.906 | 1.00 | 16.39 |
| 16213 | N | LYS | D | 247 | -56.314 | -49.645 | 17.094 | 1.00 | 16.30 |
| 16215 | CA | LYS | D | 247 | -55.540 | -50.887 | 17.121 | 1.00 | 17.05 |
| 16217 | CB | LYS | D | 247 | -56.383 | -52.073 | 16.649 | 1.00 | 17.48 |
| 16220 | CG | LYS | D | 247 | -57.436 | -52.541 | 17.630 | 1.00 | 19.90 |
| 16223 | CD | LYS | D | 247 | -57.925 | -53.931 | 17.255 | 1.00 | 23.08 |
| 16226 | CE | LYS | D | 247 | -59.383 | -54.139 | 17.593 | 1.00 | 25.04 |
| 16229 | NZ | LYS | D | 247 | -59.795 | -55.553 | 17.367 | 1.00 | 26.27 |
| 16233 | C | LYS | D | 247 | -54.289 | -50.779 | 16.247 | 1.00 | 16.81 |
| 16234 | O | LYS | D | 247 | -53.200 | -51.153 | 16.661 | 1.00 | 16.63 |
| 16235 | N | GLY | D | 248 | -54.454 | -50.257 | 15.039 | 1.00 | 16.92 |
| 16237 | CA | GLY | D | 248 | -53.341 | -50.092 | 14.125 | 1.00 | 17.02 |
| 16240 | C | GLY | D | 248 | -52.269 | -49.169 | 14.654 | 1.00 | 16.90 |

FIGURE 3 (cont.)

| A | B | C | D | E | F | G | H | I | J |
|---|---|---|---|---|---|---|---|---|---|
| 16241 | O | GLY | D | 248 | -51.081 | -49.474 | 14.546 | 1.00 | 17.20 |
| 16242 | N | GLY | D | 249 | -52.680 | -48.036 | 15.223 | 1.00 | 16.41 |
| 16244 | CA | GLY | D | 249 | -51.747 | -47.100 | 15.813 | 1.00 | 16.06 |
| 16247 | C | GLY | D | 249 | -51.014 | -47.717 | 16.989 | 1.00 | 15.69 |
| 16248 | O | GLY | D | 249 | -49.796 | -47.596 | 17.101 | 1.00 | 16.01 |
| 16249 | N | ALA | D | 250 | -51.759 | -48.394 | 17.858 | 1.00 | 15.79 |
| 16251 | CA | ALA | D | 250 | -51.186 | -49.016 | 19.051 | 1.00 | 16.02 |
| 16253 | CB | ALA | D | 250 | -52.279 | -49.611 | 19.914 | 1.00 | 16.19 |
| 16257 | C | ALA | D | 250 | -50.167 | -50.089 | 18.679 | 1.00 | 16.03 |
| 16258 | O | ALA | D | 250 | -49.136 | -50.225 | 19.342 | 1.00 | 16.78 |
| 16259 | N | LEU | D | 251 | -50.454 | -50.831 | 17.612 | 1.00 | 15.83 |
| 16261 | CA | LEU | D | 251 | -49.559 | -51.876 | 17.111 | 1.00 | 15.55 |
| 16263 | CB | LEU | D | 251 | -50.360 | -52.988 | 16.418 | 1.00 | 15.72 |
| 16266 | CG | LEU | D | 251 | -51.306 | -53.772 | 17.334 | 1.00 | 16.71 |
| 16268 | CD1 | LEU | D | 251 | -52.111 | -54.757 | 16.508 | 1.00 | 18.19 |
| 16272 | CD2 | LEU | D | 251 | -50.536 | -54.485 | 18.440 | 1.00 | 17.97 |
| 16276 | C | LEU | D | 251 | -48.481 | -51.348 | 16.158 | 1.00 | 15.20 |
| 16277 | O | LEU | D | 251 | -47.680 | -52.120 | 15.641 | 1.00 | 15.15 |
| 16278 | N | ARG | D | 252 | -48.460 | -50.039 | 15.941 | 1.00 | 14.81 |
| 16280 | CA | ARG | D | 252 | -47.419 | -49.370 | 15.150 | 1.00 | 15.10 |
| 16282 | CB | ARG | D | 252 | -46.051 | -49.450 | 15.854 | 1.00 | 15.46 |
| 16285 | CG | ARG | D | 252 | -46.094 | -49.004 | 17.304 | 1.00 | 15.63 |
| 16288 | CD | ARG | D | 252 | -44.805 | -49.174 | 18.045 | 1.00 | 15.97 |
| 16291 | NE | ARG | D | 252 | -43.856 | -48.087 | 17.821 | 1.00 | 15.98 |
| 16293 | CZ | ARG | D | 252 | -43.881 | -46.909 | 18.448 | 1.00 | 16.54 |
| 16294 | NH1 | ARG | D | 252 | -44.829 | -46.617 | 19.341 | 1.00 | 16.68 |
| 16297 | NH2 | ARG | D | 252 | -42.943 | -46.012 | 18.182 | 1.00 | 16.88 |
| 16300 | C | ARG | D | 252 | -47.336 | -49.887 | 13.712 | 1.00 | 15.16 |
| 16301 | O | ARG | D | 252 | -46.261 | -49.938 | 13.126 | 1.00 | 14.65 |
| 16302 | N | GLN | D | 253 | -48.485 | -50.269 | 13.159 | 1.00 | 15.44 |
| 16304 | CA | GLN | D | 253 | -48.597 | -50.675 | 11.766 | 1.00 | 15.82 |
| 16306 | CB | GLN | D | 253 | -49.981 | -51.279 | 11.501 | 1.00 | 16.25 |
| 16309 | CG | GLN | D | 253 | -50.278 | -52.555 | 12.264 | 1.00 | 18.91 |
| 16312 | CD | GLN | D | 253 | -51.706 | -53.028 | 12.057 | 1.00 | 20.15 |
| 16313 | OE1 | GLN | D | 253 | -52.383 | -52.604 | 11.116 | 1.00 | 25.34 |
| 16314 | NE2 | GLN | D | 253 | -52.167 | -53.904 | 12.929 | 1.00 | 24.87 |
| 16317 | C | GLN | D | 253 | -48.397 | -49.472 | 10.838 | 1.00 | 15.51 |
| 16318 | O | GLN | D | 253 | -48.758 | -48.351 | 11.191 | 1.00 | 15.60 |
| 16319 | N | GLU | D | 254 | -47.839 | -49.690 | 9.656 | 1.00 | 15.34 |
| 16321 | CA | GLU | D | 254 | -47.654 | -48.587 | 8.707 | 1.00 | 15.93 |
| 16323 | CB | GLU | D | 254 | -46.739 | -48.969 | 7.544 | 1.00 | 16.58 |
| 16326 | CG | GLU | D | 254 | -45.283 | -49.106 | 7.938 | 1.00 | 19.44 |
| 16329 | CD | GLU | D | 254 | -44.310 | -49.084 | 6.767 | 1.00 | 22.84 |
| 16330 | OE1 | GLU | D | 254 | -43.100 | -49.214 | 7.021 | 1.00 | 27.77 |
| 16331 | OE2 | GLU | D | 254 | -44.732 | -48.946 | 5.606 | 1.00 | 29.24 |
| 16332 | C | GLU | D | 254 | -48.998 | -48.120 | 8.172 | 1.00 | 15.32 |
| 16333 | O | GLU | D | 254 | -49.231 | -46.920 | 8.040 | 1.00 | 14.61 |
| 16334 | N | GLU | D | 255 | -49.876 | -49.070 | 7.854 | 1.00 | 15.71 |
| 16336 | CA | GLU | D | 255 | -51.158 | -48.743 | 7.237 | 1.00 | 16.36 |

FIGURE 3 (cont.)

| A | B | C | D | E | F | G | H | I | J |
|---|---|---|---|---|---|---|---|---|---|
| 16338 | CB | GLU | D | 255 | -51.082 | -48.830 | 5.695 | 1.00 | 16.58 |
| 16341 | CG | GLU | D | 255 | -50.077 | -47.843 | 5.087 | 1.00 | 18.91 |
| 16344 | CD | GLU | D | 255 | -50.150 | -47.698 | 3.568 | 1.00 | 22.25 |
| 16345 | OE1 | GLU | D | 255 | -49.788 | -46.608 | 3.052 | 1.00 | 23.78 |
| 16346 | OE2 | GLU | D | 255 | -50.527 | -48.668 | 2.880 | 1.00 | 25.14 |
| 16347 | C | GLU | D | 255 | -52.275 | -49.628 | 7.789 | 1.00 | 16.75 |
| 16348 | O | GLU | D | 255 | -52.050 | -50.805 | 8.106 | 1.00 | 17.67 |
| 16349 | N | VAL | D | 256 | -53.452 | -49.030 | 7.938 | 1.00 | 16.18 |
| 16351 | CA | VAL | D | 256 | -54.688 | -49.712 | 8.294 | 1.00 | 16.75 |
| 16353 | CB | VAL | D | 256 | -55.330 | -49.087 | 9.546 | 1.00 | 17.02 |
| 16355 | CG1 | VAL | D | 256 | -56.705 | -49.697 | 9.829 | 1.00 | 17.92 |
| 16359 | CG2 | VAL | D | 256 | -54.409 | -49.239 | 10.737 | 1.00 | 18.68 |
| 16363 | C | VAL | D | 256 | -55.644 | -49.539 | 7.126 | 1.00 | 16.45 |
| 16364 | O | VAL | D | 256 | -55.812 | -48.434 | 6.631 | 1.00 | 17.24 |
| 16365 | N | TYR | D | 257 | -56.268 | -50.623 | 6.687 | 1.00 | 15.73 |
| 16367 | CA | TYR | D | 257 | -57.284 | -50.575 | 5.648 | 1.00 | 15.63 |
| 16369 | CB | TYR | D | 257 | -56.874 | -51.461 | 4.473 | 1.00 | 16.29 |
| 16372 | CG | TYR | D | 257 | -55.704 | -50.880 | 3.714 | 1.00 | 17.03 |
| 16373 | CD1 | TYR | D | 257 | -54.398 | -51.197 | 4.052 | 1.00 | 20.46 |
| 16375 | CE1 | TYR | D | 257 | -53.319 | -50.634 | 3.347 | 1.00 | 19.65 |
| 16377 | CZ | TYR | D | 257 | -53.559 | -49.755 | 2.315 | 1.00 | 19.78 |
| 16378 | OH | TYR | D | 257 | -52.506 | -49.191 | 1.606 | 1.00 | 21.01 |
| 16380 | CE2 | TYR | D | 257 | -54.845 | -49.432 | 1.968 | 1.00 | 18.55 |
| 16382 | CD2 | TYR | D | 257 | -55.910 | -49.987 | 2.672 | 1.00 | 19.21 |
| 16384 | C | TYR | D | 257 | -58.596 | -51.057 | 6.247 | 1.00 | 15.08 |
| 16385 | O | TYR | D | 257 | -58.644 | -52.139 | 6.828 | 1.00 | 15.18 |
| 16386 | N | TYR | D | 258 | -59.657 | -50.265 | 6.116 | 1.00 | 14.26 |
| 16388 | CA | TYR | D | 258 | -60.935 | -50.604 | 6.733 | 1.00 | 14.38 |
| 16390 | CB | TYR | D | 258 | -61.120 | -49.887 | 8.088 | 1.00 | 14.66 |
| 16393 | CG | TYR | D | 258 | -62.410 | -50.303 | 8.741 | 1.00 | 15.21 |
| 16394 | CD1 | TYR | D | 258 | -63.555 | -49.549 | 8.566 | 1.00 | 16.15 |
| 16396 | CE1 | TYR | D | 258 | -64.746 | -49.929 | 9.119 | 1.00 | 18.18 |
| 16398 | CZ | TYR | D | 258 | -64.825 | -51.091 | 9.851 | 1.00 | 18.07 |
| 16399 | OH | TYR | D | 258 | -66.043 | -51.452 | 10.391 | 1.00 | 20.65 |
| 16401 | CE2 | TYR | D | 258 | -63.704 | -51.875 | 10.035 | 1.00 | 16.97 |
| 16403 | CD2 | TYR | D | 258 | -62.503 | -51.481 | 9.472 | 1.00 | 16.41 |
| 16405 | C | TYR | D | 258 | -62.100 | -50.292 | 5.794 | 1.00 | 14.27 |
| 16406 | O | TYR | D | 258 | -62.230 | -49.178 | 5.286 | 1.00 | 14.30 |
| 16407 | N | ASP | D | 259 | -62.953 | -51.287 | 5.592 | 1.00 | 14.28 |
| 16409 | CA | ASP | D | 259 | -64.089 | -51.201 | 4.685 | 1.00 | 14.94 |
| 16411 | CB | ASP | D | 259 | -63.626 | -51.381 | 3.235 | 1.00 | 15.16 |
| 16414 | CG | ASP | D | 259 | -64.712 | -51.055 | 2.212 | 1.00 | 16.58 |
| 16415 | OD1 | ASP | D | 259 | -65.311 | -51.988 | 1.605 | 1.00 | 17.34 |
| 16416 | OD2 | ASP | D | 259 | -65.018 | -49.889 | 1.932 | 1.00 | 18.72 |
| 16417 | C | ASP | D | 259 | -65.052 | -52.329 | 5.019 | 1.00 | 15.18 |
| 16418 | O | ASP | D | 259 | -64.672 | -53.313 | 5.648 | 1.00 | 15.59 |
| 16419 | N | SER | D | 260 | -66.285 | -52.200 | 4.559 | 1.00 | 15.42 |
| 16421 | CA | SER | D | 260 | -67.278 | -53.260 | 4.724 | 1.00 | 16.09 |
| 16423 | CB | BSER | D | 260 | -68.629 | -52.816 | 4.156 | 0.35 | 16.09 |

FIGURE 3 (cont.)

| A | B | C | D | E | F | G | H | I | J |
|---|---|---|---|---|---|---|---|---|---|
| 16424 | CB | ASER | D | 260 | -68.642 | -52.796 | 4.199 | 0.65 | 16.44 |
| 16429 | OG | BSER | D | 260 | -69.192 | -51.779 | 4.933 | 0.35 | 15.90 |
| 16430 | OG | ASER | D | 260 | -68.618 | -52.596 | 2.800 | 0.65 | 18.35 |
| 16433 | C | SER | D | 260 | -66.855 | -54.567 | 4.046 | 1.00 | 16.08 |
| 16434 | O | SER | D | 260 | -67.272 | -55.643 | 4.478 | 1.00 | 16.88 |
| 16435 | N | SER | D | 261 | -66.038 | -54.478 | 2.997 | 1.00 | 16.11 |
| 16437 | CA | SER | D | 261 | -65.723 | -55.646 | 2.180 | 1.00 | 16.14 |
| 16439 | CB | SER | D | 261 | -66.192 | -55.417 | 0.751 | 1.00 | 16.57 |
| 16442 | OG | SER | D | 261 | -65.776 | -56.501 | -0.070 | 1.00 | 17.84 |
| 16444 | C | SER | D | 261 | -64.235 | -55.962 | 2.159 | 1.00 | 15.61 |
| 16445 | O | SER | D | 261 | -63.413 | -55.077 | 1.998 | 1.00 | 14.84 |
| 16446 | N | LEU | D | 262 | -63.912 | -57.241 | 2.296 | 1.00 | 15.67 |
| 16448 | CA | LEU | D | 262 | -62.542 | -57.716 | 2.134 | 1.00 | 15.58 |
| 16450 | CB | LEU | D | 262 | -62.425 | -59.186 | 2.560 | 1.00 | 16.01 |
| 16453 | CG | LEU | D | 262 | -62.414 | -59.390 | 4.077 | 1.00 | 17.84 |
| 16455 | CD1 | LEU | D | 262 | -62.557 | -60.855 | 4.432 | 1.00 | 19.74 |
| 16459 | CD2 | LEU | D | 262 | -61.144 | -58.789 | 4.696 | 1.00 | 20.46 |
| 16463 | C | LEU | D | 262 | -62.034 | -57.547 | 0.706 | 1.00 | 15.03 |
| 16464 | O | LEU | D | 262 | -60.825 | -57.499 | 0.489 | 1.00 | 14.66 |
| 16465 | N | TRP | D | 263 | -62.933 | -57.493 | -0.275 | 1.00 | 14.43 |
| 16467 | CA | TRP | D | 263 | -62.519 | -57.213 | -1.647 | 1.00 | 14.54 |
| 16469 | CB | TRP | D | 263 | -63.708 | -57.244 | -2.609 | 1.00 | 14.72 |
| 16472 | CG | TRP | D | 263 | -64.184 | -58.633 | -2.909 | 1.00 | 13.81 |
| 16473 | CD1 | TRP | D | 263 | -64.952 | -59.420 | -2.115 | 1.00 | 15.11 |
| 16475 | NE1 | TRP | D | 263 | -65.173 | -60.632 | -2.717 | 1.00 | 13.92 |
| 16477 | CE2 | TRP | D | 263 | -64.535 | -60.654 | -3.928 | 1.00 | 13.81 |
| 16478 | CD2 | TRP | D | 263 | -63.885 | -59.411 | -4.076 | 1.00 | 13.55 |
| 16479 | CE3 | TRP | D | 263 | -63.162 | -59.172 | -5.248 | 1.00 | 12.56 |
| 16481 | CZ3 | TRP | D | 263 | -63.081 | -60.177 | -6.205 | 1.00 | 13.80 |
| 16483 | CH2 | TRP | D | 263 | -63.738 | -61.397 | -6.027 | 1.00 | 13.72 |
| 16485 | CZ2 | TRP | D | 263 | -64.462 | -61.661 | -4.895 | 1.00 | 13.27 |
| 16487 | C | TRP | D | 263 | -61.816 | -55.854 | -1.692 | 1.00 | 14.53 |
| 16488 | O | TRP | D | 263 | -60.788 | -55.690 | -2.338 | 1.00 | 15.23 |
| 16489 | N | THR | D | 264 | -62.367 | -54.888 | -0.968 | 1.00 | 13.92 |
| 16491 | CA | THR | D | 264 | -61.772 | -53.561 | -0.893 | 1.00 | 13.83 |
| 16493 | CB | THR | D | 264 | -62.729 | -52.580 | -0.208 | 1.00 | 13.63 |
| 16495 | OG1 | THR | D | 264 | -63.992 | -52.593 | -0.878 | 1.00 | 15.71 |
| 16497 | CG2 | THR | D | 264 | -62.213 | -51.139 | -0.334 | 1.00 | 13.64 |
| 16501 | C | THR | D | 264 | -60.456 | -53.549 | -0.145 | 1.00 | 14.10 |
| 16502 | O | THR | D | 264 | -59.456 | -53.082 | -0.673 | 1.00 | 14.03 |
| 16503 | N | THR | D | 265 | -60.450 | -54.031 | 1.096 | 1.00 | 14.17 |
| 16505 | CA | THR | D | 265 | -59.248 | -53.892 | 1.923 | 1.00 | 14.54 |
| 16507 | CB | THR | D | 265 | -59.495 | -54.251 | 3.393 | 1.00 | 14.50 |
| 16509 | OG1 | THR | D | 265 | -59.934 | -55.603 | 3.482 | 1.00 | 15.19 |
| 16511 | CG2 | THR | D | 265 | -60.602 | -53.385 | 4.004 | 1.00 | 15.04 |
| 16515 | C | THR | D | 265 | -58.080 | -54.723 | 1.421 | 1.00 | 14.43 |
| 16516 | O | THR | D | 265 | -56.938 | -54.322 | 1.601 | 1.00 | 15.40 |
| 16517 | N | LEU | D | 266 | -58.344 | -55.868 | 0.801 | 1.00 | 13.85 |
| 16519 | CA | LEU | D | 266 | -57.251 | -56.687 | 0.267 | 1.00 | 13.71 |

FIGURE 3 (cont.)

| A | B | C | D | E | F | G | H | I | J |
|---|---|---|---|---|---|---|---|---|---|
| 16521 | CB | LEU | D | 266 | -57.655 | -58.166 | 0.182 | 1.00 | 13.50 |
| 16524 | CG | LEU | D | 266 | -57.992 | -58.840 | 1.515 | 1.00 | 14.59 |
| 16526 | CD1 | LEU | D | 266 | -58.411 | -60.270 | 1.276 | 1.00 | 13.73 |
| 16530 | CD2 | LEU | D | 266 | -56.823 | -58.793 | 2.502 | 1.00 | 16.31 |
| 16534 | C | LEU | D | 266 | -56.731 | -56.195 | -1.084 | 1.00 | 13.82 |
| 16535 | O | LEU | D | 266 | -55.536 | -56.248 | -1.317 | 1.00 | 14.37 |
| 16536 | N | LEU | D | 267 | -57.608 | -55.732 | -1.970 | 1.00 | 13.67 |
| 16538 | CA | LEU | D | 267 | -57.182 | -55.349 | -3.320 | 1.00 | 13.99 |
| 16540 | CB | LEU | D | 267 | -58.330 | -55.507 | -4.326 | 1.00 | 14.36 |
| 16543 | CG | LEU | D | 267 | -58.775 | -56.947 | -4.600 | 1.00 | 14.27 |
| 16545 | CD1 | LEU | D | 267 | -60.002 | -56.962 | -5.487 | 1.00 | 13.76 |
| 16549 | CD2 | LEU | D | 267 | -57.645 | -57.760 | -5.240 | 1.00 | 15.52 |
| 16553 | C | LEU | D | 267 | -56.583 | -53.946 | -3.409 | 1.00 | 14.41 |
| 16554 | O | LEU | D | 267 | -55.782 | -53.677 | -4.300 | 1.00 | 14.45 |
| 16555 | N | ILE | D | 268 | -56.960 | -53.061 | -2.487 | 1.00 | 15.23 |
| 16557 | CA | ILE | D | 268 | -56.471 | -51.678 | -2.496 | 1.00 | 16.15 |
| 16559 | CB | ILE | D | 268 | -57.359 | -50.772 | -1.602 | 1.00 | 16.75 |
| 16561 | CG1 | ILE | D | 268 | -57.074 | -49.293 | -1.860 | 1.00 | 19.30 |
| 16564 | CD1 | ILE | D | 268 | -57.467 | -48.841 | -3.223 | 1.00 | 21.79 |
| 16568 | CG2 | ILE | D | 268 | -57.128 | -51.065 | -0.134 | 1.00 | 18.51 |
| 16572 | C | ILE | D | 268 | -55.025 | -51.585 | -2.039 | 1.00 | 16.20 |
| 16573 | O | ILE | D | 268 | -54.324 | -50.618 | -2.361 | 1.00 | 15.68 |
| 16574 | N | ARG | D | 269 | -54.578 | -52.578 | -1.284 | 1.00 | 17.20 |
| 16576 | CA | ARG | D | 269 | -53.202 | -52.585 | -0.815 | 1.00 | 17.96 |
| 16578 | CB | ARG | D | 269 | -52.977 | -53.664 | 0.260 | 1.00 | 19.69 |
| 16581 | CG | ARG | D | 269 | -52.833 | -55.080 | -0.226 | 1.00 | 24.02 |
| 16584 | CD | ARG | D | 269 | -53.139 | -56.152 | 0.837 | 1.00 | 29.25 |
| 16587 | NE | ARG | D | 269 | -52.596 | -55.787 | 2.151 | 1.00 | 33.30 |
| 16589 | CZ | ARG | D | 269 | -53.308 | -55.384 | 3.210 | 1.00 | 35.92 |
| 16590 | NH1 | ARG | D | 269 | -52.671 | -55.078 | 4.334 | 1.00 | 37.17 |
| 16593 | NH2 | ARG | D | 269 | -54.638 | -55.285 | 3.170 | 1.00 | 35.60 |
| 16596 | C | ARG | D | 269 | -52.264 | -52.735 | -2.014 | 1.00 | 16.85 |
| 16597 | O | ARG | D | 269 | -52.565 | -53.441 | -2.979 | 1.00 | 16.88 |
| 16598 | N | ASN | D | 270 | -51.131 | -52.045 | -1.929 | 1.00 | 16.07 |
| 16600 | CA | ASN | D | 270 | -50.146 | -51.990 | -3.002 | 1.00 | 15.26 |
| 16602 | CB | ASN | D | 270 | -50.113 | -50.560 | -3.584 | 1.00 | 15.13 |
| 16605 | CG | ASN | D | 270 | -49.121 | -50.383 | -4.748 | 1.00 | 16.00 |
| 16606 | OD1 | ASN | D | 270 | -48.871 | -49.256 | -5.175 | 1.00 | 17.02 |
| 16607 | ND2 | ASN | D | 270 | -48.574 | -51.476 | -5.262 | 1.00 | 14.33 |
| 16610 | C | ASN | D | 270 | -48.783 | -52.402 | -2.449 | 1.00 | 15.05 |
| 16611 | O | ASN | D | 270 | -47.897 | -51.558 | -2.243 | 1.00 | 14.33 |
| 16612 | N | PRO | D | 271 | -48.591 | -53.698 | -2.196 | 1.00 | 14.46 |
| 16613 | CA | PRO | D | 271 | -47.327 | -54.160 | -1.613 | 1.00 | 14.37 |
| 16615 | CB | PRO | D | 271 | -47.569 | -55.662 | -1.392 | 1.00 | 14.92 |
| 16618 | CG | PRO | D | 271 | -48.612 | -56.018 | -2.341 | 1.00 | 14.78 |
| 16621 | CD | PRO | D | 271 | -49.524 | -54.818 | -2.408 | 1.00 | 14.82 |
| 16624 | C | PRO | D | 271 | -46.129 | -53.904 | -2.523 | 1.00 | 14.44 |
| 16625 | O | PRO | D | 271 | -45.024 | -53.745 | -2.005 | 1.00 | 14.26 |
| 16626 | N | SER | D | 272 | -46.338 | -53.830 | -3.838 | 1.00 | 14.50 |

FIGURE 3 (cont.)

| A | B | C | D | E | F | G | H | I | J |
|---|---|---|---|---|---|---|---|---|---|
| 16628 | CA | SER | D | 272 | -45.229 | -53.577 | -4.753 | 1.00 | 14.79 |
| 16630 | CB | SER | D | 272 | -45.703 | -53.643 | -6.207 | 1.00 | 15.34 |
| 16633 | OG | SER | D | 272 | -46.073 | -54.968 | -6.561 | 1.00 | 17.89 |
| 16635 | C | SER | D | 272 | -44.578 | -52.230 | -4.487 | 1.00 | 14.61 |
| 16636 | O | SER | D | 272 | -43.375 | -52.077 | -4.649 | 1.00 | 13.54 |
| 16637 | N | ARG | D | 273 | -45.371 | -51.230 | -4.113 | 1.00 | 15.60 |
| 16639 | CA | ARG | D | 273 | -44.797 | -49.938 | -3.764 | 1.00 | 16.01 |
| 16641 | CB | ARG | D | 273 | -45.899 | -48.921 | -3.403 | 1.00 | 16.07 |
| 16644 | CG | ARG | D | 273 | -45.358 | -47.694 | -2.710 | 1.00 | 15.01 |
| 16647 | CD | ARG | D | 273 | -46.370 | -46.553 | -2.535 | 1.00 | 14.64 |
| 16650 | NE | ARG | D | 273 | -46.050 | -45.782 | -1.331 | 1.00 | 14.56 |
| 16652 | CZ | ARG | D | 273 | -46.860 | -44.881 | -0.791 | 1.00 | 15.26 |
| 16653 | NH1 | ARG | D | 273 | -48.007 | -44.588 | -1.362 | 1.00 | 14.99 |
| 16656 | NH2 | ARG | D | 273 | -46.516 | -44.270 | 0.328 | 1.00 | 15.71 |
| 16659 | C | ARG | D | 273 | -43.794 | -50.066 | -2.615 | 1.00 | 16.24 |
| 16660 | O | ARG | D | 273 | -42.690 | -49.522 | -2.690 | 1.00 | 16.48 |
| 16661 | N | LYS | D | 274 | -44.178 | -50.773 | -1.554 | 1.00 | 17.53 |
| 16663 | CA | LYS | D | 274 | -43.332 | -50.918 | -0.372 | 1.00 | 18.78 |
| 16665 | CB | LYS | D | 274 | -44.093 | -51.661 | 0.746 | 1.00 | 19.82 |
| 16668 | CG | LYS | D | 274 | -45.431 | -51.021 | 1.176 | 1.00 | 23.62 |
| 16671 | CD | LYS | D | 274 | -46.275 | -51.957 | 2.055 | 1.00 | 28.48 |
| 16674 | CE | LYS | D | 274 | -45.919 | -51.868 | 3.550 | 1.00 | 30.49 |
| 16677 | NZ | LYS | D | 274 | -47.100 | -51.533 | 4.423 | 1.00 | 31.15 |
| 16681 | C | LYS | D | 274 | -42.053 | -51.679 | -0.732 | 1.00 | 18.11 |
| 16682 | O | LYS | D | 274 | -40.970 | -51.381 | -0.227 | 1.00 | 17.79 |
| 16683 | N | ILE | D | 275 | -42.192 | -52.644 | -1.629 | 1.00 | 18.14 |
| 16685 | CA | ILE | D | 275 | -41.054 | -53.447 | -2.076 | 1.00 | 18.22 |
| 16687 | CB | ILE | D | 275 | -41.535 | -54.657 | -2.908 | 1.00 | 18.24 |
| 16689 | CG1 | ILE | D | 275 | -42.146 | -55.710 | -1.978 | 1.00 | 20.23 |
| 16692 | CD1 | ILE | D | 275 | -43.036 | -56.708 | -2.670 | 1.00 | 22.09 |
| 16696 | CG2 | ILE | D | 275 | -40.382 | -55.260 | -3.718 | 1.00 | 18.75 |
| 16700 | C | ILE | D | 275 | -40.078 | -52.589 | -2.857 | 1.00 | 17.74 |
| 16701 | O | ILE | D | 275 | -38.875 | -52.624 | -2.597 | 1.00 | 17.63 |
| 16702 | N | LEU | D | 276 | -40.593 | -51.801 | -3.796 | 1.00 | 17.33 |
| 16704 | CA | LEU | D | 276 | -39.729 | -50.936 | -4.600 | 1.00 | 17.66 |
| 16706 | CB | LEU | D | 276 | -40.500 | -50.263 | -5.737 | 1.00 | 18.11 |
| 16709 | CG | LEU | D | 276 | -40.921 | -51.167 | -6.894 | 1.00 | 20.10 |
| 16711 | CD1 | LEU | D | 276 | -41.724 | -50.349 | -7.893 | 1.00 | 21.41 |
| 16715 | CD2 | LEU | D | 276 | -39.721 | -51.807 | -7.576 | 1.00 | 20.17 |
| 16719 | C | LEU | D | 276 | -39.053 | -49.889 | -3.728 | 1.00 | 17.46 |
| 16720 | O | LEU | D | 276 | -37.881 | -49.592 | -3.916 | 1.00 | 17.82 |
| 16721 | N | GLU | D | 277 | -39.778 | -49.313 | -2.767 | 1.00 | 17.22 |
| 16723 | CA | GLU | D | 277 | -39.150 | -48.350 | -1.861 | 1.00 | 17.40 |
| 16725 | CB | GLU | D | 277 | -40.159 | -47.815 | -0.841 | 1.00 | 17.21 |
| 16728 | CG | GLU | D | 277 | -41.231 | -46.927 | -1.464 | 1.00 | 17.04 |
| 16731 | CD | GLU | D | 277 | -42.411 | -46.650 | -0.547 | 1.00 | 17.50 |
| 16732 | OE1 | GLU | D | 277 | -43.281 | -45.860 | -0.960 | 1.00 | 15.95 |
| 16733 | OE2 | GLU | D | 277 | -42.507 | -47.206 | 0.570 | 1.00 | 18.68 |
| 16734 | C | GLU | D | 277 | -37.959 | -48.987 | -1.141 | 1.00 | 17.92 |

FIGURE 3 (cont.)

| A | B | C | D | E | F | G | H | I | J |
|---|---|---|---|---|---|---|---|---|---|
| 16735 | O | GLU | D | 277 | -36.892 | -48.378 | -1.018 | 1.00 | 18.61 |
| 16736 | N | PHE | D | 278 | -38.140 | -50.218 | -0.687 | 1.00 | 19.15 |
| 16738 | CA | PHE | D | 278 | -37.058 | -50.932 | -0.007 | 1.00 | 19.63 |
| 16740 | CB | PHE | D | 278 | -37.585 | -52.224 | 0.610 | 1.00 | 20.25 |
| 16743 | CG | PHE | D | 278 | -36.509 | -53.121 | 1.134 | 1.00 | 22.47 |
| 16744 | CD1 | PHE | D | 278 | -35.915 | -52.866 | 2.360 | 1.00 | 25.60 |
| 16746 | CE1 | PHE | D | 278 | -34.911 | -53.705 | 2.847 | 1.00 | 27.06 |
| 16748 | CZ | PHE | D | 278 | -34.499 | -54.795 | 2.095 | 1.00 | 26.78 |
| 16750 | CE2 | PHE | D | 278 | -35.083 | -55.051 | 0.865 | 1.00 | 26.02 |
| 16752 | CD2 | PHE | D | 278 | -36.083 | -54.216 | 0.391 | 1.00 | 24.26 |
| 16754 | C | PHE | D | 278 | -35.886 | -51.224 | -0.954 | 1.00 | 20.08 |
| 16755 | O | PHE | D | 278 | -34.720 | -50.971 | -0.614 | 1.00 | 20.61 |
| 16756 | N | LEU | D | 279 | -36.185 | -51.714 | -2.154 | 1.00 | 20.00 |
| 16758 | CA | LEU | D | 279 | -35.139 | -52.038 | -3.130 | 1.00 | 20.48 |
| 16760 | CB | LEU | D | 279 | -35.732 | -52.754 | -4.346 | 1.00 | 20.36 |
| 16763 | CG | LEU | D | 279 | -36.248 | -54.166 | -4.042 | 1.00 | 19.94 |
| 16765 | CD1 | LEU | D | 279 | -37.011 | -54.761 | -5.212 | 1.00 | 19.99 |
| 16769 | CD2 | LEU | D | 279 | -35.107 | -55.106 | -3.599 | 1.00 | 19.70 |
| 16773 | C | LEU | D | 279 | -34.343 | -50.799 | -3.553 | 1.00 | 21.44 |
| 16774 | O | LEU | D | 279 | -33.124 | -50.855 | -3.697 | 1.00 | 21.55 |
| 16775 | N | TYR | D | 280 | -35.030 | -49.669 | -3.683 | 1.00 | 21.51 |
| 16777 | CA | TYR | D | 280 | -34.417 | -48.408 | -4.100 | 1.00 | 22.75 |
| 16779 | CB | TYR | D | 280 | -35.501 | -47.408 | -4.505 | 1.00 | 22.11 |
| 16782 | CG | TYR | D | 280 | -36.240 | -47.702 | -5.790 | 1.00 | 21.31 |
| 16783 | CD1 | TYR | D | 280 | -37.225 | -46.833 | -6.240 | 1.00 | 20.99 |
| 16785 | CE1 | TYR | D | 280 | -37.916 | -47.071 | -7.397 | 1.00 | 21.29 |
| 16787 | CZ | TYR | D | 280 | -37.658 | -48.201 | -8.138 | 1.00 | 20.57 |
| 16788 | OH | TYR | D | 280 | -38.363 | -48.442 | -9.289 | 1.00 | 22.36 |
| 16790 | CE2 | TYR | D | 280 | -36.682 | -49.096 | -7.720 | 1.00 | 19.70 |
| 16792 | CD2 | TYR | D | 280 | -35.996 | -48.855 | -6.543 | 1.00 | 20.32 |
| 16794 | C | TYR | D | 280 | -33.574 | -47.760 | -3.011 | 1.00 | 24.15 |
| 16795 | O | TYR | D | 280 | -32.790 | -46.845 | -3.306 | 1.00 | 26.18 |
| 16796 | N | SER | D | 281 | -33.762 | -48.178 | -1.763 | 1.00 | 24.89 |
| 16798 | CA | SER | D | 281 | -33.004 | -47.617 | -0.644 | 1.00 | 26.06 |
| 16800 | CB | SER | D | 281 | -33.744 | -47.839 | 0.679 | 1.00 | 26.00 |
| 16803 | OG | SER | D | 281 | -33.716 | -49.200 | 1.078 | 1.00 | 27.53 |
| 16805 | C | SER | D | 281 | -31.605 | -48.224 | -0.583 | 1.00 | 26.92 |
| 16806 | O | SER | D | 281 | -31.401 | -49.345 | -1.066 | 1.00 | 28.17 |
| 16807 | O2 | NAD | E | 1 | 8.751 | 2.102 | 17.407 | 1.00 | 12.17 |
| 16808 | C1 | NAD | E | 1 | 8.215 | 1.537 | 18.361 | 1.00 | 12.62 |
| 16809 | N3 | NAD | E | 1 | 8.918 | 0.857 | 19.267 | 1.00 | 12.48 |
| 16812 | C4 | NAD | E | 1 | 6.722 | 1.596 | 18.452 | 1.00 | 11.10 |
| 16813 | C5 | NAD | E | 1 | 6.021 | 2.273 | 17.473 | 1.00 | 12.25 |
| 16815 | C6 | NAD | E | 1 | 4.640 | 2.351 | 17.528 | 1.00 | 12.56 |
| 16817 | C7 | NAD | E | 1 | 4.000 | 1.747 | 18.596 | 1.00 | 12.90 |
| 16819 | C9 | NAD | E | 1 | 6.038 | 0.995 | 19.498 | 1.00 | 12.32 |
| 16821 | N8 | NAD | E | 1 | 4.707 | 1.091 | 19.524 | 1.00 | 12.37 |
| 16822 | C10 | NAD | E | 1 | 3.967 | 0.451 | 20.591 | 1.00 | 13.06 |
| 16824 | C11 | NAD | E | 1 | 3.575 | -0.985 | 20.291 | 1.00 | 12.60 |

FIGURE 3 (cont.)

| A | B | C | D | E | F | G | H | I | J |
|---|---|---|---|---|---|---|---|---|---|
| 16826 | O15 | NAD | E | 1 | 2.468 | -1.233 | 19.439 | 1.00 | 12.09 |
| 16828 | C12 | NAD | E | 1 | 3.554 | -1.648 | 21.638 | 1.00 | 12.74 |
| 16830 | O16 | NAD | E | 1 | 2.181 | -1.504 | 22.014 | 1.00 | 11.94 |
| 16832 | O14 | NAD | E | 1 | 4.553 | 0.491 | 21.875 | 1.00 | 12.96 |
| 16833 | C13 | NAD | E | 1 | 4.302 | -0.742 | 22.582 | 1.00 | 12.45 |
| 16835 | C17 | NAD | E | 1 | 5.617 | -1.358 | 23.023 | 1.00 | 12.35 |
| 16838 | O18 | NAD | E | 1 | 6.467 | -1.539 | 21.890 | 1.00 | 13.48 |
| 16839 | P19 | NAD | E | 1 | 7.989 | -2.034 | 22.131 | 1.00 | 12.97 |
| 16840 | O20 | NAD | E | 1 | 8.443 | -1.534 | 23.460 | 1.00 | 12.70 |
| 16841 | O21 | NAD | E | 1 | 8.738 | -1.691 | 20.882 | 1.00 | 12.69 |
| 16842 | O22 | NAD | E | 1 | 7.766 | -3.629 | 22.169 | 1.00 | 13.47 |
| 16843 | P23 | NAD | E | 1 | 8.806 | -4.751 | 22.678 | 1.00 | 13.64 |
| 16844 | O24 | NAD | E | 1 | 10.101 | -4.134 | 23.160 | 1.00 | 13.15 |
| 16845 | O25 | NAD | E | 1 | 8.871 | -5.753 | 21.582 | 1.00 | 14.05 |
| 16846 | O26 | NAD | E | 1 | 8.013 | -5.355 | 23.938 | 1.00 | 13.80 |
| 16847 | C27 | NAD | E | 1 | 6.907 | -6.234 | 23.755 | 1.00 | 13.48 |
| 16850 | C28 | NAD | E | 1 | 6.493 | -6.755 | 25.124 | 1.00 | 11.65 |
| 16852 | C29 | NAD | E | 1 | 7.586 | -7.673 | 25.606 | 1.00 | 11.90 |
| 16854 | O33 | NAD | E | 1 | 7.570 | -7.539 | 27.039 | 1.00 | 13.89 |
| 16856 | O32 | NAD | E | 1 | 5.292 | -7.531 | 24.977 | 1.00 | 13.75 |
| 16857 | C31 | NAD | E | 1 | 5.578 | -8.874 | 25.357 | 1.00 | 13.11 |
| 16859 | C30 | NAD | E | 1 | 7.086 | -9.059 | 25.410 | 1.00 | 13.17 |
| 16861 | O34 | NAD | E | 1 | 7.656 | -10.046 | 26.257 | 1.00 | 14.05 |
| 16862 | P35 | NAD | E | 1 | 7.592 | -11.626 | 25.953 | 1.00 | 14.24 |
| 16863 | O37 | NAD | E | 1 | 8.548 | -12.192 | 26.979 | 1.00 | 16.17 |
| 16864 | O36 | NAD | E | 1 | 6.170 | -12.045 | 26.181 | 1.00 | 14.39 |
| 16865 | O38 | NAD | E | 1 | 8.067 | -11.828 | 24.530 | 1.00 | 14.16 |
| 16866 | N39 | NAD | E | 1 | 4.820 | -9.904 | 24.671 | 1.00 | 12.28 |
| 16867 | C40 | NAD | E | 1 | 3.782 | -10.559 | 25.156 | 1.00 | 12.08 |
| 16868 | N47 | NAD | E | 1 | 3.160 | -10.434 | 26.430 | 1.00 | 11.08 |
| 16869 | C41 | NAD | E | 1 | 3.337 | -11.502 | 24.183 | 1.00 | 11.01 |
| 16870 | N42 | NAD | E | 1 | 4.137 | -11.359 | 23.121 | 1.00 | 12.14 |
| 16871 | C43 | NAD | E | 1 | 5.036 | -10.389 | 23.432 | 1.00 | 11.14 |
| 16873 | C44 | NAD | E | 1 | 2.211 | -12.337 | 24.572 | 1.00 | 11.86 |
| 16874 | N48 | NAD | E | 1 | 1.745 | -13.250 | 23.693 | 1.00 | 12.80 |
| 16877 | N45 | NAD | E | 1 | 1.676 | -12.165 | 25.809 | 1.00 | 12.12 |
| 16878 | C46 | NAD | E | 1 | 2.129 | -11.258 | 26.688 | 1.00 | 11.72 |
| 16880 | O2 | NAD | E | 2 | -27.810 | 2.961 | 9.373 | 1.00 | 13.69 |
| 16881 | C1 | NAD | E | 2 | -27.399 | 1.962 | 8.814 | 1.00 | 14.14 |
| 16882 | N3 | NAD | E | 2 | -28.218 | 1.072 | 8.262 | 1.00 | 13.27 |
| 16885 | C4 | NAD | E | 2 | -25.920 | 1.748 | 8.754 | 1.00 | 13.12 |
| 16886 | C5 | NAD | E | 2 | -25.089 | 2.696 | 9.348 | 1.00 | 13.89 |
| 16888 | C6 | NAD | E | 2 | -23.717 | 2.526 | 9.293 | 1.00 | 13.22 |
| 16890 | C7 | NAD | E | 2 | -23.187 | 1.413 | 8.671 | 1.00 | 12.77 |
| 16892 | C9 | NAD | E | 2 | -25.355 | 0.638 | 8.136 | 1.00 | 12.40 |
| 16894 | N8 | NAD | E | 2 | -24.014 | 0.504 | 8.120 | 1.00 | 12.22 |
| 16895 | C10 | NAD | E | 2 | -23.405 | -0.657 | 7.488 | 1.00 | 13.86 |
| 16897 | C11 | NAD | E | 2 | -23.185 | -1.831 | 8.429 | 1.00 | 14.57 |
| 16899 | O15 | NAD | E | 2 | -22.081 | -1.793 | 9.307 | 1.00 | 13.40 |

FIGURE 3 (cont.)

| A | B | C | D | E | F | G | H | I | J |
|---|---|---|---|---|---|---|---|---|---|
| 16901 | C12 | NAD | E | 2 | -23.317 | -3.042 | 7.538 | 1.00 | 13.49 |
| 16903 | O16 | NAD | E | 2 | -21.950 | -3.359 | 7.188 | 1.00 | 11.94 |
| 16905 | O14 | NAD | E | 2 | -24.053 | -1.152 | 6.317 | 1.00 | 13.68 |
| 16906 | C13 | NAD | E | 2 | -23.982 | -2.578 | 6.265 | 1.00 | 13.20 |
| 16908 | C17 | NAD | E | 2 | -25.392 | -3.141 | 6.106 | 1.00 | 13.38 |
| 16911 | O18 | NAD | E | 2 | -26.214 | -2.664 | 7.181 | 1.00 | 13.61 |
| 16912 | P19 | NAD | E | 2 | -27.822 | -2.915 | 7.176 | 1.00 | 12.64 |
| 16913 | O20 | NAD | E | 2 | -28.262 | -3.056 | 5.766 | 1.00 | 13.33 |
| 16914 | O21 | NAD | E | 2 | -28.456 | -1.943 | 8.119 | 1.00 | 12.86 |
| 16915 | O22 | NAD | E | 2 | -27.836 | -4.361 | 7.891 | 1.00 | 13.44 |
| 16916 | P23 | NAD | E | 2 | -29.028 | -5.470 | 7.892 | 1.00 | 13.62 |
| 16917 | O24 | NAD | E | 2 | -30.204 | -4.998 | 7.102 | 1.00 | 14.21 |
| 16918 | O25 | NAD | E | 2 | -29.196 | -5.826 | 9.322 | 1.00 | 12.90 |
| 16919 | O26 | NAD | E | 2 | -28.359 | -6.691 | 7.104 | 1.00 | 12.90 |
| 16920 | C27 | NAD | E | 2 | -27.292 | -7.462 | 7.655 | 1.00 | 13.44 |
| 16923 | C28 | NAD | E | 2 | -27.102 | -8.678 | 6.766 | 1.00 | 12.69 |
| 16925 | C29 | NAD | E | 2 | -28.358 | -9.525 | 6.749 | 1.00 | 13.24 |
| 16927 | O33 | NAD | E | 2 | -28.387 | -10.052 | 5.420 | 1.00 | 13.83 |
| 16929 | O32 | NAD | E | 2 | -26.066 | -9.470 | 7.325 | 1.00 | 12.95 |
| 16930 | C31 | NAD | E | 2 | -26.556 | -10.762 | 7.613 | 1.00 | 13.66 |
| 16932 | C30 | NAD | E | 2 | -28.083 | -10.723 | 7.595 | 1.00 | 13.71 |
| 16934 | O34 | NAD | E | 2 | -28.839 | -11.887 | 7.281 | 1.00 | 14.53 |
| 16935 | P35 | NAD | E | 2 | -29.026 | -13.101 | 8.330 | 1.00 | 14.73 |
| 16936 | O37 | NAD | E | 2 | -30.112 | -13.922 | 7.668 | 1.00 | 16.19 |
| 16937 | O36 | NAD | E | 2 | -27.704 | -13.806 | 8.360 | 1.00 | 15.06 |
| 16938 | O38 | NAD | E | 2 | -29.445 | -12.538 | 9.662 | 1.00 | 14.72 |
| 16939 | N39 | NAD | E | 2 | -25.912 | -11.445 | 8.720 | 1.00 | 12.70 |
| 16940 | C40 | NAD | E | 2 | -25.035 | -12.427 | 8.605 | 1.00 | 11.90 |
| 16941 | N47 | NAD | E | 2 | -24.462 | -12.991 | 7.428 | 1.00 | 13.06 |
| 16942 | C41 | NAD | E | 2 | -24.682 | -12.878 | 9.910 | 1.00 | 12.10 |
| 16943 | N42 | NAD | E | 2 | -25.406 | -12.135 | 10.758 | 1.00 | 12.89 |
| 16944 | C43 | NAD | E | 2 | -26.156 | -11.288 | 10.016 | 1.00 | 12.05 |
| 16946 | C44 | NAD | E | 2 | -23.699 | -13.969 | 9.979 | 1.00 | 11.69 |
| 16947 | N48 | NAD | E | 2 | -23.333 | -14.439 | 11.184 | 1.00 | 14.12 |
| 16950 | N45 | NAD | E | 2 | -23.215 | -14.455 | 8.830 | 1.00 | 13.47 |
| 16951 | C46 | NAD | E | 2 | -23.570 | -13.989 | 7.625 | 1.00 | 12.53 |
| 16953 | O2 | NAD | E | 3 | -34.117 | -35.627 | -11.946 | 1.00 | 13.66 |
| 16954 | C1 | NAD | E | 3 | -34.853 | -34.705 | -12.311 | 1.00 | 13.42 |
| 16955 | N3 | NAD | E | 3 | -34.391 | -33.677 | -13.000 | 1.00 | 13.03 |
| 16958 | C4 | NAD | E | 3 | -36.325 | -34.775 | -12.001 | 1.00 | 11.89 |
| 16959 | C5 | NAD | E | 3 | -36.792 | -35.883 | -11.292 | 1.00 | 13.56 |
| 16961 | C6 | NAD | E | 3 | -38.150 | -35.997 | -11.019 | 1.00 | 13.36 |
| 16963 | C7 | NAD | E | 3 | -39.004 | -34.994 | -11.439 | 1.00 | 13.29 |
| 16965 | C9 | NAD | E | 3 | -37.223 | -33.795 | -12.411 | 1.00 | 13.42 |
| 16967 | N8 | NAD | E | 3 | -38.527 | -33.950 | -12.115 | 1.00 | 12.62 |
| 16968 | C10 | NAD | E | 3 | -39.478 | -32.922 | -12.488 | 1.00 | 13.12 |
| 16970 | C11 | NAD | E | 3 | -39.697 | -31.833 | -11.451 | 1.00 | 12.65 |
| 16972 | O15 | NAD | E | 3 | -40.492 | -32.108 | -10.308 | 1.00 | 12.94 |
| 16974 | C12 | NAD | E | 3 | -40.048 | -30.606 | -12.267 | 1.00 | 11.65 |

FIGURE 3 (cont.)

| A | B | C | D | E | F | G | H | I | J |
|---|---|---|---|---|---|---|---|---|---|
| 16976 | O16 | NAD | E | 3 | -41.481 | -30.594 | -12.282 | 1.00 | 12.23 |
| 16978 | O14 | NAD | E | 3 | -39.247 | -32.302 | -13.734 | 1.00 | 12.68 |
| 16979 | C13 | NAD | E | 3 | -39.630 | -30.914 | -13.692 | 1.00 | 11.79 |
| 16981 | C17 | NAD | E | 3 | -38.463 | -30.048 | -14.145 | 1.00 | 13.10 |
| 16984 | O18 | NAD | E | 3 | -37.335 | -30.394 | -13.333 | 1.00 | 13.65 |
| 16985 | P19 | NAD | E | 3 | -35.865 | -29.854 | -13.703 | 1.00 | 13.36 |
| 16986 | O20 | NAD | E | 3 | -35.801 | -29.493 | -15.150 | 1.00 | 13.46 |
| 16987 | O21 | NAD | E | 3 | -34.884 | -30.820 | -13.117 | 1.00 | 12.89 |
| 16988 | O22 | NAD | E | 3 | -35.784 | -28.527 | -12.805 | 1.00 | 15.28 |
| 16989 | P23 | NAD | E | 3 | -34.948 | -27.166 | -13.045 | 1.00 | 15.47 |
| 16990 | O24 | NAD | E | 3 | -33.908 | -27.346 | -14.105 | 1.00 | 17.48 |
| 16991 | O25 | NAD | E | 3 | -34.598 | -26.666 | -11.664 | 1.00 | 17.28 |
| 16992 | O26 | NAD | E | 3 | -36.100 | -26.236 | -13.662 | 1.00 | 14.95 |
| 16993 | C27 | NAD | E | 3 | -37.149 | -25.692 | -12.871 | 1.00 | 14.37 |
| 16996 | C28 | NAD | E | 3 | -37.769 | -24.568 | -13.688 | 1.00 | 13.95 |
| 16998 | C29 | NAD | E | 3 | -36.717 | -23.526 | -13.973 | 1.00 | 13.85 |
| 17000 | O33 | NAD | E | 3 | -37.009 | -23.006 | -15.299 | 1.00 | 14.30 |
| 17002 | O32 | NAD | E | 3 | -38.792 | -23.952 | -12.897 | 1.00 | 14.19 |
| 17003 | C31 | NAD | E | 3 | -38.448 | -22.581 | -12.675 | 1.00 | 13.68 |
| 17005 | C30 | NAD | E | 3 | -36.997 | -22.373 | -13.093 | 1.00 | 13.48 |
| 17007 | O34 | NAD | E | 3 | -36.579 | -21.148 | -13.658 | 1.00 | 13.85 |
| 17008 | P35 | NAD | E | 3 | -36.236 | -19.808 | -12.833 | 1.00 | 14.31 |
| 17009 | O37 | NAD | E | 3 | -35.744 | -18.967 | -13.976 | 1.00 | 15.22 |
| 17010 | O36 | NAD | E | 3 | -37.522 | -19.353 | -12.225 | 1.00 | 13.21 |
| 17011 | O38 | NAD | E | 3 | -35.150 | -20.150 | -11.825 | 1.00 | 15.38 |
| 17012 | N39 | NAD | E | 3 | -38.813 | -22.033 | -11.372 | 1.00 | 13.30 |
| 17013 | C40 | NAD | E | 3 | -39.832 | -21.216 | -11.158 | 1.00 | 13.46 |
| 17014 | N47 | NAD | E | 3 | -40.829 | -20.743 | -12.058 | 1.00 | 12.32 |
| 17015 | C41 | NAD | E | 3 | -39.851 | -20.851 | -9.765 | 1.00 | 12.36 |
| 17016 | N42 | NAD | E | 3 | -38.788 | -21.452 | -9.220 | 1.00 | 12.24 |
| 17017 | C43 | NAD | E | 3 | -38.174 | -22.149 | -10.198 | 1.00 | 12.92 |
| 17019 | C44 | NAD | E | 3 | -40.943 | -19.964 | -9.351 | 1.00 | 13.46 |
| 17020 | N48 | NAD | E | 3 | -41.011 | -19.582 | -8.060 | 1.00 | 14.63 |
| 17023 | N45 | NAD | E | 3 | -41.834 | -19.560 | -10.272 | 1.00 | 13.04 |
| 17024 | C46 | NAD | E | 3 | -41.770 | -19.930 | -11.569 | 1.00 | 14.15 |
| 17026 | O2 | NAD | E | 4 | -67.060 | -42.510 | 4.780 | 1.00 | 16.74 |
| 17027 | C1 | NAD | E | 4 | -66.453 | -41.855 | 5.611 | 1.00 | 15.31 |
| 17028 | N3 | NAD | E | 4 | -67.048 | -41.410 | 6.729 | 1.00 | 16.22 |
| 17031 | C4 | NAD | E | 4 | -65.005 | -41.585 | 5.344 | 1.00 | 16.29 |
| 17032 | C5 | NAD | E | 4 | -64.456 | -42.091 | 4.167 | 1.00 | 15.48 |
| 17034 | C6 | NAD | E | 4 | -63.114 | -41.870 | 3.899 | 1.00 | 15.41 |
| 17036 | C7 | NAD | E | 4 | -62.353 | -41.156 | 4.800 | 1.00 | 15.97 |
| 17038 | C9 | NAD | E | 4 | -64.197 | -40.879 | 6.218 | 1.00 | 16.21 |
| 17040 | N8 | NAD | E | 4 | -62.907 | -40.676 | 5.930 | 1.00 | 14.62 |
| 17041 | C10 | NAD | E | 4 | -62.046 | -39.930 | 6.809 | 1.00 | 15.56 |
| 17043 | C11 | NAD | E | 4 | -61.998 | -38.436 | 6.527 | 1.00 | 15.57 |
| 17045 | O15 | NAD | E | 4 | -61.224 | -37.948 | 5.439 | 1.00 | 14.99 |
| 17047 | C12 | NAD | E | 4 | -61.764 | -37.799 | 7.867 | 1.00 | 15.11 |
| 17049 | O16 | NAD | E | 4 | -60.342 | -37.609 | 7.927 | 1.00 | 14.75 |

FIGURE 3 (cont.)

| A | B | C | D | E | F | G | H | I | J |
|---|---|---|---|---|---|---|---|---|---|
| 17051 | O14 | NAD | E | 4 | -62.284 | -40.104 | 8.215 | 1.00 | 15.60 |
| 17052 | C13 | NAD | E | 4 | -62.093 | -38.862 | 8.912 | 1.00 | 15.54 |
| 17054 | C17 | NAD | E | 4 | -63.364 | -38.525 | 9.697 | 1.00 | 16.51 |
| 17057 | O18 | NAD | E | 4 | -64.479 | -38.439 | 8.821 | 1.00 | 16.78 |
| 17058 | P19 | NAD | E | 4 | -65.984 | -38.339 | 9.412 | 1.00 | 17.84 |
| 17059 | O20 | NAD | E | 4 | -65.939 | -38.884 | 10.808 | 1.00 | 17.58 |
| 17060 | O21 | NAD | E | 4 | -66.912 | -38.885 | 8.382 | 1.00 | 17.04 |
| 17061 | O22 | NAD | E | 4 | -66.124 | -36.744 | 9.475 | 1.00 | 18.11 |
| 17062 | P23 | NAD | E | 4 | -67.212 | -35.875 | 10.324 | 1.00 | 19.23 |
| 17063 | O24 | NAD | E | 4 | -68.227 | -36.775 | 10.969 | 1.00 | 21.51 |
| 17064 | O25 | NAD | E | 4 | -67.695 | -34.823 | 9.372 | 1.00 | 19.94 |
| 17065 | O26 | NAD | E | 4 | -66.270 | -35.207 | 11.407 | 1.00 | 17.31 |
| 17066 | C27 | NAD | E | 4 | -65.320 | -34.187 | 11.061 | 1.00 | 18.60 |
| 17069 | C28 | NAD | E | 4 | -64.731 | -33.574 | 12.309 | 1.00 | 18.23 |
| 17071 | C29 | NAD | E | 4 | -65.859 | -32.895 | 13.051 | 1.00 | 18.79 |
| 17073 | O33 | NAD | E | 4 | -65.545 | -33.090 | 14.431 | 1.00 | 19.43 |
| 17075 | O32 | NAD | E | 4 | -63.792 | -32.549 | 11.971 | 1.00 | 18.43 |
| 17076 | C31 | NAD | E | 4 | -64.237 | -31.289 | 12.470 | 1.00 | 18.85 |
| 17078 | C30 | NAD | E | 4 | -65.680 | -31.427 | 12.899 | 1.00 | 19.84 |
| 17080 | O34 | NAD | E | 4 | -66.101 | -30.669 | 14.011 | 1.00 | 21.05 |
| 17081 | P35 | NAD | E | 4 | -66.765 | -29.203 | 13.874 | 1.00 | 22.67 |
| 17082 | O37 | NAD | E | 4 | -67.399 | -29.097 | 15.242 | 1.00 | 26.36 |
| 17083 | O36 | NAD | E | 4 | -65.539 | -28.359 | 13.794 | 1.00 | 23.44 |
| 17084 | O38 | NAD | E | 4 | -67.672 | -29.178 | 12.675 | 1.00 | 23.97 |
| 17085 | N39 | NAD | E | 4 | -63.932 | -30.102 | 11.665 | 1.00 | 17.93 |
| 17086 | C40 | NAD | E | 4 | -62.995 | -29.226 | 11.950 | 1.00 | 16.40 |
| 17087 | N47 | NAD | E | 4 | -62.062 | -29.203 | 13.038 | 1.00 | 17.28 |
| 17088 | C41 | NAD | E | 4 | -63.017 | -28.188 | 10.952 | 1.00 | 16.02 |
| 17089 | N42 | NAD | E | 4 | -63.996 | -28.518 | 10.110 | 1.00 | 16.09 |
| 17090 | C43 | NAD | E | 4 | -64.553 | -29.673 | 10.551 | 1.00 | 16.87 |
| 17092 | C44 | NAD | E | 4 | -62.015 | -27.128 | 11.155 | 1.00 | 17.11 |
| 17093 | N48 | NAD | E | 4 | -61.957 | -26.103 | 10.276 | 1.00 | 18.90 |
| 17096 | N45 | NAD | E | 4 | -61.176 | -27.192 | 12.206 | 1.00 | 17.55 |
| 17097 | C46 | NAD | E | 4 | -61.203 | -28.182 | 13.123 | 1.00 | 16.88 |
| 17099 | O28 | syr | F | 1 | 5.729 | 7.519 | 9.589 | 1.00 | 16.31 |
| 17100 | C27 | syr | F | 1 | 6.486 | 7.478 | 10.557 | 1.00 | 16.13 |
| 17101 | N29 | syr | F | 1 | 6.876 | 8.569 | 11.198 | 1.00 | 15.79 |
| 17103 | C30 | syr | F | 1 | 6.402 | 9.906 | 10.874 | 1.00 | 18.39 |
| 17106 | C31 | syr | F | 1 | 6.854 | 10.468 | 9.532 | 1.00 | 20.78 |
| 17109 | C32 | syr | F | 1 | 8.367 | 10.520 | 9.432 | 1.00 | 23.90 |
| 17112 | N33 | syr | F | 1 | 8.885 | 11.044 | 8.149 | 1.00 | 25.33 |
| 17113 | C35 | syr | F | 1 | 8.598 | 10.103 | 7.047 | 1.00 | 25.50 |
| 17117 | C34 | syr | F | 1 | 8.321 | 12.368 | 7.806 | 1.00 | 25.07 |
| 17121 | C36 | syr | F | 1 | 10.358 | 11.116 | 8.245 | 1.00 | 30.12 |
| 17124 | C37 | syr | F | 1 | 10.882 | 12.233 | 9.133 | 1.00 | 33.24 |
| 17127 | C38 | syr | F | 1 | 12.266 | 11.866 | 9.655 | 1.00 | 36.47 |
| 17130 | S39 | syr | F | 1 | 12.788 | 13.045 | 10.698 | 1.00 | 38.85 |
| 17131 | O41 | syr | F | 1 | 12.756 | 14.346 | 9.987 | 1.00 | 40.15 |
| 17132 | O40 | syr | F | 1 | 11.904 | 13.088 | 11.889 | 1.00 | 40.12 |

FIGURE 3 (cont.)

| A | B | C | D | E | F | G | H | I | J |
|---|---|---|---|---|---|---|---|---|---|
| 17133 | O42 | syr | F | 1 | 14.164 | 12.729 | 11.149 | 1.00 | 39.08 |
| 17134 | C26 | syr | F | 1 | 7.068 | 6.175 | 11.112 | 1.00 | 15.95 |
| 17137 | C25 | syr | F | 1 | 7.133 | 5.089 | 10.059 | 1.00 | 14.16 |
| 17140 | C23 | syr | F | 1 | 7.708 | 3.745 | 10.538 | 1.00 | 12.85 |
| 17142 | C24 | syr | F | 1 | 9.156 | 3.919 | 11.011 | 1.00 | 13.60 |
| 17146 | C20 | syr | F | 1 | 6.808 | 3.066 | 11.583 | 1.00 | 12.50 |
| 17148 | C21 | syr | F | 1 | 5.385 | 2.849 | 11.031 | 1.00 | 11.84 |
| 17151 | C22 | syr | F | 1 | 4.890 | 1.506 | 11.583 | 1.00 | 12.25 |
| 17154 | C14 | syr | F | 1 | 5.907 | 1.181 | 12.671 | 1.00 | 11.94 |
| 17156 | C15 | syr | F | 1 | 7.225 | 1.672 | 12.086 | 1.00 | 12.32 |
| 17157 | C19 | syr | F | 1 | 7.694 | 0.796 | 10.935 | 1.00 | 12.01 |
| 17161 | C16 | syr | F | 1 | 8.236 | 1.632 | 13.241 | 1.00 | 11.77 |
| 17163 | O18 | syr | F | 1 | 7.871 | 2.502 | 14.326 | 1.00 | 11.79 |
| 17165 | C17 | syr | F | 1 | 8.405 | 0.195 | 13.756 | 1.00 | 11.59 |
| 17168 | C12 | syr | F | 1 | 7.086 | -0.504 | 14.184 | 1.00 | 11.97 |
| 17170 | C2 | syr | F | 1 | 7.245 | -2.008 | 14.515 | 1.00 | 12.39 |
| 17171 | C8 | syr | F | 1 | 7.499 | -2.832 | 13.245 | 1.00 | 13.73 |
| 17175 | C1 | syr | F | 1 | 8.395 | -2.319 | 15.496 | 1.00 | 11.40 |
| 17178 | C6 | syr | F | 1 | 8.197 | -1.721 | 16.898 | 1.00 | 11.99 |
| 17181 | C5 | syr | F | 1 | 6.940 | -2.338 | 17.503 | 1.00 | 12.62 |
| 17183 | O7 | syr | F | 1 | 6.689 | -1.854 | 18.826 | 1.00 | 13.11 |
| 17185 | C4 | syr | F | 1 | 5.737 | -2.016 | 16.614 | 1.00 | 11.66 |
| 17188 | C3 | syr | F | 1 | 5.937 | -2.499 | 15.172 | 1.00 | 12.17 |
| 17190 | C9 | syr | F | 1 | 4.697 | -2.131 | 14.333 | 1.00 | 12.07 |
| 17193 | C10 | syr | F | 1 | 4.631 | -0.662 | 13.868 | 1.00 | 11.38 |
| 17195 | O13 | syr | F | 1 | 4.278 | 0.223 | 14.936 | 1.00 | 12.42 |
| 17197 | C11 | syr | F | 1 | 5.943 | -0.262 | 13.196 | 1.00 | 12.71 |
| 17199 | O28 | syr | F | 2 | -23.964 | 10.892 | 13.809 | 1.00 | 17.93 |
| 17200 | C27 | syr | F | 2 | -24.724 | 10.474 | 12.936 | 1.00 | 16.83 |
| 17201 | N29 | syr | F | 2 | -24.957 | 11.133 | 11.797 | 1.00 | 16.76 |
| 17203 | C30 | syr | F | 2 | -24.290 | 12.385 | 11.456 | 1.00 | 18.59 |
| 17206 | C31 | syr | F | 2 | -24.738 | 13.597 | 12.254 | 1.00 | 21.27 |
| 17209 | C32 | syr | F | 2 | -26.079 | 14.141 | 11.776 | 1.00 | 25.18 |
| 17212 | N33 | syr | F | 2 | -26.566 | 15.284 | 12.601 | 1.00 | 27.82 |
| 17213 | C35 | syr | F | 2 | -27.299 | 14.801 | 13.786 | 1.00 | 28.89 |
| 17217 | C34 | syr | F | 2 | -25.457 | 16.141 | 13.078 | 1.00 | 27.57 |
| 17221 | C36 | syr | F | 2 | -27.384 | 16.198 | 11.783 | 1.00 | 32.87 |
| 17224 | C37 | syr | F | 2 | -28.669 | 15.616 | 11.215 | 1.00 | 35.98 |
| 17227 | C38 | syr | F | 2 | -29.814 | 16.599 | 11.468 | 1.00 | 39.35 |
| 17230 | S39 | syr | F | 2 | -31.237 | 16.049 | 10.809 | 1.00 | 41.57 |
| 17231 | O41 | syr | F | 2 | -31.927 | 17.125 | 10.055 | 1.00 | 42.38 |
| 17232 | O40 | syr | F | 2 | -30.937 | 14.933 | 9.887 | 1.00 | 40.22 |
| 17233 | O42 | syr | F | 2 | -32.119 | 15.617 | 11.915 | 1.00 | 42.31 |
| 17234 | C26 | syr | F | 2 | -25.461 | 9.152 | 13.069 | 1.00 | 16.24 |
| 17237 | C25 | syr | F | 2 | -25.638 | 8.694 | 14.509 | 1.00 | 15.81 |
| 17240 | C23 | syr | F | 2 | -26.374 | 7.350 | 14.655 | 1.00 | 15.00 |
| 17242 | C24 | syr | F | 2 | -27.761 | 7.449 | 14.022 | 1.00 | 15.81 |
| 17246 | C20 | syr | F | 2 | -25.561 | 6.168 | 14.093 | 1.00 | 14.58 |
| 17248 | C21 | syr | F | 2 | -24.167 | 6.063 | 14.738 | 1.00 | 14.17 |

FIGURE 3 (cont.)

| A | B | C | D | E | F | G | H | I | J |
|---|---|---|---|---|---|---|---|---|---|
| 17251 | C22 | syr | F | 2 | -23.832 | 4.569 | 14.859 | 1.00 | 13.04 |
| 17254 | C14 | syr | F | 2 | -24.933 | 3.895 | 14.067 | 1.00 | 13.05 |
| 17256 | C15 | syr | F | 2 | -26.156 | 4.772 | 14.302 | 1.00 | 13.59 |
| 17257 | C19 | syr | F | 2 | -26.732 | 4.645 | 15.718 | 1.00 | 13.77 |
| 17261 | C16 | syr | F | 2 | -27.198 | 4.314 | 13.271 | 1.00 | 12.32 |
| 17263 | O18 | syr | F | 2 | -26.760 | 4.489 | 11.918 | 1.00 | 12.47 |
| 17265 | C17 | syr | F | 2 | -27.553 | 2.839 | 13.441 | 1.00 | 12.19 |
| 17268 | C12 | syr | F | 2 | -26.351 | 1.883 | 13.487 | 1.00 | 12.40 |
| 17270 | C2 | syr | F | 2 | -26.714 | 0.447 | 13.924 | 1.00 | 13.50 |
| 17271 | C8 | syr | F | 2 | -27.072 | 0.328 | 15.415 | 1.00 | 13.22 |
| 17275 | C1 | syr | F | 2 | -27.910 | -0.134 | 13.153 | 1.00 | 12.64 |
| 17278 | C6 | syr | F | 2 | -27.695 | -0.345 | 11.669 | 1.00 | 13.86 |
| 17281 | C5 | syr | F | 2 | -26.544 | -1.309 | 11.459 | 1.00 | 12.95 |
| 17283 | O7 | syr | F | 2 | -26.312 | -1.494 | 10.068 | 1.00 | 13.98 |
| 17285 | C4 | syr | F | 2 | -25.297 | -0.731 | 12.137 | 1.00 | 13.06 |
| 17288 | C3 | syr | F | 2 | -25.512 | -0.459 | 13.635 | 1.00 | 12.82 |
| 17290 | C9 | syr | F | 2 | -24.224 | 0.100 | 14.273 | 1.00 | 11.55 |
| 17293 | C10 | syr | F | 2 | -23.938 | 1.578 | 13.988 | 1.00 | 12.57 |
| 17295 | O13 | syr | F | 2 | -23.535 | 1.809 | 12.646 | 1.00 | 13.44 |
| 17297 | C11 | syr | F | 2 | -25.174 | 2.414 | 14.318 | 1.00 | 12.11 |
| 17299 | O28 | syr | F | 3 | -35.027 | -44.086 | -7.159 | 1.00 | 18.66 |
| 17300 | C27 | syr | F | 3 | -34.637 | -43.565 | -8.196 | 1.00 | 18.53 |
| 17301 | N29 | syr | F | 3 | -34.567 | -44.217 | -9.345 | 1.00 | 18.86 |
| 17303 | C30 | syr | F | 3 | -35.023 | -45.580 | -9.510 | 1.00 | 20.61 |
| 17306 | C31 | syr | F | 3 | -34.167 | -46.618 | -8.817 | 1.00 | 24.81 |
| 17309 | C32 | syr | F | 3 | -32.729 | -46.534 | -9.283 | 1.00 | 27.90 |
| 17312 | N33 | syr | F | 3 | -31.861 | -47.547 | -8.644 | 1.00 | 30.65 |
| 17313 | C35 | syr | F | 3 | -30.480 | -47.280 | -9.078 | 1.00 | 32.20 |
| 17317 | C34 | syr | F | 3 | -31.877 | -47.379 | -7.180 | 1.00 | 31.24 |
| 17321 | C36 | syr | F | 3 | -32.268 | -48.931 | -8.988 | 1.00 | 33.83 |
| 17324 | C37 | syr | F | 3 | -32.186 | -49.194 | -10.496 | 1.00 | 36.72 |
| 17327 | C38 | syr | F | 3 | -32.275 | -50.679 | -10.845 | 1.00 | 38.87 |
| 17330 | S39 | syr | F | 3 | -31.427 | -50.998 | -12.236 | 1.00 | 40.5 |
| 17331 | O41 | syr | F | 3 | -32.062 | -50.435 | -13.441 | 1.00 | 40.94 |
| 17332 | O40 | syr | F | 3 | -30.063 | -50.431 | -12.104 | 1.00 | 41.61 |
| 17333 | O42 | syr | F | 3 | -31.350 | -52.480 | -12.362 | 1.00 | 41.94 |
| 17334 | C26 | syr | F | 3 | -34.175 | -42.121 | -8.235 | 1.00 | 18.19 |
| 17337 | C25 | syr | F | 3 | -33.617 | -41.682 | -6.884 | 1.00 | 17.62 |
| 17340 | C23 | syr | F | 3 | -33.164 | -40.214 | -6.862 | 1.00 | 16.42 |
| 17342 | C24 | syr | F | 3 | -32.024 | -40.019 | -7.866 | 1.00 | 16.80 |
| 17346 | C20 | syr | F | 3 | -34.324 | -39.211 | -7.063 | 1.00 | 15.83 |
| 17348 | C21 | syr | F | 3 | -35.436 | -39.434 | -6.022 | 1.00 | 15.72 |
| 17351 | C22 | syr | F | 3 | -36.060 | -38.061 | -5.747 | 1.00 | 14.30 |
| 17354 | C14 | syr | F | 3 | -35.413 | -37.148 | -6.799 | 1.00 | 14.66 |
| 17356 | C15 | syr | F | 3 | -34.004 | -37.719 | -6.962 | 1.00 | 15.26 |
| 17357 | C19 | syr | F | 3 | -33.089 | -37.470 | -5.766 | 1.00 | 16.16 |
| 17361 | C16 | syr | F | 3 | -33.386 | -37.058 | -8.203 | 1.00 | 14.56 |
| 17363 | O18 | syr | F | 3 | -34.113 | -37.354 | -9.393 | 1.00 | 14.97 |
| 17365 | C17 | syr | F | 3 | -33.303 | -35.535 | -8.020 | 1.00 | 13.55 |

FIGURE 3 (cont.)

| A | B | C | D | E | F | G | H | I | J |
|---|---|---|---|---|---|---|---|---|---|
| 17368 | C12 | syr | F | 3 | -34.631 | -34.861 | -7.603 | 1.00 | 13.44 |
| 17370 | C2 | syr | F | 3 | -34.468 | -33.389 | -7.163 | 1.00 | 13.90 |
| 17371 | C8 | syr | F | 3 | -33.766 | -33.276 | -5.811 | 1.00 | 14.20 |
| 17375 | C1 | syr | F | 3 | -33.639 | -32.547 | -8.135 | 1.00 | 13.52 |
| 17378 | C6 | syr | F | 3 | -34.269 | -32.376 | -9.512 | 1.00 | 13.99 |
| 17381 | C5 | syr | F | 3 | -35.625 | -31.697 | -9.353 | 1.00 | 14.71 |
| 17383 | O7 | syr | F | 3 | -36.256 | -31.564 | -10.628 | 1.00 | 15.41 |
| 17385 | C4 | syr | F | 3 | -36.511 | -32.528 | -8.445 | 1.00 | 13.06 |
| 17388 | C3 | syr | F | 3 | -35.876 | -32.772 | -7.067 | 1.00 | 13.86 |
| 17390 | C9 | syr | F | 3 | -36.824 | -33.601 | -6.191 | 1.00 | 14.31 |
| 17393 | C10 | syr | F | 3 | -36.854 | -35.106 | -6.475 | 1.00 | 14.18 |
| 17395 | O13 | syr | F | 3 | -37.547 | -35.433 | -7.685 | 1.00 | 13.54 |
| 17397 | C11 | syr | F | 3 | -35.421 | -35.648 | -6.539 | 1.00 | 13.82 |
| 17399 | O28 | syr | F | 4 | -65.292 | -47.138 | -3.871 | 1.00 | 21.06 |
| 17400 | C27 | syr | F | 4 | -65.671 | -47.252 | -2.712 | 1.00 | 20.96 |
| 17401 | N29 | syr | F | 4 | -65.621 | -48.398 | -2.041 | 1.00 | 21.85 |
| 17403 | C30 | syr | F | 4 | -65.061 | -49.627 | -2.578 | 1.00 | 22.83 |
| 17406 | C31 | syr | F | 4 | -65.733 | -50.202 | -3.812 | 1.00 | 24.03 |
| 17409 | C32 | syr | F | 4 | -67.030 | -50.931 | -3.466 | 1.00 | 26.38 |
| 17412 | N33 | syr | F | 4 | -67.773 | -51.435 | -4.650 | 1.00 | 29.40 |
| 17413 | C35 | syr | F | 4 | -68.245 | -50.294 | -5.471 | 1.00 | 30.57 |
| 17417 | C34 | syr | F | 4 | -66.887 | -52.244 | -5.507 | 1.00 | 29.99 |
| 17421 | C36 | syr | F | 4 | -68.954 | -52.208 | -4.150 | 1.00 | 32.87 |
| 17424 | C37 | syr | F | 4 | -68.926 | -53.751 | -4.296 | 1.00 | 35.76 |
| 17427 | C38 | syr | F | 4 | -68.798 | -54.547 | -2.986 | 1.00 | 37.86 |
| 17430 | S39 | syr | F | 4 | -67.770 | -55.858 | -3.163 | 1.00 | 37.85 |
| 17431 | O41 | syr | F | 4 | -68.161 | -56.657 | -4.350 | 1.00 | 40.77 |
| 17432 | O40 | syr | F | 4 | -66.419 | -55.309 | -3.391 | 1.00 | 40.02 |
| 17433 | O42 | syr | F | 4 | -67.751 | -56.734 | -1.972 | 1.00 | 38.11 |
| 17434 | C26 | syr | F | 4 | -66.241 | -46.076 | -1.938 | 1.00 | 20.69 |
| 17437 | C25 | syr | F | 4 | -66.862 | -45.032 | -2.847 | 1.00 | 19.62 |
| 17440 | C23 | syr | F | 4 | -67.516 | -43.858 | -2.089 | 1.00 | 17.57 |
| 17442 | C24 | syr | F | 4 | -68.625 | -44.376 | -1.173 | 1.00 | 18.14 |
| 17446 | C20 | syr | F | 4 | -66.510 | -42.984 | -1.314 | 1.00 | 16.13 |
| 17448 | C21 | syr | F | 4 | -65.362 | -42.473 | -2.205 | 1.00 | 15.94 |
| 17451 | C22 | syr | F | 4 | -65.011 | -41.062 | -1.721 | 1.00 | 15.76 |
| 17454 | C14 | syr | F | 4 | -65.735 | -40.939 | -0.389 | 1.00 | 14.84 |
| 17456 | C15 | syr | F | 4 | -67.031 | -41.699 | -0.640 | 1.00 | 15.67 |
| 17457 | C19 | syr | F | 4 | -67.997 | -40.958 | -1.573 | 1.00 | 15.67 |
| 17461 | C16 | syr | F | 4 | -67.701 | -41.852 | 0.735 | 1.00 | 14.79 |
| 17463 | O18 | syr | F | 4 | -66.926 | -42.629 | 1.649 | 1.00 | 15.02 |
| 17465 | C17 | syr | F | 4 | -67.986 | -40.482 | 1.374 | 1.00 | 15.41 |
| 17468 | C12 | syr | F | 4 | -66.767 | -39.534 | 1.457 | 1.00 | 15.57 |
| 17470 | C2 | syr | F | 4 | -67.126 | -38.085 | 1.874 | 1.00 | 17.08 |
| 17471 | C8 | syr | F | 4 | -67.871 | -37.342 | 0.759 | 1.00 | 17.37 |
| 17475 | C1 | syr | F | 4 | -68.018 | -38.029 | 3.120 | 1.00 | 17.48 |
| 17478 | C6 | syr | F | 4 | -67.351 | -38.536 | 4.395 | 1.00 | 16.50 |
| 17481 | C5 | syr | F | 4 | -66.129 | -37.685 | 4.703 | 1.00 | 16.69 |
| 17483 | O7 | syr | F | 4 | -65.494 | -38.134 | 5.892 | 1.00 | 17.59 |

FIGURE 3 (cont.)

| A | B | C | D | E | F | G | H | I | J |
|---|---|---|---|---|---|---|---|---|---|
| 17485 | C4 | syr | F | 4 | -65.171 | -37.767 | 3.523 | 1.00 | 16.35 |
| 17488 | C3 | syr | F | 4 | -65.815 | -37.332 | 2.194 | 1.00 | 15.90 |
| 17490 | C9 | syr | F | 4 | -64.774 | -37.450 | 1.061 | 1.00 | 15.43 |
| 17493 | C10 | syr | F | 4 | -64.563 | -38.862 | 0.497 | 1.00 | 14.92 |
| 17495 | O13 | syr | F | 4 | -63.801 | -39.667 | 1.388 | 1.00 | 15.44 |
| 17497 | C11 | syr | F | 4 | -65.909 | -39.527 | 0.177 | 1.00 | 16.04 |
| 17499 | O12 | mes | G | 1 | 12.814 | 1.616 | -7.937 | 1.00 | 24.67 |
| 17500 | S9 | mes | G | 1 | 11.812 | 0.993 | 7.073 | 1.00 | 24.4 |
| 17501 | O10 | mes | G | 1 | 12.046 | 1.445 | 5.675 | 1.00 | 27.22 |
| 17502 | O11 | mes | G | 1 | 11.810 | -0.461 | 7.171 | 1.00 | 28.23 |
| 17503 | C8 | mes | G | 1 | 10.291 | 1.547 | 7.533 | 1.00 | 23.64 |
| 17506 | C7 | mes | G | 1 | 9.219 | 0.851 | 6.686 | 1.00 | 24.05 |
| 17509 | N1 | mes | G | 1 | 7.892 | 1.459 | 6.835 | 1.00 | 21.76 |
| 17510 | C2 | mes | G | 1 | 7.792 | 2.837 | 6.370 | 1.00 | 21.74 |
| 17513 | C3 | mes | G | 1 | 6.382 | 3.362 | 6.565 | 1.00 | 22.22 |
| 17516 | O4 | mes | G | 1 | 5.463 | 2.466 | 5.939 | 1.00 | 22.65 |
| 17517 | C5 | mes | G | 1 | 5.459 | 1.224 | 6.608 | 1.00 | 22.29 |
| 17520 | C6 | mes | G | 1 | 6.805 | 0.535 | 6.449 | 1.00 | 22.27 |
| 17523 | OW0 | HOH | W | 5 | 3.160 | 2.748 | 14.174 | 1.00 | 13.33 |
| 17526 | OW0 | HOH | W | 6 | -13.969 | 2.106 | 8.909 | 1.00 | 13.17 |
| 17529 | OW0 | HOH | W | 7 | 2.400 | -8.798 | 28.726 | 1.00 | 12.54 |
| 17532 | OW0 | HOH | W | 8 | -37.358 | -27.466 | -16.238 | 1.00 | 12.94 |
| 17535 | OW0 | HOH | W | 9 | -18.405 | -5.556 | 8.958 | 1.00 | 13.40 |
| 17538 | OW0 | HOH | W | 10 | 1.698 | -11.209 | 30.000 | 1.00 | 12.33 |
| 17541 | OW0 | HOH | W | 11 | -1.765 | -3.724 | 21.329 | 1.00 | 12.89 |
| 17544 | OW0 | HOH | W | 12 | -10.925 | 4.337 | 11.107 | 1.00 | 12.97 |
| 17547 | OW0 | HOH | W | 13 | -27.482 | -5.272 | 4.368 | 1.00 | 12.44 |
| 17550 | OW0 | HOH | W | 14 | -23.304 | -15.611 | 4.752 | 1.00 | 13.55 |
| 17553 | OW0 | HOH | W | 15 | -38.568 | -38.052 | -7.996 | 1.00 | 14.03 |
| 17556 | OW0 | HOH | W | 16 | -42.523 | -21.035 | -14.480 | 1.00 | 13.32 |
| 17559 | OW0 | HOH | W | 17 | -22.124 | 4.218 | 12.058 | 1.00 | 14.62 |
| 17562 | OW0 | HOH | W | 18 | -57.241 | -34.684 | 6.393 | 1.00 | 16.43 |
| 17565 | OW0 | HOH | W | 19 | 5.372 | 4.381 | 14.698 | 1.00 | 13.91 |
| 17568 | OW0 | HOH | W | 20 | 7.429 | -2.738 | 25.638 | 1.00 | 12.30 |
| 17571 | OW0 | HOH | W | 21 | -43.205 | -18.306 | -14.169 | 1.00 | 13.98 |
| 17574 | OW0 | HOH | W | 22 | -7.869 | 7.489 | 10.697 | 1.00 | 13.76 |
| 17577 | OW0 | HOH | W | 23 | -62.464 | -41.940 | 0.277 | 1.00 | 16.16 |
| 17580 | OW0 | HOH | W | 24 | -37.601 | -34.014 | 3.731 | 1.00 | 16.88 |
| 17583 | OW0 | HOH | W | 25 | -51.890 | -44.165 | -6.103 | 1.00 | 13.92 |
| 17586 | OW0 | HOH | W | 26 | -21.063 | -0.277 | 23.661 | 1.00 | 16.52 |
| 17589 | OW0 | HOH | W | 27 | -23.585 | -12.772 | 4.721 | 1.00 | 13.32 |
| 17592 | OW0 | HOH | W | 28 | -47.554 | -37.579 | -8.832 | 1.00 | 13.05 |
| 17595 | OW0 | HOH | W | 29 | -44.789 | -29.284 | -9.450 | 1.00 | 12.83 |
| 17598 | OW0 | HOH | W | 30 | -12.637 | 10.153 | 20.404 | 1.00 | 15.36 |
| 17601 | OW0 | HOH | W | 31 | -51.492 | -41.734 | -2.196 | 1.00 | 14.58 |
| 17604 | OW0 | HOH | W | 32 | -64.184 | -43.953 | 1.149 | 1.00 | 16.01 |
| 17607 | OW0 | HOH | W | 33 | 4.547 | -12.698 | 20.606 | 1.00 | 15.39 |
| 17610 | OW0 | HOH | W | 34 | -57.593 | -40.630 | -13.633 | 1.00 | 15.06 |
| 17613 | OW0 | HOH | W | 35 | 1.130 | -6.405 | 6.065 | 1.00 | 14.70 |

FIGURE 3 (cont.)

| A | B | C | D | E | F | G | H | I | J |
|---|---|---|---|---|---:|---:|---:|---:|---:|
| 17616 | OW0 | HOH | W | 36 | -44.196 | -11.020 | -32.107 | 1.00 | 16.83 |
| 17619 | OW0 | HOH | W | 37 | -7.703 | 11.012 | 15.980 | 1.00 | 14.52 |
| 17622 | OW0 | HOH | W | 38 | -36.691 | -39.031 | -9.765 | 1.00 | 15.37 |
| 17625 | OW0 | HOH | W | 39 | -8.515 | 10.307 | 13.378 | 1.00 | 15.27 |
| 17628 | OW0 | HOH | W | 40 | -33.690 | -3.836 | 1.566 | 1.00 | 14.84 |
| 17631 | OW0 | HOH | W | 42 | -64.366 | -32.426 | -7.447 | 1.00 | 15.75 |
| 17634 | OW0 | HOH | W | 43 | 13.829 | -0.927 | 27.823 | 1.00 | 18.08 |
| 17637 | OW0 | HOH | W | 44 | 6.013 | -8.754 | 20.864 | 1.00 | 17.34 |
| 17640 | OW0 | HOH | W | 45 | 0.034 | -7.938 | 8.119 | 1.00 | 14.81 |
| 17643 | OW0 | HOH | W | 46 | -56.124 | -42.529 | -12.173 | 1.00 | 16.46 |
| 17646 | OW0 | HOH | W | 47 | -6.043 | 10.056 | 12.231 | 1.00 | 16.79 |
| 17649 | OW0 | HOH | W | 48 | 0.481 | -7.459 | 14.982 | 1.00 | 20.81 |
| 17652 | OW0 | HOH | W | 49 | -2.691 | -12.024 | 44.776 | 1.00 | 18.21 |
| 17655 | OW0 | HOH | W | 50 | -5.049 | 3.623 | 17.688 | 1.00 | 13.00 |
| 17658 | OW0 | HOH | W | 51 | -50.211 | -47.568 | -1.329 | 1.00 | 16.60 |
| 17661 | OW0 | HOH | W | 53 | -43.072 | -44.993 | 4.292 | 1.00 | 15.66 |
| 17664 | OW0 | HOH | W | 54 | -26.700 | 10.213 | 9.719 | 1.00 | 15.99 |
| 17667 | OW0 | HOH | W | 55 | -59.871 | -28.162 | 16.222 | 1.00 | 18.10 |
| 17670 | OW0 | HOH | W | 56 | -44.477 | -45.912 | 2.023 | 1.00 | 17.50 |
| 17673 | OW0 | HOH | W | 57 | -5.031 | 3.353 | 1.827 | 1.00 | 15.82 |
| 17676 | OW0 | HOH | W | 58 | -9.557 | 9.553 | 9.816 | 1.00 | 16.46 |
| 17679 | OW0 | HOH | W | 59 | -12.214 | -9.995 | 32.224 | 1.00 | 16.98 |
| 17682 | OW0 | HOH | W | 60 | -33.711 | -42.818 | -11.633 | 1.00 | 17.75 |
| 17685 | OW0 | HOH | W | 61 | 2.971 | -13.013 | 16.601 | 1.00 | 17.88 |
| 17688 | OW0 | HOH | W | 62 | -24.105 | 5.720 | 10.859 | 1.00 | 14.78 |
| 17691 | OW0 | HOH | W | 63 | -39.094 | -31.768 | 3.016 | 1.00 | 17.91 |
| 17694 | OW0 | HOH | W | 64 | -45.953 | -17.126 | -28.993 | 1.00 | 19.15 |
| 17697 | OW0 | HOH | W | 65 | 1.078 | -6.903 | 10.646 | 1.00 | 16.77 |
| 17700 | OW0 | HOH | W | 66 | -39.190 | -18.915 | -36.465 | 1.00 | 15.66 |
| 17703 | OW0 | HOH | W | 68 | -32.763 | -4.589 | 7.887 | 1.00 | 14.84 |
| 17706 | OW0 | HOH | W | 69 | -10.435 | 8.327 | 13.391 | 1.00 | 14.30 |
| 17709 | OW0 | HOH | W | 70 | -48.632 | -44.443 | -4.209 | 1.00 | 15.61 |
| 17712 | OW0 | HOH | W | 71 | -49.471 | -40.474 | -6.170 | 1.00 | 14.81 |
| 17715 | OW0 | HOH | W | 72 | -60.414 | -30.675 | 14.967 | 1.00 | 16.51 |
| 17718 | OW0 | HOH | W | 73 | -10.326 | 8.898 | 7.223 | 1.00 | 17.12 |
| 17721 | OW0 | HOH | W | 74 | -38.778 | -31.366 | 0.016 | 1.00 | 17.73 |
| 17724 | OW0 | HOH | W | 75 | -48.121 | -44.965 | 4.403 | 1.00 | 20.28 |
| 17727 | OW0 | HOH | W | 76 | -64.715 | -37.547 | 12.805 | 1.00 | 17.42 |
| 17730 | OW0 | HOH | W | 77 | -70.865 | -36.945 | 11.028 | 1.00 | 19.36 |
| 17733 | OW0 | HOH | W | 78 | -50.092 | -45.041 | -10.167 | 1.00 | 16.38 |
| 17736 | OW0 | HOH | W | 80 | -45.682 | -29.714 | 0.480 | 1.00 | 20.84 |
| 17739 | OW0 | HOH | W | 81 | 2.069 | -13.959 | 20.830 | 1.00 | 16.49 |
| 17742 | OW0 | HOH | W | 82 | -11.231 | -4.972 | 39.517 | 1.00 | 18.75 |
| 17745 | OW0 | HOH | W | 83 | -53.619 | -40.960 | 1.536 | 1.00 | 14.31 |
| 17748 | OW0 | HOH | W | 85 | -46.180 | -17.672 | -37.651 | 1.00 | 16.50 |
| 17751 | OW0 | HOH | W | 86 | -31.272 | -27.074 | -14.177 | 1.00 | 18.33 |
| 17754 | OW0 | HOH | W | 87 | -8.473 | 0.005 | 43.758 | 1.00 | 18.40 |
| 17757 | OW0 | HOH | W | 88 | -13.536 | 9.392 | 23.022 | 1.00 | 15.07 |
| 17760 | OW0 | HOH | W | 89 | 0.112 | -18.225 | 30.231 | 1.00 | 18.19 |

FIGURE 3 (cont.)

| A | B | C | D | E | F | G | H | I | J |
|---|---|---|---|---|---|---|---|---|---|
| 17763 | OW0 | HOH | W | 90 | -23.583 | -13.771 | 14.163 | 1.00 | 17.79 |
| 17766 | OW0 | HOH | W | 91 | -65.370 | -27.386 | 7.899 | 1.00 | 20.87 |
| 17769 | OW0 | HOH | W | 92 | -51.641 | -12.333 | -31.122 | 1.00 | 18.48 |
| 17772 | OW0 | HOH | W | 93 | -21.369 | -2.824 | 19.839 | 1.00 | 15.98 |
| 17775 | OW0 | HOH | W | 94 | 8.538 | 8.289 | 13.576 | 1.00 | 15.84 |
| 17778 | OW0 | HOH | W | 95 | -41.132 | -12.235 | -25.581 | 1.00 | 20.50 |
| 17781 | OW0 | HOH | W | 96 | -50.176 | -45.800 | -7.498 | 1.00 | 16.80 |
| 17784 | OW0 | HOH | W | 98 | -57.325 | -19.217 | -12.226 | 1.00 | 20.77 |
| 17787 | OW0 | HOH | W | 99 | -7.816 | 5.006 | 14.536 | 1.00 | 12.96 |
| 17790 | OW0 | HOH | W | 100 | -42.141 | -10.500 | -18.556 | 1.00 | 17.48 |
| 17793 | OW0 | HOH | W | 101 | -5.772 | 5.441 | 3.729 | 1.00 | 16.47 |
| 17796 | OW0 | HOH | W | 102 | -10.228 | -8.724 | 38.645 | 1.00 | 22.61 |
| 17799 | OW0 | HOH | W | 103 | -24.978 | -15.995 | -10.412 | 1.00 | 21.50 |
| 17802 | OW0 | HOH | W | 104 | -21.394 | 16.961 | 9.939 | 1.00 | 21.31 |
| 17805 | OW0 | HOH | W | 105 | -27.532 | -22.625 | 0.523 | 1.00 | 22.49 |
| 17808 | OW0 | HOH | W | 106 | -26.005 | -12.037 | 13.567 | 1.00 | 18.57 |
| 17811 | OW0 | HOH | W | 107 | 11.706 | -6.650 | 15.328 | 1.00 | 21.70 |
| 17814 | OW0 | HOH | W | 108 | -20.242 | -2.818 | 22.587 | 1.00 | 16.60 |
| 17817 | OW0 | HOH | W | 109 | -28.573 | 9.826 | 6.943 | 1.00 | 18.24 |
| 17820 | OW0 | HOH | W | 110 | 11.325 | 7.659 | 10.323 | 1.00 | 22.36 |
| 17823 | OW0 | HOH | W | 111 | -34.545 | -30.119 | -26.731 | 1.00 | 21.13 |
| 17826 | OW0 | HOH | W | 112 | -42.617 | -14.503 | -31.961 | 1.00 | 18.65 |
| 17829 | OW0 | HOH | W | 113 | 10.930 | 8.997 | 12.657 | 1.00 | 22.28 |
| 17832 | OW0 | HOH | W | 114 | -63.082 | -30.667 | -5.649 | 1.00 | 18.00 |
| 17835 | OW0 | HOH | W | 115 | -22.743 | -22.048 | 7.803 | 1.00 | 20.68 |
| 17838 | OW0 | HOH | W | 116 | 4.457 | -16.096 | 37.151 | 1.00 | 16.12 |
| 17841 | OW0 | HOH | W | 117 | -32.860 | -42.024 | -14.942 | 1.00 | 20.21 |
| 17844 | OW0 | HOH | W | 118 | -58.009 | -22.186 | -27.714 | 1.00 | 19.46 |
| 17847 | OW0 | HOH | W | 119 | -43.766 | -12.258 | -10.477 | 1.00 | 21.92 |
| 17850 | OW0 | HOH | W | 120 | -29.928 | -10.195 | 11.073 | 1.00 | 21.48 |
| 17853 | OW0 | HOH | W | 121 | 8.328 | -5.870 | 46.552 | 1.00 | 23.04 |
| 17856 | OW0 | HOH | W | 122 | -63.237 | -32.105 | -2.842 | 1.00 | 18.35 |
| 17859 | OW0 | HOH | W | 123 | -24.453 | -10.640 | 17.289 | 1.00 | 19.63 |
| 17862 | OW0 | HOH | W | 124 | -11.855 | 10.278 | 11.043 | 1.00 | 19.82 |
| 17865 | OW0 | HOH | W | 125 | 3.974 | -4.952 | 43.680 | 1.00 | 21.74 |
| 17868 | OW0 | HOH | W | 126 | -32.221 | -12.635 | 6.619 | 1.00 | 18.49 |
| 17871 | OW0 | HOH | W | 127 | 16.248 | 5.924 | 26.336 | 1.00 | 20.89 |
| 17874 | OW0 | HOH | W | 128 | -43.965 | -31.668 | 21.694 | 1.00 | 22.99 |
| 17877 | OW0 | HOH | W | 129 | -29.338 | -20.457 | -5.946 | 1.00 | 23.65 |
| 17880 | OW0 | HOH | W | 130 | -32.201 | -3.617 | 15.068 | 1.00 | 19.54 |
| 17883 | OW0 | HOH | W | 131 | 12.619 | -4.375 | 22.440 | 1.00 | 15.51 |
| 17886 | OW0 | HOH | W | 132 | -45.517 | -23.821 | -38.055 | 1.00 | 21.98 |
| 17889 | OW0 | HOH | W | 133 | -50.132 | -46.854 | -3.986 | 1.00 | 17.33 |
| 17892 | OW0 | HOH | W | 134 | -56.817 | -15.729 | -16.504 | 1.00 | 21.47 |
| 17895 | OW0 | HOH | W | 135 | 8.300 | -17.983 | 31.664 | 1.00 | 22.83 |
| 17898 | OW0 | HOH | W | 136 | -43.716 | -40.739 | -24.290 | 1.00 | 20.75 |
| 17901 | OW0 | HOH | W | 137 | -38.034 | -23.401 | -2.461 | 1.00 | 20.21 |
| 17904 | OW0 | HOH | W | 138 | -37.332 | -21.541 | -6.805 | 1.00 | 18.87 |
| 17907 | OW0 | HOH | W | 139 | -58.779 | -42.194 | -15.558 | 1.00 | 22.26 |

FIGURE 3 (cont.)

| A | B | C | D | E | F | G | H | I | J |
|---|---|---|---|---|---|---|---|---|---|
| 17910 | OW0 | HOH | W | 140 | -10.168 | -16.467 | -6.034 | 1.00 | 22.30 |
| 17913 | OW0 | HOH | W | 141 | 10.231 | 9.126 | 16.325 | 1.00 | 16.79 |
| 17916 | OW0 | HOH | W | 142 | -19.548 | 10.710 | 17.395 | 1.00 | 18.70 |
| 17919 | OW0 | HOH | W | 143 | -9.676 | 3.650 | 3.058 | 1.00 | 18.79 |
| 17922 | OW0 | HOH | W | 144 | -53.281 | -43.836 | -21.712 | 1.00 | 24.79 |
| 17925 | OW0 | HOH | W | 145 | -31.959 | -27.404 | -20.679 | 1.00 | 20.78 |
| 17928 | OW0 | HOH | W | 146 | -26.836 | -8.447 | 11.395 | 1.00 | 20.34 |
| 17931 | OW0 | HOH | W | 147 | 13.038 | 4.377 | 32.227 | 1.00 | 21.64 |
| 17934 | OW0 | HOH | W | 148 | -20.999 | -5.517 | 16.212 | 1.00 | 20.13 |
| 17937 | OW0 | HOH | W | 149 | 4.525 | -17.506 | 30.244 | 1.00 | 22.79 |
| 17940 | OW0 | HOH | W | 150 | -32.280 | -1.357 | -4.997 | 1.00 | 20.46 |
| 17943 | OW0 | HOH | W | 151 | -27.192 | -4.926 | 13.638 | 1.00 | 27.01 |
| 17946 | OW0 | HOH | W | 152 | -56.571 | -29.518 | -2.109 | 1.00 | 22.13 |
| 17949 | OW0 | HOH | W | 153 | -62.513 | -19.851 | -5.792 | 1.00 | 20.88 |
| 17952 | OW0 | HOH | W | 154 | -37.414 | -50.613 | -10.474 | 1.00 | 20.20 |
| 17955 | OW0 | HOH | W | 155 | -40.510 | -12.696 | -28.519 | 1.00 | 23.01 |
| 17958 | OW0 | HOH | W | 156 | 2.830 | 13.344 | 27.970 | 1.00 | 24.67 |
| 17961 | OW0 | HOH | W | 157 | 7.472 | -6.985 | 19.672 | 1.00 | 22.18 |
| 17964 | OW0 | HOH | W | 158 | -31.050 | -12.055 | -22.699 | 1.00 | 30.38 |
| 17967 | OW0 | HOH | W | 159 | -47.426 | -45.956 | -7.043 | 1.00 | 21.22 |
| 17970 | OW0 | HOH | W | 160 | 17.043 | -5.640 | 43.857 | 1.00 | 21.26 |
| 17973 | OW0 | HOH | W | 161 | -32.980 | -12.370 | -15.457 | 1.00 | 19.37 |
| 17976 | OW0 | HOH | W | 162 | 8.777 | -10.500 | 22.312 | 1.00 | 20.59 |
| 17979 | OW0 | HOH | W | 163 | 1.368 | 6.276 | 6.136 | 1.00 | 21.51 |
| 17982 | OW0 | HOH | W | 164 | -8.847 | 8.324 | 21.899 | 1.00 | 21.51 |
| 17985 | OW0 | HOH | W | 165 | -5.534 | -7.933 | 13.137 | 1.00 | 25.03 |
| 17988 | OW0 | HOH | W | 166 | -13.160 | -1.120 | -5.473 | 1.00 | 23.89 |
| 17991 | OW0 | HOH | W | 167 | -42.866 | -10.327 | -21.238 | 1.00 | 22.56 |
| 17994 | OW0 | HOH | W | 168 | -46.700 | -52.498 | 9.243 | 1.00 | 24.38 |
| 17997 | OW0 | HOH | W | 169 | -45.887 | -26.385 | 14.787 | 1.00 | 21.29 |
| 18000 | OW0 | HOH | W | 170 | -3.690 | 4.666 | -0.190 | 1.00 | 22.34 |
| 18003 | OW0 | HOH | W | 171 | -9.547 | -17.730 | 2.636 | 1.00 | 20.70 |
| 18006 | OW0 | HOH | W | 172 | 1.010 | -18.305 | 32.901 | 1.00 | 21.57 |
| 18009 | OW0 | HOH | W | 173 | -27.658 | 13.678 | 8.549 | 1.00 | 28.50 |
| 18012 | OW0 | HOH | W | 174 | -33.836 | -15.532 | -33.204 | 1.00 | 25.82 |
| 18015 | OW0 | HOH | W | 176 | -9.282 | 6.051 | 12.485 | 1.00 | 11.86 |
| 18018 | OW0 | HOH | W | 177 | -50.367 | -42.439 | -4.579 | 1.00 | 12.26 |
| 18021 | OW0 | HOH | W | 178 | 11.319 | -11.950 | 41.315 | 1.00 | 17.07 |
| 18024 | OW0 | HOH | W | 179 | -10.506 | -8.799 | 41.179 | 1.00 | 22.68 |
| 18027 | OW0 | HOH | W | 180 | -12.190 | -13.758 | -12.289 | 1.00 | 20.41 |
| 18030 | OW0 | HOH | W | 181 | -53.158 | -10.739 | -18.312 | 1.00 | 21.04 |
| 18033 | OW0 | HOH | W | 182 | -39.554 | -20.344 | -5.592 | 1.00 | 23.14 |
| 18036 | OW0 | HOH | W | 183 | -58.831 | -19.886 | -21.059 | 1.00 | 19.42 |
| 18039 | OW0 | HOH | W | 184 | -39.845 | -9.165 | -18.036 | 1.00 | 25.77 |
| 18042 | OW0 | HOH | W | 185 | 10.813 | -10.921 | 27.404 | 1.00 | 18.53 |
| 18045 | OW0 | HOH | W | 186 | -41.730 | -47.115 | 5.086 | 1.00 | 24.01 |
| 18048 | OW0 | HOH | W | 187 | -61.917 | -44.966 | -7.946 | 1.00 | 20.01 |
| 18051 | OW0 | HOH | W | 188 | -19.906 | 1.432 | 29.536 | 1.00 | 21.88 |
| 18054 | OW0 | HOH | W | 189 | 4.912 | -14.789 | 39.537 | 1.00 | 20.92 |

FIGURE 3 (cont.)

| A | B | C | D | E | F | G | H | I | J |
|---|---|---|---|---|---|---|---|---|---|
| 18057 | OW0 | HOH | W | 190 | -50.340 | -53.076 | -9.985 | 1.00 | 26.60 |
| 18060 | OW0 | HOH | W | 191 | -9.417 | -18.952 | -6.826 | 1.00 | 23.96 |
| 18063 | OW0 | HOH | W | 192 | -38.372 | -44.937 | -2.609 | 1.00 | 21.01 |
| 18066 | OW0 | HOH | W | 193 | -56.644 | -52.391 | 12.783 | 1.00 | 26.23 |
| 18069 | OW0 | HOH | W | 194 | -7.154 | -17.926 | -2.156 | 1.00 | 23.68 |
| 18072 | OW0 | HOH | W | 195 | -66.717 | -48.488 | 0.619 | 1.00 | 20.03 |
| 18075 | OW0 | HOH | W | 196 | -29.930 | -33.875 | -23.417 | 1.00 | 22.67 |
| 18078 | OW0 | HOH | W | 197 | -48.549 | -15.955 | -31.943 | 1.00 | 24.95 |
| 18081 | OW0 | HOH | W | 198 | -24.108 | 16.539 | 9.776 | 1.00 | 22.27 |
| 18084 | OW0 | HOH | W | 199 | -62.999 | -28.125 | -14.418 | 1.00 | 25.08 |
| 18087 | OW0 | HOH | W | 200 | -3.601 | -18.614 | 7.961 | 1.00 | 22.46 |
| 18090 | OW0 | HOH | W | 201 | -44.438 | -37.268 | 26.089 | 1.00 | 22.26 |
| 18093 | OW0 | HOH | W | 202 | 0.532 | 14.738 | 23.517 | 1.00 | 22.34 |
| 18096 | OW0 | HOH | W | 203 | -62.081 | -22.916 | -15.715 | 1.00 | 22.40 |
| 18099 | OW0 | HOH | W | 204 | -5.135 | -14.543 | -1.823 | 1.00 | 24.53 |
| 18102 | OW0 | HOH | W | 205 | -64.980 | -26.647 | 3.537 | 1.00 | 23.24 |
| 18105 | OW0 | HOH | W | 206 | 4.386 | 14.879 | 9.762 | 1.00 | 24.03 |
| 18108 | OW0 | HOH | W | 207 | -48.813 | -12.030 | -31.633 | 1.00 | 25.78 |
| 18111 | OW0 | HOH | W | 208 | -9.966 | -10.165 | 17.887 | 1.00 | 31.47 |
| 18114 | OW0 | HOH | W | 209 | -10.102 | 11.048 | 20.429 | 1.00 | 26.61 |
| 18117 | OW0 | HOH | W | 210 | 6.918 | 14.306 | 21.078 | 1.00 | 22.67 |
| 18120 | OW0 | HOH | W | 211 | -62.437 | -45.019 | -14.011 | 1.00 | 26.58 |
| 18123 | OW0 | HOH | W | 212 | -2.958 | 0.686 | 8.008 | 1.00 | 25.75 |
| 18126 | OW0 | HOH | W | 213 | -65.845 | -31.471 | 8.155 | 1.00 | 26.66 |
| 18129 | OW0 | HOH | W | 214 | -38.253 | -29.441 | 4.645 | 1.00 | 25.37 |
| 18132 | OW0 | HOH | W | 215 | -52.645 | -40.045 | -13.399 | 1.00 | 23.21 |
| 18135 | OW0 | HOH | W | 216 | -55.337 | -53.220 | 7.911 | 1.00 | 25.74 |
| 18138 | OW0 | HOH | W | 217 | -52.753 | -47.064 | -4.508 | 1.00 | 21.80 |
| 18141 | OW0 | HOH | W | 218 | -10.575 | -10.994 | 37.163 | 1.00 | 24.60 |
| 18144 | OW0 | HOH | W | 219 | -26.456 | -9.153 | -18.769 | 1.00 | 24.83 |
| 18147 | OW0 | HOH | W | 220 | -35.430 | 7.438 | 3.711 | 1.00 | 25.73 |
| 18150 | OW0 | HOH | W | 221 | -31.225 | -17.601 | -14.486 | 1.00 | 33.18 |
| 18153 | OW0 | HOH | W | 222 | -67.567 | -49.660 | 3.741 | 1.00 | 21.92 |
| 18156 | OW0 | HOH | W | 223 | -14.412 | 11.680 | 24.092 | 1.00 | 22.22 |
| 18159 | OW0 | HOH | W | 224 | -29.657 | -28.389 | -7.131 | 1.00 | 25.41 |
| 18162 | OW0 | HOH | W | 225 | -63.190 | -25.352 | 7.516 | 1.00 | 20.99 |
| 18165 | OW0 | HOH | W | 226 | -53.596 | -24.293 | -33.203 | 1.00 | 23.55 |
| 18168 | OW0 | HOH | W | 227 | -8.459 | 16.641 | 7.054 | 1.00 | 27.01 |
| 18171 | OW0 | HOH | W | 229 | -8.567 | -9.165 | 43.067 | 1.00 | 23.21 |
| 18174 | OW0 | HOH | W | 230 | -3.649 | 0.152 | -4.673 | 1.00 | 23.80 |
| 18177 | OW0 | HOH | W | 231 | -69.845 | -40.672 | 16.319 | 1.00 | 23.89 |
| 18180 | OW0 | HOH | W | 232 | -9.793 | 14.825 | 17.468 | 1.00 | 27.77 |
| 18183 | OW0 | HOH | W | 233 | 19.188 | 4.350 | 4.555 | 1.00 | 26.21 |
| 18186 | OW0 | HOH | W | 234 | -5.748 | 12.057 | 10.445 | 1.00 | 26.02 |
| 18189 | OW0 | HOH | W | 235 | -45.888 | -28.184 | 21.431 | 1.00 | 25.39 |
| 18192 | OW0 | HOH | W | 236 | 12.533 | -0.637 | 46.753 | 1.00 | 25.86 |
| 18195 | OW0 | HOH | W | 237 | -35.957 | -9.155 | -23.033 | 1.00 | 22.15 |
| 18198 | OW0 | HOH | W | 238 | -71.080 | -47.817 | 15.103 | 1.00 | 26.65 |
| 18201 | OW0 | HOH | W | 240 | -10.340 | 7.705 | -4.987 | 1.00 | 25.15 |

FIGURE 3 (cont.)

| A | B | C | D | E | F | G | H | I | J |
|---|---|---|---|---|---|---|---|---|---|
| 18204 | OW0 | HOH | W | 241 | -30.388 | -17.475 | -27.757 | 1.00 | 27.53 |
| 18207 | OW0 | HOH | W | 242 | -29.344 | -31.938 | -2.430 | 1.00 | 26.91 |
| 18210 | OW0 | HOH | W | 243 | -59.487 | -46.574 | -14.831 | 1.00 | 26.42 |
| 18213 | OW0 | HOH | W | 244 | -40.639 | -50.126 | 2.221 | 1.00 | 28.73 |
| 18216 | OW0 | HOH | W | 245 | -45.408 | -13.753 | -32.846 | 1.00 | 25.99 |
| 18219 | OW0 | HOH | W | 246 | -58.768 | -18.983 | 6.313 | 1.00 | 25.71 |
| 18222 | OW0 | HOH | W | 247 | -32.618 | -20.058 | -12.199 | 1.00 | 24.98 |
| 18225 | OW0 | HOH | W | 248 | -2.580 | -9.550 | -0.531 | 1.00 | 24.03 |
| 18228 | OW0 | HOH | W | 249 | -51.020 | -16.853 | -33.405 | 1.00 | 26.40 |
| 18231 | OW0 | HOH | W | 250 | -12.041 | 8.554 | -2.460 | 1.00 | 28.29 |
| 18234 | OW0 | HOH | W | 251 | -57.305 | -17.080 | -18.906 | 1.00 | 25.77 |
| 18237 | OW0 | HOH | W | 252 | 7.156 | -8.694 | 2.222 | 1.00 | 25.66 |
| 18240 | OW0 | HOH | W | 253 | -23.758 | -23.212 | 5.347 | 1.00 | 25.40 |
| 18243 | OW0 | HOH | W | 254 | -36.798 | 4.629 | 14.730 | 1.00 | 28.30 |
| 18246 | OW0 | HOH | W | 255 | -6.432 | -14.579 | 40.123 | 1.00 | 25.01 |
| 18249 | OW0 | HOH | W | 256 | -2.342 | 3.418 | -2.175 | 1.00 | 26.65 |
| 18252 | OW0 | HOH | W | 257 | -53.778 | -10.106 | -20.902 | 1.00 | 26.07 |
| 18255 | OW0 | HOH | W | 258 | 13.288 | -7.236 | 21.507 | 1.00 | 28.59 |
| 18258 | OW0 | HOH | W | 259 | -61.725 | -31.466 | 1.366 | 1.00 | 21.28 |
| 18261 | OW0 | HOH | W | 260 | -13.012 | 10.068 | 7.456 | 1.00 | 26.12 |
| 18264 | OW0 | HOH | W | 261 | -59.143 | -36.100 | -19.615 | 1.00 | 26.51 |
| 18267 | OW0 | HOH | W | 262 | -27.803 | -6.209 | 11.652 | 1.00 | 25.18 |
| 18270 | OW0 | HOH | W | 263 | -48.955 | -51.868 | 7.139 | 1.00 | 29.29 |
| 18273 | OW0 | HOH | W | 264 | -40.489 | -28.830 | -3.248 | 1.00 | 19.64 |
| 18276 | OW0 | HOH | W | 265 | -63.723 | -23.828 | -18.161 | 1.00 | 25.99 |
| 18279 | OW0 | HOH | W | 266 | -46.457 | -25.970 | 20.142 | 1.00 | 25.17 |
| 18282 | OW0 | HOH | W | 267 | -51.201 | -44.238 | -19.699 | 1.00 | 26.14 |
| 18285 | OW0 | HOH | W | 270 | -64.581 | -22.626 | -23.955 | 1.00 | 24.82 |
| 18288 | OW0 | HOH | W | 271 | -8.518 | -18.957 | 0.220 | 1.00 | 25.72 |
| 18291 | OW0 | HOH | W | 272 | -4.903 | -14.971 | -10.304 | 1.00 | 27.69 |
| 18294 | OW0 | HOH | W | 273 | -37.605 | -29.451 | 7.487 | 1.00 | 36.34 |
| 18297 | OW0 | HOH | W | 274 | -37.905 | -11.916 | -28.841 | 1.00 | 20.81 |
| 18300 | OW0 | HOH | W | 275 | -29.480 | -17.850 | -12.399 | 1.00 | 24.35 |
| 18303 | OW0 | HOH | W | 276 | -30.877 | -0.503 | 19.834 | 1.00 | 24.80 |
| 18306 | OW0 | HOH | W | 277 | -38.746 | -23.236 | 0.132 | 1.00 | 30.94 |
| 18309 | OW0 | HOH | W | 278 | 7.042 | 14.153 | 10.235 | 1.00 | 24.33 |
| 18312 | OW0 | HOH | W | 279 | -36.480 | -0.333 | 5.176 | 1.00 | 20.24 |
| 18315 | OW0 | HOH | W | 280 | 15.884 | -8.312 | 44.333 | 1.00 | 28.11 |
| 18318 | OW0 | HOH | W | 281 | -0.297 | -7.890 | 0.232 | 1.00 | 22.17 |
| 18321 | OW0 | HOH | W | 282 | -35.486 | -11.067 | 1.523 | 1.00 | 26.97 |
| 18324 | OW0 | HOH | W | 283 | -45.926 | -20.885 | 7.139 | 1.00 | 44.84 |
| 18327 | OW0 | HOH | W | 284 | -61.977 | -29.018 | 29.362 | 1.00 | 37.50 |
| 18330 | OW0 | HOH | W | 285 | -15.903 | -4.472 | 34.600 | 1.00 | 22.26 |
| 18333 | OW0 | HOH | W | 286 | -20.812 | 6.999 | -5.144 | 1.00 | 24.21 |
| 18336 | OW0 | HOH | W | 287 | -31.491 | -14.815 | -16.242 | 1.00 | 23.70 |
| 18339 | OW0 | HOH | W | 288 | -72.368 | -34.371 | 4.276 | 1.00 | 24.47 |
| 18342 | OW0 | HOH | W | 289 | -53.540 | -56.120 | -3.123 | 1.00 | 27.28 |
| 18345 | OW0 | HOH | W | 290 | -30.004 | -25.072 | -12.494 | 1.00 | 28.70 |
| 18348 | OW0 | HOH | W | 291 | -35.002 | -49.562 | -11.116 | 1.00 | 22.24 |

FIGURE 3 (cont.)

| A | B | C | D | E | F | G | H | I | J |
|---|---|---|---|---|---|---|---|---|---|
| 18351 | OW0 | HOH | W | 293 | -33.549 | -11.608 | 8.795 | 1.00 | 28.82 |
| 18354 | OW0 | HOH | W | 294 | 14.452 | -7.776 | 31.115 | 1.00 | 27.58 |
| 18357 | OW0 | HOH | W | 295 | -72.431 | -34.473 | 10.610 | 1.00 | 29.40 |
| 18360 | OW0 | HOH | W | 296 | -21.031 | -5.168 | 24.116 | 1.00 | 28.11 |
| 18363 | OW0 | HOH | W | 297 | -31.863 | -13.045 | 10.726 | 1.00 | 26.59 |
| 18366 | OW0 | HOH | W | 298 | 10.320 | -13.084 | 23.899 | 1.00 | 26.77 |
| 18369 | OW0 | HOH | W | 299 | -12.808 | 8.161 | 30.529 | 1.00 | 24.26 |
| 18372 | OW0 | HOH | W | 300 | -2.914 | 18.689 | 12.738 | 1.00 | 23.60 |
| 18375 | OW0 | HOH | W | 301 | -18.270 | 9.802 | -1.767 | 1.00 | 25.62 |
| 18378 | OW0 | HOH | W | 302 | -7.258 | 15.618 | 27.123 | 1.00 | 27.73 |
| 18381 | OW0 | HOH | W | 303 | -25.489 | 12.395 | 15.797 | 1.00 | 27.05 |
| 18384 | OW0 | HOH | W | 304 | -48.865 | -54.255 | -5.589 | 1.00 | 30.51 |
| 18387 | OW0 | HOH | W | 305 | 1.047 | -10.349 | 7.561 | 1.00 | 27.50 |
| 18390 | OW0 | HOH | W | 306 | 7.856 | -21.381 | 34.620 | 1.00 | 30.83 |
| 18393 | OW0 | HOH | W | 307 | -48.471 | -45.315 | 14.846 | 1.00 | 30.20 |
| 18396 | OW0 | HOH | W | 308 | -44.675 | -44.143 | -20.716 | 1.00 | 23.88 |
| 18399 | OW0 | HOH | W | 309 | -62.027 | -54.153 | -4.459 | 1.00 | 26.43 |
| 18402 | OW0 | HOH | W | 310 | -3.815 | -17.516 | 15.090 | 1.00 | 27.30 |
| 18405 | OW0 | HOH | W | 311 | -53.048 | -19.556 | 9.947 | 1.00 | 29.57 |
| 18408 | OW0 | HOH | W | 312 | 10.753 | -6.514 | 10.479 | 1.00 | 34.78 |
| 18411 | OW0 | HOH | W | 313 | -36.380 | 3.671 | 1.448 | 1.00 | 28.05 |
| 18414 | OW0 | HOH | W | 314 | -1.661 | -20.037 | 29.246 | 1.00 | 26.80 |
| 18417 | OW0 | HOH | W | 316 | -33.945 | -40.059 | -1.106 | 1.00 | 38.52 |
| 18420 | OW0 | HOH | W | 317 | -5.759 | 14.790 | 24.690 | 1.00 | 27.42 |
| 18423 | OW0 | HOH | W | 318 | -63.951 | -45.304 | -9.634 | 1.00 | 23.44 |
| 18426 | OW0 | HOH | W | 319 | -40.575 | -31.029 | 15.729 | 1.00 | 26.40 |
| 18429 | OW0 | HOH | W | 320 | 0.844 | -17.443 | 23.281 | 1.00 | 31.23 |
| 18432 | OW0 | HOH | W | 321 | -47.105 | -45.700 | -10.135 | 1.00 | 25.74 |
| 18435 | OW0 | HOH | W | 322 | -30.540 | -32.946 | 6.342 | 1.00 | 33.75 |
| 18438 | OW0 | HOH | W | 323 | 13.846 | -10.878 | 40.681 | 1.00 | 20.78 |
| 18441 | OW0 | HOH | W | 324 | -36.933 | -36.044 | 9.625 | 1.00 | 23.21 |
| 18444 | OW0 | HOH | W | 325 | -52.809 | -48.610 | -1.298 | 1.00 | 26.95 |
| 18447 | OW0 | HOH | W | 326 | -56.879 | -35.192 | 29.412 | 1.00 | 25.90 |
| 18450 | OW0 | HOH | W | 328 | -4.706 | 11.224 | 14.521 | 1.00 | 22.53 |
| 18453 | OW0 | HOH | W | 329 | -15.033 | -5.938 | 18.283 | 1.00 | 26.89 |
| 18456 | OW0 | HOH | W | 330 | -8.118 | 6.992 | 3.457 | 1.00 | 29.08 |
| 18459 | OW0 | HOH | W | 331 | -11.360 | -14.453 | 30.730 | 1.00 | 30.22 |
| 18462 | OW0 | HOH | W | 332 | -40.563 | -23.004 | 8.766 | 1.00 | 28.63 |
| 18465 | OW0 | HOH | W | 333 | -4.570 | -18.722 | 4.095 | 1.00 | 24.32 |
| 18468 | OW0 | HOH | W | 334 | -27.198 | -20.743 | 7.367 | 1.00 | 29.55 |
| 18471 | OW0 | HOH | W | 335 | -36.570 | -24.752 | -8.857 | 1.00 | 27.52 |
| 18474 | OW0 | HOH | W | 336 | -4.406 | -17.300 | -2.295 | 1.00 | 29.36 |
| 18477 | OW0 | HOH | W | 337 | -26.968 | -0.641 | 28.021 | 1.00 | 31.99 |
| 18480 | OW0 | HOH | W | 338 | -5.803 | 7.574 | 31.791 | 1.00 | 24.96 |
| 18483 | OW0 | HOH | W | 339 | -37.901 | -44.366 | -20.377 | 1.00 | 26.69 |
| 18486 | OW0 | HOH | W | 340 | 2.788 | -14.073 | 9.565 | 1.00 | 28.44 |
| 18489 | OW0 | HOH | W | 342 | 5.291 | -11.336 | 2.718 | 1.00 | 29.33 |
| 18492 | OW0 | HOH | W | 343 | 0.056 | -17.754 | 4.264 | 1.00 | 29.73 |
| 18495 | OW0 | HOH | W | 344 | -5.980 | -0.954 | -4.530 | 1.00 | 23.30 |

FIGURE 3 (cont.)

| A | B | C | D | E | F | G | H | I | J |
|---|---|---|---|---|---|---|---|---|---|
| 18498 | OW0 | HOH | W | 345 | -29.003 | 11.548 | 9.368 | 1.00 | 26.80 |
| 18501 | OW0 | HOH | W | 346 | -23.132 | -10.904 | 19.761 | 1.00 | 35.51 |
| 18504 | OW0 | HOH | W | 347 | -1.407 | -9.845 | -3.107 | 1.00 | 30.69 |
| 18507 | OW0 | HOH | W | 348 | -53.798 | -49.517 | -5.461 | 1.00 | 37.45 |
| 18510 | OW0 | HOH | W | 349 | -13.686 | -1.143 | -12.337 | 1.00 | 32.42 |
| 18513 | OW0 | HOH | W | 350 | -13.580 | 17.339 | 5.484 | 1.00 | 24.55 |
| 18516 | OW0 | HOH | W | 351 | 13.903 | -9.607 | 43.225 | 1.00 | 23.19 |
| 18519 | OW0 | HOH | W | 352 | -60.262 | -17.580 | -21.781 | 1.00 | 25.69 |
| 18522 | OW0 | HOH | W | 353 | -52.844 | -55.809 | -13.467 | 1.00 | 28.53 |
| 18525 | OW0 | HOH | W | 354 | -6.591 | -13.605 | 42.723 | 1.00 | 25.11 |
| 18528 | OW0 | HOH | W | 355 | -8.506 | 17.798 | 11.713 | 1.00 | 24.54 |
| 18531 | OW0 | HOH | W | 356 | -3.830 | -13.879 | -4.200 | 1.00 | 26.92 |
| 18534 | OW0 | HOH | W | 357 | -11.681 | -20.350 | -5.993 | 1.00 | 27.86 |
| 18537 | OW0 | HOH | W | 358 | 12.774 | -2.705 | 48.606 | 1.00 | 32.76 |
| 18540 | OW0 | HOH | W | 359 | -44.938 | -28.225 | 23.890 | 1.00 | 26.70 |
| 18543 | OW0 | HOH | W | 360 | -56.969 | -14.034 | -29.181 | 1.00 | 25.04 |
| 18546 | OW0 | HOH | W | 362 | -66.900 | -45.851 | 20.144 | 1.00 | 28.35 |
| 18549 | OW0 | HOH | W | 363 | -37.469 | -0.629 | 18.071 | 1.00 | 32.58 |
| 18552 | OW0 | HOH | W | 364 | -21.322 | -5.735 | 27.240 | 1.00 | 35.64 |
| 18555 | OW0 | HOH | W | 365 | -2.703 | -7.322 | -10.898 | 1.00 | 28.00 |
| 18558 | OW0 | HOH | W | 366 | 6.561 | -19.125 | 33.881 | 1.00 | 28.24 |
| 18561 | OW0 | HOH | W | 367 | -3.303 | -18.148 | -4.554 | 1.00 | 25.16 |
| 18564 | OW0 | HOH | W | 368 | -33.725 | -6.458 | 9.912 | 1.00 | 29.75 |
| 18567 | OW0 | HOH | W | 369 | -16.850 | 6.238 | 39.214 | 1.00 | 32.73 |
| 18570 | OW0 | HOH | W | 370 | -59.715 | -39.584 | -5.559 | 1.00 | 28.64 |
| 18573 | OW0 | HOH | W | 371 | -61.575 | -24.026 | 24.172 | 1.00 | 28.92 |
| 18576 | OW0 | HOH | W | 372 | -37.037 | -31.854 | -31.885 | 1.00 | 31.51 |
| 18579 | OW0 | HOH | W | 373 | -9.915 | -2.000 | 45.285 | 1.00 | 24.74 |
| 18582 | OW0 | HOH | W | 374 | -36.231 | -12.027 | -33.152 | 1.00 | 27.77 |
| 18585 | OW0 | HOH | W | 375 | -13.395 | -6.811 | -13.569 | 1.00 | 32.62 |
| 18588 | OW0 | HOH | W | 376 | -42.877 | -29.923 | 23.593 | 1.00 | 30.90 |
| 18591 | OW0 | HOH | W | 377 | -60.773 | -41.179 | -16.925 | 1.00 | 28.65 |
| 18594 | OW0 | HOH | W | 378 | -20.937 | 11.984 | 19.253 | 1.00 | 25.02 |
| 18597 | OW0 | HOH | W | 379 | -12.290 | -6.568 | 41.405 | 1.00 | 27.25 |
| 18600 | OW0 | HOH | W | 380 | -64.538 | -53.812 | -3.383 | 1.00 | 23.47 |
| 18603 | OW0 | HOH | W | 381 | -35.694 | -12.611 | -30.298 | 1.00 | 30.62 |
| 18606 | OW0 | HOH | W | 383 | 9.818 | 11.435 | 12.764 | 1.00 | 24.30 |
| 18609 | OW0 | HOH | W | 385 | -8.769 | 9.525 | 5.220 | 1.00 | 28.62 |
| 18612 | OW0 | HOH | W | 386 | -62.118 | -53.986 | 7.261 | 1.00 | 27.18 |
| 18615 | OW0 | HOH | W | 387 | 3.706 | -6.504 | 10.132 | 1.00 | 27.74 |
| 18618 | OW0 | HOH | W | 388 | -37.714 | -48.162 | 2.304 | 1.00 | 30.25 |
| 18621 | OW0 | HOH | W | 389 | -13.036 | -13.429 | 28.981 | 1.00 | 29.51 |
| 18624 | OW0 | HOH | W | 390 | -41.283 | -39.436 | -1.810 | 1.00 | 28.81 |
| 18627 | OW0 | HOH | W | 391 | -62.301 | -25.071 | -13.762 | 1.00 | 24.83 |
| 18630 | OW0 | HOH | W | 392 | -31.210 | -15.600 | 9.701 | 1.00 | 28.85 |
| 18633 | OW0 | HOH | W | 393 | -6.075 | -16.250 | 21.654 | 1.00 | 28.42 |
| 18636 | OW0 | HOH | W | 394 | -46.551 | -9.866 | -23.520 | 1.00 | 33.59 |
| 18639 | OW0 | HOH | W | 395 | -37.774 | -8.946 | -26.992 | 1.00 | 33.88 |
| 18642 | OW0 | HOH | W | 397 | -15.081 | 9.649 | 30.184 | 1.00 | 23.30 |

FIGURE 3 (cont.)

| A | B | C | D | E | F | G | H | I | J |
|---|---|---|---|---|---|---|---|---|---|
| 18645 | OW0 | HOH | W | 398 | 16.972 | -13.730 | 34.822 | 1.00 | 28.64 |
| 18648 | OW0 | HOH | W | 399 | -44.271 | -53.547 | -9.591 | 1.00 | 29.37 |
| 18651 | OW0 | HOH | W | 400 | 16.945 | -3.915 | 45.956 | 1.00 | 34.07 |
| 18654 | OW0 | HOH | W | 401 | 10.941 | 18.797 | 15.634 | 1.00 | 31.38 |
| 18657 | OW0 | HOH | W | 402 | -36.405 | -45.691 | -1.181 | 1.00 | 24.16 |
| 18660 | OW0 | HOH | W | 403 | -10.684 | 19.073 | 18.741 | 1.00 | 27.95 |
| 18663 | OW0 | HOH | W | 404 | -15.947 | -0.760 | 42.197 | 1.00 | 27.69 |
| 18666 | OW0 | HOH | W | 405 | -39.088 | -34.392 | 11.658 | 1.00 | 30.88 |
| 18669 | OW0 | HOH | W | 407 | -22.298 | -5.753 | 14.299 | 1.00 | 30.26 |
| 18672 | OW0 | HOH | W | 408 | 2.062 | -11.300 | -0.597 | 1.00 | 36.53 |
| 18675 | OW0 | HOH | W | 409 | -1.286 | -19.062 | 34.575 | 1.00 | 33.94 |
| 18678 | OW0 | HOH | W | 410 | -11.028 | -20.623 | 5.831 | 1.00 | 32.87 |
| 18681 | OW0 | HOH | W | 411 | -15.819 | 11.553 | 26.533 | 1.00 | 29.12 |
| 18684 | OW0 | HOH | W | 412 | -30.509 | -16.904 | -30.347 | 1.00 | 43.18 |
| 18687 | OW0 | HOH | W | 413 | -54.968 | -56.305 | -10.204 | 1.00 | 30.99 |
| 18690 | OW0 | HOH | W | 414 | -25.437 | -17.724 | 13.728 | 1.00 | 33.57 |
| 18693 | OW0 | HOH | W | 415 | -2.654 | 17.495 | 9.330 | 1.00 | 27.17 |
| 18696 | OW0 | HOH | W | 416 | -17.049 | -2.680 | 36.519 | 1.00 | 28.71 |
| 18699 | OW0 | HOH | W | 417 | -15.673 | 15.186 | 21.499 | 1.00 | 30.76 |
| 18702 | OW0 | HOH | W | 418 | -15.874 | 9.857 | 32.745 | 1.00 | 33.08 |
| 18705 | OW0 | HOH | W | 420 | -26.421 | -12.501 | 17.570 | 1.00 | 30.34 |
| 18708 | OW0 | HOH | W | 421 | 1.504 | -14.079 | 14.635 | 1.00 | 30.61 |
| 18711 | OW0 | HOH | W | 422 | -56.500 | -15.066 | -23.319 | 1.00 | 29.79 |
| 18714 | OW0 | HOH | W | 423 | -16.530 | -24.545 | -2.193 | 1.00 | 29.50 |
| 18717 | OW0 | HOH | W | 424 | -12.731 | 12.937 | 10.897 | 1.00 | 39.31 |
| 18720 | OW0 | HOH | W | 426 | -6.094 | -18.915 | 13.035 | 1.00 | 32.52 |
| 18723 | OW0 | HOH | W | 428 | -32.941 | -50.902 | -18.961 | 1.00 | 32.99 |
| 18726 | OW0 | HOH | W | 429 | -44.113 | -26.160 | 16.852 | 1.00 | 31.24 |
| 18729 | OW0 | HOH | W | 430 | -11.752 | -19.209 | -3.613 | 1.00 | 25.94 |
| 18732 | OW0 | HOH | W | 431 | -33.162 | -44.863 | -5.298 | 1.00 | 28.90 |
| 18735 | OW0 | HOH | W | 433 | -45.084 | -11.201 | -8.280 | 1.00 | 34.55 |
| 18738 | OW0 | HOH | W | 434 | -2.717 | 3.699 | 46.035 | 1.00 | 29.96 |
| 18741 | OW0 | HOH | W | 436 | -44.025 | -20.308 | 2.812 | 1.00 | 31.50 |
| 18744 | OW0 | HOH | W | 438 | -14.537 | -7.673 | 36.525 | 1.00 | 30.71 |
| 18747 | OW0 | HOH | W | 439 | -7.539 | -19.609 | -4.534 | 1.00 | 26.39 |
| 18750 | OW0 | HOH | W | 440 | -2.634 | 8.620 | 0.399 | 1.00 | 31.25 |
| 18753 | OW0 | HOH | W | 441 | -8.302 | -17.813 | 25.727 | 1.00 | 31.43 |
| 18756 | OW0 | HOH | W | 442 | -33.455 | -30.698 | -28.963 | 1.00 | 41.91 |
| 18759 | OW0 | HOH | W | 444 | -49.699 | -46.855 | -13.558 | 1.00 | 31.32 |
| 18762 | OW0 | HOH | W | 445 | -39.672 | -13.469 | -9.710 | 1.00 | 26.08 |
| 18765 | OW0 | HOH | W | 446 | -16.058 | 4.331 | 18.700 | 1.00 | 34.03 |
| 18768 | OW0 | HOH | W | 447 | -17.671 | -0.707 | 31.115 | 1.00 | 27.75 |
| 18771 | OW0 | HOH | W | 448 | -10.700 | 12.310 | 33.920 | 1.00 | 38.15 |
| 18774 | OW0 | HOH | W | 449 | -19.100 | 8.775 | -4.201 | 1.00 | 28.23 |
| 18777 | OW0 | HOH | W | 450 | -72.598 | -34.907 | -1.489 | 1.00 | 27.54 |
| 18780 | OW0 | HOH | W | 451 | -37.910 | -34.806 | 22.808 | 1.00 | 29.80 |
| 18783 | OW0 | HOH | W | 452 | -50.596 | -23.185 | 24.234 | 1.00 | 28.13 |
| 18786 | OW0 | HOH | W | 453 | -39.841 | -45.218 | 10.659 | 1.00 | 29.59 |
| 18789 | OW0 | HOH | W | 454 | -45.509 | -52.769 | -12.965 | 1.00 | 25.19 |

FIGURE 3 (cont.)

| A | B | C | D | E | F | G | H | I | J |
|---|---|---|---|---|---|---|---|---|---|
| 18792 | OW0 | HOH | W | 455 | -26.257 | -20.190 | 9.877 | 1.00 | 33.71 |
| 18795 | OW0 | HOH | W | 458 | -13.799 | -20.923 | -7.681 | 1.00 | 31.12 |
| 18798 | OW0 | HOH | W | 459 | 9.418 | -9.040 | 44.613 | 1.00 | 31.24 |
| 18801 | OW0 | HOH | W | 460 | -39.700 | -46.915 | 6.860 | 1.00 | 30.19 |
| 18804 | OW0 | HOH | W | 461 | -55.979 | -28.739 | -29.600 | 1.00 | 29.08 |
| 18807 | OW0 | HOH | W | 462 | -65.033 | -31.061 | -13.532 | 1.00 | 23.41 |
| 18810 | OW0 | HOH | W | 465 | -31.048 | -26.571 | -29.971 | 1.00 | 29.32 |
| 18813 | OW0 | HOH | W | 466 | -36.654 | -3.577 | -1.152 | 1.00 | 33.65 |
| 18816 | OW0 | HOH | W | 467 | -45.535 | -9.373 | -21.146 | 1.00 | 35.79 |
| 18819 | OW0 | HOH | W | 468 | 0.609 | -7.757 | -2.459 | 1.00 | 29.63 |
| 18822 | OW0 | HOH | W | 469 | -16.451 | -3.277 | 32.122 | 1.00 | 32.88 |
| 18825 | OW0 | HOH | W | 470 | -2.735 | -6.841 | 49.722 | 1.00 | 29.17 |
| 18828 | OW0 | HOH | W | 471 | -65.338 | -30.636 | -24.548 | 1.00 | 31.25 |
| 18831 | OW0 | HOH | W | 472 | -19.088 | 0.637 | 33.378 | 1.00 | 33.25 |
| 18834 | OW0 | HOH | W | 473 | -50.633 | -29.798 | -36.139 | 1.00 | 31.11 |
| 18837 | OW0 | HOH | W | 474 | 9.192 | -14.753 | 26.000 | 1.00 | 25.07 |
| 18840 | OW0 | HOH | W | 475 | 17.018 | 0.044 | 30.109 | 1.00 | 36.34 |
| 18843 | OW0 | HOH | W | 476 | -24.949 | -5.044 | 19.888 | 1.00 | 36.18 |
| 18846 | OW0 | HOH | W | 477 | -54.507 | -53.813 | 13.818 | 1.00 | 31.64 |
| 18849 | OW0 | HOH | W | 478 | -30.091 | -0.006 | -11.086 | 1.00 | 35.00 |
| 18852 | OW0 | HOH | W | 482 | -20.610 | 2.641 | 31.813 | 1.00 | 37.42 |
| 18855 | OW0 | HOH | W | 484 | -25.532 | -23.597 | 2.282 | 1.00 | 30.71 |
| 18858 | OW0 | HOH | W | 486 | -64.609 | -22.399 | 10.458 | 1.00 | 31.67 |
| 18861 | OW0 | HOH | W | 487 | 16.932 | -0.067 | 22.891 | 1.00 | 30.57 |
| 18864 | OW0 | HOH | W | 488 | -58.168 | -15.758 | -21.081 | 1.00 | 30.20 |
| 18867 | OW0 | HOH | W | 489 | -46.600 | -48.543 | -7.085 | 1.00 | 33.74 |
| 18870 | OW0 | HOH | W | 490 | -54.317 | -50.893 | -15.774 | 1.00 | 29.36 |
| 18873 | OW0 | HOH | W | 491 | -57.157 | -16.380 | 14.173 | 1.00 | 32.16 |
| 18876 | OW0 | HOH | W | 492 | 2.345 | -17.230 | 36.277 | 1.00 | 31.13 |
| 18879 | OW0 | HOH | W | 493 | -32.419 | -45.859 | -12.912 | 1.00 | 27.08 |
| 18882 | OW0 | HOH | W | 494 | -27.687 | -22.639 | -2.233 | 1.00 | 28.05 |
| 18885 | OW0 | HOH | W | 497 | -50.273 | -48.879 | -15.412 | 1.00 | 46.28 |
| 18888 | OW0 | HOH | W | 498 | -56.600 | -21.350 | -32.027 | 1.00 | 40.63 |
| 18891 | OW0 | HOH | W | 499 | -13.718 | 18.047 | 8.906 | 1.00 | 30.27 |
| 18894 | OW0 | HOH | W | 500 | -48.141 | -49.051 | -0.489 | 1.00 | 33.22 |
| 18897 | OW0 | HOH | W | 501 | -34.398 | -20.239 | -5.962 | 1.00 | 26.31 |
| 18900 | OW0 | HOH | W | 502 | -59.702 | -21.121 | 16.655 | 1.00 | 31.19 |
| 18903 | OW0 | HOH | W | 503 | -27.477 | 18.555 | 2.591 | 1.00 | 31.48 |
| 18906 | OW0 | HOH | W | 504 | -49.875 | -24.271 | 26.689 | 1.00 | 33.41 |
| 18909 | OW0 | HOH | W | 505 | -16.546 | -10.860 | 30.920 | 1.00 | 39.53 |
| 18912 | OW0 | HOH | W | 506 | -45.696 | -41.578 | -25.946 | 1.00 | 29.86 |
| 18915 | OW0 | HOH | W | 507 | -63.436 | -41.314 | 34.375 | 1.00 | 35.31 |
| 18918 | OW0 | HOH | W | 508 | -52.733 | -32.974 | -27.462 | 1.00 | 35.28 |
| 18921 | OW0 | HOH | W | 509 | -50.079 | -51.017 | 0.775 | 1.00 | 29.75 |
| 18924 | OW0 | HOH | W | 510 | -27.821 | -27.489 | -21.645 | 1.00 | 36.47 |
| 18927 | OW0 | HOH | W | 511 | -13.516 | -9.972 | 34.666 | 1.00 | 32.67 |
| 18930 | OW0 | HOH | W | 512 | -20.209 | 11.160 | 26.051 | 1.00 | 30.90 |
| 18933 | OW0 | HOH | W | 513 | -11.062 | 10.738 | 3.843 | 1.00 | 28.99 |
| 18936 | OW0 | HOH | W | 515 | 6.418 | 5.033 | 47.899 | 1.00 | 28.62 |

FIGURE 3 (cont.)

| A | B | C | D | E | F | G | H | I | J |
|---|---|---|---|---|---|---|---|---|---|
| 18939 | OW0 | HOH | W | 516 | -49.687 | -19.874 | -37.460 | 1.00 | 36.05 |
| 18942 | OW0 | HOH | W | 517 | -65.701 | -19.157 | -9.131 | 1.00 | 38.40 |
| 18945 | OW0 | HOH | W | 518 | -57.640 | -18.264 | -9.917 | 1.00 | 37.06 |
| 18948 | OW0 | HOH | W | 519 | 2.486 | 16.054 | 21.565 | 1.00 | 32.08 |
| 18951 | OW0 | HOH | W | 520 | -59.185 | -18.089 | -13.748 | 1.00 | 37.57 |
| 18954 | OW0 | HOH | W | 521 | -39.347 | -9.282 | -15.415 | 1.00 | 28.47 |
| 18957 | OW0 | HOH | W | 523 | -67.566 | -51.893 | -0.108 | 1.00 | 31.71 |
| 18960 | OW0 | HOH | W | 524 | -2.061 | 16.586 | 6.336 | 1.00 | 35.98 |
| 18963 | OW0 | HOH | W | 525 | -39.430 | -3.446 | 11.094 | 1.00 | 31.95 |
| 18966 | OW0 | HOH | W | 528 | 7.785 | -9.738 | 48.207 | 1.00 | 33.07 |
| 18969 | OW0 | HOH | W | 530 | -18.073 | 12.719 | 25.918 | 1.00 | 36.54 |
| 18972 | OW0 | HOH | W | 531 | -58.529 | -19.023 | -2.956 | 1.00 | 29.57 |
| 18975 | OW0 | HOH | W | 532 | -44.578 | -42.328 | -28.269 | 1.00 | 41.03 |
| 18978 | OW0 | HOH | W | 534 | -62.763 | -32.102 | 31.943 | 1.00 | 37.06 |
| 18981 | OW0 | HOH | W | 535 | -1.636 | -9.374 | -9.486 | 1.00 | 32.15 |
| 18984 | OW0 | HOH | W | 536 | 9.768 | 15.243 | 10.622 | 1.00 | 38.05 |
| 18987 | OW0 | HOH | W | 537 | -8.934 | -19.171 | 7.039 | 1.00 | 35.97 |
| 18990 | OW0 | HOH | W | 538 | -33.907 | -22.089 | -10.376 | 1.00 | 31.10 |
| 18993 | OW0 | HOH | W | 539 | 6.905 | -6.657 | 17.277 | 1.00 | 31.28 |
| 18996 | OW0 | HOH | W | 542 | -44.743 | -42.956 | -23.096 | 1.00 | 29.69 |
| 18999 | OW0 | HOH | W | 544 | -4.504 | -16.432 | 40.724 | 1.00 | 33.95 |
| 19002 | OW0 | HOH | W | 545 | -38.664 | -32.741 | 17.308 | 1.00 | 32.11 |
| 19005 | OW0 | HOH | W | 546 | -67.425 | -51.110 | -14.488 | 1.00 | 35.68 |
| 19008 | OW0 | HOH | W | 547 | -52.658 | -34.447 | -22.208 | 1.00 | 26.99 |
| 19011 | OW0 | HOH | W | 548 | -48.176 | -25.147 | 34.605 | 1.00 | 35.16 |
| 19014 | OW0 | HOH | W | 549 | -22.804 | 20.072 | 21.180 | 1.00 | 45.74 |
| 19017 | OW0 | HOH | W | 550 | 12.080 | 8.634 | 36.491 | 1.00 | 32.88 |
| 19020 | OW0 | HOH | W | 551 | -8.841 | 21.071 | 11.431 | 1.00 | 34.30 |
| 19023 | OW0 | HOH | W | 552 | -63.675 | -49.886 | 23.656 | 1.00 | 38.75 |
| 19026 | OW0 | HOH | W | 554 | -19.525 | -17.148 | 16.831 | 1.00 | 35.38 |
| 19029 | OW0 | HOH | W | 555 | -59.553 | -19.831 | -27.686 | 1.00 | 26.18 |
| 19032 | OW0 | HOH | W | 556 | -47.681 | -30.942 | 32.267 | 1.00 | 31.60 |
| 19035 | OW0 | HOH | W | 558 | -2.291 | -11.981 | 0.426 | 1.00 | 28.90 |
| 19038 | OW0 | HOH | W | 559 | -4.750 | -15.367 | 47.709 | 1.00 | 39.25 |
| 19041 | OW0 | HOH | W | 560 | -65.806 | -32.169 | -3.667 | 1.00 | 35.46 |
| 19044 | OW0 | HOH | W | 562 | -17.437 | -10.533 | -16.296 | 1.00 | 34.42 |
| 19047 | OW0 | HOH | W | 564 | -33.398 | -3.310 | 17.572 | 1.00 | 31.60 |
| 19050 | OW0 | HOH | W | 566 | -5.896 | -7.339 | 48.765 | 1.00 | 32.27 |
| 19053 | OW0 | HOH | W | 567 | -50.675 | -15.097 | -4.492 | 1.00 | 29.37 |
| 19056 | OW0 | HOH | W | 568 | -38.944 | -33.504 | -33.477 | 1.00 | 39.95 |
| 19059 | OW0 | HOH | W | 571 | -14.223 | -20.671 | 12.061 | 1.00 | 32.48 |
| 19062 | OW0 | HOH | W | 572 | -67.268 | -47.382 | 22.282 | 1.00 | 50.74 |
| 19065 | OW0 | HOH | W | 573 | 3.281 | -17.655 | 22.834 | 1.00 | 34.58 |
| 19068 | OW0 | HOH | W | 574 | -5.702 | 14.693 | 10.132 | 1.00 | 32.40 |
| 19071 | OW0 | HOH | W | 575 | -11.243 | 14.624 | 9.771 | 1.00 | 37.28 |
| 19074 | OW0 | HOH | W | 576 | 2.749 | 5.936 | 3.950 | 1.00 | 30.45 |
| 19077 | OW0 | HOH | W | 578 | -62.203 | -16.917 | -20.098 | 1.00 | 38.72 |
| 19080 | OW0 | HOH | W | 580 | -12.387 | -2.647 | 44.353 | 1.00 | 48.36 |
| 19083 | OW0 | HOH | W | 581 | -43.752 | -10.106 | -16.524 | 1.00 | 31.54 |

FIGURE 3 (cont.)

| A | B | C | D | E | F | G | H | I | J |
|---|---|---|---|---|---|---|---|---|---|
| 19086 | OW0 | HOH | W | 582 | -7.354 | -19.038 | 3.852 | 1.00 | 57.83 |
| 19089 | OW0 | HOH | W | 583 | -64.054 | -25.053 | 1.484 | 1.00 | 31.88 |
| 19092 | OW0 | HOH | W | 584 | -13.768 | -25.250 | -1.843 | 1.00 | 35.26 |
| 19095 | OW0 | HOH | W | 585 | -8.589 | -7.417 | 45.243 | 1.00 | 35.13 |
| 19098 | OW0 | HOH | W | 586 | 11.350 | -10.436 | 43.963 | 1.00 | 25.78 |
| 19101 | OW0 | HOH | W | 587 | 10.253 | -8.062 | 47.024 | 1.00 | 33.26 |
| 19104 | OW0 | HOH | W | 588 | -60.492 | -35.039 | 33.564 | 1.00 | 30.90 |
| 19107 | OW0 | HOH | W | 589 | -11.858 | -20.603 | -1.371 | 1.00 | 30.08 |
| 19110 | OW0 | HOH | W | 591 | -66.898 | -33.417 | 7.201 | 1.00 | 31.51 |
| 19113 | OW0 | HOH | W | 592 | 1.391 | 14.903 | 29.762 | 1.00 | 30.67 |
| 19116 | OW0 | HOH | W | 593 | -11.800 | 18.567 | 3.944 | 1.00 | 37.87 |
| 19119 | OW0 | HOH | W | 594 | -67.323 | -40.595 | -6.207 | 1.00 | 34.96 |
| 19122 | OW0 | HOH | W | 595 | 18.041 | -10.017 | 43.820 | 1.00 | 33.21 |
| 19125 | OW0 | HOH | W | 596 | -59.397 | -20.934 | 0.873 | 1.00 | 34.30 |
| 19128 | OW0 | HOH | W | 597 | -53.886 | -53.056 | -17.213 | 1.00 | 32.38 |
| 19131 | OW0 | HOH | W | 598 | -5.240 | -7.670 | -11.610 | 1.00 | 35.07 |
| 19134 | OW0 | HOH | W | 599 | -55.540 | -10.508 | -17.058 | 1.00 | 33.73 |
| 19137 | OW0 | HOH | W | 600 | -31.472 | -52.639 | -2.035 | 1.00 | 44.20 |
| 19140 | OW0 | HOH | W | 601 | -1.496 | 19.752 | 16.578 | 1.00 | 30.16 |
| 19143 | OW0 | HOH | W | 602 | -51.477 | -57.592 | -2.784 | 1.00 | 37.10 |
| 19146 | OW0 | HOH | W | 603 | -58.367 | -37.864 | -24.952 | 1.00 | 34.96 |
| 19149 | OW0 | HOH | W | 604 | 9.069 | 16.102 | 18.827 | 1.00 | 35.39 |
| 19152 | OW0 | HOH | W | 605 | -45.862 | -43.864 | 23.966 | 1.00 | 32.20 |
| 19155 | OW0 | HOH | W | 606 | -6.133 | 6.478 | 41.672 | 1.00 | 35.34 |
| 19158 | OW0 | HOH | W | 607 | -29.917 | -23.302 | 1.823 | 1.00 | 39.63 |
| 19161 | OW0 | HOH | W | 608 | -28.396 | -7.050 | -19.485 | 1.00 | 37.35 |
| 19164 | OW0 | HOH | W | 609 | 17.828 | -10.152 | 38.439 | 1.00 | 40.49 |
| 19167 | OW0 | HOH | W | 610 | -67.104 | -46.801 | -6.067 | 1.00 | 31.67 |
| 19170 | OW0 | HOH | W | 611 | -57.493 | -44.912 | -14.700 | 1.00 | 47.65 |
| 19173 | OW0 | HOH | W | 612 | 19.616 | -6.016 | 43.565 | 1.00 | 34.99 |
| 19176 | OW0 | HOH | W | 613 | -61.247 | -13.332 | -12.193 | 1.00 | 37.70 |
| 19179 | OW0 | HOH | W | 614 | -23.821 | -35.035 | -9.705 | 1.00 | 32.77 |
| 19182 | OW0 | HOH | W | 615 | -46.580 | -28.574 | 26.146 | 1.00 | 32.12 |
| 19185 | OW0 | HOH | W | 616 | 16.303 | -6.043 | 32.016 | 1.00 | 33.14 |
| 19188 | OW0 | HOH | W | 618 | -40.197 | -31.208 | 12.876 | 1.00 | 35.35 |
| 19191 | OW0 | HOH | W | 619 | -26.466 | -2.444 | -17.832 | 1.00 | 39.51 |
| 19194 | OW0 | HOH | W | 620 | 12.442 | -11.212 | 25.352 | 1.00 | 31.34 |
| 19197 | OW0 | HOH | W | 621 | -21.038 | -23.524 | 9.080 | 1.00 | 34.35 |
| 19200 | OW0 | HOH | W | 622 | -30.036 | -4.851 | 15.707 | 1.00 | 33.39 |
| 19203 | OW0 | HOH | W | 623 | -35.345 | -37.381 | 11.278 | 1.00 | 32.98 |
| 19206 | OW0 | HOH | W | 625 | 11.973 | -7.654 | 12.629 | 1.00 | 33.05 |
| 19209 | OW0 | HOH | W | 626 | -38.060 | 1.365 | 3.422 | 1.00 | 33.60 |
| 19212 | OW0 | HOH | W | 627 | -25.998 | 17.027 | 16.355 | 1.00 | 33.69 |
| 19215 | OW0 | HOH | W | 628 | 16.730 | -13.989 | 38.719 | 1.00 | 28.05 |
| 19218 | OW0 | HOH | W | 629 | 1.312 | 14.758 | 26.114 | 1.00 | 30.40 |
| 19221 | OW0 | HOH | W | 630 | -31.059 | -21.069 | 6.237 | 1.00 | 32.58 |
| 19224 | OW0 | HOH | W | 632 | -27.067 | 18.630 | 9.304 | 1.00 | 51.53 |
| 19227 | OW0 | HOH | W | 633 | 4.976 | 4.236 | 3.559 | 1.00 | 36.16 |
| 19230 | OW0 | HOH | W | 634 | 10.053 | -13.365 | 21.320 | 1.00 | 34.67 |

FIGURE 3 (cont.)

| A | B | C | D | E | F | G | H | I | J |
|---|---|---|---|---|---|---|---|---|---|
| 19233 | OW0 | HOH | W | 635 | 14.582 | 5.940 | 33.697 | 1.00 | 39.50 |
| 19236 | OW0 | HOH | W | 636 | -36.322 | -6.128 | 6.265 | 1.00 | 32.50 |
| 19239 | OW0 | HOH | W | 637 | -11.957 | -11.265 | 41.352 | 1.00 | 36.22 |
| 19242 | OW0 | HOH | W | 638 | -34.114 | -1.478 | -6.927 | 1.00 | 57.15 |
| 19245 | OW0 | HOH | W | 640 | -11.156 | -16.215 | -12.721 | 1.00 | 29.42 |
| 19248 | OW0 | HOH | W | 641 | -14.161 | -8.520 | 38.924 | 1.00 | 37.53 |
| 19251 | OW0 | HOH | W | 642 | -54.017 | -34.214 | -29.062 | 1.00 | 33.45 |
| 19254 | OW0 | HOH | W | 644 | -9.639 | 12.615 | 22.567 | 1.00 | 38.95 |
| 19257 | OW0 | HOH | W | 645 | -48.284 | -23.859 | -38.901 | 1.00 | 33.57 |
| 19260 | OW0 | HOH | W | 646 | -29.375 | -31.538 | -23.871 | 1.00 | 35.54 |
| 19263 | OW0 | HOH | W | 648 | -65.998 | -59.323 | 2.613 | 1.00 | 30.37 |
| 19266 | OW0 | HOH | W | 649 | -26.222 | -7.873 | 19.776 | 1.00 | 37.55 |
| 19269 | OW0 | HOH | W | 650 | -60.832 | -25.412 | 26.455 | 1.00 | 35.18 |
| 19272 | OW0 | HOH | W | 653 | -28.434 | -25.889 | -10.201 | 1.00 | 41.73 |
| 19275 | OW0 | HOH | W | 654 | -41.584 | -48.402 | -19.987 | 1.00 | 32.92 |
| 19278 | OW0 | HOH | W | 655 | 4.618 | 13.802 | 23.941 | 1.00 | 40.04 |
| 19281 | OW0 | HOH | W | 656 | -42.634 | -36.879 | -39.680 | 1.00 | 40.50 |
| 19284 | OW0 | HOH | W | 658 | -41.097 | -8.315 | -22.234 | 1.00 | 36.77 |
| 19287 | OW0 | HOH | W | 659 | -36.262 | -31.820 | -0.233 | 1.00 | 36.04 |
| 19290 | OW0 | HOH | W | 660 | -31.563 | -13.279 | -27.023 | 1.00 | 32.92 |
| 19293 | OW0 | HOH | W | 661 | -59.872 | -21.301 | 19.380 | 1.00 | 42.11 |
| 19296 | OW0 | HOH | W | 662 | 8.769 | 11.776 | 3.852 | 1.00 | 40.03 |
| 19299 | OW0 | HOH | W | 664 | -4.846 | -20.253 | 31.952 | 1.00 | 37.38 |
| 19302 | OW0 | HOH | W | 665 | -52.163 | -51.481 | -6.307 | 1.00 | 33.32 |
| 19305 | OW0 | HOH | W | 667 | -56.461 | -45.430 | 33.446 | 1.00 | 33.57 |
| 19308 | OW0 | HOH | W | 668 | -44.169 | -10.849 | -12.824 | 1.00 | 32.95 |
| 19311 | OW0 | HOH | W | 669 | -37.021 | -35.601 | 13.584 | 1.00 | 35.95 |
| 19314 | OW0 | HOH | W | 670 | -67.656 | -26.521 | -19.504 | 1.00 | 44.88 |
| 19317 | OW0 | HOH | W | 671 | -22.630 | 9.603 | -7.429 | 1.00 | 35.89 |
| 19320 | OW0 | HOH | W | 672 | -10.098 | 22.024 | 13.804 | 1.00 | 33.60 |
| 19323 | OW0 | HOH | W | 673 | 1.206 | 5.563 | 1.723 | 1.00 | 42.76 |
| 19326 | OW0 | HOH | W | 674 | -69.116 | -49.736 | 0.535 | 1.00 | 34.84 |
| 19329 | OW0 | HOH | W | 675 | -51.481 | -21.919 | -35.833 | 1.00 | 32.27 |
| 19332 | OW0 | HOH | W | 677 | -43.934 | -29.836 | -37.737 | 1.00 | 27.30 |
| 19335 | OW0 | HOH | W | 678 | -66.549 | -31.199 | -15.761 | 1.00 | 34.89 |
| 19338 | OW0 | HOH | W | 679 | -26.262 | -19.785 | 12.305 | 1.00 | 38.53 |
| 19341 | OW0 | HOH | W | 680 | -20.410 | 9.369 | -11.805 | 1.00 | 34.00 |
| 19344 | OW0 | HOH | W | 681 | -66.724 | -30.272 | -1.345 | 1.00 | 38.95 |
| 19347 | OW0 | HOH | W | 682 | -8.638 | 6.754 | 0.799 | 1.00 | 44.52 |
| 19350 | OW0 | HOH | W | 683 | 17.621 | 5.444 | 24.172 | 1.00 | 30.13 |
| 19353 | OW0 | HOH | W | 684 | -53.014 | -15.222 | 17.209 | 1.00 | 30.83 |
| 19356 | OW0 | HOH | W | 685 | -47.078 | -50.821 | -7.867 | 1.00 | 37.87 |
| 19359 | OW0 | HOH | W | 686 | 15.304 | -7.432 | 23.090 | 1.00 | 35.43 |
| 19362 | OW0 | HOH | W | 688 | -35.512 | -26.803 | -9.125 | 1.00 | 36.82 |
| 19365 | OW0 | HOH | W | 689 | -38.836 | -18.124 | -4.639 | 1.00 | 53.40 |
| 19368 | OW0 | HOH | W | 690 | 17.003 | 3.749 | 27.769 | 1.00 | 36.19 |
| 19371 | OW0 | HOH | W | 691 | -60.119 | -36.090 | -24.278 | 1.00 | 43.60 |
| 19374 | OW0 | HOH | W | 692 | -51.050 | -56.022 | -11.487 | 1.00 | 33.02 |
| 19377 | OW0 | HOH | W | 693 | -36.246 | -41.579 | 19.104 | 1.00 | 33.41 |

FIGURE 3 (cont.)

| A | B | C | D | E | F | G | H | I | J |
|---|---|---|---|---|---:|---:|---:|---:|---:|
| 19380 | OW0 | HOH | W | 694 | -19.897 | -4.241 | -18.623 | 1.00 | 34.79 |
| 19383 | OW0 | HOH | W | 695 | -10.617 | -12.300 | 16.955 | 1.00 | 45.30 |
| 19386 | OW0 | HOH | W | 696 | -73.005 | -47.500 | 13.394 | 1.00 | 37.81 |
| 19389 | OW0 | HOH | W | 702 | 10.017 | 16.666 | 8.468 | 1.00 | 36.22 |
| 19392 | OW0 | HOH | W | 704 | -31.147 | -2.610 | 18.119 | 1.00 | 54.59 |
| 19395 | OW0 | HOH | W | 705 | -47.768 | -53.036 | -16.206 | 1.00 | 36.04 |
| 19398 | OW0 | HOH | W | 707 | -9.074 | -15.171 | 39.874 | 1.00 | 36.28 |
| 19401 | OW0 | HOH | W | 709 | -69.961 | -29.222 | 0.924 | 1.00 | 42.01 |
| 19404 | OW0 | HOH | W | 712 | -17.061 | -6.896 | 36.123 | 1.00 | 45.99 |
| 19407 | OW0 | HOH | W | 713 | -40.722 | -46.617 | 15.983 | 1.00 | 40.93 |
| 19410 | OW0 | HOH | W | 714 | -16.605 | -24.960 | -4.977 | 1.00 | 36.33 |
| 19413 | OW0 | HOH | W | 715 | -30.994 | -0.774 | 22.714 | 1.00 | 34.31 |
| 19416 | OW0 | HOH | W | 716 | -26.391 | 22.050 | 10.789 | 1.00 | 39.05 |
| 19419 | OW0 | HOH | W | 717 | -43.591 | -39.821 | -0.076 | 1.00 | 67.11 |
| 19422 | OW0 | HOH | W | 719 | -39.138 | -11.928 | -4.250 | 1.00 | 31.47 |
| 19425 | OW0 | HOH | W | 720 | -43.136 | -35.161 | 27.280 | 1.00 | 31.46 |
| 19428 | OW0 | HOH | W | 721 | -61.123 | -19.172 | -16.004 | 1.00 | 34.80 |
| 19431 | OW0 | HOH | W | 722 | -23.777 | -2.071 | 20.439 | 1.00 | 32.59 |
| 19434 | OW0 | HOH | W | 724 | 18.246 | -0.713 | 27.402 | 1.00 | 34.36 |
| 19437 | OW0 | HOH | W | 725 | -67.358 | -33.512 | 4.810 | 1.00 | 37.89 |
| 19440 | OW0 | HOH | W | 727 | -45.486 | -43.267 | -30.949 | 1.00 | 33.17 |
| 19443 | OW0 | HOH | W | 728 | 15.900 | -5.563 | 24.762 | 1.00 | 35.93 |
| 19446 | OW0 | HOH | W | 729 | -41.068 | -34.214 | 26.029 | 1.00 | 49.12 |
| 19449 | OW0 | HOH | W | 730 | 7.567 | 10.216 | 43.625 | 1.00 | 37.91 |
| 19452 | OW0 | HOH | W | 731 | -6.278 | 14.052 | 17.387 | 1.00 | 34.97 |
| 19455 | OW0 | HOH | W | 732 | -59.030 | -18.809 | -30.103 | 1.00 | 40.61 |
| 19458 | OW0 | HOH | W | 733 | 13.254 | 10.427 | 30.892 | 1.00 | 37.64 |
| 19461 | OW0 | HOH | W | 734 | -41.995 | -44.138 | 11.750 | 1.00 | 27.03 |
| 19464 | OW0 | HOH | W | 735 | -64.782 | -41.465 | -15.022 | 1.00 | 39.84 |
| 19467 | OW0 | HOH | W | 736 | -14.979 | 10.336 | -0.914 | 1.00 | 43.58 |
| 19470 | OW0 | HOH | W | 737 | -28.043 | -34.320 | -21.765 | 1.00 | 37.29 |
| 19473 | OW0 | HOH | W | 738 | -13.688 | -20.369 | -10.241 | 1.00 | 39.21 |
| 19476 | OW0 | HOH | W | 739 | -51.892 | -46.122 | -11.472 | 1.00 | 35.05 |
| 19479 | OW0 | HOH | W | 740 | -4.322 | 15.825 | 21.292 | 1.00 | 41.38 |
| 19482 | OW0 | HOH | W | 741 | -30.755 | -6.480 | -17.423 | 1.00 | 35.62 |
| 19485 | OW0 | HOH | W | 742 | -27.967 | -14.179 | -19.214 | 1.00 | 49.89 |
| 19488 | OW0 | HOH | W | 743 | -47.006 | -47.608 | 1.873 | 1.00 | 42.29 |
| 19491 | OW0 | HOH | W | 744 | -30.643 | -11.702 | -25.087 | 1.00 | 37.49 |
| 19494 | OW0 | HOH | W | 745 | -29.059 | -35.598 | -25.541 | 1.00 | 38.24 |
| 19497 | OW0 | HOH | W | 747 | -8.082 | 9.647 | 41.013 | 1.00 | 36.41 |
| 19500 | OW0 | HOH | W | 748 | -32.664 | -30.994 | 9.186 | 1.00 | 63.48 |
| 19503 | OW0 | HOH | W | 749 | 10.538 | -8.675 | 19.567 | 1.00 | 42.51 |
| 19506 | OW0 | HOH | W | 750 | -72.547 | -36.262 | 27.156 | 1.00 | 36.91 |
| 19509 | OW0 | HOH | W | 751 | -8.930 | -12.405 | 43.587 | 1.00 | 42.37 |
| 19512 | OW0 | HOH | W | 752 | 0.494 | 17.082 | 19.139 | 1.00 | 38.31 |
| 19515 | OW0 | HOH | W | 753 | -31.505 | 13.662 | 17.292 | 1.00 | 60.40 |
| 19518 | OW0 | HOH | W | 754 | 6.603 | 16.466 | 19.778 | 1.00 | 36.93 |
| 19521 | OW0 | HOH | W | 755 | -35.166 | -28.339 | -7.207 | 1.00 | 42.29 |
| 19524 | OW0 | HOH | W | 756 | -19.294 | 7.363 | -7.418 | 1.00 | 34.43 |

FIGURE 3 (cont.)

| A | B | C | D | E | F | G | H | I | J |
|---|---|---|---|---|---|---|---|---|---|
| 19527 | OW0 | HOH | W | 757 | -54.686 | -57.608 | 16.972 | 1.00 | 36.60 |
| 19530 | OW0 | HOH | W | 758 | -32.044 | -52.618 | 0.457 | 1.00 | 38.92 |
| 19533 | OW0 | HOH | W | 759 | -4.233 | 20.706 | 16.194 | 1.00 | 39.99 |
| 19536 | OW0 | HOH | W | 760 | -3.994 | -18.564 | 33.720 | 1.00 | 40.93 |
| 19539 | OW0 | HOH | W | 761 | -32.708 | 11.632 | 3.446 | 1.00 | 36.04 |
| 19542 | OW0 | HOH | W | 762 | 12.810 | -22.865 | 33.542 | 1.00 | 38.80 |
| 19545 | OW0 | HOH | W | 763 | -56.811 | -45.771 | -16.961 | 1.00 | 43.84 |
| 19548 | OW0 | HOH | W | 764 | -31.646 | -12.047 | 13.260 | 1.00 | 33.74 |
| 19551 | OW0 | HOH | W | 765 | -55.431 | -9.480 | -12.229 | 1.00 | 38.17 |
| 19554 | OW0 | HOH | W | 766 | -12.447 | 10.594 | 34.748 | 1.00 | 39.80 |
| 19557 | OW0 | HOH | W | 767 | -29.840 | -26.591 | -23.881 | 1.00 | 36.62 |
| 19560 | OW0 | HOH | W | 768 | 13.262 | 3.019 | 3.991 | 1.00 | 37.73 |
| 19563 | OW0 | HOH | W | 769 | -66.074 | -21.844 | -3.360 | 1.00 | 36.97 |
| 19566 | OW0 | HOH | W | 770 | -31.757 | 4.237 | -6.397 | 1.00 | 44.01 |
| 19569 | OW0 | HOH | W | 771 | -35.638 | -28.528 | -0.284 | 1.00 | 40.71 |
| 19572 | OW0 | HOH | W | 772 | -36.329 | -3.327 | -7.081 | 1.00 | 42.09 |
| 19575 | OW0 | HOH | W | 773 | 10.384 | 11.173 | 37.668 | 1.00 | 44.23 |
| 19578 | OW0 | HOH | W | 774 | -55.959 | -12.272 | -8.510 | 1.00 | 38.89 |
| 19581 | OW0 | HOH | W | 775 | -9.526 | 19.066 | 9.679 | 1.00 | 37.48 |
| 19584 | OW0 | HOH | W | 776 | -12.091 | 13.094 | 36.356 | 1.00 | 83.93 |
| 19587 | OW0 | HOH | W | 777 | -48.122 | -22.033 | 13.717 | 1.00 | 32.16 |
| 19590 | OW0 | HOH | W | 778 | -29.884 | -57.538 | -15.106 | 1.00 | 37.56 |
| 19593 | OW0 | HOH | W | 781 | -55.440 | -55.656 | 15.488 | 1.00 | 45.33 |
| 19596 | OW0 | HOH | W | 782 | -77.359 | -42.349 | 2.721 | 1.00 | 36.78 |
| 19599 | OW0 | HOH | W | 783 | -51.682 | -54.394 | -6.114 | 1.00 | 36.80 |
| 19602 | OW0 | HOH | W | 784 | 14.393 | 9.772 | 36.079 | 1.00 | 46.32 |
| 19605 | OW0 | HOH | W | 786 | -4.168 | 8.948 | 36.783 | 1.00 | 38.35 |
| 19608 | OW0 | HOH | W | 788 | -67.029 | -62.944 | -2.015 | 1.00 | 43.68 |
| 19611 | OW0 | HOH | W | 789 | -40.428 | -9.824 | -7.912 | 1.00 | 40.49 |
| 19614 | OW0 | HOH | W | 790 | -62.915 | -42.548 | -16.630 | 1.00 | 38.89 |
| 19617 | OW0 | HOH | W | 791 | -52.825 | -42.089 | 34.703 | 1.00 | 44.91 |
| 19620 | OW0 | HOH | W | 792 | -37.552 | -6.135 | -0.749 | 1.00 | 40.57 |
| 19623 | OW0 | HOH | W | 793 | -32.051 | -50.026 | 3.277 | 1.00 | 40.84 |
| 19626 | OW0 | HOH | W | 794 | -61.101 | -37.685 | -19.278 | 1.00 | 33.57 |
| 19629 | OW0 | HOH | W | 795 | -35.870 | 4.997 | -2.357 | 1.00 | 34.64 |
| 19632 | OW0 | HOH | W | 796 | -48.401 | -42.176 | 29.325 | 1.00 | 33.75 |
| 19635 | OW0 | HOH | W | 797 | -47.950 | -22.167 | 9.426 | 1.00 | 43.02 |
| 19638 | OW0 | HOH | W | 798 | -9.631 | 12.051 | 17.952 | 1.00 | 44.53 |
| 19641 | OW0 | HOH | W | 799 | -17.675 | -15.179 | 20.745 | 1.00 | 33.06 |
| 19644 | OW0 | HOH | W | 800 | -43.305 | -46.921 | 22.593 | 1.00 | 39.81 |
| 19647 | OW0 | HOH | W | 801 | -20.782 | 8.437 | -9.449 | 1.00 | 42.40 |
| 19650 | OW0 | HOH | W | 802 | -57.684 | -31.986 | -30.064 | 1.00 | 33.96 |
| 19653 | OW0 | HOH | W | 804 | -26.942 | -23.675 | -10.310 | 1.00 | 58.56 |
| 19656 | OW0 | HOH | W | 805 | -14.169 | -12.275 | -14.305 | 1.00 | 37.78 |
| 19659 | OW0 | HOH | W | 806 | 4.512 | -10.629 | 11.073 | 1.00 | 62.46 |
| 19662 | OW0 | HOH | W | 807 | -55.536 | -53.490 | 10.686 | 1.00 | 34.19 |
| 19665 | OW0 | HOH | W | 808 | -29.716 | -7.934 | -21.962 | 1.00 | 46.49 |
| 19668 | OW0 | HOH | W | 809 | -68.867 | -30.200 | 10.493 | 1.00 | 35.43 |
| 19671 | OW0 | HOH | W | 810 | -37.859 | -2.833 | 1.358 | 1.00 | 30.01 |

FIGURE 3 (cont.)

| A | B | C | D | E | F | G | H | I | J |
|---|---|---|---|---|---|---|---|---|---|
| 19674 | OW0 | HOH | W | 811 | -5.658 | 17.637 | 10.271 | 1.00 | 37.75 |
| 19677 | OW0 | HOH | W | 812 | -35.655 | -4.316 | -14.578 | 1.00 | 45.68 |
| 19680 | OW0 | HOH | W | 813 | -48.672 | -10.144 | -11.962 | 1.00 | 41.34 |
| 19683 | OW0 | HOH | W | 815 | -66.302 | -28.821 | -22.538 | 1.00 | 32.85 |
| 19686 | OW0 | HOH | W | 817 | -19.660 | 11.882 | 21.576 | 1.00 | 42.70 |
| 19689 | OW0 | HOH | W | 818 | -35.500 | -25.126 | -0.426 | 1.00 | 40.31 |
| 19692 | OW0 | HOH | W | 819 | -40.612 | -34.307 | -39.693 | 1.00 | 43.85 |
| 19695 | OW0 | HOH | W | 820 | 18.240 | -6.505 | 37.034 | 1.00 | 35.11 |
| 19698 | OW0 | HOH | W | 821 | -45.574 | -24.089 | 13.762 | 1.00 | 45.88 |
| 19701 | OW0 | HOH | W | 822 | 2.636 | -18.229 | 7.809 | 1.00 | 37.80 |
| 19704 | OW0 | HOH | W | 823 | -39.559 | -36.000 | -33.339 | 1.00 | 42.54 |
| 19707 | OW0 | HOH | W | 824 | -42.762 | -50.816 | 4.232 | 1.00 | 40.10 |
| 19710 | OW0 | HOH | W | 825 | -59.622 | -22.613 | 22.458 | 1.00 | 40.70 |
| 19713 | OW0 | HOH | W | 826 | -3.359 | 18.940 | 5.502 | 1.00 | 35.51 |
| 19716 | OW0 | HOH | W | 827 | -13.151 | -12.145 | 31.220 | 1.00 | 46.20 |
| 19719 | OW0 | HOH | W | 828 | 16.141 | 5.856 | 42.112 | 1.00 | 39.02 |
| 19722 | OW0 | HOH | W | 829 | 18.163 | -12.576 | 36.994 | 1.00 | 39.33 |
| 19725 | OW0 | HOH | W | 830 | -57.292 | -54.828 | 6.687 | 1.00 | 36.64 |
| 19728 | OW0 | HOH | W | 832 | -5.079 | -16.834 | 17.316 | 1.00 | 36.66 |
| 19731 | OW0 | HOH | W | 833 | -10.725 | -13.524 | 41.783 | 1.00 | 41.27 |
| 19734 | OW0 | HOH | W | 834 | -82.850 | -43.281 | -3.974 | 1.00 | 68.81 |
| 19737 | OW0 | HOH | W | 835 | 17.484 | -2.357 | 30.637 | 1.00 | 40.45 |
| 19740 | OW0 | HOH | W | 836 | -35.868 | -45.327 | 5.468 | 1.00 | 38.20 |
| 19743 | OW0 | HOH | W | 837 | 4.009 | -15.974 | 8.040 | 1.00 | 39.43 |
| 19746 | OW0 | HOH | W | 838 | -39.838 | -47.566 | 9.290 | 1.00 | 35.40 |
| 19749 | OW0 | HOH | W | 839 | -27.605 | -30.355 | -18.042 | 1.00 | 33.99 |
| 19752 | OW0 | HOH | W | 840 | -28.935 | -24.491 | -16.081 | 1.00 | 45.79 |
| 19755 | OW0 | HOH | W | 841 | -64.004 | -22.823 | 17.751 | 1.00 | 44.21 |
| 19758 | OW0 | HOH | W | 842 | -47.187 | -48.498 | 20.354 | 1.00 | 40.78 |
| 19761 | OW0 | HOH | W | 843 | 5.285 | 16.794 | 28.520 | 1.00 | 37.70 |
| 19764 | OW0 | HOH | W | 844 | 6.390 | -0.377 | -6.559 | 1.00 | 45.09 |
| 19767 | OW0 | HOH | W | 846 | 0.384 | 18.462 | 29.518 | 1.00 | 46.71 |
| 19770 | OW0 | HOH | W | 847 | -41.002 | -24.170 | -38.432 | 1.00 | 37.53 |
| 19773 | OW0 | HOH | W | 848 | -2.900 | -15.615 | -5.945 | 1.00 | 36.12 |
| 19776 | OW0 | HOH | W | 849 | -37.122 | -47.509 | 5.891 | 1.00 | 44.64 |
| 19779 | OW0 | HOH | W | 850 | -27.338 | -38.389 | -19.373 | 1.00 | 37.10 |
| 19782 | OW0 | HOH | W | 854 | -4.183 | -16.105 | 19.886 | 1.00 | 38.61 |
| 19785 | OW0 | HOH | W | 855 | -51.682 | -22.616 | 29.880 | 1.00 | 41.30 |
| 19788 | OW0 | HOH | W | 856 | -37.460 | -31.614 | 14.578 | 1.00 | 59.71 |
| 19791 | OW0 | HOH | W | 857 | -49.160 | -25.909 | -40.459 | 1.00 | 41.14 |
| 19794 | OW0 | HOH | W | 858 | 0.016 | 7.033 | -0.046 | 1.00 | 36.24 |
| 19797 | OW0 | HOH | W | 859 | -59.126 | -11.753 | -11.012 | 1.00 | 36.47 |
| 19800 | OW0 | HOH | W | 860 | -34.286 | 1.299 | 20.047 | 1.00 | 40.57 |
| 19803 | OW0 | HOH | W | 861 | 13.242 | -7.593 | 10.337 | 1.00 | 71.27 |
| 19806 | OW0 | HOH | W | 863 | 14.746 | -9.638 | 25.820 | 1.00 | 40.18 |
| 19809 | OW0 | HOH | W | 864 | -4.571 | -19.731 | 20.575 | 1.00 | 51.81 |
| 19812 | OW0 | HOH | W | 865 | 1.644 | -6.935 | 17.186 | 1.00 | 37.29 |
| 19815 | OW0 | HOH | W | 866 | -66.287 | -26.968 | -7.564 | 1.00 | 44.38 |
| 19818 | OW0 | HOH | W | 867 | 16.948 | 3.018 | 35.159 | 1.00 | 47.77 |

FIGURE 3 (cont.)

| A | B | C | D | E | F | G | H | I | J |
|---|---|---|---|---|---:|---:|---:|---:|---:|
| 19821 | OW0 | HOH | W | 868 | -11.024 | -10.624 | 15.182 | 1.00 | 35.33 |
| 19824 | OW0 | HOH | W | 869 | 7.088 | 4.193 | -0.030 | 1.00 | 51.08 |
| 19827 | OW0 | HOH | W | 870 | -7.434 | -21.688 | 3.656 | 1.00 | 41.59 |
| 19830 | OW0 | HOH | W | 873 | -46.613 | -22.921 | 11.534 | 1.00 | 33.34 |
| 19833 | OW0 | HOH | W | 876 | -2.361 | 11.976 | 39.041 | 1.00 | 36.22 |
| 19836 | OW0 | HOH | W | 878 | -51.068 | -15.457 | 15.052 | 1.00 | 39.60 |
| 19839 | OW0 | HOH | W | 879 | -54.972 | -55.010 | -6.490 | 1.00 | 30.59 |
| 19842 | OW0 | HOH | W | 880 | 3.628 | -9.273 | 9.225 | 1.00 | 40.80 |
| 19845 | OW0 | HOH | W | 882 | -38.610 | -17.831 | 0.472 | 1.00 | 40.04 |
| 19848 | OW0 | HOH | W | 883 | -68.133 | -22.820 | -5.238 | 1.00 | 36.26 |
| 19851 | OW0 | HOH | W | 885 | -35.149 | -45.201 | 3.093 | 1.00 | 43.85 |
| 19854 | OW0 | HOH | W | 886 | -30.943 | -19.307 | -10.012 | 1.00 | 37.86 |
| 19857 | OW0 | HOH | W | 887 | -10.796 | 13.045 | 1.516 | 1.00 | 43.43 |
| 19860 | OW0 | HOH | W | 888 | -69.426 | -50.123 | -13.195 | 1.00 | 51.67 |
| 19863 | OW0 | HOH | W | 889 | -34.703 | -36.016 | -28.224 | 1.00 | 40.05 |
| 19866 | OW0 | HOH | W | 890 | -37.421 | -39.936 | 27.372 | 1.00 | 67.80 |
| 19869 | OW0 | HOH | W | 891 | 1.869 | -6.985 | 49.016 | 1.00 | 34.65 |
| 19872 | OW0 | HOH | W | 892 | -40.199 | -9.857 | -26.501 | 1.00 | 40.03 |
| 19875 | OW0 | HOH | W | 893 | -16.714 | 1.738 | 42.998 | 1.00 | 40.48 |
| 19878 | OW0 | HOH | W | 895 | -36.394 | -37.186 | 23.137 | 1.00 | 42.92 |
| 19881 | OW0 | HOH | W | 896 | -65.078 | -27.604 | -16.027 | 1.00 | 34.82 |
| 19884 | OW0 | HOH | W | 897 | 2.317 | 3.405 | 0.582 | 1.00 | 41.64 |
| 19887 | OW0 | HOH | W | 898 | -52.345 | -24.555 | 1.090 | 1.00 | 73.50 |
| 19890 | OW0 | HOH | W | 899 | -64.444 | -28.268 | -5.710 | 1.00 | 43.44 |
| 19893 | OW0 | HOH | W | 900 | -5.096 | 10.816 | 37.919 | 1.00 | 39.66 |
| 19896 | OW0 | HOH | W | 901 | -8.372 | -13.870 | 50.589 | 1.00 | 52.33 |
| 19899 | OW0 | HOH | W | 903 | -74.053 | -34.203 | 8.585 | 1.00 | 51.28 |
| 19902 | OW0 | HOH | W | 906 | 0.042 | 4.179 | -1.874 | 1.00 | 46.75 |
| 19905 | OW0 | HOH | W | 907 | 17.933 | 6.336 | 2.929 | 1.00 | 38.77 |
| 19908 | OW0 | HOH | W | 908 | -41.448 | -49.817 | -22.321 | 1.00 | 47.58 |
| 19911 | OW0 | HOH | W | 909 | -31.552 | -25.040 | -9.299 | 1.00 | 34.16 |
| 19914 | OW0 | HOH | W | 910 | -59.315 | -53.265 | 9.414 | 1.00 | 41.55 |
| 19917 | OW0 | HOH | W | 911 | -70.283 | -32.756 | 4.028 | 1.00 | 31.41 |
| 19920 | OW0 | HOH | W | 912 | -34.961 | -24.335 | -10.428 | 1.00 | 33.51 |
| 19923 | OW0 | HOH | W | 913 | -33.234 | -9.985 | -27.561 | 1.00 | 55.18 |
| 19926 | OW0 | HOH | W | 914 | -37.711 | 6.063 | 0.088 | 1.00 | 46.08 |
| 19929 | OW0 | HOH | W | 915 | -69.174 | -42.189 | -6.029 | 1.00 | 46.43 |
| 19932 | OW0 | HOH | W | 916 | 12.084 | 17.747 | 13.015 | 1.00 | 41.31 |
| 19935 | OW0 | HOH | W | 917 | -41.426 | -31.339 | 25.608 | 1.00 | 41.89 |
| 19938 | OW0 | HOH | W | 918 | -38.872 | -43.866 | -22.854 | 1.00 | 39.36 |
| 19941 | OW0 | HOH | W | 919 | -9.967 | -12.524 | 46.380 | 1.00 | 47.84 |
| 19944 | OW0 | HOH | W | 920 | -30.654 | -43.148 | -20.731 | 1.00 | 44.73 |
| 19947 | OW0 | HOH | W | 921 | -57.529 | -50.581 | 29.387 | 1.00 | 40.94 |
| 19950 | OW0 | HOH | W | 922 | -68.348 | -51.800 | -8.628 | 1.00 | 33.32 |
| 19953 | OW0 | HOH | W | 924 | -5.598 | 2.467 | 45.208 | 1.00 | 60.61 |
| 19956 | OW0 | HOH | W | 925 | -33.318 | -47.199 | 5.987 | 1.00 | 54.17 |
| 19959 | OW0 | HOH | W | 926 | -39.923 | -9.539 | -4.203 | 1.00 | 42.98 |
| 19962 | OW0 | HOH | W | 927 | -16.440 | -10.663 | 33.647 | 1.00 | 37.94 |
| 19965 | OW0 | HOH | W | 928 | -35.639 | 10.921 | 6.734 | 1.00 | 38.25 |

FIGURE 3 (cont.)

| A | B | C | D | E | F | G | H | I | J |
|---|---|---|---|---|---|---|---|---|---|
| 19968 | OW0 | HOH | W | 929 | -55.719 | -22.820 | -33.886 | 1.00 | 44.58 |
| 19971 | OW0 | HOH | W | 930 | -25.078 | 9.378 | 34.902 | 1.00 | 46.02 |
| 19974 | OW0 | HOH | W | 931 | 17.449 | 8.156 | 27.075 | 1.00 | 36.23 |
| 19977 | OW0 | HOH | W | 932 | -29.463 | -0.322 | -16.097 | 1.00 | 46.29 |
| 19980 | OW0 | HOH | W | 933 | -66.282 | -45.104 | -8.326 | 1.00 | 35.61 |
| 19983 | OW0 | HOH | W | 934 | 14.022 | -7.932 | 19.302 | 1.00 | 42.82 |
| 19986 | OW0 | HOH | W | 935 | -14.742 | -1.872 | -10.466 | 1.00 | 39.42 |
| 19989 | OW0 | HOH | W | 937 | -40.118 | -12.307 | -7.157 | 1.00 | 40.24 |
| 19992 | OW0 | HOH | W | 938 | 3.747 | -18.269 | 27.316 | 1.00 | 36.90 |
| 19995 | OW0 | HOH | W | 940 | -40.173 | -7.196 | -10.553 | 1.00 | 70.95 |
| 19998 | OW0 | HOH | W | 941 | -34.965 | -26.627 | -36.508 | 1.00 | 36.90 |
| 20001 | OW0 | HOH | W | 942 | -69.541 | -37.196 | 33.046 | 1.00 | 41.43 |
| 20004 | OW0 | HOH | W | 943 | -64.583 | -18.064 | -19.899 | 1.00 | 41.08 |
| 20007 | OW0 | HOH | W | 944 | -34.848 | -28.690 | 8.183 | 1.00 | 72.86 |
| 20010 | OW0 | HOH | W | 945 | -62.341 | -24.467 | 28.579 | 1.00 | 46.99 |
| 20013 | OW0 | HOH | W | 946 | -38.484 | -7.648 | 4.600 | 1.00 | 54.11 |
| 20016 | OW0 | HOH | W | 947 | 19.087 | -5.770 | 39.595 | 1.00 | 35.81 |
| 20019 | OW0 | HOH | W | 948 | -63.132 | -19.501 | 10.206 | 1.00 | 38.27 |
| 20022 | OW0 | HOH | W | 949 | -49.477 | -53.505 | 1.187 | 1.00 | 40.75 |
| 20025 | OW0 | HOH | W | 950 | -17.808 | 4.759 | 17.118 | 1.00 | 35.60 |
| 20028 | OW0 | HOH | W | 952 | -8.030 | -21.650 | 35.429 | 1.00 | 52.22 |
| 20031 | OW0 | HOH | W | 953 | -39.167 | -16.387 | -3.125 | 1.00 | 45.03 |
| 20034 | OW0 | HOH | W | 954 | -38.987 | 1.727 | 20.771 | 1.00 | 38.95 |
| 20037 | OW0 | HOH | W | 955 | -6.387 | 14.246 | 21.047 | 1.00 | 34.68 |
| 20040 | OW0 | HOH | W | 956 | -33.396 | 8.751 | -3.654 | 1.00 | 42.65 |
| 20043 | OW0 | HOH | W | 957 | -24.428 | 11.316 | 0.325 | 1.00 | 31.05 |
| 20046 | OW0 | HOH | W | 958 | -7.130 | -1.308 | -15.391 | 1.00 | 52.64 |
| 20049 | OW0 | HOH | W | 959 | -64.600 | -23.243 | 6.931 | 1.00 | 50.93 |
| 20052 | OW0 | HOH | W | 960 | -32.257 | 16.537 | 14.398 | 1.00 | 70.89 |
| 20055 | OW0 | HOH | W | 961 | 10.768 | 2.090 | 49.006 | 1.00 | 49.36 |
| 20058 | OW0 | HOH | W | 962 | -41.930 | -24.941 | 15.108 | 1.00 | 42.31 |
| 20061 | OW0 | HOH | W | 963 | -46.459 | -9.495 | -13.435 | 1.00 | 42.60 |
| 20064 | OW0 | HOH | W | 964 | 4.118 | -19.248 | 32.272 | 1.00 | 30.84 |
| 20067 | OW0 | HOH | W | 965 | -64.627 | -54.933 | 8.563 | 1.00 | 48.19 |
| 20070 | OW0 | HOH | W | 966 | -31.060 | 11.642 | 0.870 | 1.00 | 54.05 |
| 20073 | OW0 | HOH | W | 967 | -52.073 | -34.644 | -31.083 | 1.00 | 40.92 |
| 20076 | OW0 | HOH | W | 968 | -26.505 | -21.583 | -5.243 | 1.00 | 38.89 |
| 20079 | OW0 | HOH | W | 969 | -36.071 | -7.193 | 8.555 | 1.00 | 36.11 |
| 20082 | OW0 | HOH | W | 970 | -33.308 | -5.852 | 14.029 | 1.00 | 37.98 |
| 20085 | OW0 | HOH | W | 971 | -45.182 | -19.371 | -1.636 | 1.00 | 43.54 |
| 20088 | OW0 | HOH | W | 972 | -6.399 | 14.162 | 0.218 | 1.00 | 36.96 |
| 20091 | OW0 | HOH | W | 973 | -64.505 | -21.347 | 13.135 | 1.00 | 36.45 |
| 20094 | OW0 | HOH | W | 974 | -3.345 | -17.470 | 36.267 | 1.00 | 36.91 |
| 20097 | OW0 | HOH | W | 975 | -52.237 | -26.680 | -35.964 | 1.00 | 42.41 |
| 20100 | OW0 | HOH | W | 976 | -73.620 | -36.656 | 14.116 | 1.00 | 39.66 |
| 20103 | OW0 | HOH | W | 977 | 12.320 | -8.497 | 17.174 | 1.00 | 39.02 |
| 20106 | OW0 | HOH | W | 978 | -48.653 | -46.657 | 19.852 | 1.00 | 43.50 |
| 20109 | OW0 | HOH | W | 979 | -27.920 | -23.231 | 6.185 | 1.00 | 48.95 |
| 20112 | OW0 | HOH | W | 980 | -17.047 | -22.472 | -13.450 | 1.00 | 39.84 |

FIGURE 3 (cont.)

| A | B | C | D | E | F | G | H | I | J |
|---|---|---|---|---|---:|---:|---:|---:|---:|
| 20115 | OW0 | HOH | W | 982 | -8.008 | 1.600 | 45.804 | 1.00 | 43.09 |
| 20118 | OW0 | HOH | W | 983 | -35.197 | -46.740 | -20.576 | 1.00 | 38.94 |
| 20121 | OW0 | HOH | W | 987 | 17.699 | -10.934 | 29.750 | 1.00 | 38.39 |
| 20124 | OW0 | HOH | W | 988 | -14.404 | 6.071 | 40.012 | 1.00 | 44.29 |
| 20127 | OW0 | HOH | W | 989 | -73.890 | -41.371 | -10.051 | 1.00 | 58.50 |
| 20130 | OW0 | HOH | W | 990 | -0.814 | 21.930 | 8.967 | 1.00 | 36.20 |
| 20133 | OW0 | HOH | W | 991 | -33.349 | -6.552 | -18.034 | 1.00 | 38.88 |
| 20136 | OW0 | HOH | W | 993 | 9.809 | 13.396 | 36.339 | 1.00 | 42.08 |
| 20139 | OW0 | HOH | W | 994 | -59.738 | -59.995 | 31.673 | 1.00 | 65.76 |
| 20142 | OW0 | HOH | W | 995 | -14.680 | -4.460 | -13.662 | 1.00 | 56.29 |
| 20145 | OW0 | HOH | W | 996 | -42.253 | -48.661 | 15.351 | 1.00 | 32.85 |
| 20148 | OW0 | HOH | W | 997 | -49.843 | -43.751 | -26.738 | 1.00 | 52.96 |
| 20151 | OW0 | HOH | W | 998 | -76.909 | -34.239 | 11.799 | 1.00 | 71.95 |
| 20154 | OW0 | HOH | W | 999 | -68.992 | -24.468 | 12.625 | 1.00 | 50.36 |
| 20157 | OW0 | HOH | W1000 | | -56.372 | -12.440 | -15.144 | 1.00 | 41.24 |
| 20160 | OW0 | HOH | W1001 | | -12.311 | 2.465 | 48.515 | 1.00 | 62.66 |
| 20163 | OW0 | HOH | W1003 | | -21.100 | 11.371 | 23.636 | 1.00 | 42.05 |
| 20166 | OW0 | HOH | W1004 | | -71.877 | -36.106 | 21.471 | 1.00 | 45.79 |
| 20169 | OW0 | HOH | W1005 | | -28.931 | -16.667 | -19.543 | 1.00 | 60.88 |
| 20172 | OW0 | HOH | W1007 | | -41.789 | -28.361 | 18.044 | 1.00 | 40.43 |
| 20175 | OW0 | HOH | W1008 | | -55.757 | -27.022 | -32.832 | 1.00 | 43.19 |
| 20178 | OW0 | HOH | W1009 | | 4.734 | 3.262 | 1.002 | 1.00 | 36.59 |
| 20181 | OW0 | HOH | W1010 | | 16.356 | -16.668 | 36.026 | 1.00 | 34.31 |
| 20184 | OW0 | HOH | W1011 | | 2.797 | 17.917 | 19.785 | 1.00 | 39.05 |
| 20187 | OW0 | HOH | W1012 | | -58.303 | -22.552 | -30.309 | 1.00 | 40.43 |
| 20190 | OW0 | HOH | W1013 | | -71.948 | -42.116 | 19.372 | 1.00 | 41.05 |
| 20193 | OW0 | HOH | W1014 | | -60.568 | -40.290 | -19.285 | 1.00 | 43.98 |
| 20196 | OW0 | HOH | W1015 | | -57.931 | -56.708 | 5.290 | 1.00 | 42.97 |
| 20199 | OW0 | HOH | W1018 | | -18.403 | 4.084 | 38.629 | 1.00 | 42.32 |
| 20202 | OW0 | HOH | W1019 | | -7.110 | 19.249 | 4.983 | 1.00 | 35.74 |
| 20205 | OW0 | HOH | W1020 | | 4.929 | -12.004 | 13.264 | 1.00 | 38.23 |
| 20208 | OW0 | HOH | W1021 | | -30.597 | -27.789 | -32.345 | 1.00 | 45.36 |
| 20211 | OW0 | HOH | W1022 | | -10.230 | -14.044 | 37.786 | 1.00 | 48.03 |
| 20214 | OW0 | HOH | W1023 | | -31.665 | -7.291 | 12.543 | 1.00 | 40.60 |
| 20217 | OW0 | HOH | W1024 | | -36.817 | -45.781 | 1.341 | 1.00 | 38.68 |
| 20220 | OW0 | HOH | W1026 | | -40.485 | -43.095 | 27.340 | 1.00 | 46.74 |
| 20223 | OW0 | HOH | W1028 | | -1.383 | -2.223 | -10.825 | 1.00 | 69.68 |
| 20226 | OW0 | HOH | W1029 | | -29.143 | -2.800 | 15.173 | 1.00 | 46.39 |
| 20229 | OW0 | HOH | W1031 | | -38.320 | -41.713 | 20.469 | 1.00 | 46.17 |
| 20232 | OW0 | HOH | W1032 | | -50.209 | -55.615 | 13.019 | 1.00 | 55.75 |
| 20235 | OW0 | HOH | W1033 | | -20.663 | -33.177 | -3.663 | 1.00 | 44.36 |
| 20238 | OW0 | HOH | W1035 | | -11.639 | -16.832 | 25.766 | 1.00 | 44.01 |
| 20241 | OW0 | HOH | W1036 | | -56.651 | -22.166 | 22.432 | 1.00 | 41.00 |
| 20244 | OW0 | HOH | W1037 | | -48.873 | -9.925 | -9.447 | 1.00 | 43.22 |
| 20247 | OW0 | HOH | W1042 | | 2.952 | -9.710 | 6.976 | 1.00 | 43.32 |
| 20250 | OW0 | HOH | W1045 | | -38.501 | -49.638 | 13.160 | 1.00 | 45.32 |
| 20253 | OW0 | HOH | W1046 | | -70.746 | -34.091 | 20.360 | 1.00 | 40.13 |
| 20256 | OW0 | HOH | W1047 | | -61.836 | -19.757 | -8.305 | 1.00 | 43.54 |
| 20259 | OW0 | HOH | W1048 | | -7.818 | -5.601 | 46.908 | 1.00 | 46.26 |

FIGURE 3 (cont.)

| A | B | C | D E | F | G | H | I | J |
|---|---|---|---|---|---|---|---|---|
| 20262 | OW0 | HOH | W1049 | -29.710 | -7.018 | 13.925 | 1.00 | 33.51 |
| 20265 | OW0 | HOH | W1050 | -2.726 | 13.600 | 41.159 | 1.00 | 45.38 |
| 20268 | OW0 | HOH | W1051 | -57.424 | -38.776 | -7.294 | 1.00 | 75.52 |
| 20271 | OW0 | HOH | W1052 | -41.023 | -13.901 | -4.550 | 1.00 | 39.16 |
| 20274 | OW0 | HOH | W1053 | -56.807 | -17.727 | -7.304 | 1.00 | 39.68 |
| 20277 | OW0 | HOH | W1054 | -80.001 | -43.121 | -10.681 | 1.00 | 52.38 |
| 20280 | OW0 | HOH | W1057 | 15.423 | 9.831 | 27.145 | 1.00 | 42.46 |
| 20283 | OW0 | HOH | W1058 | -57.777 | -22.043 | 5.427 | 1.00 | 36.01 |
| 20286 | OW0 | HOH | W1059 | 14.639 | -19.923 | 34.915 | 1.00 | 43.98 |
| 20289 | OW0 | HOH | W1060 | -70.489 | -50.054 | -9.096 | 1.00 | 60.78 |
| 20292 | OW0 | HOH | W1062 | -1.673 | -18.586 | -0.450 | 1.00 | 39.97 |
| 20295 | OW0 | HOH | W1063 | -28.617 | -6.872 | 19.681 | 1.00 | 38.22 |
| 20298 | OW0 | HOH | W1064 | -3.728 | 7.260 | -3.229 | 1.00 | 49.98 |
| 20301 | OW0 | HOH | W1065 | -16.890 | -15.736 | 18.418 | 1.00 | 47.11 |
| 20304 | OW0 | HOH | W1066 | 12.762 | 8.853 | 6.615 | 1.00 | 54.85 |
| 20307 | OW0 | HOH | W1067 | -18.810 | -7.861 | -18.727 | 1.00 | 48.56 |
| 20310 | OW0 | HOH | W1068 | -48.577 | -11.610 | -15.975 | 1.00 | 44.79 |
| 20313 | OW0 | HOH | W1069 | -29.664 | -14.893 | -27.824 | 1.00 | 40.76 |
| 20316 | OW0 | HOH | W1070 | -64.771 | -20.042 | -23.937 | 1.00 | 49.48 |
| 20319 | OW0 | HOH | W1071 | -30.494 | -55.455 | -16.807 | 1.00 | 46.76 |
| 20322 | OW0 | HOH | W1072 | -50.987 | -32.240 | -30.796 | 1.00 | 42.72 |
| 20325 | OW0 | HOH | W1073 | -43.511 | -48.803 | 3.062 | 1.00 | 53.01 |
| 20328 | OW0 | HOH | W1075 | -50.671 | -55.168 | -8.447 | 1.00 | 35.64 |
| 20331 | OW0 | HOH | W1076 | -72.402 | -39.789 | 20.321 | 1.00 | 53.33 |
| 20334 | OW0 | HOH | W1078 | -38.246 | 7.951 | 23.844 | 1.00 | 37.64 |
| 20337 | OW0 | HOH | W1079 | -40.096 | -38.367 | -32.751 | 1.00 | 42.40 |
| 20340 | OW0 | HOH | W1081 | -34.771 | -37.138 | 20.454 | 1.00 | 46.16 |
| 20343 | OW0 | HOH | W1082 | -7.513 | -9.275 | 49.910 | 1.00 | 44.31 |
| 20346 | OW0 | HOH | W1083 | -12.399 | -18.529 | -12.082 | 1.00 | 39.14 |
| 20349 | OW0 | HOH | W1084 | -44.256 | -25.571 | 24.245 | 1.00 | 42.11 |
| 20352 | OW0 | HOH | W1085 | -58.728 | -13.781 | -9.049 | 1.00 | 38.98 |
| 20355 | OW0 | HOH | W1087 | 6.362 | -15.612 | 19.655 | 1.00 | 38.93 |
| 20358 | OW0 | HOH | W1088 | -22.463 | 9.564 | -1.993 | 1.00 | 36.61 |
| 20361 | OW0 | HOH | W1089 | -14.766 | -7.538 | 41.232 | 1.00 | 40.29 |
| 20364 | OW0 | HOH | W1090 | -33.993 | -7.224 | -26.469 | 1.00 | 43.07 |
| 20367 | OW0 | HOH | W1091 | -52.630 | -21.935 | 0.867 | 1.00 | 71.53 |
| 20370 | OW0 | HOH | W1092 | -7.979 | -0.376 | 47.755 | 1.00 | 47.90 |
| 20373 | OW0 | HOH | W1093 | 0.535 | -20.168 | 20.581 | 1.00 | 41.49 |
| 20376 | OW0 | HOH | W1095 | -45.846 | -29.828 | 28.346 | 1.00 | 41.50 |
| 20379 | OW0 | HOH | W1096 | 18.939 | 3.791 | 21.696 | 1.00 | 44.84 |
| 20382 | OW0 | HOH | W1097 | -71.581 | -31.266 | -9.268 | 1.00 | 35.68 |
| 20385 | OW0 | HOH | W1098 | -41.976 | -24.803 | 12.426 | 1.00 | 49.38 |
| 20388 | OW0 | HOH | W1099 | -9.052 | -17.943 | 39.833 | 1.00 | 57.55 |
| 20391 | OW0 | HOH | W1100 | -29.991 | -6.798 | 17.428 | 1.00 | 54.44 |
| 20394 | OW0 | HOH | W1101 | 19.553 | -8.796 | 41.899 | 1.00 | 40.55 |
| 20397 | OW0 | HOH | W1102 | 16.202 | -0.069 | -3.821 | 1.00 | 50.72 |
| 20400 | OW0 | HOH | W1103 | -36.720 | -9.647 | -0.666 | 1.00 | 33.93 |
| 20403 | OW0 | HOH | W1104 | -57.895 | -57.479 | 17.618 | 1.00 | 43.20 |
| 20406 | OW0 | HOH | W1105 | -50.283 | -42.052 | 32.661 | 1.00 | 42.12 |

FIGURE 3 (cont.)

| A | B | C | D | E | F | G | H | I | J |
|---|---|---|---|---|---|---|---|---|---|
| 20409 | OW0 | | HOH | W1106 | -70.626 | -28.266 | 9.870 | 1.00 | 50.61 |
| 20412 | OW0 | | HOH | W1107 | -3.246 | -15.399 | -8.434 | 1.00 | 45.02 |
| 20415 | OW0 | | HOH | W1108 | -57.811 | -21.137 | 2.958 | 1.00 | 48.65 |
| 20418 | OW0 | | HOH | W1109 | -73.405 | -33.400 | -3.509 | 1.00 | 38.67 |
| 20421 | OW0 | | HOH | W1110 | -52.781 | -53.042 | 6.868 | 1.00 | 50.55 |
| 20424 | OW0 | | HOH | W1111 | -7.940 | -18.296 | 18.415 | 1.00 | 40.73 |
| 20427 | OW0 | | HOH | W1112 | -47.285 | -24.915 | 27.137 | 1.00 | 48.07 |
| 20430 | OW0 | | HOH | W1113 | 10.881 | -4.098 | 49.833 | 1.00 | 39.14 |
| 20433 | OW0 | | HOH | W1114 | -20.053 | 14.219 | -0.401 | 1.00 | 38.53 |
| 20436 | OW0 | | HOH | W1115 | -67.728 | -27.901 | 0.951 | 1.00 | 44.30 |
| 20439 | OW0 | | HOH | W1116 | -30.075 | -17.092 | 11.627 | 1.00 | 46.09 |
| 20442 | OW0 | | HOH | W1117 | -66.860 | -26.265 | 29.407 | 1.00 | 51.18 |
| 20445 | OW0 | | HOH | W1118 | -70.232 | -28.254 | 12.565 | 1.00 | 41.66 |
| 20448 | OW0 | | HOH | W1119 | -16.219 | -22.383 | 12.934 | 1.00 | 48.31 |
| 20451 | OW0 | | HOH | W1120 | 0.633 | -20.078 | 24.274 | 1.00 | 47.42 |
| 20454 | OW0 | | HOH | W1121 | -16.067 | -0.211 | -14.058 | 1.00 | 43.40 |
| 20457 | OW0 | | HOH | W1122 | -14.610 | -4.817 | -11.054 | 1.00 | 49.17 |
| 20460 | OW0 | | HOH | W1123 | -7.519 | -20.767 | 28.984 | 1.00 | 48.13 |
| 20463 | OW0 | | HOH | W1125 | 8.748 | -17.029 | 27.225 | 1.00 | 34.21 |
| 20466 | OW0 | | HOH | W1126 | -59.717 | -52.108 | 29.125 | 1.00 | 51.14 |
| 20469 | OW0 | | HOH | W1128 | 16.740 | 3.721 | 30.593 | 1.00 | 46.28 |
| 20472 | OW0 | | HOH | W1129 | -14.916 | -14.602 | 32.920 | 1.00 | 46.58 |
| 20475 | OW0 | | HOH | W1130 | 10.652 | 13.149 | 5.112 | 1.00 | 45.35 |
| 20478 | OW0 | | HOH | W1131 | 6.320 | 17.862 | 32.533 | 1.00 | 41.63 |
| 20481 | OW0 | | HOH | W1132 | -3.709 | 20.457 | 20.058 | 1.00 | 58.14 |
| 20484 | OW0 | | HOH | W1134 | -17.946 | -1.901 | 40.367 | 1.00 | 44.24 |
| 20487 | OW0 | | HOH | W1135 | -24.254 | -4.250 | 22.226 | 1.00 | 46.02 |
| 20490 | OW0 | | HOH | W1136 | -38.130 | -6.373 | 9.787 | 1.00 | 52.32 |
| 20493 | OW0 | | HOH | W1137 | 17.397 | 7.168 | 19.700 | 1.00 | 32.83 |
| 20496 | OW0 | | HOH | W1138 | -3.616 | -19.603 | 25.017 | 1.00 | 38.54 |
| 20499 | OW0 | | HOH | W1139 | -73.095 | -32.921 | 6.564 | 1.00 | 42.40 |
| 20502 | OW0 | | HOH | W1140 | -50.465 | -45.499 | -16.196 | 1.00 | 50.42 |
| 20505 | OW0 | | HOH | W1143 | -2.524 | 0.614 | 50.624 | 1.00 | 53.50 |
| 20508 | OW0 | | HOH | W1144 | 17.502 | -3.624 | 32.935 | 1.00 | 46.30 |
| 20511 | OW0 | | HOH | W1145 | -27.527 | -17.849 | -16.495 | 1.00 | 42.94 |
| 20514 | OW0 | | HOH | W1146 | -9.763 | 21.627 | 18.817 | 1.00 | 40.36 |
| 20517 | OW0 | | HOH | W1147 | -33.107 | -32.960 | 15.334 | 1.00 | 54.05 |
| 20520 | OW0 | | HOH | W1148 | -83.149 | -42.853 | -1.227 | 1.00 | 44.69 |
| 20523 | OW0 | | HOH | W1149 | -41.631 | -31.292 | -37.670 | 1.00 | 42.10 |
| 20526 | OW0 | | HOH | W1151 | -38.032 | -22.400 | 4.550 | 1.00 | 35.51 |
| 20529 | OW0 | | HOH | W1152 | 15.172 | -7.936 | 27.597 | 1.00 | 53.74 |
| 20532 | OW0 | | HOH | W1153 | -35.108 | -5.397 | 11.639 | 1.00 | 58.93 |
| 20535 | OW0 | | HOH | W1154 | 6.671 | 15.287 | 23.808 | 1.00 | 47.42 |
| 20538 | OW0 | | HOH | W1155 | -16.755 | -4.125 | -11.865 | 1.00 | 45.88 |
| 20541 | OW0 | | HOH | W1156 | -2.619 | 7.470 | 38.965 | 1.00 | 45.39 |
| 20544 | OW0 | | HOH | W1157 | -45.599 | -53.205 | -19.771 | 1.00 | 47.88 |
| 20547 | OW0 | | HOH | W1158 | -66.836 | -48.254 | 30.074 | 1.00 | 40.28 |
| 20550 | OW0 | | HOH | W1159 | -2.890 | -1.064 | -7.040 | 1.00 | 35.35 |
| 20553 | OW0 | | HOH | W1160 | 1.777 | 17.346 | 26.771 | 1.00 | 50.37 |

FIGURE 3 (cont.)

| A | B | C | D | E | F | G | H | I | J |
|---|---|---|---|---|---|---|---|---|---|
| 20556 | OW0 | HOH | | W1161 | -31.137 | -37.150 | -25.615 | 1.00 | 44.13 |
| 20559 | OW0 | HOH | | W1162 | -65.698 | -22.663 | -21.450 | 1.00 | 46.48 |
| 20562 | OW0 | HOH | | W1163 | -24.888 | 6.422 | 19.466 | 1.00 | 41.96 |
| 20565 | OW0 | HOH | | W1164 | -12.137 | -26.208 | 4.044 | 1.00 | 51.85 |
| 20568 | OW0 | HOH | | W1166 | -35.483 | -39.186 | -28.609 | 1.00 | 41.16 |
| 20571 | OW0 | HOH | | W1168 | -25.007 | -39.283 | -14.140 | 1.00 | 44.75 |
| 20574 | OW0 | HOH | | W1169 | -56.664 | -11.772 | -12.471 | 1.00 | 42.61 |
| 20577 | OW0 | HOH | | W1170 | -27.525 | 10.827 | -4.639 | 1.00 | 74.29 |
| 20580 | OW0 | HOH | | W1173 | -59.609 | -35.406 | -29.609 | 1.00 | 45.50 |
| 20583 | OW0 | HOH | | W1175 | -61.201 | -17.800 | -11.164 | 1.00 | 46.58 |
| 20586 | OW0 | HOH | | W1176 | 16.124 | -14.528 | 29.107 | 1.00 | 48.06 |
| 20589 | OW0 | HOH | | W1177 | -43.681 | -38.904 | 27.882 | 1.00 | 42.65 |
| 20592 | OW0 | HOH | | W1179 | -56.571 | -24.107 | -31.340 | 1.00 | 40.76 |
| 20595 | OW0 | HOH | | W1180 | -9.106 | -24.791 | 4.799 | 1.00 | 40.24 |
| 20598 | OW0 | HOH | | W1181 | -50.980 | -52.861 | 4.706 | 1.00 | 45.79 |
| 20601 | OW0 | HOH | | W1182 | -44.337 | -11.461 | -23.885 | 1.00 | 43.61 |
| 20604 | OW0 | HOH | | W1183 | -68.687 | -28.229 | -13.591 | 1.00 | 47.38 |
| 20607 | OW0 | HOH | | W1184 | -58.184 | -28.074 | -32.301 | 1.00 | 46.62 |
| 20610 | OW0 | HOH | | W1185 | -6.584 | 16.429 | 18.312 | 1.00 | 44.42 |
| 20613 | OW0 | HOH | | W1186 | -20.056 | -11.895 | -18.491 | 1.00 | 44.74 |
| 20616 | OW0 | HOH | | W1189 | -48.919 | -10.944 | -18.164 | 1.00 | 35.64 |
| 20619 | OW0 | HOH | | W1191 | -52.490 | -25.458 | -1.457 | 1.00 | 77.69 |
| 20622 | OW0 | HOH | | W1192 | -76.225 | -47.338 | -6.315 | 1.00 | 52.45 |
| 20625 | OW0 | HOH | | W1193 | -34.593 | -18.050 | -5.173 | 1.00 | 52.58 |
| 20628 | OW0 | HOH | | W1196 | -70.737 | -32.503 | 7.923 | 1.00 | 39.96 |
| 20631 | OW0 | HOH | | W1197 | -35.994 | -1.949 | -3.892 | 1.00 | 44.29 |
| 20634 | OW0 | HOH | | W1198 | -48.113 | -44.763 | 21.547 | 1.00 | 47.90 |
| 20637 | OW0 | HOH | | W1199 | 15.703 | 12.364 | 26.350 | 1.00 | 45.16 |
| 20640 | OW0 | HOH | | W1200 | -52.771 | -35.203 | -33.616 | 1.00 | 41.80 |
| 20643 | OW0 | HOH | | W1201 | -50.570 | -24.251 | -0.857 | 1.00 | 55.23 |
| 20646 | OW0 | HOH | | W1202 | -10.899 | -3.767 | -14.520 | 1.00 | 40.03 |
| 20649 | OW0 | HOH | | W1203 | -21.248 | -11.958 | 28.904 | 1.00 | 55.28 |
| 20652 | OW0 | HOH | | W1205 | -46.662 | -48.868 | 3.997 | 1.00 | 61.08 |
| 20655 | OW0 | HOH | | W1206 | 10.386 | -19.301 | 30.868 | 1.00 | 43.78 |
| 20658 | OW0 | HOH | | W1207 | -16.126 | -16.382 | 22.473 | 1.00 | 44.98 |
| 20661 | OW0 | HOH | | W1208 | -14.346 | -20.139 | -12.831 | 1.00 | 57.95 |
| 20664 | OW0 | HOH | | W1209 | -33.377 | -25.865 | -7.592 | 1.00 | 59.43 |
| 20667 | OW0 | HOH | | W1210 | -44.423 | -31.903 | 27.798 | 1.00 | 58.57 |
| 20670 | OW0 | HOH | | W1211 | 6.181 | -6.565 | 48.760 | 1.00 | 47.14 |
| 20673 | OW0 | HOH | | W1212 | -67.440 | -42.606 | -8.060 | 1.00 | 62.41 |
| 20676 | OW0 | HOH | | W1213 | -1.372 | -20.890 | 26.602 | 1.00 | 37.08 |
| 20679 | OW0 | HOH | | W1214 | 18.017 | 6.363 | 40.078 | 1.00 | 40.48 |
| 20682 | OW0 | HOH | | W1215 | -35.852 | -47.466 | 13.332 | 1.00 | 51.28 |
| 20685 | OW0 | HOH | | W1217 | -27.671 | 6.817 | -5.841 | 1.00 | 57.98 |
| 20688 | OW0 | HOH | | W1218 | -18.392 | 13.878 | 22.447 | 1.00 | 34.32 |
| 20691 | OW0 | HOH | | W1219 | 12.929 | -16.692 | 28.731 | 1.00 | 45.08 |
| 20694 | OW0 | HOH | | W1220 | -73.964 | -34.468 | 12.687 | 1.00 | 42.58 |
| 20697 | OW0 | HOH | | W1221 | -63.408 | -39.207 | 36.175 | 1.00 | 46.21 |
| 20700 | OW0 | HOH | | W1222 | -34.522 | -34.404 | 19.481 | 1.00 | 53.41 |

FIGURE 3 (cont.)

| A | B | C | D E | F | G | H | I | J |
|---|---|---|---|---|---|---|---|---|
| 20703 | OW0 | HOH | W1223 | -24.478 | -15.270 | 16.261 | 1.00 | 39.52 |
| 20706 | OW0 | HOH | W1224 | -25.645 | -24.875 | 6.360 | 1.00 | 41.55 |
| 20709 | OW0 | HOH | W1225 | -36.770 | -6.608 | -23.090 | 1.00 | 43.22 |
| 20712 | OW0 | HOH | W1226 | -31.401 | -24.001 | -0.369 | 1.00 | 43.93 |
| 20715 | OW0 | HOH | W1227 | -26.394 | -35.078 | -2.770 | 1.00 | 41.00 |
| 20718 | OW0 | HOH | W1228 | -2.737 | -18.176 | 19.705 | 1.00 | 59.88 |
| 20721 | OW0 | HOH | W1229 | -72.269 | -53.221 | -4.991 | 1.00 | 73.80 |
| 20724 | OW0 | HOH | W1230 | -3.407 | 2.823 | -4.500 | 1.00 | 36.84 |
| 20727 | OW0 | HOH | W1231 | -0.792 | -16.881 | 36.725 | 1.00 | 43.29 |
| 20730 | OW0 | HOH | W1232 | -59.010 | -27.779 | 28.351 | 1.00 | 45.57 |
| 20733 | OW0 | HOH | W1233 | -18.727 | 6.765 | -18.782 | 1.00 | 48.70 |
| 20736 | OW0 | HOH | W1234 | 19.698 | -3.670 | 17.499 | 1.00 | 46.16 |
| 20739 | OW0 | HOH | W1235 | -38.977 | -50.811 | 4.295 | 1.00 | 39.88 |
| 20742 | OW0 | HOH | W1236 | -37.800 | -47.003 | -20.180 | 1.00 | 41.60 |
| 20745 | OW0 | HOH | W1237 | -69.965 | -24.328 | -10.630 | 1.00 | 59.55 |
| 20748 | OW0 | HOH | W1238 | -49.493 | -50.918 | -16.821 | 1.00 | 45.36 |
| 20751 | OW0 | HOH | W1239 | 10.837 | -7.555 | 7.634 | 1.00 | 38.50 |
| 20754 | OW0 | HOH | W1240 | -54.758 | -19.770 | 18.974 | 1.00 | 43.35 |
| 20757 | OW0 | HOH | W1241 | -71.917 | -45.906 | 16.673 | 1.00 | 40.04 |
| 20760 | OW0 | HOH | W1243 | -72.760 | -33.044 | -10.916 | 1.00 | 50.33 |
| 20763 | OW0 | HOH | W1244 | -30.151 | 18.244 | 14.650 | 1.00 | 70.40 |
| 20766 | OW0 | HOH | W1245 | -53.030 | -17.328 | 12.346 | 1.00 | 43.39 |
| 20769 | OW0 | HOH | W1246 | 16.409 | 10.739 | 16.328 | 1.00 | 41.04 |
| 20772 | OW0 | HOH | W1247 | 8.809 | 2.812 | -2.186 | 1.00 | 57.81 |
| 20775 | OW0 | HOH | W1248 | -50.003 | -37.300 | 33.441 | 1.00 | 88.77 |
| 20778 | OW0 | HOH | W1249 | -17.791 | 12.935 | 12.675 | 1.00 | 87.04 |
| 20781 | OW0 | HOH | W1250 | -4.651 | 4.270 | 47.868 | 1.00 | 50.20 |
| 20784 | OW0 | HOH | W1251 | -58.966 | -18.968 | 15.509 | 1.00 | 38.27 |
| 20787 | OW0 | HOH | W1252 | -65.232 | -43.274 | -19.409 | 1.00 | 44.64 |
| 20790 | OW0 | HOH | W1253 | -66.456 | -51.699 | 18.200 | 1.00 | 39.06 |
| 20793 | OW0 | HOH | W1254 | -27.222 | -35.708 | -0.364 | 1.00 | 44.15 |
| 20796 | OW0 | HOH | W1255 | -71.173 | -55.007 | -6.670 | 1.00 | 43.68 |
| 20799 | OW0 | HOH | W1258 | -32.274 | -40.992 | -2.830 | 1.00 | 44.49 |
| 20802 | OW0 | HOH | W1259 | -75.537 | -48.480 | 4.539 | 1.00 | 44.66 |
| 20805 | OW0 | HOH | W1260 | -31.689 | -56.690 | -11.146 | 1.00 | 58.40 |
| 20808 | OW0 | HOH | W1261 | -15.793 | -17.323 | 14.629 | 1.00 | 37.74 |
| 20811 | OW0 | HOH | W1262 | 1.040 | -9.307 | -8.956 | 1.00 | 56.83 |
| 20814 | OW0 | HOH | W1263 | -30.199 | -22.245 | -9.833 | 1.00 | 43.87 |
| 20817 | OW0 | HOH | W1264 | 1.887 | -19.958 | 29.091 | 1.00 | 45.07 |
| 20820 | OW0 | HOH | W1266 | -25.175 | -32.149 | -2.485 | 1.00 | 57.62 |
| 20823 | OW0 | HOH | W1268 | -71.875 | -24.431 | -6.772 | 1.00 | 47.78 |
| 20826 | OW0 | HOH | W1269 | -54.416 | -31.197 | 33.637 | 1.00 | 49.62 |
| 20829 | OW0 | HOH | W1270 | -73.114 | -35.977 | -11.735 | 1.00 | 63.01 |
| 20832 | OW0 | HOH | W1271 | -48.732 | -17.912 | -2.637 | 1.00 | 38.14 |
| 20835 | OW0 | HOH | W1272 | 14.282 | -0.789 | 0.573 | 1.00 | 62.99 |
| 20838 | OW0 | HOH | W1273 | 18.336 | 9.548 | 21.168 | 1.00 | 34.07 |
| 20841 | OW0 | HOH | W1274 | -11.020 | 17.182 | 8.299 | 1.00 | 46.72 |
| 20844 | OW0 | HOH | W1275 | -56.308 | -32.583 | 34.647 | 1.00 | 55.39 |
| 20847 | OW0 | HOH | W1276 | -53.059 | -6.933 | -11.008 | 1.00 | 49.54 |

FIGURE 3 (cont.)

| A | B | C | D | E | F | G | H | I | J |
|---|---|---|---|---|---|---|---|---|---|
| 20850 | OW0 | HOH | W1277 | | -33.682 | 1.731 | -10.555 | 1.00 | 53.85 |
| 20853 | OW0 | HOH | W1278 | | -14.041 | -10.365 | -16.079 | 1.00 | 48.12 |
| 20856 | OW0 | HOH | W1279 | | -42.378 | -45.923 | -20.138 | 1.00 | 35.23 |
| 20859 | OW0 | HOH | W1280 | | 12.714 | -0.371 | 3.775 | 1.00 | 35.48 |
| 20862 | OW0 | HOH | W1281 | | 12.827 | -4.783 | -5.925 | 1.00 | 56.80 |
| 20865 | OW0 | HOH | W1282 | | 15.546 | -10.905 | 15.275 | 1.00 | 60.98 |
| 20868 | OW0 | HOH | W1284 | | -45.383 | -51.845 | -16.888 | 1.00 | 33.34 |
| 20871 | OW0 | HOH | W1285 | | -13.613 | -16.936 | 17.499 | 1.00 | 79.24 |
| 20874 | OW0 | HOH | W1287 | | 16.482 | -8.689 | 29.618 | 1.00 | 37.76 |
| 20877 | OW0 | HOH | W1291 | | -28.175 | -23.749 | -13.771 | 1.00 | 42.52 |
| 20880 | OW0 | HOH | W1293 | | -65.329 | -52.850 | 21.012 | 1.00 | 56.30 |
| 20883 | OW0 | HOH | W1294 | | -41.616 | -39.694 | 10.011 | 1.00 | 87.08 |
| 20886 | OW0 | HOH | W1295 | | 12.058 | 13.341 | 29.858 | 1.00 | 46.88 |
| 20889 | OW0 | HOH | W1297 | | -39.100 | 5.300 | 17.170 | 1.00 | 42.82 |
| 20892 | OW0 | HOH | W1298 | | 15.979 | -4.376 | 8.803 | 1.00 | 53.37 |
| 20895 | OW0 | HOH | W1299 | | -40.893 | -28.377 | 22.616 | 1.00 | 37.82 |
| 20898 | OW0 | HOH | W1301 | | -9.731 | -14.252 | 53.144 | 1.00 | 47.09 |
| 20901 | OW0 | HOH | W1302 | | -65.772 | -24.484 | -25.482 | 1.00 | 40.45 |
| 20904 | OW0 | HOH | W1303 | | -38.314 | -7.741 | -2.664 | 1.00 | 48.75 |
| 20907 | OW0 | HOH | W1304 | | -65.777 | -42.463 | -12.776 | 1.00 | 47.45 |
| 20910 | OW0 | HOH | W1305 | | -73.581 | -35.041 | -9.287 | 1.00 | 69.68 |
| 20913 | OW0 | HOH | W1307 | | -33.109 | -25.987 | -1.041 | 1.00 | 51.86 |
| 20916 | OW0 | HOH | W1308 | | 10.009 | 15.445 | 32.303 | 1.00 | 56.80 |
| 20919 | OW0 | HOH | W1309 | | 15.213 | 0.213 | 2.947 | 1.00 | 55.22 |
| 20922 | OW0 | HOH | W1310 | | -39.310 | -12.548 | 4.050 | 1.00 | 46.57 |
| 20925 | OW0 | HOH | W1311 | | -63.711 | -29.882 | 30.883 | 1.00 | 44.90 |
| 20928 | OW0 | HOH | W1312 | | -60.629 | -17.328 | -17.871 | 1.00 | 45.19 |
| 20931 | O | HOH | W1313 | | 18.096 | -17.288 | 32.008 | 1.00 | 43.08 |
| 20934 | O | HOH | W1314 | | -0.725 | -19.760 | 18.506 | 1.00 | 47.87 |
| 20937 | O | HOH | W1315 | | 2.784 | -17.968 | 17.062 | 1.00 | 41.58 |
| 20940 | O | HOH | W1316 | | 8.786 | -6.266 | 15.134 | 1.00 | 31.36 |
| 20943 | O | HOH | W1317 | | 13.948 | 12.635 | 19.907 | 1.00 | 38.11 |
| 20946 | O | HOH | W1318 | | -14.806 | 20.441 | 21.077 | 1.00 | 48.05 |
| 20949 | O | HOH | W1319 | | -16.523 | 8.583 | -3.527 | 1.00 | 43.38 |
| 20952 | O | HOH | W1320 | | -69.923 | -46.278 | -8.180 | 1.00 | 52.94 |
| 20955 | O | HOH | W1321 | | 3.341 | 18.468 | 32.535 | 1.00 | 38.33 |
| 20958 | O | HOH | W1322 | | -2.204 | 17.591 | 30.197 | 1.00 | 46.88 |
| 20961 | O | HOH | W1323 | | 8.952 | 15.133 | 34.661 | 1.00 | 54.33 |
| 20964 | O | HOH | W1324 | | -56.474 | -61.843 | 19.424 | 1.00 | 57.03 |
| 20967 | O | HOH | W1325 | | -57.814 | -56.179 | 13.495 | 1.00 | 42.32 |
| 20970 | O | HOH | W1326 | | -6.015 | -0.478 | -8.037 | 1.00 | 43.90 |
| 20973 | O | HOH | W1327 | | -6.284 | -1.023 | -9.908 | 1.00 | 35.26 |
| 20976 | O | HOH | W1328 | | -7.759 | 1.172 | -9.379 | 1.00 | 35.57 |
| 20979 | O | HOH | W1329 | | -41.769 | -43.019 | -27.379 | 1.00 | 38.35 |
| 20982 | O | HOH | W1330 | | -42.194 | -42.123 | -31.281 | 1.00 | 39.14 |
| 20985 | O | HOH | W1331 | | 14.488 | -2.677 | 24.360 | 1.00 | 5.98 |
| 20988 | O | HOH | W1332 | | -34.373 | -3.676 | 5.309 | 1.00 | 5.59 |
| 20991 | O | HOH | W1333 | | -30.223 | -27.633 | -17.087 | 1.00 | 8.68 |
| 20994 | O | HOH | W1334 | | -71.728 | -39.096 | 13.203 | 1.00 | 11.55 |

FIGURE 3 (cont.)

| A | B | C | D | E | F | G | H | I | J |
|---|---|---|---|---|---|---|---|---|---|
| 20997 | O | HOH | W1335 | | -30.338 | -43.697 | -8.950 | 1.00 | 24.11 |
| 21000 | O | HOH | W1336 | | -26.758 | -41.983 | -12.111 | 1.00 | 29.90 |
| 21003 | O | HOH | W1337 | | -31.181 | -43.613 | -12.256 | 1.00 | 28.94 |
| 21006 | O | HOH | W1338 | | 10.323 | 17.960 | 6.257 | 1.00 | 32.75 |
| 21009 | O | HOH | W1339 | | -25.949 | -43.186 | -9.766 | 1.00 | 38.58 |
| 21012 | O | HOH | W1340 | | -74.247 | -42.254 | -4.739 | 1.00 | 45.45 |
| 21015 | O | HOH | W1341 | | -74.625 | -45.718 | 0.029 | 1.00 | 42.82 |
| 21018 | O | HOH | W1342 | | -63.430 | -20.386 | -15.195 | 1.00 | 37.69 |
| 21021 | O | HOH | W1343 | | 18.424 | -2.159 | 21.765 | 1.00 | 40.03 |
| 21024 | O | HOH | W1344 | | -28.087 | -22.697 | -7.053 | 1.00 | 41.76 |
| 21027 | O | HOH | W1345 | | -25.654 | -39.647 | -8.858 | 1.00 | 42.51 |
| 21030 | O | HOH | W1346 | | -10.757 | 9.807 | 29.597 | 1.00 | 18.03 |
| 21033 | O | HOH | W1347 | | -78.865 | -44.013 | -1.225 | 1.00 | 43.61 |
| 21036 | O | HOH | W1348 | | -28.005 | -44.403 | -15.406 | 1.00 | 45.05 |
| 21039 | O | HOH | W1349 | | -28.996 | -21.253 | -13.131 | 1.00 | 38.28 |
| 21042 | O | HOH | W1350 | | -34.080 | -44.458 | -2.158 | 1.00 | 40.43 |
| 21045 | O | HOH | W1351 | | -30.270 | -20.427 | -22.355 | 1.00 | 40.60 |
| 21048 | O | HOH | W1352 | | -12.490 | -14.016 | 26.257 | 1.00 | 39.34 |
| 21051 | O | HOH | W1353 | | -72.331 | -28.725 | 26.203 | 1.00 | 39.11 |
| 21054 | O | HOH | W1354 | | 12.455 | -9.862 | -2.273 | 1.00 | 40.17 |
| 21057 | O | HOH | W1355 | | -56.399 | -37.983 | -34.218 | 1.00 | 41.06 |
| 21060 | O | HOH | W1356 | | -68.102 | -47.191 | -15.728 | 1.00 | 42.12 |
| 21063 | O | HOH | W1357 | | -18.064 | -25.313 | 7.485 | 1.00 | 42.37 |
| 21066 | O | HOH | W1358 | | -37.955 | -6.382 | -25.464 | 1.00 | 38.45 |
| 21069 | O | HOH | W1359 | | -22.184 | -20.389 | 14.547 | 1.00 | 42.79 |
| 21072 | O | HOH | W1360 | | -12.421 | -8.344 | 45.312 | 1.00 | 45.86 |
| 21075 | O | HOH | W1361 | | -86.637 | -44.414 | -1.657 | 1.00 | 42.32 |
| 21078 | O | HOH | W1362 | | -43.149 | -44.187 | 26.867 | 1.00 | 41.21 |
| 21081 | O | HOH | W1363 | | -68.844 | -54.135 | 8.237 | 1.00 | 42.37 |
| 21084 | O | HOH | W1364 | | -23.818 | -21.782 | -12.741 | 1.00 | 40.25 |
| 21087 | O | HOH | W1365 | | -30.594 | -37.373 | 11.717 | 1.00 | 40.44 |
| 21090 | O | HOH | W1366 | | 4.521 | -11.975 | -0.127 | 1.00 | 38.84 |
| 21093 | O | HOH | W1367 | | -59.011 | -30.143 | 34.591 | 1.00 | 42.68 |
| 21096 | O | HOH | W1368 | | -29.988 | -47.044 | -15.081 | 1.00 | 39.85 |
| 21099 | O | HOH | W1369 | | -48.928 | -50.163 | 22.069 | 1.00 | 39.86 |
| 21102 | O | HOH | W1370 | | -74.093 | -41.494 | 16.966 | 1.00 | 37.82 |
| 21105 | O | HOH | W1371 | | -15.795 | -0.031 | -16.596 | 1.00 | 39.99 |
| 21108 | O | HOH | W1372 | | -43.819 | -56.476 | -6.717 | 1.00 | 38.97 |
| 21111 | O | HOH | W1373 | | -58.181 | -8.340 | -20.846 | 1.00 | 42.09 |
| 21114 | O | HOH | W1374 | | -23.487 | 9.158 | -11.308 | 1.00 | 37.80 |
| 21117 | O | HOH | W1375 | | 0.801 | 9.979 | 45.346 | 1.00 | 39.07 |
| 21120 | O | HOH | W1376 | | 13.974 | 12.196 | 13.994 | 1.00 | 41.70 |
| 21123 | O | HOH | W1377 | | -38.422 | -40.042 | -31.486 | 1.00 | 44.56 |
| 21126 | O | HOH | W1378 | | -63.501 | -43.835 | -11.853 | 1.00 | 38.04 |
| 21129 | O | HOH | W1379 | | -51.965 | -9.062 | -6.971 | 1.00 | 40.87 |
| 21132 | O | HOH | W1380 | | -16.058 | 15.884 | 27.986 | 1.00 | 47.35 |
| 21135 | O | HOH | W1381 | | -21.824 | -24.781 | 4.373 | 1.00 | 40.47 |
| 21138 | O | HOH | W1382 | | -45.322 | -13.930 | -4.317 | 1.00 | 42.60 |
| 21141 | O | HOH | W1383 | | -25.331 | -41.526 | -17.322 | 1.00 | 47.10 |

FIGURE 3 (cont.)

| A | B | C | D | E | F | G | H | I | J |
|---|---|---|---|---|---|---|---|---|---|
| 21144 | O | HOH | W1384 | | -29.594 | -10.968 | 17.972 | 1.00 | 41.17 |
| 21147 | O | HOH | W1385 | | -50.710 | -48.871 | 28.892 | 1.00 | 42.81 |
| 21150 | O | HOH | W1386 | | -63.946 | -22.712 | 23.998 | 1.00 | 37.65 |
| 21153 | O | HOH | W1387 | | -69.553 | -53.959 | 0.118 | 1.00 | 41.90 |
| 21156 | O | HOH | W1388 | | -28.851 | -29.069 | -3.979 | 1.00 | 44.27 |
| 21159 | O | HOH | W1389 | | -48.182 | -22.178 | 23.313 | 1.00 | 41.63 |
| 21162 | O | HOH | W1390 | | -17.628 | 10.041 | -18.992 | 1.00 | 41.83 |
| 21165 | O | HOH | W1391 | | -33.865 | -16.473 | -35.971 | 1.00 | 41.00 |
| 21168 | O | HOH | W1392 | | 10.743 | -7.614 | -3.480 | 1.00 | 42.63 |
| 21171 | O | HOH | W1393 | | -22.946 | -24.502 | 0.404 | 1.00 | 44.11 |
| 21174 | O | HOH | W1394 | | -29.252 | -21.552 | -17.491 | 1.00 | 41.76 |
| 21177 | O | HOH | W1395 | | -62.536 | -36.646 | -21.204 | 1.00 | 39.65 |
| 21180 | O | HOH | W1396 | | 3.638 | 20.109 | 21.008 | 1.00 | 42.52 |
| 21183 | O | HOH | W1397 | | 9.649 | 7.530 | 46.604 | 1.00 | 44.53 |
| 21186 | O | HOH | W1398 | | 15.051 | -7.044 | 4.413 | 1.00 | 41.41 |
| 21189 | O | HOH | W1399 | | -67.924 | -24.553 | -8.393 | 1.00 | 41.29 |
| 21192 | O | HOH | W1400 | | -67.124 | -52.232 | -19.913 | 1.00 | 42.75 |
| 21195 | O | HOH | W1401 | | -28.793 | 5.301 | -15.618 | 1.00 | 45.15 |
| 21198 | O | HOH | W1402 | | -25.129 | -35.296 | -19.164 | 1.00 | 40.26 |
| 21201 | O | HOH | W1403 | | 2.859 | 9.653 | -7.062 | 1.00 | 44.45 |
| 21204 | O | HOH | W1404 | | -73.519 | -38.873 | 25.404 | 1.00 | 45.11 |
| 21207 | O | HOH | W1405 | | -26.609 | -47.583 | -11.685 | 1.00 | 44.69 |
| 21210 | O | HOH | W1406 | | -61.527 | -19.034 | -25.509 | 1.00 | 43.43 |
| 21213 | O | HOH | W1407 | | -64.726 | -27.112 | -29.501 | 1.00 | 48.26 |
| 21216 | O | HOH | W1408 | | 9.240 | -10.488 | 15.070 | 1.00 | 41.83 |
| 21219 | O | HOH | W1409 | | -33.366 | -9.172 | -22.210 | 1.00 | 40.59 |
| 21222 | O | HOH | W1410 | | -29.963 | -24.016 | -2.756 | 1.00 | 42.70 |
| 21225 | O | HOH | W1411 | | -37.028 | -31.913 | 19.357 | 1.00 | 40.72 |
| 21228 | O | HOH | W1412 | | -59.141 | -12.954 | -19.001 | 1.00 | 42.19 |
| 21231 | O | HOH | W1413 | | -36.156 | -10.186 | 6.767 | 1.00 | 38.39 |
| 21234 | O | HOH | W1414 | | -41.516 | -50.551 | 19.356 | 1.00 | 46.20 |
| 21237 | O | HOH | W1415 | | -2.321 | 15.372 | 23.575 | 1.00 | 47.07 |
| 21240 | O | HOH | W1416 | | -12.119 | -4.719 | 47.509 | 1.00 | 42.66 |
| 21243 | O | HOH | W1417 | | -9.354 | 6.417 | -16.213 | 1.00 | 41.97 |
| 21246 | O | HOH | W1418 | | -73.557 | -33.299 | 1.728 | 1.00 | 42.41 |
| 21249 | O | HOH | W1419 | | -21.337 | 20.358 | 28.076 | 1.00 | 46.61 |
| 21252 | O | HOH | W1420 | | -35.775 | -30.515 | 1.997 | 1.00 | 40.56 |
| 21255 | O | HOH | W1421 | | -68.477 | -20.490 | -24.594 | 1.00 | 42.08 |
| 21258 | O | HOH | W1422 | | -35.441 | -52.200 | 11.972 | 1.00 | 45.22 |
| 21261 | O | HOH | W1423 | | -67.497 | -27.459 | -1.749 | 1.00 | 43.82 |
| 21264 | O | HOH | W1424 | | -20.747 | -19.987 | -15.392 | 1.00 | 43.41 |
| 21267 | O | HOH | W1425 | | -58.078 | -50.609 | -16.710 | 1.00 | 47.18 |
| 21270 | O | HOH | W1426 | | -1.405 | -14.756 | -2.162 | 1.00 | 39.06 |
| 21273 | O | HOH | W1427 | | -18.679 | 2.686 | 40.884 | 1.00 | 39.91 |
| 21276 | O | HOH | W1428 | | -25.966 | 11.325 | -11.442 | 1.00 | 43.38 |
| 21279 | O | HOH | W1429 | | -41.743 | -54.854 | 2.045 | 1.00 | 43.87 |
| 21282 | O | HOH | W1430 | | -9.926 | -19.720 | 16.088 | 1.00 | 50.72 |
| 21285 | O | HOH | W1431 | | 8.128 | -14.931 | 16.977 | 1.00 | 45.07 |
| 21288 | O | HOH | W1432 | | -48.262 | -55.165 | -8.121 | 1.00 | 43.00 |

FIGURE 3 (cont.)

| A | B | C | D | E | F | G | H | I | J |
|---|---|---|---|---|---|---|---|---|---|
| 21291 | O | HOH | W1433 | | -50.106 | -57.579 | -8.631 | 1.00 | 41.39 |
| 21294 | O | HOH | W1434 | | -76.001 | -35.355 | 17.245 | 1.00 | 44.95 |
| 21297 | O | HOH | W1435 | | -30.392 | -19.047 | -16.185 | 1.00 | 37.61 |
| 21300 | O | HOH | W1436 | | -31.321 | -49.943 | -5.443 | 1.00 | 37.32 |

SEQUENCE LISTING

```
<160> NUMBER OF SEQ ID NOS: 13

<210> SEQ ID NO 1
<211> LENGTH: 292
<212> TYPE: PRT
<213> ORGANISM: Homo sapiens
<220> FEATURE:
<221> NAME/KEY: MISC_FEATURE
<222> LOCATION: (1)..(292)
<223> OTHER INFORMATION: Amino acid sequence for full-length human wild
      type 11-beta-hydroxysteroid dehydrogenase type 1

<400> SEQUENCE: 1

Met Ala Phe Met Lys Lys Tyr Leu Leu Pro Ile Leu Gly Leu Phe Met
1               5                   10                  15

Ala Tyr Tyr Tyr Tyr Ser Ala Asn Glu Glu Phe Arg Pro Glu Met Leu
                20                  25                  30

Gln Gly Lys Lys Val Ile Val Thr Gly Ala Ser Lys Gly Ile Gly Arg
            35                  40                  45

Glu Met Ala Tyr His Leu Ala Lys Met Gly Ala His Val Val Val Thr
        50                  55                  60

Ala Arg Ser Lys Glu Thr Leu Gln Lys Val Val Ser His Cys Leu Glu
65                  70                  75                  80

Leu Gly Ala Ala Ser Ala His Tyr Ile Ala Gly Thr Met Glu Asp Met
                85                  90                  95

Thr Phe Ala Glu Gln Phe Val Ala Gln Ala Gly Lys Leu Met Gly Gly
            100                 105                 110

Leu Asp Met Leu Ile Leu Asn His Ile Thr Asn Thr Ser Leu Asn Leu
        115                 120                 125

Phe His Asp Asp Ile His His Val Arg Lys Ser Met Glu Val Asn Phe
    130                 135                 140

Leu Ser Tyr Val Val Leu Thr Val Ala Ala Leu Pro Met Leu Lys Gln
145                 150                 155                 160

Ser Asn Gly Ser Ile Val Val Val Ser Ser Leu Ala Gly Lys Val Ala
                165                 170                 175

Tyr Pro Met Val Ala Ala Tyr Ser Ala Ser Lys Phe Ala Leu Asp Gly
            180                 185                 190
```

```
Phe Phe Ser Ser Ile Arg Lys Glu Tyr Ser Val Ser Arg Val Asn Val
        195                 200                 205

Ser Ile Thr Leu Cys Val Leu Gly Leu Ile Asp Thr Glu Thr Ala Met
    210                 215                 220

Lys Ala Val Ser Gly Ile Val His Met Gln Ala Ala Pro Lys Glu Glu
225                 230                 235                 240

Cys Ala Leu Glu Ile Ile Lys Gly Gly Ala Leu Arg Gln Glu Glu Val
                245                 250                 255

Tyr Tyr Asp Ser Ser Leu Trp Thr Thr Leu Leu Ile Arg Asn Pro Cys
            260                 265                 270

Arg Lys Ile Leu Glu Phe Leu Tyr Ser Thr Ser Tyr Asn Met Asp Arg
        275                 280                 285

Phe Ile Asn Lys
    290

<210> SEQ ID NO 2
<211> LENGTH: 807
<212> TYPE: DNA
<213> ORGANISM: Homo sapiens
<220> FEATURE:
<221> NAME/KEY: misc_feature
<222> LOCATION: (1)..(807)
<223> OTHER INFORMATION: Human cDNA sequence encoding residues 24-292 of
      11-beta-hydroxysteroid dehydrogenase type 1

<400> SEQUENCE: 2
aacgaggaat tcagaccaga gatgctccaa ggaaagaaag tgattgtcac aggggccagc      60
aaagggatcg gaagagagat ggcttatcat ctggcgaaga tgggagccca tgtggtggtg     120
acagcgaggt caaaagaaac tctacagaag gtggtatccc actgcctgga gcttggagca     180
gcctcagcac actacattgc tggcaccatg gaagacatga ccttcgcaga gcaatttgtt     240
gcccaagcag gaaagctcat gggaggacta gacatgctca ttctcaacca catccccaac     300
acttctttga atcttttttca tgatgatatt caccatgtgc gcaaaagcat ggaagtcaac     360
ttcctcagtt acgtggtcct gactgtagct gccttgccca tgctgaagca gagcaatgga     420
agcattgttg tcgtctcctc tctggctggg aaagtggctt atccaatggt tgctgcctat     480
tctgcaagca gtttgctttt ggatgggttc ttctcctcca tcagaaagga atattcagtg     540
tccagggtca atgtatcaat cactctctgt gttcttggcc tcatagacac agaaacagcc     600
atgaaggcag tttctgggat agtccatatg caagcagctc caaaggagga atgtgccctg     660
gagatcatca aaggggggagc tctgcgccaa gaagaagtgt attatgacag ctcactctgg     720
accactcttc tgatcagaaa tccatgcagg aagatcctgg aatttctcta ctcaacgagc     780
tataatatgg acagattcat aaacaag                                         807

<210> SEQ ID NO 3
<211> LENGTH: 705
<212> TYPE: DNA
<213> ORGANISM: Homo sapiens
<220> FEATURE:
<221> NAME/KEY: misc_feature
<222> LOCATION: (1)..(705)
<223> OTHER INFORMATION: Human cDNA sequence encoding residues 24-258 of
      11-beta-hydroxysteroid dehydrogenase type 1

<400> SEQUENCE: 3
aacgaggaat tcagaccaga gatgctccaa ggaaagaaag tgattgtcac aggggccagc      60
aaagggatcg gaagagagat ggcttatcat ctggcgaaga tgggagccca tgtggtggtg     120
```

```
acagcgaggt caaaagaaac tctacagaag gtggtatccc actgcctgga gcttggagca      180
gcctcagcac actacattgc tggcaccatg aagacatga ccttcgcaga gcaatttgtt       240
gcccaagcag gaaagctcat gggaggacta gacatgctca ttctcaacca catcaccaac      300
acttctttga atcttttca tgatgatatt caccatgtgc gcaaaagcat ggaagtcaac      360
ttcctcagtt acgtggtcct gactgtagct gccttgccca tgctgaagca gagcaatgga      420
agcattgttg tcgtctcctc tctggctggg aaagtggctt atccaatggt tgctgcctat      480
tctgcaagca gtttgcttt ggatgggttc ttctcctcca tcagaaagga atattcagtg       540
tccagggtca atgtatcaat cactctctgt gttcttggcc tcatagacac agaaacagcc      600
atgaaggcag tttctgggat agtccatatg caagcagctc caaggagga atgtgccctg       660 gagatcatca aaggggagc tctgcgccaa gaagaagtgt attat                       705
```

<210> SEQ ID NO 4
<211> LENGTH: 732
<212> TYPE: DNA
<213> ORGANISM: Homo sapiens
<220> FEATURE:
<221> NAME/KEY: misc_feature
<222> LOCATION: (1)..(732)
<223> OTHER INFORMATION: Human cDNA sequence encoding residues 24-267 of
      11-beta-hydroxysteroid dehydrogenase type 1

<400> SEQUENCE: 4

```
aacgaggaat tcagaccaga gatgctccaa ggaaagaaag tgattgtcac aggggccagc      60
aaagggatcg gaagagagat ggcttatcat ctggcgaaga tgggagccca tgtggtggtg      120
acagcgaggt caaaagaaac tctacagaag gtggtatccc actgcctgga gcttggagca      180
gcctcagcac actacattgc tggcaccatg aagacatga ccttcgcaga gcaatttgtt       240
gcccaagcag gaaagctcat gggaggacta gacatgctca ttctcaacca catcaccaac      300
acttctttga atcttttca tgatgatatt caccatgtgc gcaaaagcat ggaagtcaac      360
ttcctcagtt acgtggtcct gactgtagct gccttgccca tgctgaagca gagcaatgga      420
agcattgttg tcgtctcctc tctggctggg aaagtggctt atccaatggt tgctgcctat      480
tctgcaagca gtttgcttt ggatgggttc ttctcctcca tcagaaagga atattcagtg       540
tccagggtca atgtatcaat cactctctgt gttcttggcc tcatagacac agaaacagcc      600
atgaaggcag tttctgggat agtccatatg caagcagctc caaggagga atgtgccctg       660 gagatcatca aaggggagc tctgcgccaa gaagaagtgt attatgacag ctcactctgg      720
accactcttc tg                                                          732
```

<210> SEQ ID NO 5
<211> LENGTH: 286
<212> TYPE: PRT
<213> ORGANISM: Artificial
<220> FEATURE:
<223> OTHER INFORMATION: Amino acid sequence for residues 24-292 of
      11-beta-hydroxysteroid dehydrogenase type 1 with a N-terminal
      MKHQHQHQHQHQQPL tag

<400> SEQUENCE: 5

```
Met Lys His Gln His Gln His Gln His Gln His Gln Gln Pro
1               5                   10                  15

Leu Asn Glu Glu Phe Arg Pro Glu Met Leu Gln Gly Lys Lys Val Ile
                20                  25                  30

Val Thr Gly Ala Ser Lys Gly Ile Gly Arg Glu Met Ala Tyr His Leu
            35                  40                  45
```

Ala Lys Met Gly Ala His Val Val Thr Ala Arg Ser Lys Glu Thr
 50                  55                  60

Leu Gln Lys Val Val Ser His Cys Leu Glu Leu Gly Ala Ala Ser Ala
65                  70                  75                  80

His Tyr Ile Ala Gly Thr Met Glu Asp Met Thr Phe Ala Glu Gln Phe
                 85                  90                  95

Val Ala Gln Ala Gly Lys Leu Met Gly Gly Leu Asp Met Leu Ile Leu
            100                 105                 110

Asn His Ile Thr Asn Thr Ser Leu Asn Leu Phe His Asp Asp Ile His
        115                 120                 125

His Val Arg Lys Ser Met Glu Val Asn Phe Leu Ser Tyr Val Val Leu
    130                 135                 140

Thr Val Ala Ala Leu Pro Met Leu Lys Gln Ser Asn Gly Ser Ile Val
145                 150                 155                 160

Val Val Ser Ser Leu Ala Gly Lys Val Ala Tyr Pro Met Val Ala Ala
                165                 170                 175

Tyr Ser Ala Ser Lys Phe Ala Leu Asp Gly Phe Phe Ser Ser Ile Arg
            180                 185                 190

Lys Glu Tyr Ser Val Ser Arg Val Asn Val Ser Ile Thr Leu Cys Val
        195                 200                 205

Leu Gly Leu Ile Asp Thr Glu Thr Ala Met Lys Ala Val Ser Gly Ile
    210                 215                 220

Val His Met Gln Ala Ala Pro Lys Glu Glu Cys Ala Leu Glu Ile Ile
225                 230                 235                 240

Lys Gly Gly Ala Leu Arg Gln Glu Glu Val Tyr Tyr Asp Ser Ser Leu
                245                 250                 255

Trp Thr Thr Leu Leu Ile Arg Asn Pro Cys Arg Lys Ile Leu Glu Phe
            260                 265                 270

Leu Tyr Ser Thr Ser Tyr Asn Met Asp Arg Phe Ile Asn Lys
        275                 280                 285

<210> SEQ ID NO 6
<211> LENGTH: 252
<212> TYPE: PRT
<213> ORGANISM: Artificial
<220> FEATURE:
<223> OTHER INFORMATION: Amino acid sequence for residues 24-258 of
      11-beta-hydroxysteroid dehydrogenase type 1 with a N-terminal
      MKHQHQHQHQHQQPL tag

<400> SEQUENCE: 6

Met Lys His Gln His Gln His Gln His Gln His Gln His Gln Gln Pro
1               5                   10                  15

Leu Asn Glu Glu Phe Arg Pro Glu Met Leu Gln Gly Lys Lys Val Ile
            20                  25                  30

Val Thr Gly Ala Ser Lys Gly Ile Gly Arg Glu Met Ala Tyr His Leu
        35                  40                  45

Ala Lys Met Gly Ala His Val Val Thr Ala Arg Ser Lys Glu Thr
    50                  55                  60

Leu Gln Lys Val Val Ser His Cys Leu Glu Leu Gly Ala Ala Ser Ala
65                  70                  75                  80

His Tyr Ile Ala Gly Thr Met Glu Asp Met Thr Phe Ala Glu Gln Phe
                85                  90                  95

Val Ala Gln Ala Gly Lys Leu Met Gly Gly Leu Asp Met Leu Ile Leu
            100                 105                 110

```
Asn His Ile Thr Asn Thr Ser Leu Asn Leu Phe His Asp Asp Ile His
        115                 120                 125
His Val Arg Lys Ser Met Glu Val Asn Phe Leu Ser Tyr Val Val Leu
    130                 135                 140
Thr Val Ala Ala Leu Pro Met Leu Lys Gln Ser Asn Gly Ser Ile Val
145                 150                 155                 160
Val Val Ser Ser Leu Ala Gly Lys Val Ala Tyr Pro Met Val Ala Ala
                165                 170                 175
Tyr Ser Ala Ser Lys Phe Ala Leu Asp Gly Phe Phe Ser Ser Ile Arg
            180                 185                 190
Lys Glu Tyr Ser Val Ser Arg Val Asn Val Ser Ile Thr Leu Cys Val
        195                 200                 205
Leu Gly Leu Ile Asp Thr Glu Thr Ala Met Lys Ala Val Ser Gly Ile
    210                 215                 220
Val His Met Gln Ala Ala Pro Lys Glu Glu Cys Ala Leu Glu Ile Ile
225                 230                 235                 240
Lys Gly Gly Ala Leu Arg Gln Glu Glu Val Tyr Tyr
                245                 250
```

<210> SEQ ID NO 7
<211> LENGTH: 261
<212> TYPE: PRT
<213> ORGANISM: Artificial
<220> FEATURE:
<223> OTHER INFORMATION: Amino acid sequence for residues 24-267 of
      11-beta-hydroxysteroid dehydrogenase type 1 with a N-terminal
      MKHQHQHQHQHQQPL tag

<400> SEQUENCE: 7

```
Met Lys His Gln His Gln His Gln His Gln His Gln Gln Pro
1               5                   10                  15
Leu Asn Glu Glu Phe Arg Pro Glu Met Leu Gln Gly Lys Lys Val Ile
            20                  25                  30
Val Thr Gly Ala Ser Lys Gly Ile Gly Arg Glu Met Ala Tyr His Leu
        35                  40                  45
Ala Lys Met Gly Ala His Val Val Val Thr Ala Arg Ser Lys Glu Thr
    50                  55                  60
Leu Gln Lys Val Val Ser His Cys Leu Glu Leu Gly Ala Ala Ser Ala
65                  70                  75                  80
His Tyr Ile Ala Gly Thr Met Glu Asp Met Thr Phe Ala Glu Gln Phe
                85                  90                  95
Val Ala Gln Ala Gly Lys Leu Met Gly Gly Leu Asp Met Leu Ile Leu
            100                 105                 110
Asn His Ile Thr Asn Thr Ser Leu Asn Leu Phe His Asp Asp Ile His
        115                 120                 125
His Val Arg Lys Ser Met Glu Val Asn Phe Leu Ser Tyr Val Val Leu
    130                 135                 140
Thr Val Ala Ala Leu Pro Met Leu Lys Gln Ser Asn Gly Ser Ile Val
145                 150                 155                 160
Val Val Ser Ser Leu Ala Gly Lys Val Ala Tyr Pro Met Val Ala Ala
                165                 170                 175
Tyr Ser Ala Ser Lys Phe Ala Leu Asp Gly Phe Phe Ser Ser Ile Arg
            180                 185                 190
Lys Glu Tyr Ser Val Ser Arg Val Asn Val Ser Ile Thr Leu Cys Val
        195                 200                 205
Leu Gly Leu Ile Asp Thr Glu Thr Ala Met Lys Ala Val Ser Gly Ile
```

```
                210              215              220
Val His Met Gln Ala Ala Pro Lys Glu Glu Cys Ala Leu Glu Ile Ile
225              230              235              240

Lys Gly Gly Ala Leu Arg Gln Glu Glu Val Tyr Tyr Asp Ser Ser Leu
            245              250              255

Trp Thr Thr Leu Leu
            260

<210> SEQ ID NO 8
<211> LENGTH: 24
<212> TYPE: DNA
<213> ORGANISM: Artificial
<220> FEATURE:
<223> OTHER INFORMATION: DNA sequence encoding PCR Primer hsd1_24-f

<400> SEQUENCE: 8
aacgaggaat tcagaccaga gatg                                         24

<210> SEQ ID NO 9
<211> LENGTH: 29
<212> TYPE: DNA
<213> ORGANISM: Artificial
<220> FEATURE:
<223> OTHER INFORMATION: DNA sequence encoding PCR Primer hsd1_292-r

<400> SEQUENCE: 9
cttgtttatg aatctgtcca tattatagc                                    29

<210> SEQ ID NO 10
<211> LENGTH: 23
<212> TYPE: DNA
<213> ORGANISM: Artificial
<220> FEATURE:
<223> OTHER INFORMATION: DNA sequence encoding PCR Primer hsdC272Sqcf

<400> SEQUENCE: 10
tcagaaatcc atccaggaag atc                                          23

<210> SEQ ID NO 11
<211> LENGTH: 23
<212> TYPE: DNA
<213> ORGANISM: Artificial
<220> FEATURE:
<223> OTHER INFORMATION: DNA sequence encoding PCR Primer hsdC272Sqcr

<400> SEQUENCE: 11
gatcttcctg gatggatttc tga                                          23

<210> SEQ ID NO 12
<211> LENGTH: 27
<212> TYPE: DNA
<213> ORGANISM: Artificial
<220> FEATURE:
<223> OTHER INFORMATION: DNA sequence encoding PCR Primer hsd1-258-r

<400> SEQUENCE: 12
ataatacact tcttcttggc gcagagc                                      27

<210> SEQ ID NO 13
<211> LENGTH: 27
<212> TYPE: DNA
<213> ORGANISM: Artificial
<220> FEATURE:
<223> OTHER INFORMATION: DNA sequence encoding PCR Primer hsd1-267-r
```

```
<400> SEQUENCE: 13
cagaagagtg gtccagagtg agctgtc                                                27
```

US 7,241,604 B1

CRYSTALLIZATION OF 11-BETA-HYDROXYSTEROID DEHYDROGENASE TYPE 1

FIELD OF THE INVENTION

The present invention relates to a member of a family of short chain dehydrogenases/reductases (SDRs) and more specifically to a particular SDR known as 11-Beta-Hydroxysteroid Dehydrogenase type 1 (HSD11B1). Provided is HSD11B1 in crystalline form, methods of forming crystals comprising HSD11B1, methods of using crystals comprising HSD11B1, a crystal structure of HSD11B1, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising HSD11B1 and particularly crystals comprising HSD11B1 that have sufficient size and quality to obtain useful information about the structural properties of HSD11B1 and molecules are complexes that may associated with HSD11B1.

In one embodiment, a composition is provided that comprises a protein in crystalline form wherein at least a portion of the protein has 55%, 65%, 75%, 85%, 90%, 95%, 97%, 99% or greater identity with residues 24-292 of SEQ. ID No. 1.

In one embodiment, a composition is provided that comprises a protein in crystalline form wherein at least a portion of the protein has 55%, 65%, 75%, 85%, 90%, 95%, 97%, 99% or greater identity with residues 24-258 of SEQ. ID No. 1.

In one embodiment, a composition is provided that comprises a protein in crystalline form wherein at least a portion of the protein has 55%, 65%, 75%, 85%, 90%, 95%, 97%, 99% or greater identity with residues 24-267 of SEQ. ID No. 1.

In one variation, the protein has activity characteristic of HSD11B1. For example, the protein may optionally be inhibited by inhibitors of wild type HSD11B1. The protein crystal may also diffract X-rays for a determination of structure coordinates to a resolution of 4 Å, 3.5 Å, 3.0 Å or less.

In one variation, the protein crystal has a crystal lattice in a $P2_1$ space group. The protein crystal may also have a crystal lattice having unit dimensions, +/−5%, of a=56.4 Å, b=152.5 Å, c=73.8 Å, $\alpha$=90.0°, $\beta$=92.2°, and $\gamma$=90.0°.

In one variation, the protein crystal has a crystal lattice in a $P4_12_12$ space group. The protein crystal may also have a crystal lattice having unit cell dimensions, +/−5%, of a=114 Å, b=114 Å, c=157 Å, $\alpha$=90°, $\beta$=90°, and $\gamma$=90°.

In one variation, the protein crystal has a crystal lattice in a $P3_121$ space group. The protein crystal may also have a crystal lattice having unit cell dimensions, +/−5%, of a=86.2 Å, b=86.2 Å, c=146.7 Å, $\alpha$=90.0°, $\beta$=90.0°, and $\gamma$=120°.

The present invention is also directed to crystallizing HSD11B1. The present invention is also directed to the conditions useful for crystallizing HSD11B1. It should be recognized that a wide variety of crystallization methods can be used in combination with the crystallization conditions to form crystals comprising HSD11B1 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 24-292 of SEQ. ID No. 1; and storing the crystallization volume under conditions suitable for crystal formation.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 24-258 of SEQ. ID No. 1; and storing the crystallization volume under conditions suitable for crystal formation.

In one embodiment, a method is provided for forming crystals of a protein comprising: forming a crystallization volume comprising: a protein wherein at least a portion of the protein has 55%, 65%, 75%, 85%, 90% 95%, 97%, 99% or greater identity with residues 24-267 of SEQ. ID No. 1; and storing the crystallization volume under conditions suitable for crystal formation.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 24-292 of SEQ. ID No. 1 in a concentration between 1 mg/ml-50 mg/ml, a pH between 4-10 and a temperature of 1° C.-25° C.; 5-50% w/v of precipitant wherein the precipitant comprises one or more members of the group consisting of PEG MME having a molecular weight range between 1000-10000, PEG having a molecular weight range between 100-10000, 0.01-3.5 M Sodium, potassium or ammonium phosphate, and 0.01-3.5M Sodium, potassium or ammonium sulfate. Buffers that may be used include, but are not limited to tris, bicine, phosphate, cacodylate, acetate, citrate, HEPES, PIPES, MES and combinations thereof. Optionally 0.05 to 2.5M additives wherein the additives comprise a monovalent and/or divalent salt (for example, sodium, lithium, magnesium, calcium, and the like).

The method may optionally further comprise forming a protein crystal that has a crystal lattice in a $P2_1$ space group.

The method also optionally further comprises forming a protein crystal that has a crystal lattice having unit cell dimensions, +/−5%, of a=56.4 Å, b=152.5 Å, c=73.8 Å, α=90.0°, β=92.2°, and γ=90.0°. The invention also relates to protein crystals formed by these methods.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 24-258 of SEQ. ID No. 1 in a concentration between 1 mg/ml-50 mg/ml, a pH between 4-10 and a temperature of 1° C.-25° C.; 5-50% w/v of precipitant wherein the precipitant comprises one or more members of the group consisting of PEG MME having a molecular weight range between 1000-10000, PEG having a molecular weight range between 100-10000, 0.01-3.5 M Sodium, potassium or ammonium phosphate, and 0.01-3.5M Sodium, potassium or ammonium sulfate. Buffers that may be used include, but are not limited to tris, bicine, phosphate, cacodylate, acetate, citrate, HEPES, PIPES, MES and combinations thereof. Optionally 0.05 to 2.5M additives wherein the additives comprise a monovalent and/or divalent salt (for example, sodium, lithium, magnesium, calcium, and the like).

The method may optionally further comprise forming a protein crystal that has a crystal lattice in a $P4_12_12$ space group. The method also optionally further comprises forming a protein crystal that has a crystal lattice having unit cell dimensions, +/−5%, of a=114 Å, b=114 Å, c=157 Å, α=90°, β=90°, and γ=90°. The invention also relates to protein crystals formed by these methods.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 24-267 of SEQ. ID No. 1 in a concentration between 1 mg/ml-50 mg/ml, a pH between 4-10 and a temperature of 1° C.-25° C.; 5-50% w/v of precipitant wherein the precipitant comprises one or more members of the group consisting of PEG MME having a molecular weight range between 1000-10000, PEG having a molecular weight range between 100-10000, 0.01-3.5 M Sodium, potassium or ammonium phosphate, and 0.01-3.5M Sodium, potassium or ammonium sulfate. Buffers that may be used include, but are not limited to tris, bicine, phosphate, cacodylate, acetate, citrate, HEPES, PIPES, MES and combinations thereof. Optionally 0.05 to 2.5M additives wherein the additives comprise a monovalent and/or divalent salt (for example, sodium, lithium, magnesium, calcium, and the like).

The method may optionally further comprise forming a protein crystal that has a crystal lattice in a $P3_121$ space group. The method also optionally further comprises forming a protein crystal that has a crystal lattice having unit cell dimensions, +/−5%, of a=86.2 Å, b=86.2 Å, c=146.7 Å, α=90.0°, β=90.0°, and γ=120°. The invention also relates to protein crystals formed by these methods.

The present invention is also directed to a composition comprising an isolated protein that comprises or consists of one or more of the protein sequence(s) of HSD11B1 taught herein for crystallizing HSD11B1. The present invention is also directed to a composition comprising an isolated nucleic acid molecule that comprises or consists of the nucleotides for expressing the protein sequence of HSD11B1 taught herein for crystallizing HSD11B1.

The present invention is also directed to an expression vector that may be used to express the isolated proteins taught herein for crystallizing HSD11B1. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for HSD11B1 as well as structure coordinates that are comparatively similar to these structure coordinates. It is noted that these comparatively similar structure coordinates may encompass proteins with similar sequences and/or structures, such as other SDRs. For example, machine-readable data storage media is provided having data storage material encoded with machine-readable data that comprises structure coordinates that are comparatively similar to the structure coordinates of HSD11B1. The present invention is also directed to a machine readable data storage medium having data storage material encoded with machine readable data, which, when read by an appropriate machine, can display a three dimensional representation of all or a portion of a structure of HSD11B1 or a model that is comparatively similar to the structure of all or a portion of HSD11B1.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1. The amino acids being overlaid and compared need not to be identical when the RMSD calculation is performed on alpha carbons and main chain atoms but the amino acids being overlaid and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.34, 0.22 and 0.17 when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.34 | 0.22 | 0.17 |
| (4 Angstrom set) | main-chain atoms[1] | 0.32 | 0.21 | 0.16 |
| | all non-hydrogen[2] | 0.45 | 0.29 | 0.22 |
| Table 3 | alpha-carbon atoms[1] | 1.06 | 0.70 | 0.53 |
| (7 Angstrom set) | main-chain atoms[1] | 1.12 | 0.74 | 0.56 |
| | all non-hydrogen[2] | 1.16 | 0.77 | 0.58 |
| Table 4 | alpha-carbon atoms[1] | 2.01 | 1.32 | 1.00 |
| (10 Angstrom set) | main-chain atoms[1] | 1.98 | 1.31 | 0.99 |
| | all non-hydrogen[2] | 2.27 | 1.50 | 1.14 |

TABLE 1-continued

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| 24-292 of SEQ. ID No. 1 | alpha-carbon atoms[1] | 1.61 | 1.06 | 0.80 |
| | main-chain atoms[1] | 1.59 | 1.05 | 0.80 |
| | all non-hydrogen[2] | 1.77 | 1.16 | 0.88 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

The present invention is also directed to a three-dimensional structure of all or a portion of HSD11B1. This three-dimensional structure may be used to identify binding sites, to provide mutants having desirable binding properties, and ultimately, to design, characterize, or identify ligands capable of interacting with HSD11B1. Ligands that interact with HSD11B1 may be any type of atom, compound, protein or chemical group that binds to or otherwise associates with the protein. Examples of types of ligands include natural substrates for HSD11B1, inhibitors of HSD11B1, and heavy atoms. The inhibitors of HSD11B1 may optionally be used as drugs to treat therapeutic indications by modifying the in vivo activity of HSD11B1.

In various embodiments, methods are provided for displaying a three dimensional representation of a structure of a protein comprising:
taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;
computing a three dimensional representation of a structure based on the structure coordinates; and
displaying the three dimensional representation.

The present invention is also directed to a method for solving a three-dimensional crystal structure of a target protein using the structure of HSD11B1.

In various embodiments, computational methods are provided comprising:
taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;
computing phases based on the structural coordinates;
computing an electron density map based on the computed phases; and
determining a three-dimensional crystal structure based on the computed electron density map.

In various embodiments, computational methods are provided comprising:
taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

These methods may optionally further comprise determining a three-dimensional crystal structure based upon the computed three-dimensional electron density map.

The present invention is also directed to using a crystal structure of HSD11B1, in particular the structure coordinates of HSD11B1 and the surface contour defined by them, in methods for screening, designing, or optimizing molecules or other chemical entities that interact with and preferably inhibit HSD11B1.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of HSD11B1 and/or its structure coordinates to evaluate the ability of entities to associate with HSD11B1. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:
creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;
performing a fitting operation between the entity and the computer model; and
analyzing results of the fitting operation to quantify an association between the entity and the model.

In other embodiments, methods are provided for identifying entities that can associate with a protein comprising:
generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 24-292 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 24-258 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 24-267 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein binding modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 24-292 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 24-258 of SEQ. ID No. 1.

In other embodiments, methods are provided for identifying entities that can associated with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 24-267 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HSD11B1, or a portion thereof;

performing a fitting program operation between computer models of the entity to be evaluated and the binding pocket in order to provide an energy-minimized configuration of the entity in the binding pocket;

and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HSD11B1, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of HSD11B1. For example, the protein may optionally be inhibited by inhibitors of wild type HSD11B1.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 24-292 of SEQ. ID No. 1; and performing rational drug design using a three dimensional structure that is based on the obtained structure coordinates.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 24-258 of SEQ. ID No. 1; and performing rational drug design using a three dimensional structure that is based on the obtained structure coordinates.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 24-267 of SEQ. ID No. 1; and performing rational drug design using a three dimensional structure that is based on the obtained structure coordinates.

The protein crystals may optionally have a crystal lattice with a $P2_1$ space group and unit cell dimensions, +/−5%, of a=56.4 Å, b=152.5 Å, c=73.8 Å, $\alpha$=90.0°, $\beta$=92.2°, and $\gamma$=90.0°.

The protein crystals may optionally have a crystal lattice with a $P4_12_12$ space group and unit cell dimensions, +/−5%, of, a=114 Å, b=114 Å, c=157 Å, $\alpha$=90°, $\beta$=90°, and $\gamma$=90°.

The protein crystals may optionally have a crystal lattice with a $P3_121$ space group and unit cell dimensions, +/−5%, of, 86.2 86.2 146.7 90 90 90.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, 3, 4, 5, 6, 7, 8, 9, 10, 11, 12, and 13 referred to in this application.

FIG. 3 lists a set of atomic structure coordinates for HSD11B1 as derived by X-ray crystallography from a crystal that comprises the protein of SEQ. ID No. 5. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2A:
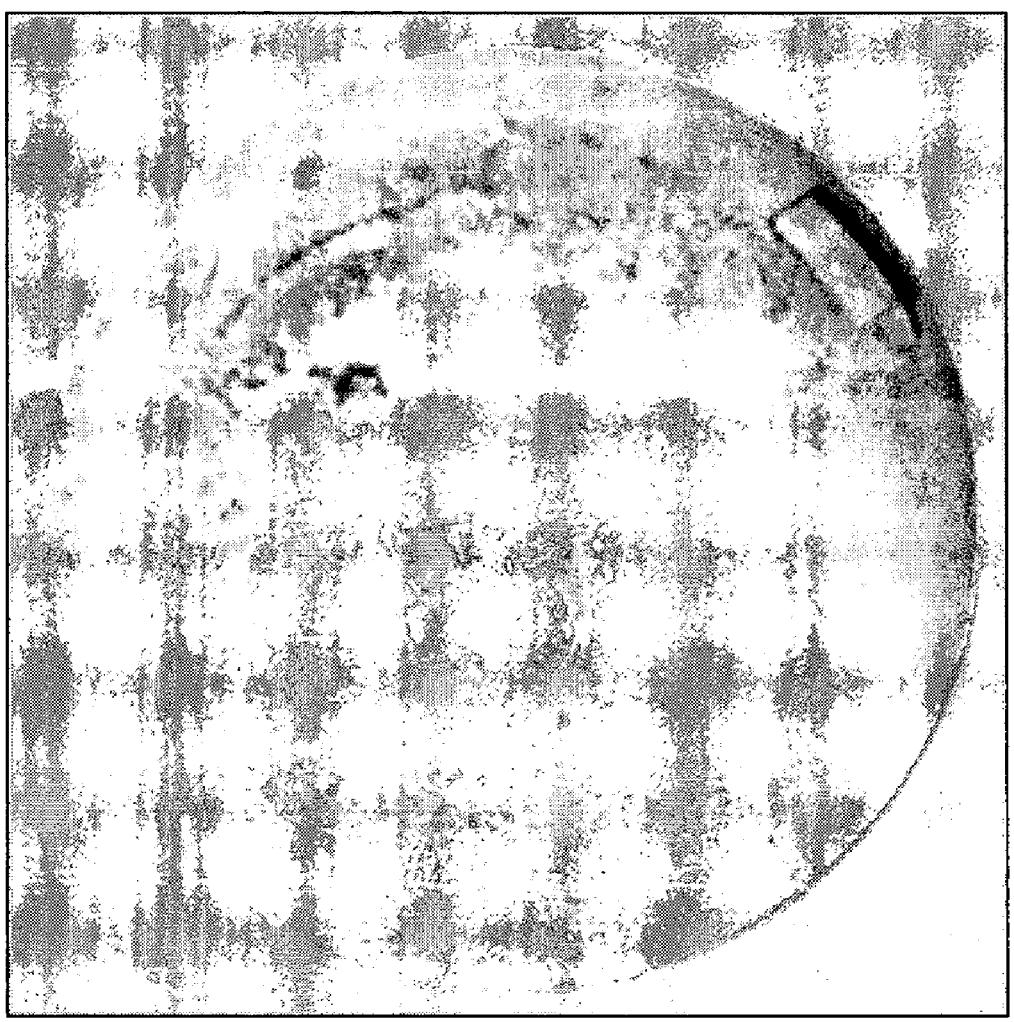
FIG. 2A illustrates a crystal of HSD11B1 corresponding to SEQ. ID No. 5, having a crystal lattice in a $P2_1$ space group and unit cell dimensions, +/−5%, of a=56.4 Å, b=152.5 Å, c=73.8 Å, $\alpha$=90.0°, $\beta$=92.2°, and $\gamma$=90.0°.

The present invention relates to a member of a family of short chain dehydrogenases and more specifically to a particular SDR known as 11-beta-hydroxysteroid dehydrogenase type 1 (HSD11B1). Provided is HSD11B1 in crystalline form, methods of forming crystals comprising HSD11B1, methods of using crystals comprising HSD11B1, a crystal structure of HSD11B1, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. HSD11B1

The dehydrogenase HSD11B1 belongs to the short chain dehydrogenase subfamily. The protein encoded by HSD11B1 is a microsomal enzyme that catalyzes the conversion of the stress hormone cortisol to the inactive metabolite cortisone. In addition, the encoded protein can catalyze the reverse reaction, the conversion of cortisone to cortisol.

HSD11B1 is important in regulating local concentrations of glucocorticoids in various tissue types, for example, adipose, vascular, brain, testis, ocular and placental.

Disregulation of HSD11B1 is implicated in such areas as the metabolic syndrome and Cushing's disease, hypertension, cognitive function and ocular function.

In one embodiment, HSD11B1 comprises the wild-type form of full length HSD11B1, set forth herein as SEQ. ID No. 1 (GenBank Accession Number NM_005525; Tannin, G. M., Agarwal, A. K., Monder, C., New, M. I. and White, P. C., "The human gene for 11 beta-hydroxysteroid dehydrogenase. Structure, tissue distribution, and chromosomal localization;" J. Biol. Chem. 266 (25), 16653-16658 (1991)).

In another embodiment, HSD11B1 comprises residues 24-292 of SEQ. ID No. 1 which comprises the active site domain of wild-type HSD11B1 that is represented in the set of structural coordinates shown in FIG. 3.

In another embodiment, HSD11B1 comprises residues 24-258 of SEQ. ID No. 1 which comprises the active site domain of wild-type HSD11B1.

In another embodiment, HSD11B1 comprises residues 24-267 of SEQ. ID No. 1 which comprises the active site domain of wild-type HSD11B1.

It should be recognized that the invention may be readily extended to various variants of wild-type HSD11B1 and variants of fragments thereof. In another embodiment, HSD11B1 comprises a sequence wherein at least a portion of the sequence has 55%, 65%, 75%, 85%, 90%, 95%, 97%, 99% or greater identity with SEQ. ID No. 1.

It is also noted that the above sequences of HSD11B1 are also intended to encompass isoforms, mutants and fusion proteins of these sequences. An example of a fusion protein is provided by SEQ. ID Nos. 5, 6, and 7, which include an N-terminal MKHQHQHQHQHQHQQPL tag that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the HSD11B1 amino acids shown in Table 2 encompass a 4-Angstrom radius around the HSD11B1 active site and thus are likely to interact with any active site inhibitor of HSD11B1. Applicants have also determined that the amino acids of Table 3 encompass a 7-Angstrom radius around the HSD11B1 active site. Further it has been determined that the amino acids of Table 4 encompass a 10-Angstrom radius around the HSD11B1 active site. It is noted that there is one HSD11B1 molecule in the asymmetric unit, referred to as chain A. Structural coordinates appear in FIG. 3. It is noted that the sequence and structure of the residues in the active site may also be conserved and hence pertinent to other HSD11B1 variants and homologs.

One or more of the sets of amino acids set forth in the tables is preferably conserved in a variant of HSD11B1. Hence, HSD11B1 may optionally comprise a sequence wherein at least a portion of the sequence has 55%, 65%, 75%, 85%, 90%, 95%, 97%, 99% or greater identity with any one of the above sequences (e.g., all of SEQ. ID No. 1; residues 24-292 of SEQ. ID No. 1; residues 24-258 of SEQ. ID No. 1; and residues 24-267 of SEQ. ID No. 1) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the HSD11B1 active site.

| | | |
|---|---|---|
| ILE 46 | ASN 119 | ILE 121 |
| THR 124 | VAL 168 | SER 169 |
| SER 170 | LYS 187 | LEU 215 |
| GLY 216 | LEU 217 | ILE 218 |
| THR 220 | ALA 223 | ALA 226 |
| TYR 284 | | |

TABLE 3

Amino Acids encompassed by a 7-Angstrom radius around the HSD11B1 active site.

| | | |
|---|---|---|
| THR 40 | GLY 41 | LYS 44 |
| GLY 45 | ILE 46 | GLY 47 |
| ARG 48 | MET 50 | ASN 119 |
| HIS 120 | ILE 121 | THR 124 |
| SER 125 | LEU 126 | ASN 143 |
| TYR 147 | VAL 167 | VAL 168 |
| SER 169 | SER 170 | LEU 171 |
| ALA 172 | GLY 173 | TYR 177 |
| PRO 178 | MET 179 | VAL 180 |
| TYR 183 | SER 184 | LYS 187 |
| LEU 190 | CYS 213 | VAL 214 |
| LEU 215 | GLY 216 | LEU 217 |
| ILE 218 | ASP 219 | THR 220 |
| GLY 221 | THR 222 | ALA 223 |
| MET 224 | ALA 226 | VAL 227 |
| VAL 231 | GLN 234 | ALA 235 |
| CYS 241 | ILE 245 | TYR 280 |
| TYR 284 | | |

TABLE 4

Amino Acids encompassed by a 10-Angstrom radius around the HSD11B1 active site.

| | | |
|---|---|---|
| VAL 39 | THR 40 | GLY 41 |
| ALA 42 | SER 43 | LYS 44 |
| GLY 45 | ILE 46 | GLY 47 |
| ARG 48 | GLU 49 | MET 50 |
| ILE 117 | LEU 118 | ASN 119 |
| HIS 120 | ILE 121 | THR 122 |
| ASN 123 | THR 124 | SER 125 |
| LEU 126 | ASN 127 | HIS 135 |
| SER 139 | VAL 142 | ASN 143 |
| PHE 144 | TYR 147 | VAL 166 |
| VAL 167 | VAL 168 | SER 169 |
| SER 170 | LEU 171 | ALA 172 |
| GLY 173 | LYS 174 | VAL 175 |
| ALA 176 | TYR 177 | PRO 178 |

TABLE 4-continued

Amino Acids encompassed by a 10-Angstrom radius around the HSD11B1 active site.

| | | |
|---|---|---|
| MET 179 | VAL 180 | ALA 181 |
| VAL 182 | TYR 183 | SER 184 |
| ALA 187 | SER 186 | LYS 187 |
| PHE 188 | LEU 190 | SER 196 |
| LEU 212 | CYS 213 | VAL 214 |
| LEU 215 | GLY 216 | LEU 217 |
| ILE 218 | ASP 219 | THR 220 |
| GLU 221 | THR 222 | ALA 223 |
| MET 224 | LYS 225 | ALA 226 |
| VAL 227 | SER 228 | GLY 229 |
| ILE 230 | VAL 231 | HIS 232 |
| MET 233 | GLN 234 | ALA 235 |
| ALA 236 | PRO 237 | LYS 238 |
| CYS 241 | ALA 242 | ILE 245 |
| TYR 258 | ASP 259 | SER 260 |
| THR 264 | ILE 268 | LEU 276 |
| GLU 277 | TYR 280 | SER 281 |
| SER 283 | TYR 284 | ASN 285 |
| MET 286 | ARG 288 | PHE 289 |

With the benefit of the crystal structure and guidance provided by Tables 2, 3 and 4, a wide variety of HSD11B1 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of HSD11B1.

Variants of HSD11B1 may be insertional variants in which one or more amino acid residues are introduced into a predetermined site in the HSD11B1 sequence. For instance, insertional variants can be fusions of heterologous proteins or polypeptides to the amino or carboxyl terminus of the subunits.

Variants of HSD11B1 also may be substitutional variants in which at least one residue has been removed and a different residue inserted in its place. Non-natural amino acids (i.e., amino acids not normally found in native proteins), as well as isosteric analogs (amino acid or otherwise) may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the HSD11B1 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution with bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding HSD11B1 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type HSD11B1 is functional in the sense that the resulting protein is capable of associating with at least one same chemical entity that is also capable of selectively associating with a protein comprising the wild-type HSD11B1 (e.g., residues 24-292 of SEQ. ID No. 1, residues 24-258 of SEQ. ID No. 1, and residues 24-267 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of HSD11B1, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of HSD11B1 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of HSD11B1 will be apparent to those having skills in the art, particularly in view of the three dimensional structure of HSD11B1 provided herein.

2. Cloning, Expression and Purification of HSD11B1

The gene encoding HSD11B1 can be isolated from RNA, cDNA or cDNA libraries. In this case, the portion of the gene encoding amino acid residues 24-292 (SEQ. ID No. 1), corresponding to the active site of HSD11B1, was isolated and is shown as SEQ. ID No. 2. In addition, the portion of the gene encoding amino acids residues 24-258 (SEQ. ID No. 1), corresponding to the active side of HSD11B1, was isolated and is shown as SEQ. ID No. 3. Also, the portion of the gene encoding amino acid residues 24-267 (SEQ. ID No. 1), corresponding to the active site of HSD11B1, was isolated and is shown as SEQ. ID No. 4.

Construction of expression vectors and recombinant proteins from the DNA sequence encoding HSD11B1 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of HSD11B1. Example 1 provides one such expression system.

Once expressed, purification steps are employed to produce HSD11B1 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

HSD11B1 may optionally be affinity labeled during cloning, preferably with an N-terminal MKHQHQHQHQHQHQQPL tag, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising HSD11B1

One aspect of the present invention relates to methods for forming crystals comprising HSD11B1 as well as crystals comprising HSD11B1.

In one embodiment, a method for forming crystals comprising HSD11B1 is provided comprising forming a crystallization volume comprising HSD11B1, one or more precipitants, optionally a buffer, optionally a monovalent and/or divalent salt and optionally an organic solvent; and storing the crystallization volume under conditions suitable for crystal formation.

In yet another embodiment, a method for forming crystals comprising HSD11B1 is provided comprising forming a crystallization volume comprising HSD11B1 in solution comprising the components shown in Table 5; and storing the crystallization volume under conditions suitable for crystal formation.

TABLE 5

Precipitant 5-50% w/v of precipitant wherein the precipitant comprises one or more members of the group consisting of PEG MME having a molecular weight range between 1000-10000, PEG having a molecular weight range between 100-10000, and 0.01-2.0 M Sodium, potassium or ammonium phosphate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 3.5 M additives wherein the additives comprise a monovalent and/or divalent salt (for example, sodium, lithium, magnesium, calcium, and the like)

Protein Concentration 1 mg/ml-50 mg/ml

Temperature

1° C.-25° C.

In yet another embodiment, a method for forming crystals comprising HSD11B1 is provided comprising forming a crystallization volume comprising HSD11B1; introducing crystals comprising HSD11B1 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising HSD11B1 and crystals comprising HSD11B1 according to the invention are not intended to be limited to the wild type, full length HSD11B1 shown in SEQ. ID No. 1 and fragments comprising residues 24-292, residues 24-258, and residues 24-267 of SEQ. ID No. 1. Rather, it should be recognized that the invention may be extended to various other fragments and variants of wild-type HSD11B1 as described above.

It should also be understood that forming crystals comprising HSD11B1 and crystals comprising HSD11B1 according to the invention may be such that HSD11B1 is optionally complexed with one or more ligands and one or more copies of the same ligand. The ligand used to form the complex may be any ligand capable of binding to HSD11B1. In one variation, the ligand is a natural substrate. In another variation, the ligand is an inhibitor.

In one particular embodiment, HSD11B1 crystals have a crystal lattice in the $P2_1$ space group. HSD11B1 crystals may also optionally have unit cell dimensions, +/−5%, of a=56.4 Å, b=152.5 Å, c=73.8 Å, $\alpha$=90.0°, $\beta$=92.2°, and $\gamma$=90.0°. HSD11B1 crystals also preferably are capable of diffracting X-rays for determination of atomic coordinates to a resolution of 4 Å, 3.5 Å, 3.0 Å or better.

In one particular embodiment, HSD11B1 crystals have a crystal lattice in the $P2_1$ space group. HSD11B1 crystals may also optionally have unit cell dimensions, +/−5%, of a=114 Å, b=114 Å, c=157 Å, $\alpha$=90°, $\beta$=90°, and $\gamma$=90°. HSD11B1 crystals also preferably are capable of diffracting X-rays for determination of atomic coordinates to a resolution of 4 Å, 3.5 Å, 3.0 Å or better.

In one particular embodiment, HSD11B1 crystals have a crystal lattice in the $P2_1$ space group. HSD11B1 crystals may also optionally have unit cell dimensions, +/−5%, of a=86.2 Å, b=86.2 Å, c=146.7 Å, $\alpha$=90.0°, $\beta$=90.0°, and $\gamma$=120°. HSD11B1 crystals also preferably are capable of diffracting X-rays for determination of atomic coordinates to a resolution of 4 Å, 3.5 Å, 3.0 Å or better.

Crystals comprising HSD11B1 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens et al. (2000) *Curr. Opin. Struct. Biol.*: 10(5):558-63, and U.S. Pat. Nos. 6,296,673; 5,419,278; and 5,096,676.

In one variation, crystals comprising HSD11B1 are formed by mixing substantially pure HSD11B1 with an aqueous buffer containing a precipitant at a concentration just below a concentration necessary to precipitate the protein. One suitable precipitant for crystallizing HSD11B1 is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a HSD11B1 complex were obtained. In order to accomplish this, systematic broad screen crystallization trials were performed on an HSD11B1 complex using the sitting drop technique. In each experiment, a 100 nL mixture of HSD11B1 complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Figure 2B:
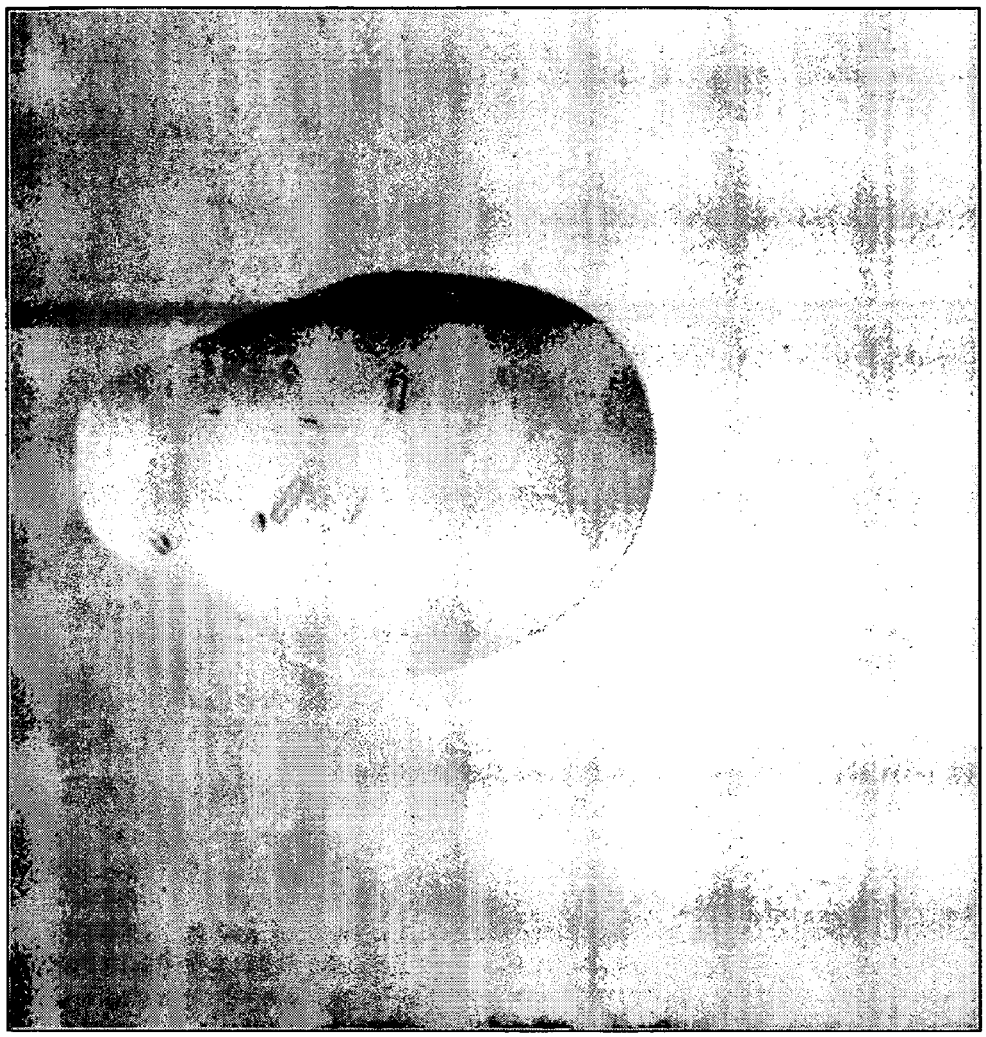
FIG. 2B illustrates a crystal of HSD11B1 corresponding to SEQ. ID No. 6, having a crystal lattice in a $P3_121$ space group and unit cell dimensions, +/−5%, of a=86.2 Å, b=86.2 Å, c=146.7 Å, $\alpha$=90.0°, $\beta$=90.0°, and $\gamma$=120°.
Figure 2C:
FIG. 2C illustrates a crystal of HSD11B1 corresponding to SEQ. ID No. 7, having a crystal lattice in a $P4_12_12$ space group and unit cell dimensions, +/−5%, of a=114 Å, b=114 Å, c=157 Å, $\alpha$=90°, $\beta$=90°, and $\gamma$=90°.

Based on the crystallization experiments that were performed, a thorough understanding of how different crystallization conditions affect HSD11B1 crystallization was obtained. Based on this understanding, a series of crystallization conditions were identified that may be used to form crystals comprising HSD11B1. These conditions are summarized in Table 5. A particular example of crystallization conditions that may be used to form diffraction quality crystals of the HSD11B1 complex is detailed in Example 2. FIGS. 2a, 2B, and 2C illustrate crystals of the HSD11B1 complex formed using the crystallization conditions provided in Table 5.

One skilled in the art will recognize that the crystallization conditions provided in Table 5 and Example 2 can be varied and still yield protein crystals comprising HSD11B1. For example, it is noted that variations on the crystallization conditions described herein can be readily determined by taking the conditions provided in Table 5 and performing fine screens around those conditions by varying the type and concentration of the components in order to determine additional suitable conditions for crystallizing HSD11B1, variants of HSD11B1, and ligand complexes thereof.

Crystals comprising HSD11B1 have a wide range of uses. For example, now that crystals comprising HSD11B1 have been produced, it is noted that crystallization may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising HSD11B1 according to the present invention, the crystals so formed can be used by this crystallization technique to initiate crystal growth of other HSD11B1 comprising crystals, including HSD11B1 complexed to other ligands.

As will be described herein in greater detail, crystals may also be used to perform X-ray or neutron diffraction analysis in order to determine the three-dimensional structure of HSD11B1 and, in particular, to assist in the identification of its active site. Knowledge of the binding site region allows rational design and construction of ligands including inhibitors. Crystallization and structural determination of HSD11B1 mutants having altered bioactivity allows the evaluation of whether such changes are caused by general structure deformation or by side chain alterations at the substitution site.

4. X-Ray Data Collection and Structure Determination

Crystals comprising HSD11B1 may be obtained as described above in Section 3. As described herein, these crystals may then be used to perform X-ray data collection and for structure determination.

In one embodiment, described in Example 2, crystals of HSD11B1 were obtained where HSD11B1 has the sequence of residues shown in SEQ. ID No. 5. These particular crystals were used to determine the three dimensional structure of HSD11B1.

Diffraction data was collected from cryocooled crystals (100K) of HSD11B1 at the Advanced Light Source (ALS) beam line 5.0.3 using an ADSC Quantum CCD detector. The diffraction pattern of the HSD11B1 crystals displayed symmetry consistent with space group $P2_1$ with unit cell dimensions a=56.4 Å, b=152.5 Å, c=73.8 Å, α=90.0°, β=92.2°, and γ=90.0° (+/−5%). Data were collected and integrated to 1.55 Å with the HKL2000 program package (Otwinowski, Z. and Minor, W., *Meth. Enzymol.* 276:307 (1997)).

The structure solution for HSD11B1 in the space group $P2_1$ with unit cell dimensions a=56.4 Å, b=152.5 Å, c=73.8 Å, α=90.0°, β=92.2°, and γ=90.0° (+/−5%) was obtained by Multiwavelength Anomalous dispersion (MAD) methods with a HSD11B1 crystal derivitized with Lutetium Acetate. Data sets extending to 2.4 Å were collected using x-rays of wavelength 1.3412 Å, 1.3408 Å, 1.3404 Å, and 1.2782 Å and phases were calculated with the program SHARP (La Fortelle, E de & Bricogne G. *Methods Enzymol.* 276:472 (1997)). All subsequent crystallographic calculations were performed using the CCP4 program package (Collaborative Computational Project, N. The CCP4 Suite: Programs for Protein Crystallography. *Acta Crystallogr.* D50, 760-763 (1994)). Multiple rounds of manual fitting of the HSD11B1 sequence into the experimental electron density maps were performed with Xfit (McRee, D. E., *J. Struct. Biol.* 125:156 (1999)). Initial manual fitting was interspersed with restrained least-squares refinement in REFMAC against data from 10.0 to 2.5 Å to give a model that was used to phase a high resolution non-derivitized 1.55 Å HSD11B1 data set. All subsequent stages of refinement against the high resolution data were performed with bulk solvent corrections and anisotropic scaling, and excluded 5% of $R_{free}$ reflections for cross-validation. The data collection and data refinement statistics are given in Table 6.

TABLE 6

| Crystal data | |
| --- | --- |
| Space group | $P2_1$ |
| Unit cell dimensions | a = 56.4 Å |
| | b = 152.5 Å |
| | c = 73.8 Å |
| | α = 90.0° |
| | β = 92.2° |
| | γ = 90.0° |
| Data collection | |
| X-ray source | ALS BL 5.0.2 |
| Wavelength [Å] | 1.00 |
| Resolution [Å] | 1.55 |
| Observations (unique) | 169082 |

TABLE 6-continued

| | | |
|---|---|---|
| Redundancy | | 2.9 |
| Completeness | overall (outer shell) | 92.2 (69)% |
| I/σ(I) | overall (outer shell) | 14.2 (2.2) |
| $R_{symm}^{1}$ | overall (outer shell) | 0.04 (.31) |
| Refinement | | |
| Reflections used | | 160594 |
| R-factor | | 16.1% |
| $R_{free}$ | | 18.4% |
| r.m.s bonds | | 0.009 Å |
| r.m.s angles | | 1.48° |

During structure determination, where the unit cell dimensions were a=56.4 Å, b=152.5 Å, c=73.8 Å, α=90.0°, β=92.2°, and γ=90.0°, it was realized that the asymmetric unit comprised four HSD11B1 molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 5. This is due to different numbering schemes used in the course of the structure refinement. Since Gln14 is the first residue visible in the electron density maps it was assigned as residue 0. Thus all the other residues in the structure coordinates are similarly number 14 residues lower than shown in SEQ. ID No. 3. Also, because of insufficient electron density, structure coordinates are not reported for the following residues: In molecule A, these residues comprise those before position 1, and C-terminal residues 270-273. In molecule B, these residues comprise those before position 0 and C-terminal residues 270-273. In molecule C, these residues comprise those before position zero, loop residues 211-214, and C-terminal residues 261-273. In molecule D, these residues comprise those before position 0, loop residues 211-214, and C-terminal residues 261-273. The final coordinate set additionally includes 1260 solvent molecules modeled as water, four molecules of the cofactor NADP+, and four molecules of the steroidal detergent CHAPS In another embodiment, described in Example 2, crystals of HSD11B1 were obtained where HSD11B1 has the sequence of residues shown in SEQ. ID No. 6. These particular crystals were also used to determine the three dimensional structure of HSD11B1.

Diffraction data was collected from cryocooled crystals (100K) of HSD11B1 at the Advanced Light Source (ALS) beam line 5.0.3 using an ADSC Quantum CCD detector. The diffraction pattern of the HSD11B1 crystals displayed symmetry consistent with space group P3$_1$21 with unit cell dimensions a=86.2 Å, b=86.2 Å, c=146.7 Å, α=90.0°, β=90.0°, and γ=120° (+/−5%). Data were collected and integrated to 2.30 Å with the HKL2000 program package (Otwinowski, Z. and Minor, W., *Meth. Enzymol.* 276:307 (1997)).

The structure solution for HSD11B1 in the space group P3$_1$21 with unit cell dimensions a=86.2 Å, b=86.2 Å, c=146.7 Å, α=90.0°, β=90.0°, and γ=120° (+/−5%) was obtained by molecular replacement with the P2$_1$ crystal form. All subsequent crystallographic calculations were performed using the CCP4 program package (Collaborative Computational Project, N. The CCP4 Suite: Programs for Protein Crystallography. *Acta Crystallogr.* D50, 760-763 (1994)). Multiple rounds of manual fitting of the HSD11B1 sequence into the experimental electron density maps were performed with Xfit (McRee, D. E., *J. Struct. Biol.* 125:156 (1999)). Initial manual fitting was interspersed with restrained least-squares refinement in REFMAC against data from 20.0 to 2.3 Å with bulk solvent corrections and anisotropic scaling. 5% of the data was excluded for cross-validation. The data collection and data refinement statistics are given in Table 7.

TABLE 7

| | | |
|---|---|---|
| Crystal data | | |
| Space group | | P3$_1$21 |
| Unit cell dimensions | | a = 86.2 Å |
| | | b = 86.2 Å |
| | | c = 146.7 Å |
| | | α = 90.0° |
| | | β = 90.0° |
| | | γ = 120.0° |
| Data collection | | |
| X-ray source | | ALS BL 5.0.3 |
| Wavelength [Å] | | 1.00 |
| Resolution [Å] | | 2.30 |
| Observations (unique) | | 30611 |
| Redundancy | | 4.3 |
| Completeness | overall (outer shell) | 99.6 (99.6)% |
| I/σ(I) | overall (outer shell) | 18 (2.2) |
| $R_{symm}^{1}$ | overall (outer shell) | 0.076 (0.54) |
| Refinement | | |
| Reflections used | | |
| R-factor | | 18.0% |
| $R_{free}$ | | 23.4% |
| r.m.s bonds | | 0.011 Å |
| r.m.s angles | | 1.53° |

In another embodiment, described in Example 2, crystals of HSD11B1 were obtained where HSD11B1 has the sequence of residues shown in SEQ. ID No. 7. These particular crystals were also used to determine the three dimensional structure of HSD11B1.

Diffraction data was collected from cryocooled crystals (100K) of HSD11B1 at the Advanced Light Source (ALS) beam line 5.0.3 using an ADSC Quantum CCD detector. The diffraction pattern of the HSD11B1 crystals displayed symmetry consistent with space group P4$_1$2$_1$2 with unit cell dimensions 114 114 157 90 90 (+/−5%). Data were collected and integrated to 2.30 Å with the HKL2000 program package (Otwinowski, Z. and Minor, W., *Met. Enzymol.* 276:307 (1997)).

The structure solution for HSD11B1 in the space group P4$_1$2$_1$2 with unit cell dimensions a=114 Å, b=114 Å, c=157 Å, α=90°, β=90°, and γ=90° (+/−5%) was obtained by molecular replacement with the P2$_1$ crystal form. All subsequent crystallographic calculations were performed using the CCP4 program package (Collaborative Computational Project, N. The CCP4 Suite: Programs for Protein Crystallography. *Acta Crystallogr.* D50, 760-763 (1994)). Multiple rounds of manual fitting of the HSD11B1 sequence into the experimental electron density maps were performed with Xfit (McRee, D. E., *J. Struct. Biol.* 125:156 (1999)). Initial manual fitting was interspersed with restrained least-squares refinement in REFMAC against data from 10.0 to 2.3 Å with bulk solvent corrections and anisotropic scaling. 5% of the data was excluded for for cross-validation. The data collection and data refinement statistics are given in Table 8.

TABLE 8

| Crystal data | | |
|---|---|---|
| Space group | | $P4_12_12$ |
| Unit cell dimensions | | a = 114 Å |
| | | b = 114 Å |
| | | c = 157 Å |
| | | α = 90.0° |
| | | β = 90.0° |
| | | γ = 90.0° |
| Data collection | | |
| X-ray source | | ALS BL 5.0.3 |
| Wavelength [Å] | | 1.00 |
| Resolution [Å] | | 2.30 |
| Observations (unique) | | 49660 |
| Redundancy | | 5.1 |
| Completeness | overall (outer shell) | 99.6 (100)% |
| I/σ(I) | overall (outer shell) | 14.0 (2.2) |
| $R_{symm}^1$ | overall (outer shell) | 0.10 (.42) |
| Refinement | | |
| Reflections used | | 47075 |
| R-factor | | 20.2% |
| $R_{free}$ | | 22.2% |
| r.m.s bonds | | 0.008 Å |
| r.m.s angles | | 1.50° |

It is noted that other crystals comprising HSD11B1 including different HSD11B1 variants, fragments, and complexes thereof may also be used.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of the ligands that could associate with those pockets. The term "binding pocket" as used herein refers to a region of the protein that, as a result of its shape, favorably associates with a ligand.

These variations in coordinates may be generated because of mathematical manipulations of the HSD11B1 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of HSD11B1 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1.

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a target protein from the atomic coordinates of a reference protein or portions of thereof. The structure coordinates for HSD11B1, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1AE1 was identified as having the smallest RMSD values relative to the structure coordinates provided herein. Table 9 below provides a series of RMSD values that were calculated by the above described process using the structure coordinates in FIG. 3 as the reference protein and the structure coordinates from PDB code: 1AE1 (Jimsonweed tropinone reductase-I complex with NADP) as the target protein.

TABLE 9

| AA RESIDUES USED TO PERFORM RMSD COMPARISON WITH PDB:1VR2 | PORTION OF EACH AA RESIDUE USED TO PERFORM RMSD COMPARISON WITH PDB:1AE1 | RMSD [Å] |
|---|---|---|
| Table 2 (4 Angstrom set) | alpha-carbon atoms[1] | 0.68 |
| | main-chain atoms[1] | 0.64 |
| | all non-hydrogen[2] | 0.89 |
| Table 3 (7 Angstrom set) | alpha-carbon atoms[1] | 2.11 |
| | main-chain atoms[1] | 2.24 |
| | all non-hydrogen[2] | 2.32 |
| Table 4 (10 Angstrom set) | alpha-carbon atoms[1] | 4.01 |
| | main-chain atoms[1] | 3.96 |
| | all non-hydrogen[2] | 4.54 |
| 24-292 of SEQ. ID No. 1 | alpha-carbon atoms[1] | 3.21 |
| | main-chain atoms[1] | 3.18 |
| | all non-hydrogen[2] | 3.53 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

It is noted that mutants and variants of HSD11B1, as well as other SDRs, are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3, or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted, there are many different ways to express the surface contours of the HSD11B1 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. HSD11B1 Structure

The present invention is also directed to a three-dimensional crystal structure of HSD11B1. This crystal structure may be used to identify binding sites, to provide mutants having desirable binding properties, and ultimately, to design, characterize, or identify ligands that interact with HSD11B1 as well as other structurally similar proteins.

The three-dimensional crystal structure of HSD11B1 may be generated, as is known in the art, from the structure coordinates shown in FIG. 3 and similar such coordinates.

Figure 4:
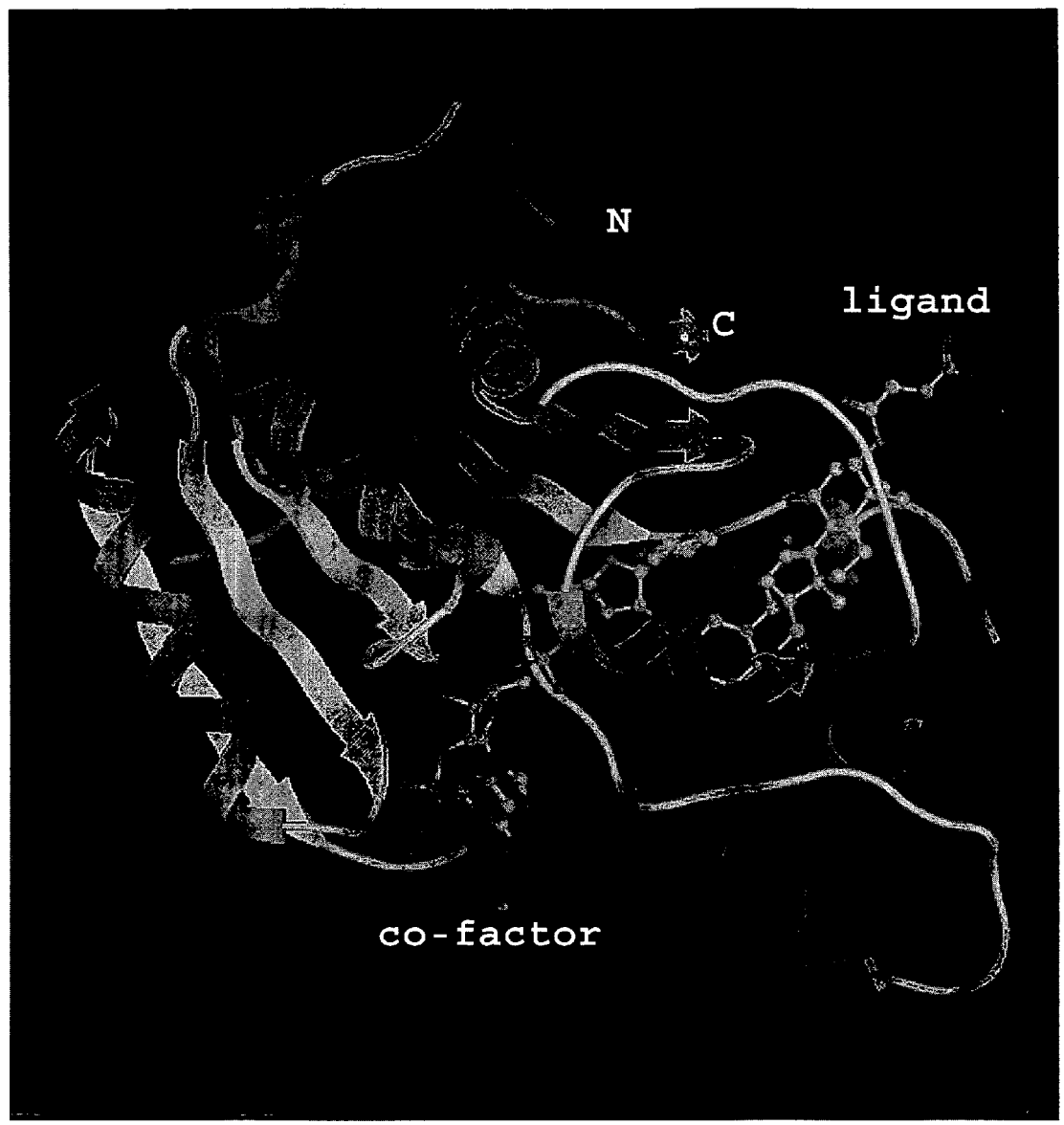
FIG. 4 illustrates a ribbon diagram overview of the structure of HSD11B1, highlighting secondary structural elements of the protein.

FIG. 4 illustrates a ribbon diagram overview of the structure of HSD11B1.

Figure 5:
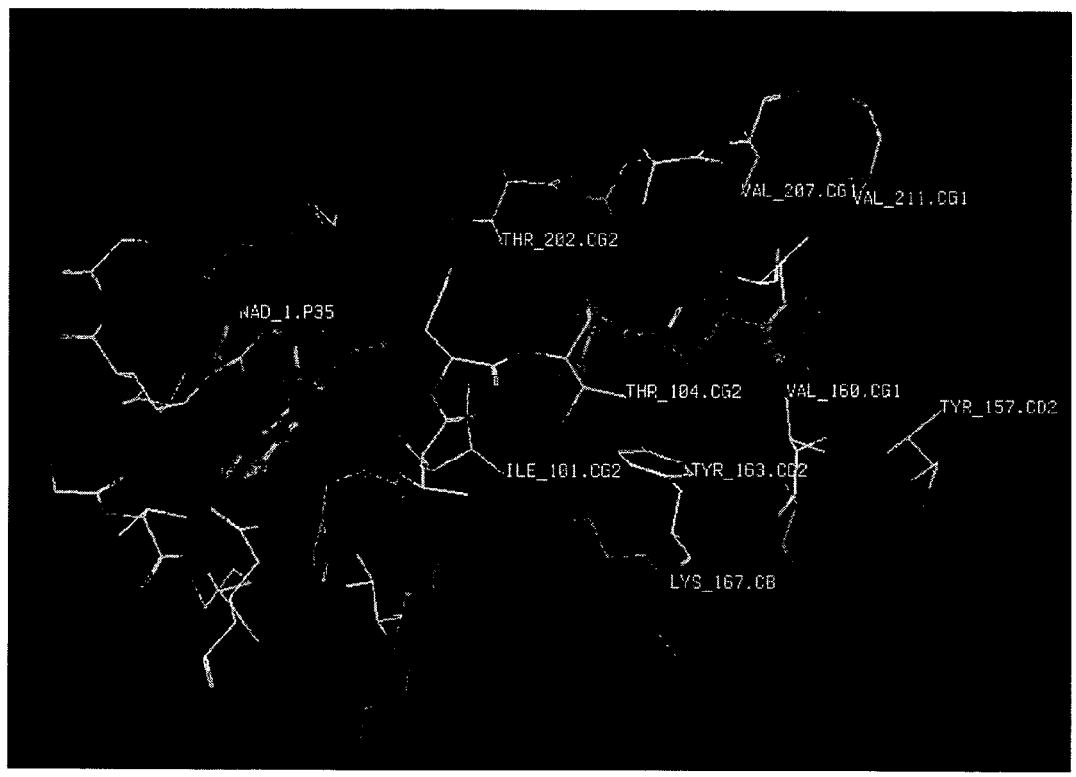
FIG. 5 illustrates the HSD11B1 binding site of HSD11B1 based on the determined crystal structure for the molecule in the asymmetric unit corresponding to the coordinates shown in FIG. 3.

FIG. 5 illustrates the binding site of HSD11B1 based on the determined crystal structure corresponding to the coordinates shown in FIG. 3.

6. HSD11B1 Active Site and Ligand Interaction

The terms "binding site" or "binding pocket", as used herein, refer to a region of a protein that, as a result of its shape, favorably associates with a ligand or substrate. The term "HSD11B1-like binding pocket" refers to a portion of a molecule or molecular complex whose shape is sufficiently similar to the HSD11B1 binding pockets as to bind common ligands. This commonality of shape may be quantitatively defined based on a comparison to a reference point, that reference point being the structure coordinates provided herein. For example, the commonality of shape may be quantitatively defined based on a root mean square deviation (RMSD) from the structure coordinates of the backbone atoms of the amino acids that make up the binding pockets in HSD11B1 (as set forth in FIG. 3).

The "active site binding pockets" or "active site" of HSD11B1 refers to the area on the surface of HSD11B1 where the substrate binds.

FIG. 5 illustrates the substrate binding site of HSD11B1 based on the determined crystal structure for the molecule in the asymmetric unit corresponding to the structure coordinates shown in FIG. 3. The catalytic site for the substrate is located as in FIG. 5.

The substrate binding site of SDRs is a primary target for the design of small molecule inhibitors. The substrate binding site appears well conserved among SDRs and involves residues comprising a relatively hydrophobic pocket. The structure of the substrate binding pocket in the HSD11B1 complex shows considerable sequence variability with other SDRs, which is reflective of diversity among SDR subfamilies. The substrate binding pocket shows subtle differences in substrate site architecture that may be explored to confer specificity of inhibition.

In resolving the crystal structure of HSD11B1, Applicants determined that HSD11B1 amino acids shown in Table 2 (above) are encompassed within a 4-Angstrom radius around the HSD11B1 active site and therefore are likely close enough to interact with an active site inhibitor of HSD11B1. Applicants have also determined that the amino acids shown in Table 3 (above) are encompassed within a 7-Angstrom radius around the HSD11B1 active site. Further, the amino acids shown in Table 4 (above) are encompassed within a 10-Angstrom radius around the HSD11B1 active site. Due to their proximity to the active site, the amino acids in the 4, 7, and/or 10 Angstrom sets are preferably conserved in variants of HSD11B1. While it is desirable to largely conserve these residues, it should be recognized however that variants may also involve varying 1, 2, 3, 4 or more of the residues set forth in Tables 2, 3 and 4, for example, in order to evaluate the roles these amino acids play in the binding pocket.

With the knowledge of the HSD11B1 crystal structure provided herein, Applicants are able to know the contour of an HSD11B1 binding pocket based on the relative positioning of the 4, 7, and/or 10 Angstroms sets of amino acids. Again, it is noted that it may be desirable to form variants where 1, 2, 3, 4 or more of the residues set forth in Tables 2, 3 and 4 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acids residues specified in Column 2 of Table 1 of each set of structure coordinates are superimposed and the root mean square deviation is based only on those amino acid residues in the structure coordinates that are also present in the portion of the protein specified in Column 1 of Table 1.

As noted above, there are many different ways to express the surface contours of the HSD11B1 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of HSD11B1 may be different than that set forth for HSD11B1. Corresponding amino acids in other isoforms of HSD11B1 are easily identified by visual inspection of the amino acid sequences or by using commercially available homology software programs, as further described below.

7. System For Displaying the Three Dimensional Structure of HSD11B1

The present invention is also directed to machine-readable data storage media having data storage material encoded with machine-readable data that comprises structure coordinates for HSD11B1. The present invention is also directed to a machine readable data storage media having data storage material encoded with machine readable data, which, when read by an appropriate machine, can display a three dimensional representation of a structure of HSD11B1.

All or a portion of the HSD11B1 coordinate data shown in FIG. 3, when used in conjunction with a computer programmed with software to translate those coordinates into the three-dimensional structure of HSD11B1 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of HSD11B1 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an HSD11B1-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising HSD11B1 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other HSD11B1-like enzymes, and isoforms of HSD11B1.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
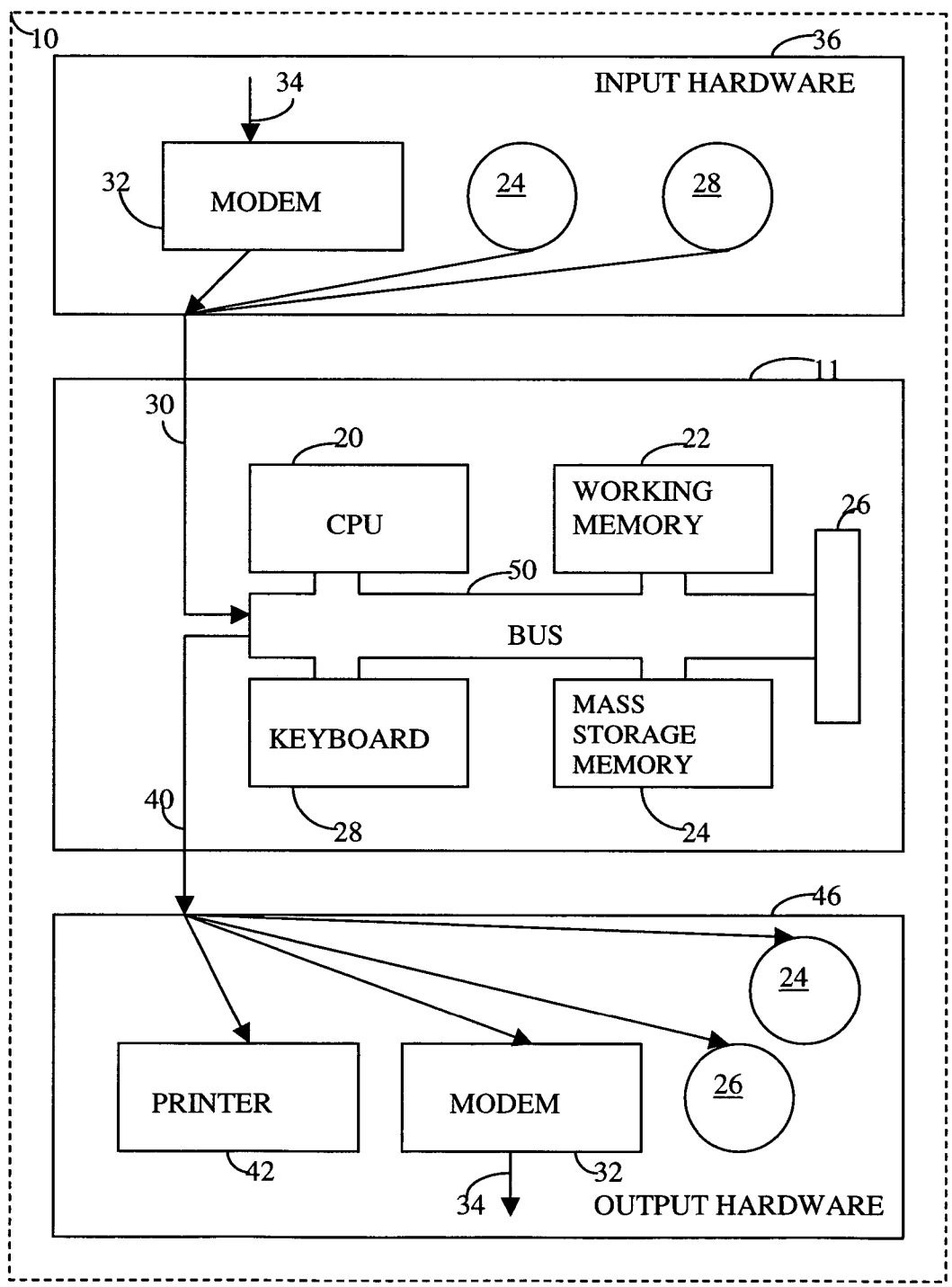
FIG. 6 illustrates a system that may be used to carry out instructions for displaying a crystal structure of HSD11B1 encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices coupled to computer 11 by output lines 40, may similarly implement output hardware 46. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46; coordinates data accesses from mass storage 24 and accesses to and from working memory 22; and determines the sequence of data processing steps. A number of programs may be used to process the machine-readable data of this invention. Such programs are discussed in reference to using the three dimensional structure of HSD11B1 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of HSD11B1

The three-dimensional crystal structure of the present invention may be used to identify HSD11B1 binding sites, be used as a molecular replacement model to solve the structure of unknown crystallized proteins, to design mutants having desirable binding properties, and ultimately, to design, characterize and identify entities capable of interacting with HSD11B1 and other structurally similar proteins, as well as other uses that would be recognized by one of ordinary skill in the art. Such entities may be chemical entities or proteins. The term "chemical entity," as used herein, refers to chemical compounds, complexes of at least two chemical compounds, and fragments of such compounds.

The HSD11B1 structure coordinates provided herein are useful for screening and identifying drugs that inhibit HSD11B1 and other structurally similar proteins. For example, the structure encoded by the data may be computationally evaluated for its ability to associate with putative substrates or ligands. Such compounds that associate with HSD11B1 may inhibit HSD11B1, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with HSD11B1 or a fragment or variant thereof by using all or a portion of the structure coordinates provided in FIG. 3 or functional equivalents thereof. A method is also provided for evaluating the potential of an entity to associate with HSD11B1 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an HSD11B1-like binding pocket. One embodiment of the method comprises: using all or a portion of the structure coordinates provided herein to generate a three-dimensional structure of an HSD11B1-like binding pocket; employing the three-dimensional structure to design or select a potential ligand; synthesizing the potential ligand; and contacting the synthesized potential ligand with a protein comprising an HSD11B1-like binding pocket to determine the ability of the potential ligand to interact with the protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an HSD11B1-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an HSD11B1-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for HSD11B1, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity and contacting a protein having an HSD11B1-like binding pocket with the synthesized entity.

With the structure provided herein, the present invention for the first time permits the use of molecular design techniques to identify, select or design potential inhibitors of HSD11B1, based on the structure of an HSD11B1-like binding pocket. Such a predictive model is valuable in light of the high costs associated with the preparation and testing of the many diverse compounds that may possibly bind to the HSD11B1 protein.

According to this invention, a potential HSD11B1 inhibitor may now be evaluated for its ability to bind an HSD11B1-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an HSD11B1-like binding pocket may be computationally evaluated using a series of steps in which chemical entities or fragments are screened and selected for their ability to associate with the HSD11B1-like binding pockets.

One skilled in the art may use one of several methods to screen entities (whether chemical or protein) for their ability to associate with an HSD11B1-like binding pocket. This process may begin by visual inspection of, for example, an HSD11B1-like binding pocket on a computer screen based on the HSD11B1 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)) available from Oxford University, Oxford, UK; MCSS (A. Miranker et al., "Functionality Maps of Binding Sites: A Multiple Copy Simultaneous Search Method", Proteins: Structure, Function and Genetics, 11, pp. 29-34 (1991)) available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)) available from Scripps Research Institute, La Jolla, Calif.; and DOCK (I. D. Kuntz et al., "A Geometric Approach to Macromolecule-Ligand Interactions", J. Mol. Biol., 161, pp. 269-288 (1982)) available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of HSD11B1. This may then be followed by manual model building using software such as MOE, QUANTA or Sybyl [Tripos Associates, St. Louis, Mo.].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems," Special Pub., Royal Chem. Soc., 78, pp. 182-196 (1989); G. Lauri and P. A. Bartlett, "CAVEAT: a Program to Facilitate the Design of Organic Molecules," J. Comput. Aided Mol. Des., 8, pp. 51-66 (1994)) available from the University of California, Berkeley, Calif.; 3D Database systems such as ISIS (MDL Information Systems, San Leandro, Calif.) reviewed in Y. C. Martin, "3D Database Searching in Drug Design", J. Med. Chem., 35, pp. 2145-2154 (1992); and HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994)) available from Molecular Simulations, San Diego, Calif.

Instead of proceeding to build an inhibitor of an HSD11B1-like binding pocket in a step-wise fashion one fragment or entity at a time as described above, inhibitory or other HSD11B1 binding compounds may be designed as a whole or "de novo" using either an empty binding site or optionally including some portion(s) of a known inhibitor (s). There are many de novo ligand design methods including: LUDI (H. -J. Bohm, "The Computer Program LUDI: A New Method for the De Novo Design of Enzyme Inhibitors", J. Comp. Aid. Molec. Design, 6, pp. 61-78 (1992)) available from Molecular Simulations Incorporated, San Diego, Calif.; LEGEND (Y. Nishibata et al., Tetrahedron, 47, p. 8985 (1991)) available from Molecular Simulations Incorporated, San Diego, Calif.; LEAPFROG available from Tripos Associates, St. Louis, Mo.; and SPROUT (V. Gillet et al., "SPROUT: A Program for Structure Generation)", J. Comput. Aided Mol. Design, 7, pp. 127-153 (1993)), available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an HSD11B1 binding pocket may be tested and optimized by computational evaluation. For example, an effective HSD11B1 binding pocket inhibitor preferably demonstrates a relatively small difference in energy between its bound and free states (i.e., a small deformation energy of binding). Thus, the most efficient HSD11B1 binding pocket inhibitors should preferably be designed with deformation energy of binding of not greater than about 10 kcal/mole, and more preferably, not greater than 7 kcal/mole. HSD11B1 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an HSD11B1 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an HSD11B1 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an HSD11B1-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set froth in FIG. 3 as a molecular replacement model.

By using molecular replacement, all or part of the structure coordinates of the HSD11B1 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of HSD11B1 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol. 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of HSD11B1 can be resolved by this method.

In one embodiment, the method of molecular replacement is utilized to obtain structural information about the present invention and any other HSD11B1-like molecule. The structure coordinates of HSD11B1, as provided by this invention, are particularly useful in solving the structure of other isoforms of HSD11B1 or HSD11B1 complexes.

The structure coordinates of HSD11B1 as provided by this invention are useful in solving the structure of HSD11B1 variants that have amino acid substitutions, additions and/or deletions (referred to collectively as "HSD11B1 mutants", as compared to naturally occurring HSD11B1). These HSD11B1 mutants may optionally be crystallized in co-complex with a ligand, such as an inhibitor, substrate analogue or a suicide substrate. The crystal structures of a series of such complexes may then be solved by molecular replacement and compared with that of HSD11B1. Potential sites for modification within the various binding sites of the enzyme may thus be identified. This information provides an additional tool for determining the most efficient binding interactions such as, for example, increased hydrophobic interactions, between HSD11B1 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known HSD11B1 inhibitors, and more importantly, to design new HSD11B1 inhibitors.

The structure coordinates described above may also be used to derive the dihedral angles, phi and psi, that define the conformation of the amino acids in the protein backbone. As will be understood by those skilled in the art, the $\text{phi}_n$ angle refers to the rotation around the bond between the alpha-carbon and the nitrogen, and the $\text{psi}_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of HSD11B1

Crystals, crystallization conditions and the diffraction pattern of HSD11B1 that can be generated from the crystals also have a range of uses. One particular use relates to screening entities that are not known ligands of HSD11B1 for their ability to bind to HSD11B1. For example, with the availability of crystallization conditions, crystals and diffraction patterns of HSD11B1 provided according to the present invention, it is possible to take a crystal of HSD11B1; expose the crystal to one or more entities that may be a ligand of HSD11B1; and determine whether a ligand/HSD11B1 complex is formed. The crystals of HSD11B1 may be exposed to potential ligands by various methods, including but not limited to, soaking a crystal in a solution of one or more potential ligands or co-crystallizing HSD11B1 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/HSD11B1 complex(es) may be used to design new ligands that bind tighter, bind more specifically, have better biological activity or have better safety profiles than known ligands.

In one embodiment, a method is provided for identifying a ligand that binds to HSD11B1 comprising: (a) attempting to crystallize a protein that comprises a sequence wherein at least a portion of the sequence has 55%, 65%, 75%, 85%, 90%, 95%, 97%, 99% or greater identity with SEQ. ID No. 5 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In one embodiment, a method is provided for identifying a ligand that binds to HSD11B1 comprising: (a) attempting to crystallize a protein that comprises a sequence wherein at least a portion of the sequence has 55%, 65%, 75%, 85%, 90%, 95%, 97%, 99% or greater identity with SEQ. ID No. 6 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In one embodiment, a method is provided for identifying a ligand that binds to HSD11B1 comprising: (a) attempting to crystallize a protein that comprises a sequence wherein at least a portion of the sequence has 55%, 65%, 75%, 85%, 90%, 95%, 97%, 99% or greater identity with SEQ. ID No. 7 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to HSD11B1 comprising: soaking a crystal of a protein wherein at least a portion of the protein has 55%, 65%, 75%, 85%, 90%, 95%, 97%, 99% or greater identity with SEQ. ID No. 5 with one or more entities; determining whether a ligand/protein complex was formed by comparing an X-ray diffraction pattern of a crystal of the protein that has not been soaked with the one or more entities to the crystal that has been soaked with the one or more entities.

In another embodiment, a method is provided for identifying a ligand that binds to HSD11B1 comprising: soaking a crystal of a protein wherein at least a portion of the protein has 55%, 65%, 75%, 85%, 90%, 95%, 97%, 99% or greater identity with SEQ. ID No. 6 with one or more entities; determining whether a ligand/protein complex was formed by comparing an X-ray diffraction pattern of a crystal of the protein that has not been soaked with the one or more entities to the crystal that has been soaked with the one or more entities.

In another embodiment, a method is provided for identifying a ligand that binds to HSD11B1 comprising: soaking a crystal of a protein wherein at least a portion of the protein has 55%, 65%, 75%, 85%, 90%, 95%, 97%, 99% or greater identity with SEQ. ID No. 7 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-HSD11B1 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of HSD11B1 from *E. Coli*

Residues 24 to 292 of 11-β-hydroxysteroid dehydrogenase isoform 1 (SEQ. ID No. 5) were amplified from IMAGE clone 5193867 (ATCC clone 7277078) using PCR with the primers hsd1_24-f: 5'-AACGAGGAATTCAGAC-CAGAGATG-3' (SEQ. ID No. 8) and hsd1-292-r: 5'-TTACTTGTTTATGAATCTGTCCAT-3' (SEQ. ID No. 9). The resulting PCR product was topocloned into the pBAD-ThioE vector (Invitrogen) that was modified by inserting a DNA sequence that codes for MKHQHQHQHQHQHQQPL at the cloning site and adapted for TOPOcloning PCR (Invitrogen). Residues 24-292 of 11-β-hydroxysteroid dehydrogenase isoform 1 were generated fused with MKHQHQHQHQHQHQQPL at the N-terminus under control of an ara promoter. One point mutation C272S was made in the final construct by quick change PCR mutagenesis using the primers hsdC272Sqcf: 5'-TCAGAAATCCATCCAGGAAGATC-3' (SEQ. ID No. 10) and hsdC272Sqcr: 5'-GATCTTCCTGGATG-GATTTCTGA-3' (SEQ. ID No. 11).

Residues 24-258 and residues 24-267 of 11-β-hydroxysteroid dehydrogenase isoform 1 (SEQ. ID Nos. 6 and 7) were also amplified. The plasmid described above was used to generate 2 C-terminal truncations using PCR with primers hsd1_24-f: 5'-AACGAGGAATTCAGACCAGAGATG-3' (SEQ. ID No. 8) and hsd1-258-r: 5'-ATAATACACTTCT-TCTTGGCGCAGAGC-3' (SEQ. ID No. 12) to amplify residues 24 to 258 of 11-β-hydroxysteroid dehydrogenase isoform 1 (SEQ. ID No. 6) and hsd1_24-f: 5'-AACGAG-GAATTCAGACCAGAGATG-3' (SEQ. ID No. 8) and hsd1-267-r: 5'-CAGAAGAGTGGTCCAGAGTGAGCTGTC-3' (SEQ. ID No. 13) to amplify residues 24-267 of 11-β-hydroxysteroid dehydrogenase isoform 1 (SEQ. ID No. 7). The resulting PCR products were topocloned and expressed by the same method described above.

*E. coli* DH10b-Tir (Invitrogen) or BL21 (DE3) (Invitrogen), harboring the HSD11B1 expression plasmid, were grown overnight at 37° C., in Luria broth (LB) supplemented to 0.05 mg/ml kanamycin (Km). 15 mls of saturated culture was then used to inoculate one liter of fresh LB (0.05 mg/ml Km). When this culture reached an optical density of 0.4 (λ=600 nm), the growth temperature was shifted from 37° C. to 25° C. After an additional 2 hours of growth, arabinose and corticosterone were added to a final concentration of 0.2% (w/w), and 0.25 mM, respectively. Cells were harvested approximately 14 hours following induction, and were immediately frozen at −80° C. The cell pellets from each liter of cell culture were thawed and resuspended in 50 ml of lysis buffer (30 mM CHAPS or 1 mM corticosterone, 50 mM Tris-HCl, pH 7.9, 0.15 M NaCl, 0.5 μl/ml benzonase, 1 μl/ml ReadyLyse). Following a 30-minute incubation at room temperature, the lysates were clarified by centrifugation. The resulting supernatant was loaded on 6 ml of Probond resin (Invitrogen), previously equilibrated with wash buffer (4 mM CHAPS or 1 mM corticosterone, 50 mM Tris-HCl, pH 7.9, 0.25 M NaCl, 40 mM imidazole), and then washed with 10 column volumes of wash buffer. HSD11B1 was then eluted with 3 column volumes of wash buffer supplemented to 0.2 M imidazole. The eluate of purified HSD11B1 was extensively dialysed against 4 mM CHAPS or 1 mM corticosterone, 25 mM Tris-HCl, pH 7.9, 0.25 M NaCl, and concentrated to 10 mg/ml. Size exclusion chromatography demonstrated that this method of purification yields monodispersive HSD11B1.

Example 2

Crystallization of HSD11B1

This example describes the crystallization of HSD11B1. It is noted that the precise crystallization conditions used may be further varied, for example by performing a fine screen based on these crystallization conditions.

Crystals of HSD11B1 protein samples corresponding to SEQ. ID No. 5 were obtained after an extensive and broad screen of conditions, followed by optimization. Diffraction quality crystals were grown in 100/nl sitting droplets using the vapor diffusion method. 50/nl comprising HSD11B1 (12.1 mg/ml) was mixed with 50/nl from a reservoir solution (100/μl) comprising: 22% PEG 3350; and 0.1M MES buffer pH=6.5. Crystals from the resulting solution were incubated over a period of two weeks at 20° C. These crystals could also be obtained from MPEG 2000, MPEG 5000, PEG 2000, PEG 4000 and PEG 6000 at 20° C. Crystals typically appeared after 3-5 days and grew to a maximum size within 7-10 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of the HSD11B1 produced as described is illustrated in FIG. 2A.

Crystals of HSD11B1 protein samples corresponding to SEQ. ID No. 6 were also obtained. 50/nl comprising HSD11B1 (19.1 mg/ml) was mixed with 50/nl from a reservoir solution (100/µl) comprising: 65% Methyl-Pentanediol; and 0.1M Bicine buffer pH=9.0. Crystals from the resulting solution typically appeared after three weeks at 4° C. Crystals were flash frozen directly in mother liquor by immersion in liquid nitrogen and then stored under liquid nitrogen. A crystal of the HSD11B1 produced as described is illustrated in FIG. 2B.

In addition, crystals of HSD11B1 protein samples corresponding to SEQ. ID No. 7 were obtained. 50/nl comprising HSD11B1 (9.5 mg/ml) was mixed with 50/nl from a reservoir solution (100/µl) comprising: 2.25M Sodium Chloride; 0.08M Monobasic Sodium Phosphate, and 0.02M Dibasic Ammonium Phosphate. Crystals from the resulting solution typically appeared after 3 days at 20° C. Crystals could also be obtained using Sodium Chloride concentrations ranging between 1.0M and 3.5M. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of the HSD11B1 produced as described is illustrated in FIG. 2C.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

We claim:

1. A composition comprising a protein in crystalline form wherein the protein consists of SEQ ID No: 5 and wherein the protein crystal has a crystal lattice in a $P2_1$ space group and unit cell dimensions, +/− 5% of a=56.4 Å, b=152.5 Å, c=73.8 Å, α=90°, β=92.2° and γ=90°.

2. A composition according to claim 1 wherein the protein crystal diffracts X-rays for a determination of structure coordinates to a resolution greater than 3.0 Angstroms.

3. A method for forming a crystal of a protein comprising: forming a crystallization volume comprising a precipitant solution and a protein that consists of SEQ ID No: 5 and wherein the protein crystal has a crystal lattice in a $P2_1$ space group and unit cell dimensions, +/− 5% of a=56.4 Å, b=152.5 Å, c=73.8 Å, α=90°, β=92.2° and γ=90°; and storing the crystallization volume under conditions suitable for crystal formation of the protein.

4. A method according to claim 3 wherein the protein diffracts X-rays for a determination of structure coordinates to a resolution greater than 3.0 Angstroms.

5. A method according to claim 3, the method further comprising diffracting the protein crystal to produce a diffraction pattern and solving the structure of the protein from the diffraction pattern.

6. A soluble protein consisting of SEQ ID No: 5.

7. A non-crystalline protein consisting of SEQ ID No: 5.

8. An isolated soluble protein consisting of SEQ ID No: 5.

9. An isolated non-crystalline protein consisting of SEQ ID No: 5.

* * * * *